United States Patent
Lee et al.

(10) Patent No.: US 8,993,783 B2
(45) Date of Patent: *Mar. 31, 2015

(54) COMPOUND FOR ORGANIC PHOTOELECTRIC DEVICE AND ORGANIC PHOTOELECTRIC DEVICE INCLUDING THE SAME

(71) Applicants: Kyoung-Mi Lee, Uiwang-si (KR); Dal-Ho Huh, Uiwang-si (KR); Dong-Wan Ryu, Uiwang-si (KR); Sung-Hyun Jung, Uiwang-si (KR); Mi-Young Chae, Uiwang-si (KR)

(72) Inventors: Kyoung-Mi Lee, Uiwang-si (KR); Dal-Ho Huh, Uiwang-si (KR); Dong-Wan Ryu, Uiwang-si (KR); Sung-Hyun Jung, Uiwang-si (KR); Mi-Young Chae, Uiwang-si (KR)

(73) Assignee: Cheil Industries, Inc., Gumi-si, Kyeongsangbuk-do (KR)

(*) Notice: Subject to any disclaimer, the term of this patent is extended or adjusted under 35 U.S.C. 154(b) by 128 days.

This patent is subject to a terminal disclaimer.

(21) Appl. No.: 13/691,872

(22) Filed: Dec. 3, 2012

(65) Prior Publication Data

US 2013/0087776 A1  Apr. 11, 2013

Related U.S. Application Data

(63) Continuation of application No. PCT/KR2010/007545, filed on Oct. 29, 2010.

(30) Foreign Application Priority Data

Jun. 1, 2010 (KR) .......................... 10-2010-0052014

(51) Int. Cl.

| | | |
|---|---|---|
| C07C 209/86 | (2006.01) | |
| H01L 51/50 | (2006.01) | |
| C07D 209/80 | (2006.01) | |
| C07D 209/86 | (2006.01) | |
| C09K 11/06 | (2006.01) | |
| H01L 51/00 | (2006.01) | |
| H05B 33/10 | (2006.01) | |
| C07D 403/12 | (2006.01) | |
| C07D 405/12 | (2006.01) | |
| C07D 405/14 | (2006.01) | |
| C07D 409/12 | (2006.01) | |
| C07D 409/14 | (2006.01) | |
| C09B 57/00 | (2006.01) | |
| H01L 51/42 | (2006.01) | |

(52) U.S. Cl.
CPC ............ *C07D 209/80* (2013.01); *C07D 209/86* (2013.01); *C09K 11/06* (2013.01); *H01L 51/0054* (2013.01); *H01L 51/0072* (2013.01); *H05B 33/10* (2013.01); *C07D 403/12* (2013.01); *C07D 405/12* (2013.01); *C07D 405/14* (2013.01); *C07D 409/12* (2013.01); *C07D 409/14* (2013.01); *H01L 51/0052* (2013.01); *C09B 57/00* (2013.01); *C09B 57/008* (2013.01); *H01L 51/006* (2013.01); *H01L 51/0061* (2013.01); *H01L 51/0074* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0059* (2013.01); *H01L 51/42* (2013.01); *Y02E 10/549* (2013.01); *H01L 51/0055* (2013.01); *H01L 51/0081* (2013.01); *H01L 51/5056* (2013.01)

USPC .......................................... 548/440; 257/40

(58) Field of Classification Search
None
See application file for complete search history.

(56) References Cited

U.S. PATENT DOCUMENTS

| | | |
|---|---|---|
| 2006/0051613 A1 | 3/2006 | Tomita et al. |
| 2006/0073357 A1 | 4/2006 | Brunner et al. |
| 2006/0088728 A1 | 4/2006 | Kwong et al. |

(Continued)

FOREIGN PATENT DOCUMENTS

| | | |
|---|---|---|
| KR | 10 2005-0100673 A | 10/2005 |
| KR | 10 2009-0035729 A | 4/2009 |
| WO | WO 2004/074399 A1 | 9/2004 |

(Continued)

OTHER PUBLICATIONS

Search Report in PCT/KR2010/007545 dated Aug. 1, 2011 (Lee, et al.).

*Primary Examiner* — Nyeemah A Grazier
(74) *Attorney, Agent, or Firm* — Lee & Morse, P.C.

(57) ABSTRACT

A compound for an organic photoelectric device, the compound being represented by the following Chemical Formula 1:

[Chemical Formula 1]

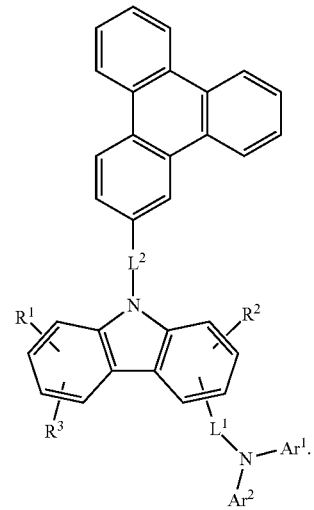

16 Claims, 5 Drawing Sheets

(56) References Cited

U.S. PATENT DOCUMENTS

2008/0124572 A1 5/2008 Mizuki et al.
2013/0105771 A1* 5/2013 Ryu et al. ................... 257/40
2014/0070199 A1* 3/2014 Jung et al. .................. 257/40

FOREIGN PATENT DOCUMENTS

| WO | WO 2006/047119 A1 | 5/2006 |
| WO | WO 2007/043484 A1 | 4/2007 |
| WO | WO 2008/062636 A1 | 5/2008 |

* cited by examiner

COMPOUND FOR ORGANIC PHOTOELECTRIC DEVICE AND ORGANIC PHOTOELECTRIC DEVICE INCLUDING THE SAME

CROSS-REFERENCE TO RELATED APPLICATIONS

This application is a continuation of pending International Application No. PCT/KR2010/007545, entitled "COMPOUND FOR ORGANIC PHOTOELECTRIC DEVICE AND ORGANIC PHOTOELECTRIC DEVICE INCLUDING THE SAME," which was filed on Oct. 29, 2010, the entire contents of which are hereby incorporated by reference.

This application claims priority to and the benefit of Korean Patent Application No. 10-2010-0052014, filed on Jun. 1, 2010, in the Korean Intellectual Property Office, and entitled: "COMPOUND FOR ORGANIC PHOTOELECTRIC DEVICE AND ORGANIC PHOTOELECTRIC DEVICE INCLUDING THE SAME," the entire contents of which are hereby incorporated by reference.

BACKGROUND

1. Field

Embodiments relate to a compound for an organic photoelectric device and an organic photoelectric device including the same.

2. Description of the Related Art

An organic photoelectric device is, in a broad sense, a device for transforming photo-energy to electrical energy or conversely, a device for transforming electrical energy to photo-energy.

An organic photoelectric device may be classified as follows in accordance with its driving principles. A first organic photoelectric device is an electronic device driven as follows: excitons are generated in an organic material layer by photons from an external light source; the excitons are separated into electrons and holes; and the electrons and holes are transferred to different electrodes as a current source (voltage source).

A second organic photoelectric device is an electronic device driven as follows: a voltage or a current is applied to at least two electrodes to inject holes and/or electrons into an organic material semiconductor positioned at an interface of the electrodes, and the device is driven by the injected electrons and holes.

SUMMARY

Embodiments are directed to a compound for an organic photoelectric device, the compound being represented by the following Chemical Formula 1:

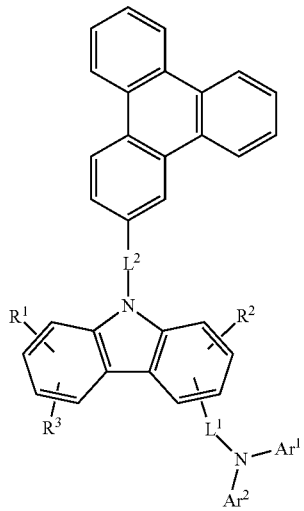

[Chemical Formula 1]

In Chemical Formula 1,
$L^1$ and $L^2$ may each independently be selected from the group of a single bond, a substituted or unsubstituted C2 to C6 alkenylene group, a substituted or unsubstituted C2 to C6 alkynylene group, a substituted or unsubstituted C6 to C30 arylene group, and a substituted or unsubstituted C2 to C30 heteroarylene group, $R^1$ to $R^3$ may each independently be selected from the group of hydrogen, a substituted or unsubstituted C1 to C6 alkyl group, a substituted or unsubstituted C6 to C30 aryl group, and a substituted or unsubstituted C2 to C30 heteroaryl group, and $Ar^1$ and $Ar^2$ may each independently be a substituted or unsubstituted C6 to C30 aryl group, or a substituted or unsubstituted C2 to C30 heteroaryl group.

The $Ar^1$ and $Ar^2$ may each independently be selected from the group of a substituted or unsubstituted phenyl group, a substituted or unsubstituted naphthalenyl group, a substituted or unsubstituted fluorenyl group, a substituted or unsubstituted biphenyl group, a substituted or unsubstituted dibenzofuranyl group, a substituted or unsubstituted dibenzothiophenyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, and a substituted or unsubstituted phenoxazinyl group.

The compound may be represented by one of the following Chemical Formulae 2 to 4:

[Chemical Formula 2]

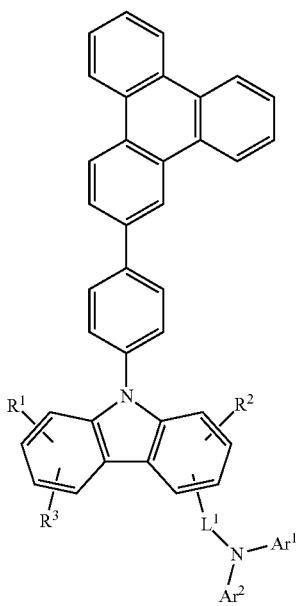

[Chemical Formula 3]

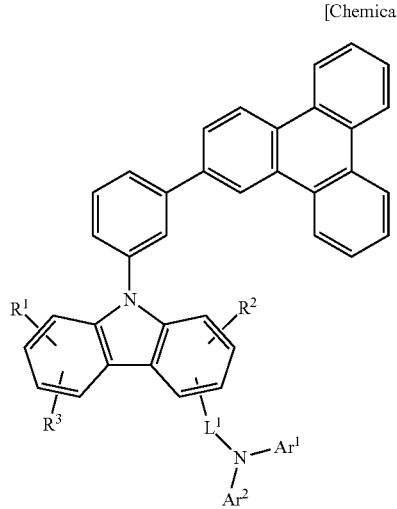

[Chemical Formula 4]

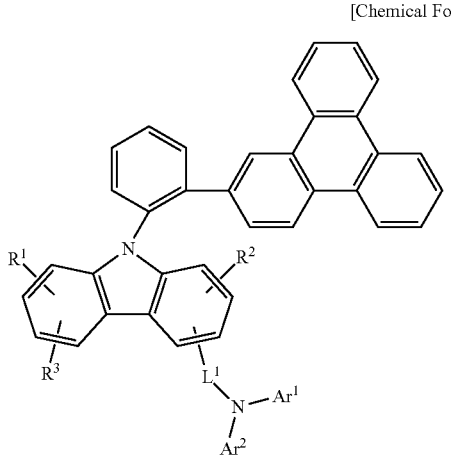

In Chemical Formulae 2 to 4, $L^1$ may be selected from the group of a single bond, a substituted or unsubstituted C2 to C6 alkenylene group, a substituted or unsubstituted C2 to C6 alkynylene group, a substituted or unsubstituted C6 to C30 arylene group, and a substituted or unsubstituted C2 to C30 heteroarylene group, $R^1$ to $R^3$ may each independently be selected from the group of hydrogen, a substituted or unsubstituted C1 to C6 alkyl group, a substituted or unsubstituted C6 to C30 aryl group, and a substituted or unsubstituted C2 to C30 heteroaryl group, and $Ar^1$ and $Ar^2$ may each independently be a substituted or unsubstituted C6 to C30 aryl group, or a substituted or unsubstituted C2 to C30 heteroaryl group.

The $Ar^1$ and $Ar^2$ may each independently be selected from the group of a substituted or unsubstituted phenyl group, a substituted or unsubstituted naphthalenyl group, a substituted or unsubstituted fluorenyl group, a substituted or unsubstituted biphenyl group, a substituted or unsubstituted dibenzofuranyl group, a substituted or unsubstituted dibenzothiophenyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, and a substituted or unsubstituted phenoxazinyl.

The compound may be represented by the following Chemical Formula 5:

[Chemical Formula 5]

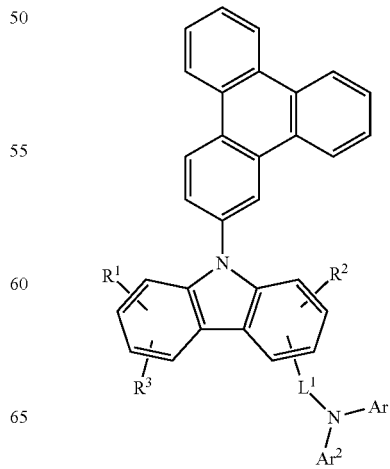

In Chemical Formula 5,

L¹ may be selected from the group of a single bond, a substituted or unsubstituted C2 to C6 alkenylene group, a substituted or unsubstituted C2 to C6 alkynylene group, a substituted or unsubstituted C6 to C30 arylene group, and a substituted or unsubstituted C2 to C30 heteroarylene group, R¹ to R³ may each independently be selected from the group of hydrogen, a substituted or unsubstituted C1 to C6 alkyl group, a substituted or unsubstituted C6 to C30 aryl group, and a substituted or unsubstituted C2 to C30 heteroaryl group, and Ar¹ and Ar² may each independently be a substituted or unsubstituted C6 to C30 aryl group, or a substituted or unsubstituted C2 to C30 heteroaryl group.

The Ar¹ and Ar² may each independently be selected from the group of a substituted or unsubstituted phenyl group, a substituted or unsubstituted naphthalenyl group, a substituted or unsubstituted fluorenyl group, a substituted or unsubstituted biphenyl group, a substituted or unsubstituted dibenzofuranyl group, a substituted or unsubstituted dibenzothiophenyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, and a substituted or unsubstituted phenoxazinyl group.

Embodiments are also directed to a compound for an organic photoelectric device, the compound being represented by one of the following Chemical Formulae 6 to 18 or A-1 to A-251:

[Chemical Formula 6]

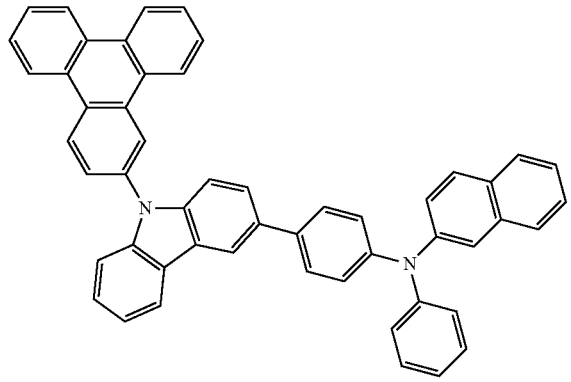

[Chemical Formula 7]

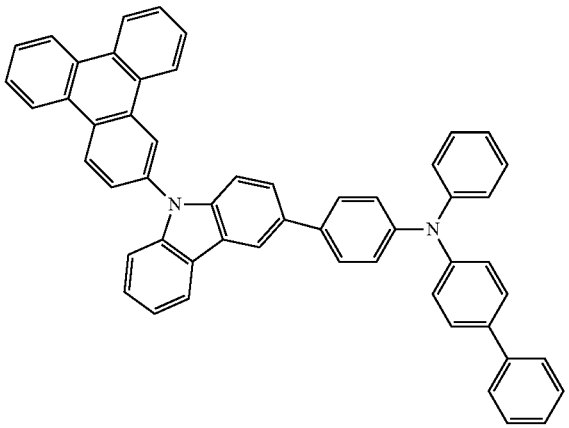

[Chemical Formula 8]

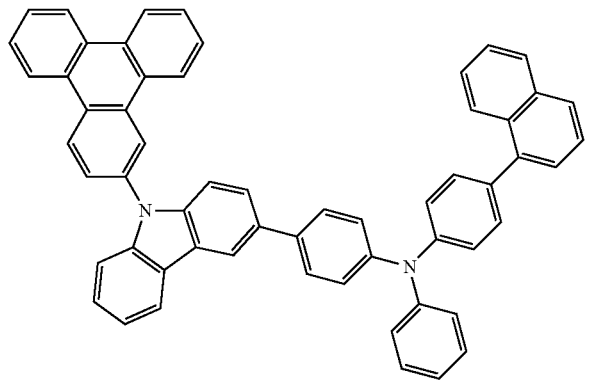

[Chemical Formula 9]

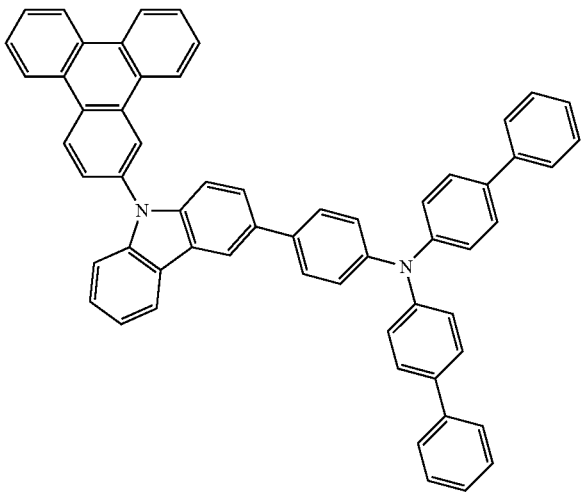

-continued
[Chemical Formula 10]
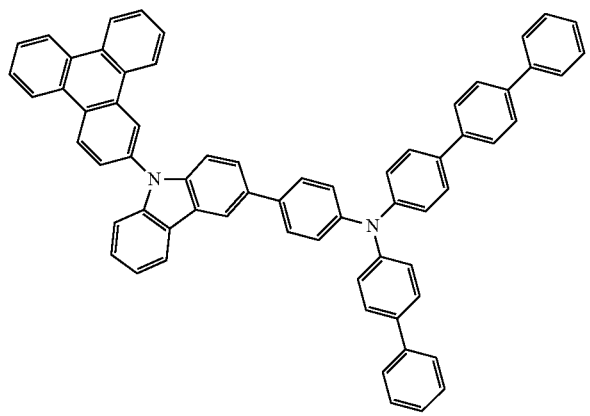
[Chemical Formula 11]
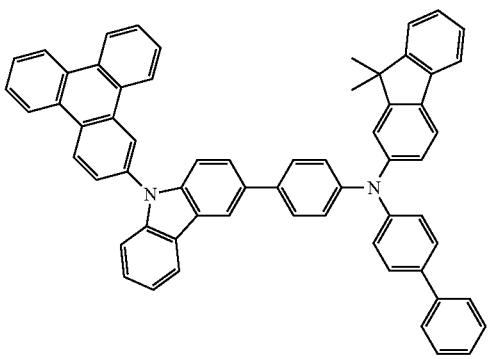
[Chemical Formula 12]
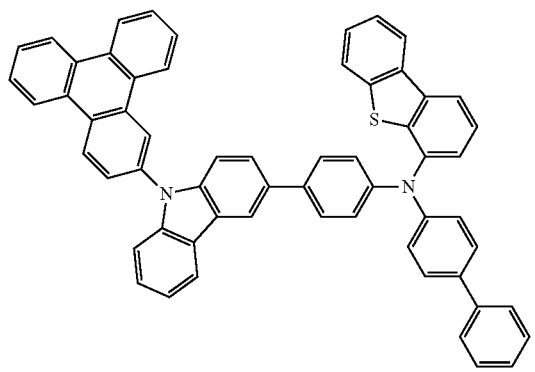
[Chemical Formula 13]
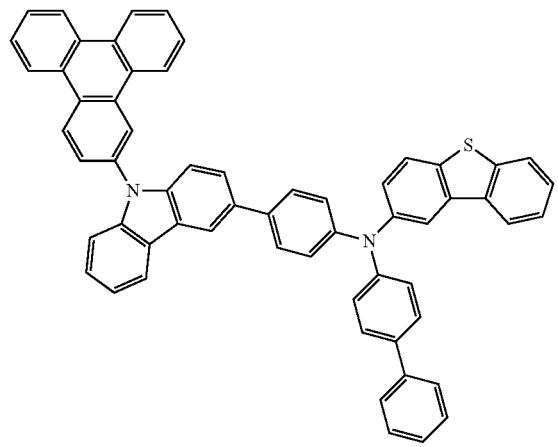
[Chemical Formula 14]
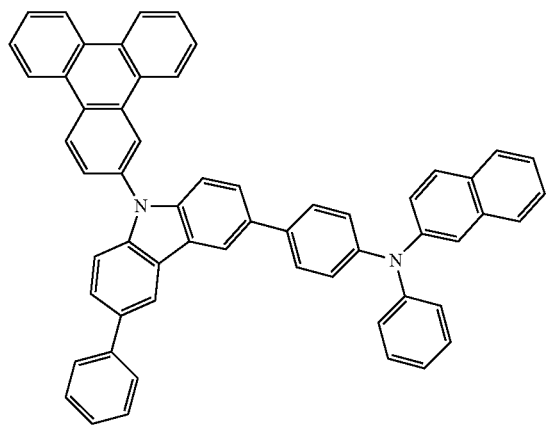
[Chemical Formula 15]
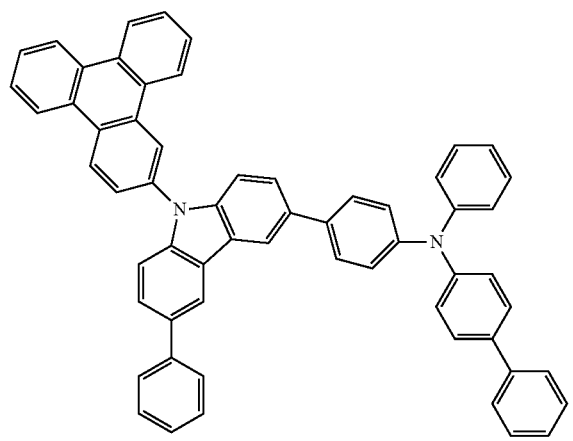

-continued
[Chemical Formula 16]
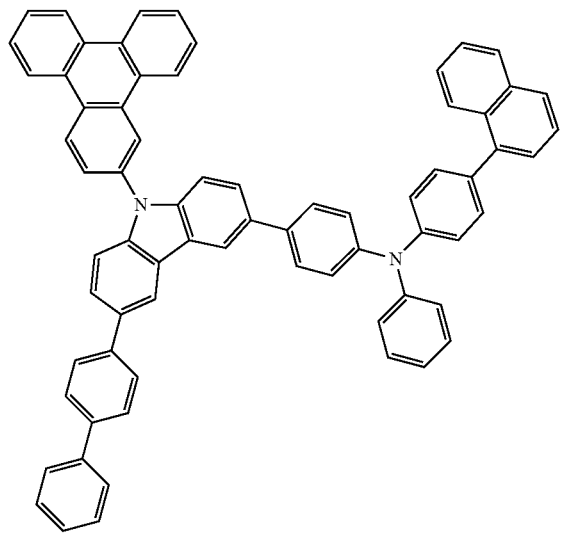
[Chemical Formula 17]
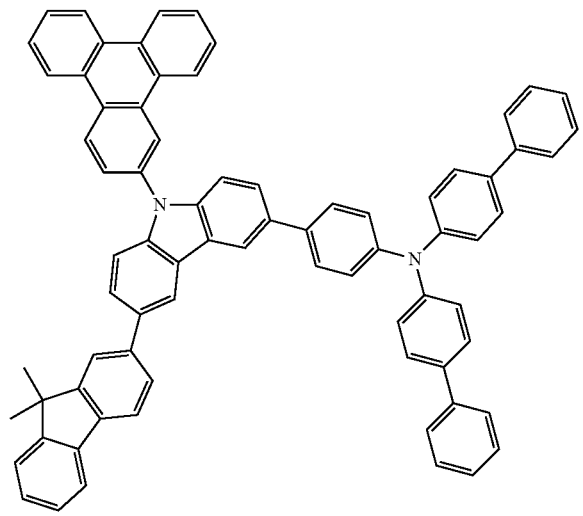
[Chemical Formula 18]
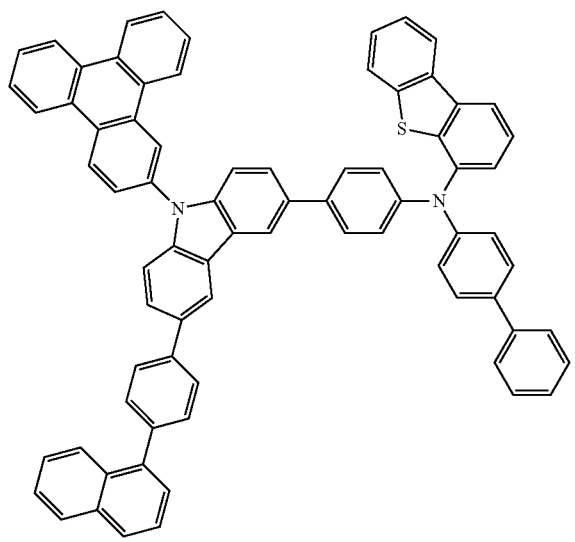
[A-1]
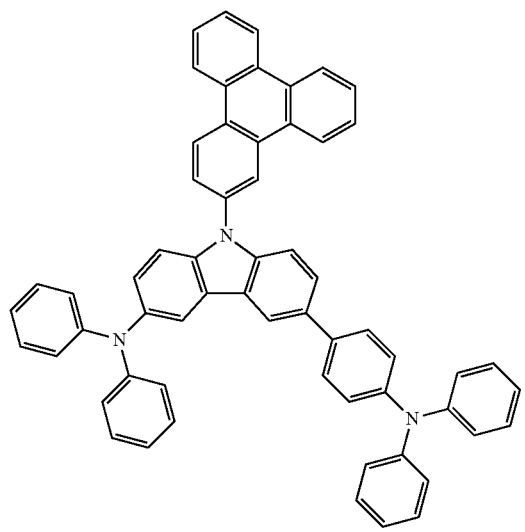
[A-2]
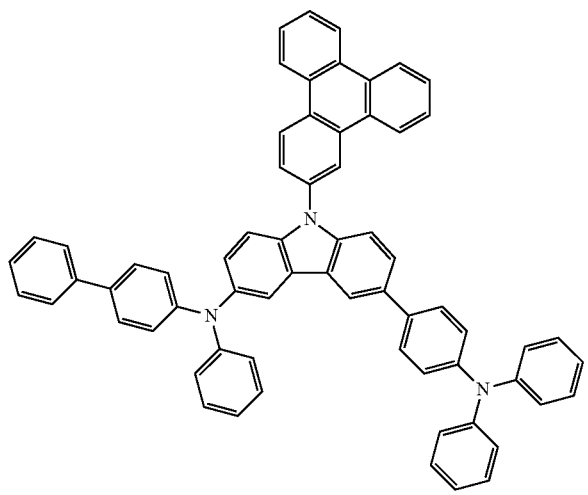
[A-3]
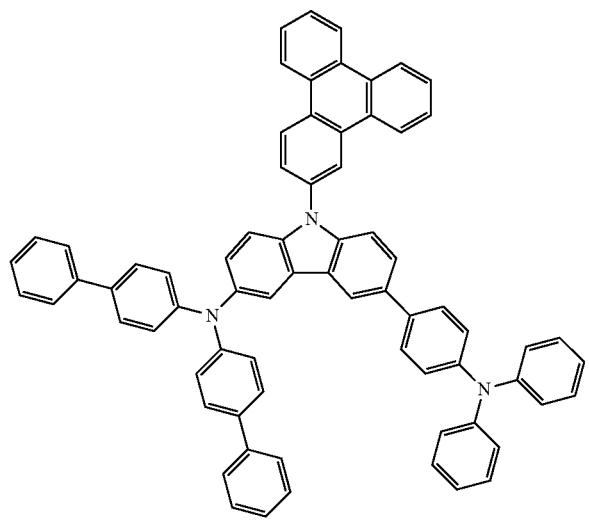

-continued
[A-4]
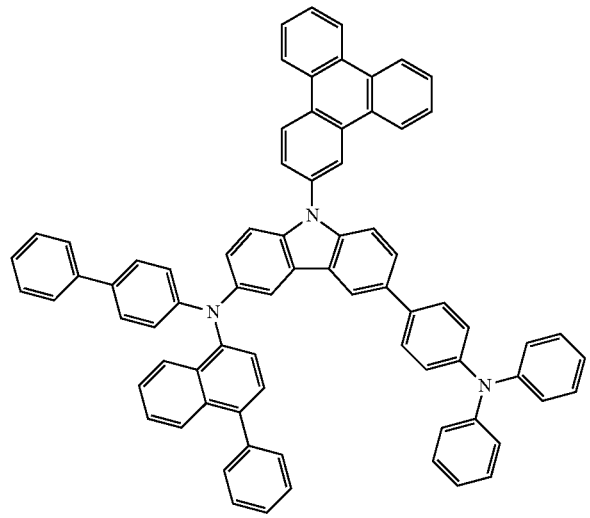
[A-5]
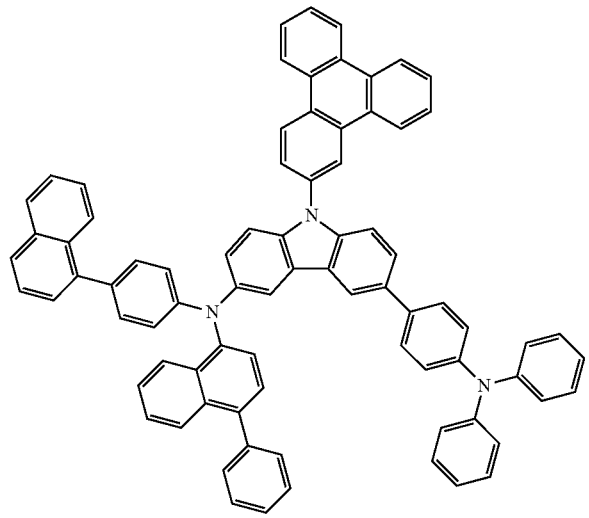
[A-6]
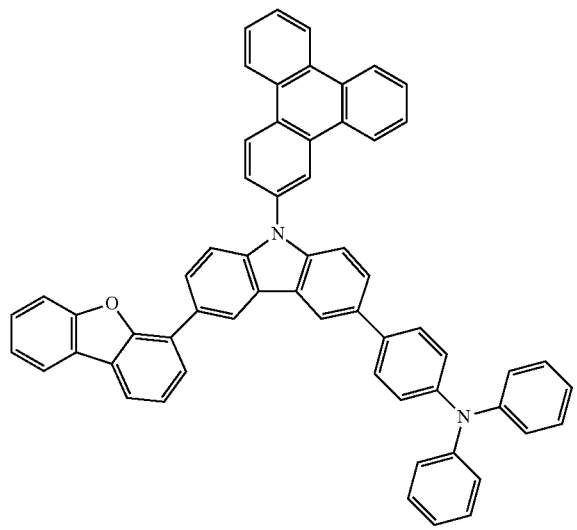
[A-7]
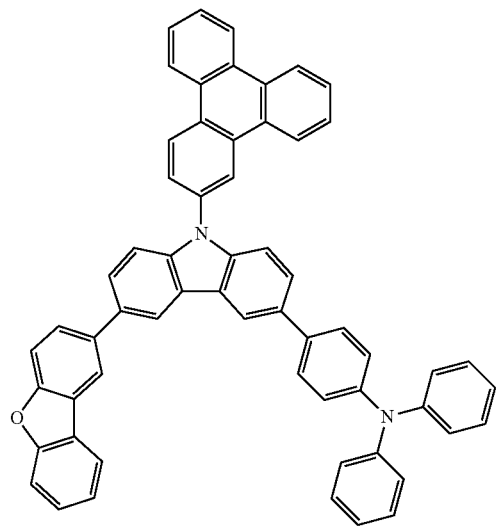
[A-8]
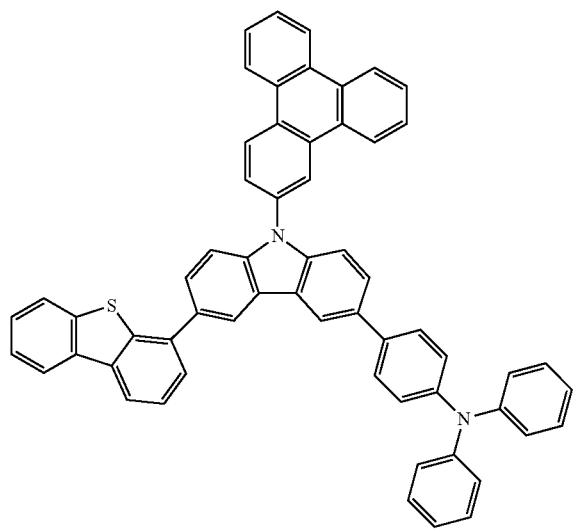
[A-9]
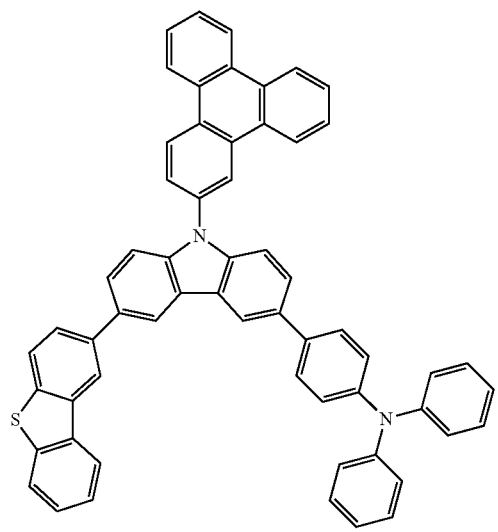

[A-10]
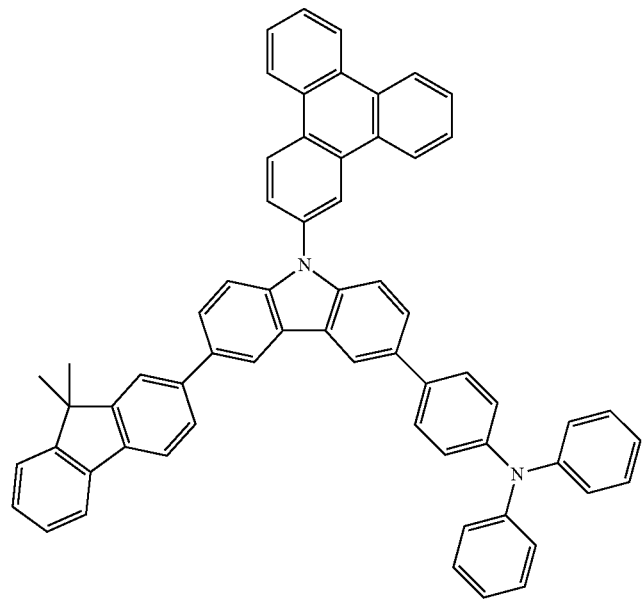
[A-11]
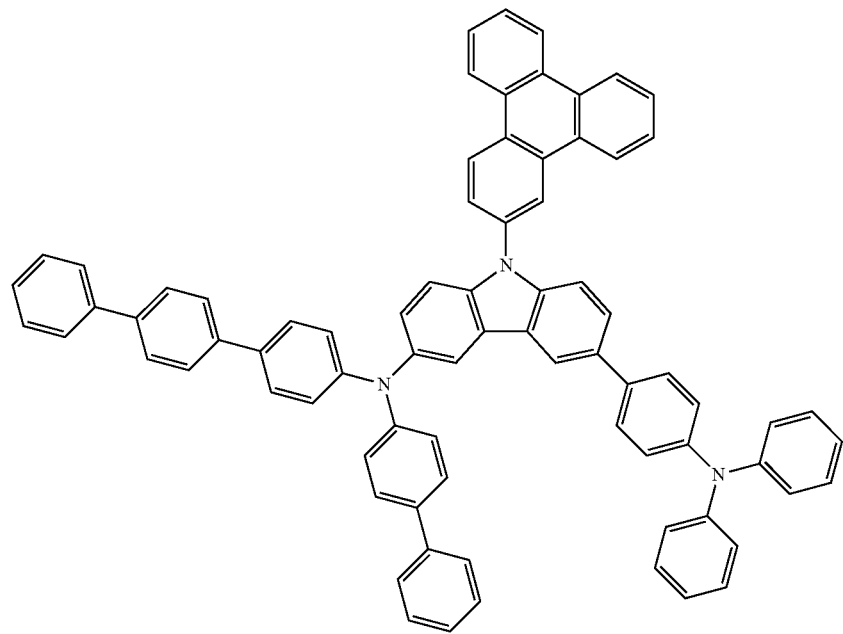

-continued
[A-12]
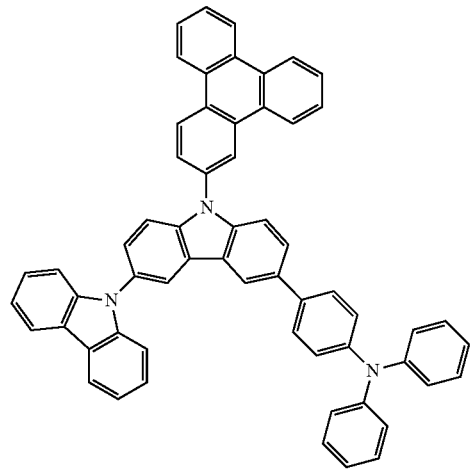
[A-13]
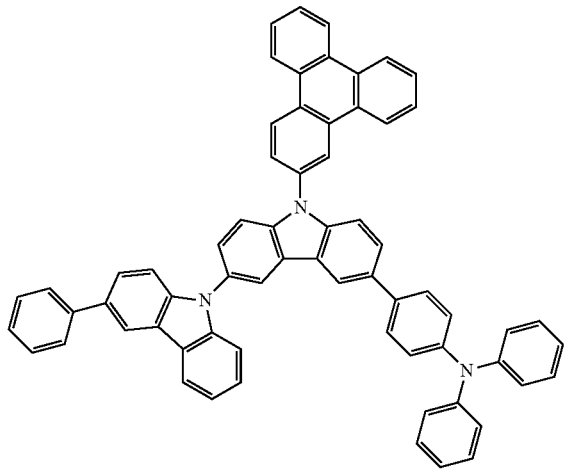
[A-14]
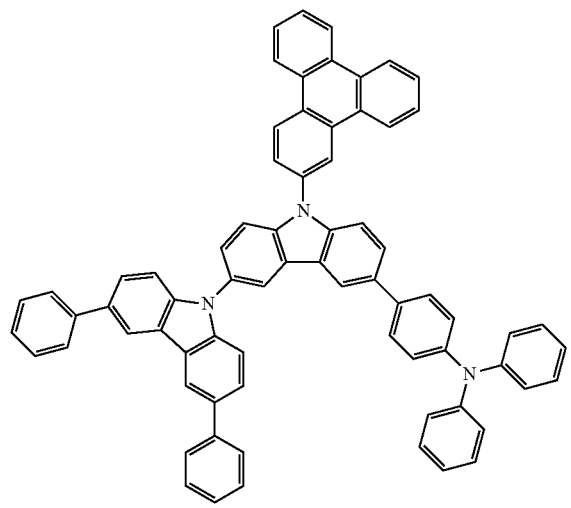
[A-15]
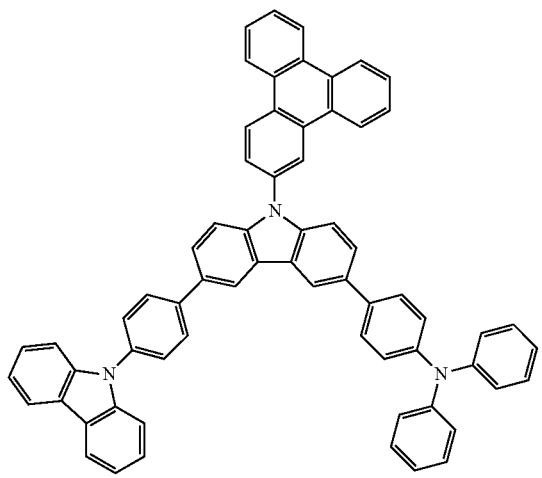
[A-16]
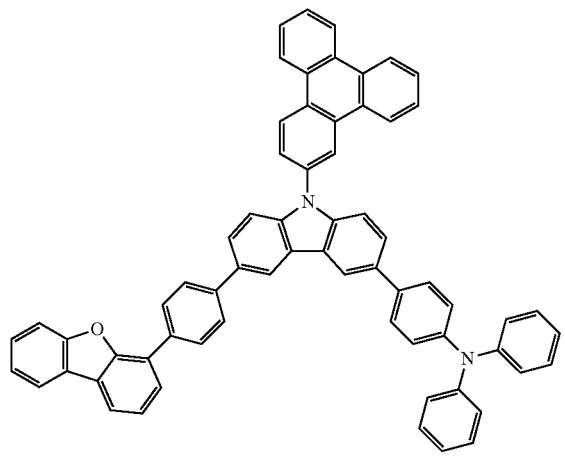
[A-17]
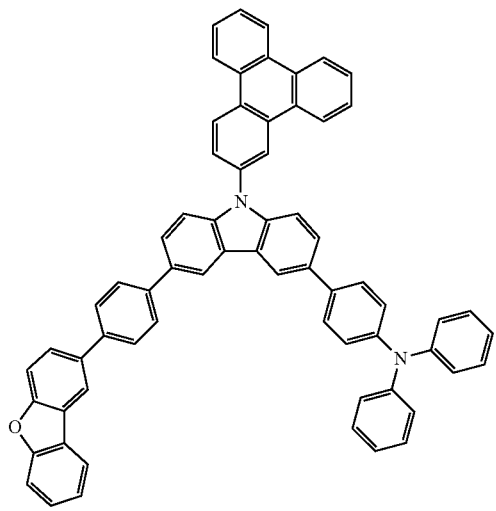

-continued
[A-18]
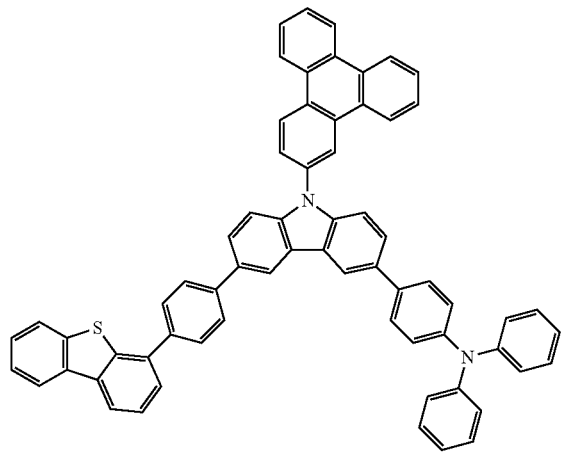
[A-19]
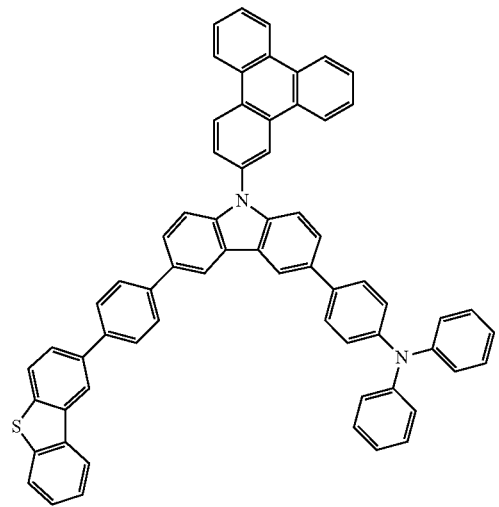
[A-20]
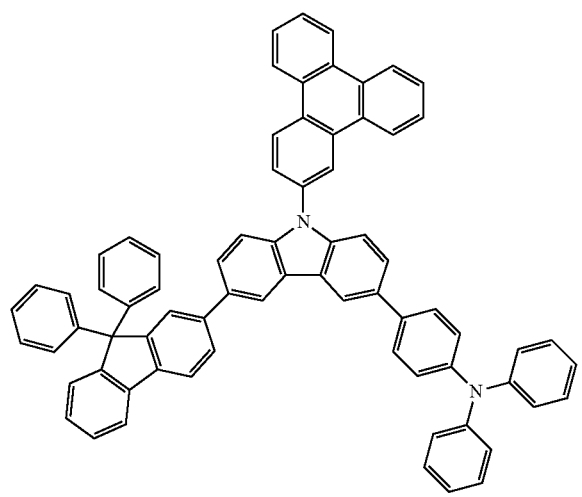
[A-21]
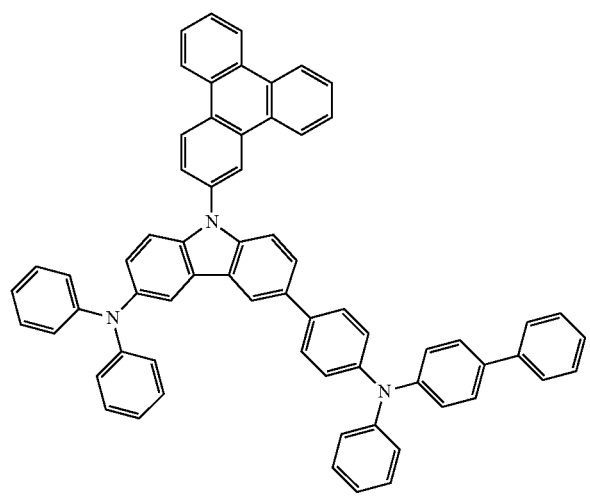
[A-22]
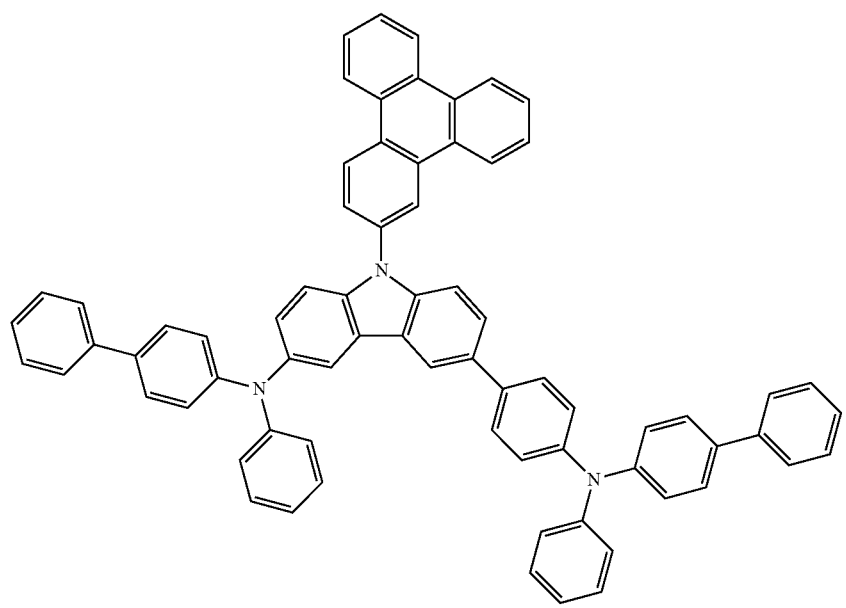

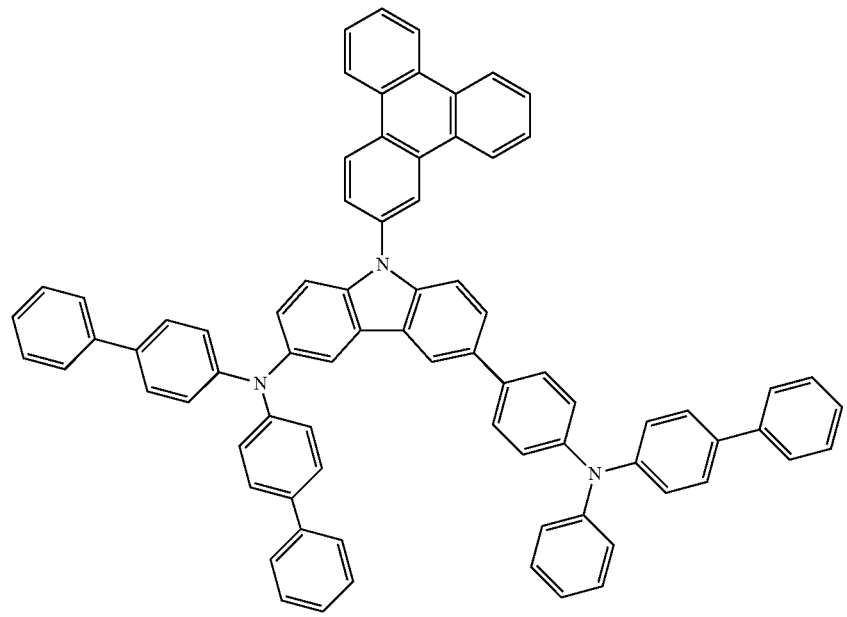
[A-23]
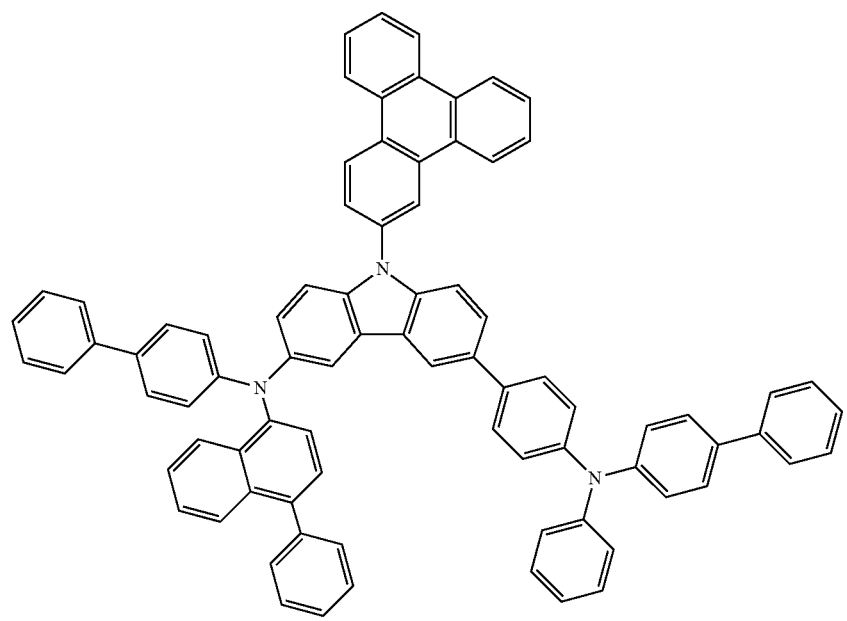
[A-24]

[A-25]
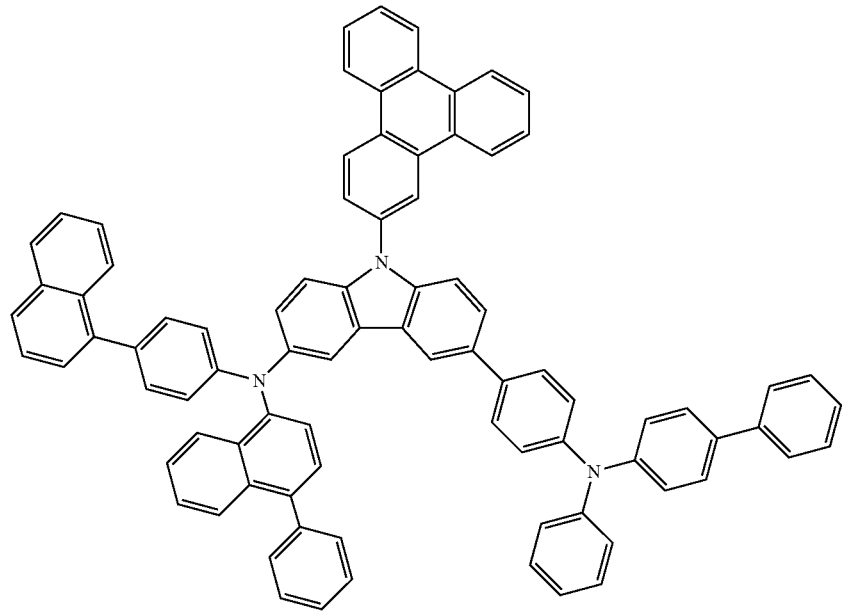
[A-26]
[A-27]
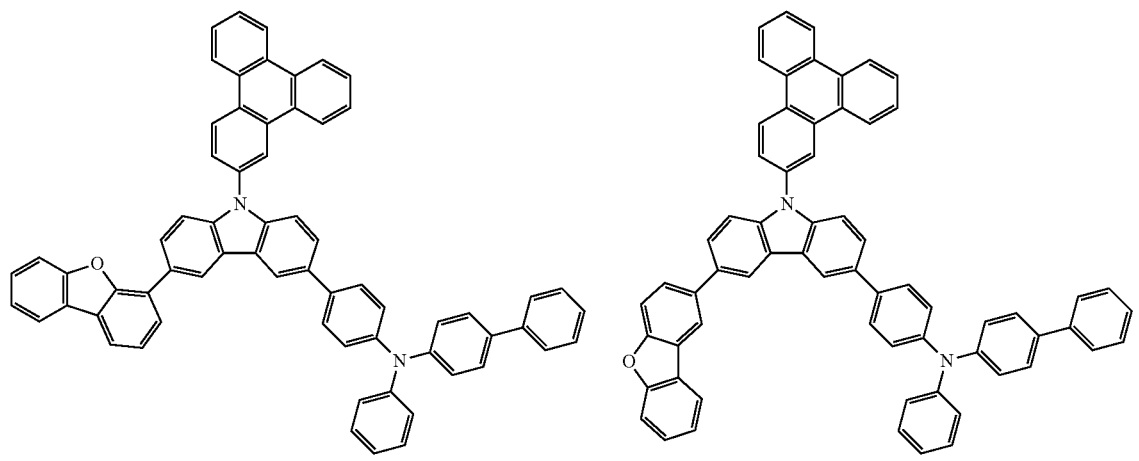
[A-28]
[A-29]
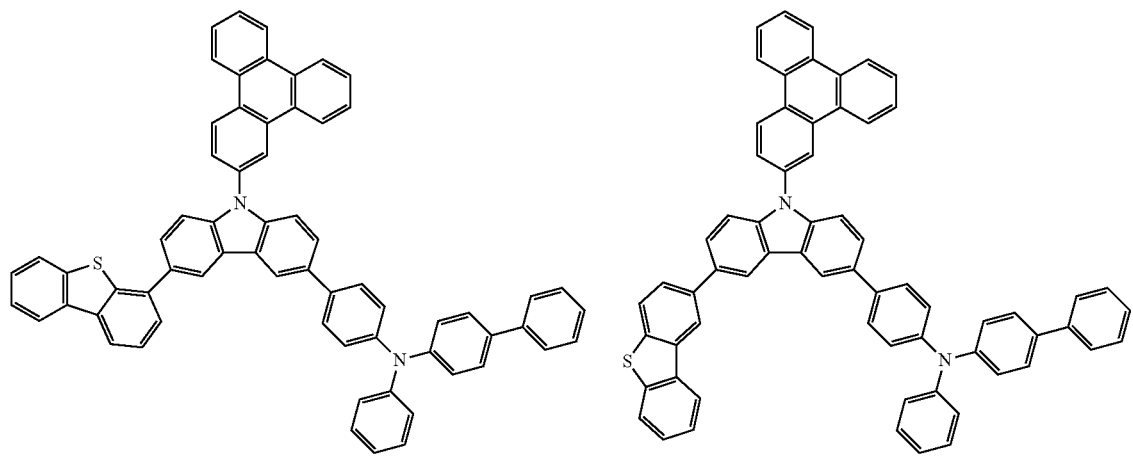

-continued
[A-30]
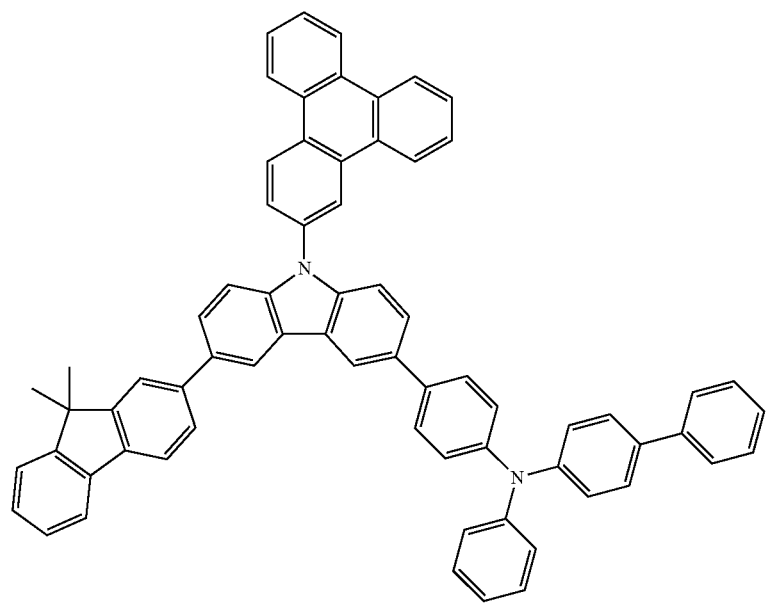
[A-31]
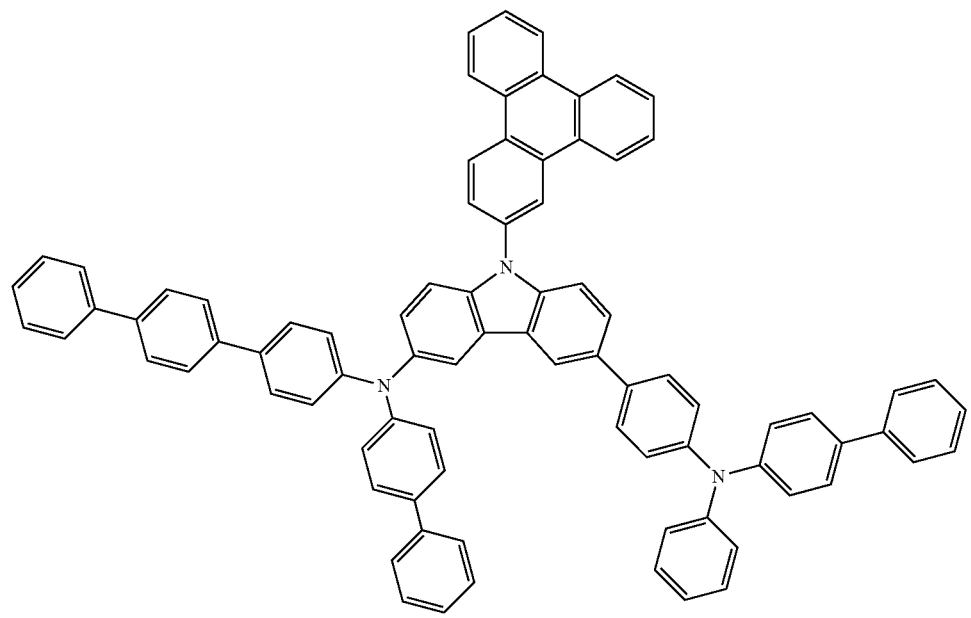

[A-32]
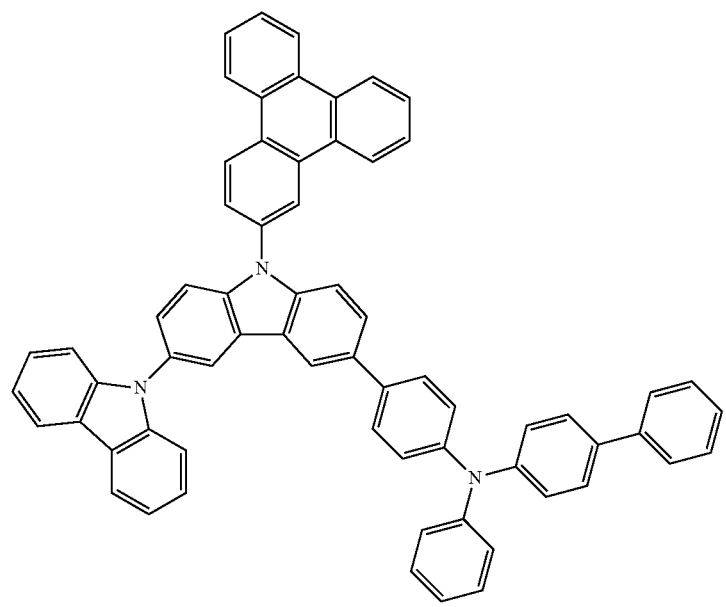
[A-33]
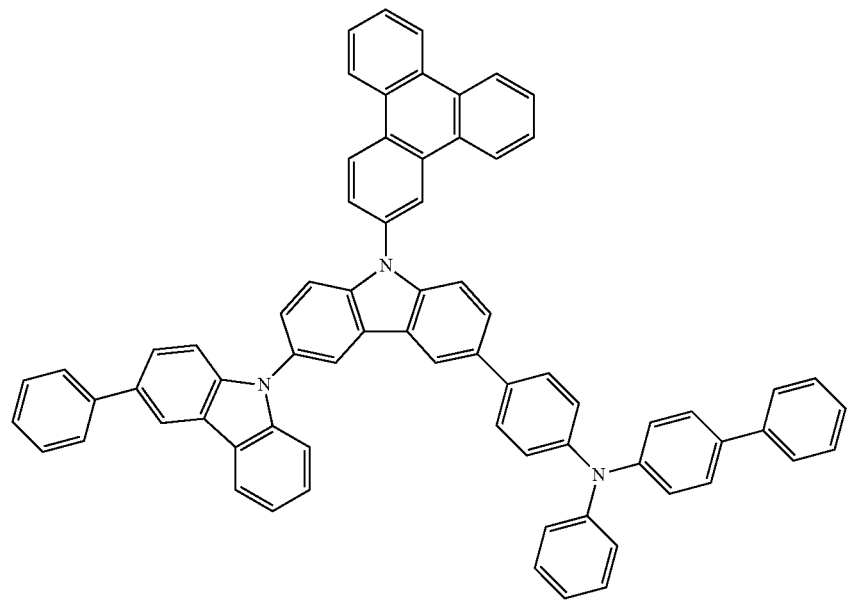

[A-34]
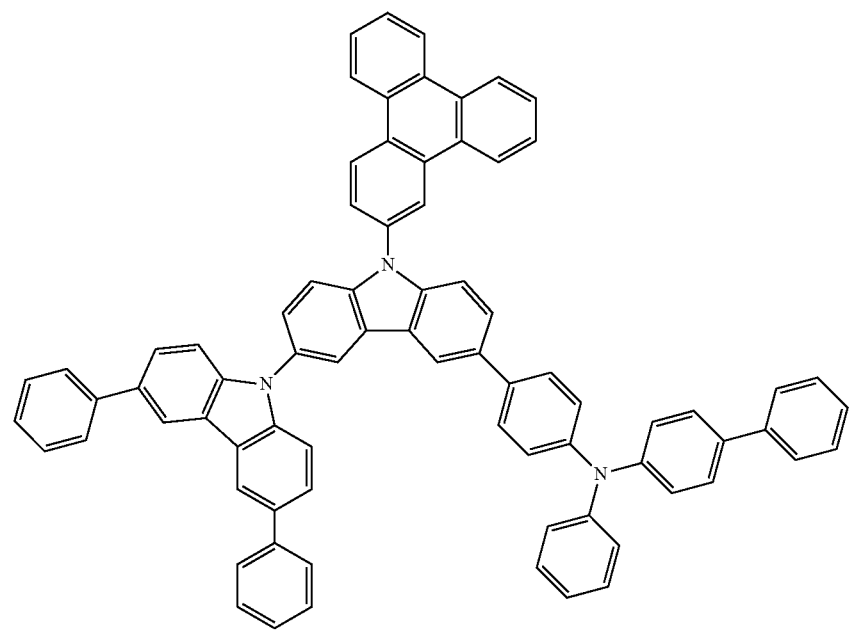
[A-35]
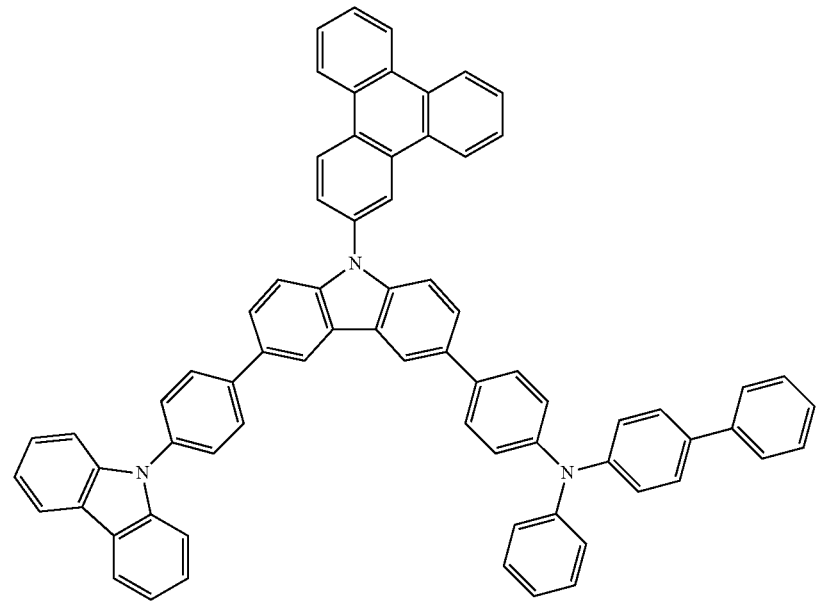

-continued
[A-36]
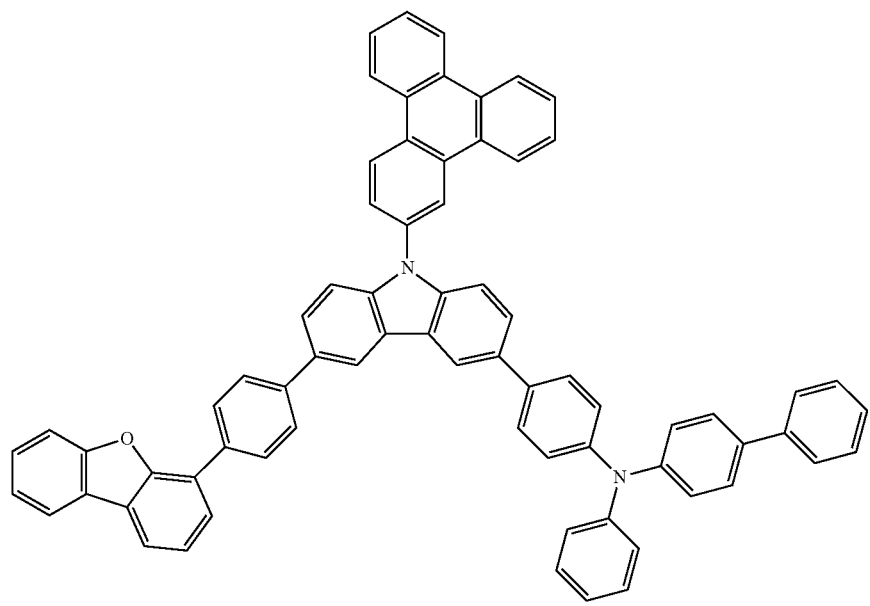
[A-37]
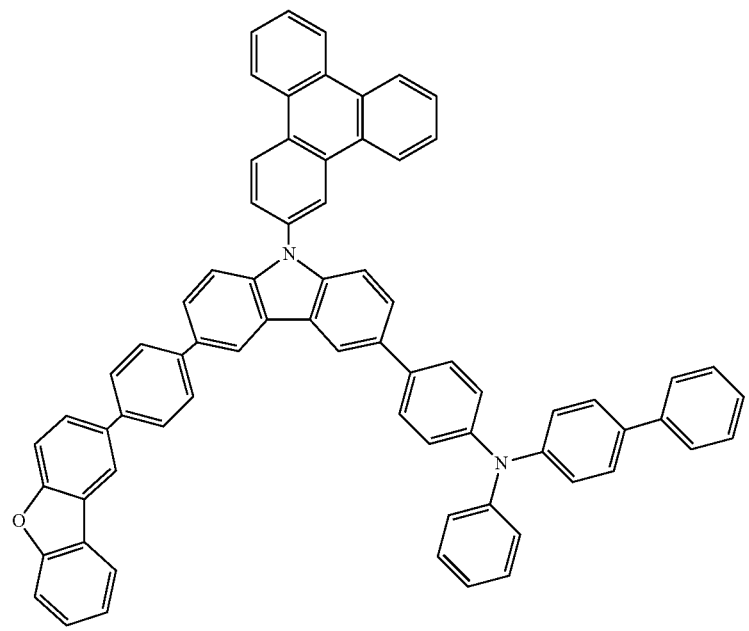

-continued
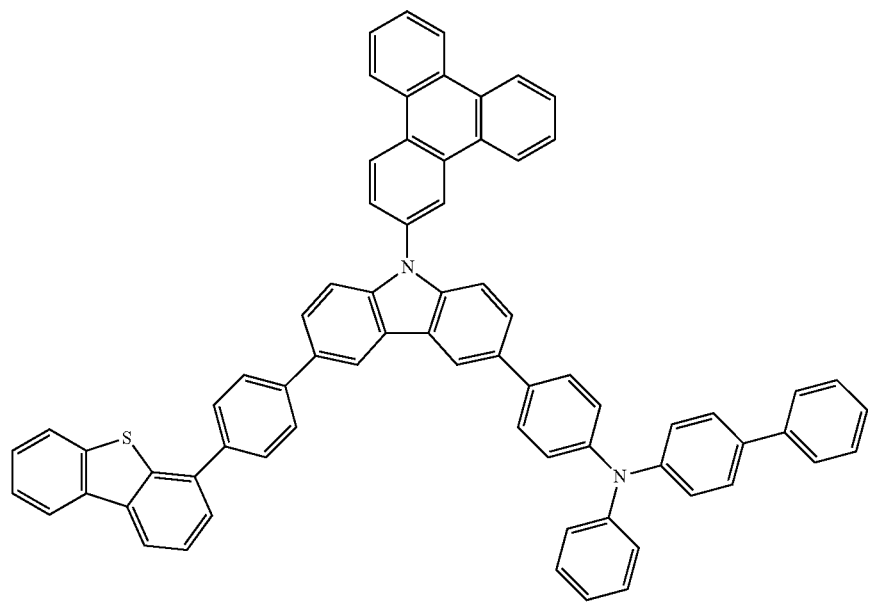
[A-38]
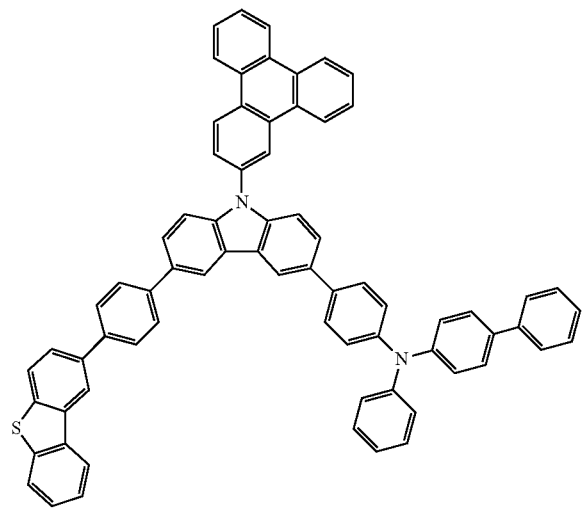
[A-39]

[A-40]
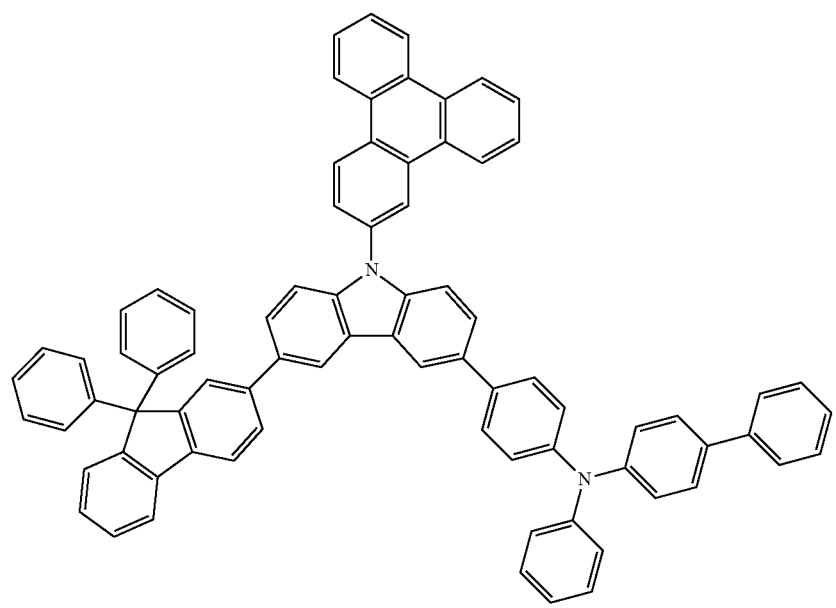
[A-41]
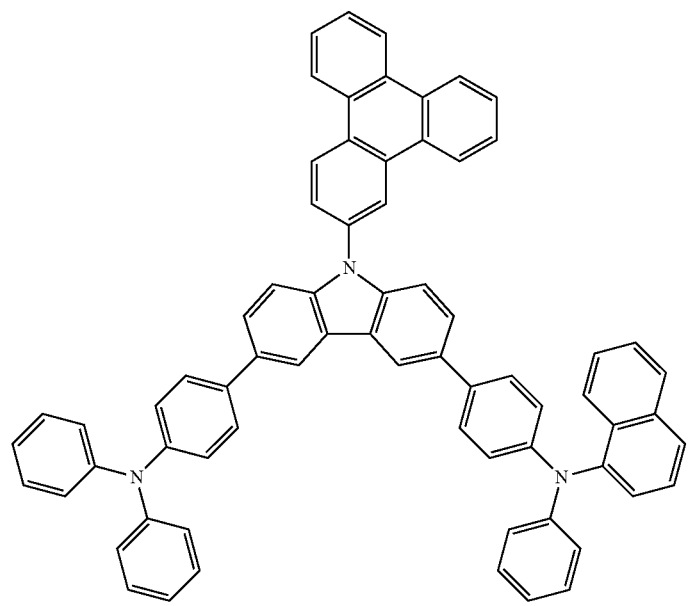

-continued
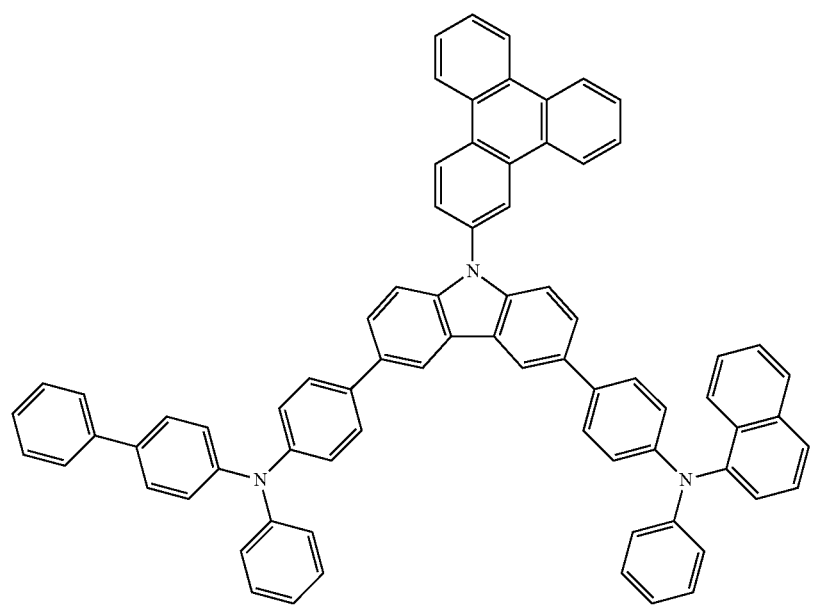
[A-42]
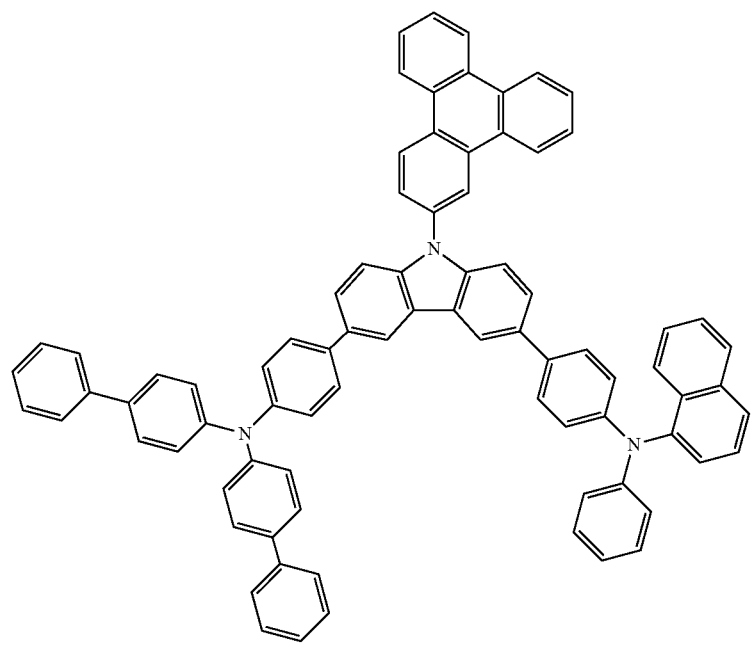
[A-43]

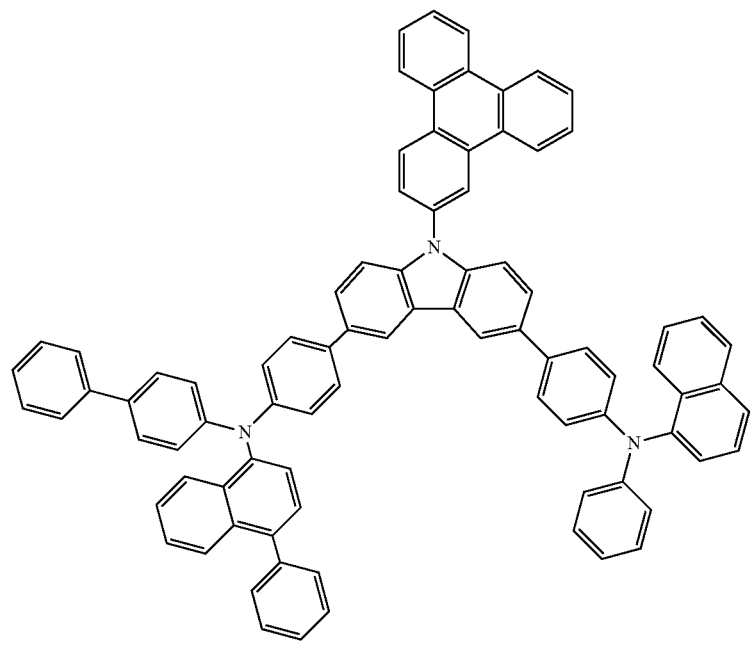
[A-44]
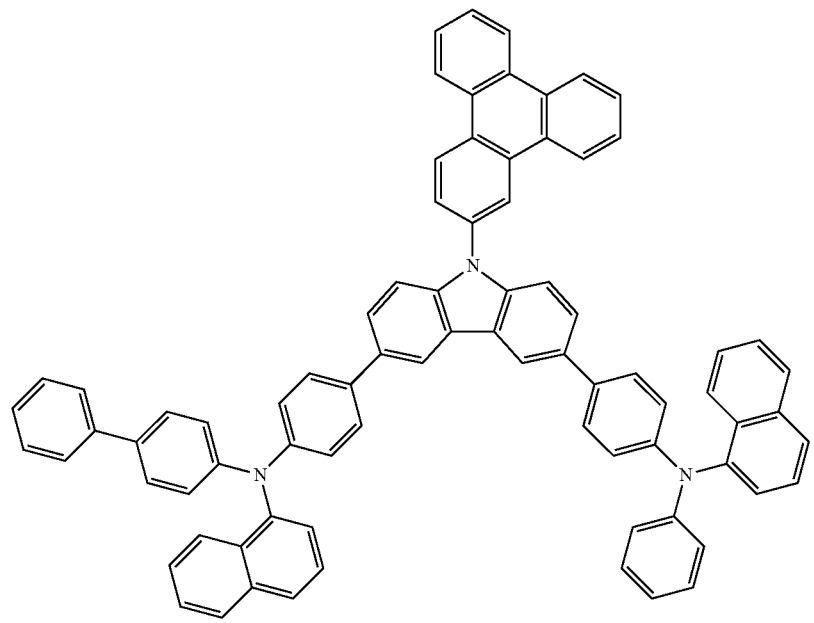
[A-45]

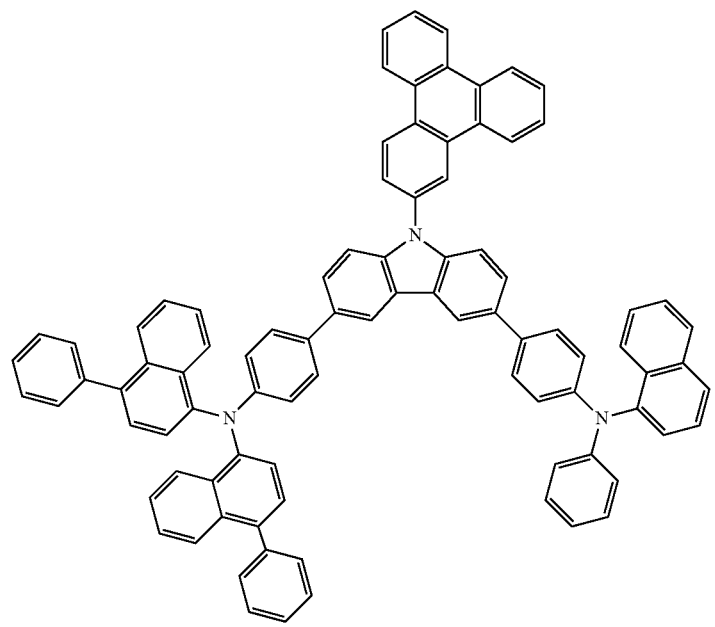
[A-46]
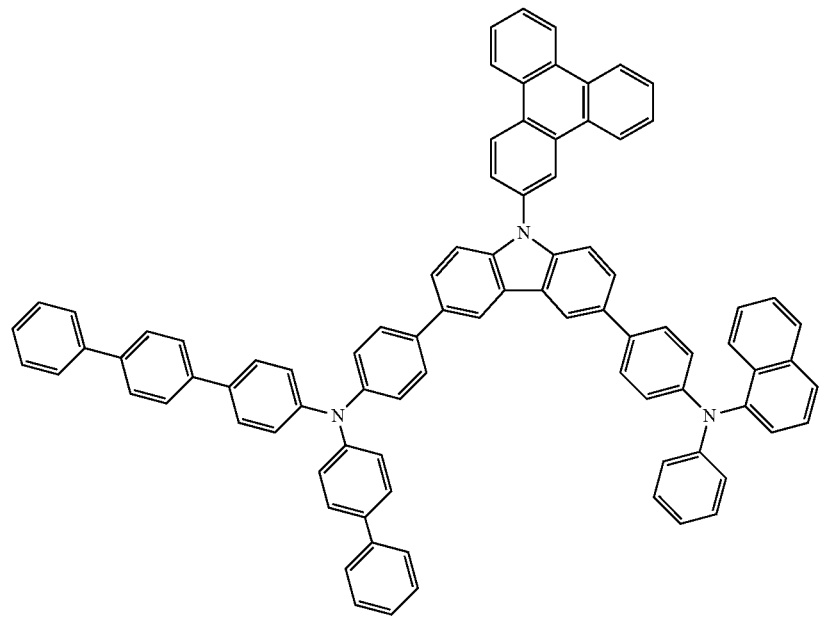
[A-47]

[A-48]
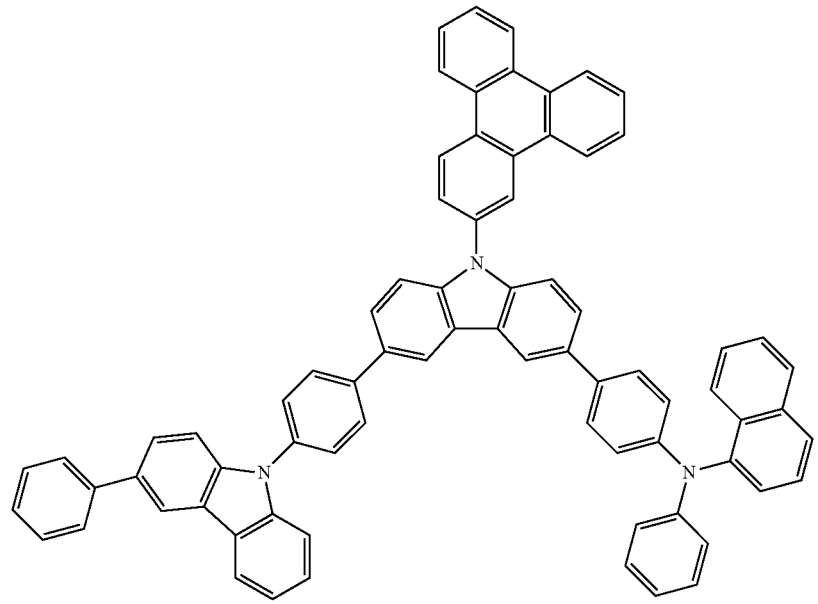
[A-49]
[A-50]
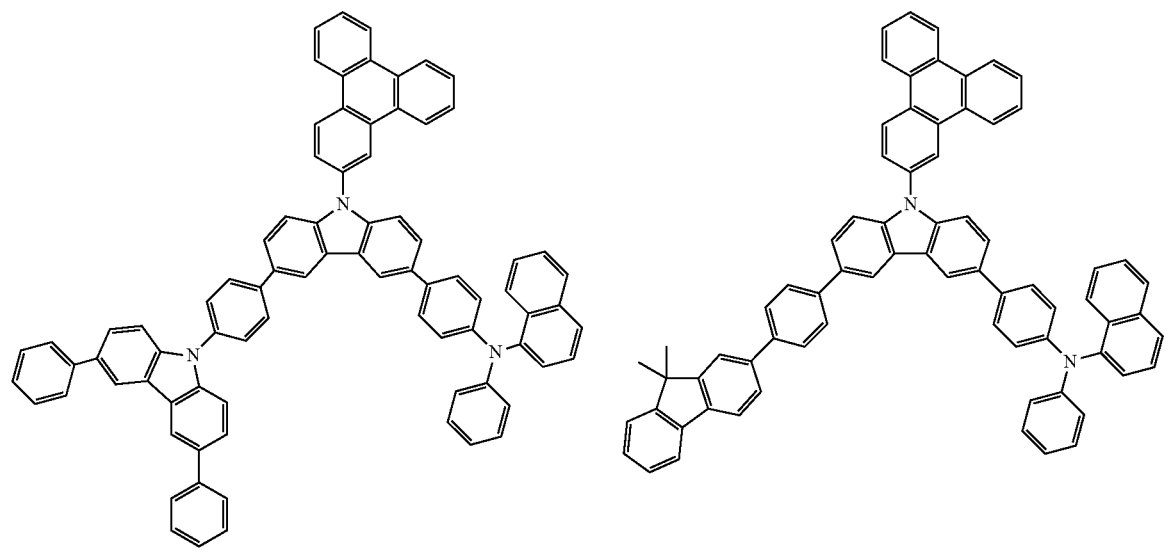

-continued
[A-51]
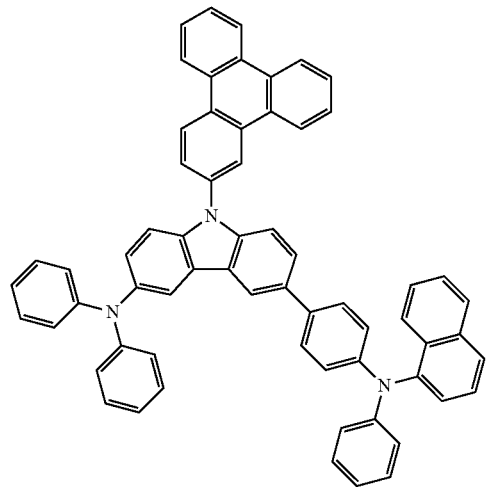
[A-52]
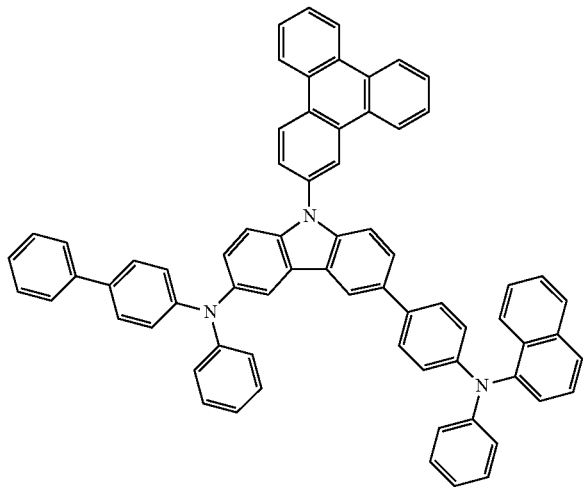
[A-53]
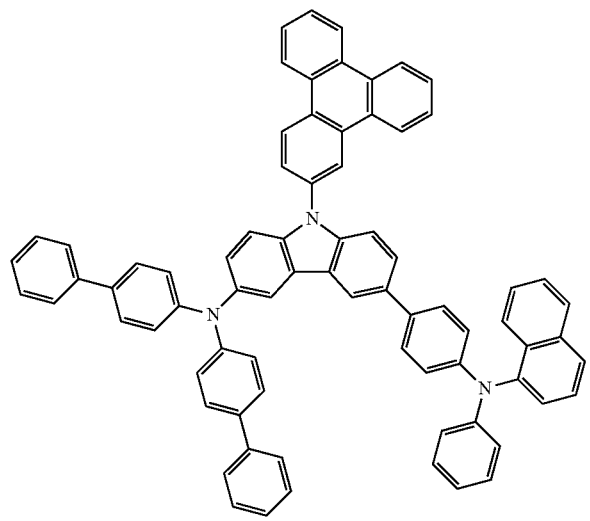
[A-54]
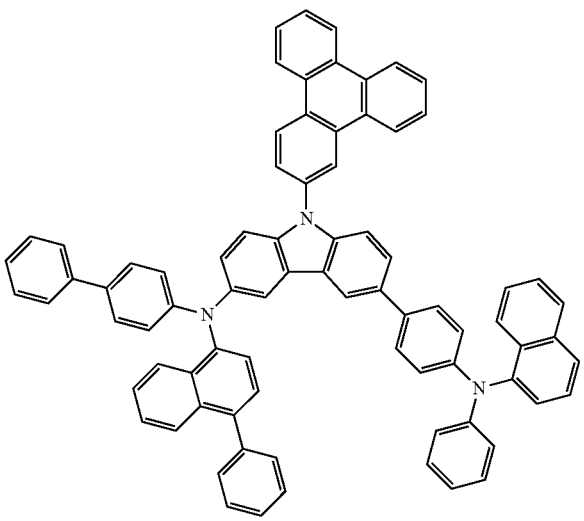
[A-55]
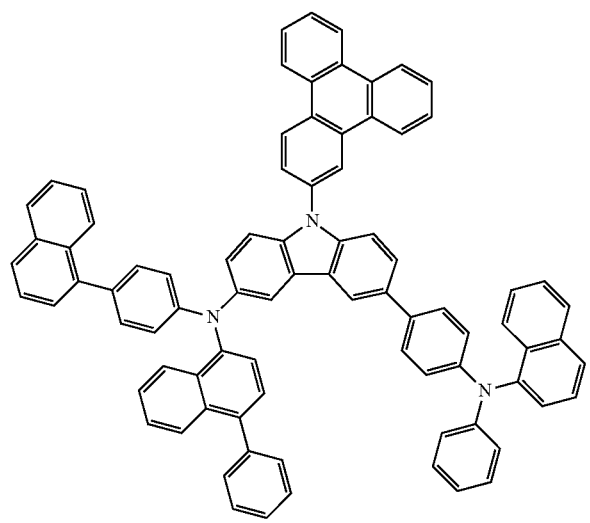
[A-56]
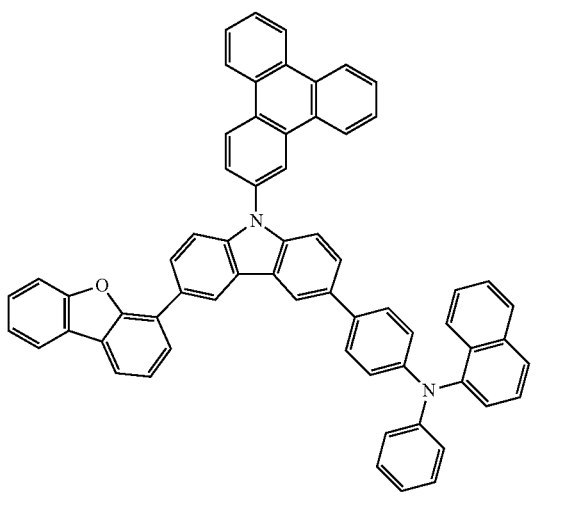

-continued
[A-57]
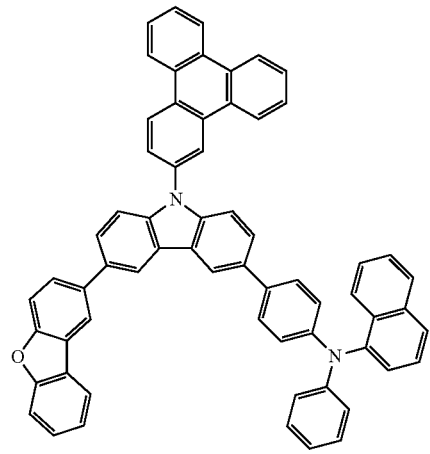
[A-58]
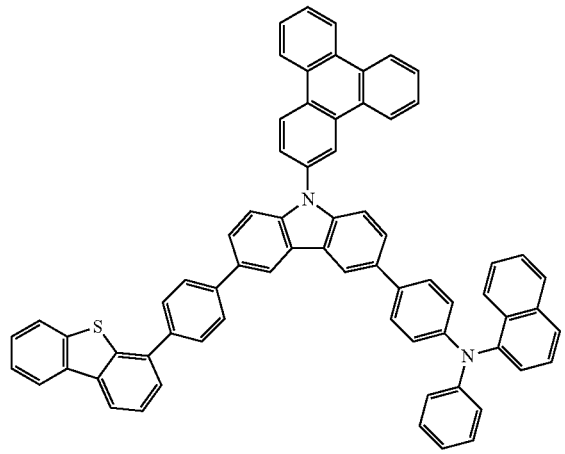
[A-59]
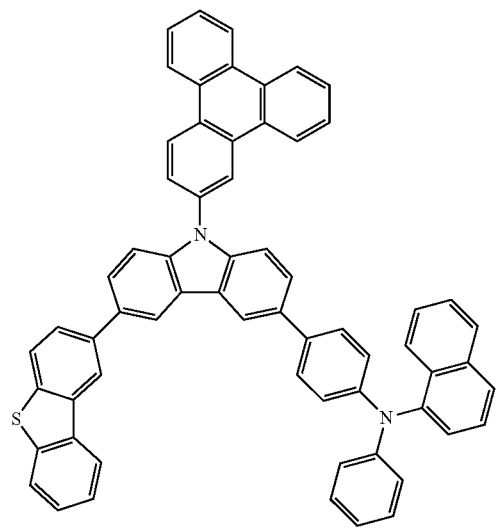
[A-60]
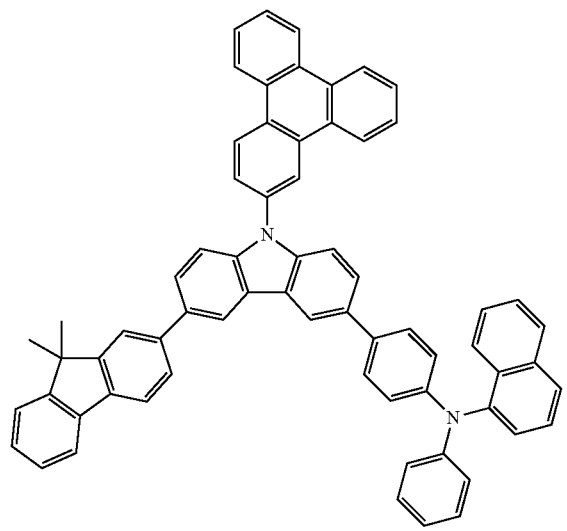
[A-61]
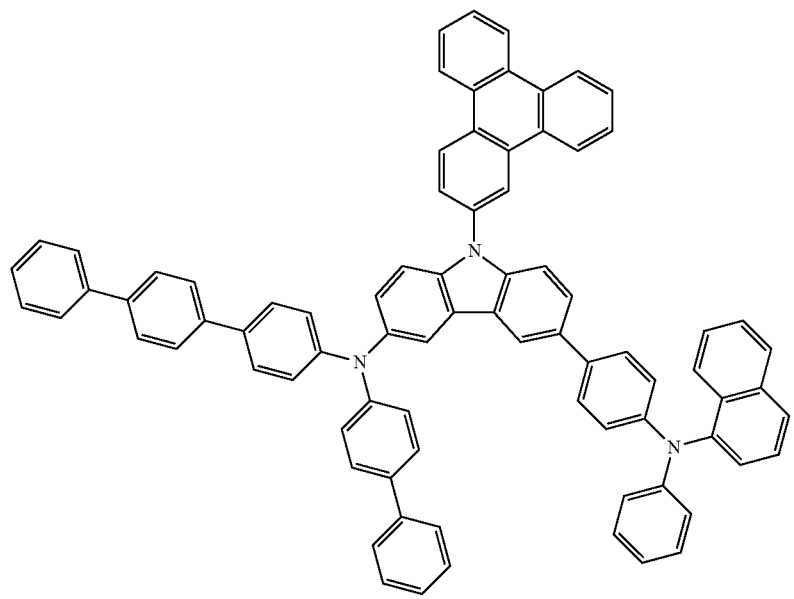

-continued
[A-62]
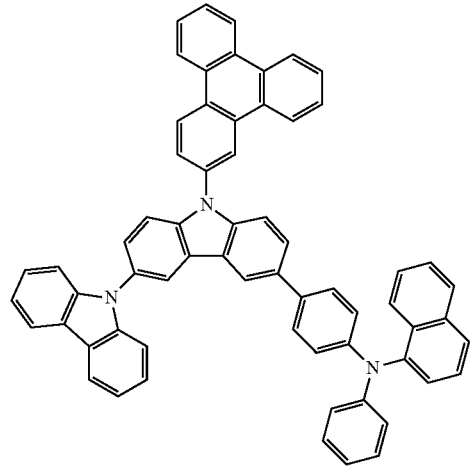
[A-63]
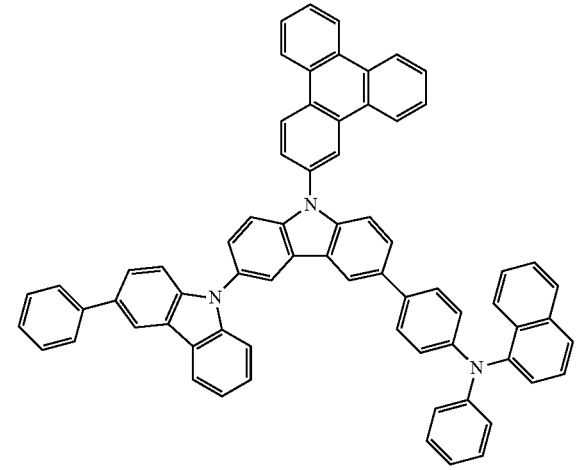
[A-64]
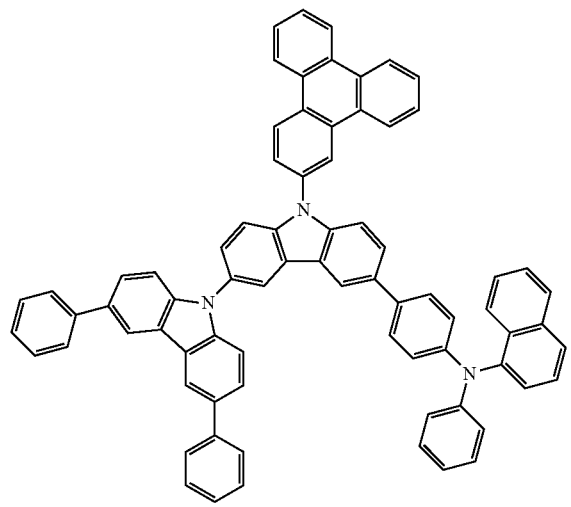
[A-65]
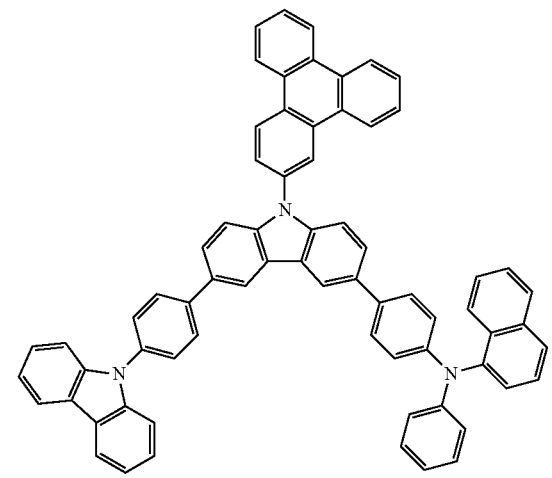
[A-66]
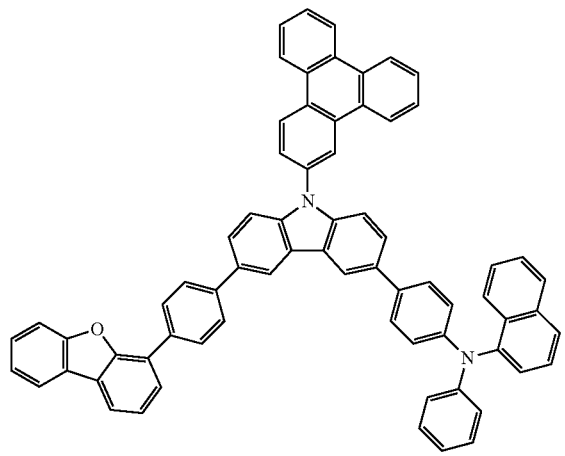
[A-67]
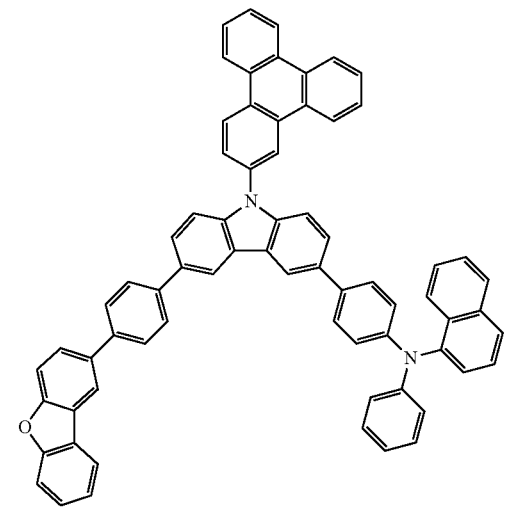

-continued
[A-68]
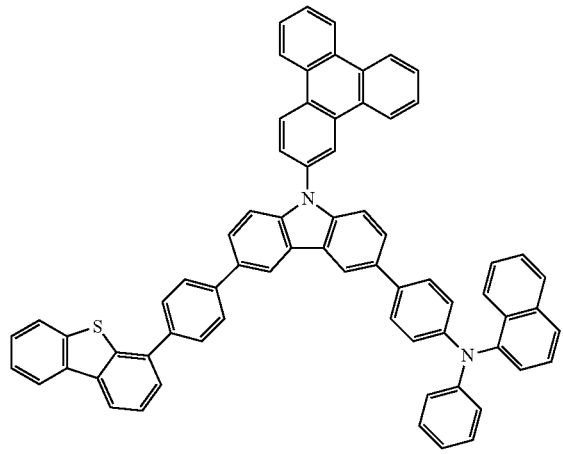
[A-69]
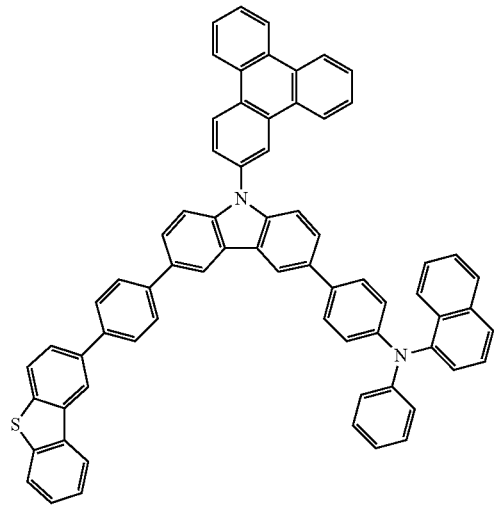
[A-70]
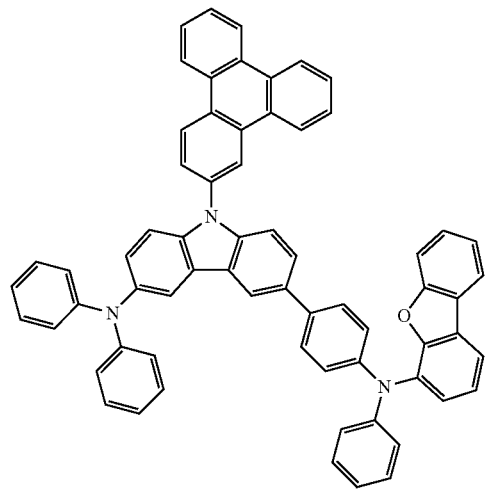
[A-71]
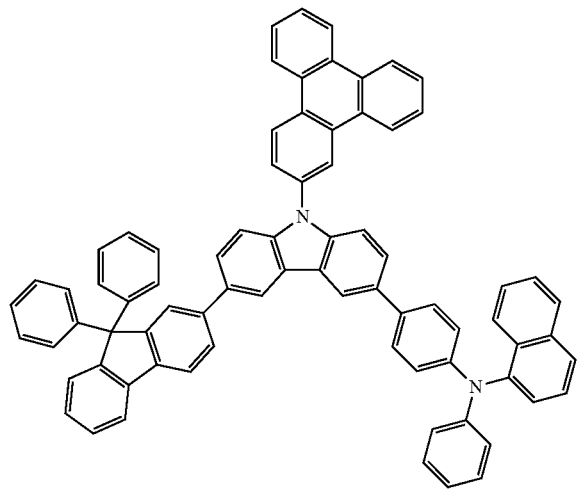
[A-72]
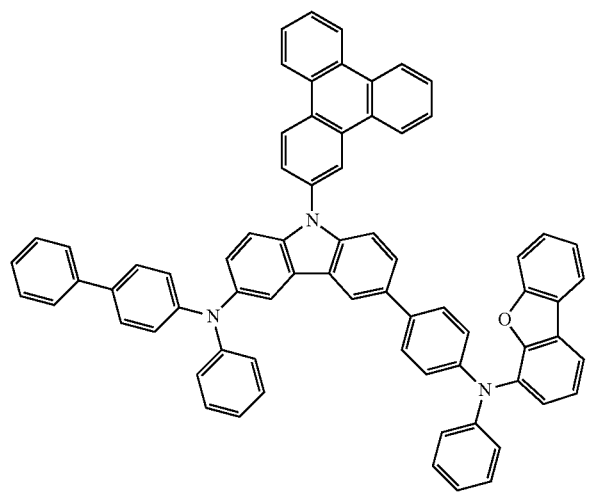
[A-73]
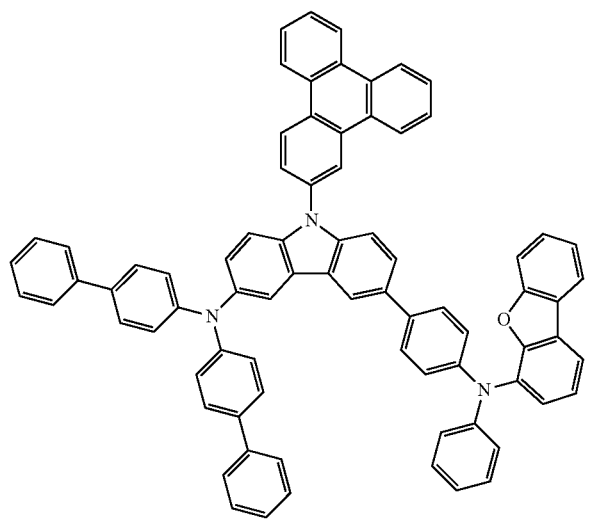

-continued
[A-74]
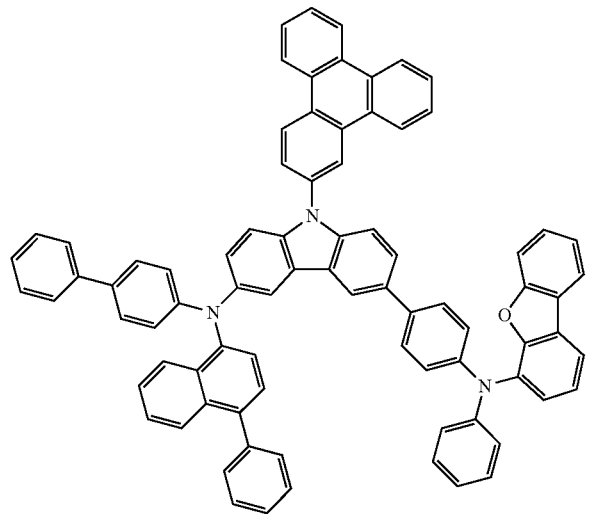
[A-75]
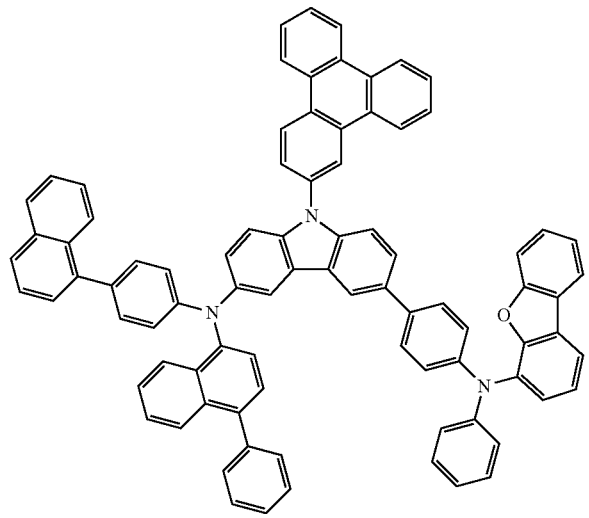
[A-76]
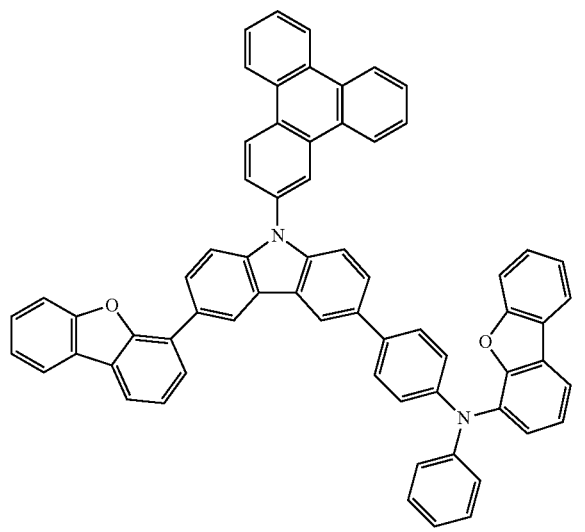
[A-77]
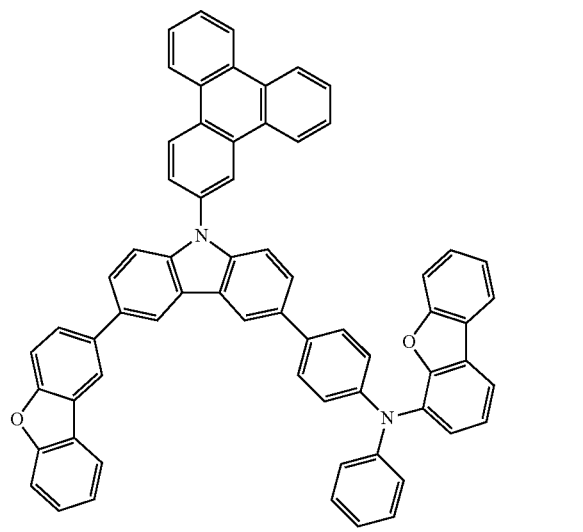
[A-78]
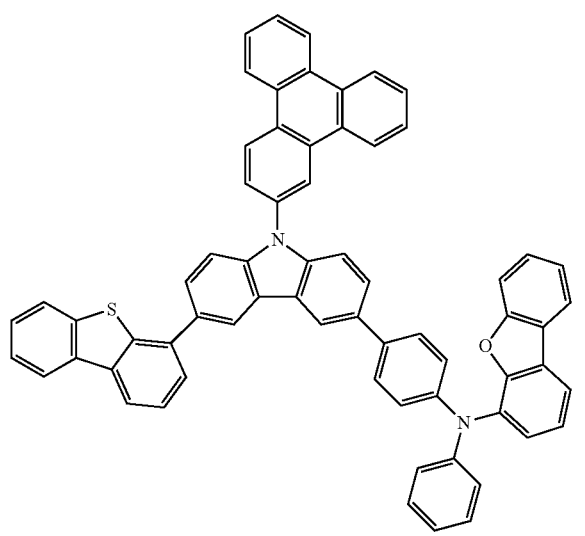
[A-79]
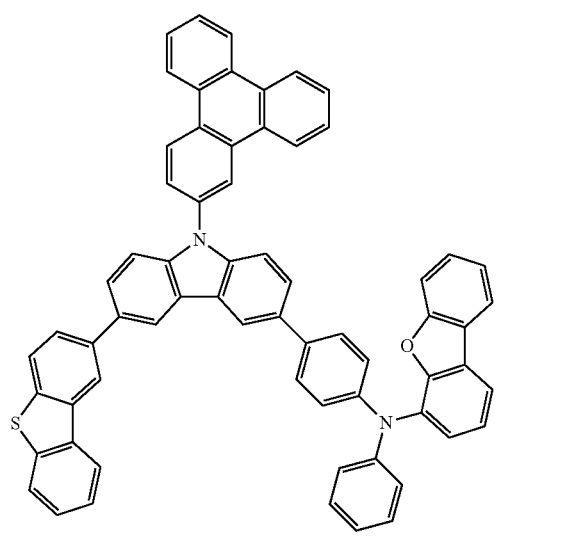

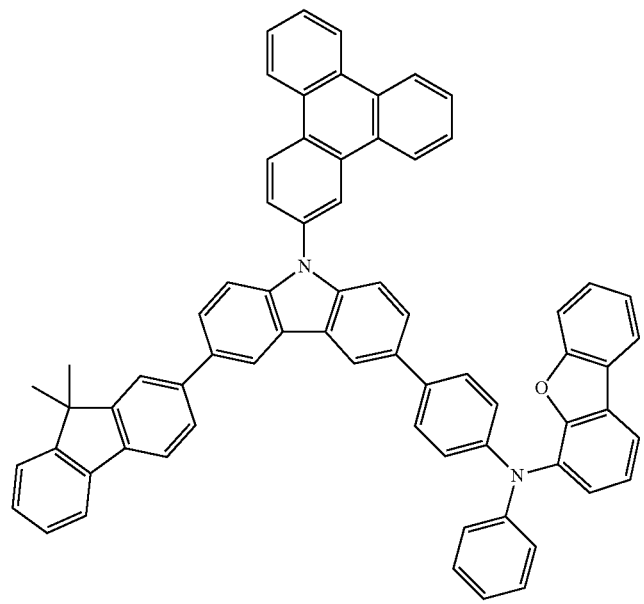
[A-80]
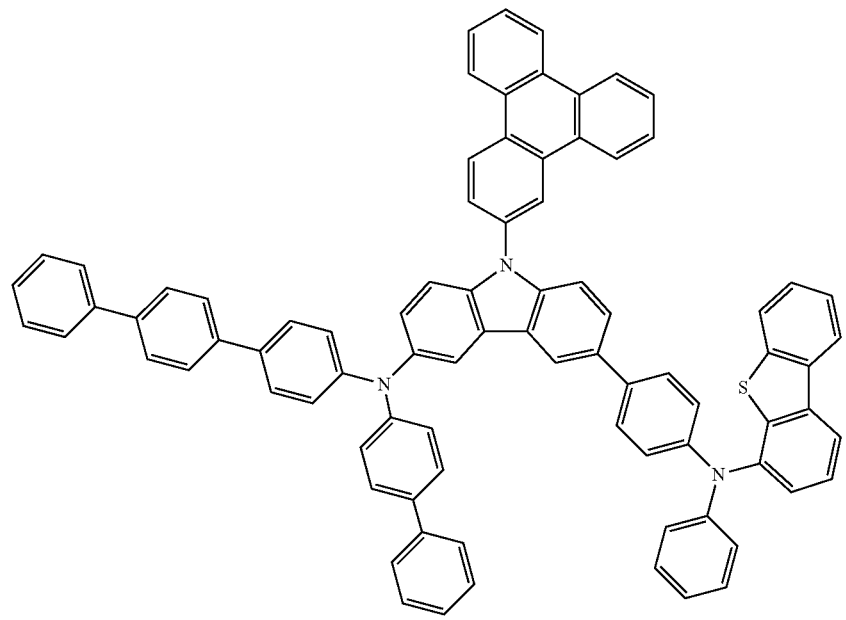
[A-81]

-continued
[A-82]
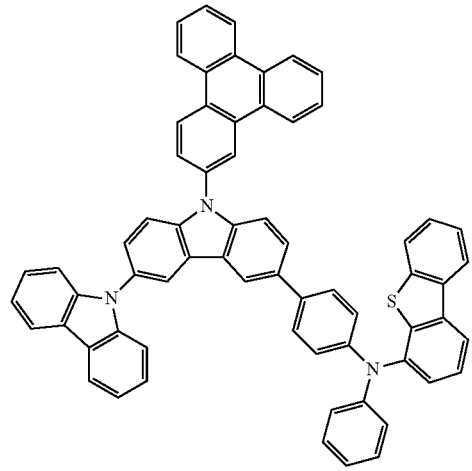
[A-83]
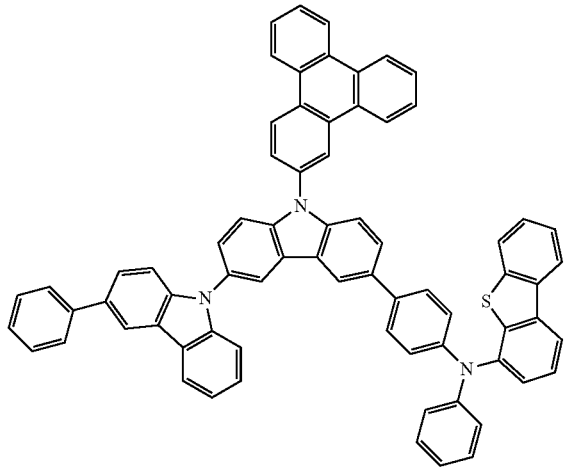
[A-84]
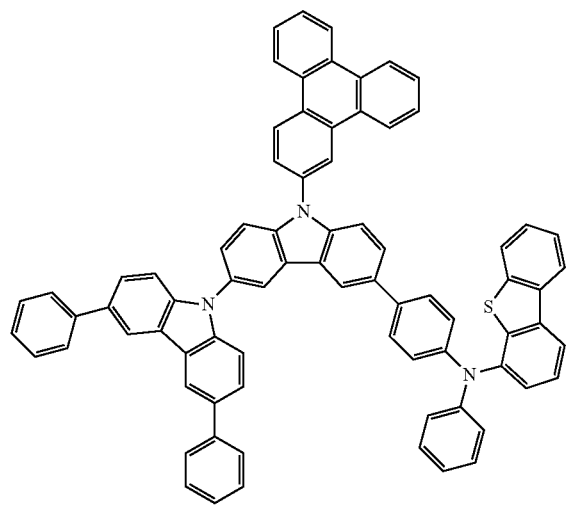
[A-85]
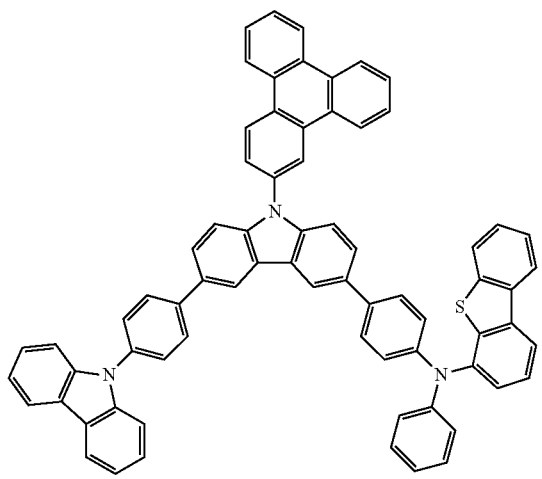
[A-86]
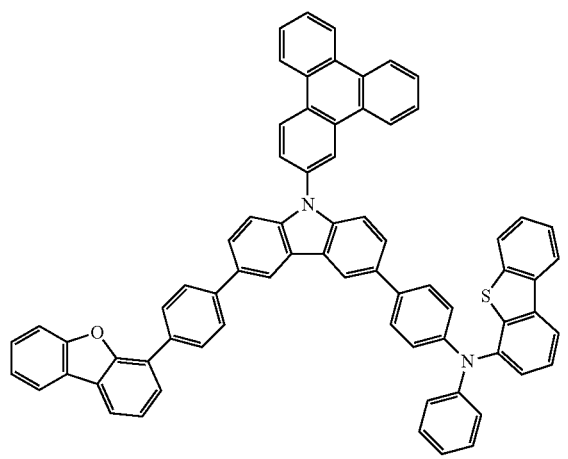
[A-87]
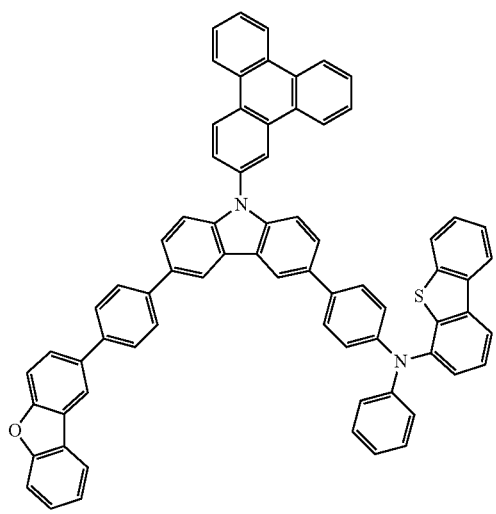

[A-88]
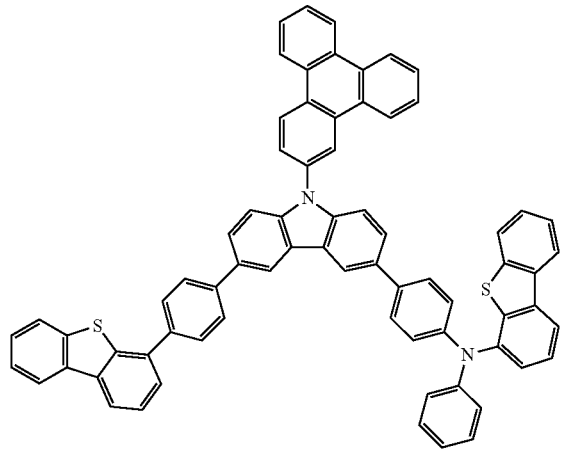
[A-89]
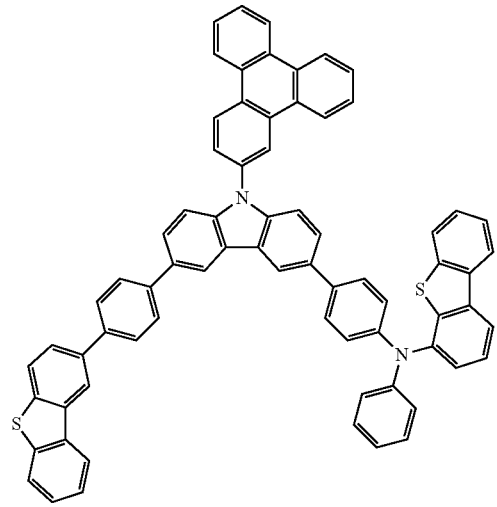
[A-90]
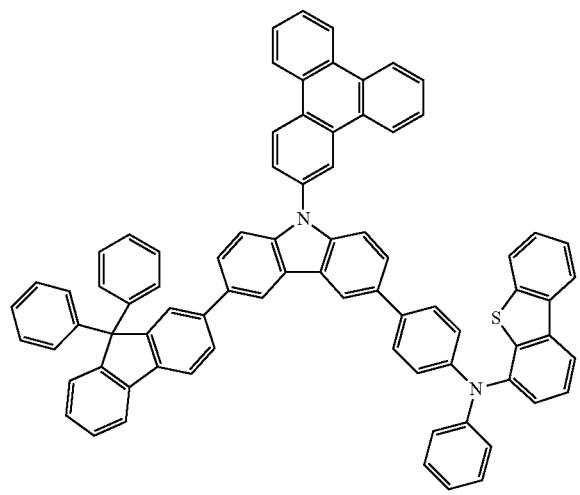
[A-91]
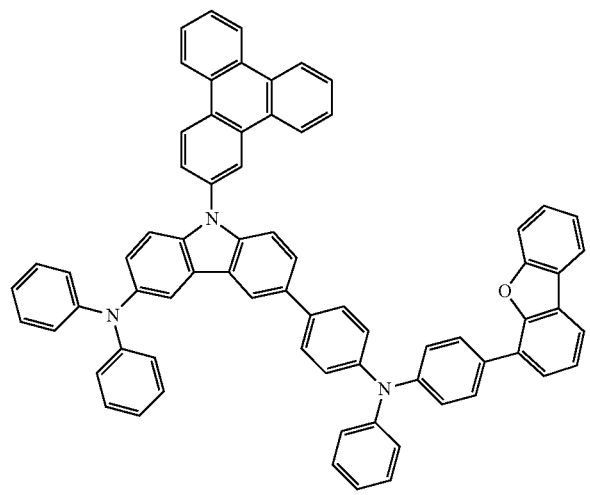
[A-92]
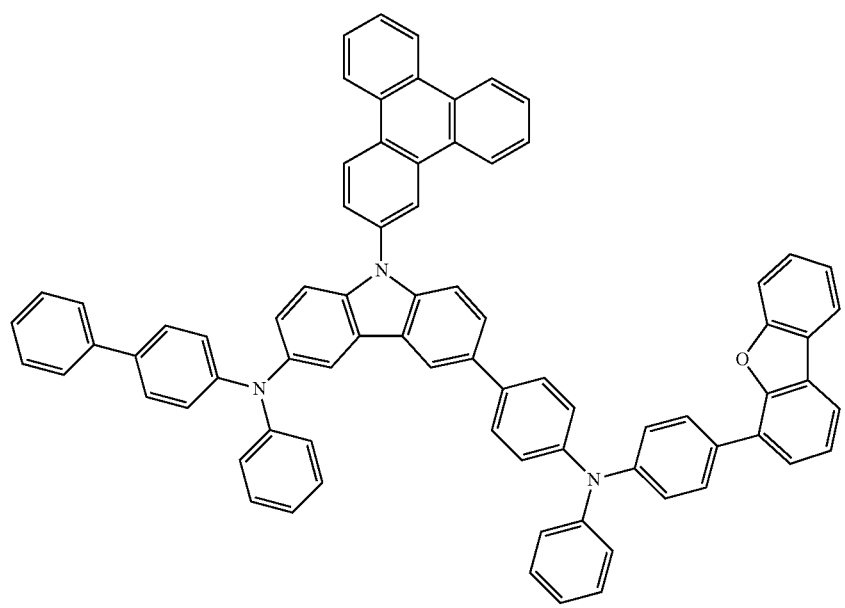

[A-93]
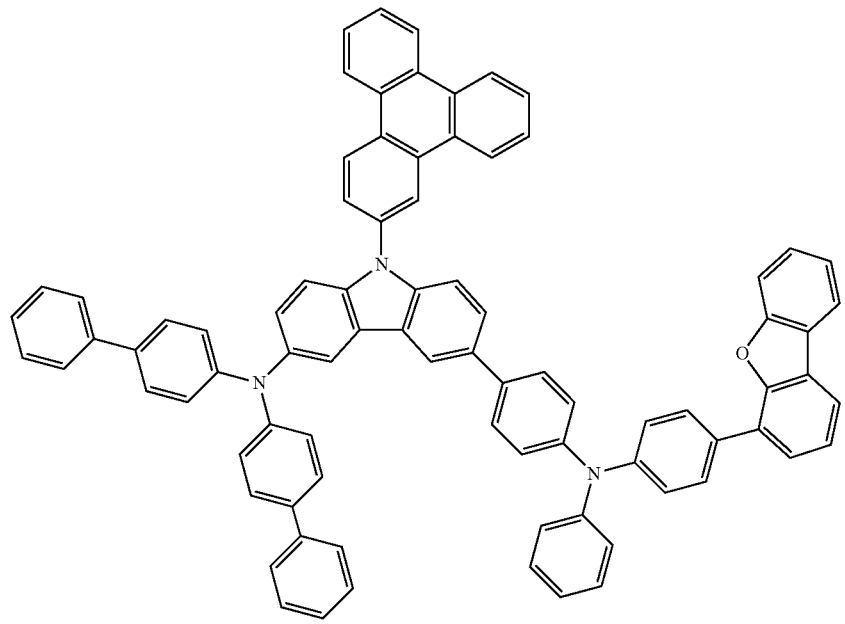
[A-94]
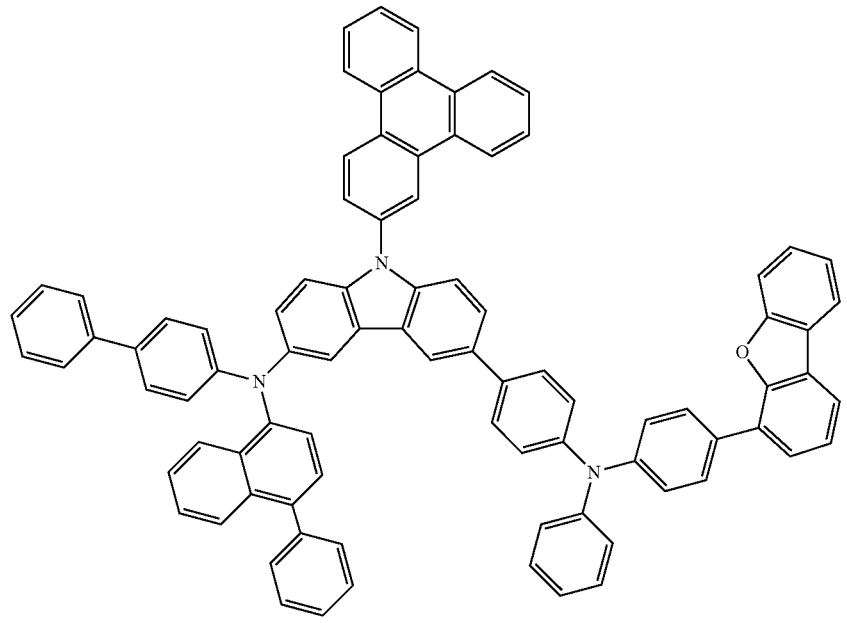

[A-95]
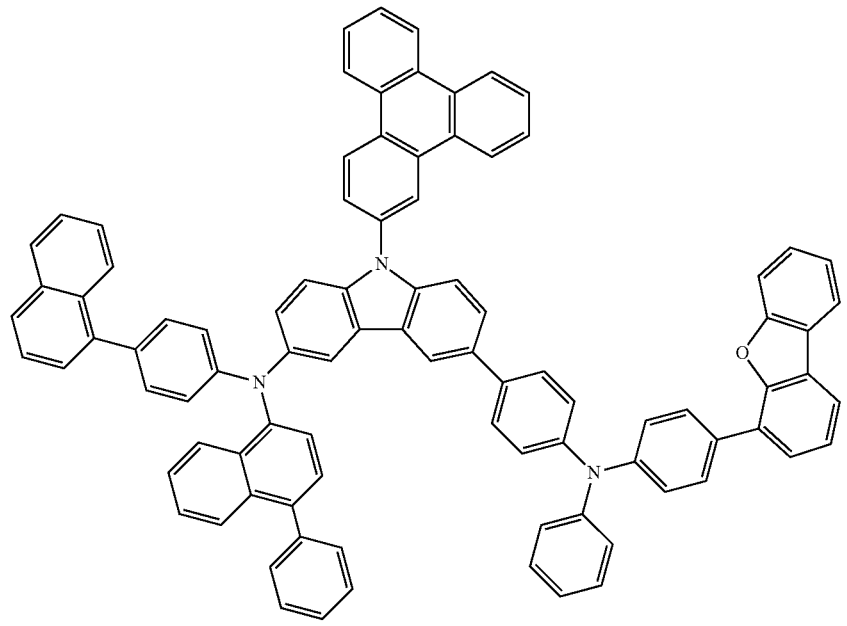
[A-96]
[A-97]
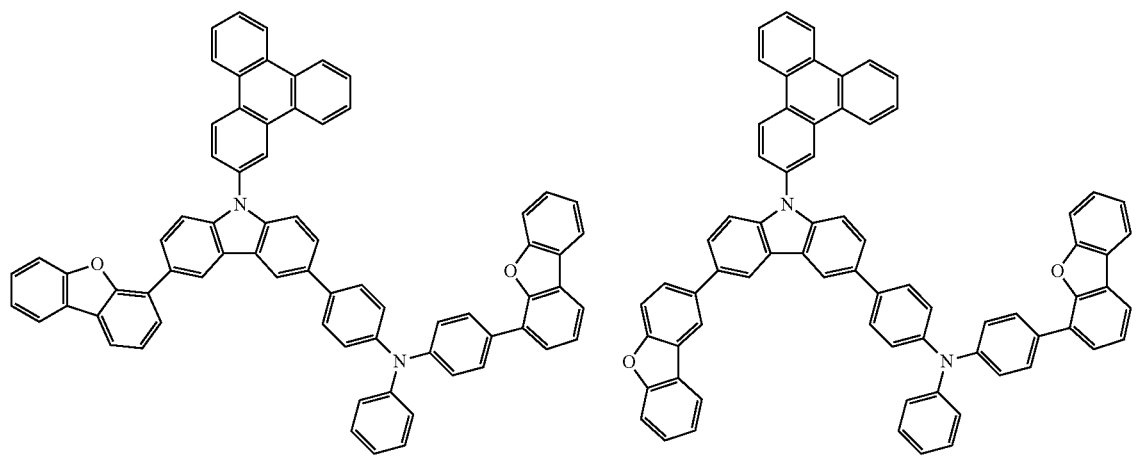
[A-98]
[A-99]
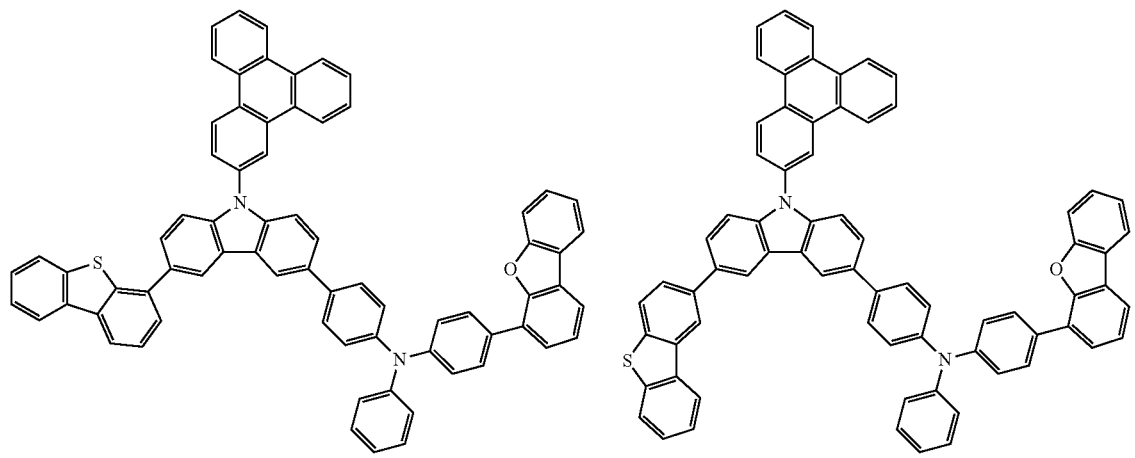

-continued
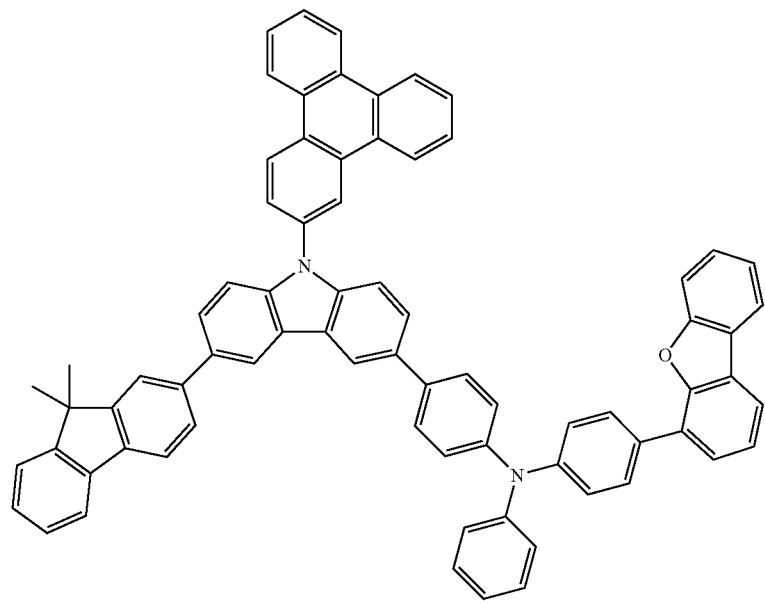
[A-100]
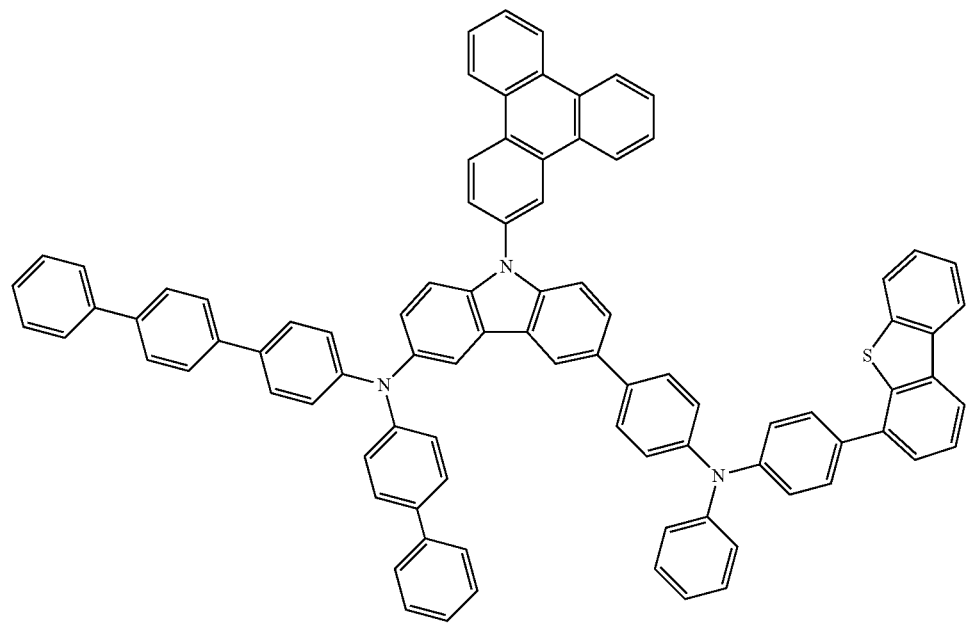
[A101]

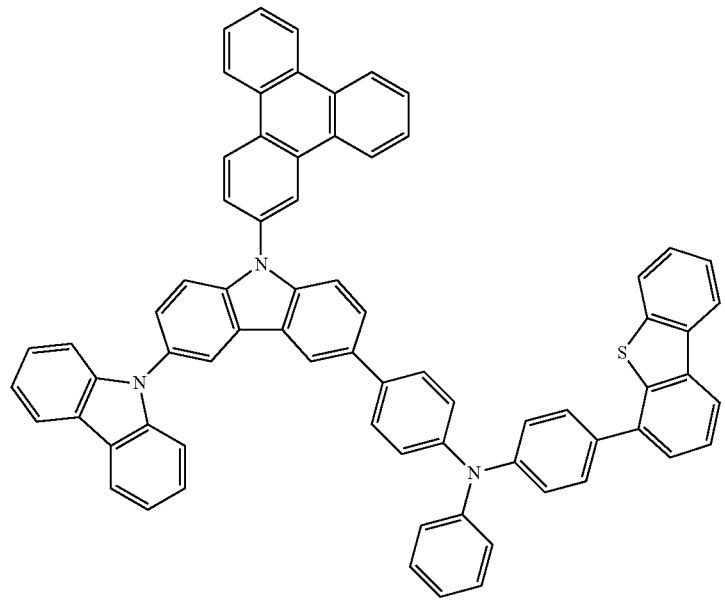
[A-102]
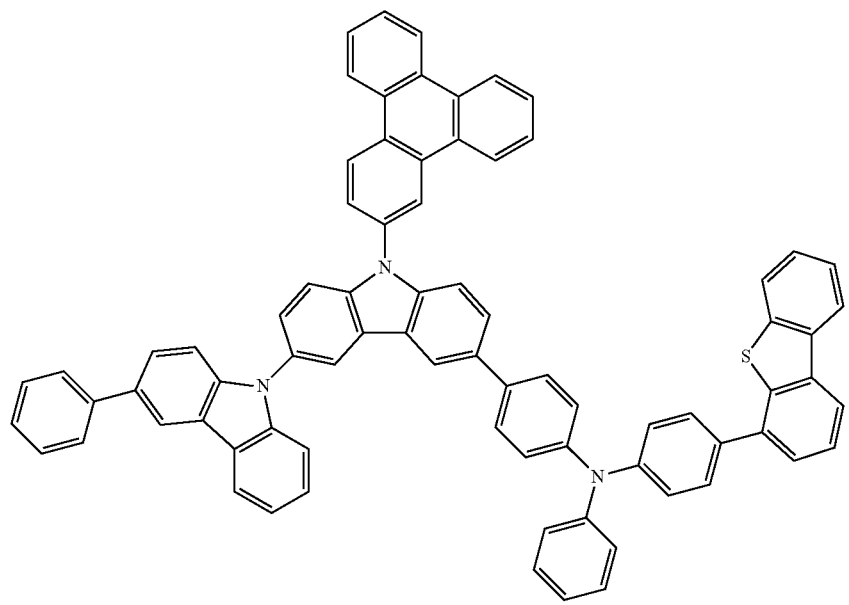
[A-103]

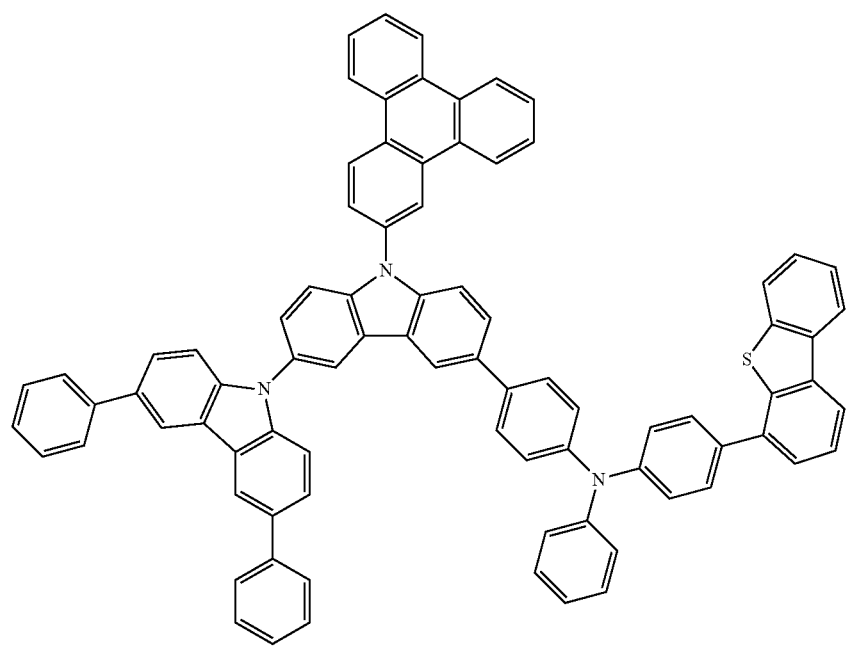
[A-104]
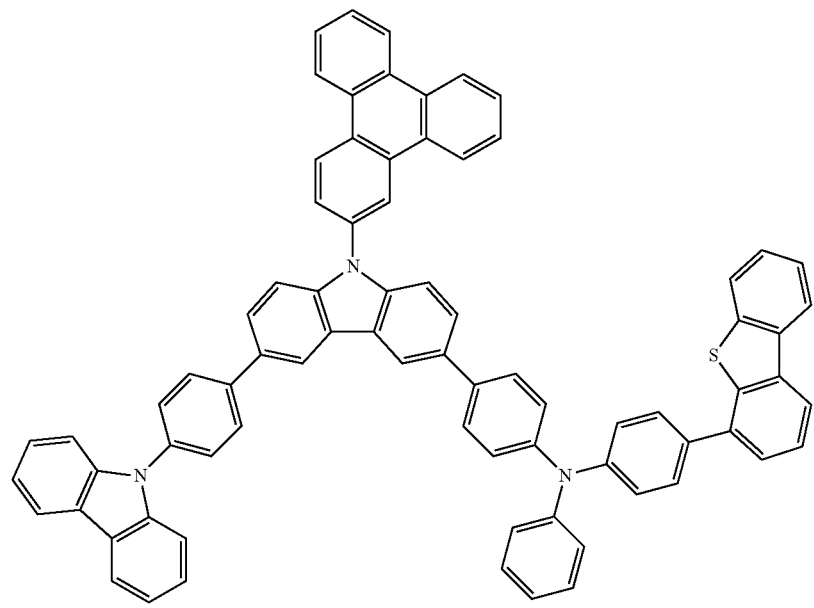
[A-105]

-continued
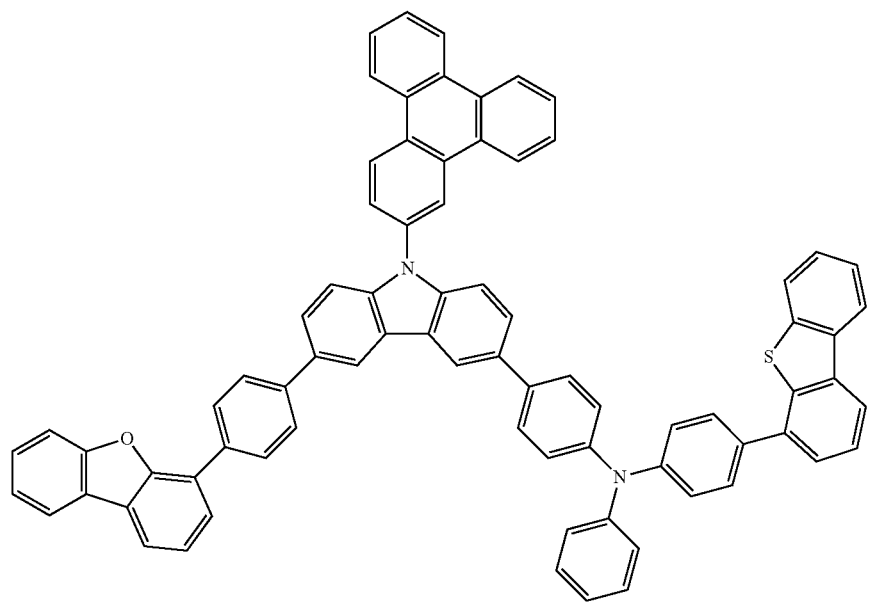
[A-106]
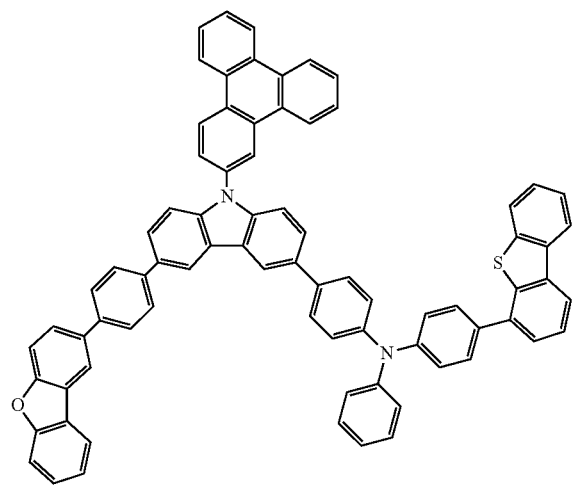
[A-107]

-continued
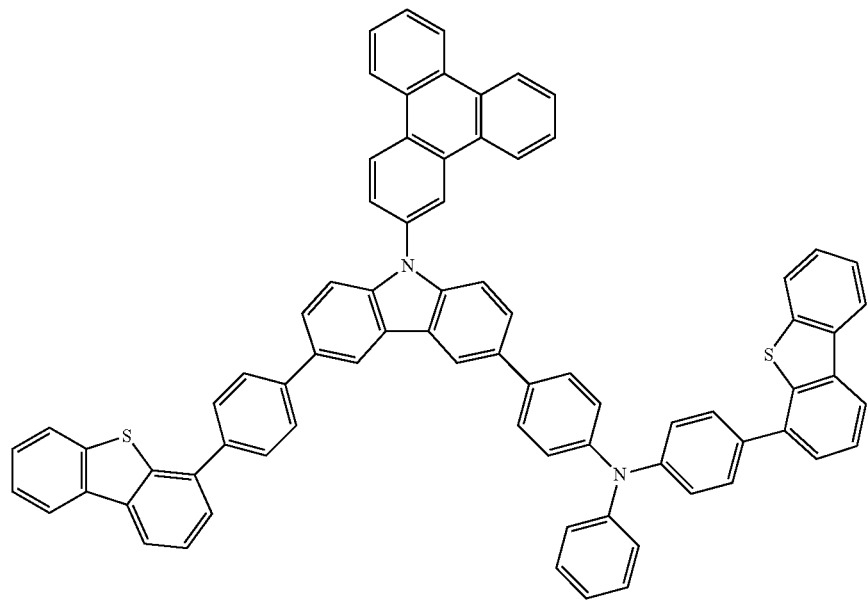
[A-108]
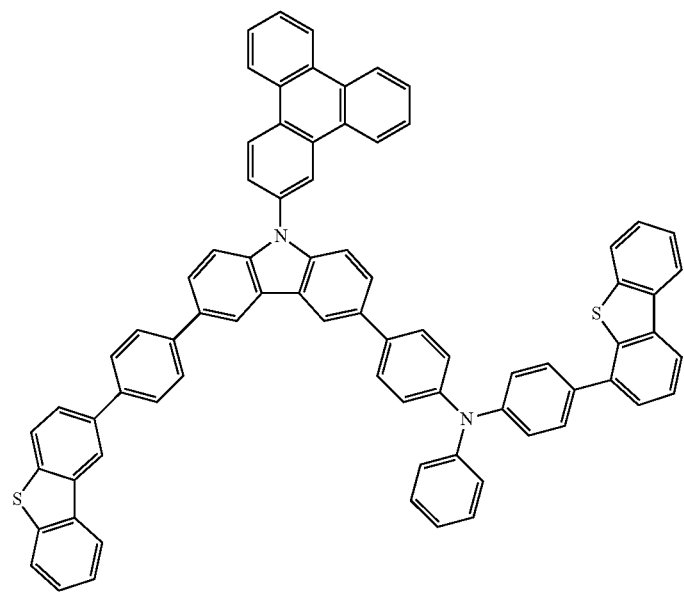
[A-109]

[A-110]
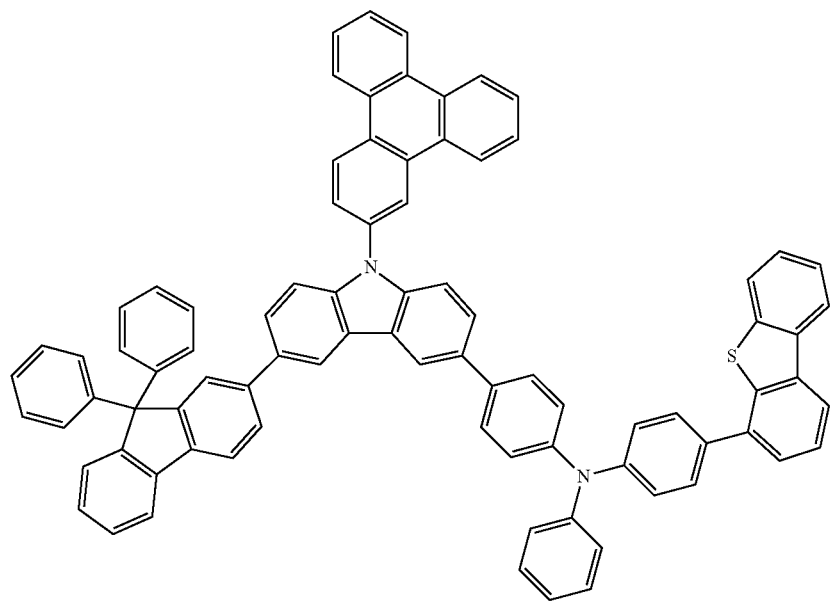
[A-111]
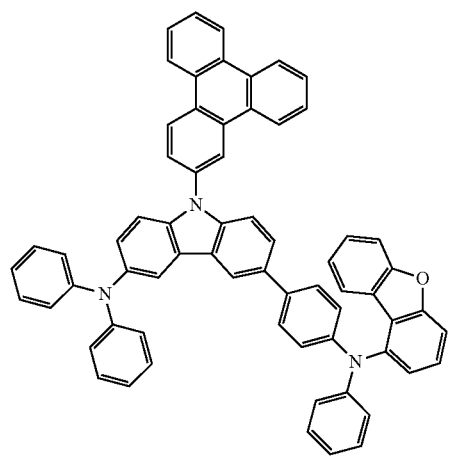
[A-112]
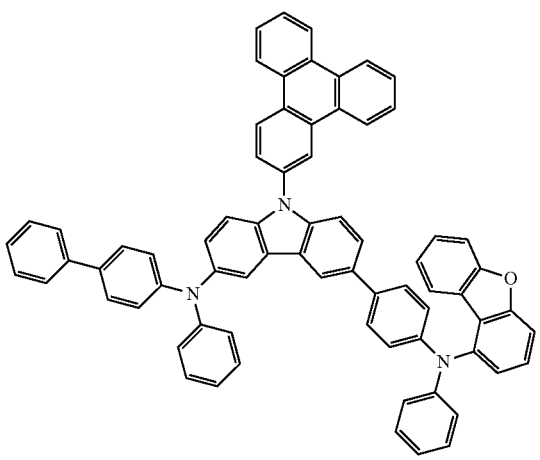
[A-113]
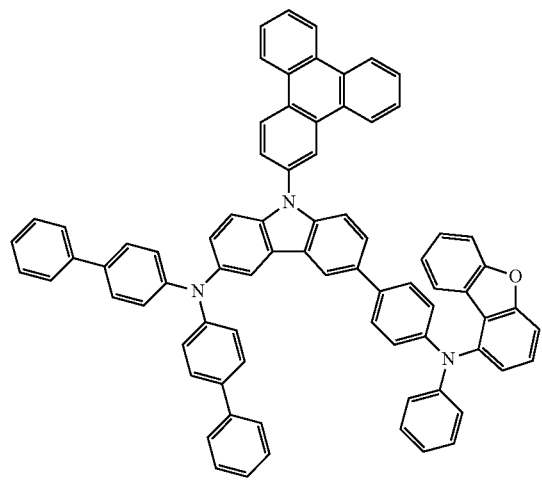
[A-114]
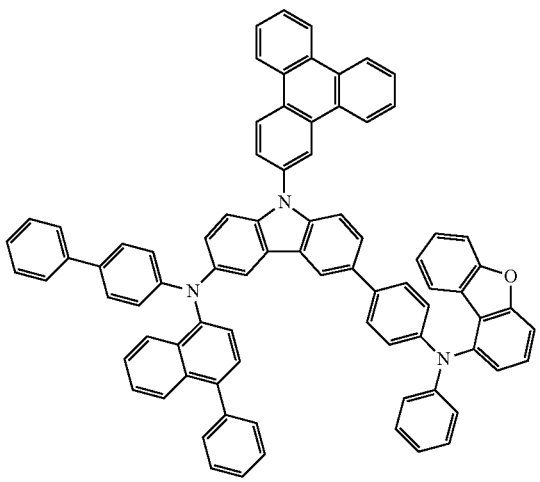

-continued
[A-115]
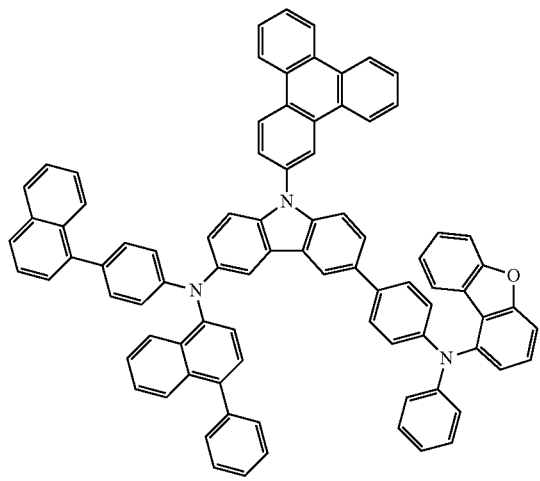
[A-116]
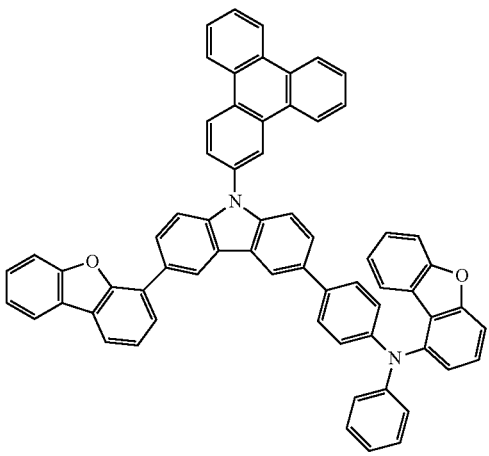
[A-117]
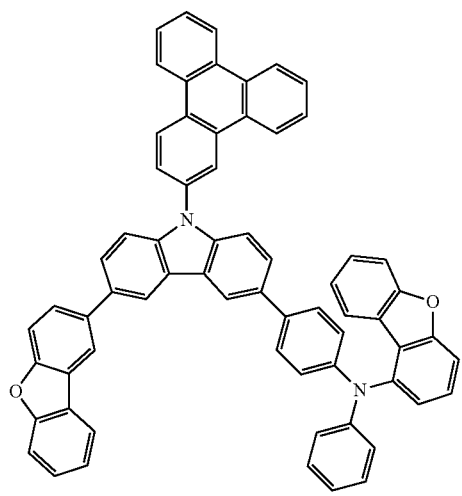
[A-118]
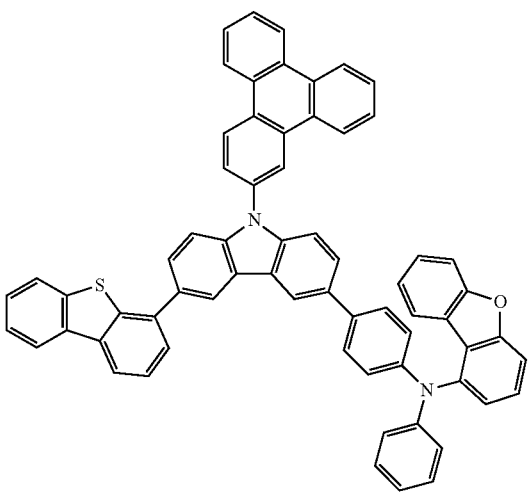
[A-119]
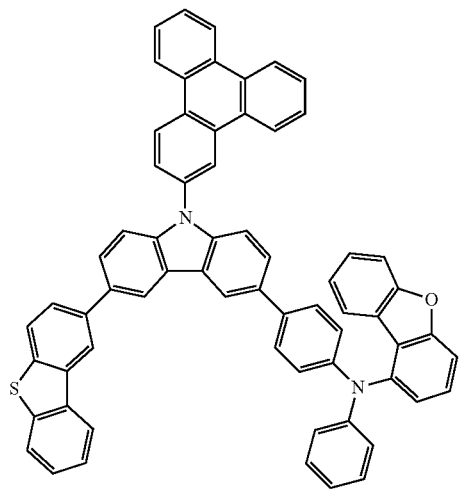
[A-120]
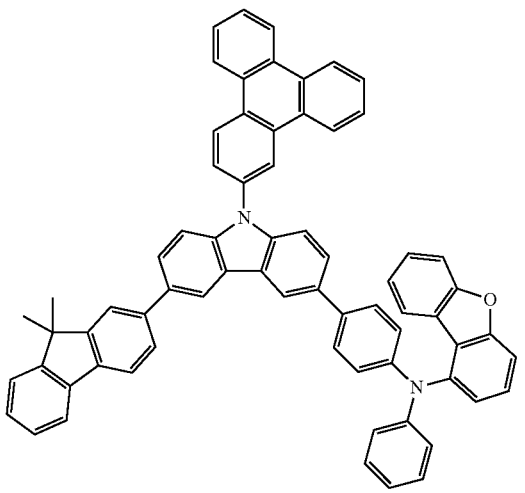

-continued
[A-121]
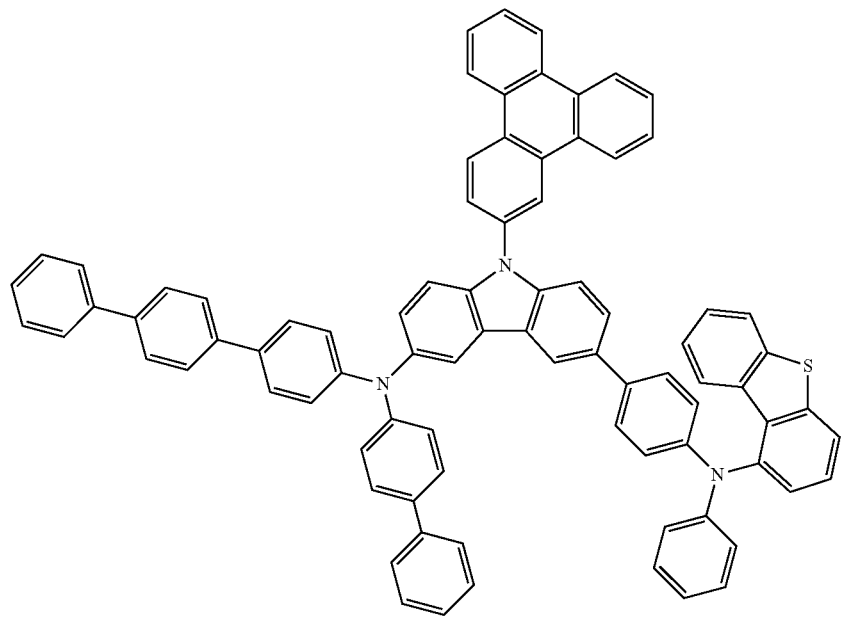
[A-122]
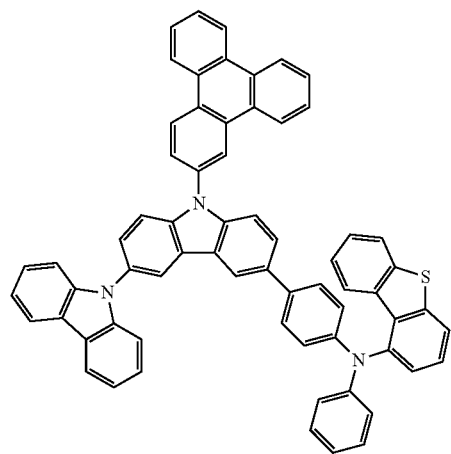
[A-123]
[A-124]
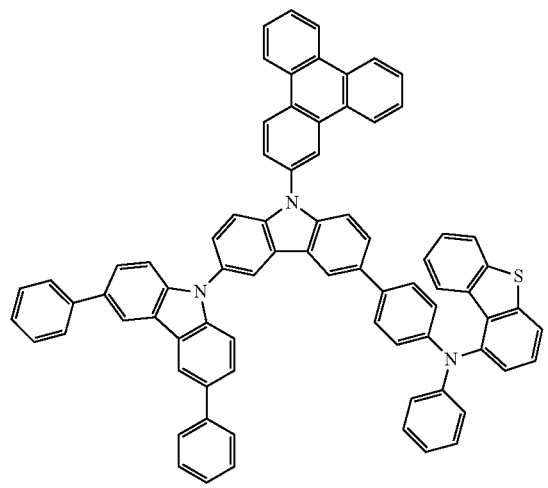
[A-125]
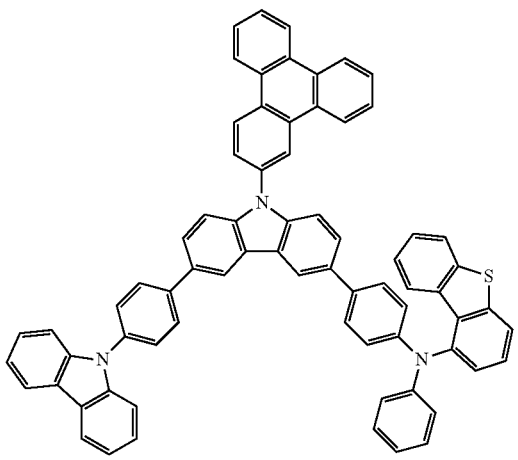

[A-126]
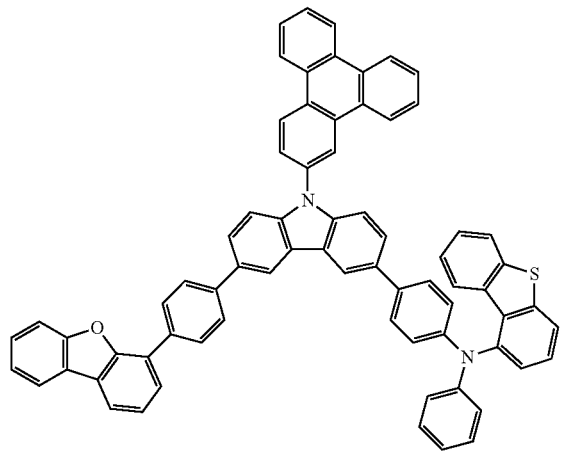
[A-127]
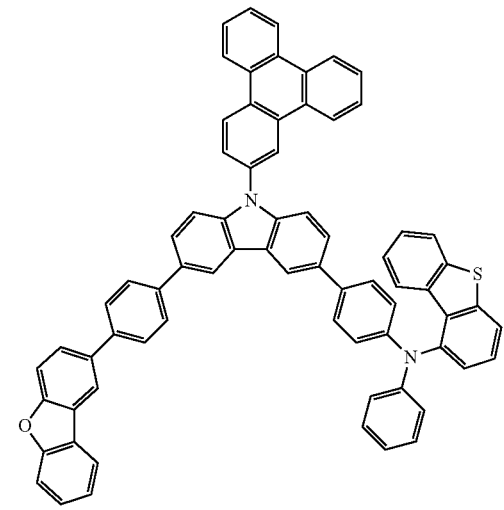
[A-128]
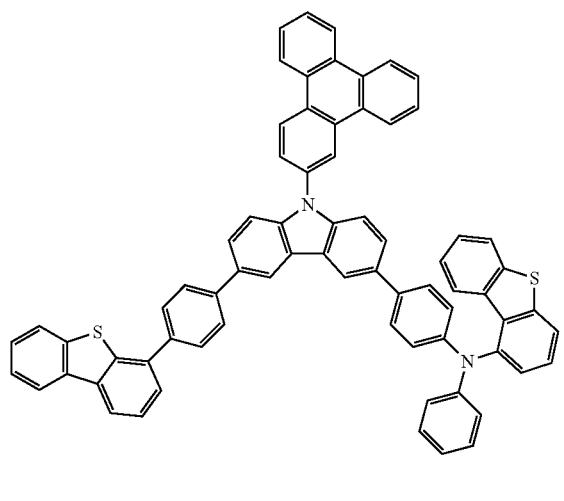
[A-129]
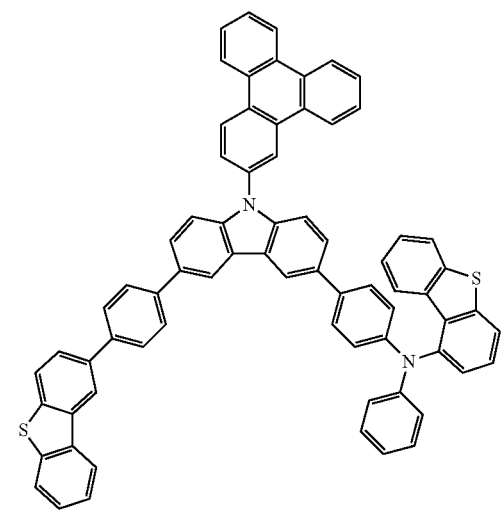
[A-130]
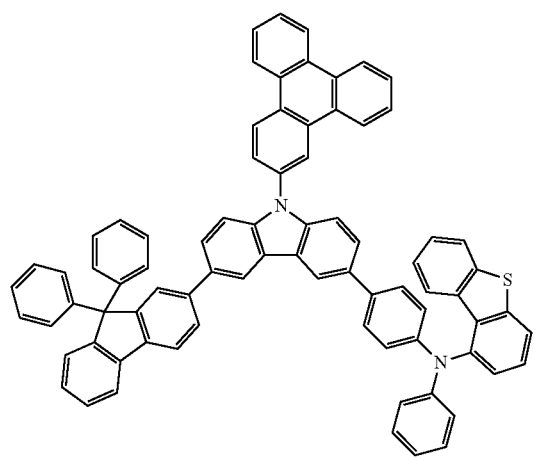
[A-131]
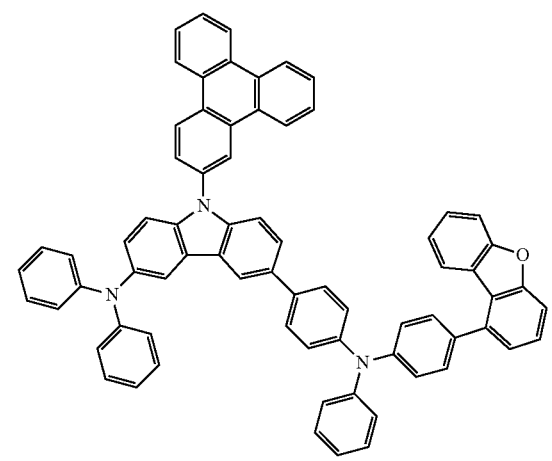

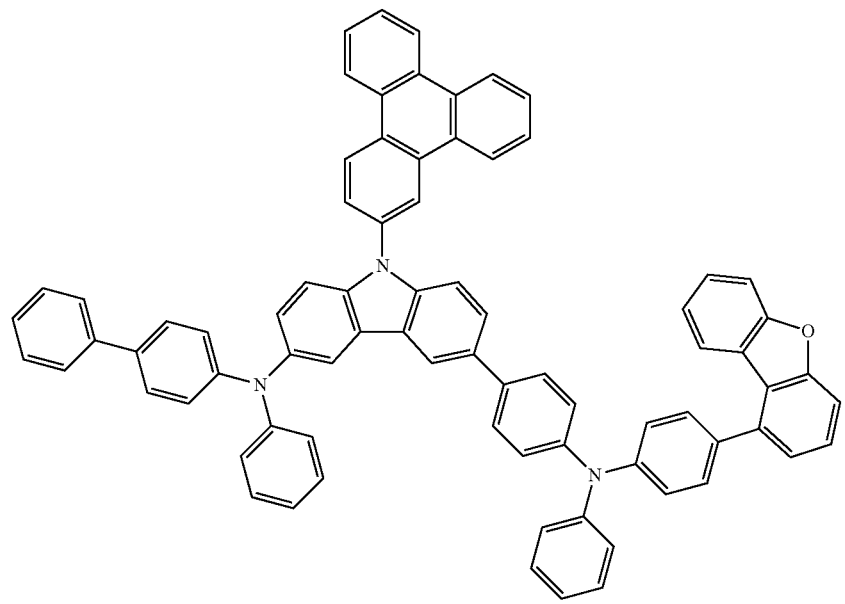
[A-132]
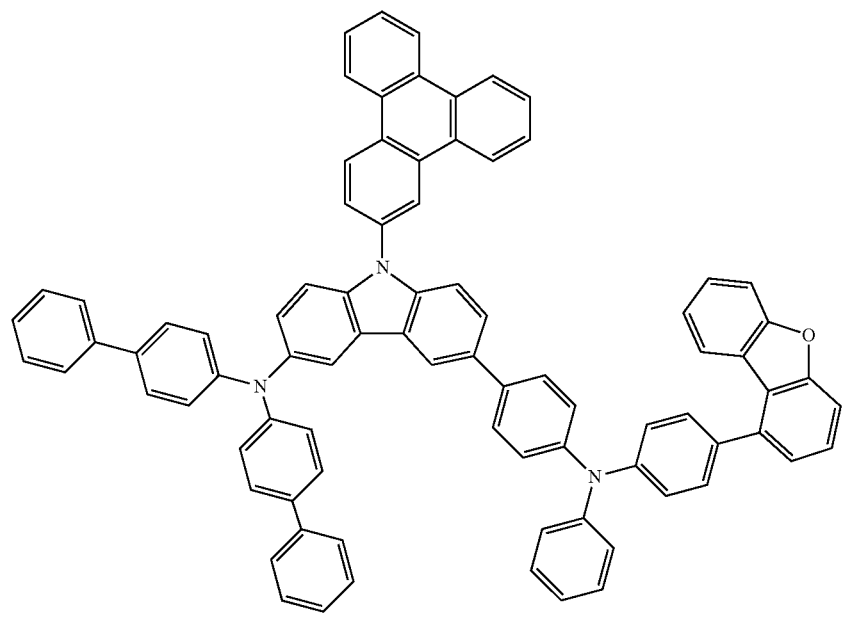
[A-133]

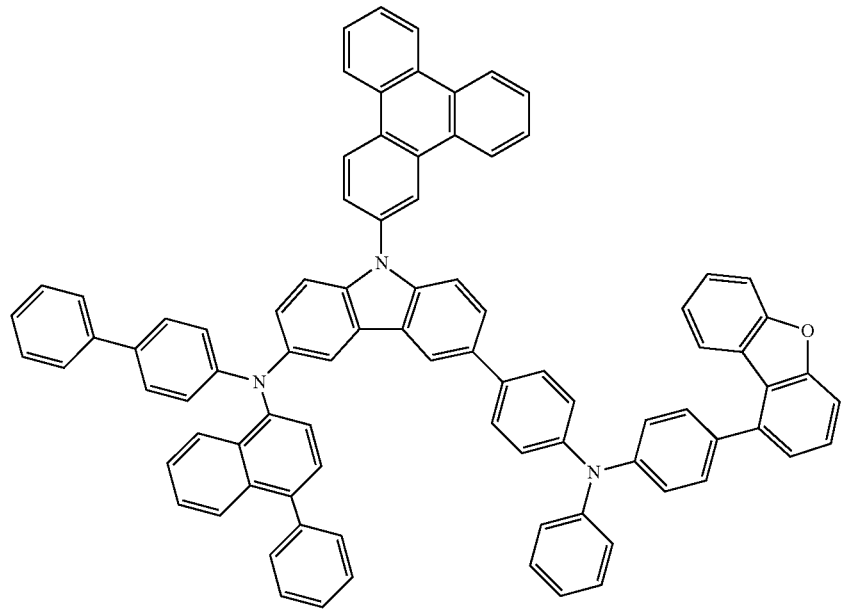
[A-134]
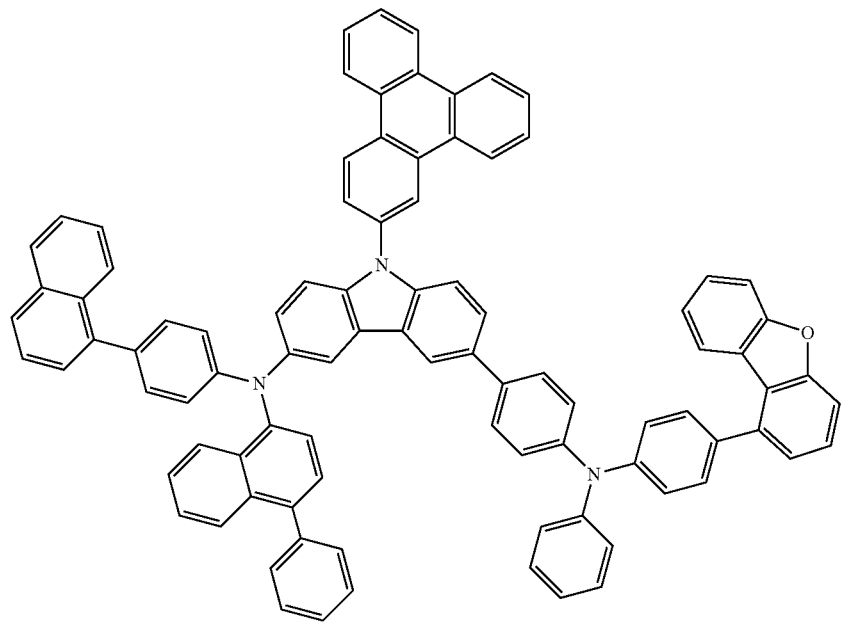
[A-135]

-continued
[A-136]
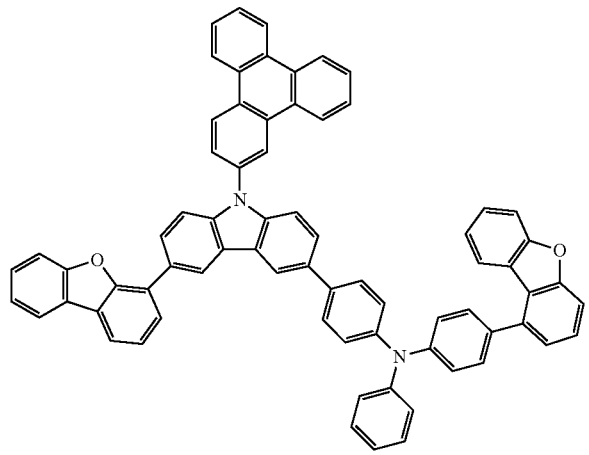
[A-137]
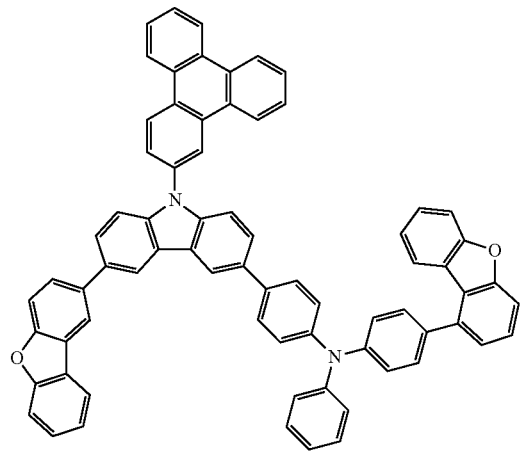
[A-138]
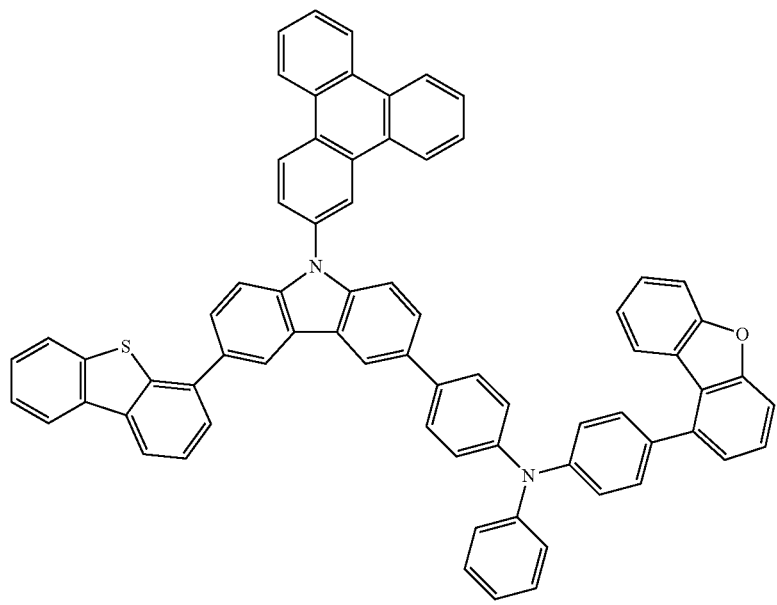
[A-139]
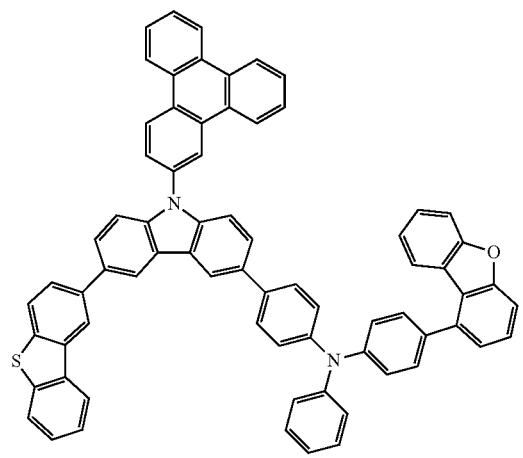
[A-140]
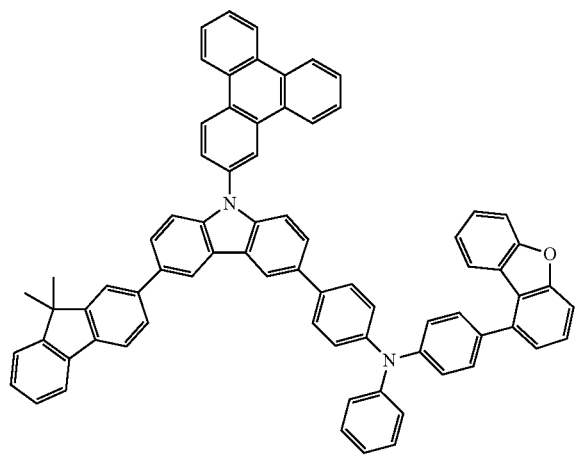

[A-141]
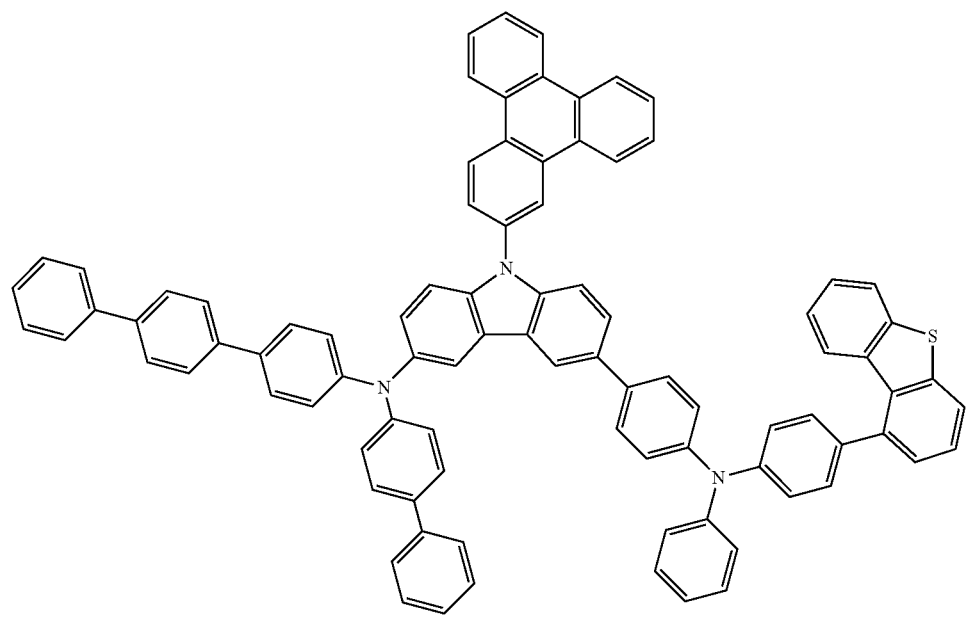
[A-142]
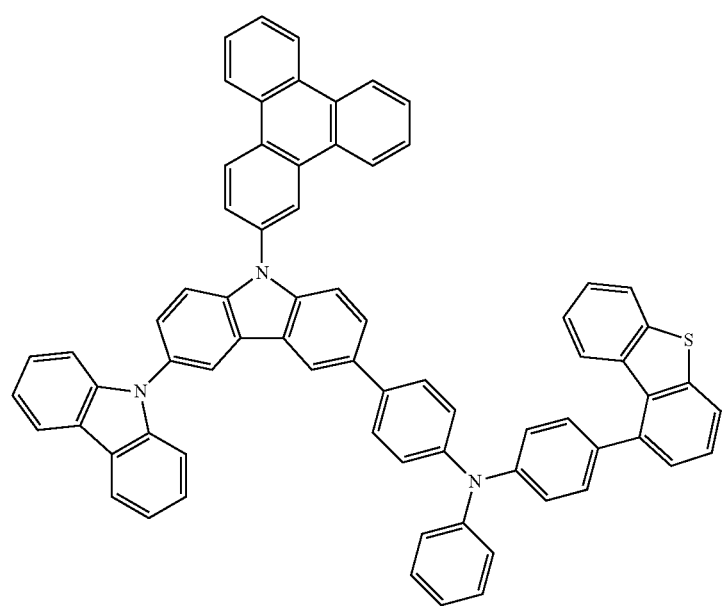

[A-143]
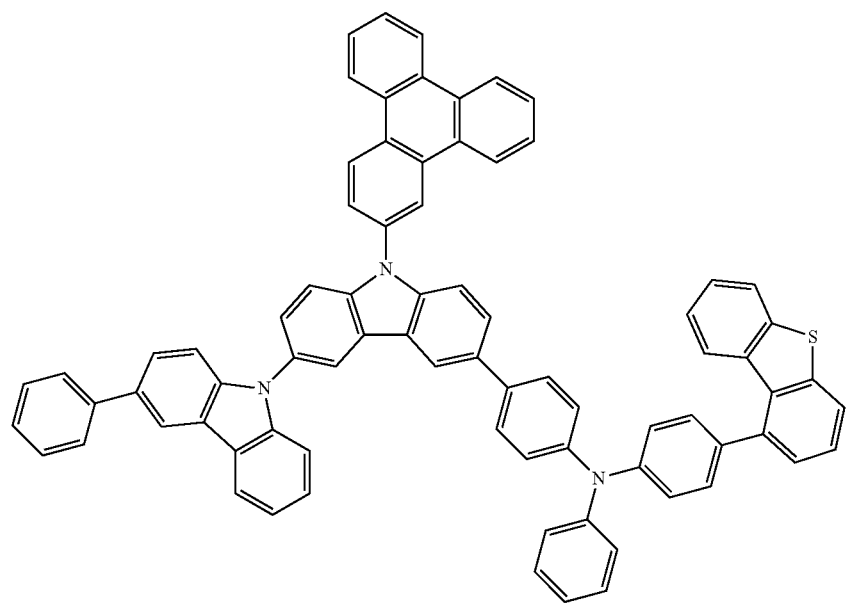
[A-144]
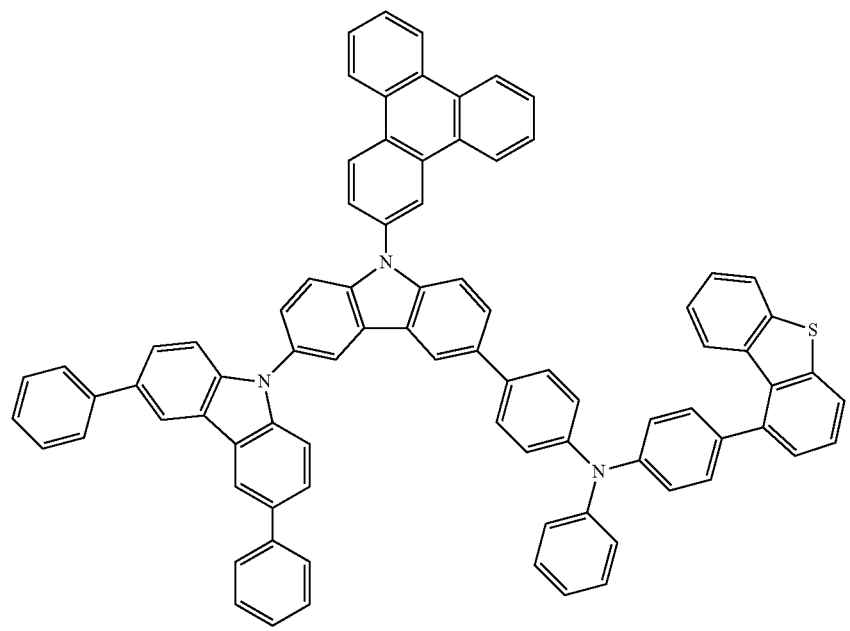

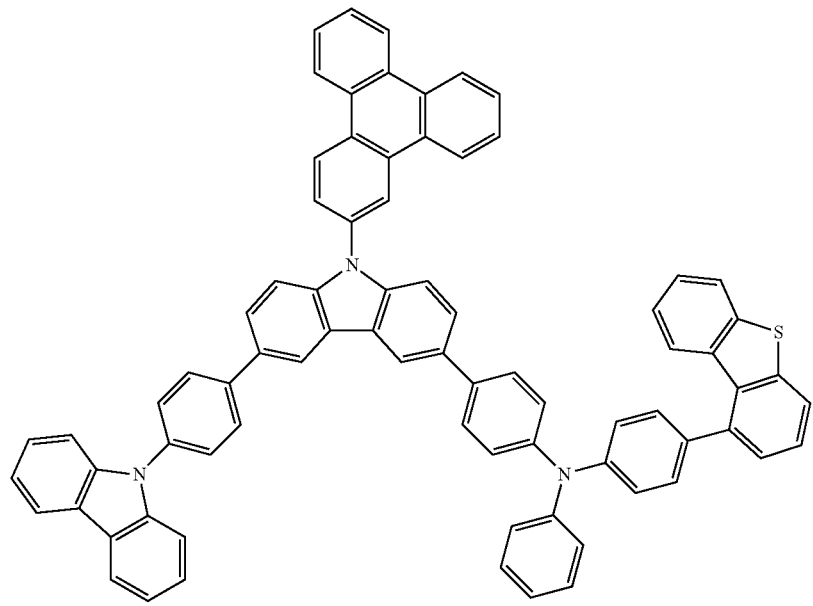
[A-145]
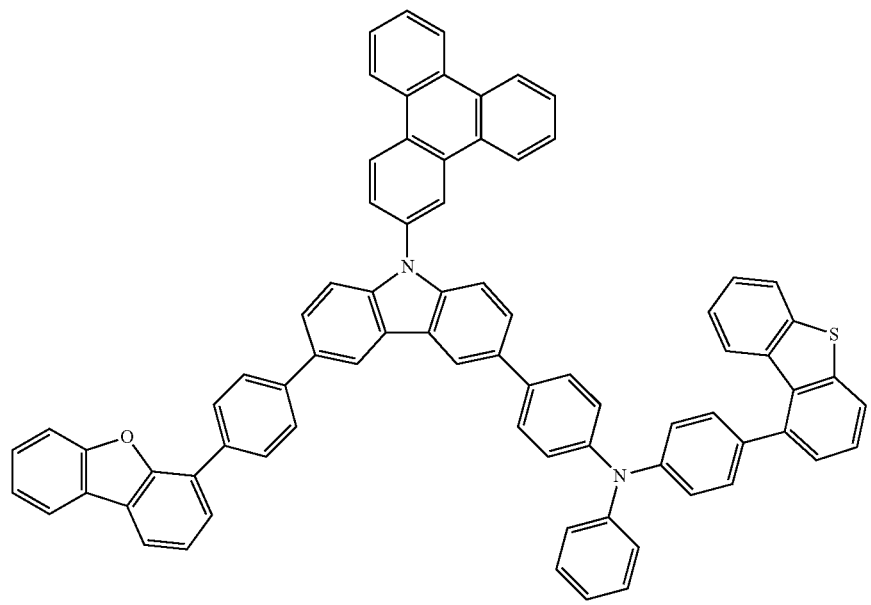
[A-146]

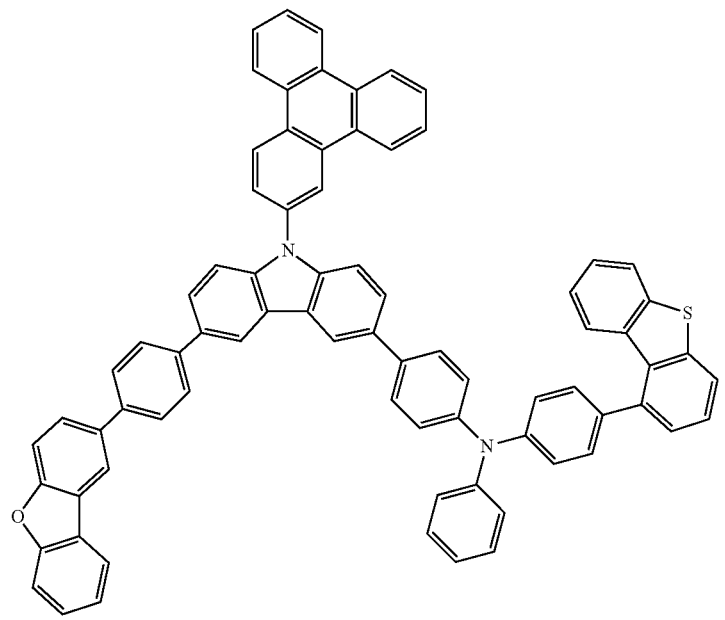
[A-147]
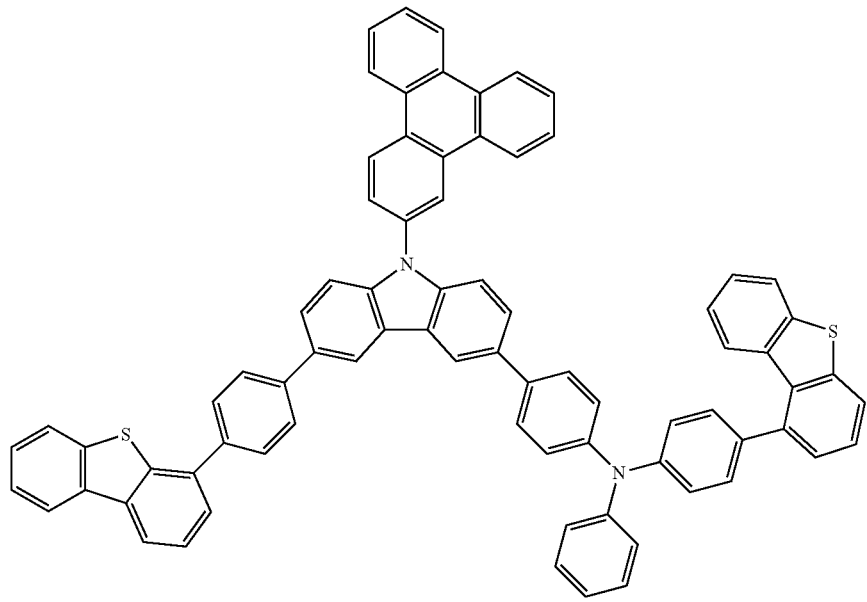
[A-148]

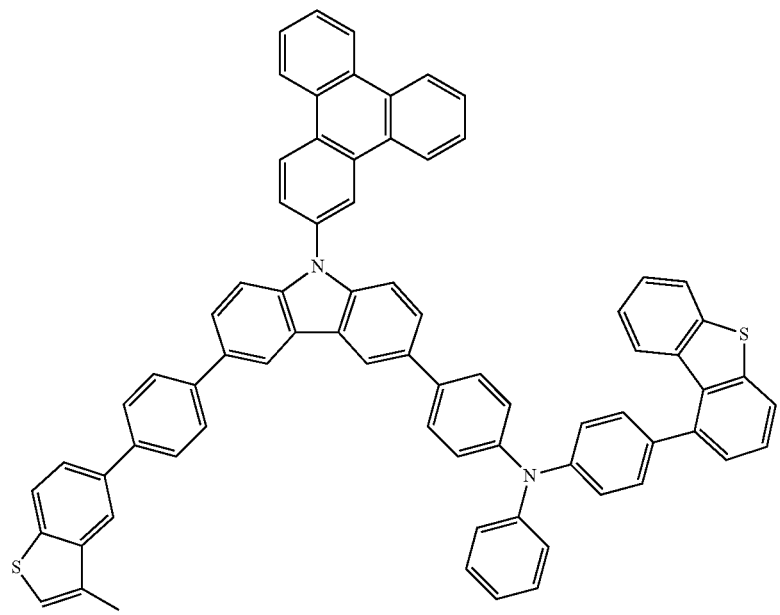
[A-149]
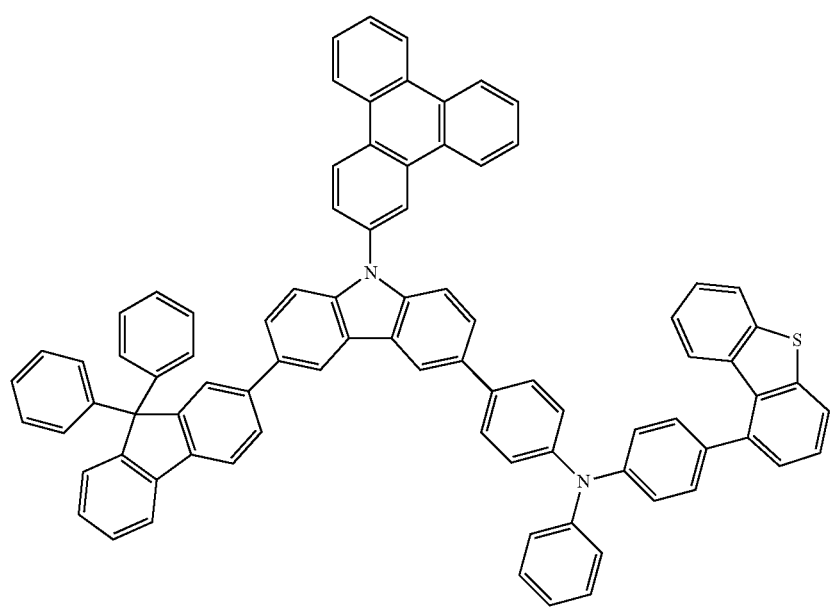
[A-150]

[A-151]
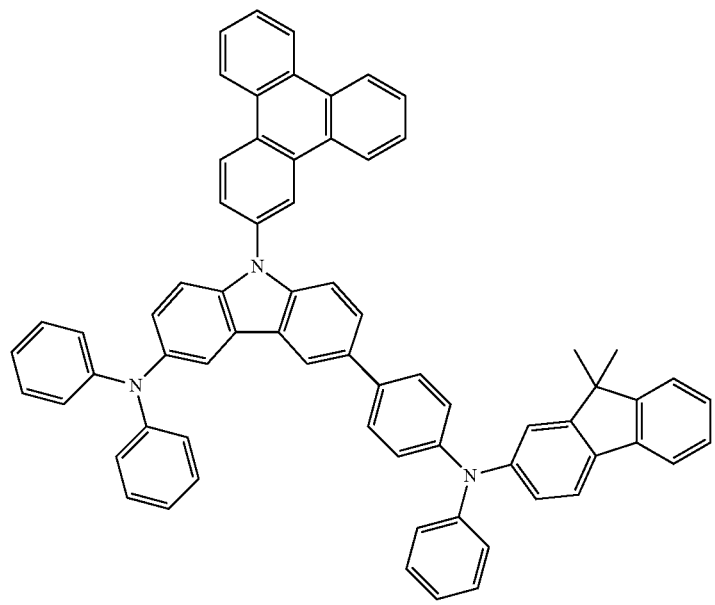
[A-152]
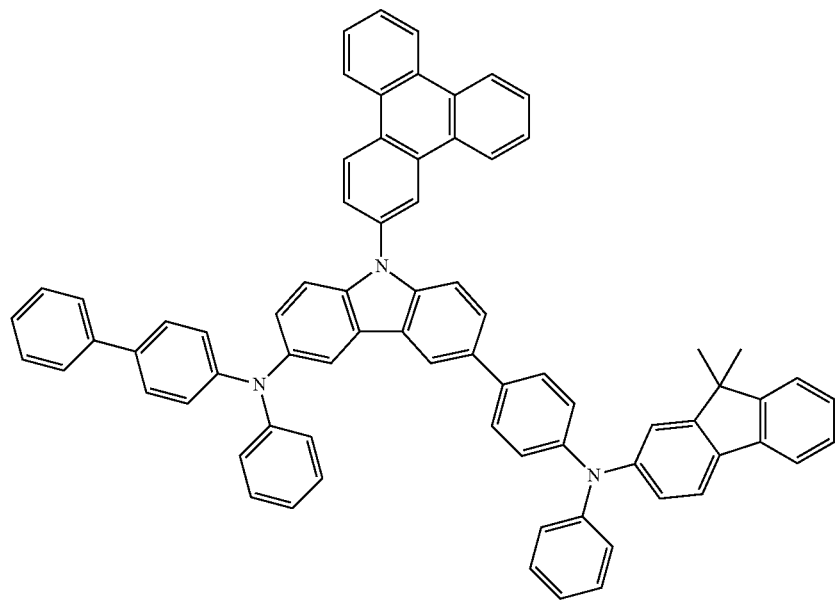

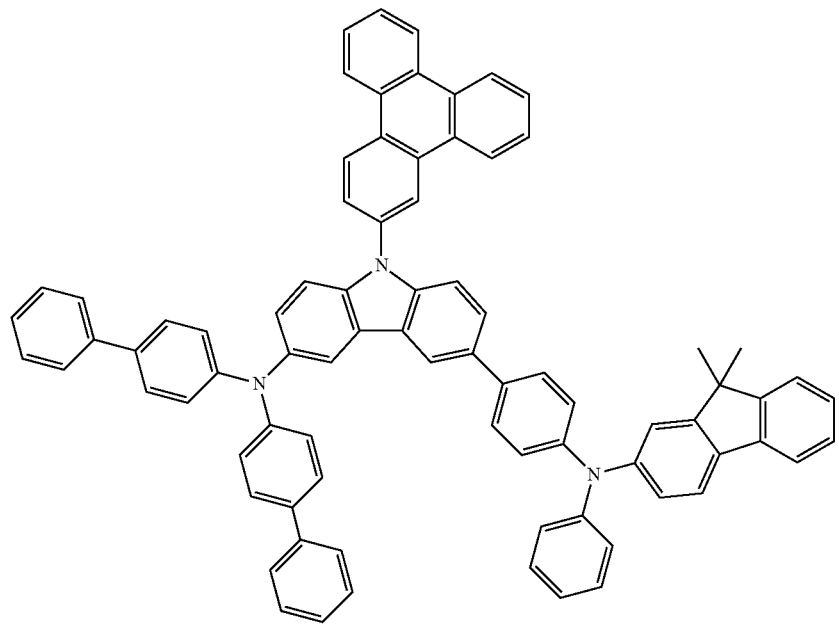
[A-153]
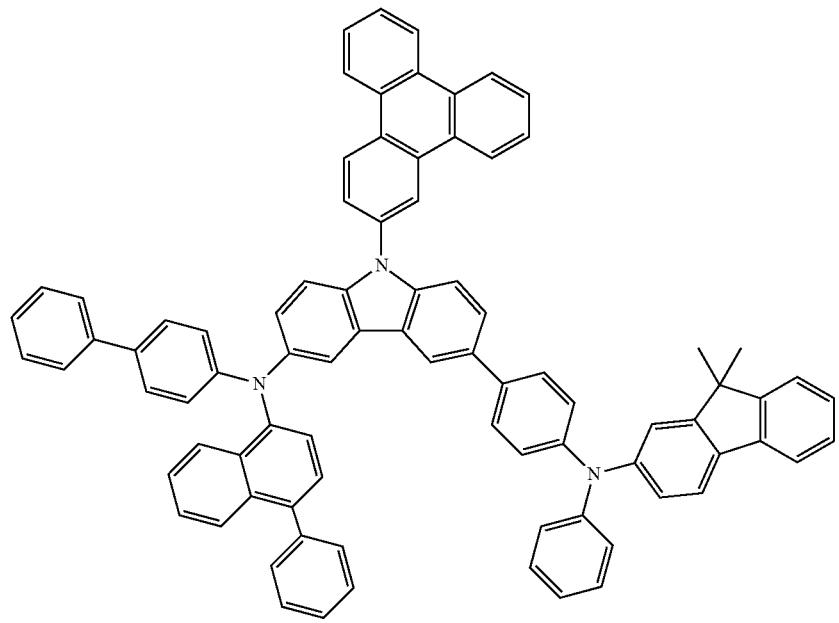
[A-154]

[A-155]
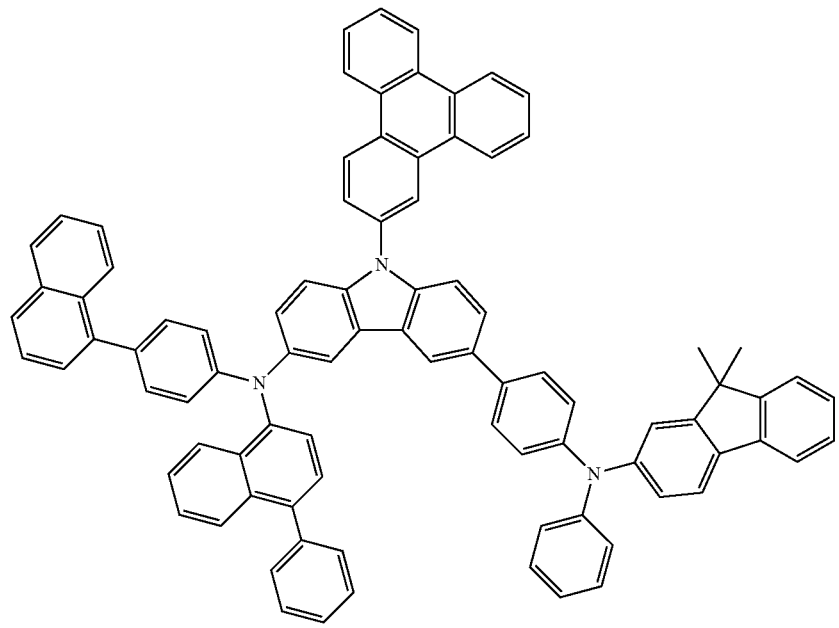
[A-156]
[A-157]
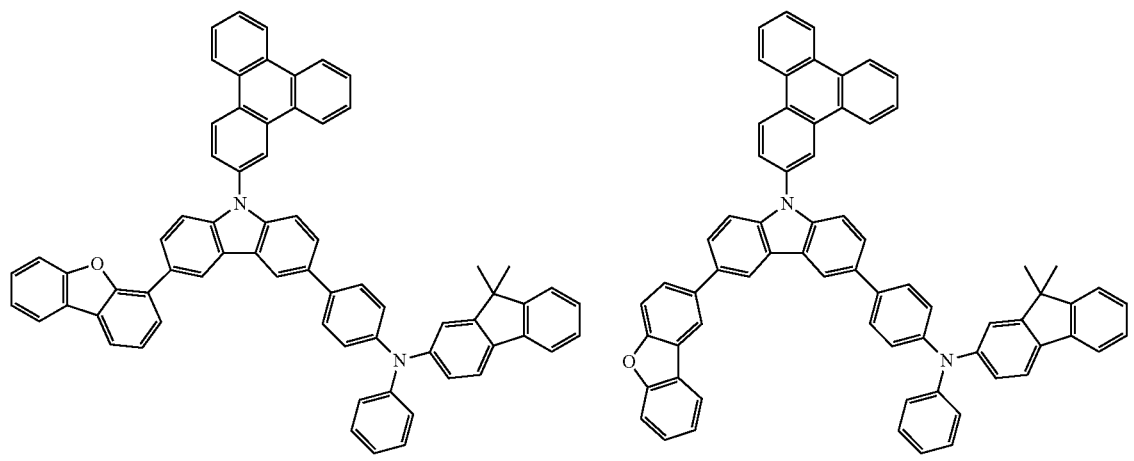
[A-158]
[A-159]
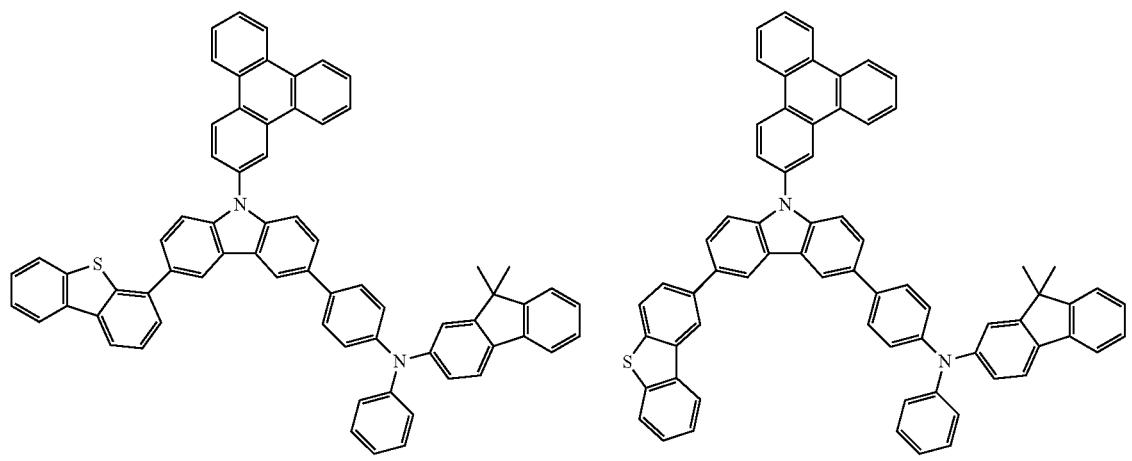

[A-160]
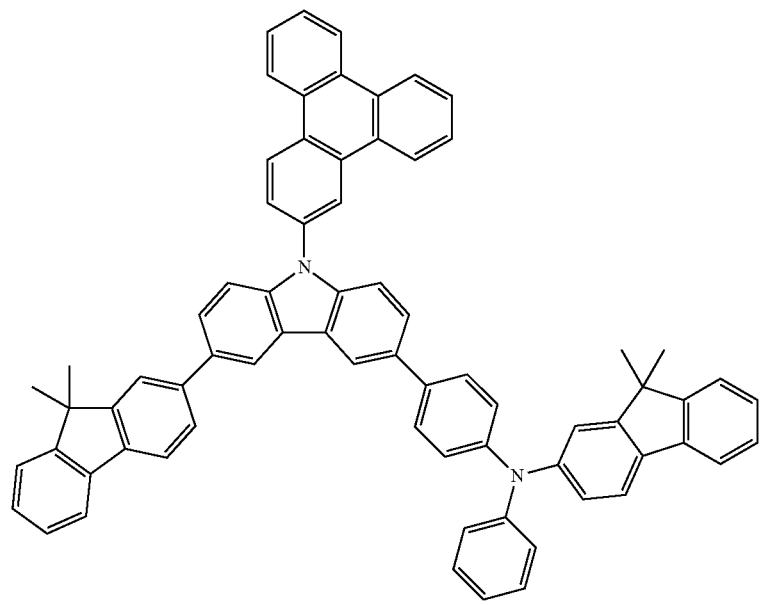
[A-161]
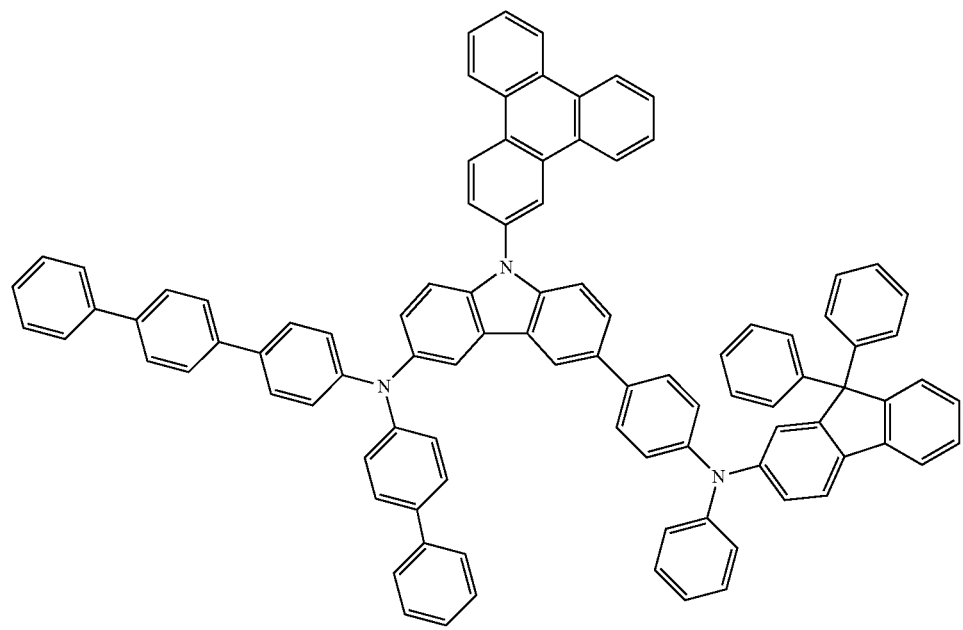

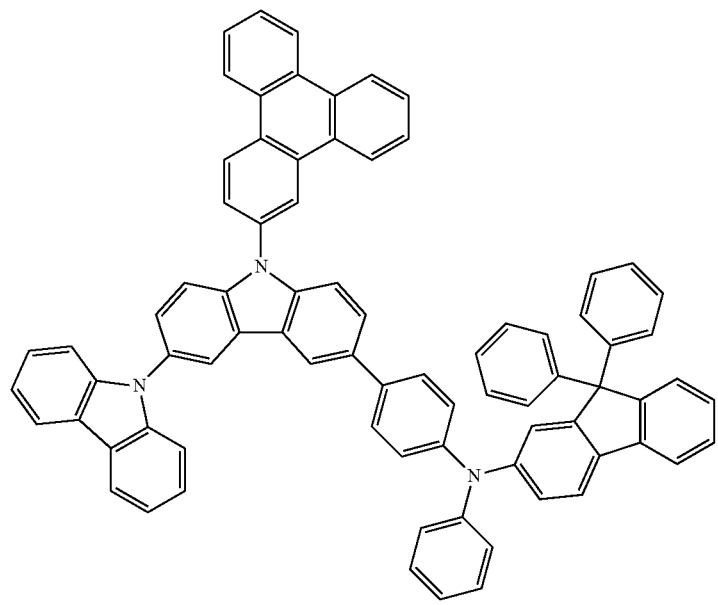
[A-162]
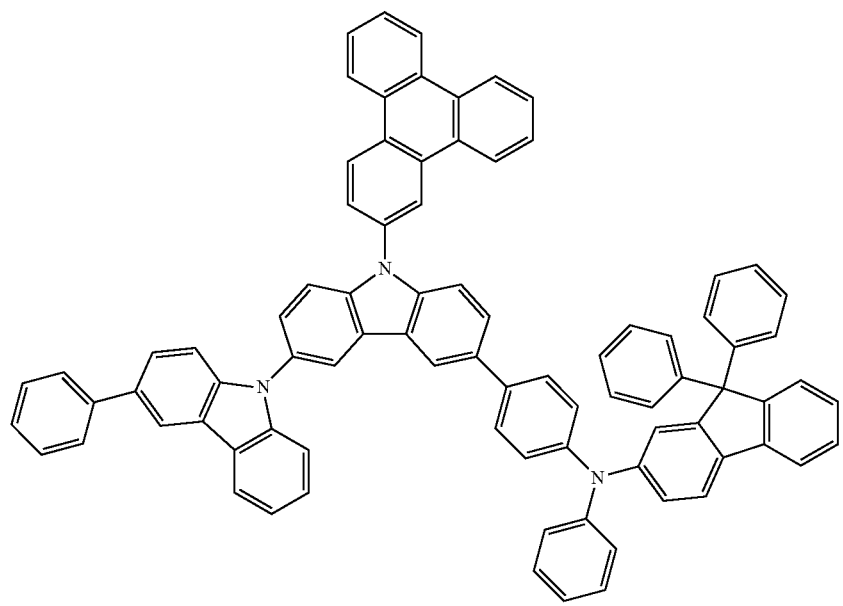
[A-163]

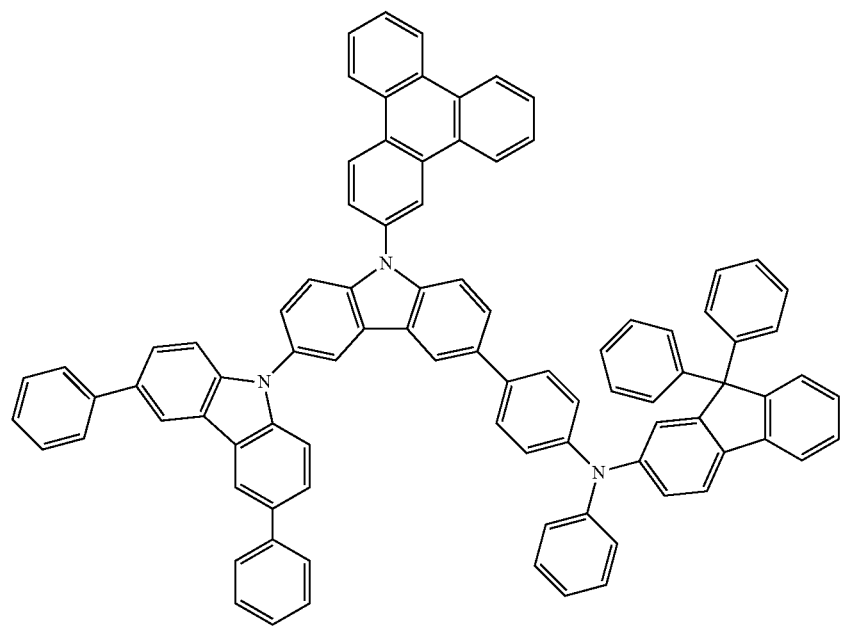
[A-164]
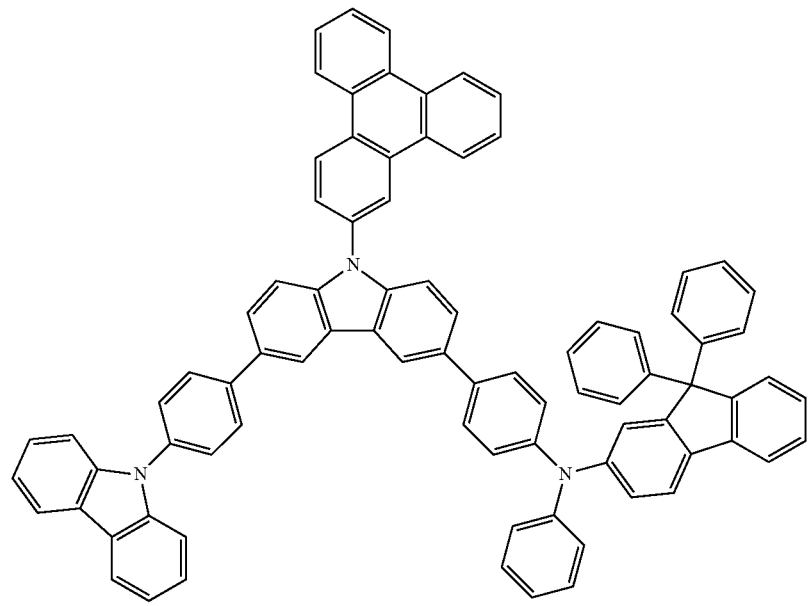
[A-165]

-continued
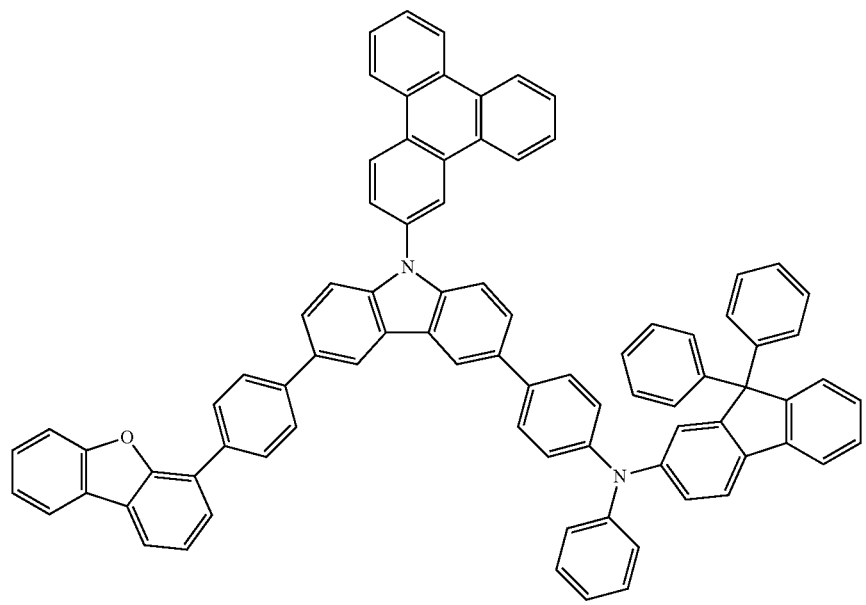
[A-166]
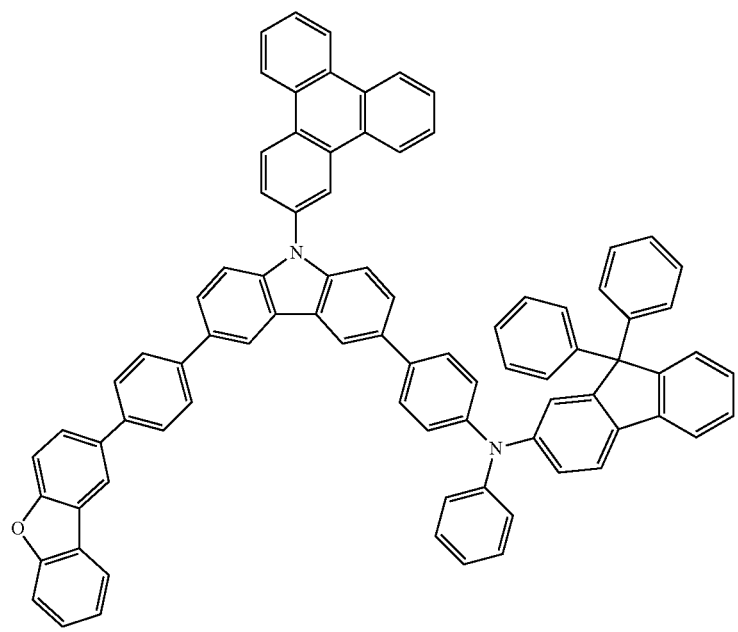
[A-167]

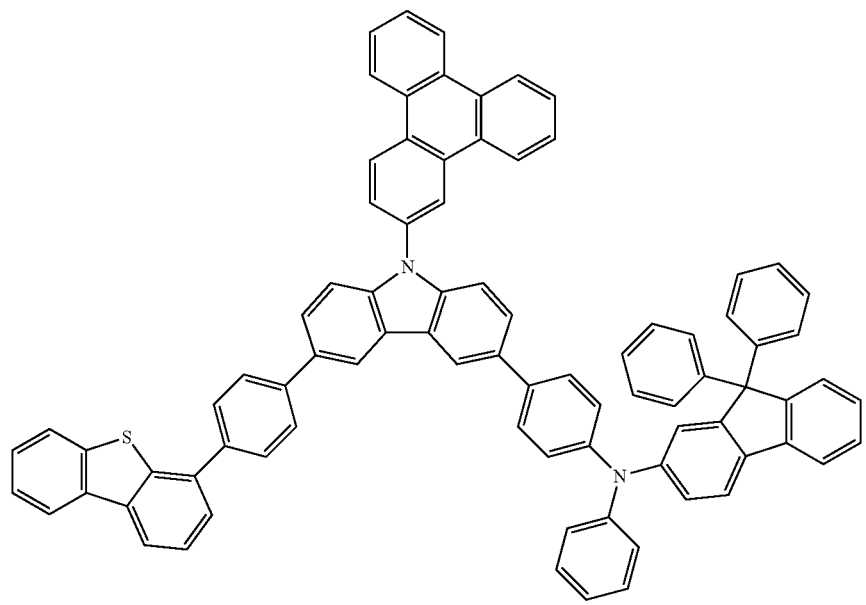
[A-168]
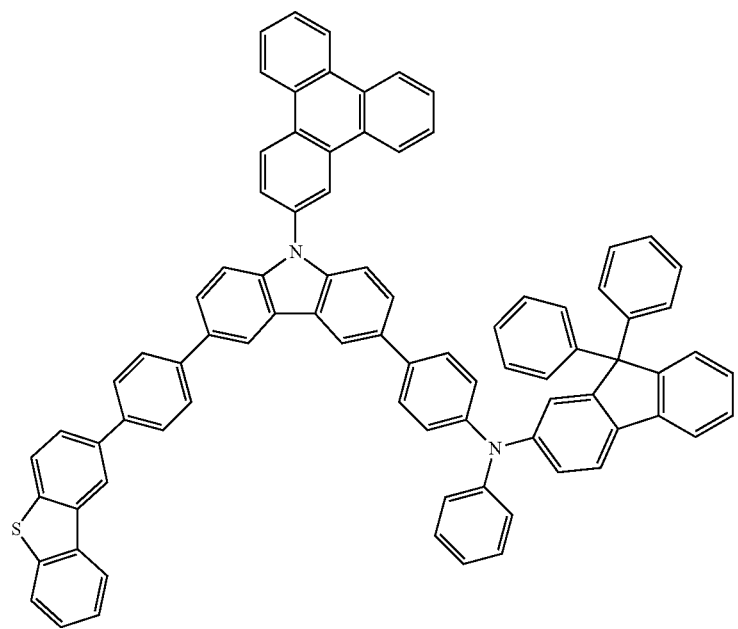
[A-169]

[A-170]
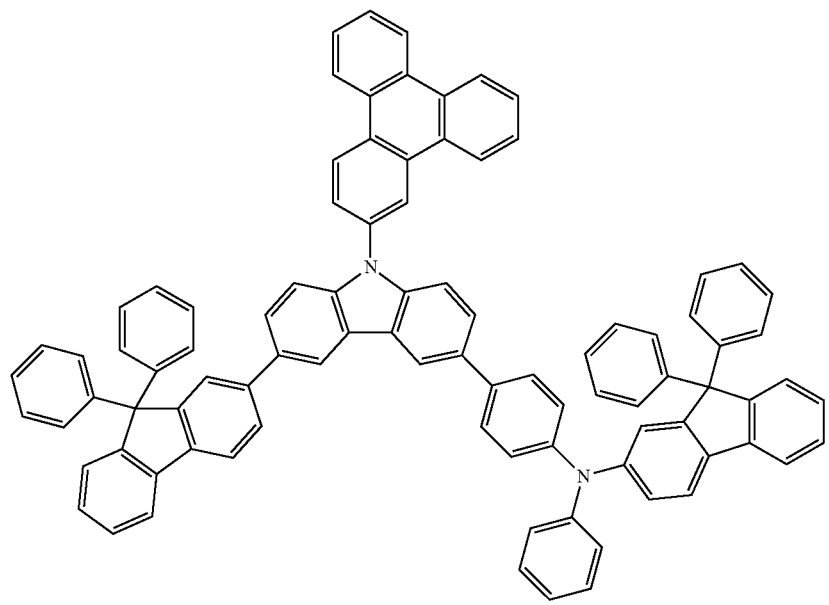
[A-171]
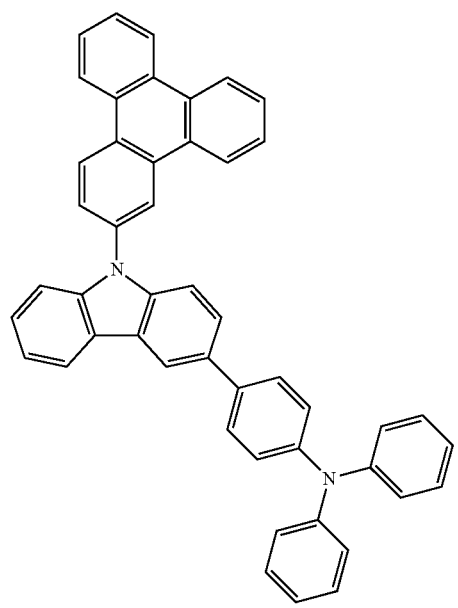
[A-172]
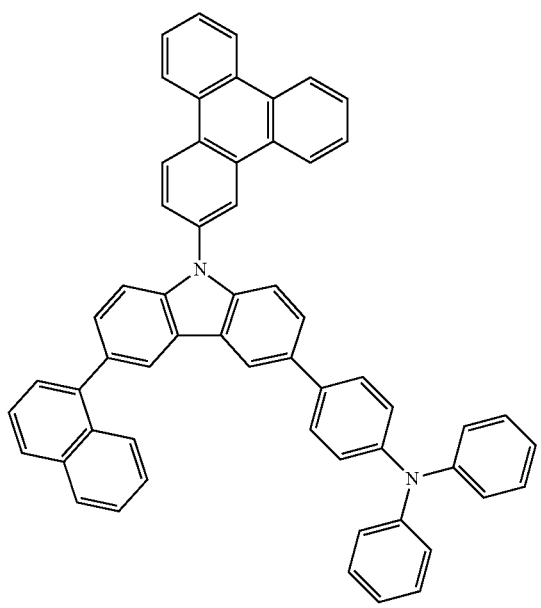

[A-173]
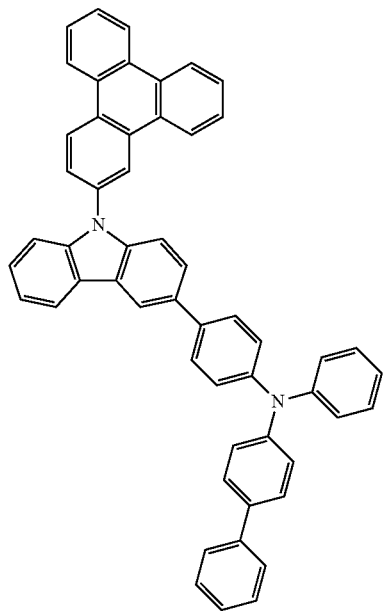
[A-174]
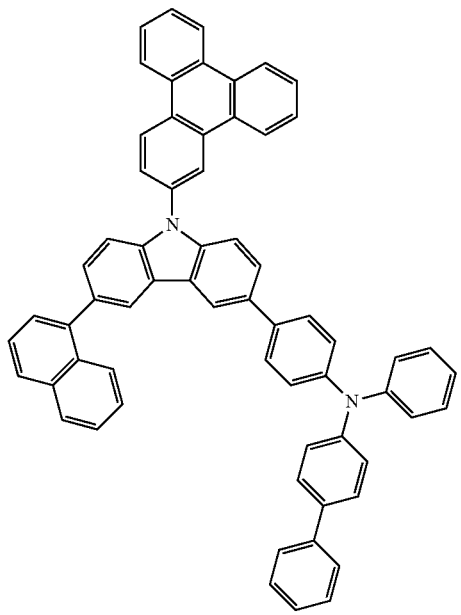
[A-175]
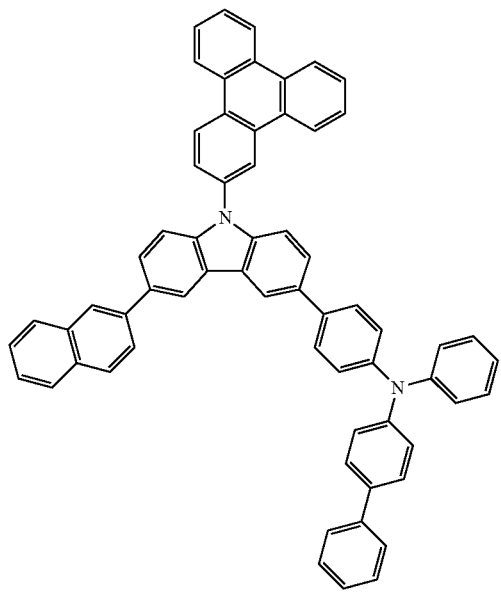
[A-176]
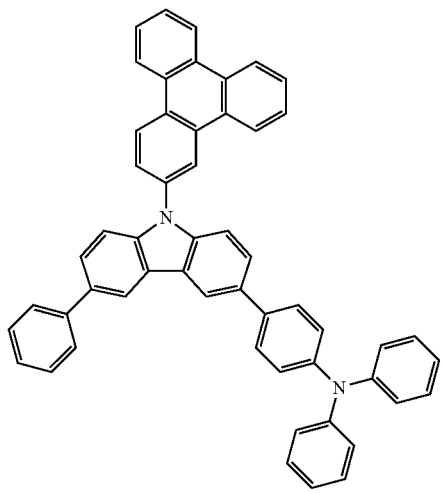

-continued
[A-177]
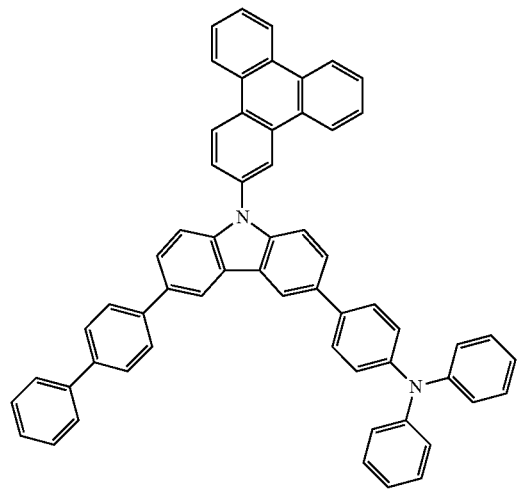
[A-178]
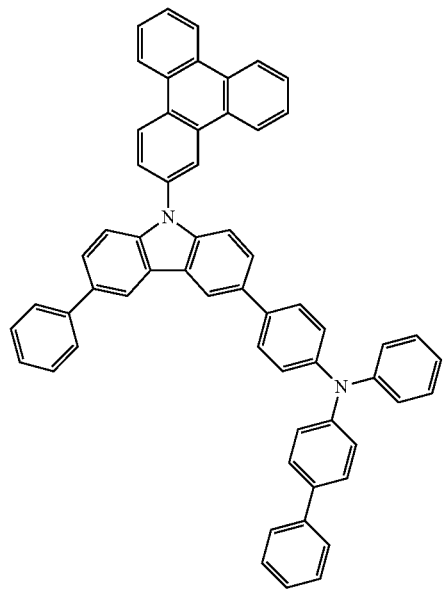
[A-179]
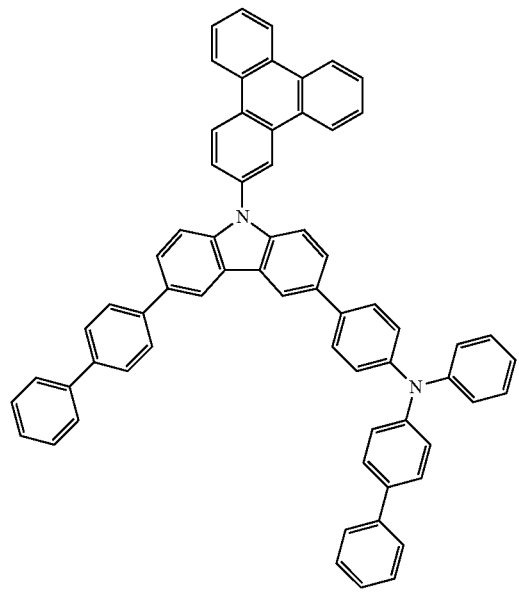
[A-180]
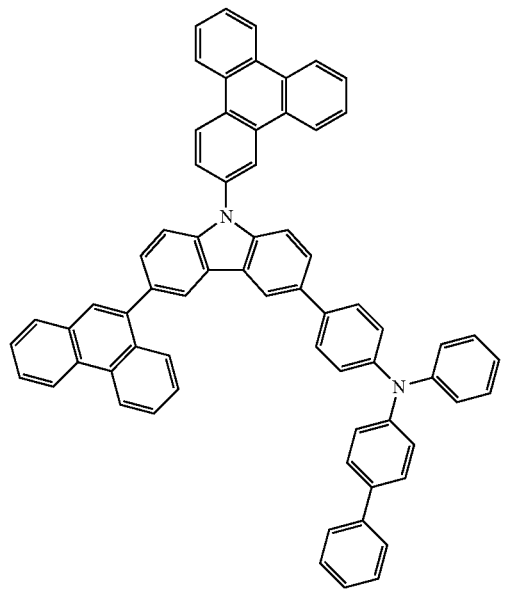

-continued
[A-181]
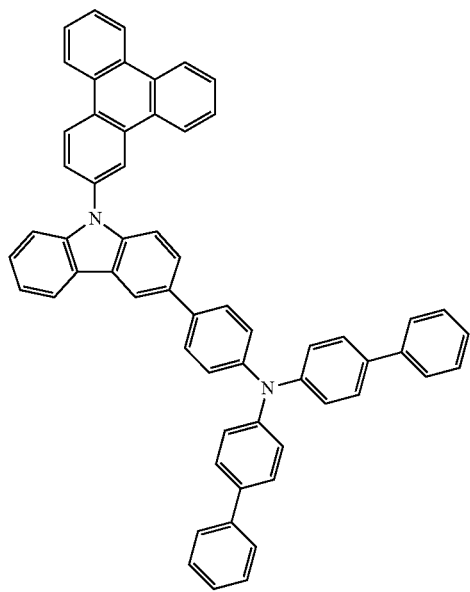
[A-182]
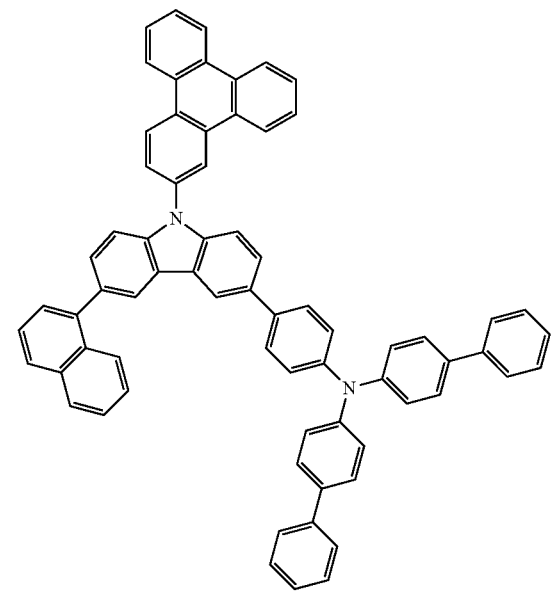
[A-183]
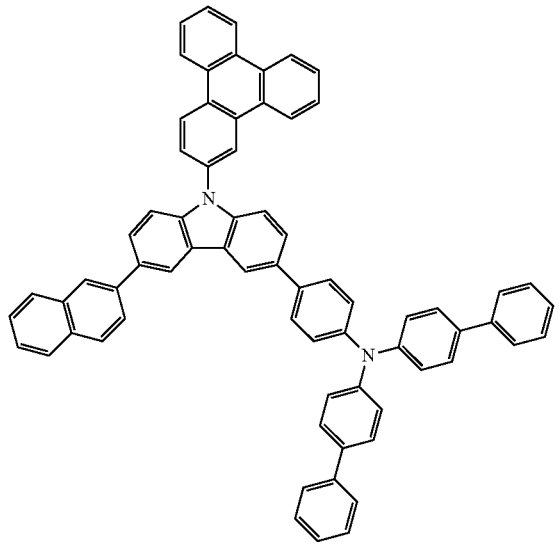
[A-184]
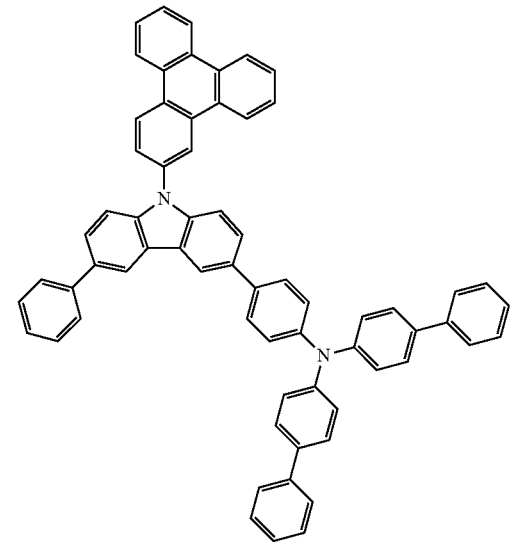

-continued
[A-185]
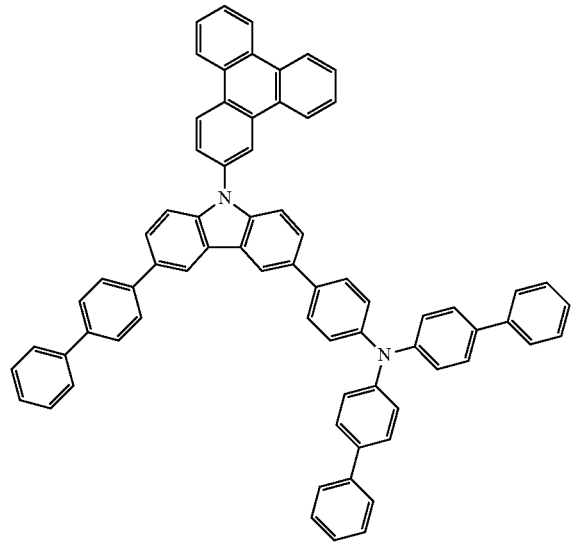
[A-186]
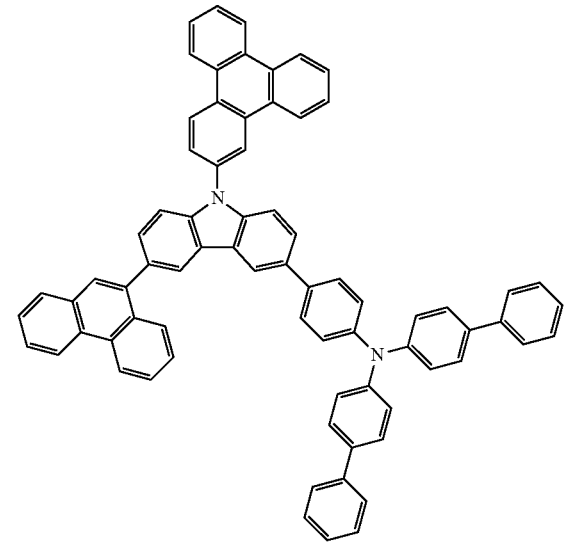
[A-187]
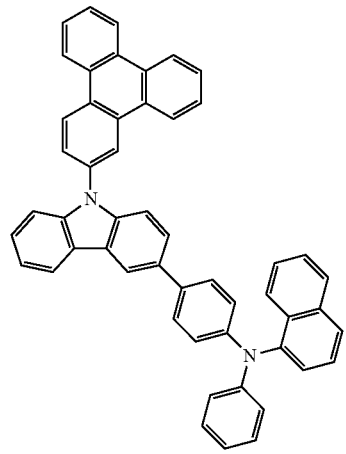
[A-188]
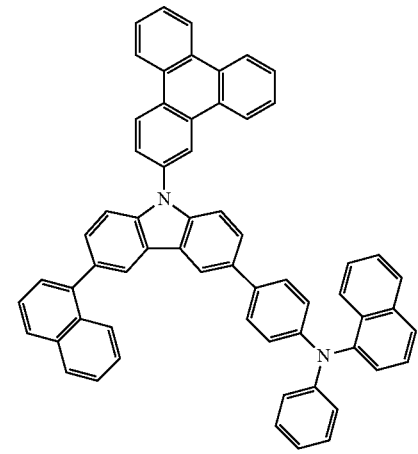
[A-189]
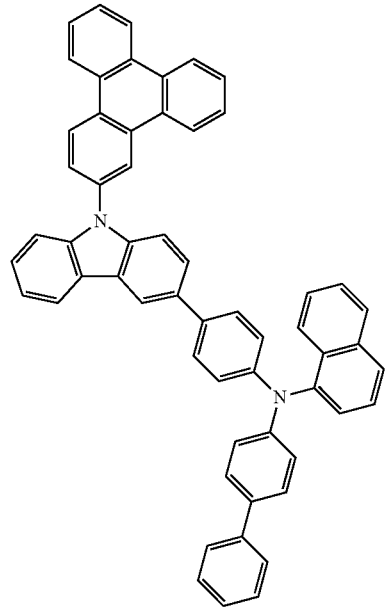
[A-190]
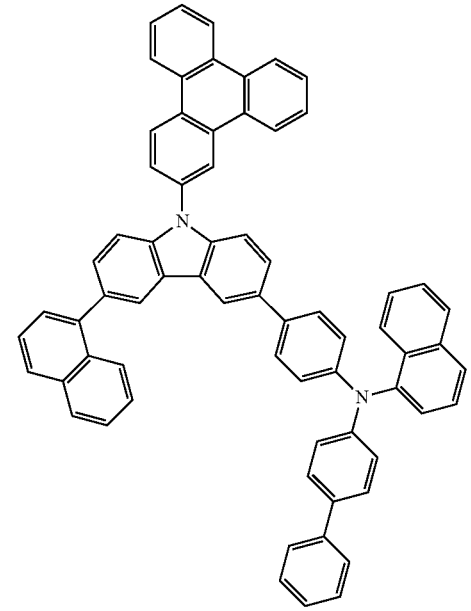

-continued
[A-191]
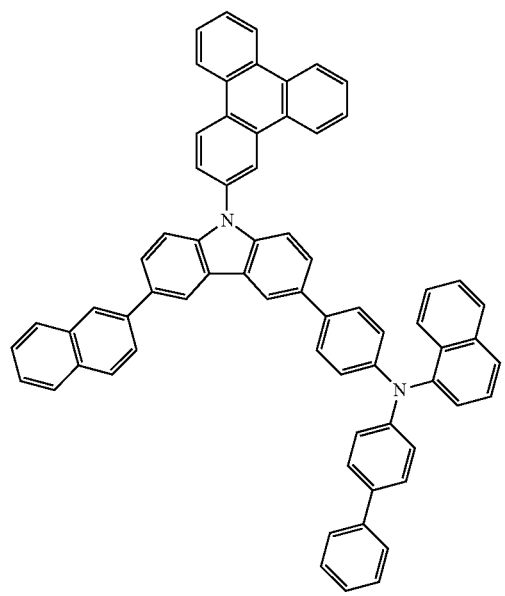
[A-192]
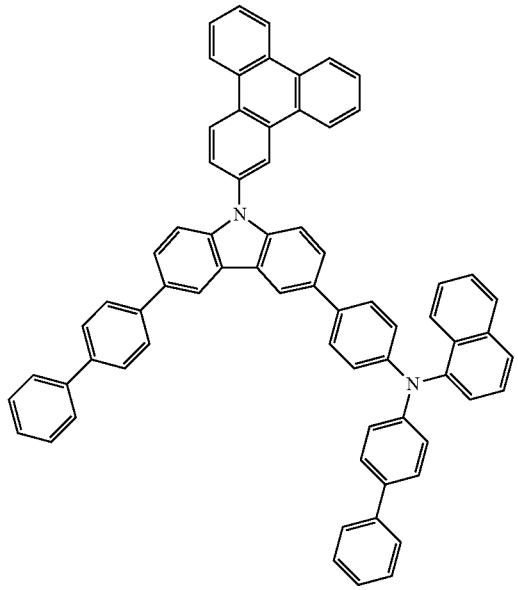
[A-193]
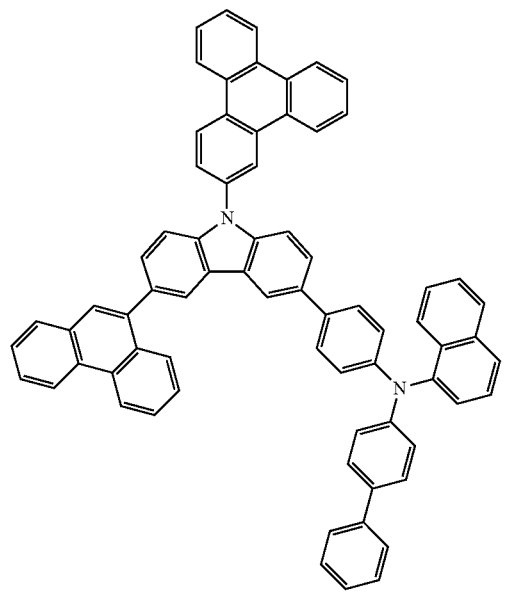
[A-194]
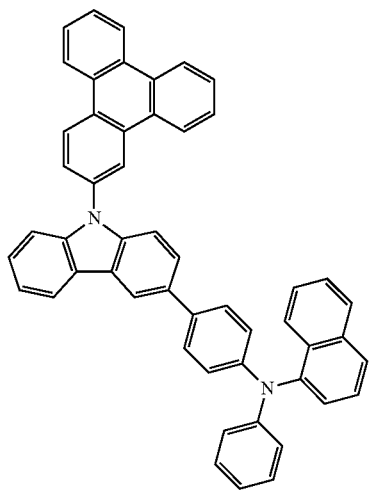

-continued
[A-195]
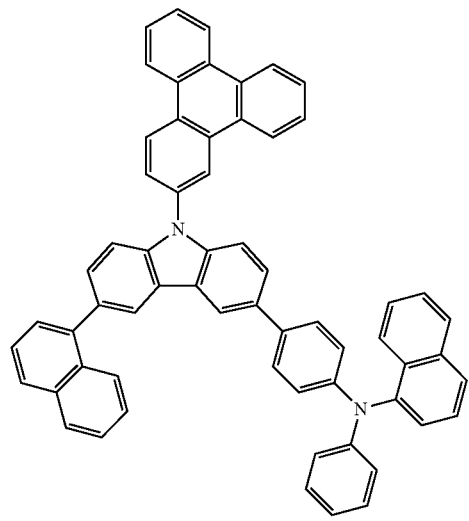
[A-196]
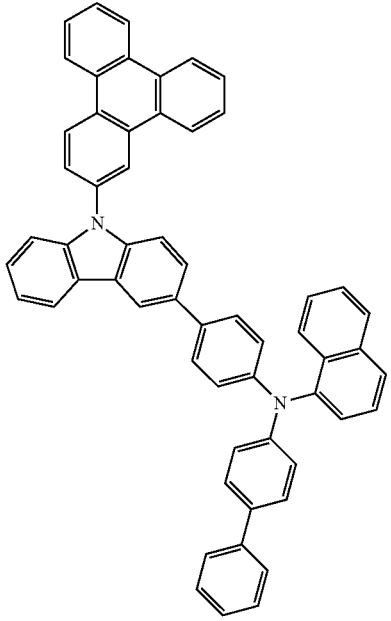
[A-197]
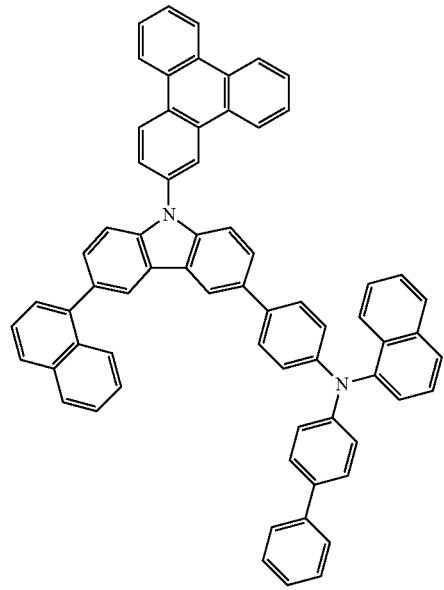
[A-198]
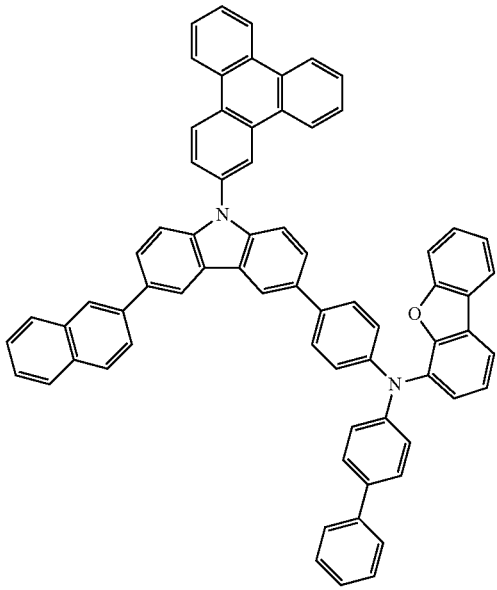

-continued
[A-199]
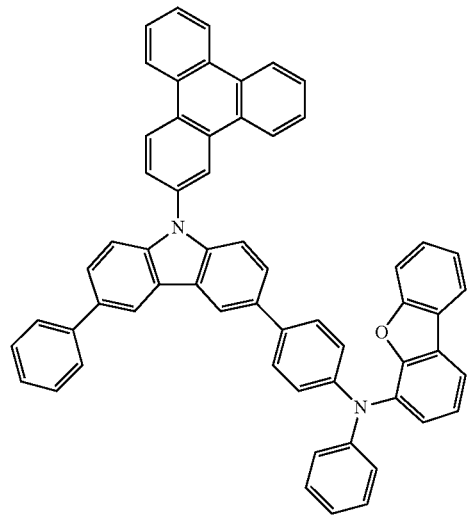
[A-200]
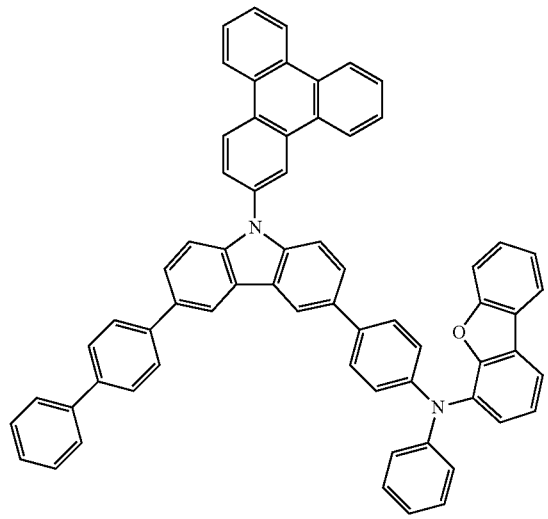
[A-201]
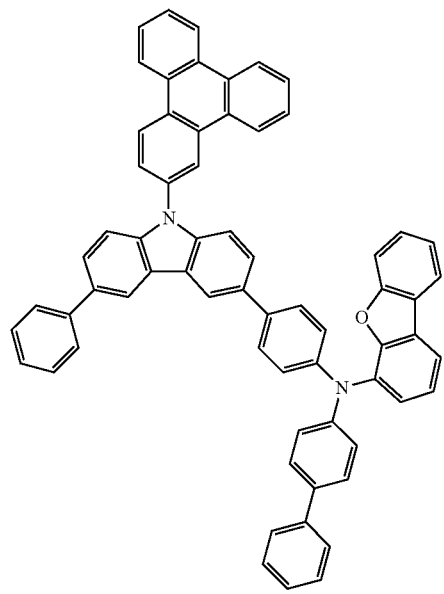
[A-202]
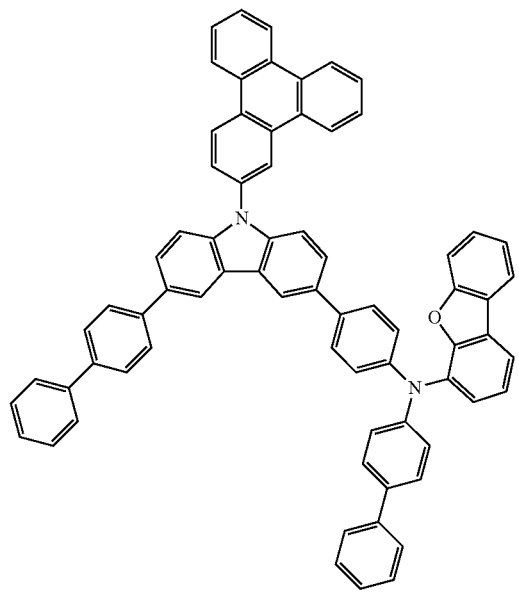

-continued
[A-203]
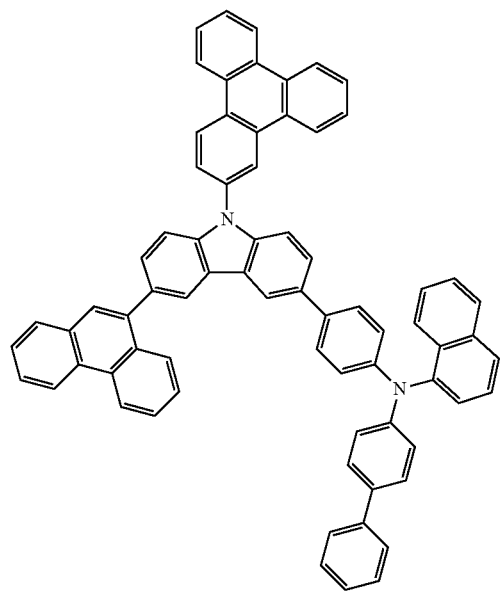
[A-204]
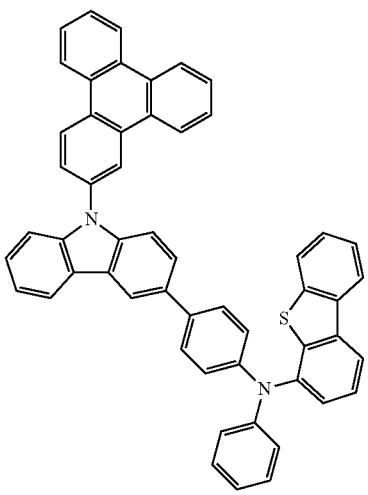
[A-205]
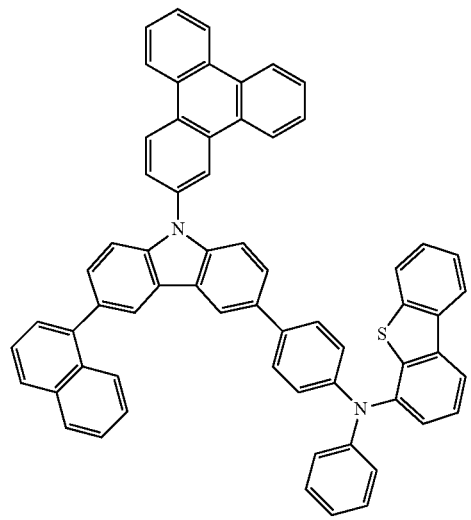
[A-206]
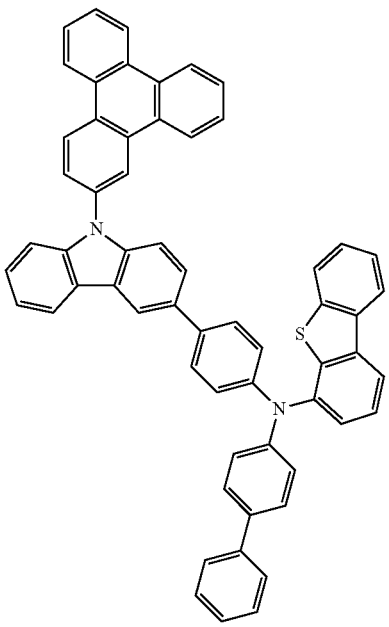

-continued
[A-207]
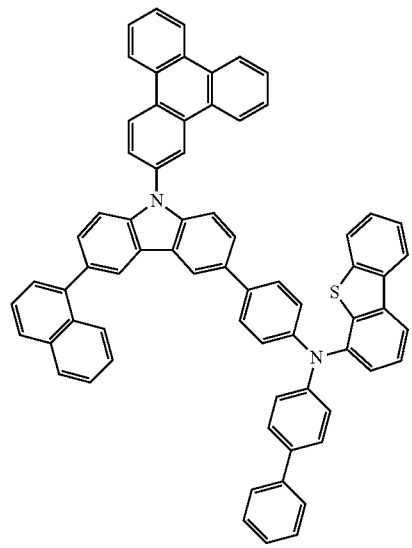
[A-208]
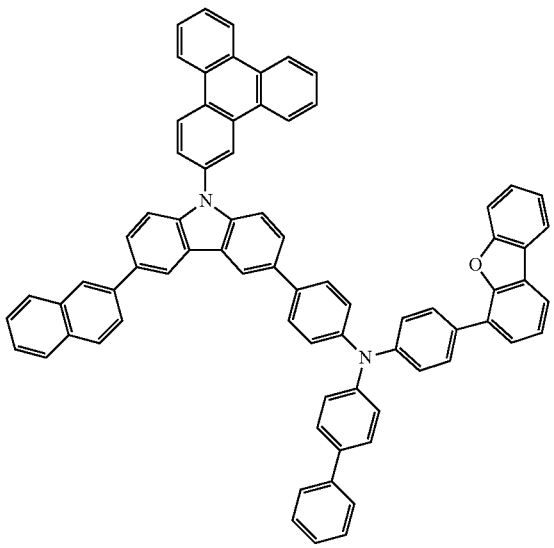
[A-209]
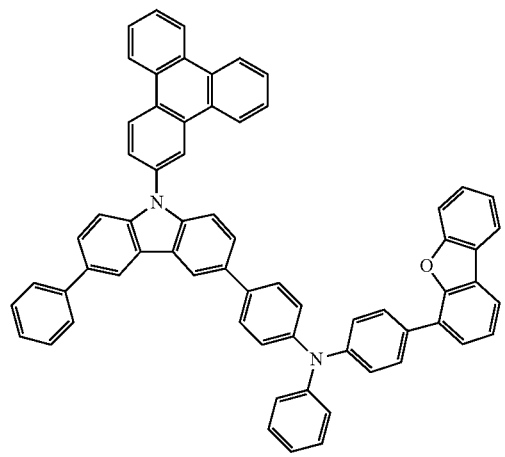
[A-210]
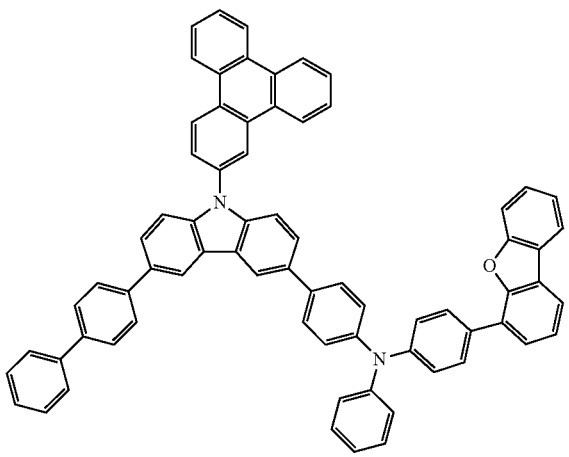
[A-211]
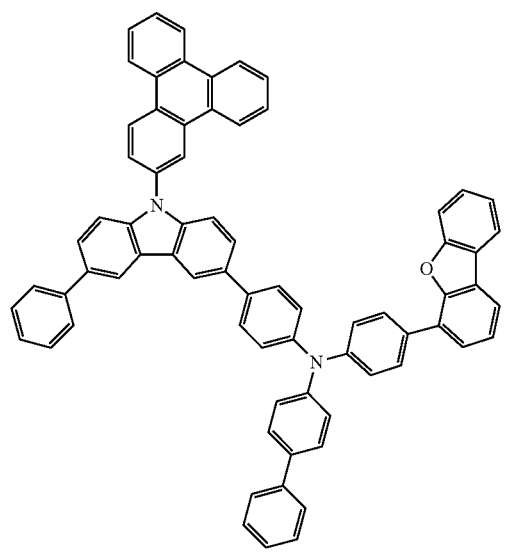
[A-212]
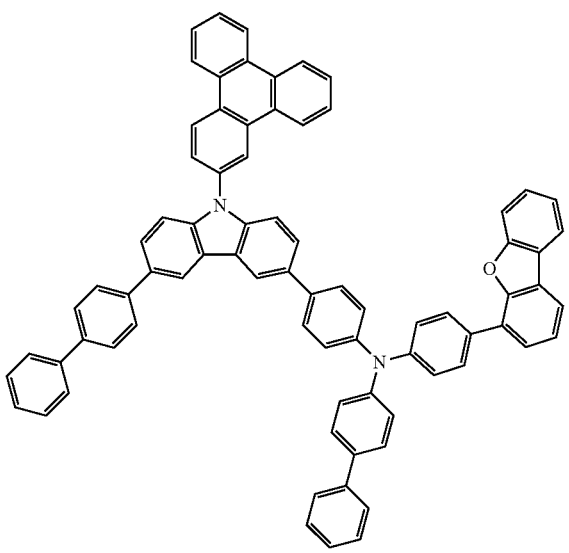

-continued
[A-213]
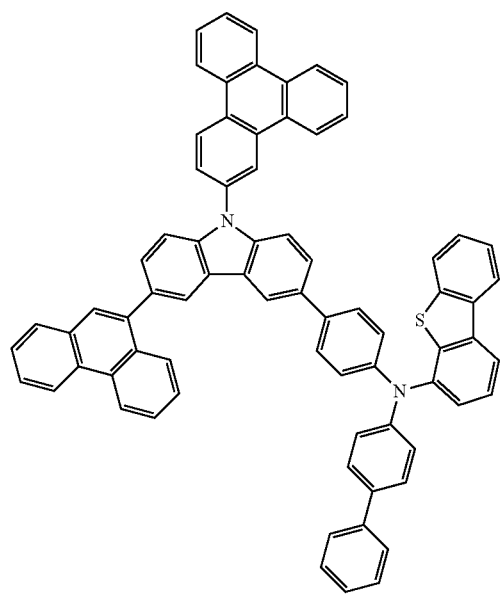
[A-214]
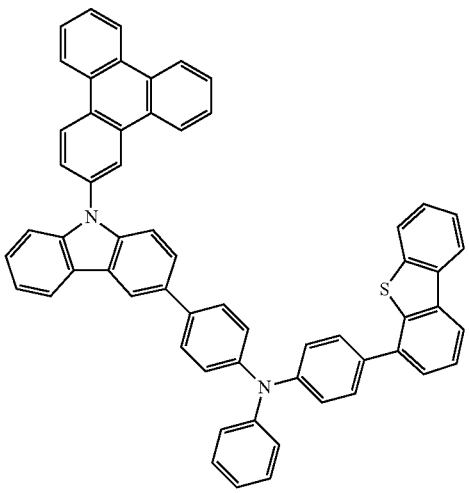
[A-215]
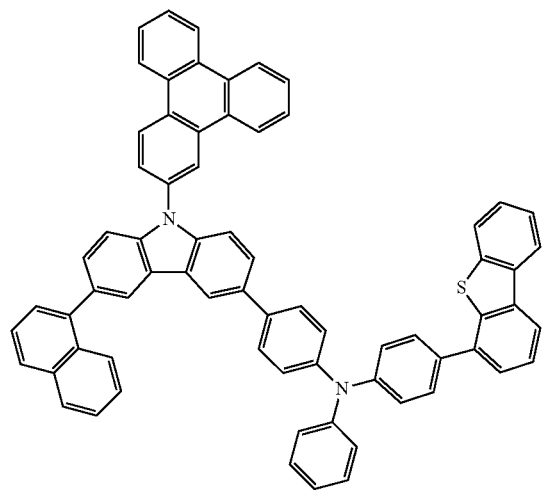
[A-216]
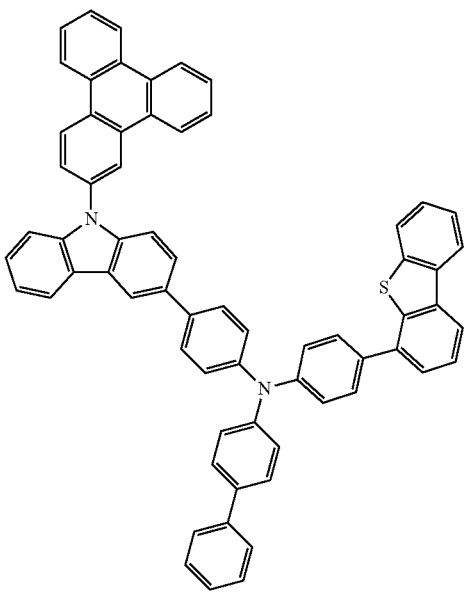

-continued
[A-217]
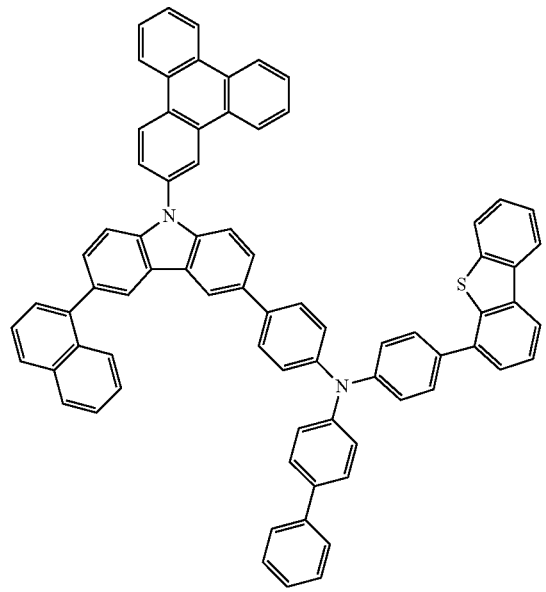
[A-218]
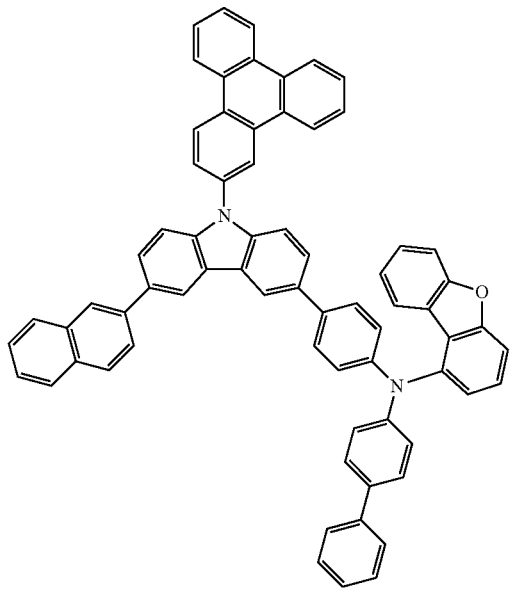
[A-219]
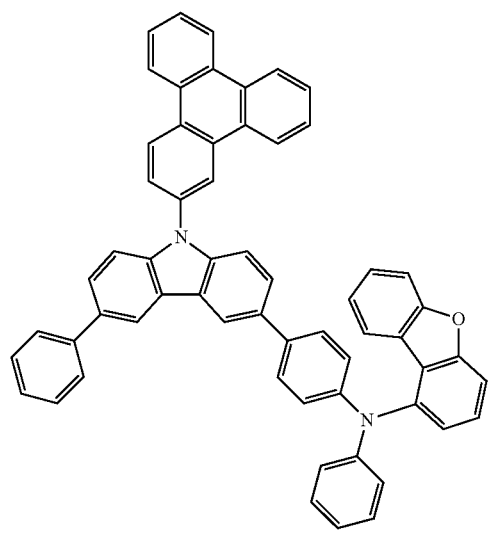
[A-220]
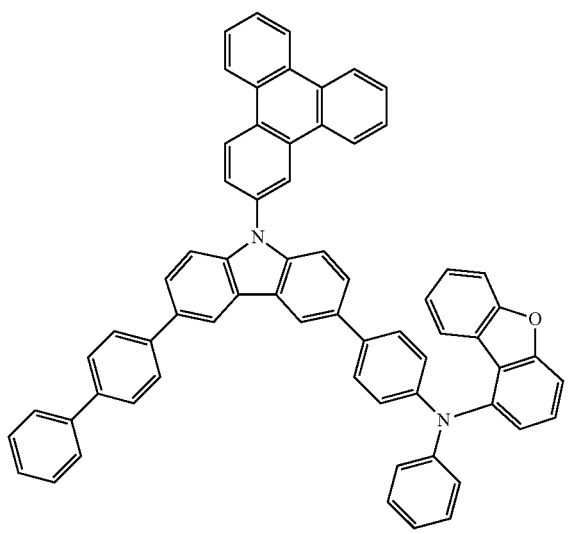

[A-221]
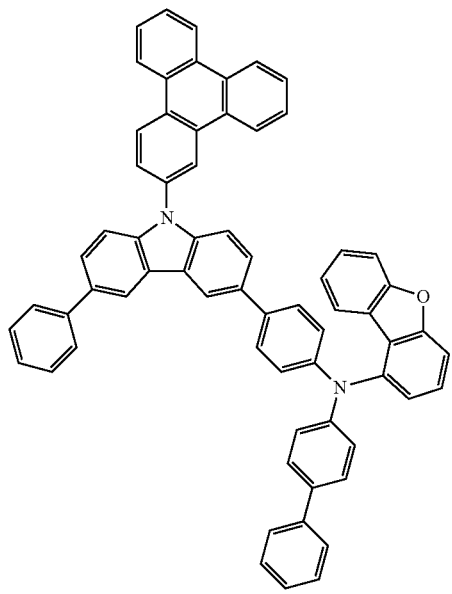
[A-222]
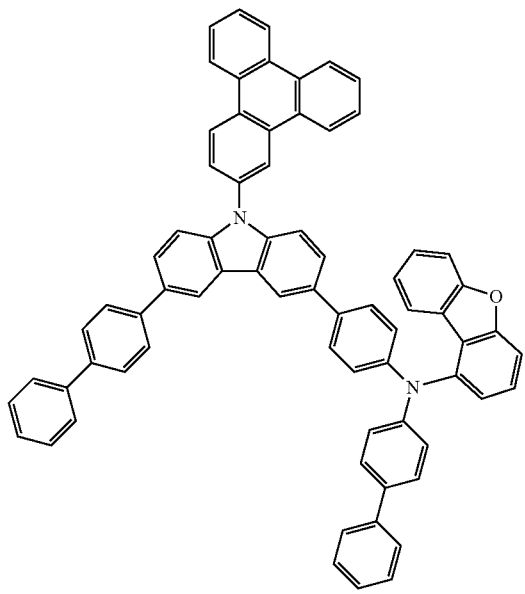
[A-223]
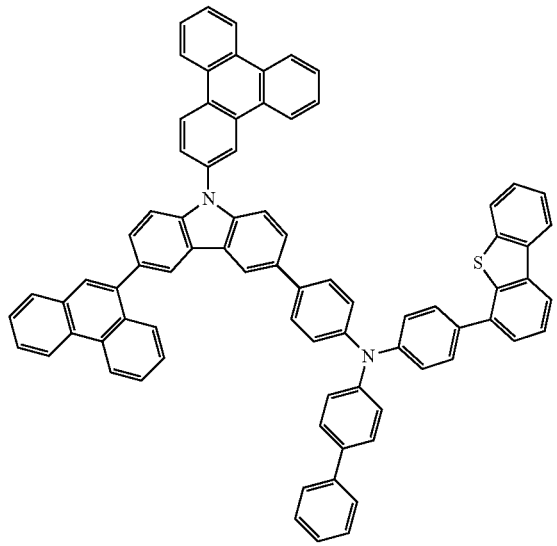
[A-224]
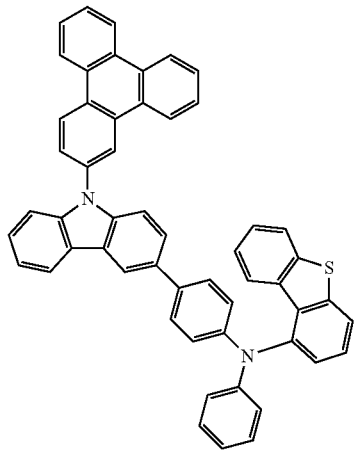

-continued
[A-225]
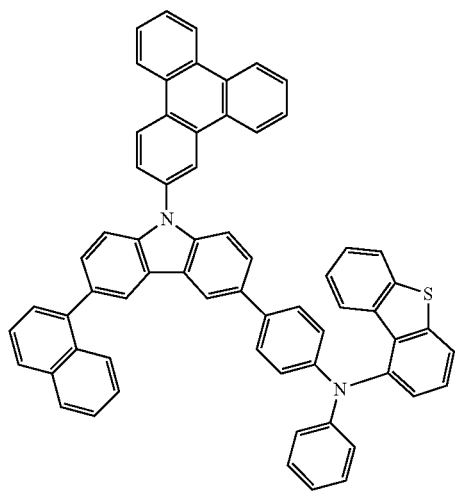
[A-226]
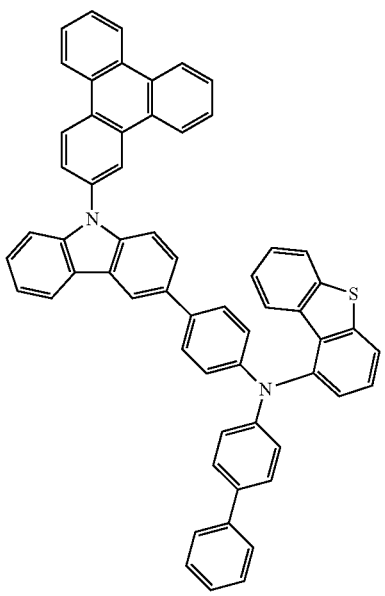
[A-227]
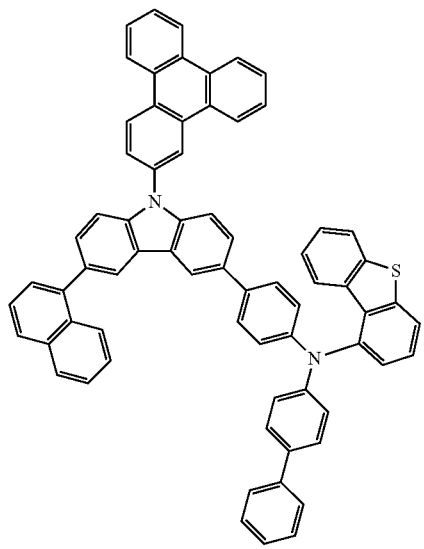
[A-228]
[A-229]
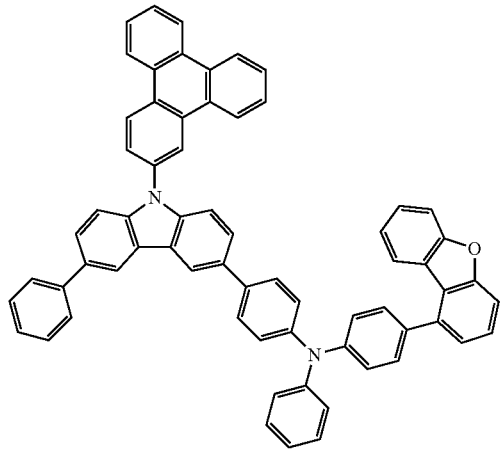
[A-230]
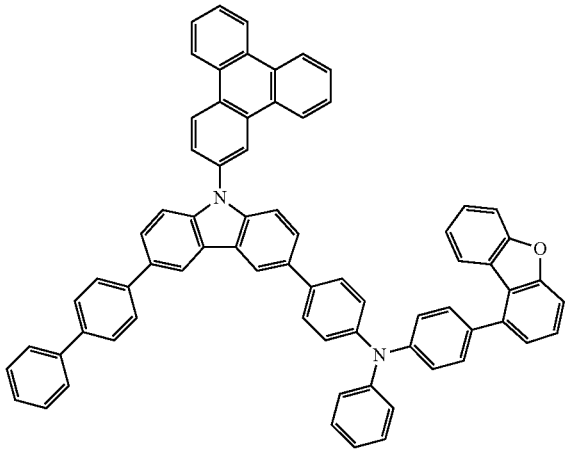

-continued
[A-231]
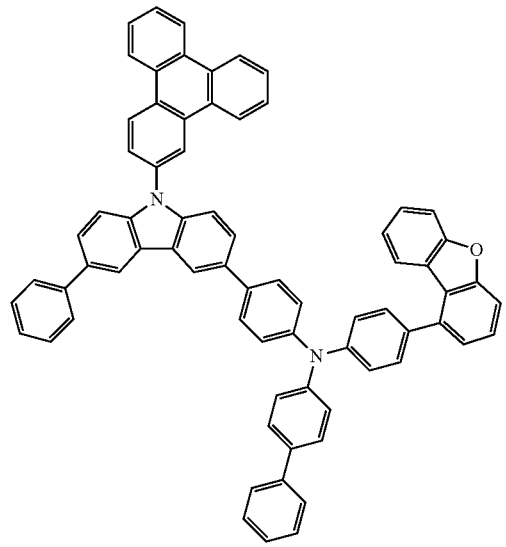
[A-232]
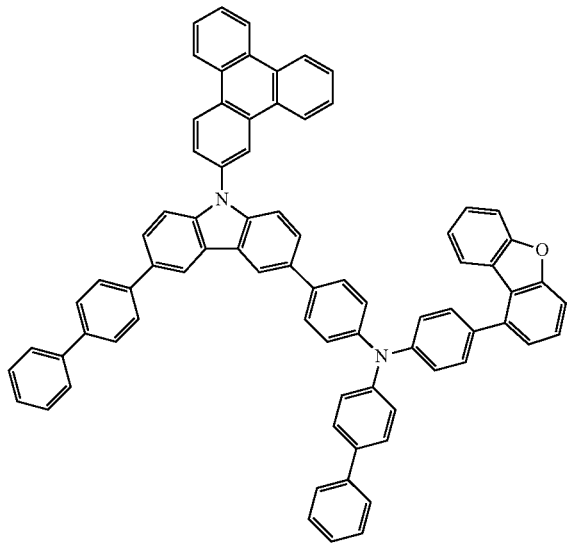
[A-233]
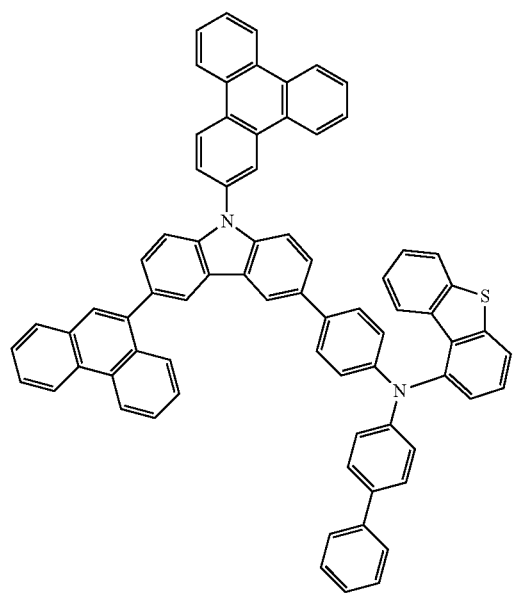
[A-234]
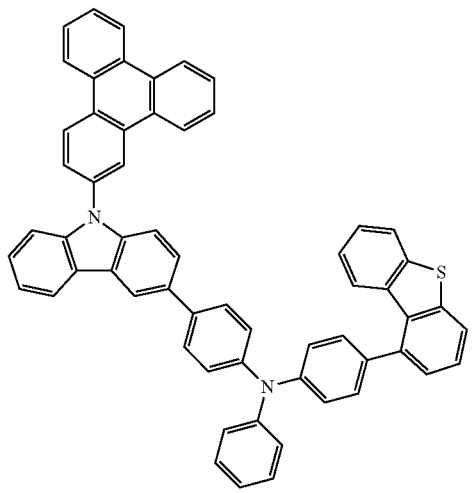

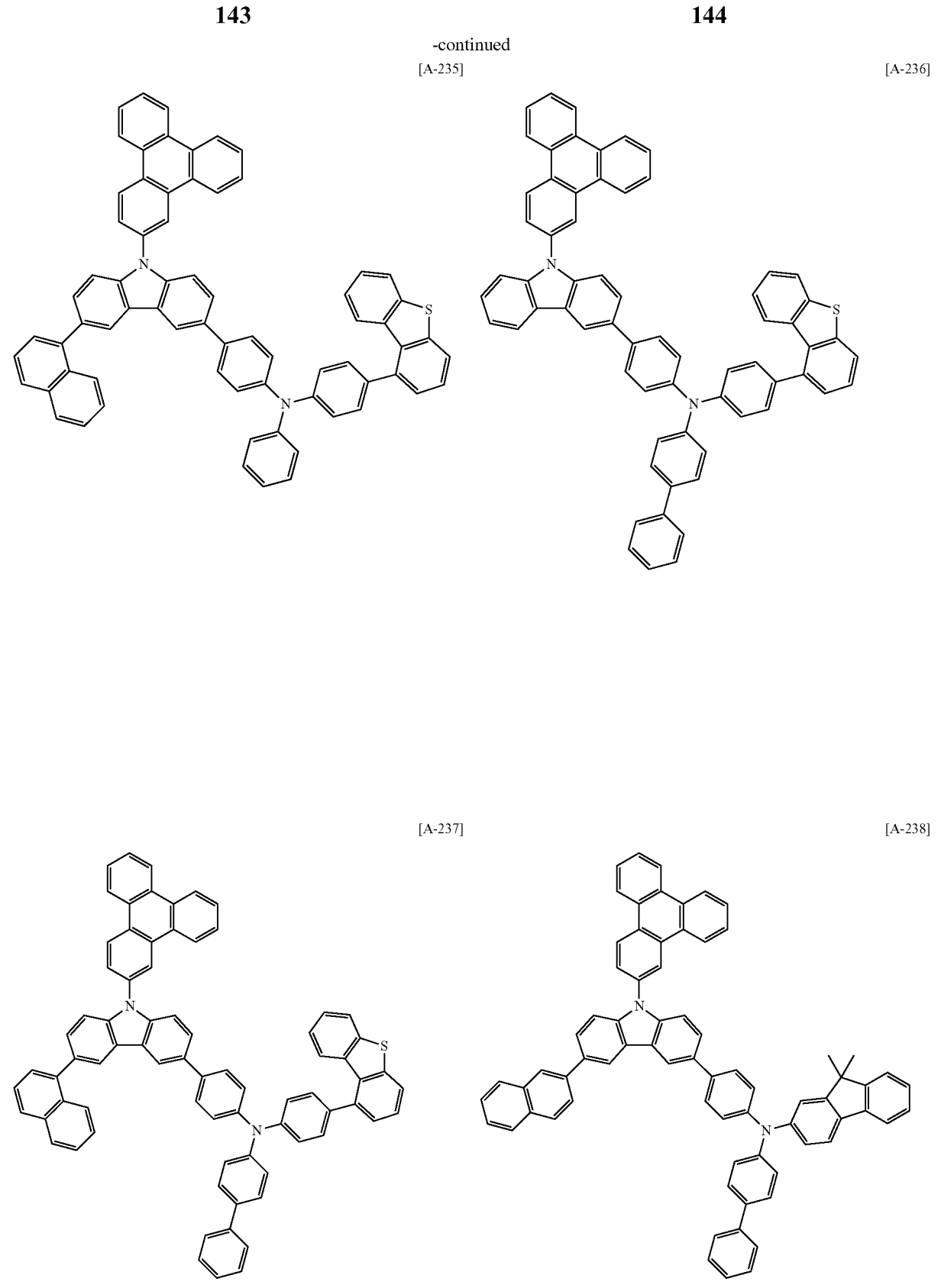

-continued

[A-235]

[A-236]

[A-237]

[A-238]

-continued
[A-239]
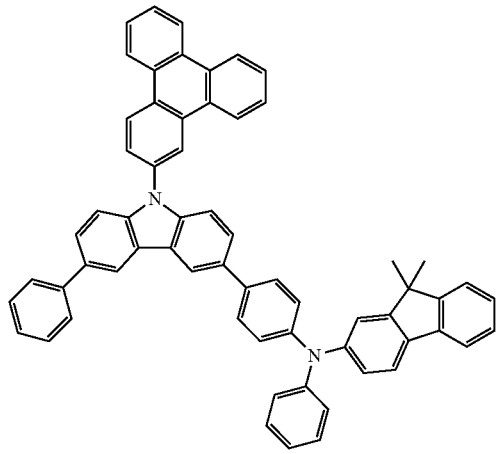
[A-240]
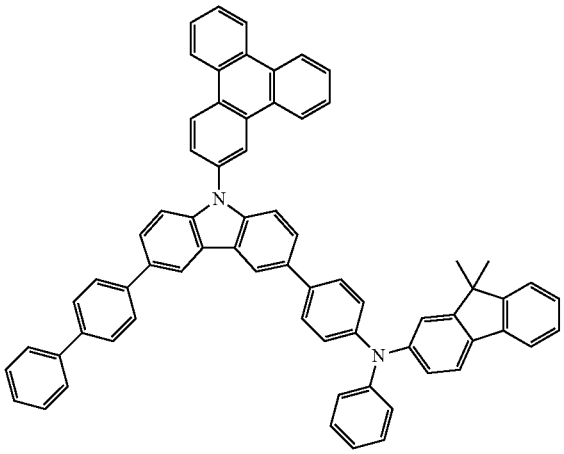
[A-241]
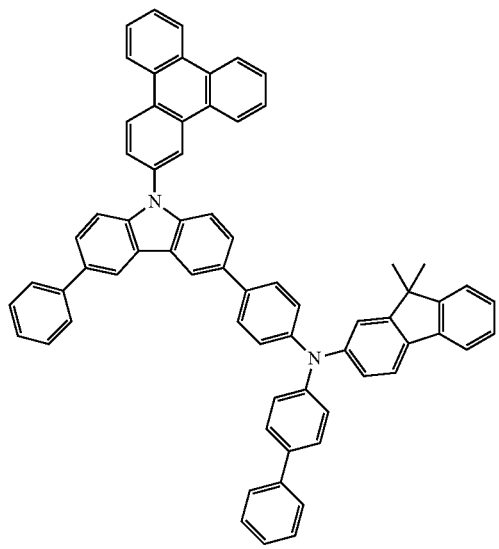
[A-242]
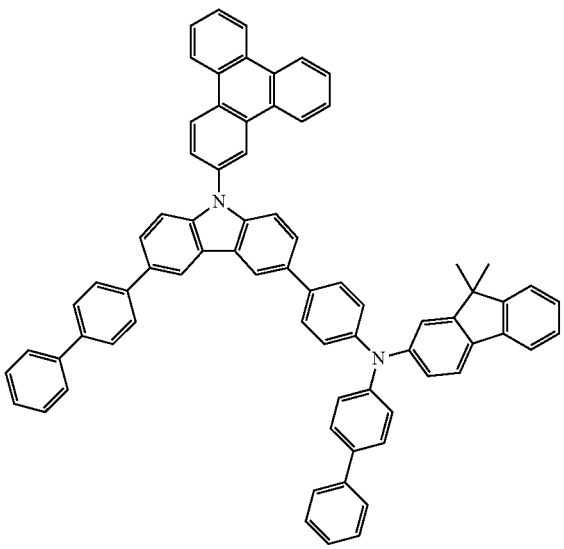
[A-243]
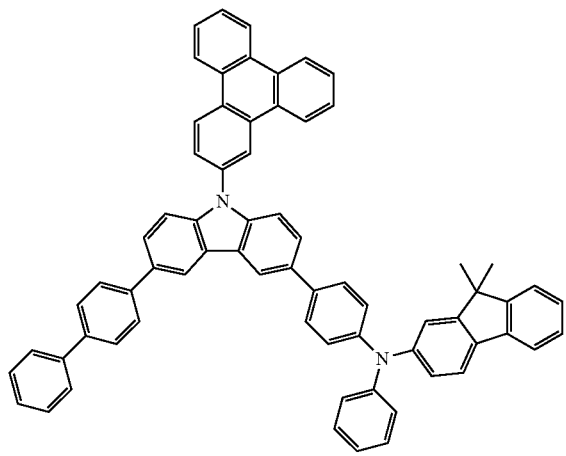
[A-244]
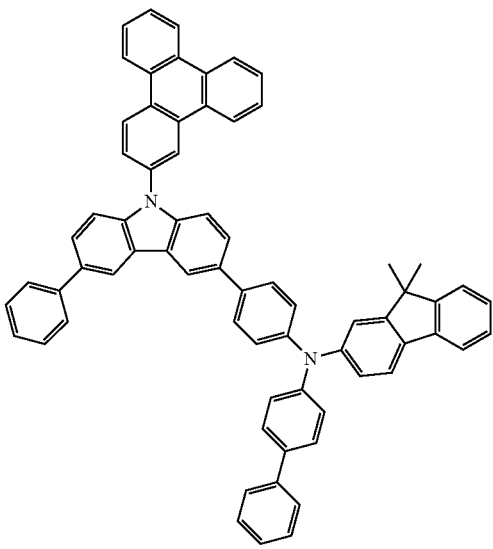

[A-245]
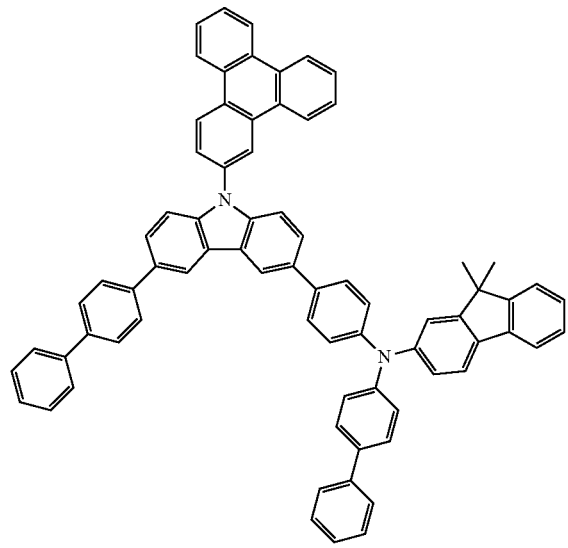
[A-246]
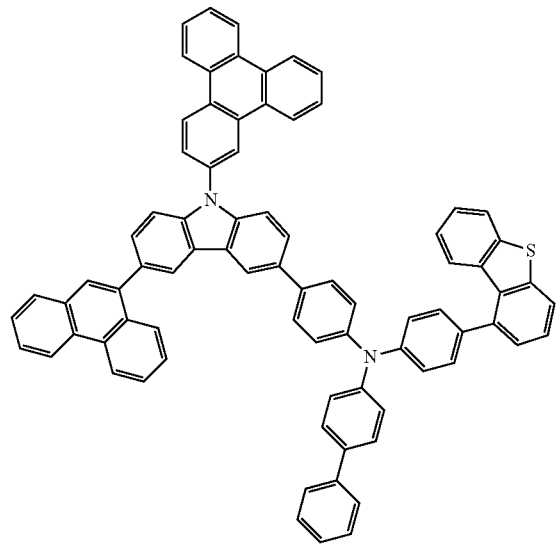
[A-247]
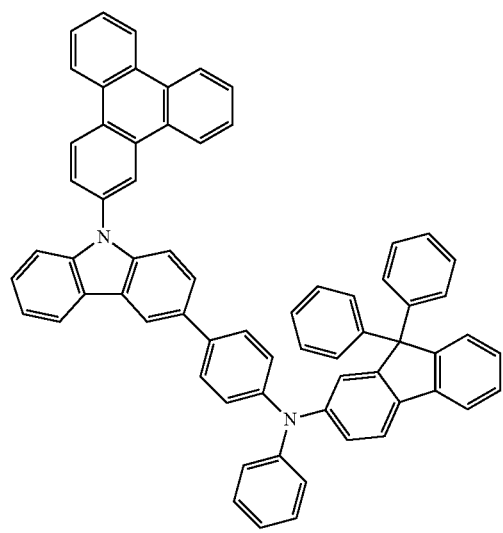
[A-248]
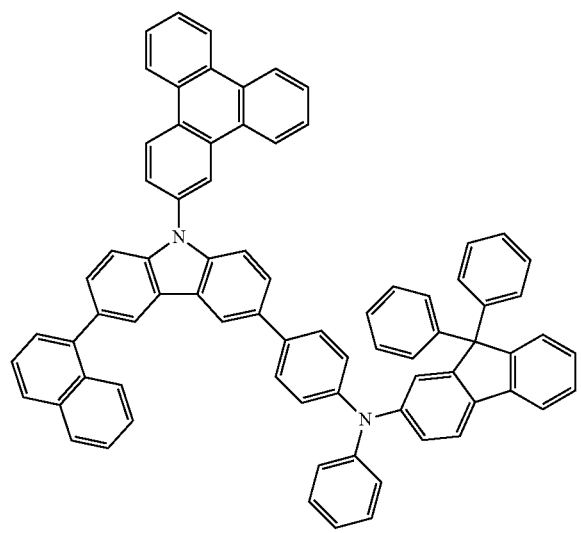

[A-249]
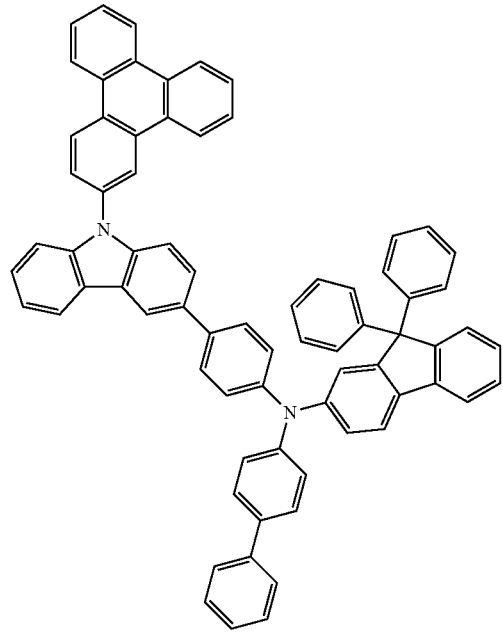
[A-250]
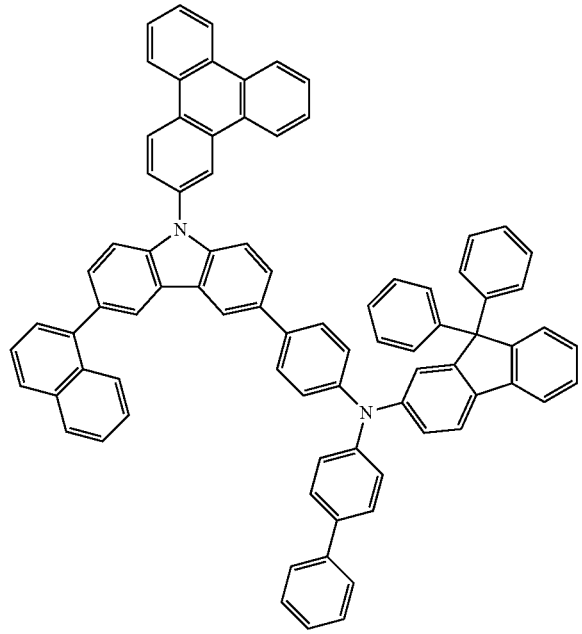
[A-251]
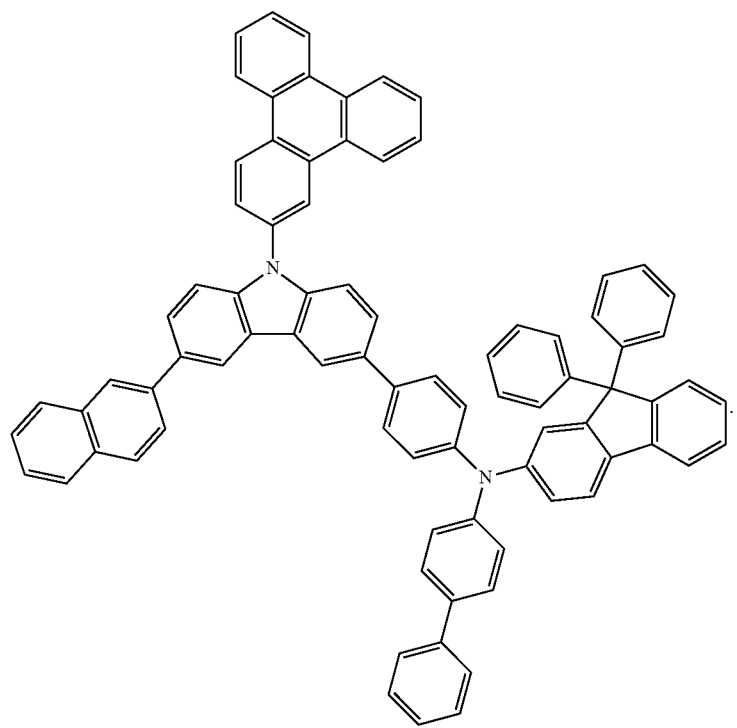

Embodiments are also directed to a compound for an organic photoelectric device, the compound being represented by one of the following Chemical Formulae 6 to 18 or A-252 to A-336
[A-252]
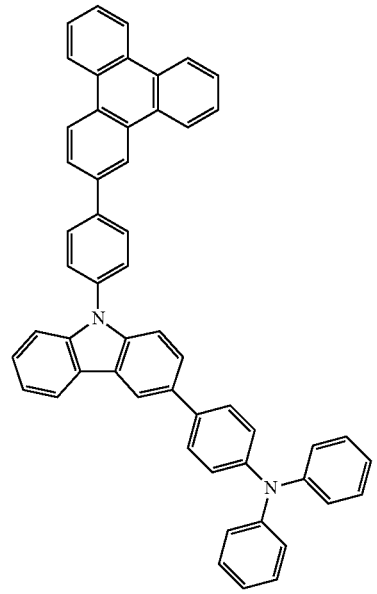
[A-253]
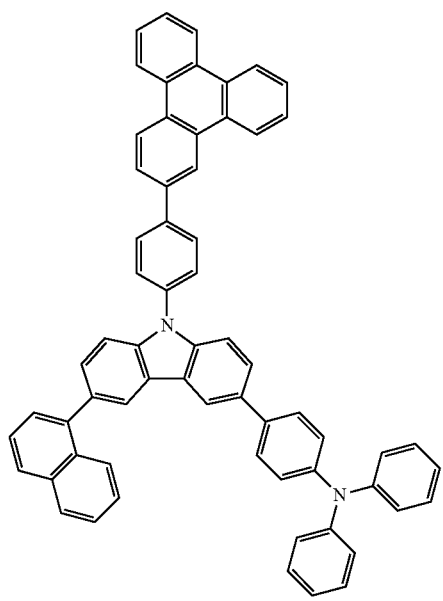
[A-254]
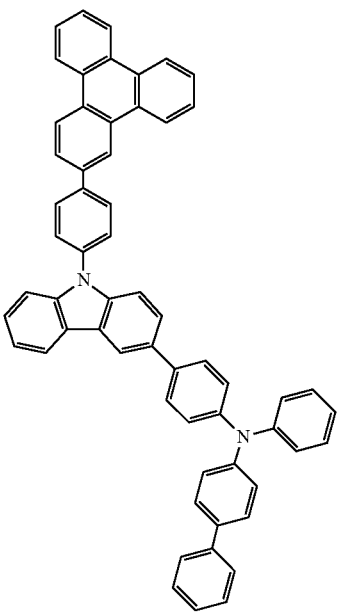
[A-255]
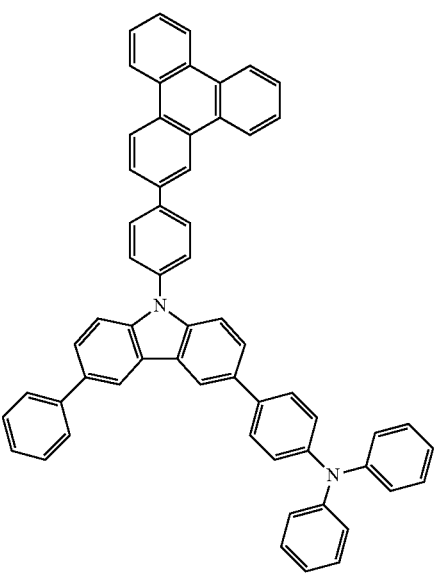

[A-256]
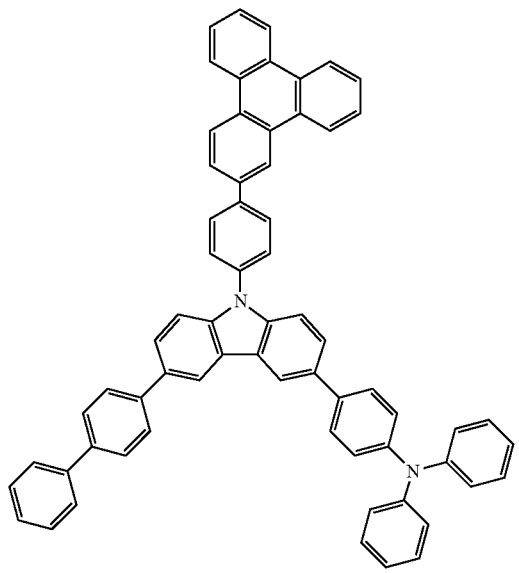
[A-258]
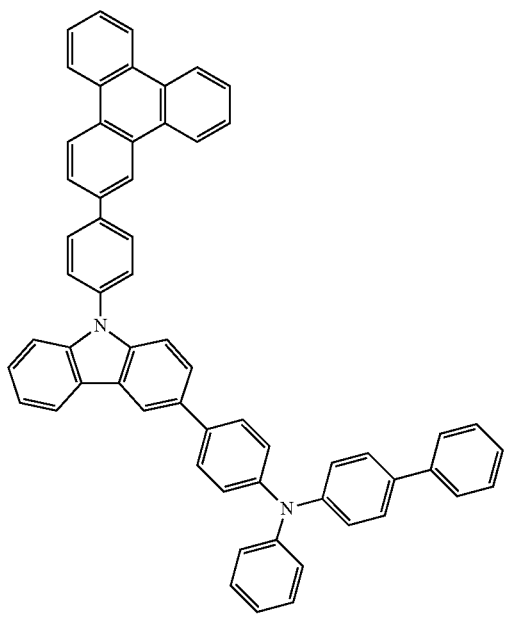
[A-257]
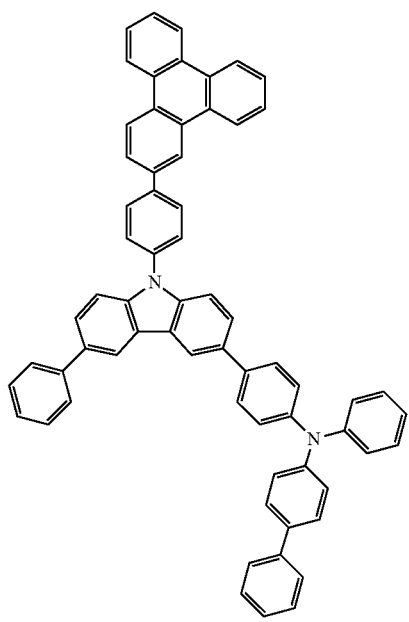
[A-259]
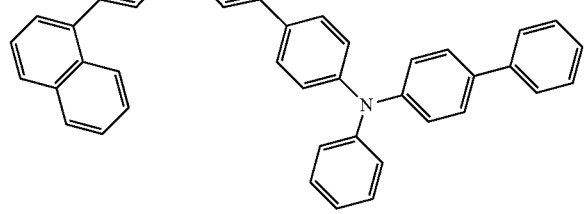

[A-260]
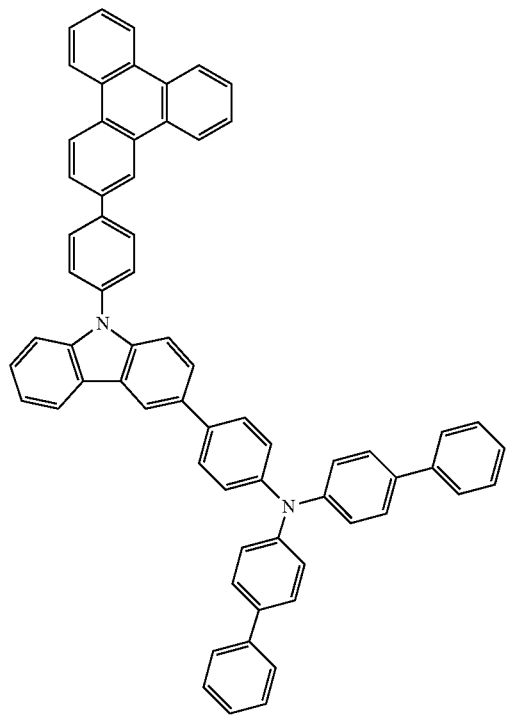
[A-262]
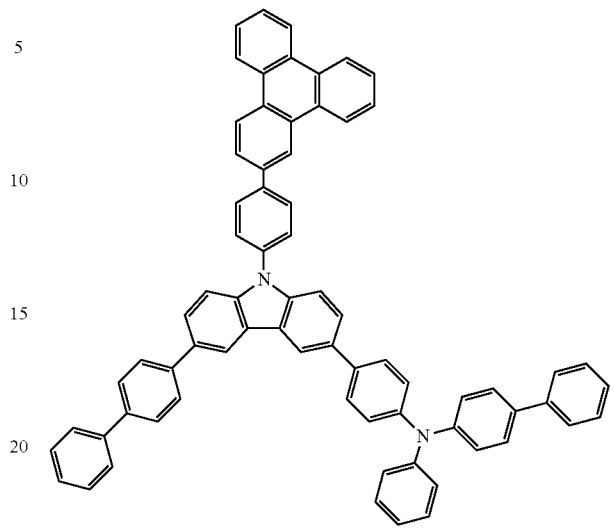
[A-261]
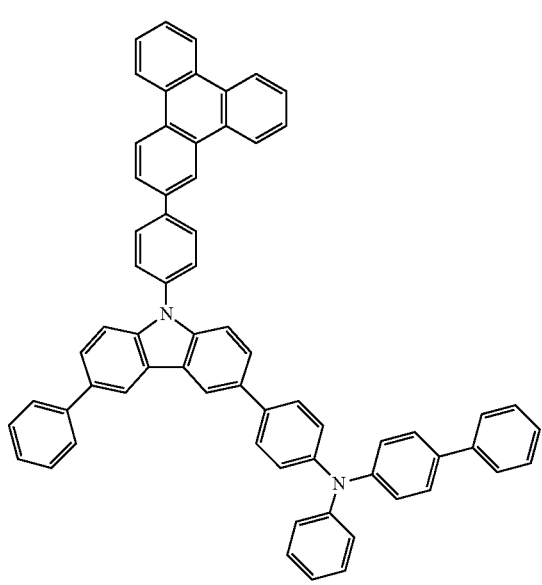
[A-263]
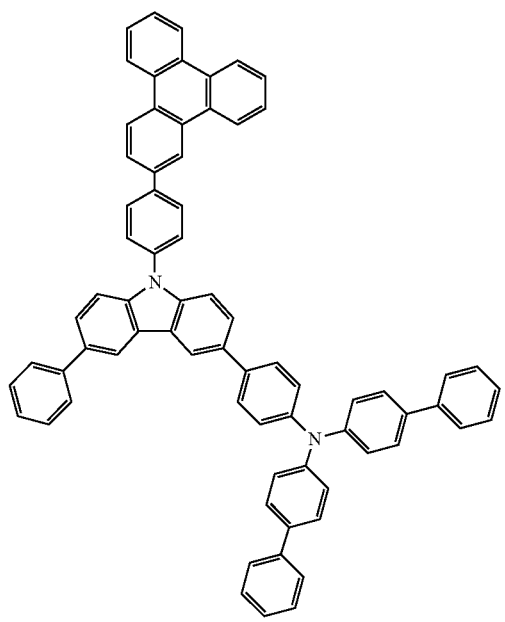

[A-264]
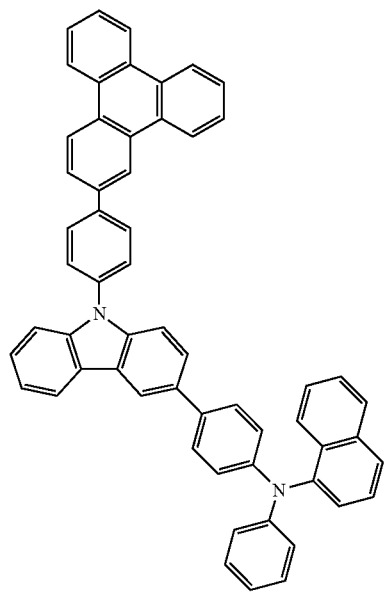
[A-266]
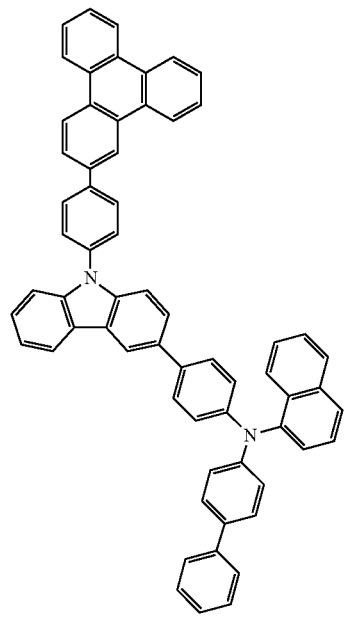
[A-265]
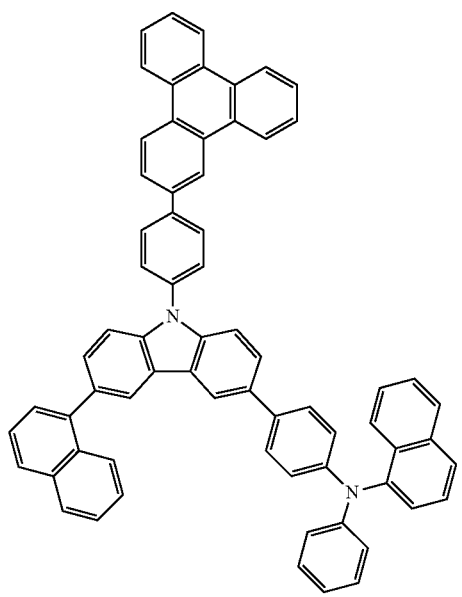
[A-267]
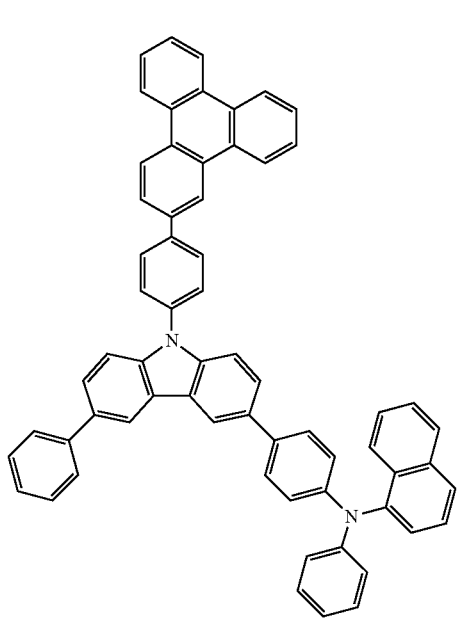

[A-268]
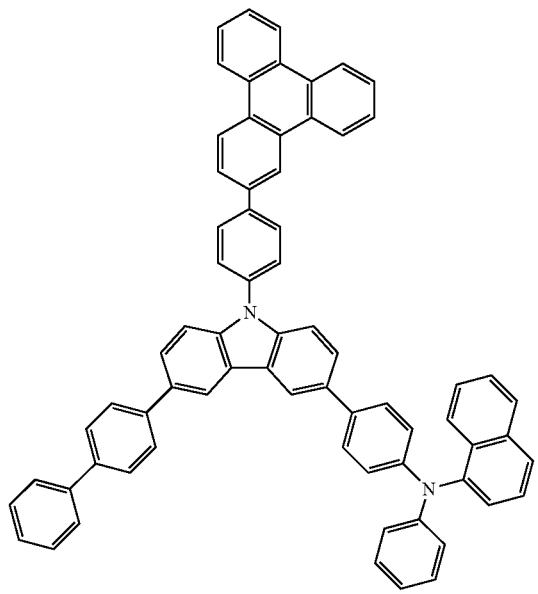
[A-270]
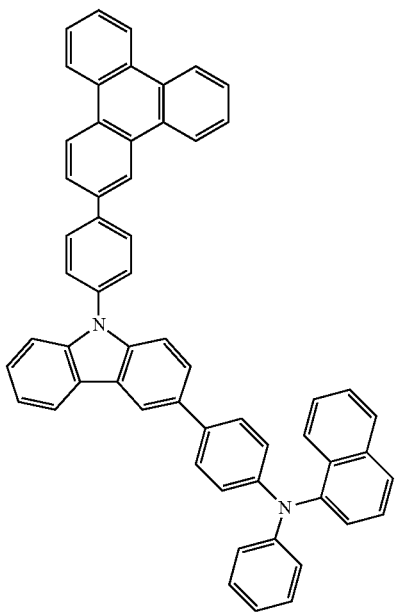
[A-269]
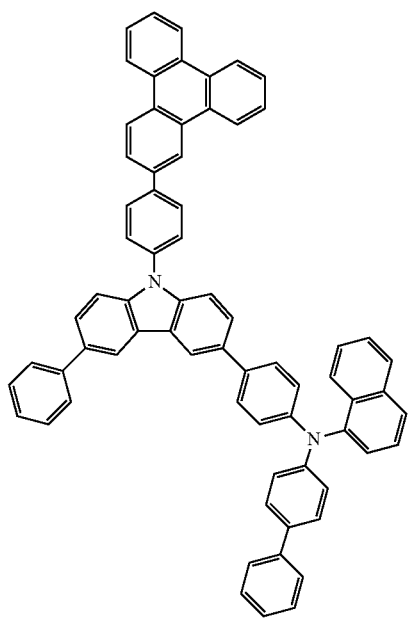
[A-271]
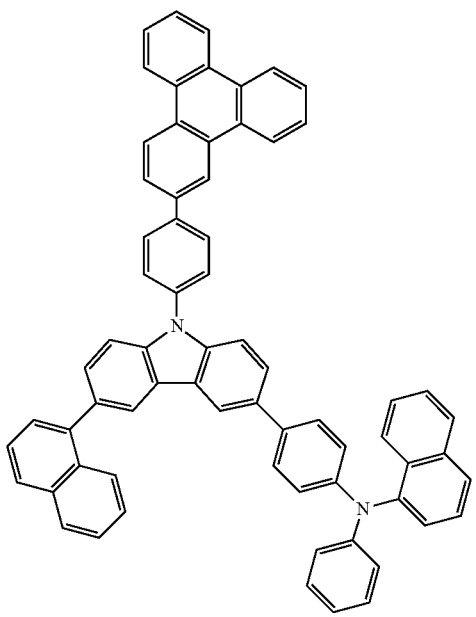

[A-272]
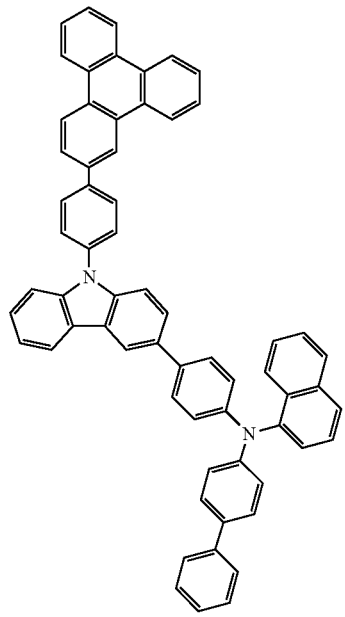
[A-274]
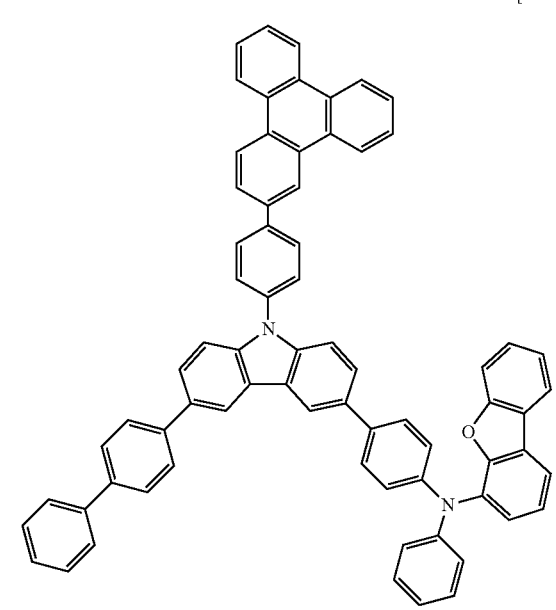
[A-273]
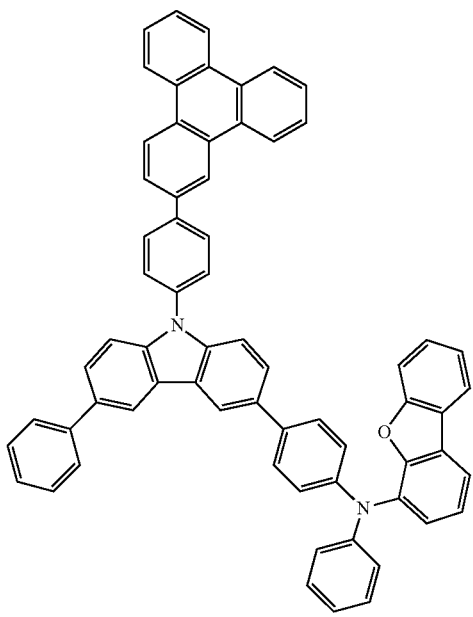
[A-275]
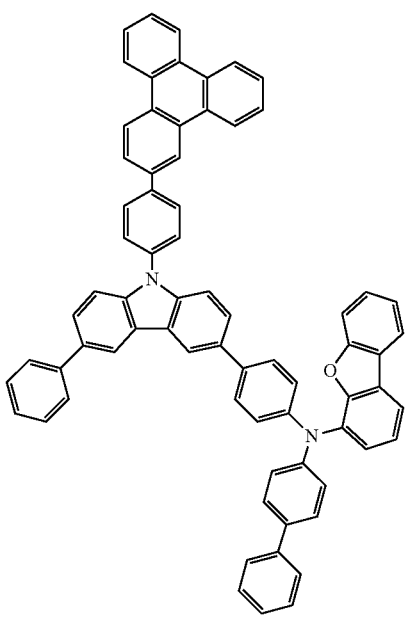

[A-276]
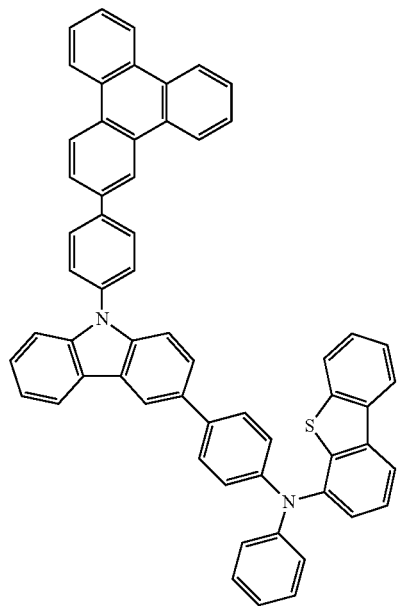
[A-278]
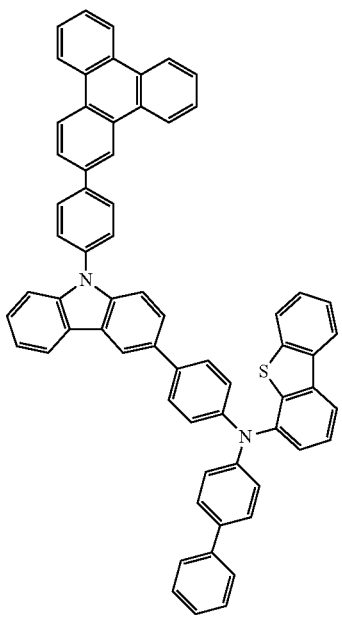
[A-277]
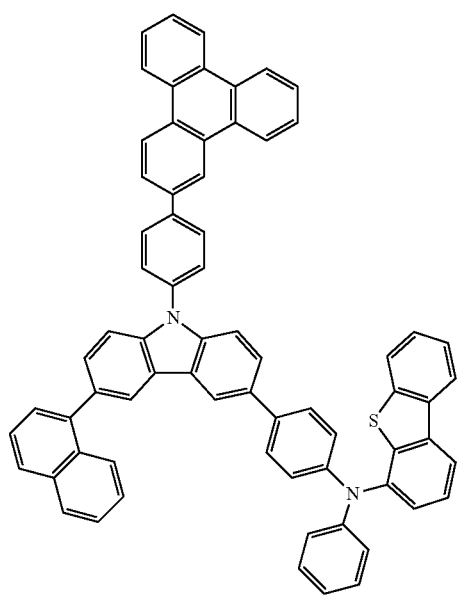
[A-279]
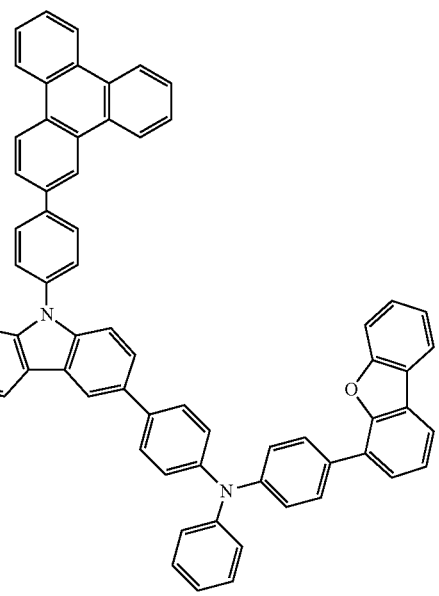

[A-280]
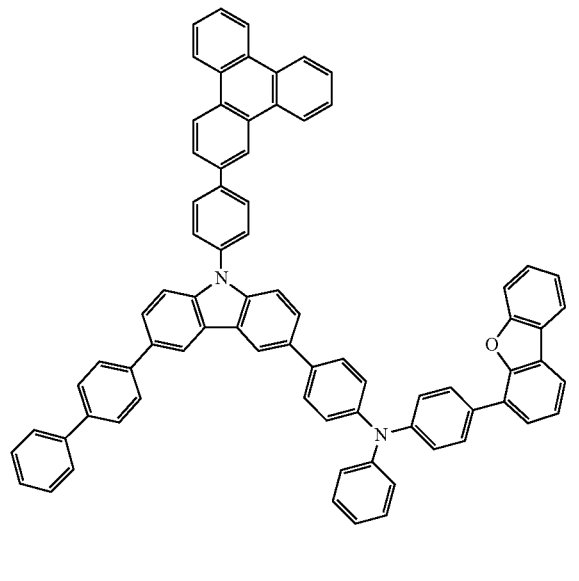
[A-281]
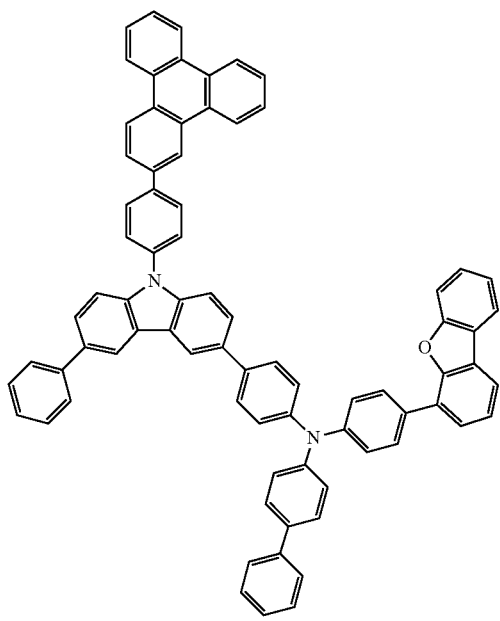
[A-282]
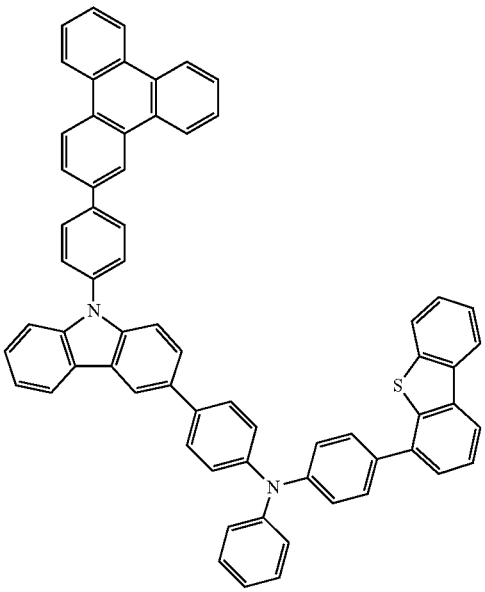
[A-283]
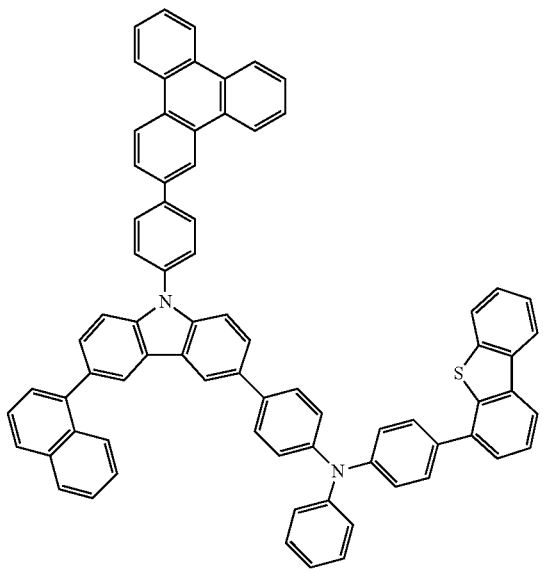

[A-284]
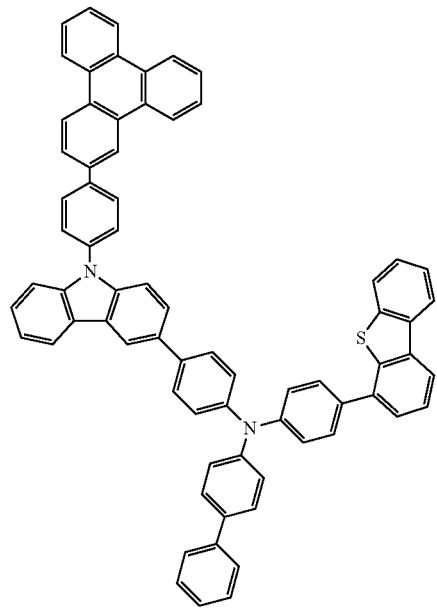
[A-285]
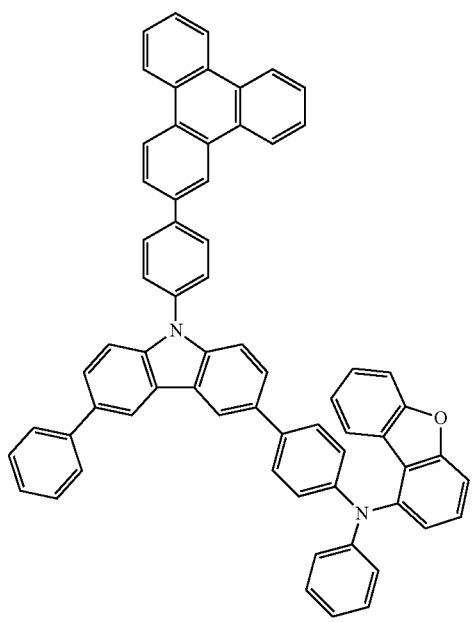
[A-286]
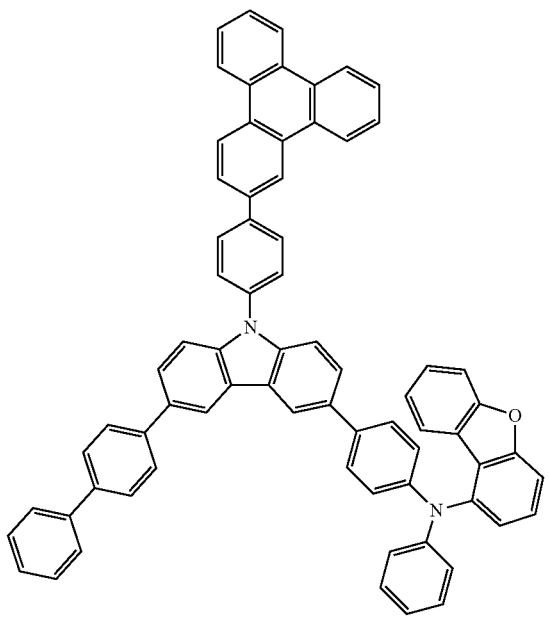
[A-287]
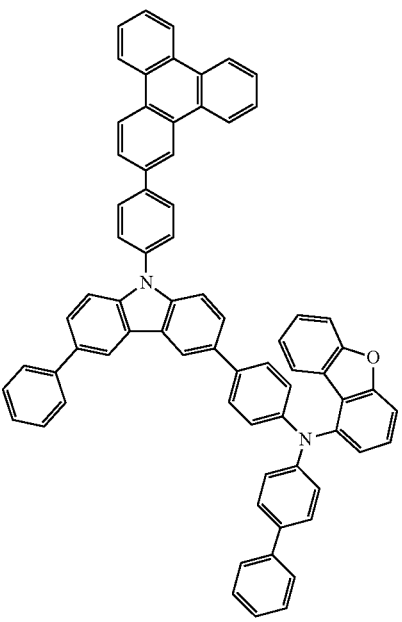

[A-288]
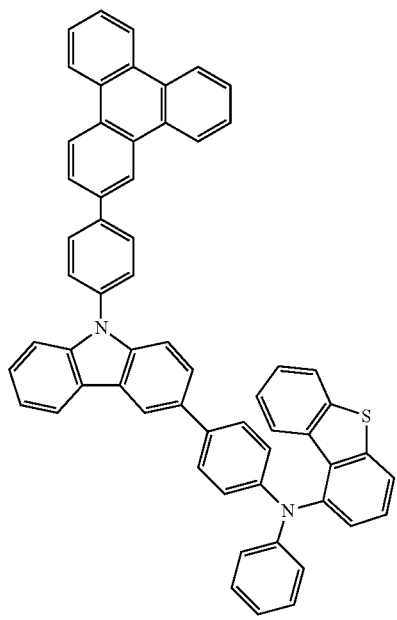
[A-290]
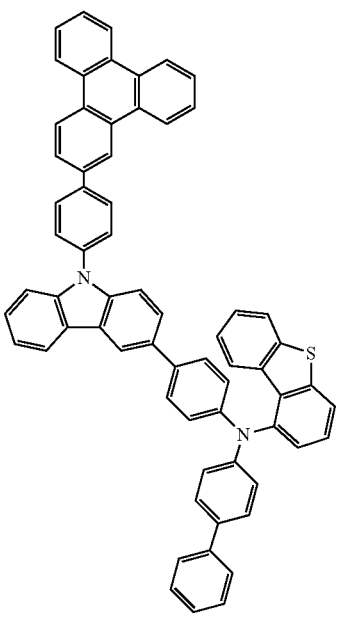
[A-289]
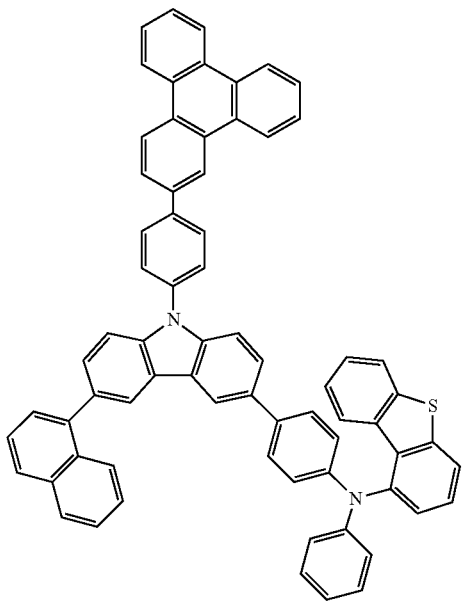
[A-291]
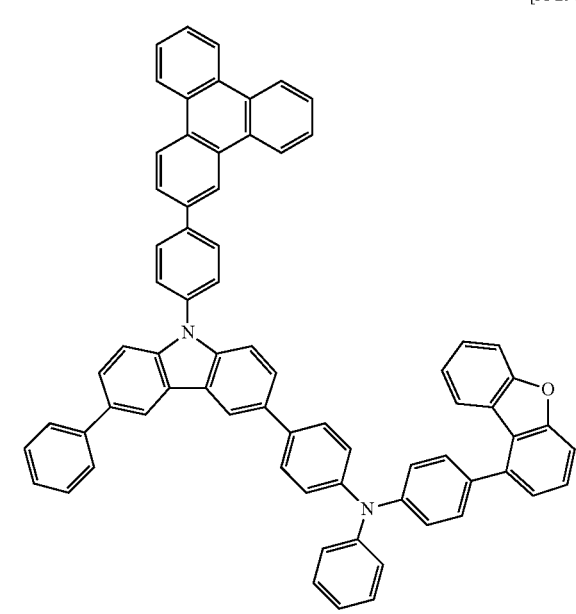

[A-292]
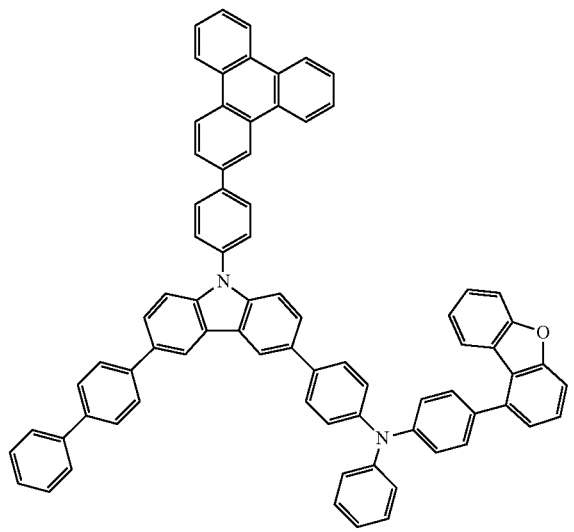
[A-294]
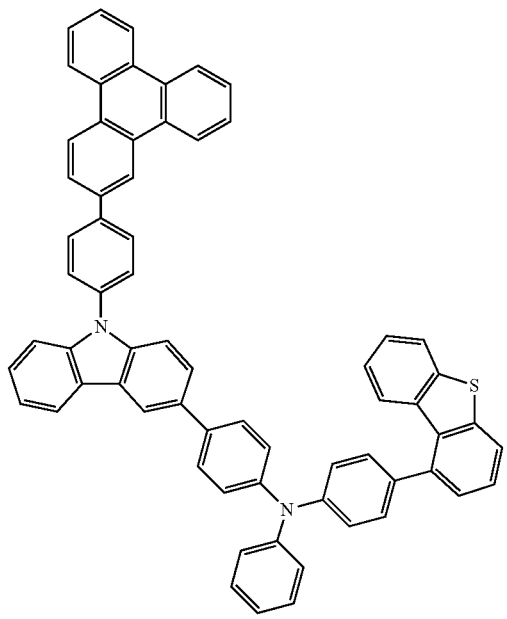
[A-293]
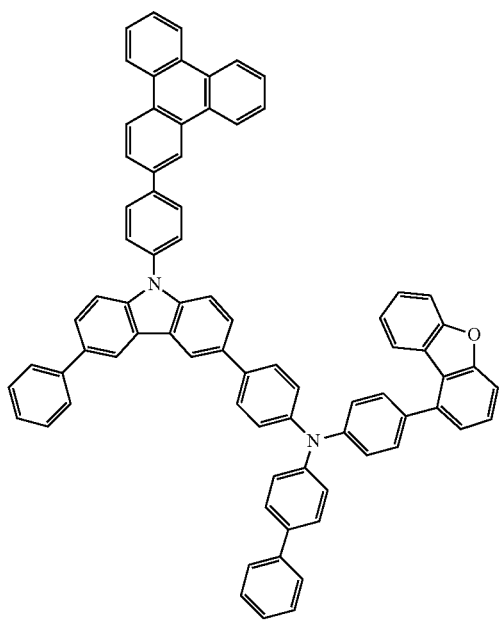
[A-295]
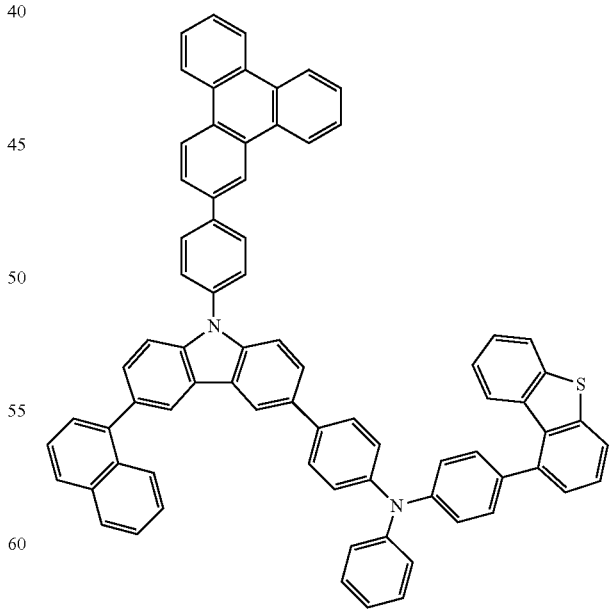

-continued
[A-296]
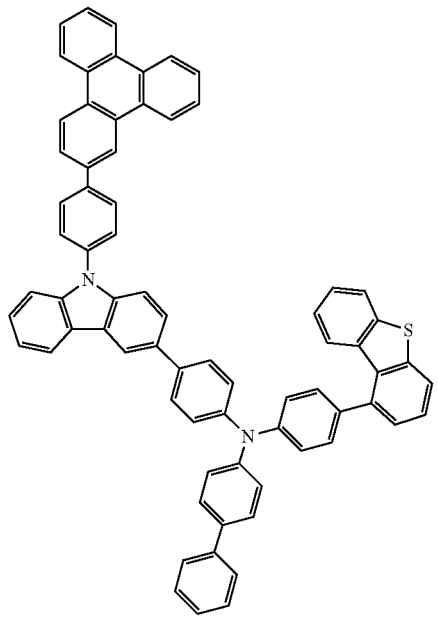
[A-298]
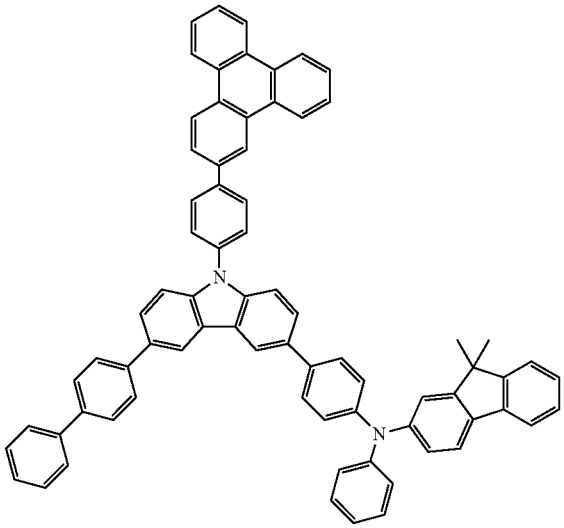
[A-297]
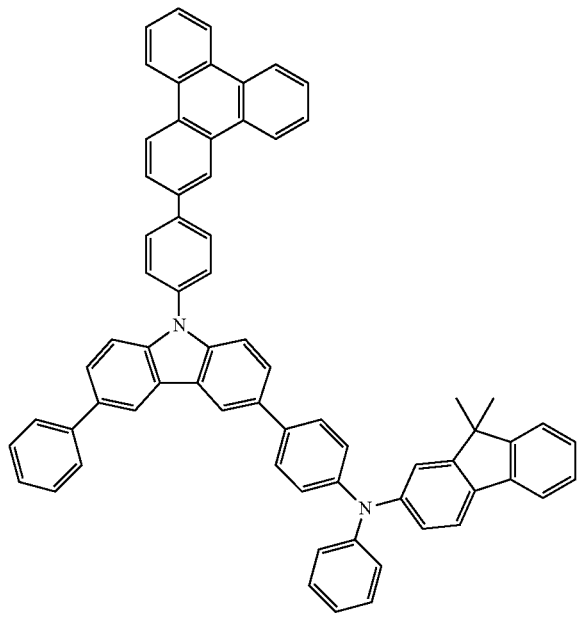
[A-299]
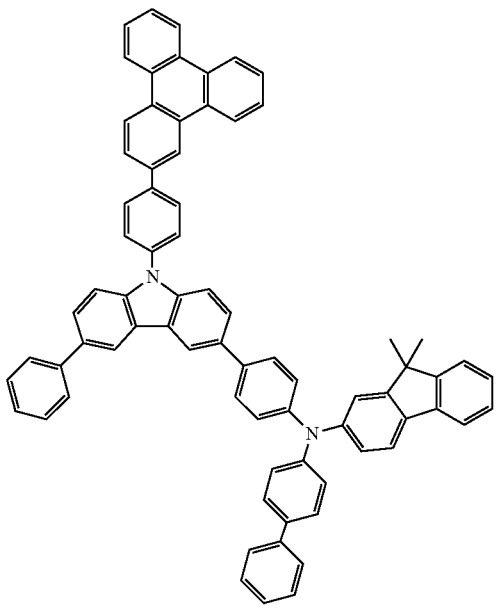

[A-300]
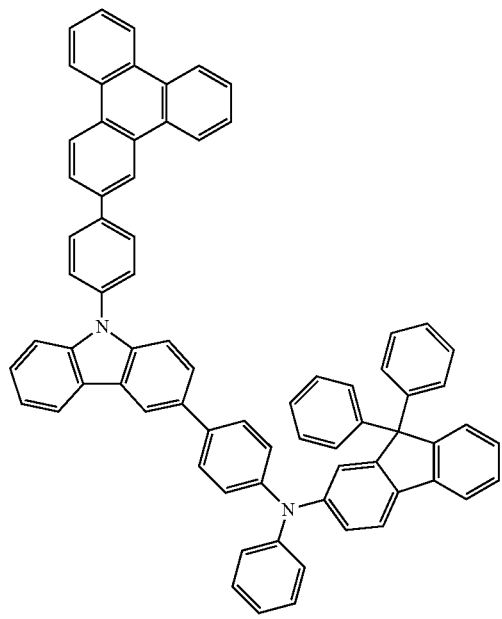
[A-302]
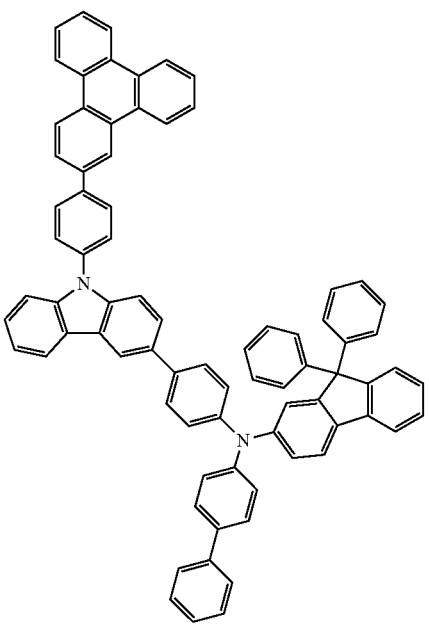
[A-301]
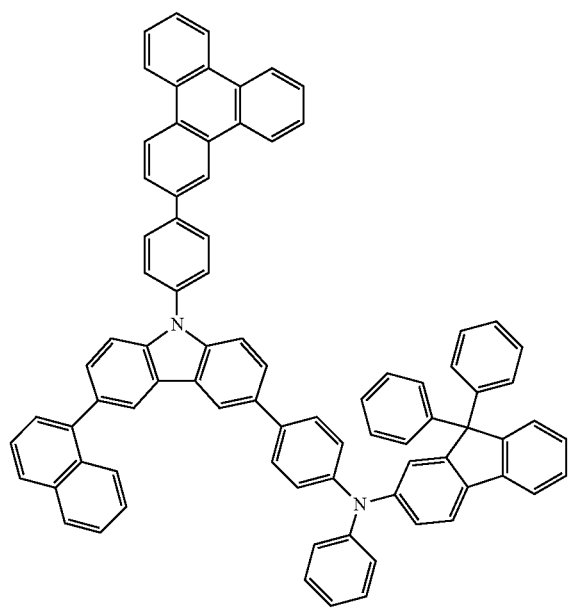
[A-303]
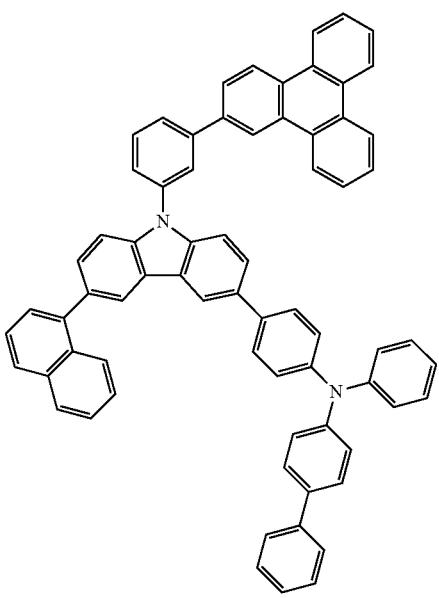

[A-304]
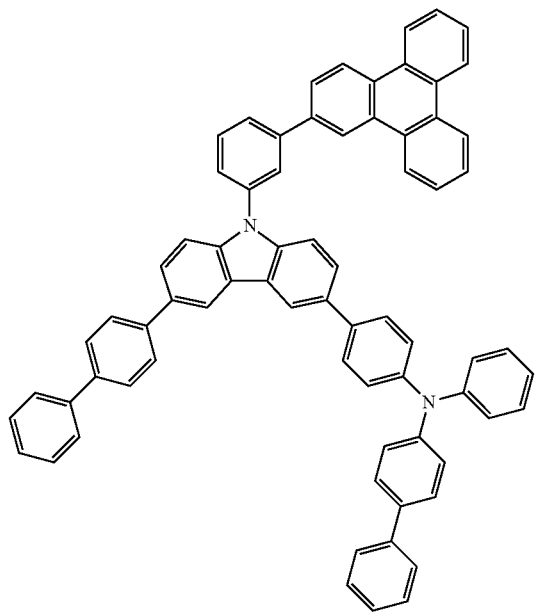
[A-306]
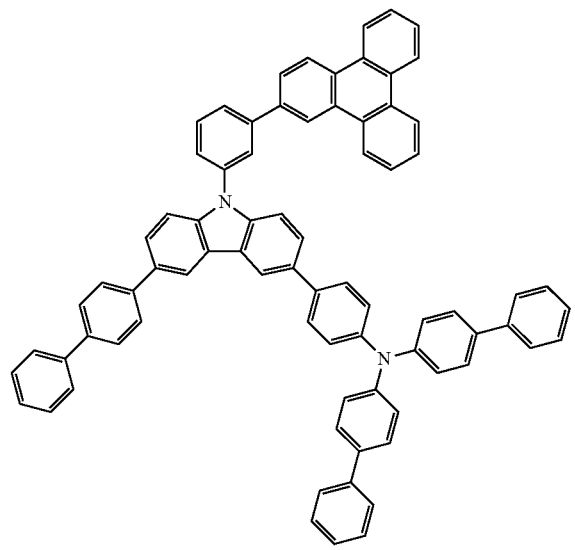
[A-305]
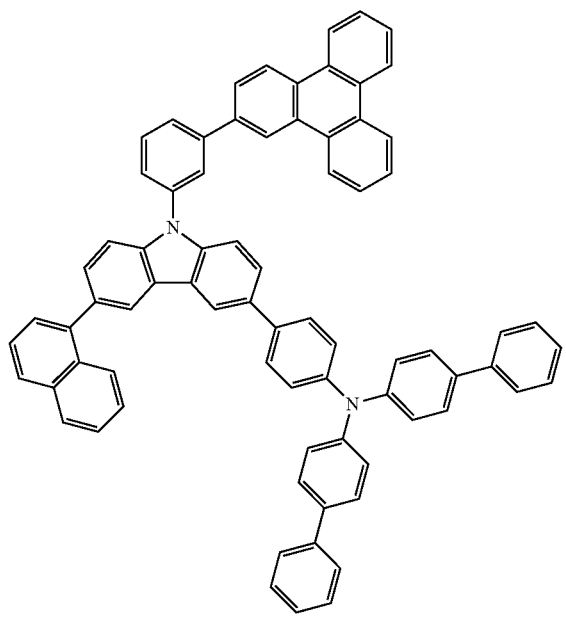
[A-307]
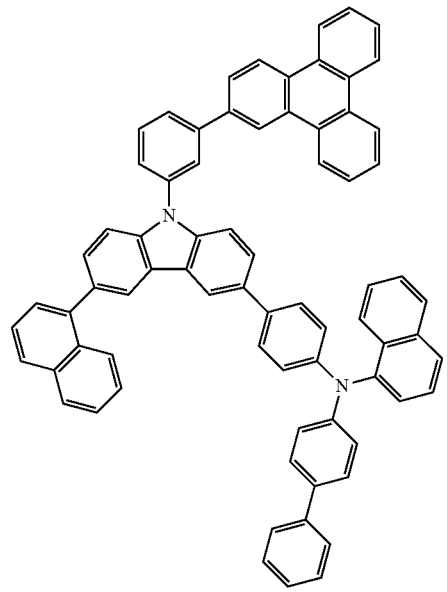

[A-308]
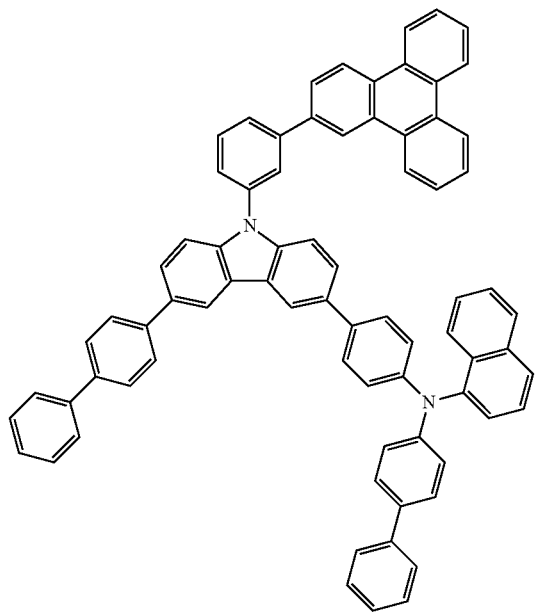
[A-310]
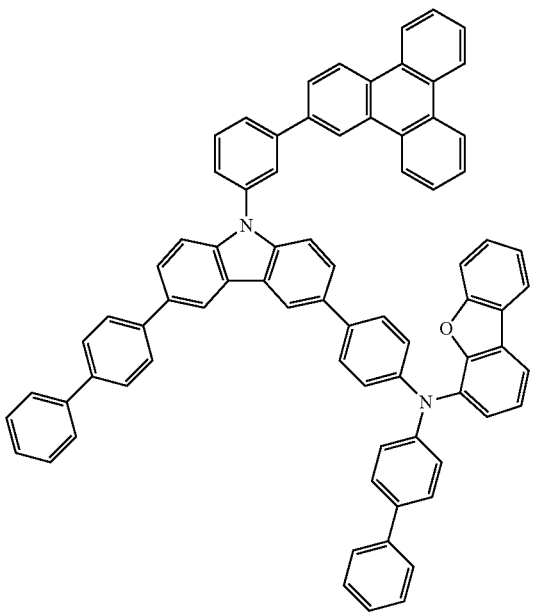
[A-309]
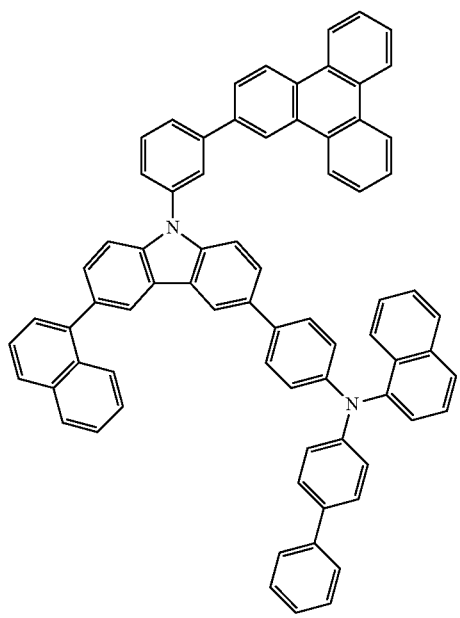
[A-311]
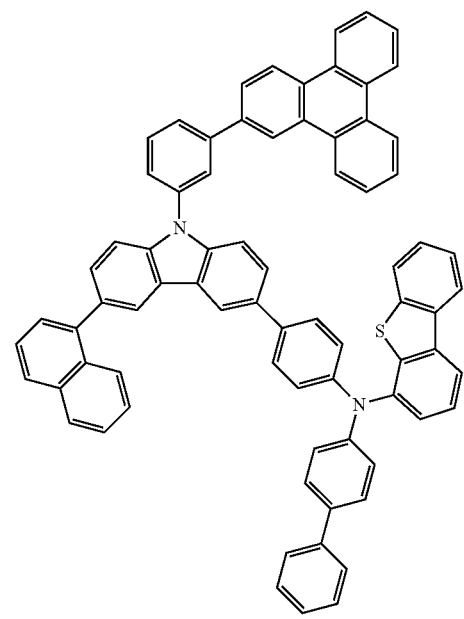

[A-312]
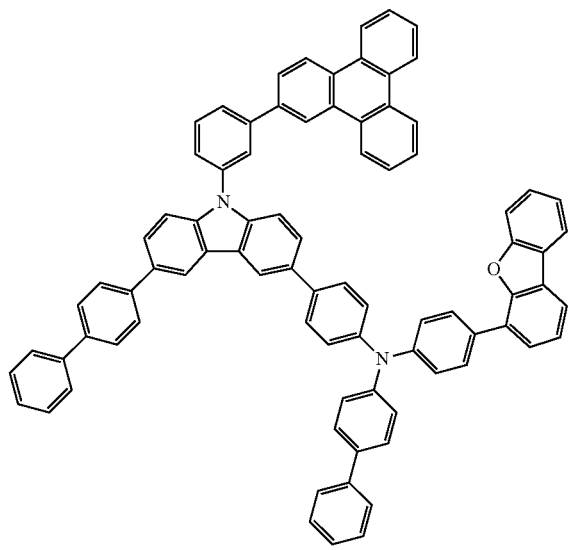
[A-314]
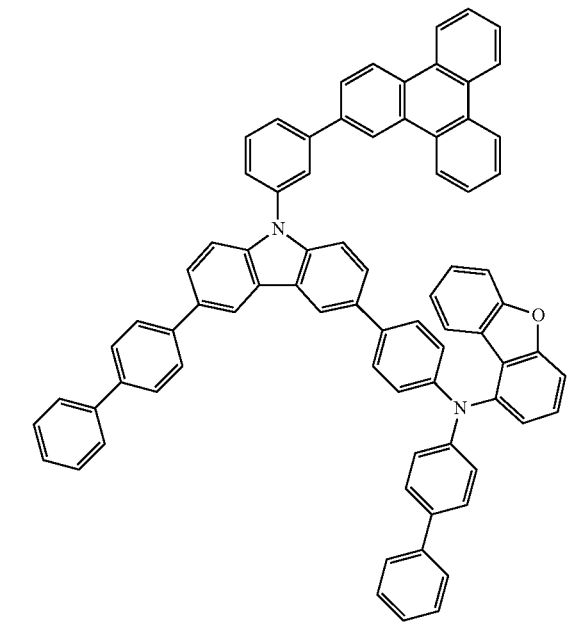
[A-313]
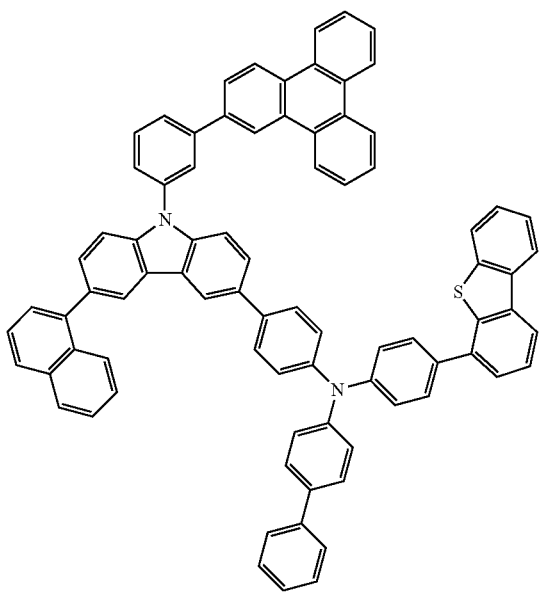
[A-315]
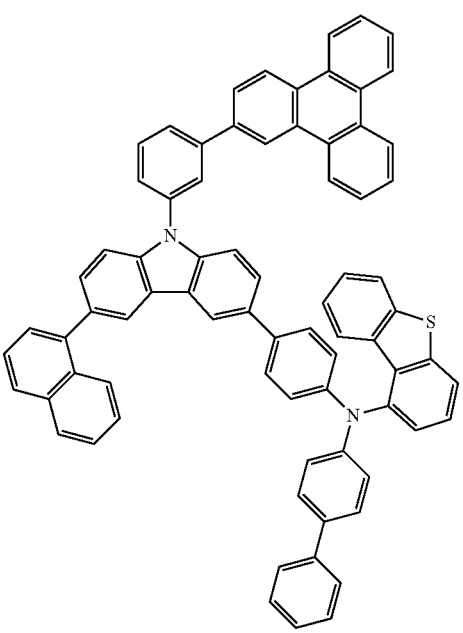

[A-316]
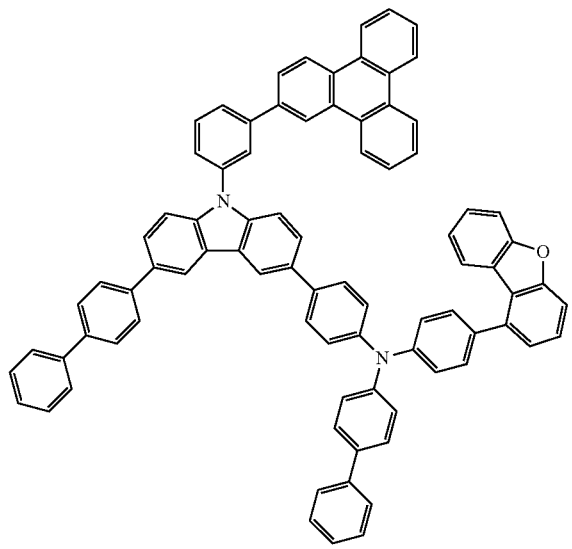
[A-318]
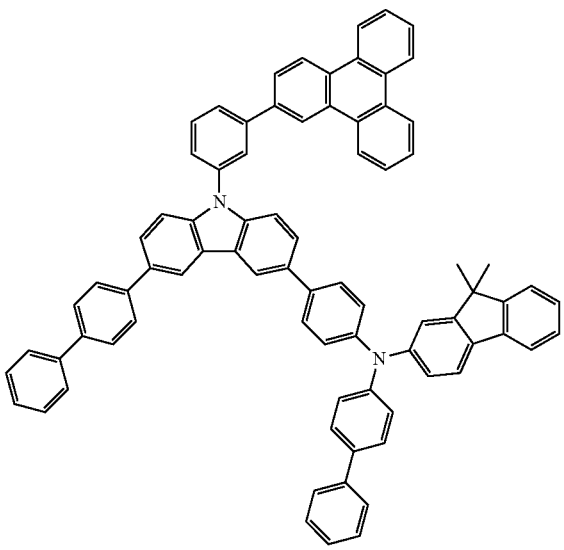
[A-317]
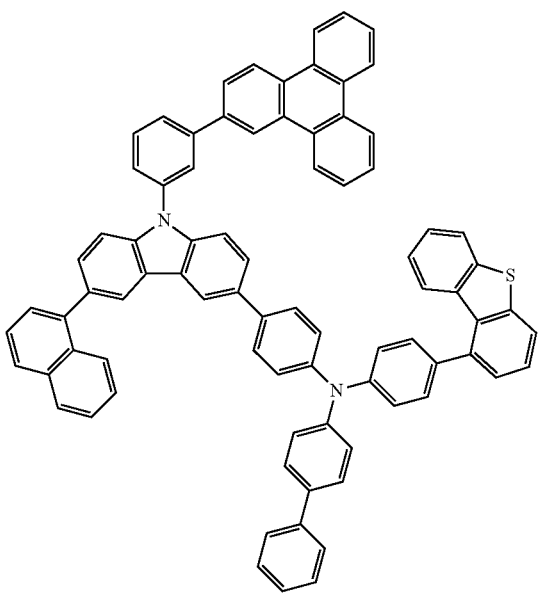
[A-319]
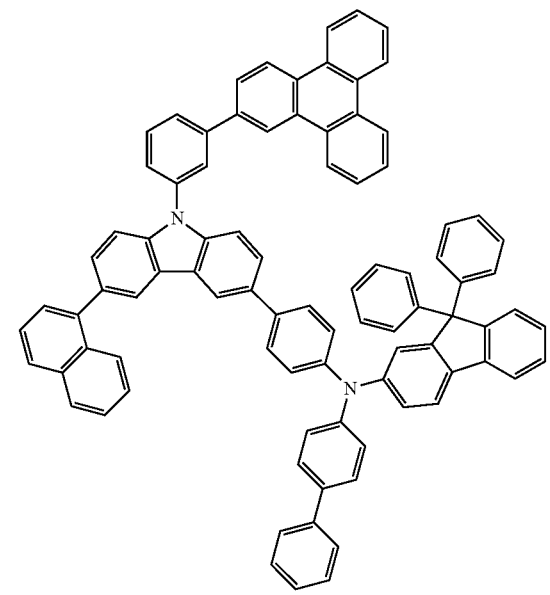

[A-320]
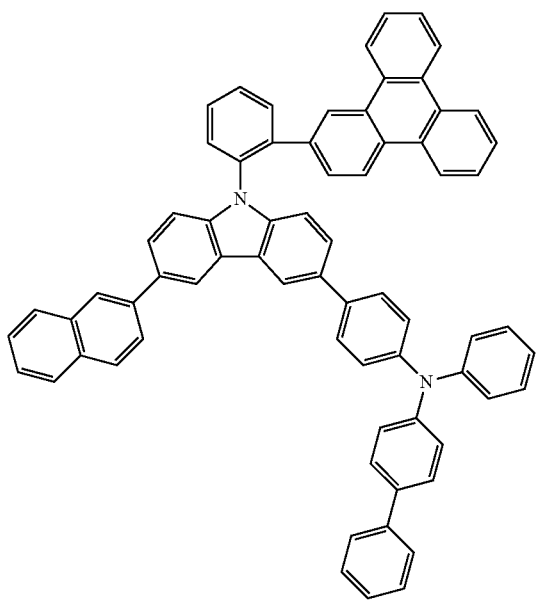
[A-322]
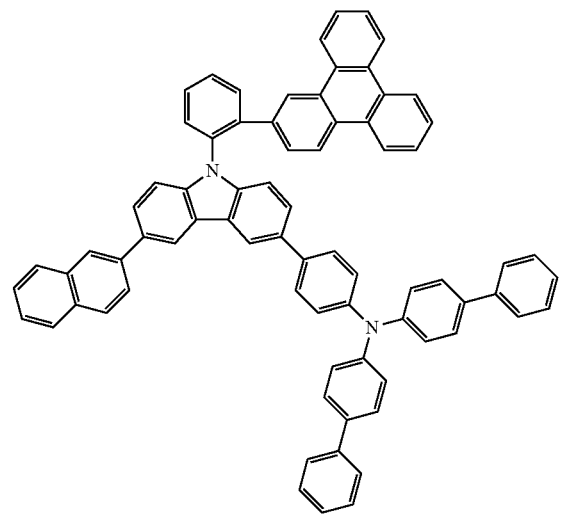
[A-321]
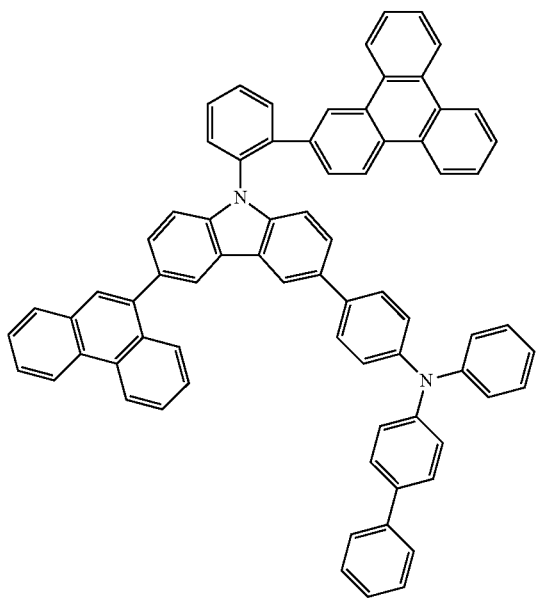
[A-323]
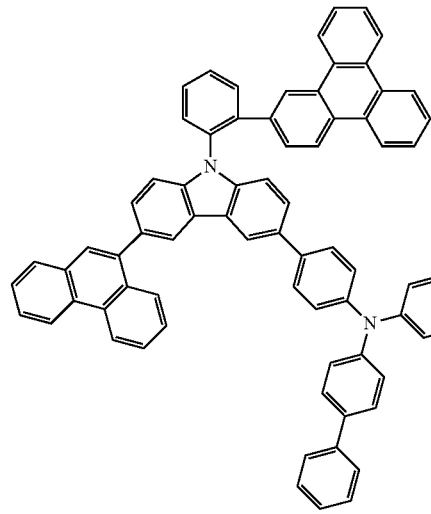

[A-324]
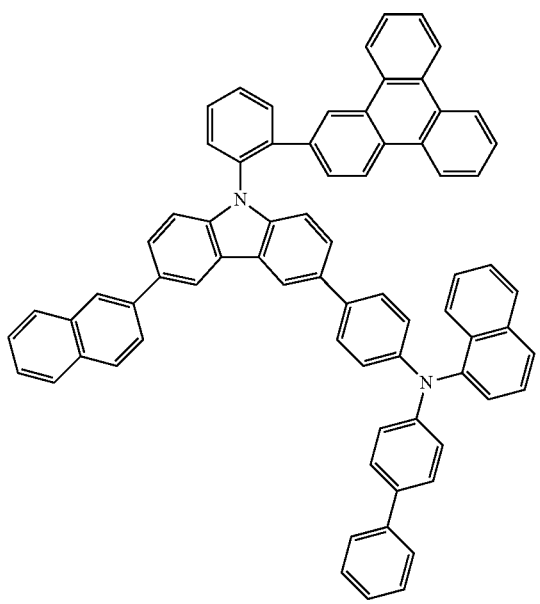
[A-326]
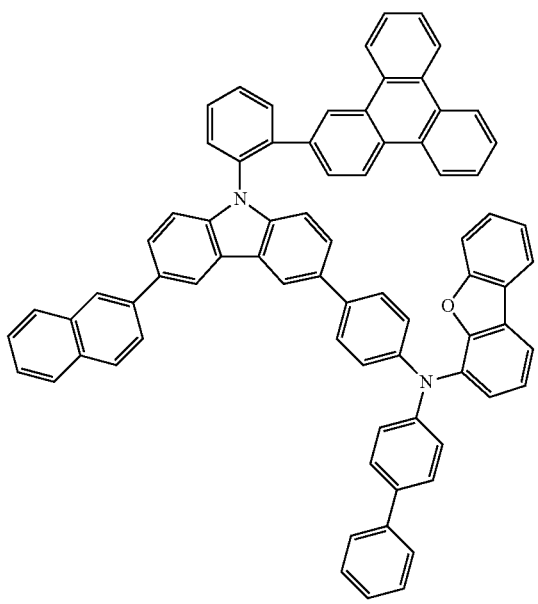
[A-325]
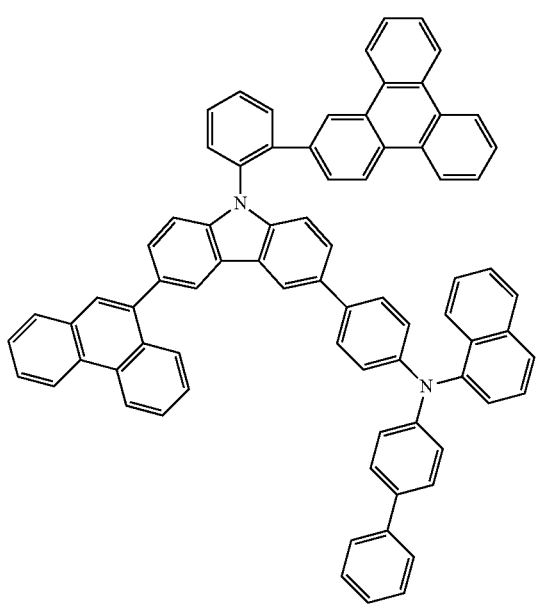
[A-327]
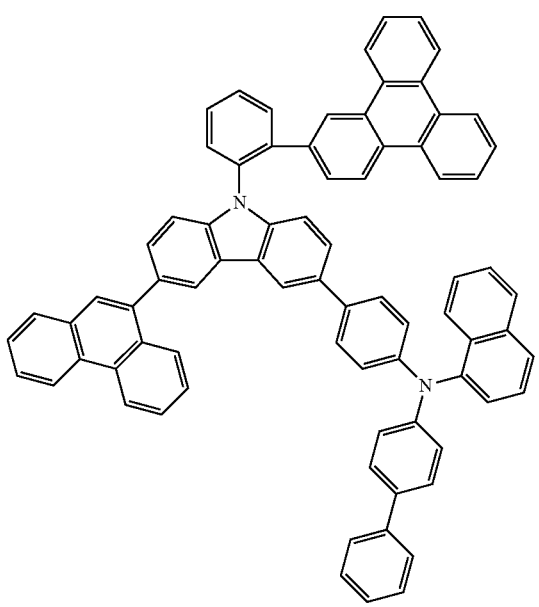

[A-328]
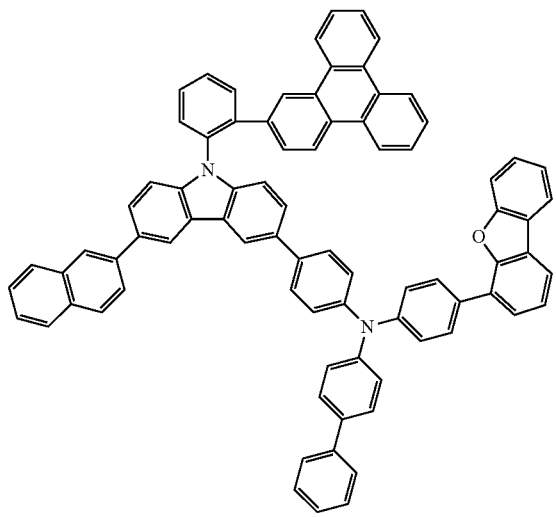
[A-329]
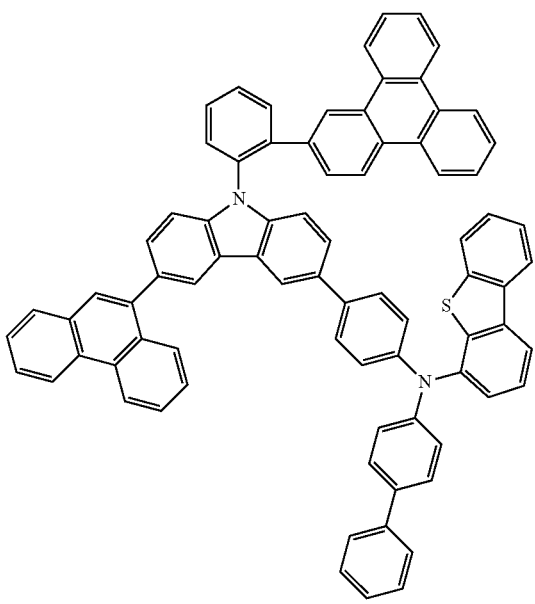
[A-330]
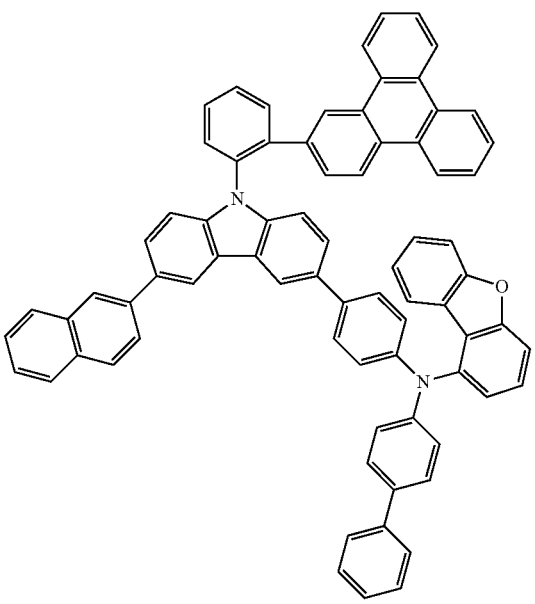
[A-331]
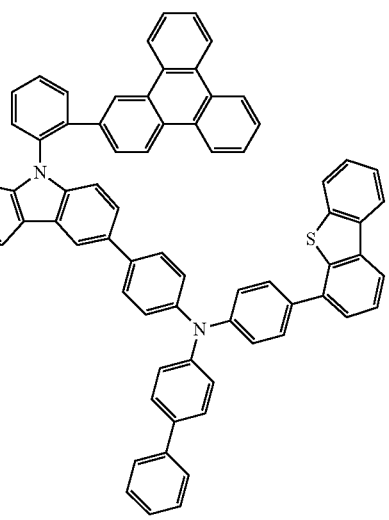

[A-332]
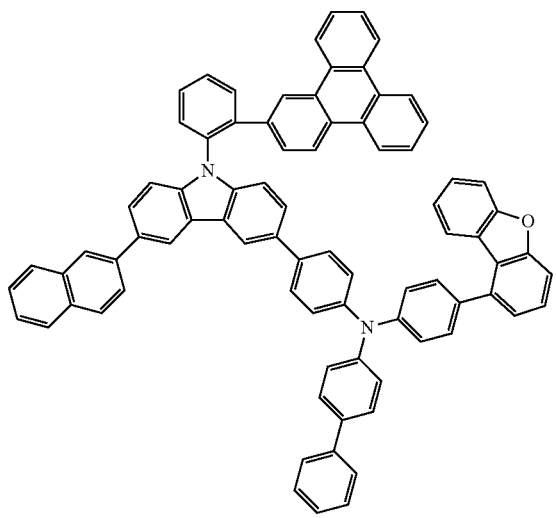
[A-333]
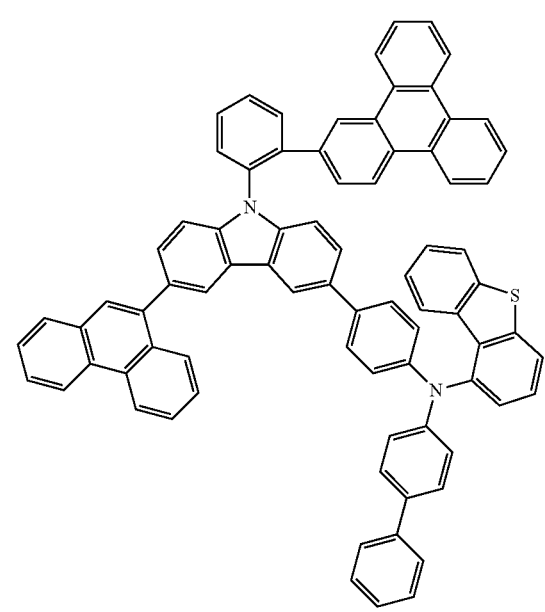
[A-334]
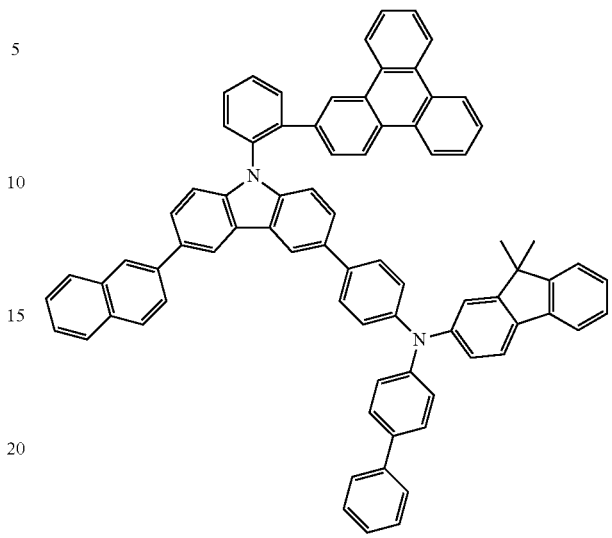
[A-335]
[A-336]

The organic photoelectric device may be selected from the group of an organic light emitting diode, an organic solar cell, an organic transistor, an organic photo conductor drum, and an organic memory device.

Embodiments are also directed to an organic light emitting diode, including an anode, a cathode, and one or more organic thin layers between the anode and the cathode. At least one of the organic thin layers may include a compound for an organic photoelectric device according to an embodiment.

At least one of the organic thin layers may include an emission layer, a hole transport layer (HTL), a hole injection layer (HIL), an electron transport layer (ETL), an electron injection layer (EIL), a hole blocking layer, or a combination thereof.

The compound may be included in an electron transport layer (ETL) or an electron injection layer (EIL).

The compound may be included in an emission layer.

The compound may be used as a phosphorescent or fluorescent host material in an emission layer.

The compound may be used as a fluorescent blue dopant material in an emission layer.

Embodiments are also directed to a display device including an organic light emitting diode according to an embodiment.

BRIEF DESCRIPTION OF THE DRAWINGS

Features will become apparent to those of skill in the art by describing in detail example embodiments with reference to the attached drawings in which.

DETAILED DESCRIPTION

Figure 1:
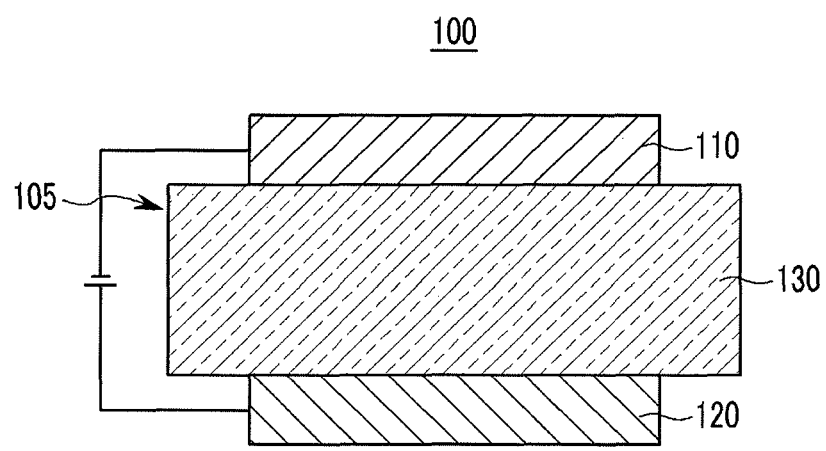
FIGS. 1 to 5 illustrate cross-sectional views of organic photoelectric devices according to embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, when specific definition is not otherwise provided, the term "substituted" refers to one substituted with a C1 to C30 alkyl group; a C1 to C10 alkylsilyl group; a C3 to C30 cycloalkyl group; a C6 to C30 aryl group; a C2 to C30 heteroaryl group; a C1 to C10 alkoxy group; a fluoro group, a C1 to C10 trifluoroalkyl group such as a trifluoromethyl group; or a cyano group.

As used herein, when specific definition is not otherwise provided, the term "hetero" refers to one including 1 to 3 hetero atoms selected from the group of N, O, S, and P, and remaining carbons in one functional group.

As used herein, when a definition is not otherwise provided, the term "combination thereof" refers to at least two substituents bound to each other by a linker, or at least two substituents condensed to each other.

In the specification, when a definition is not otherwise provided, the term "alkyl group" may refer to "a saturated group" without any alkene group or alkyne group. When a definition is not otherwise provided, the term "alkenyl group" may refer to a substituent of at least one carbon-carbon double bond of at least two carbons, and the "alkynyl group" may refer to a substituent of at least one carbon-carbon triple bond of at least two carbons. The alkyl group may be branched, linear, or cyclic.

The alkyl group may be a C1 to C20 alkyl group, and specifically a C1 to C6 lower alkyl group, a C7 to C 10 medium-sized alkyl group, or a C11 to C20 higher alkyl group.

For example, a C1 to C4 alkyl group may have 1 to 4 carbon atoms and may be selected from the group of methyl, ethyl, propyl, iso-propyl, n-butyl, iso-butyl, sec-butyl, and t-butyl.

Typical examples of an alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

Typical examples of an alkenyl group may be an ethenyl group, a propenyl group, a butenyl group, and the like. Also, typical examples of an alkynyl group may be an ethynyl group, a propynyl group, a butynyl group, and the like.

The term "aromatic group" may refer to a substituent including all elements of the cycle having p-orbitals which form conjugation. Examples may include an aryl group and a heteroaryl group.

The "aryl group" may refer to a monocyclic or fused ring polycyclic (i.e., rings sharing adjacent pairs of carbon atoms) substituent.

The term "heteroaryl group" may refer to an aryl group including 1 to 3 hetero atoms selected from the group of N, O, S, and P, and remaining carbons in one functional group. The aryl group may be a fused ring cyclic group where each cycle may include the 1 to 3 heteroatoms.

"Spiro structure" may refer to a plurality of cyclic structures having a contact point of one carbon. The Spiro structure may include a compound having a spiro structure or a substituent having a spiro structure.

A compound for an organic photoelectric device according to an embodiment includes a core structure including a triphenylenyl group coupled to nitrogen of a carbazole. The compound may further include an amine group coupled to the carbazole.

Embodiments may provide a core structure having excellent hole properties due to a triphenylenyl group and a carbazole core having excellent hole properties. The compound may be used for, e.g., a light emitting host, and may be used with a suitable dopant in an emission layer.

In an embodiment, the compound for an organic photoelectric device includes a core part and various substituents for substituting the core part and thus may have various energy band gaps. The compound may be used in, e.g., a hole injection layer (HIL) and transport layer, an emission layer, etc.

The compound may have an appropriate energy level depending on the substituents and thus, may fortify hole transport capability of an organic photoelectric device and bring about excellent effects on efficiency and driving voltage and also, have excellent electrochemical and thermal stability and thus, may improve life-span characteristic during the operation of the organic photoelectric device.

According to an embodiment, a compound for an organic photoelectric device represented by the following Chemical Formula 1 is provided.

[Chemical Formula 1]

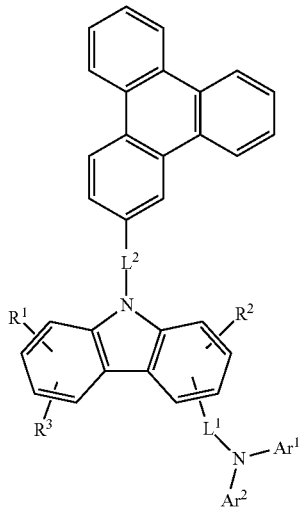

In Chemical Formula 1, $L^1$ and $L^2$ may each independently be selected from the group of a single bond, a substituted or unsubstituted C2 to C6 alkenylene group, a substituted or unsubstituted C2 to C6 alkynylene group, a substituted or unsubstituted C6 to C30 arylene group, and a substituted or unsubstituted C2 to C30 heteroarylene group.

$L^1$ and $L^2$ may increase a triplet energy band gap by controlling the total π-conjugation length of compound, which may be useful for application to an emission layer of an organic photoelectric device as a phosphorescent host.

$L^1$ and $L^2$ may each independently be a single bond. Other examples of $L^1$ and/or $L^2$ include an ethenylene group, an ethynylenyl group, a phenylene group, a biphenylene group, a naphthalene group, a terphenylene group, and the like.

$R^1$ to $R^3$ may each independently be selected from the group of hydrogen, a substituted or unsubstituted C1 to C6 alkyl group, a substituted or unsubstituted C6 to C30 aryl group, and a substituted or unsubstituted C2 to C30 heteroaryl group.

A selected combination of the substituents may provide a compound having excellent thermal stability and/or oxidation resistance. A selected combination of the substituents may provide a bipolar structure, which may improve transporting capability of holes and electrons and improve luminous efficiency and performance of a device.

Selection of the substituents may provide a compound having a bulky structure and thus lower crystallinity. The compound having lower crystallinity may improve life-span of a device.

Examples of $R^1$ to $R^3$ are hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 an aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 an arylthiol group, a substituted or unsubstituted C1 to C20 heterocyclothiol group, a substituted or unsubstituted C1 to C20 ureide group, a substituted or unsubstituted C3 to C40 silyl group, and the like.

$Ar^1$ and $Ar^2$ may each independently be a substituted or unsubstituted C6 to C30 aryl group, or a substituted or unsubstituted C2 to C30 heteroaryl group. In Chemical Formula 1, $Ar^1$ and $Ar^2$ are two substituents of the amine group substituted in the carbazole core.

The amine group may increase a hole transport capability of the compound for the organic photoelectric device in an organic light emitting diode, and may improve the suitability of the compound for use as a hole injection material or hole transport material.

More specific examples of $Ar^1$ and $Ar^2$ include a substituted or unsubstituted phenyl group, a substituted or unsubstituted naphthalenyl group, a substituted or unsubstituted fluorenyl group, a substituted or unsubstituted biphenyl group, a substituted or unsubstituted dibenzofuranyl group, a substituted or unsubstituted dibenzothiophenyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, and the like.

A selected combination of the $Ar^1$ and $Ar^2$ may introduce another substituent and provide a compound having various energy band gaps as well as hole properties compensated by the amine group. The compound may have an suitable energy level depending on the substituents and thus, may fortify electron transport capability or electron transport capability of an organic photoelectric device and may bring about excellent effects on efficiency and driving voltage and also, may have excellent electrochemical and thermal stability and thus, may improve life-span characteristic during the operation of the organic photoelectric device.

At least one of the substituents bonded to the core may be a substituent having excellent electron properties.

Accordingly, the compound may be suitable for an emission layer by complementing excellent hole properties of its carbazole structure with electron properties. For example, the compound may be used as a host material for an emission layer.

The compound for an organic photoelectric device may be represented by one of the following Chemical Formulae 2 to 4.

[Chemical Formula 2]

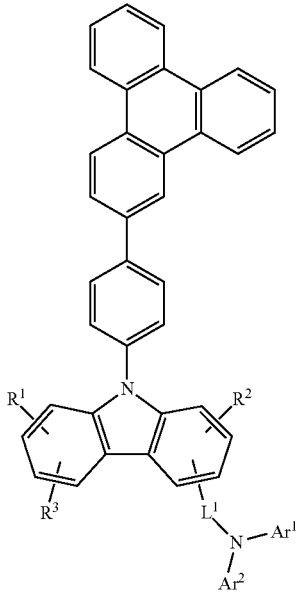

[Chemical Formula 3]

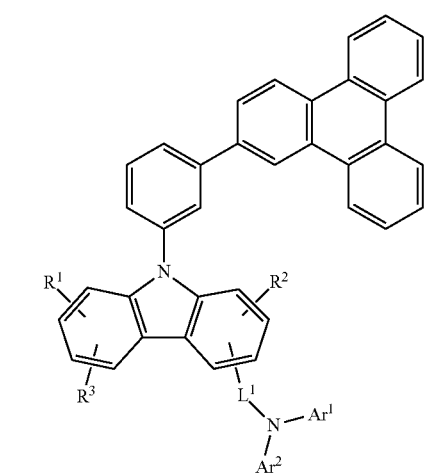

[Chemical Formula 4]

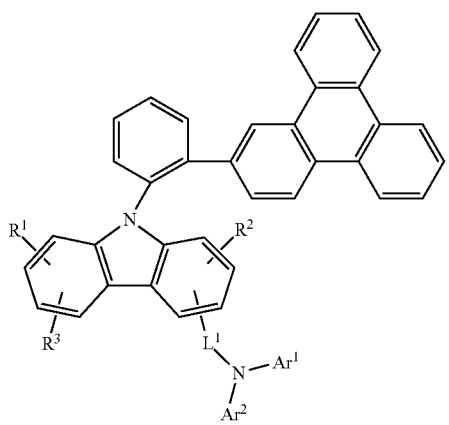

In Chemical Formulae 2 to 4, $L^1$, $R^1$ to $R^3$, $Ar^1$ and $Ar^2$ may be the same as in Chemical Formula 1 and thus their description will not be repeated.

The compounds represented by the above Chemical Formulae 2 to 4 may be a compound of the above Chemical Formula 1 where $L^2$ is phenylene.

The compound represented by the above Chemical Formula 2 may have a structure where a triphenylenyl group is bonded at a para-position of the phenylene. The compound represented by the above Chemical Formula 3 may have a structure where a triphenylenyl group is bonded at a meta-position of the phenylene. The compound represented by the above Chemical Formula 4 may have a structure where a triphenylenyl group is bonded at an ortho-position of the phenylene.

When the triphenylenyl group is bonded at an ortho-position of the phenylene, a conjugation length in a molecule may decrease to provided a wider band gap and a higher triplet excitation energy.

When the triphenylenyl group is bonded at a meta-position of the phenylene, the compound may have a desirable glass transition temperature and good solubility to be subjected to chemical treatment.

When the triphenylenyl group is bonded at a para-position of the phenylene, the compound may have improved electrochemical stability and may have good thermal stability due to a higher melting point.

Desired band gaps and triplet excitation energy may be obtained according to substitution positions of phenylene and a triphenylenyl group, and the compound having an appropriate energy level may fortify hole transport capability or electron transport capability of an organic photoelectric device and may bring about excellent effects on efficiency and driving voltage and also, may have excellent electrochemical and thermal stability and thus, may improve life-span characteristic during the operation of the organic photoelectric device.

The compound for an organic photoelectric device may be represented by the following Chemical Formula 5.

[Chemical Formula 5]

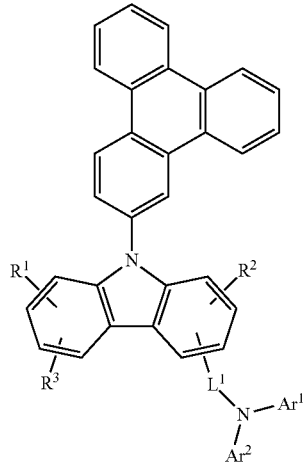

In Chemical Formula 5, $L^1$, $R^1$ to $R^3$, $Ar^1$ and $Ar^2$ may be the same as in Chemical Formula 1 and thus their description will not be repeated.

The compound represented by the above Chemical Formula 5 may be a compound of the above Chemical Formula 1 where $L^2$ is a single bond. A triphenylenyl group may be bonded to carbazole directly at the nitrogen of carbazole, which may be unstable for a radical, such that the compound may be stabilized.

In the compound, the triphenylenyl group has a bulky structure and may cause a resonance effect and thus, may suppress a side reaction possibly occurring in a solid state and improve performance of an organic light emitting diode.

In addition, the triphenylenyl group may make the compound bulky and thus, may have an effect on lowering crystallinity and increasing life-span.

The triphenylenyl group may provide a wider band gap and high triplet excitation energy relative to other substituents and thus may be bonded with carbazole but may not decrease the band gap or triplet excitation energy of the compound.

The compound for an organic photoelectric device represented by the above Chemical Formula 1 may be represented by one of the following Chemical Formulae 6 to 18 or A-1 to A-251.

[Chemical Formula 6]

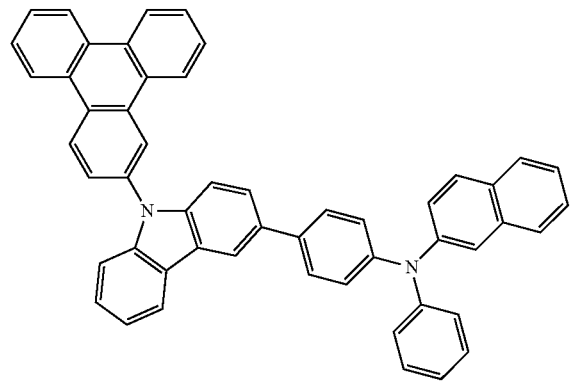

[Chemical Formula 7]

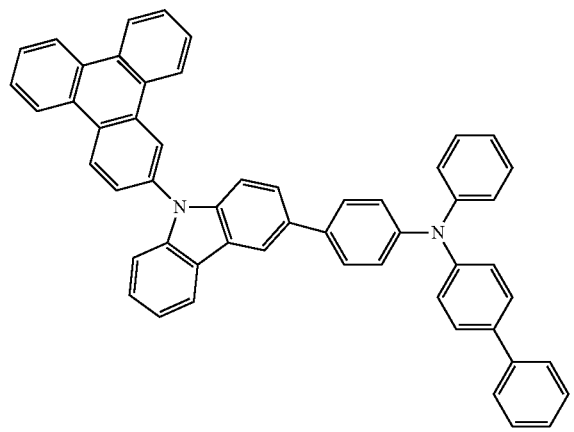

[Chemical Formula 8]

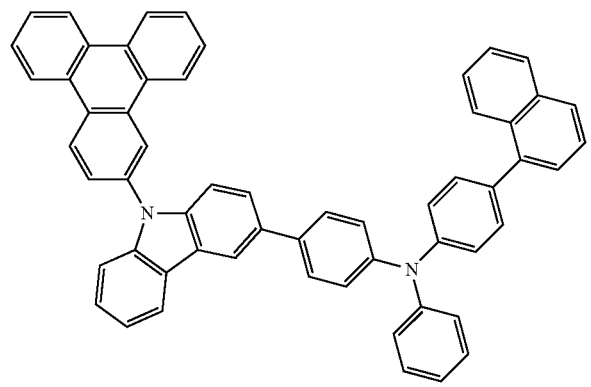

[Chemical Formula 9]

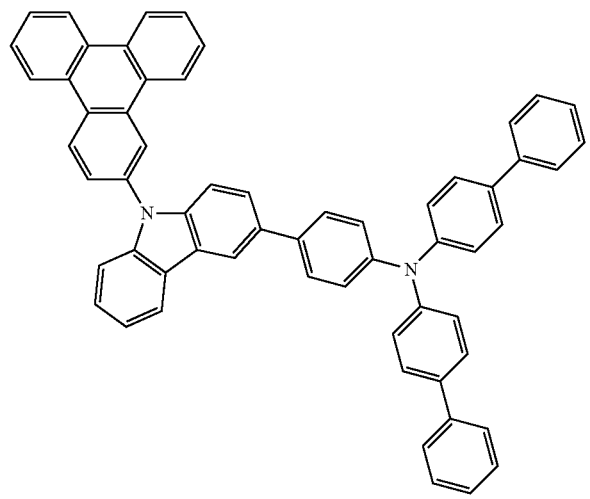

-continued
[Chemical Formula 10]
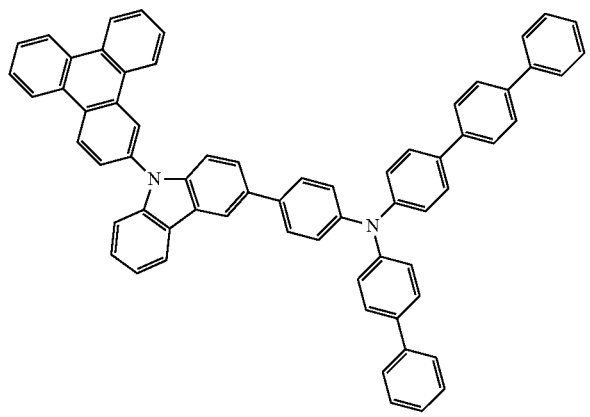
[Chemical Formula 11]
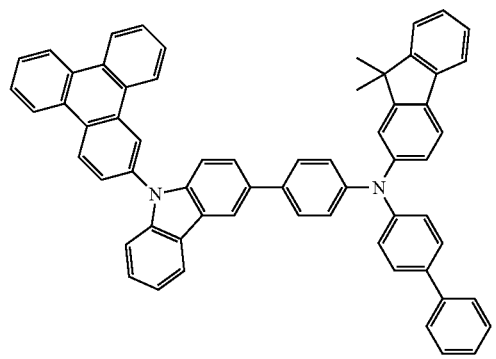
[Chemical Formula 12]
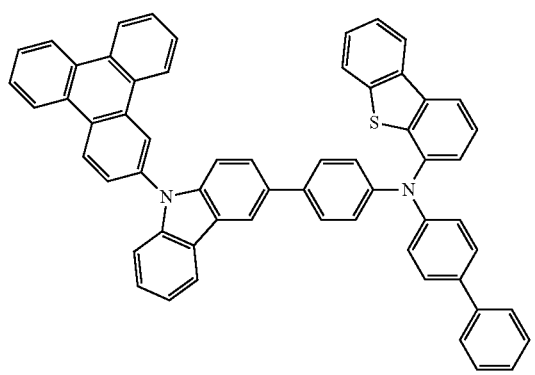
[Chemical Formula 13]
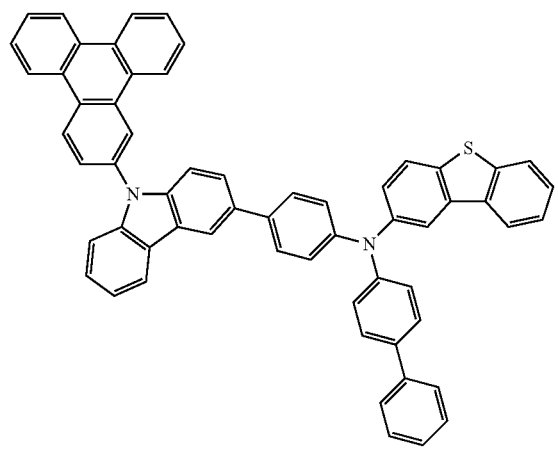
[Chemical Formula 14]
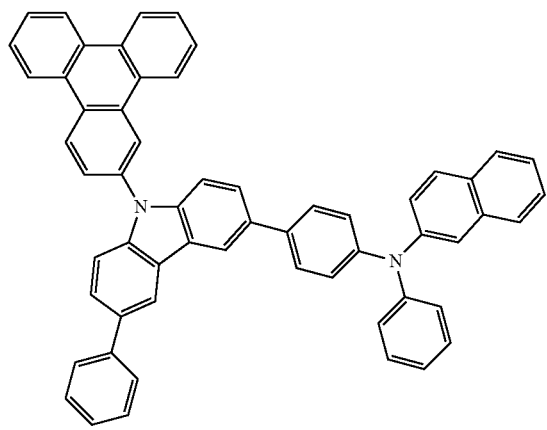
[Chemical Formula 15]
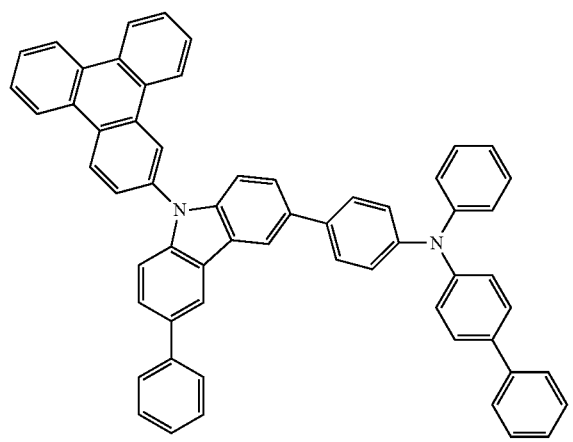

-continued
[Chemical Formula 16]
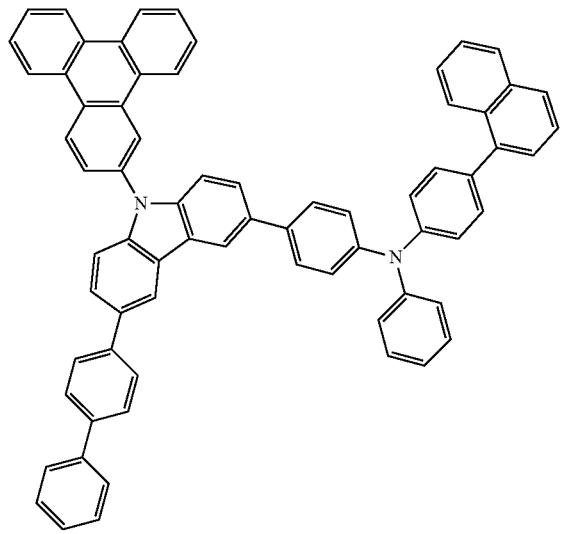
[Chemical Formula 17]
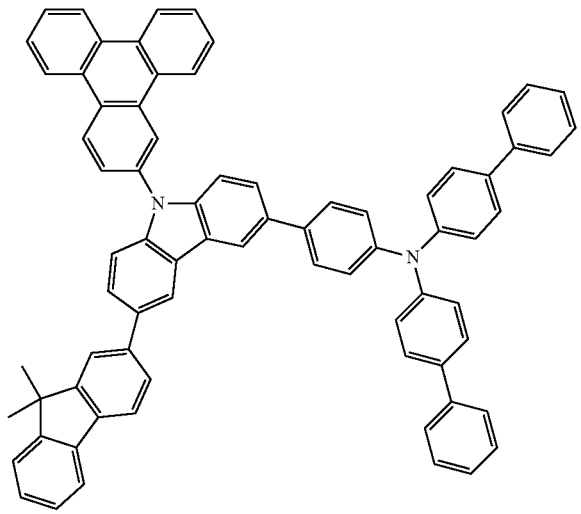
[Chemical Formula 18]
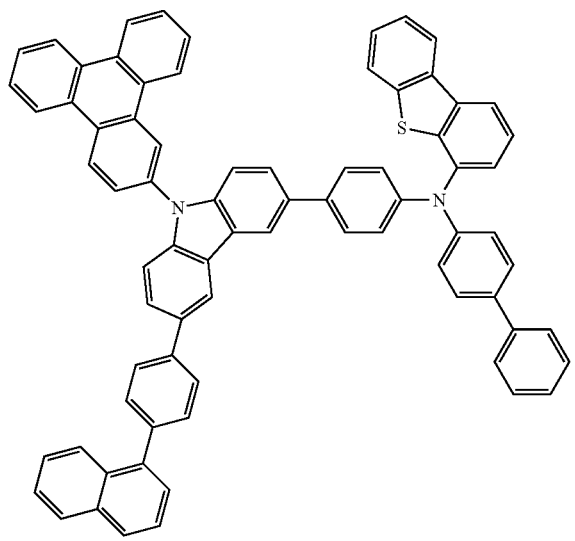
[A-1]
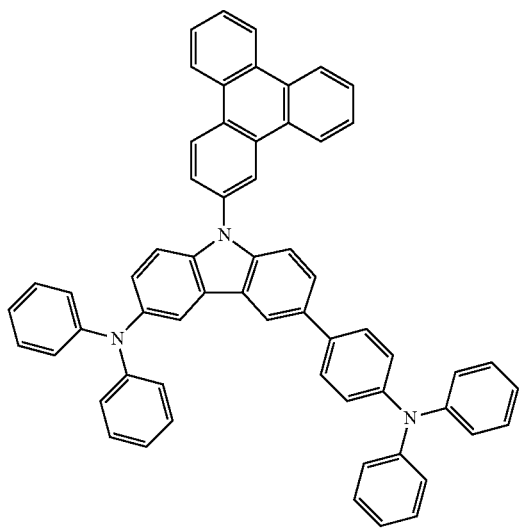
[A-2]
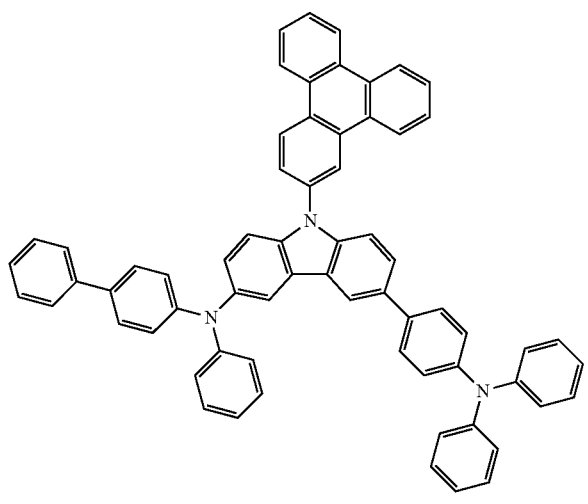
[A-3]
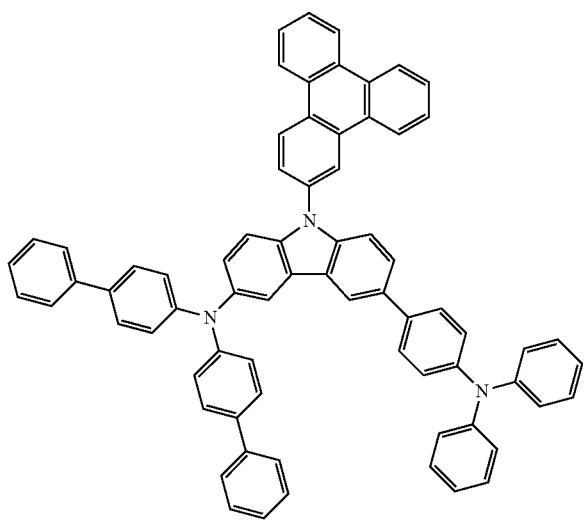

-continued
[A-4]
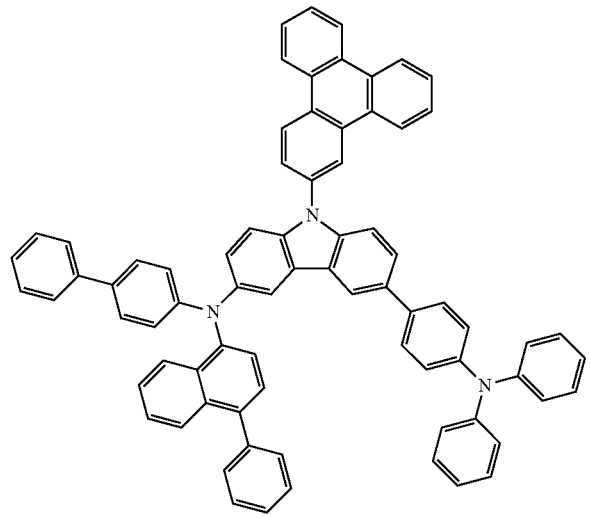
[A-5]
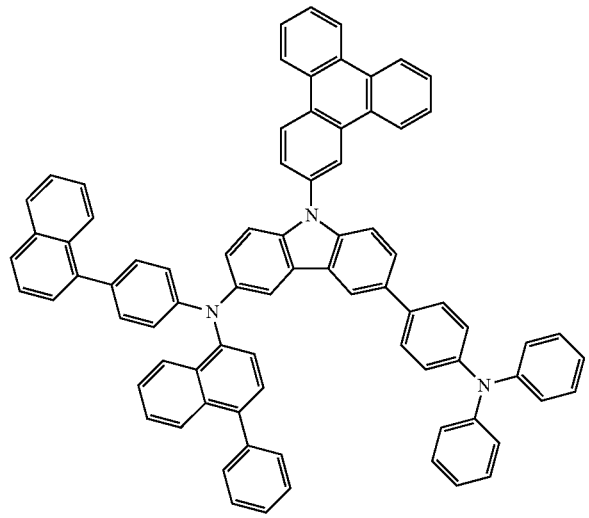
[A-6]
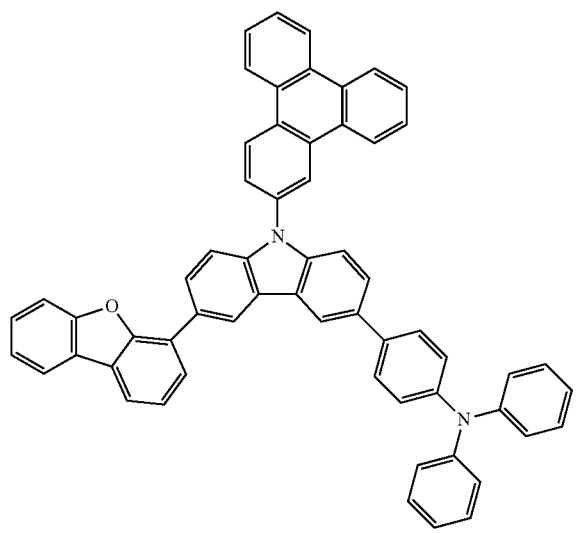
[A-7]
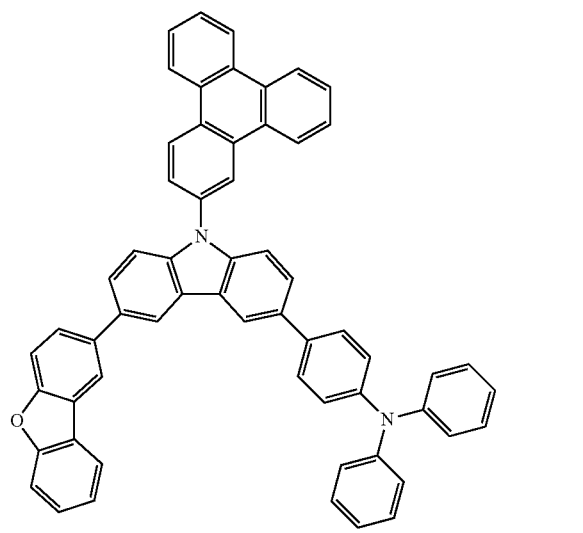
[A-8]
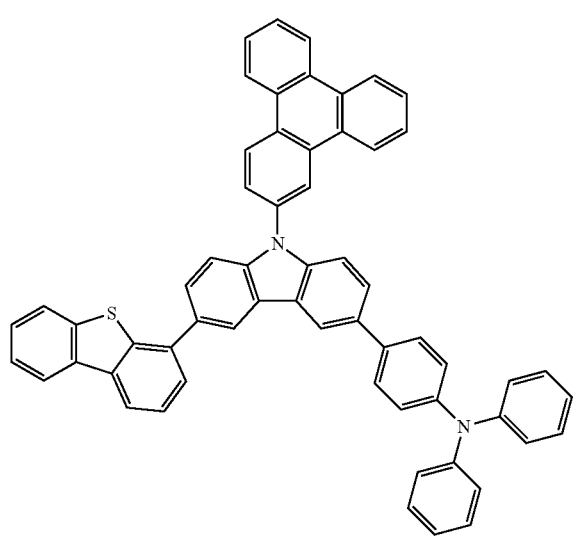
[A-9]
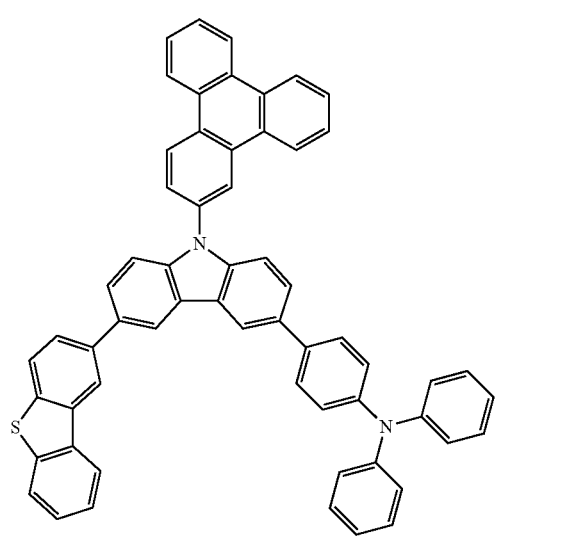

[A-10]
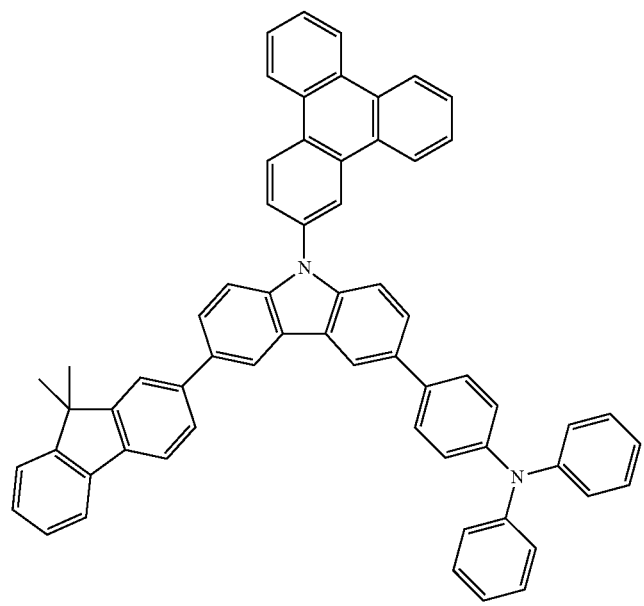
[A-11]
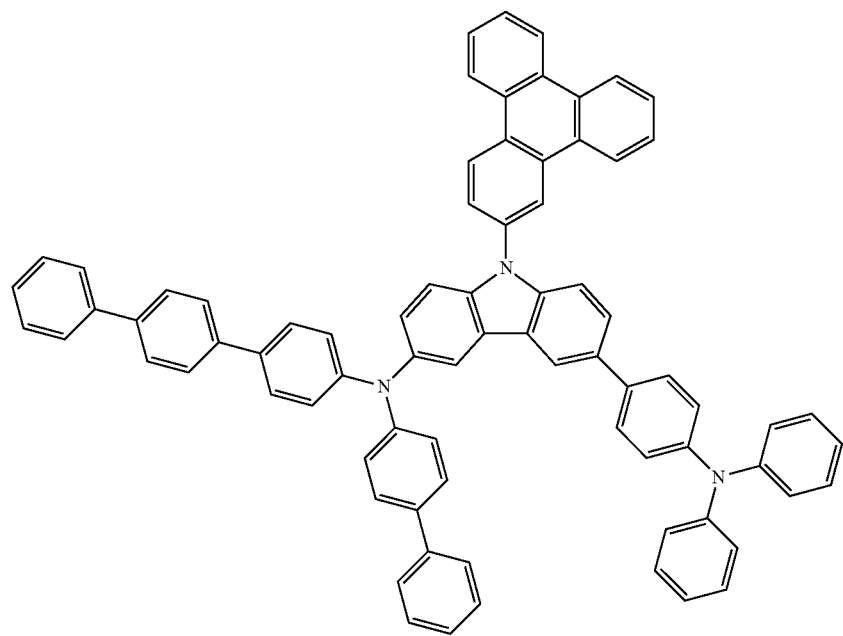

-continued
[A-12]
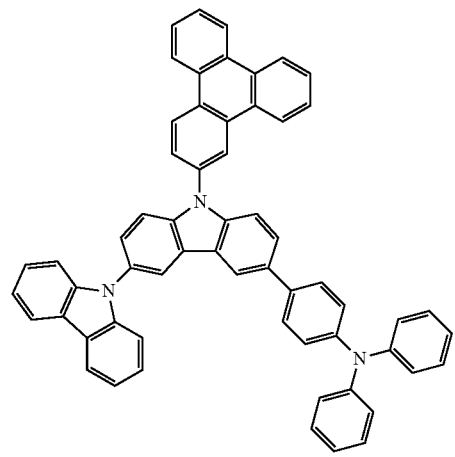
[A-13]
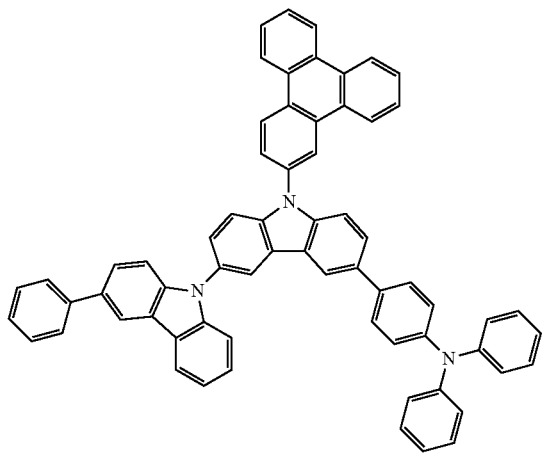
[A-14]
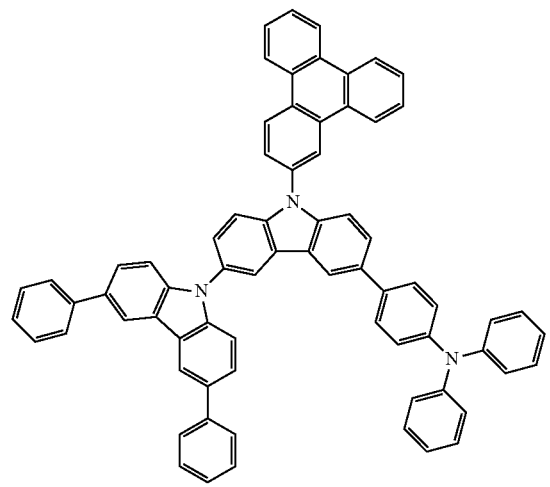
[A-15]
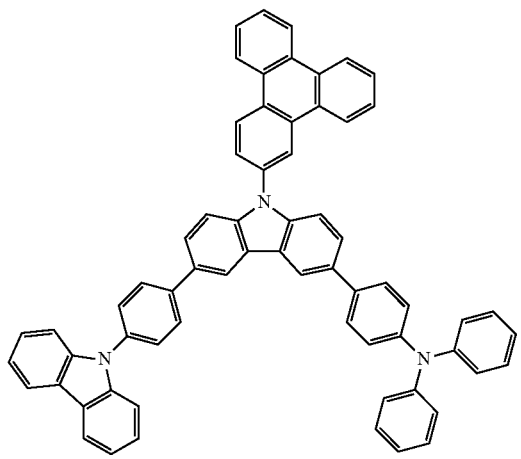
[A-16]
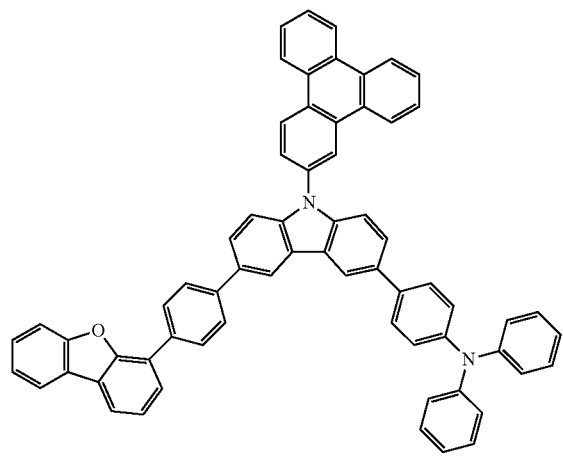
[A-17]
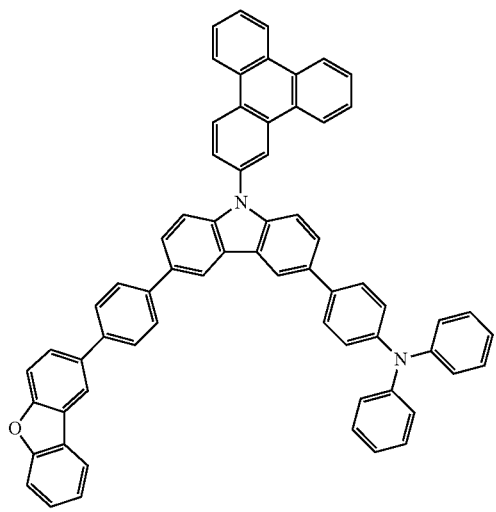

[A-18]
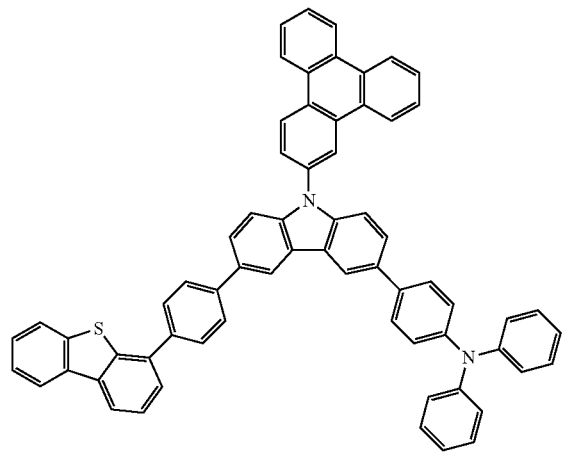
[A-19]
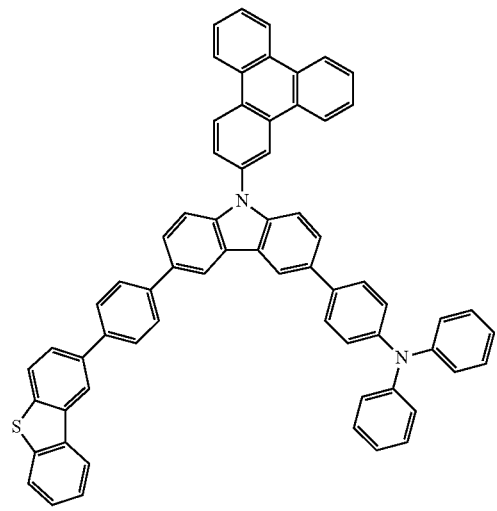
[A-20]
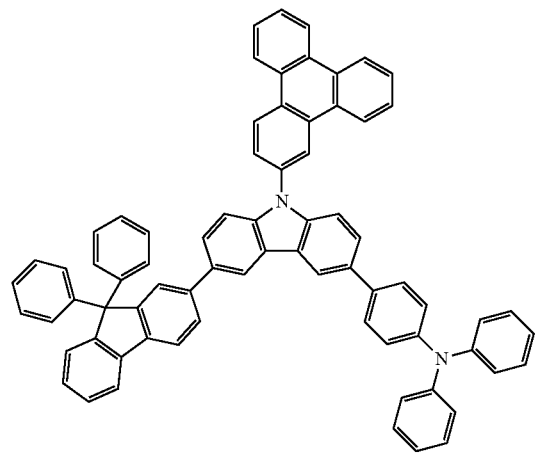
[A-21]
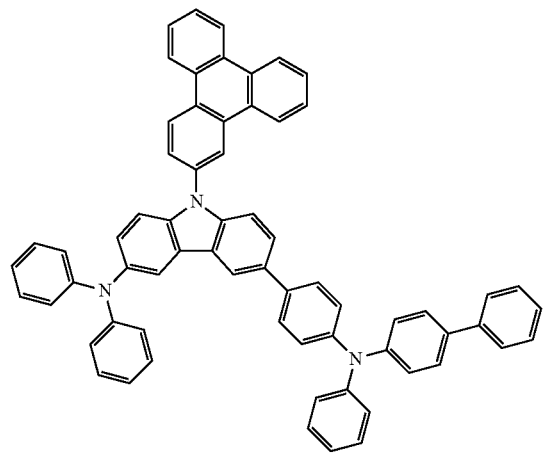
[A-22]
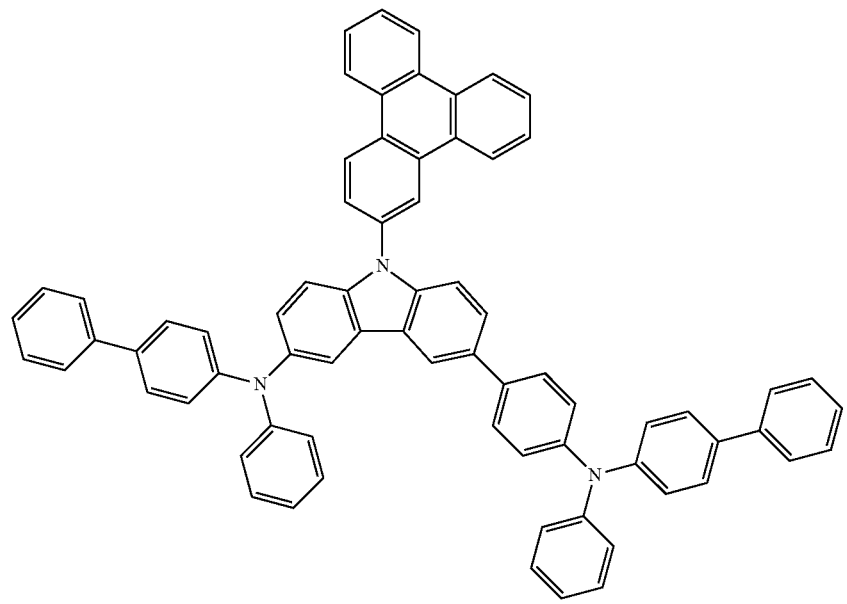

-continued
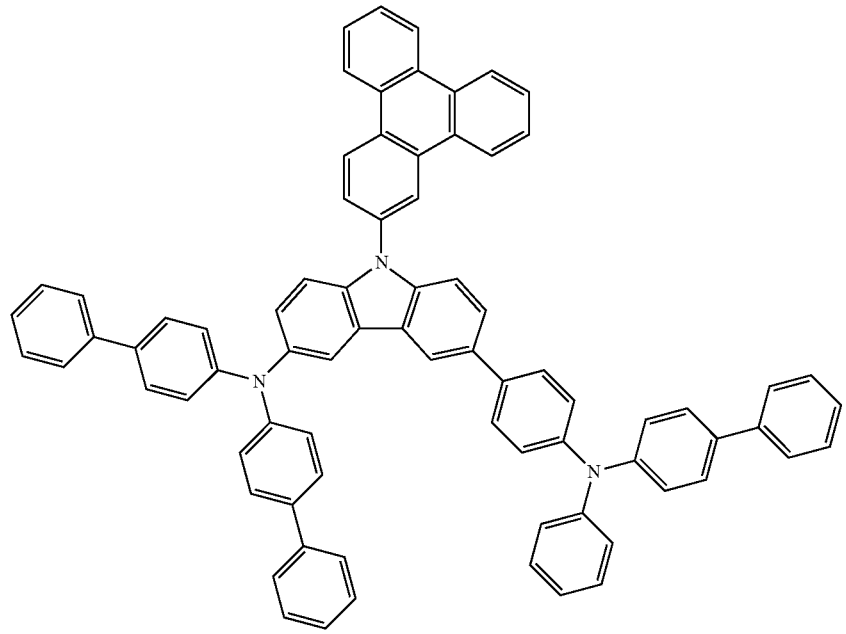
[A-23]
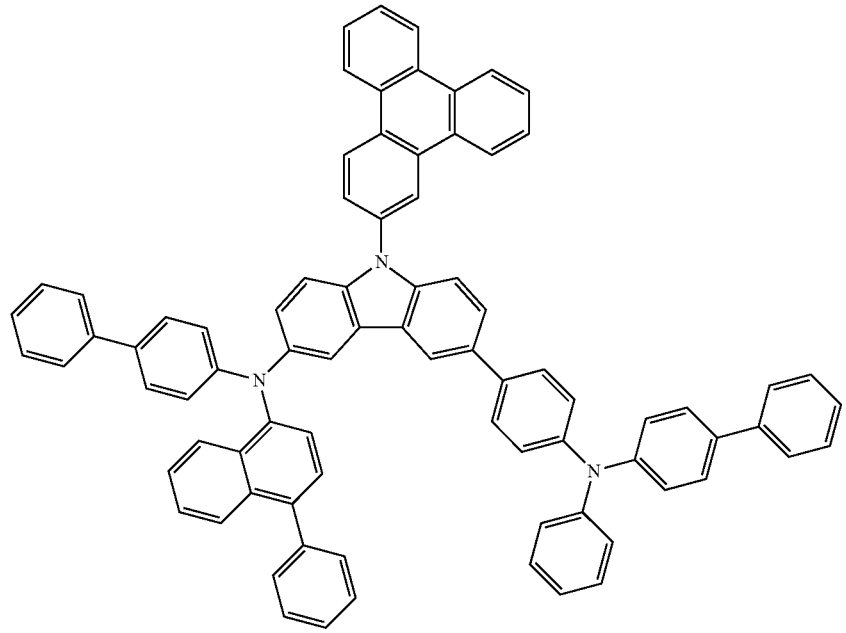
[A-24]

-continued
[A-25]
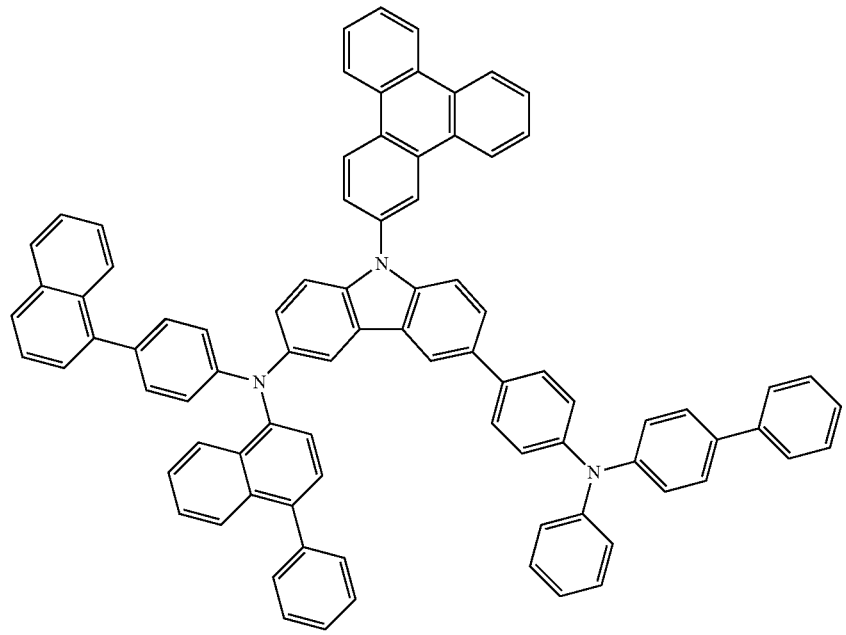
[A-26] [A-27]
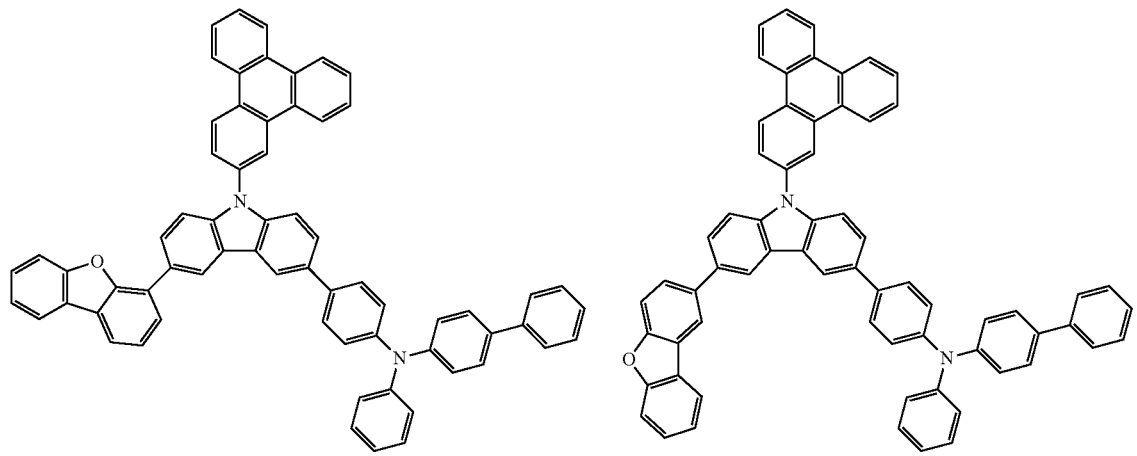
[A-28] [A-29]
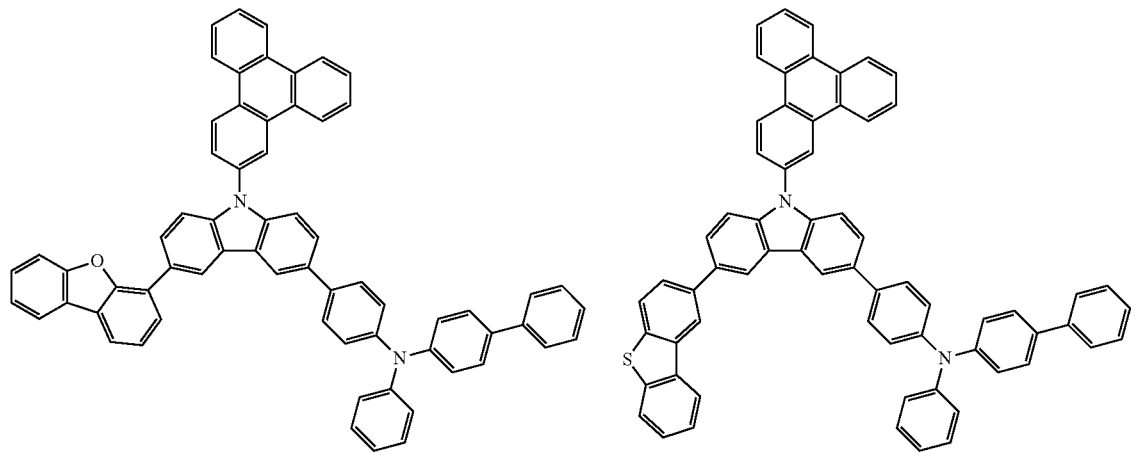

[A-30]
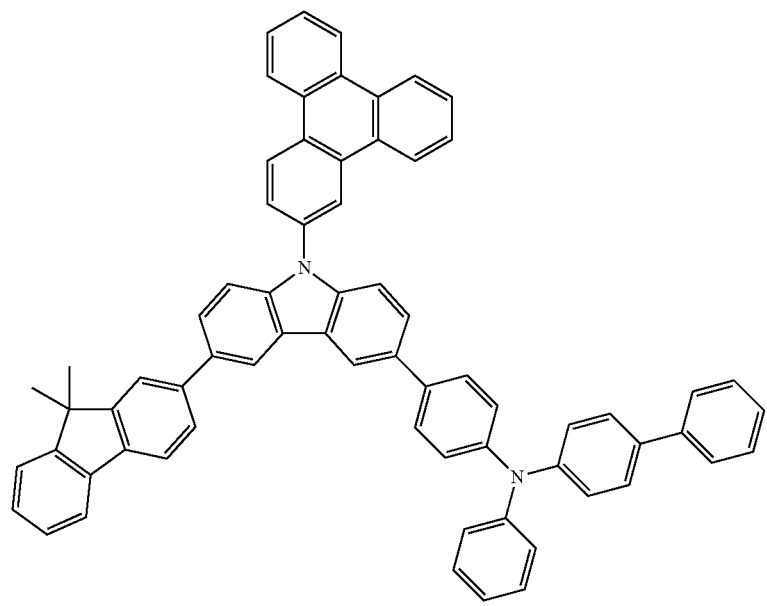
[A-31]
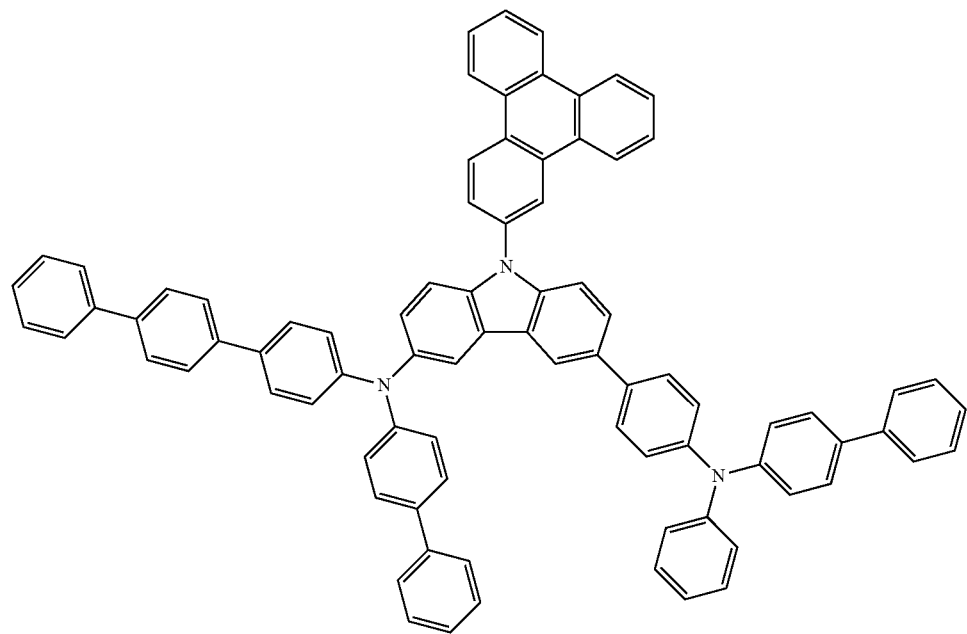

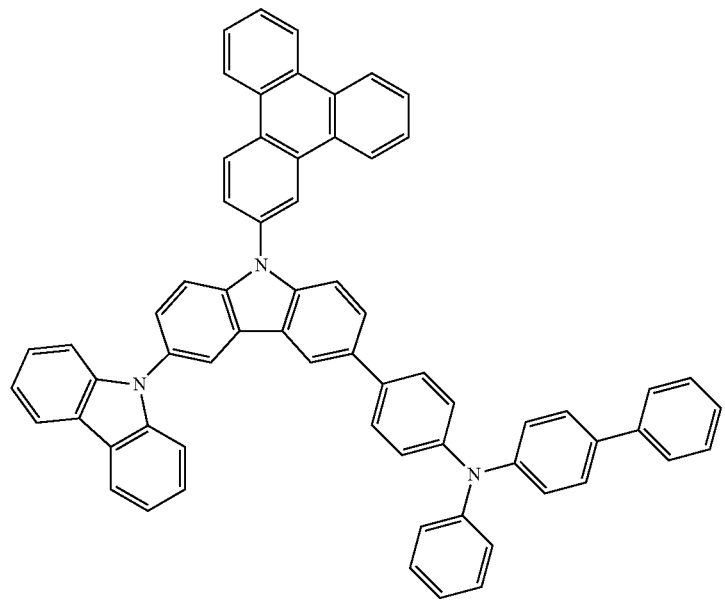
[A-32]
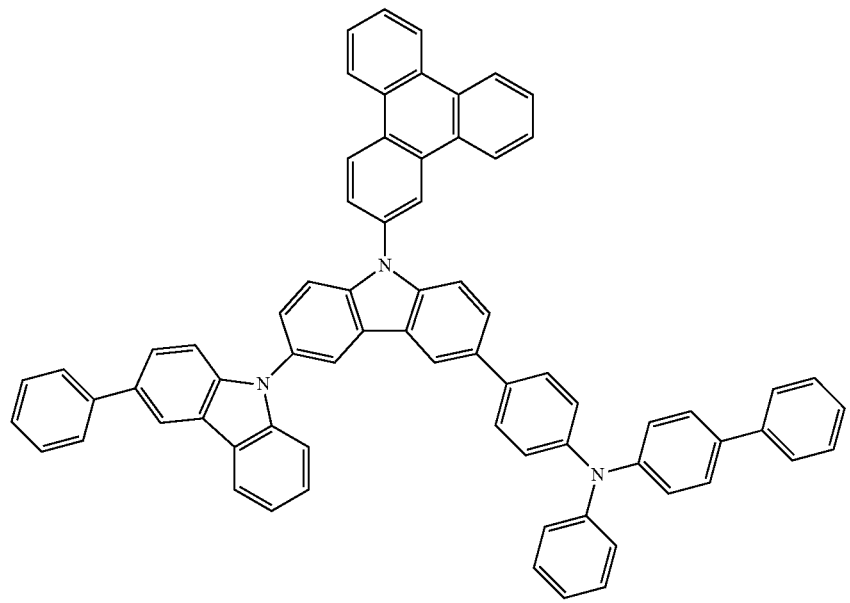
[A-33]

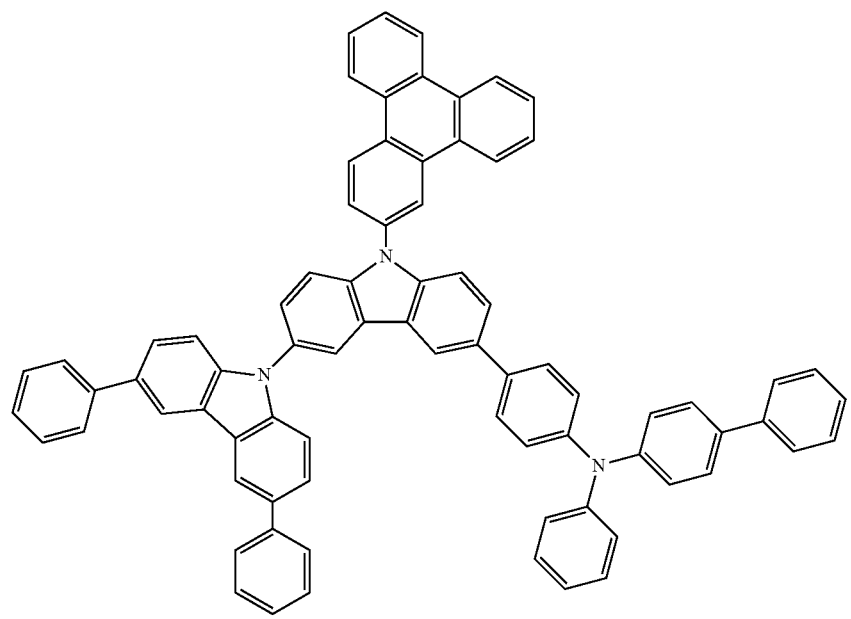
[A-34]
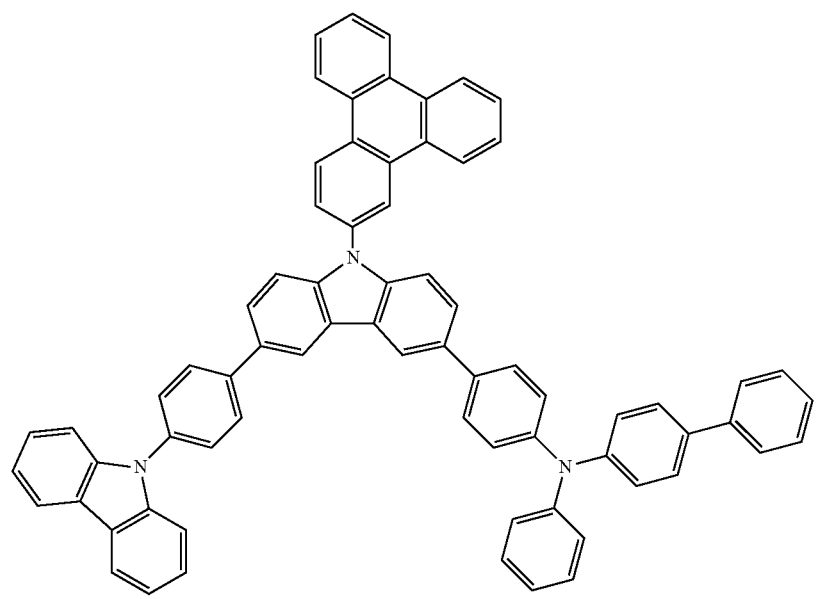
[A-35]

[A-36]
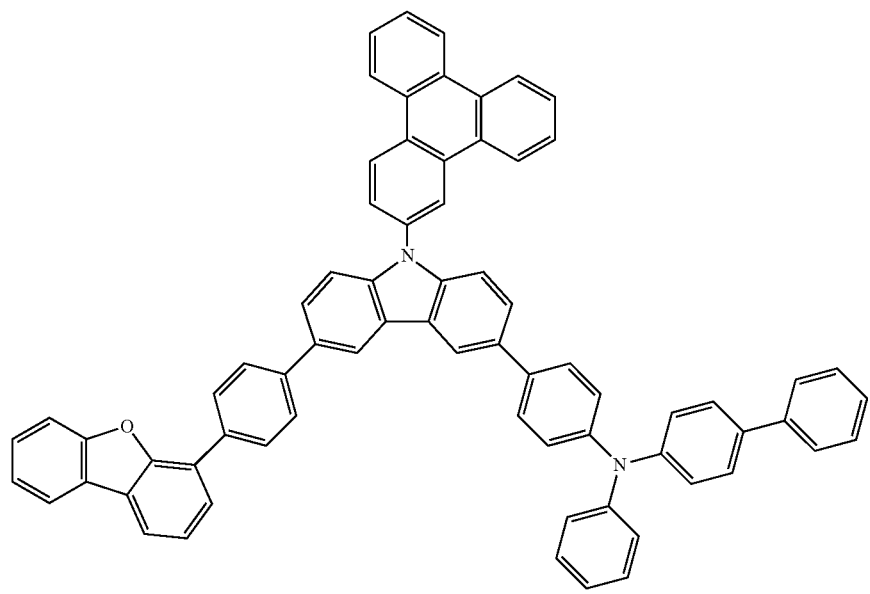
[A-37]
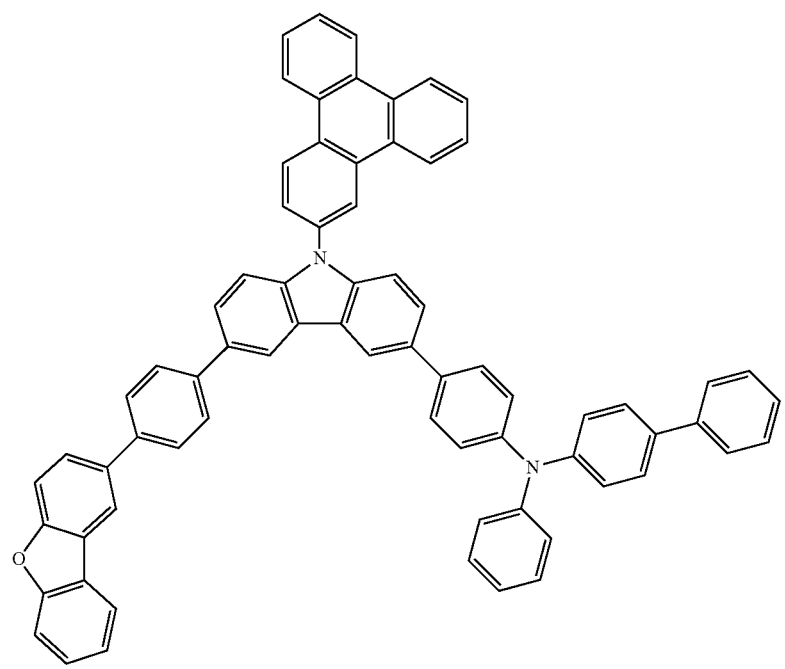

[A-38]
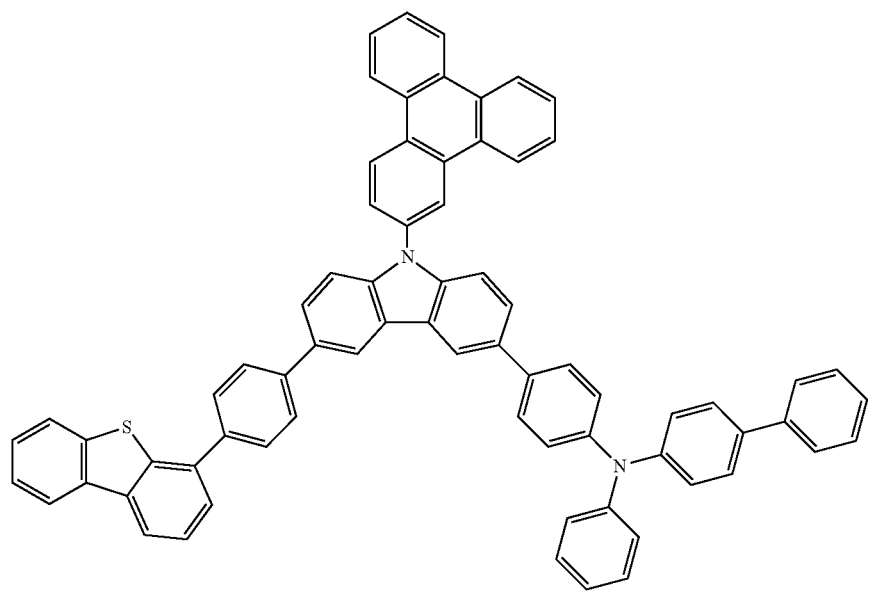
[A-39]
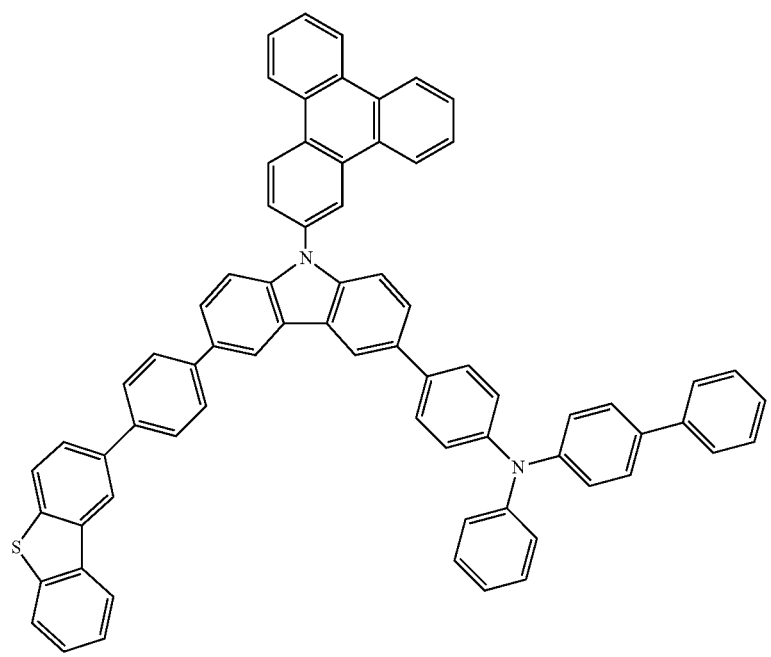

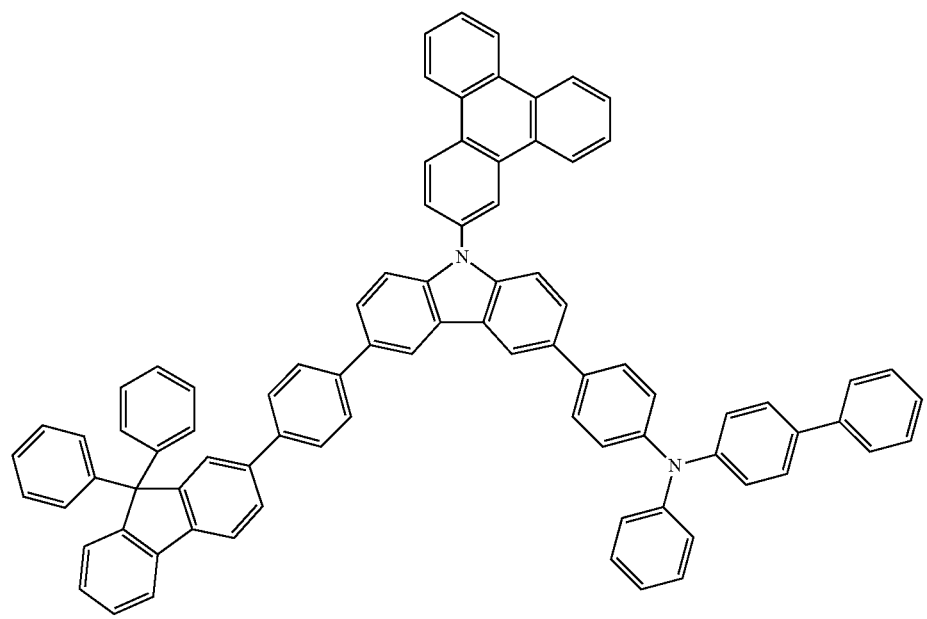
[A-40]
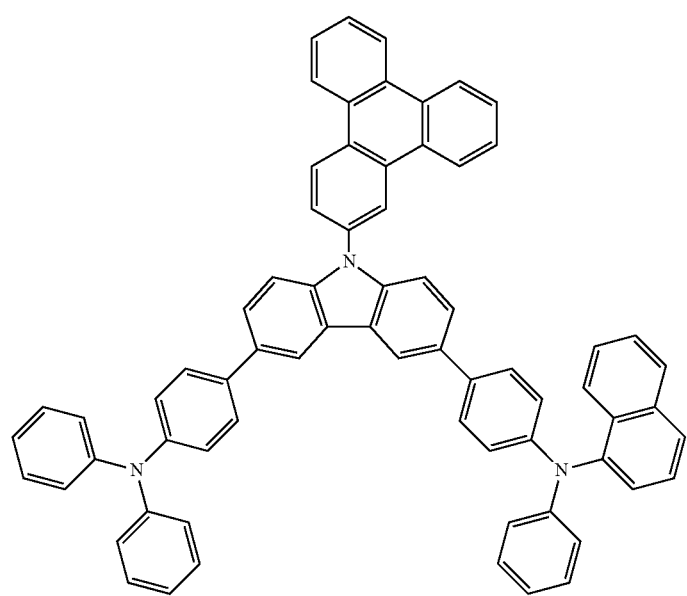
[A-41]

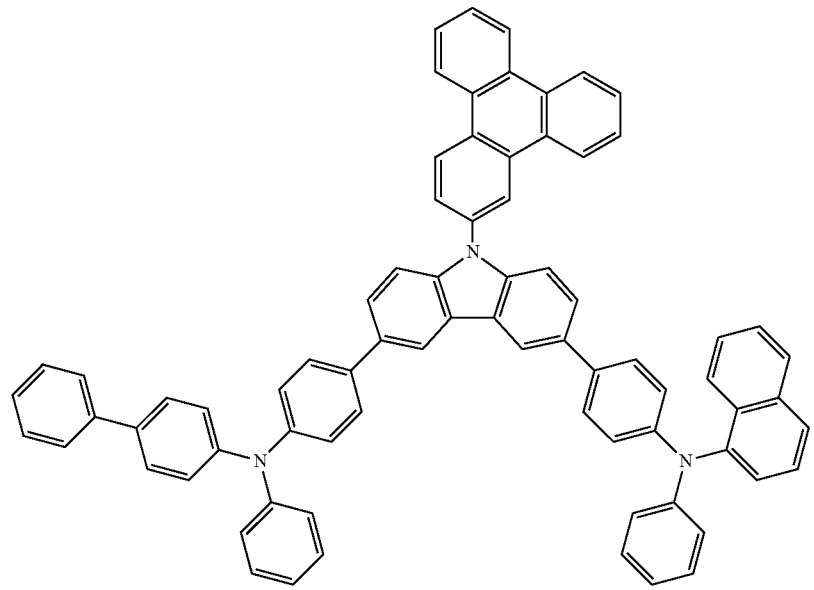
[A-42]
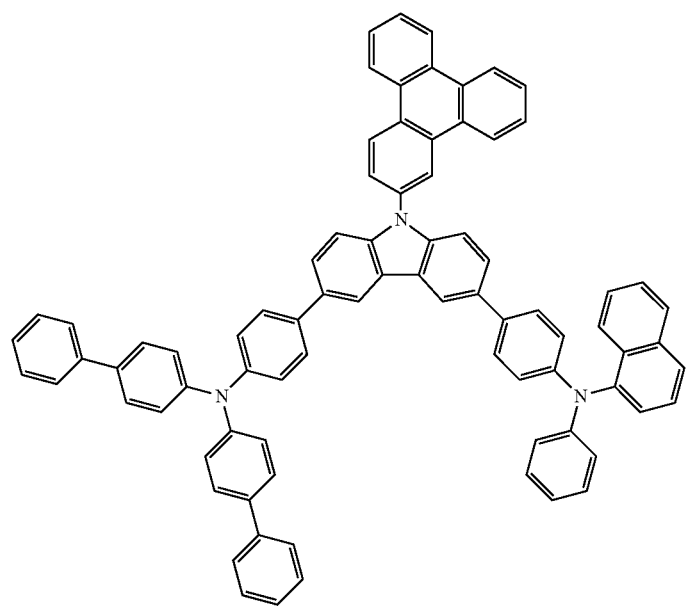
[A-43]

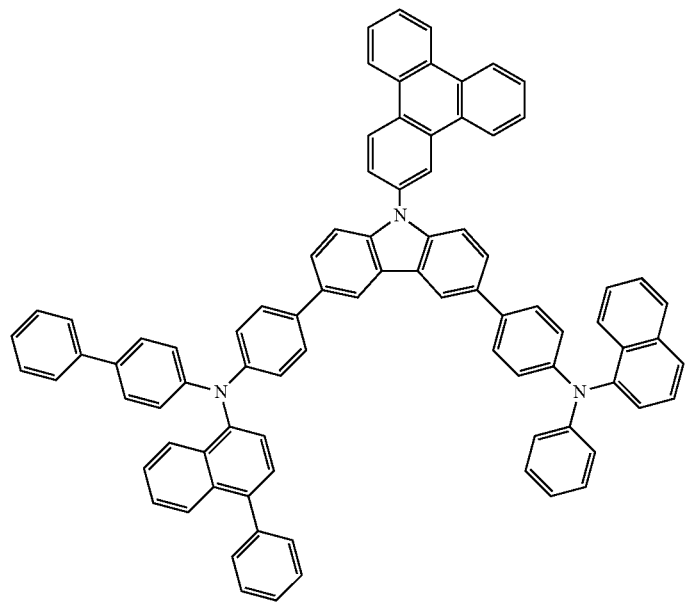
[A-44]
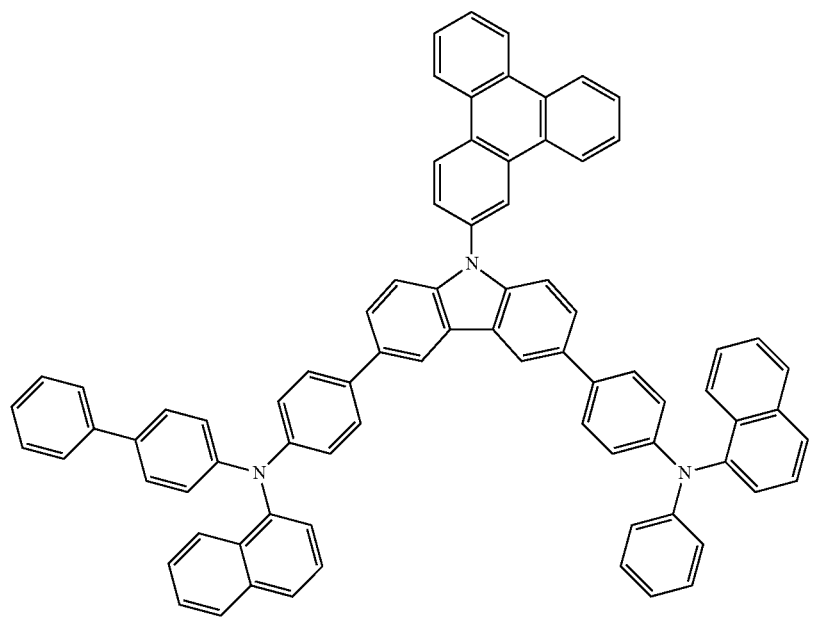
[A-45]

[A-46]
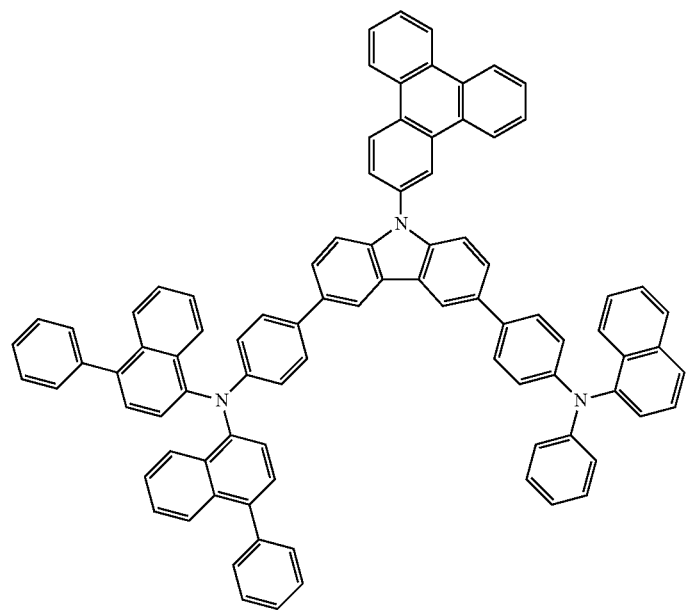
[A-47]
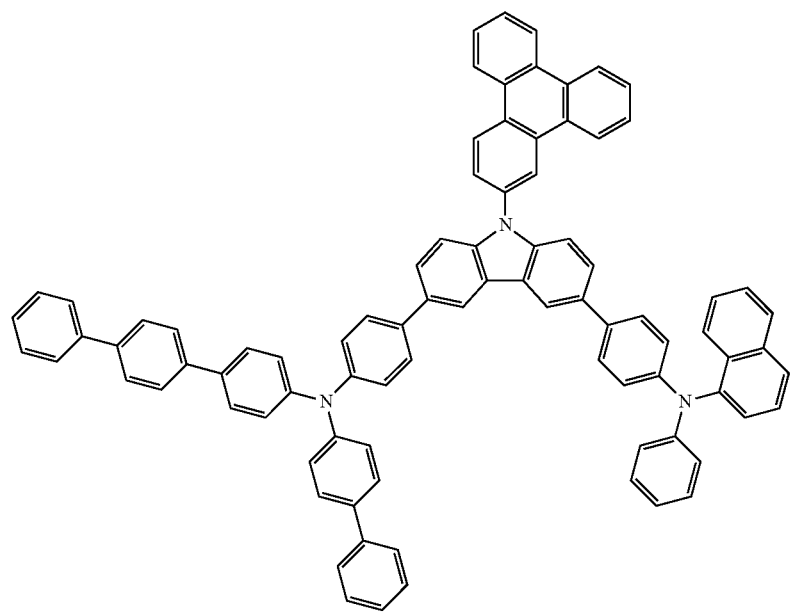

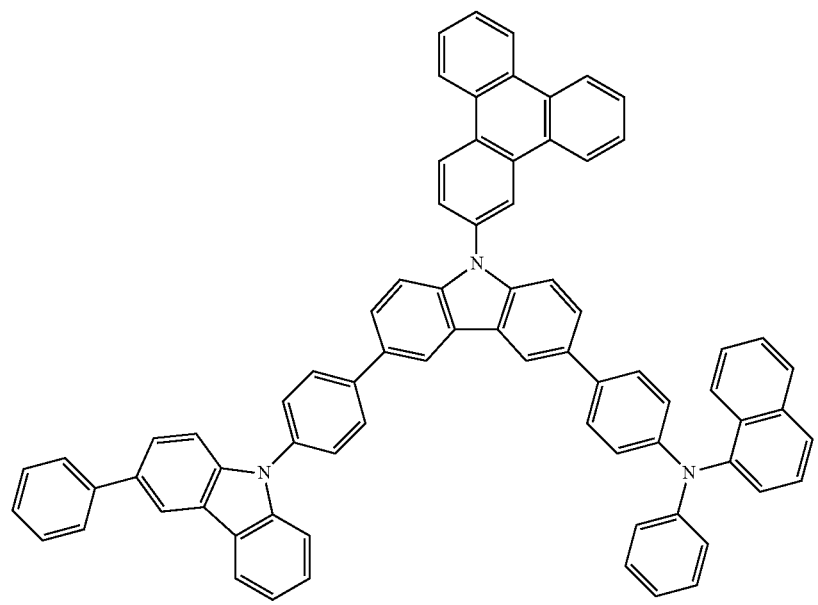
[A-48]
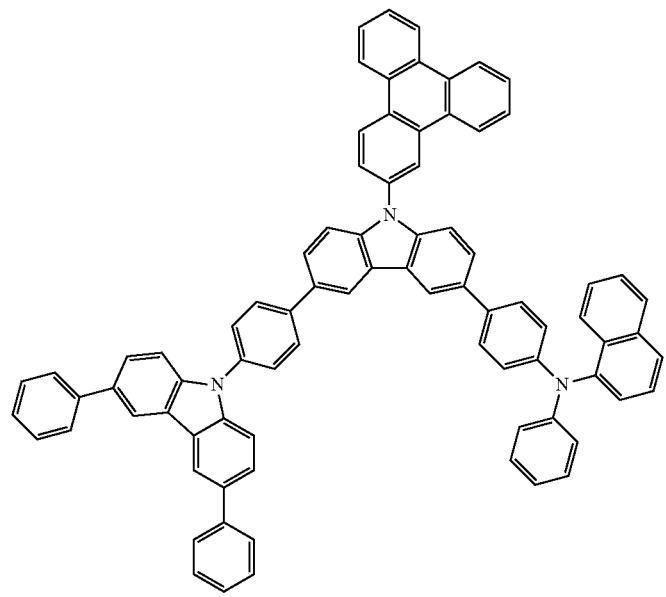
[A-49]

-continued
[A-50]
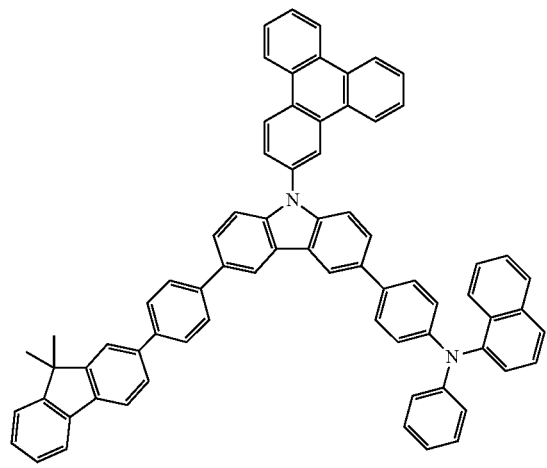
[A-51]
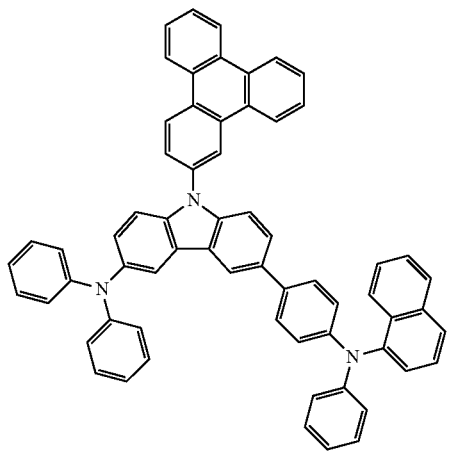
[A-52]
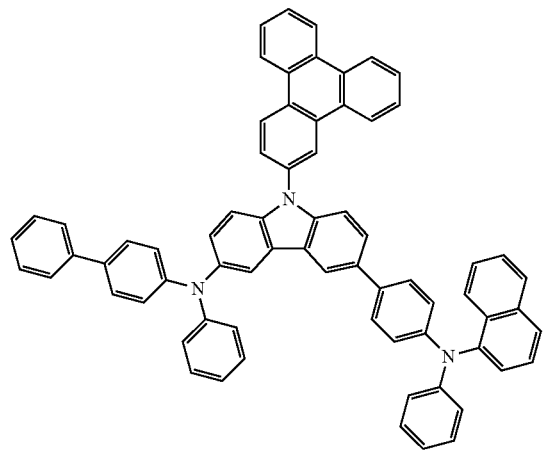
[A-53]
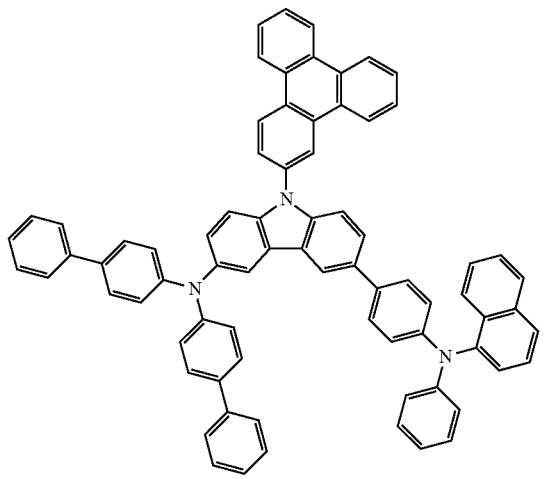
[A-54]
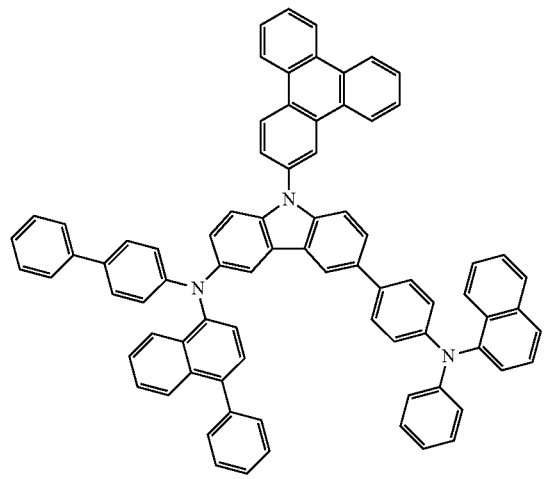
[A-55]
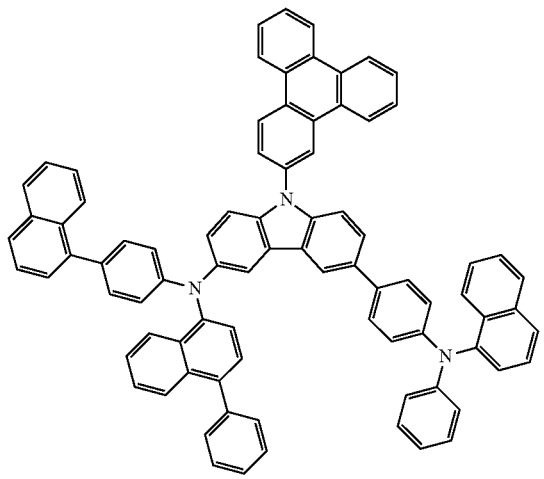

[A-56]
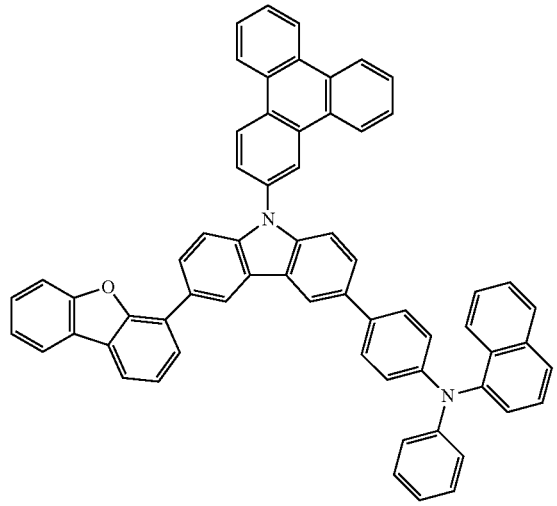
[A-57]
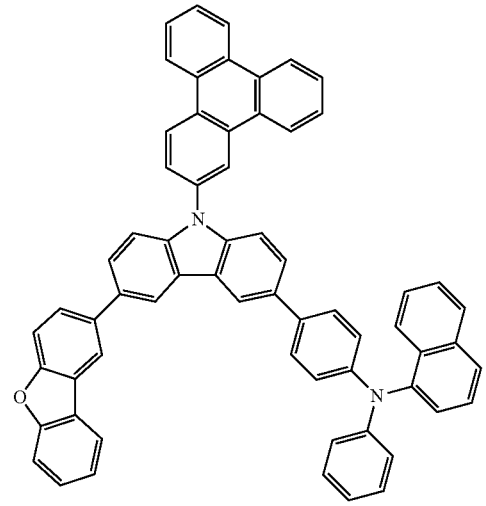
[A-58]
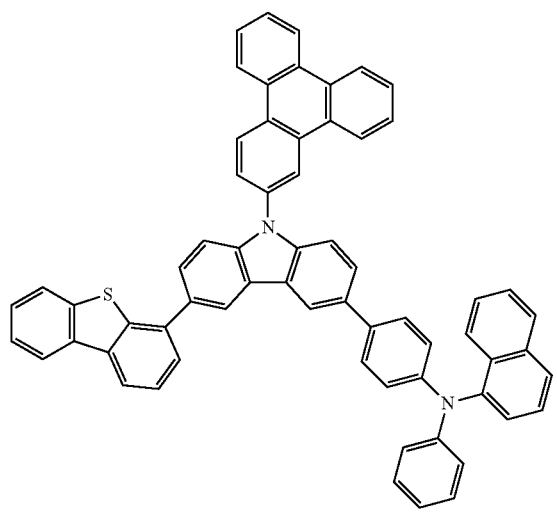
[A-59]
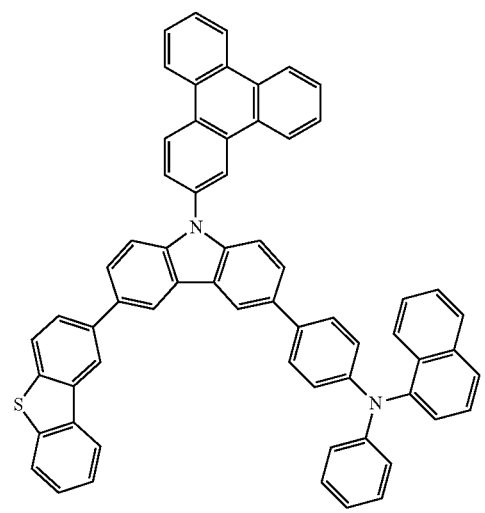
[A-60]
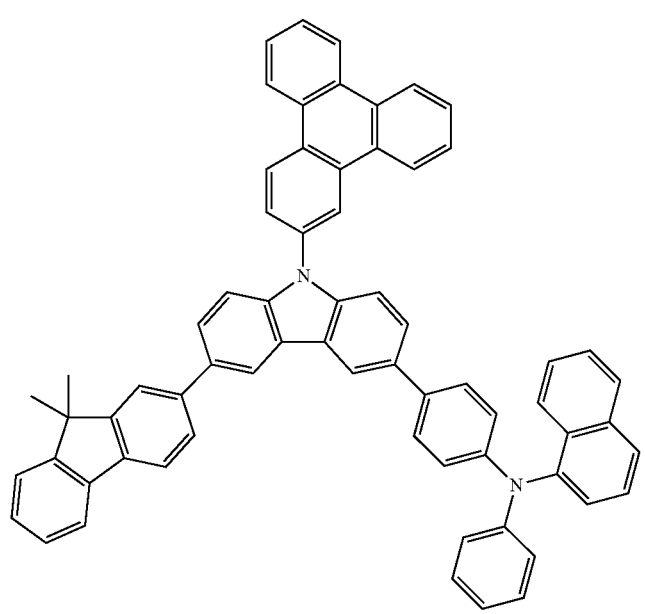

[A-61]
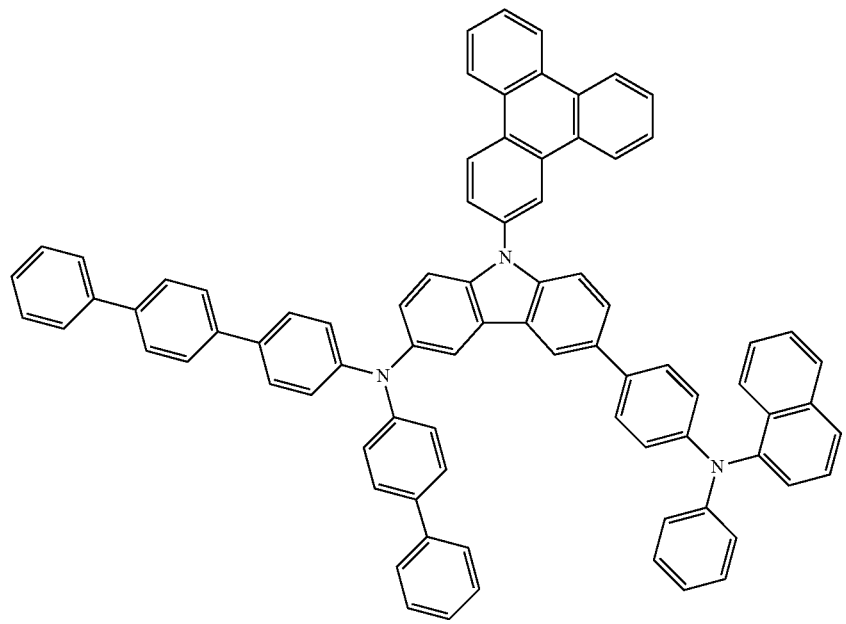
[A-62]
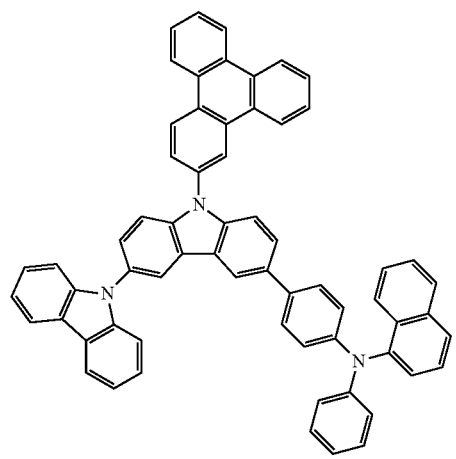
[A-63]
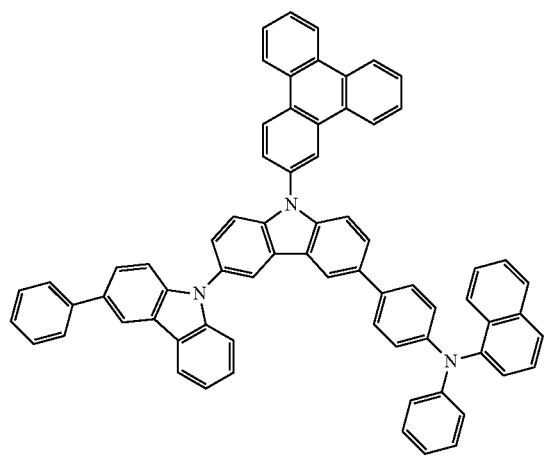
[A-64]
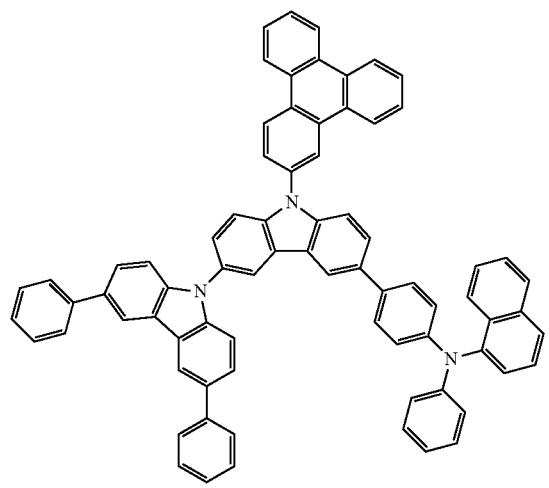
[A-65]
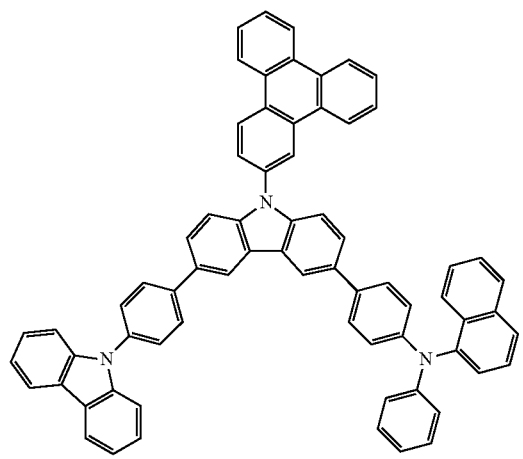

-continued
[A-66]
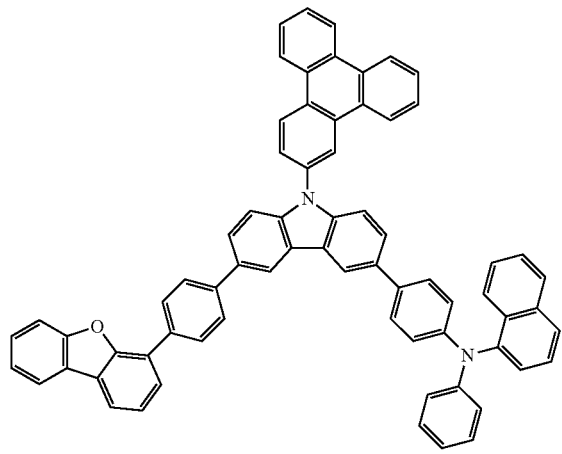
[A-67]
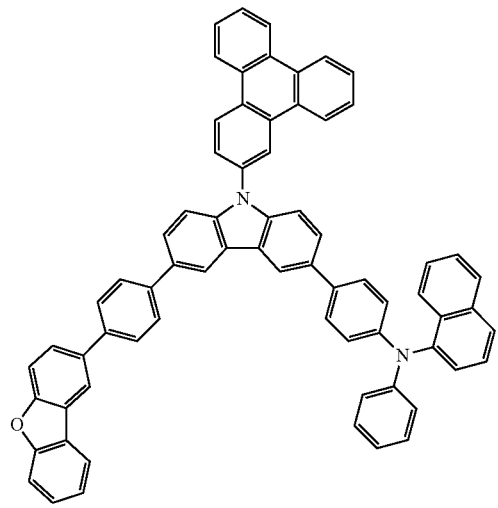
[A-68]
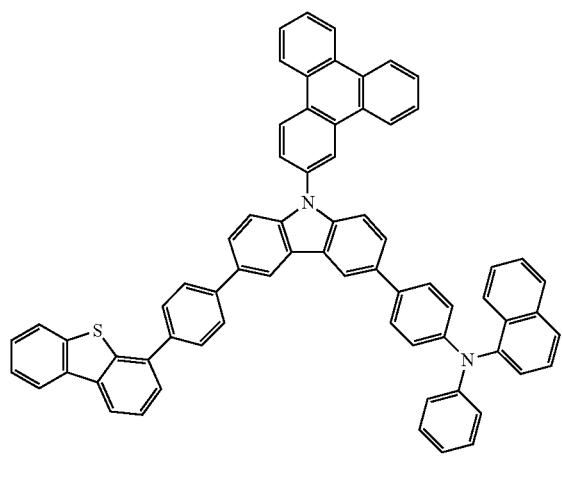
[A-69]
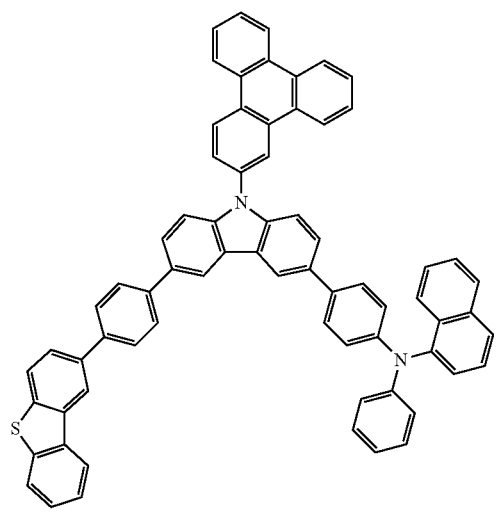
[A-70]
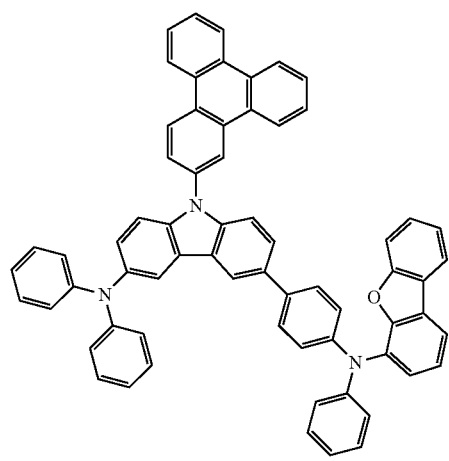
[A-71]
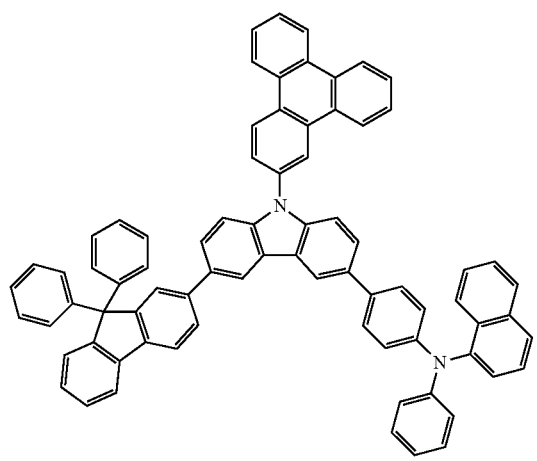

-continued
[A-72]
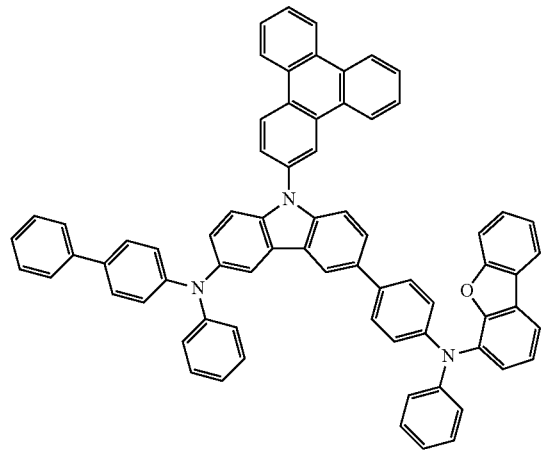
[A-73]
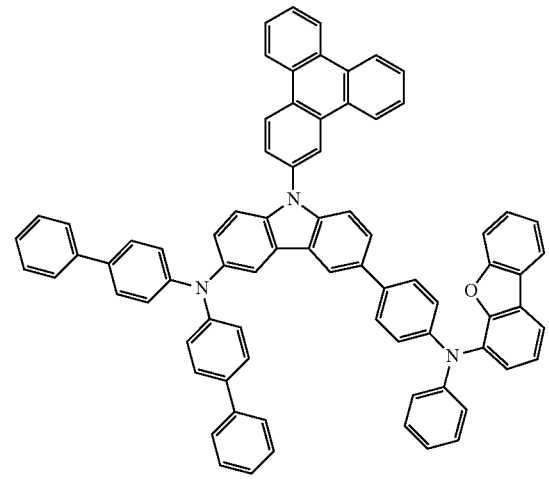
[A-74]
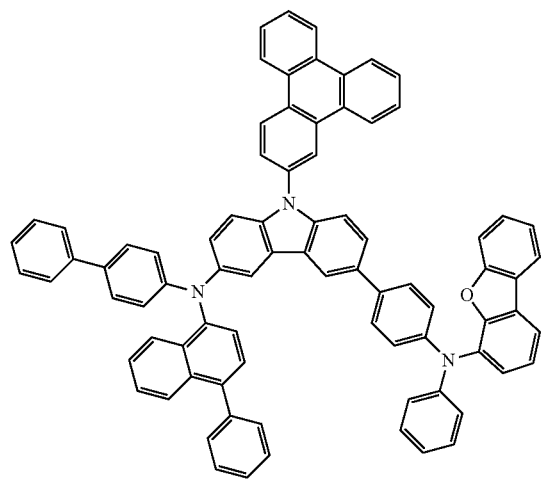
[A-75]
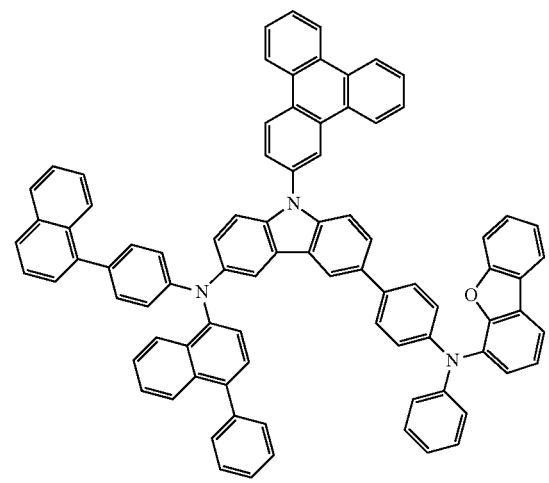
[A-76]
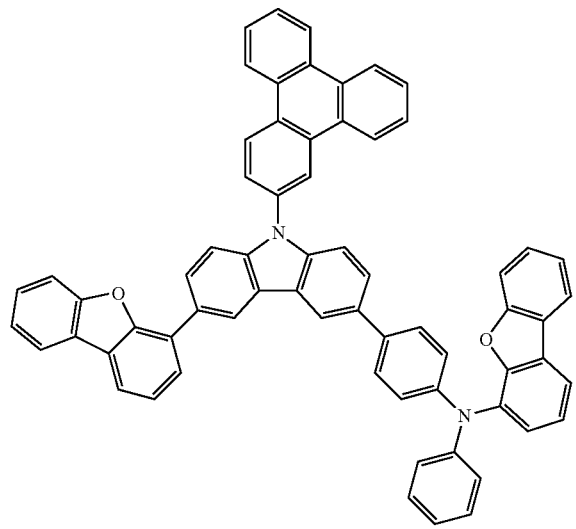
[A-77]
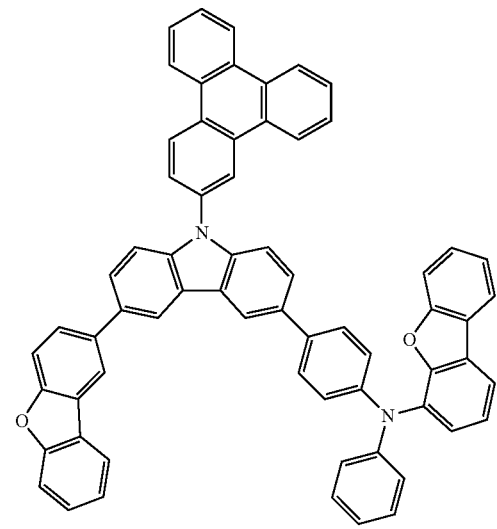

[A-78]
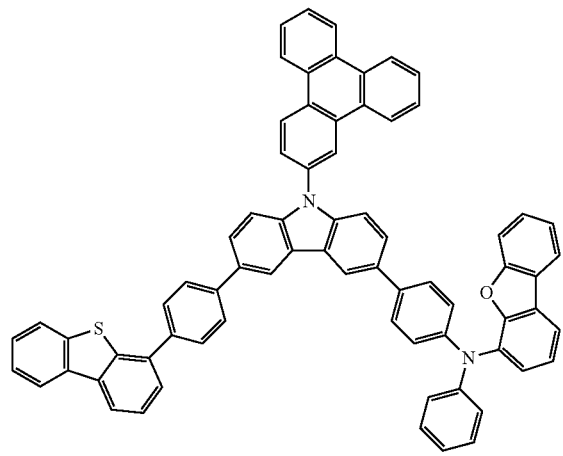
[A-79]
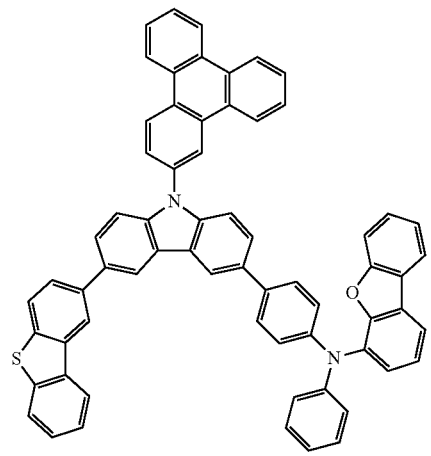
[A-80]
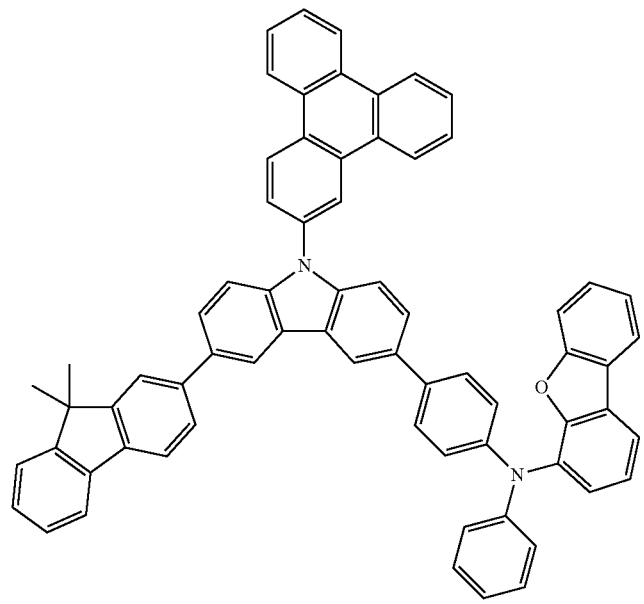

-continued
[A-81]
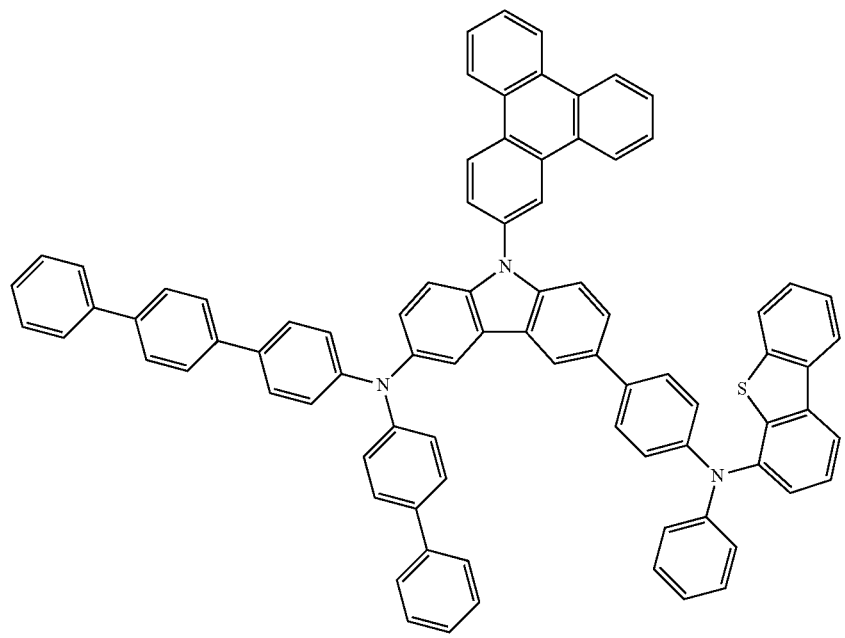
[A-82]
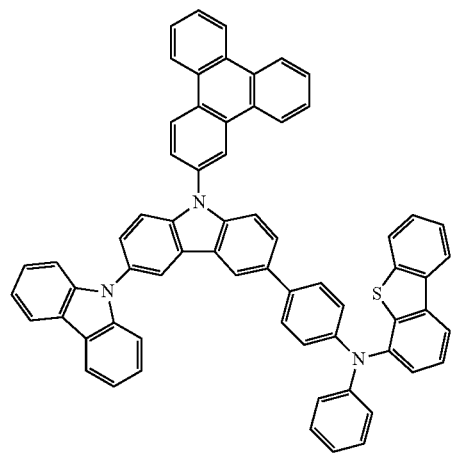
[A-83]
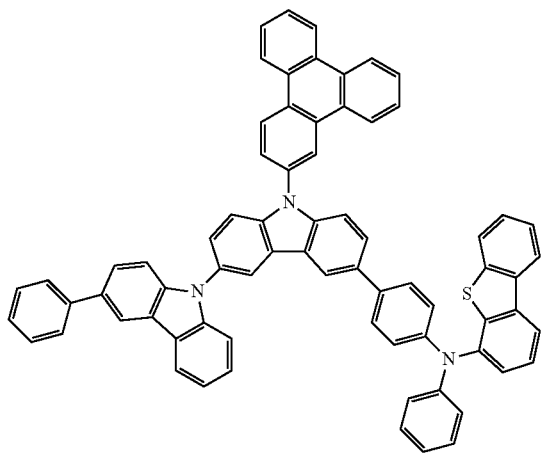
[A-84]
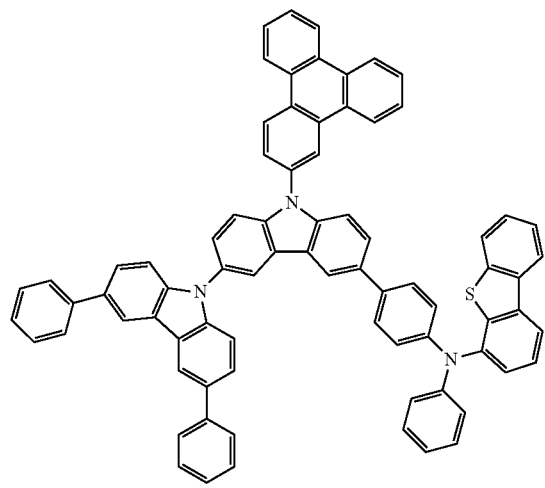
[A-85]
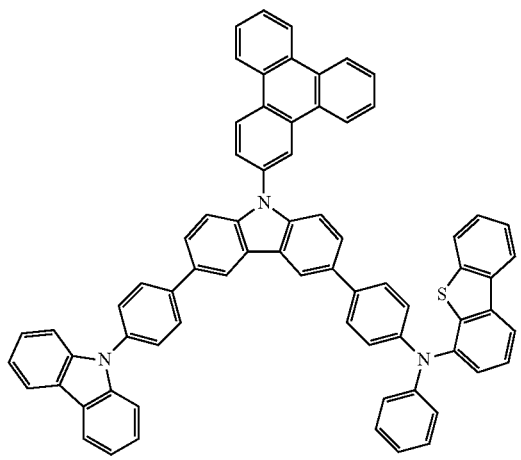

-continued
[A-86]
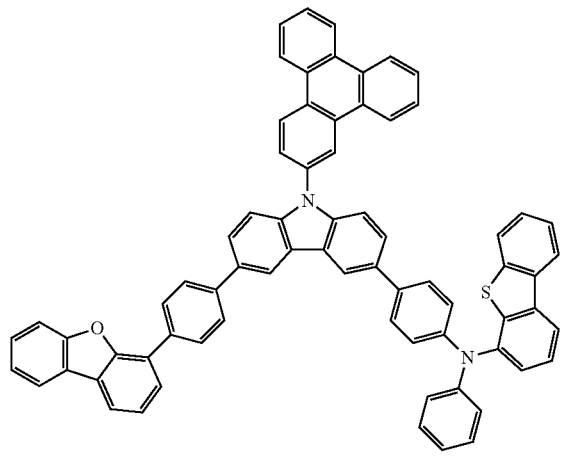
[A-87]
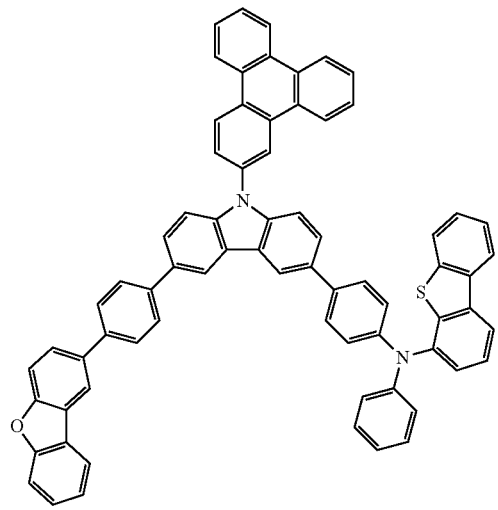
[A-88]
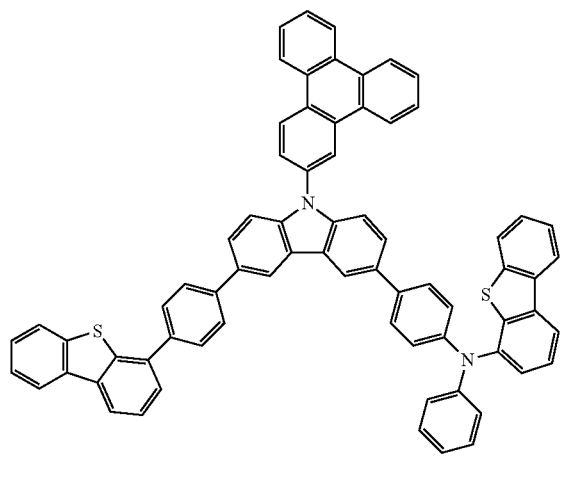
[A-89]
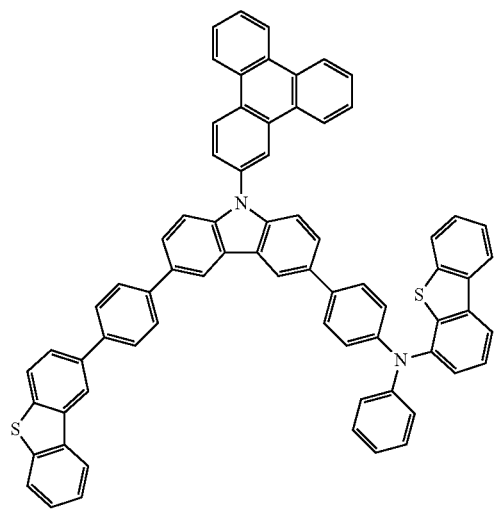
[A-90]
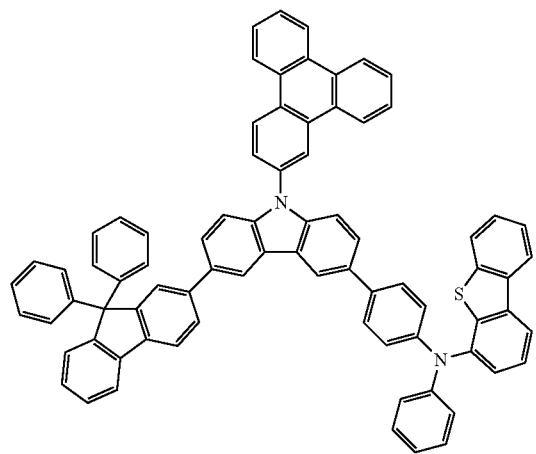
[A-91]
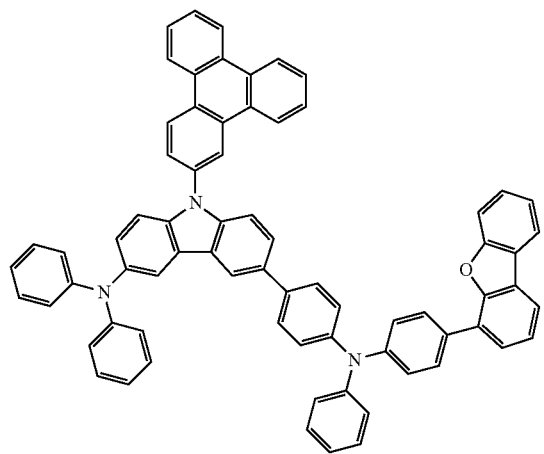

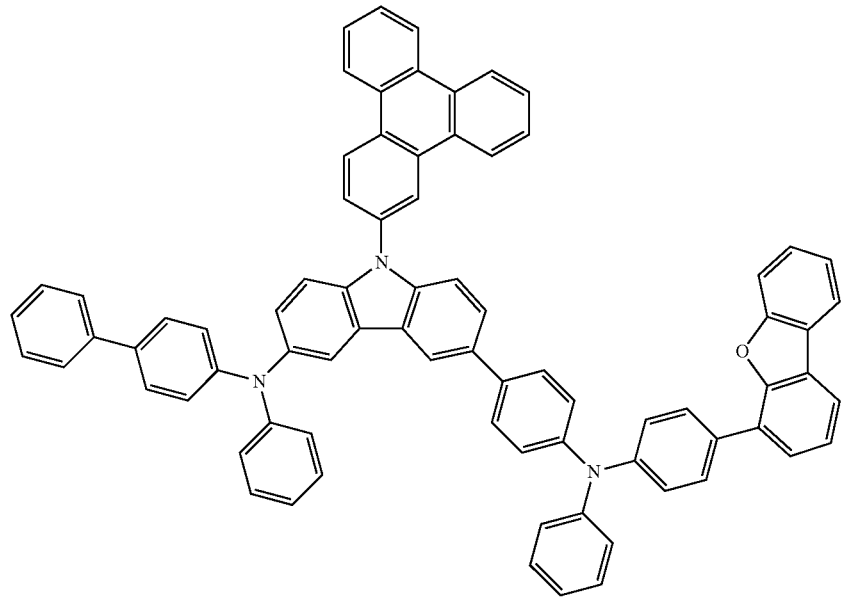
[A-92]
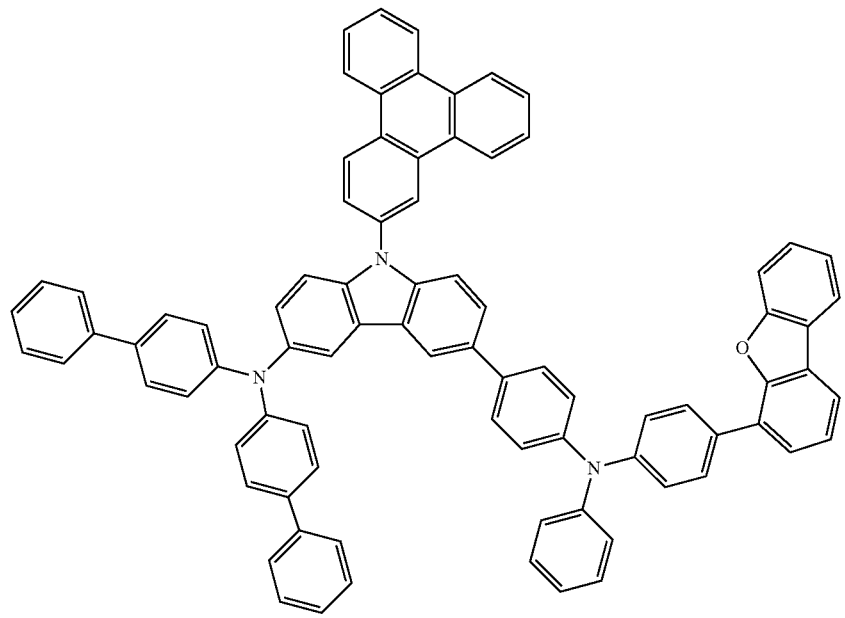
[A-93]

-continued
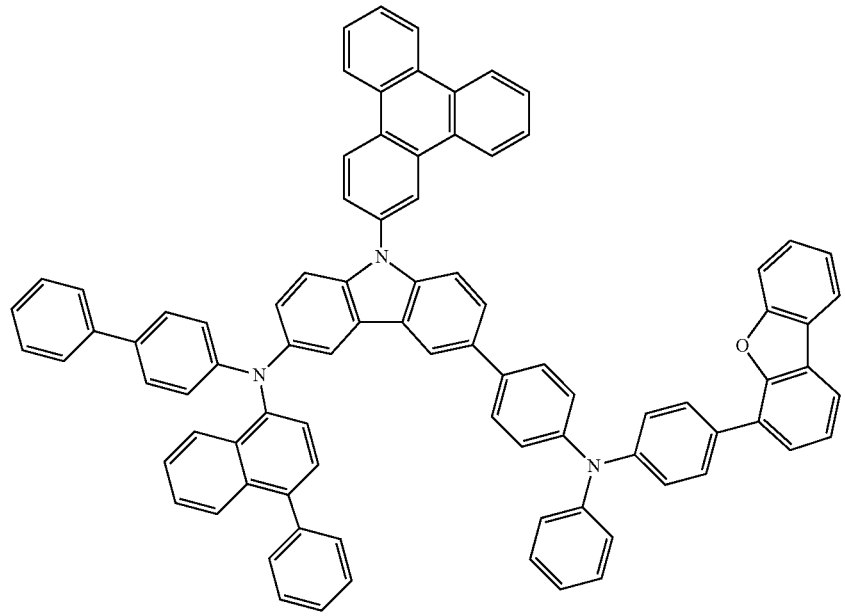
[A-94]
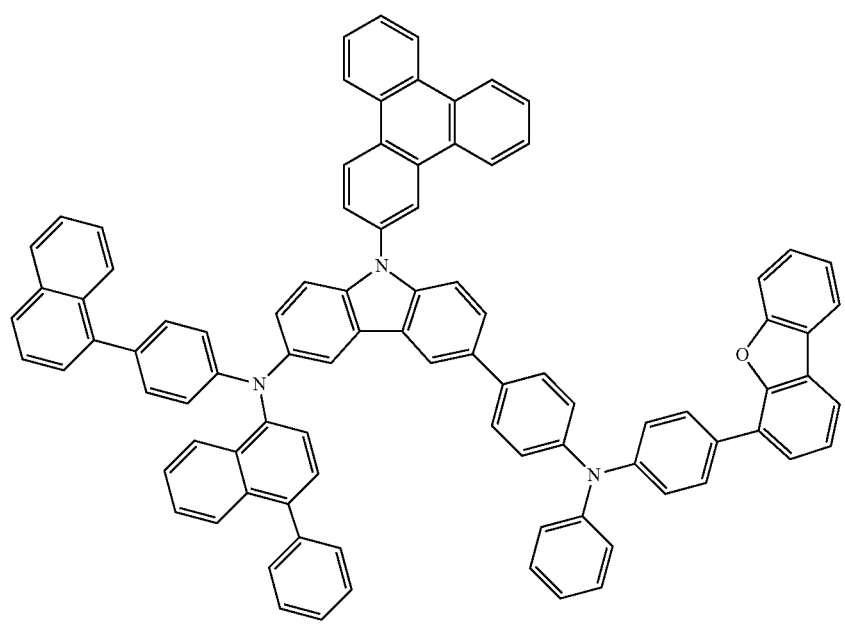
[A-95]

-continued
[A-96]
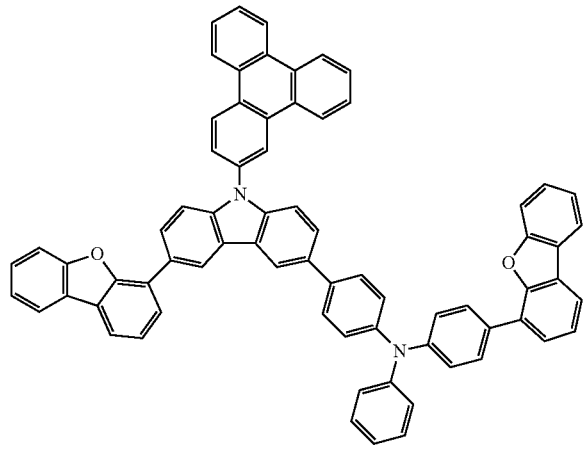
[A-97]
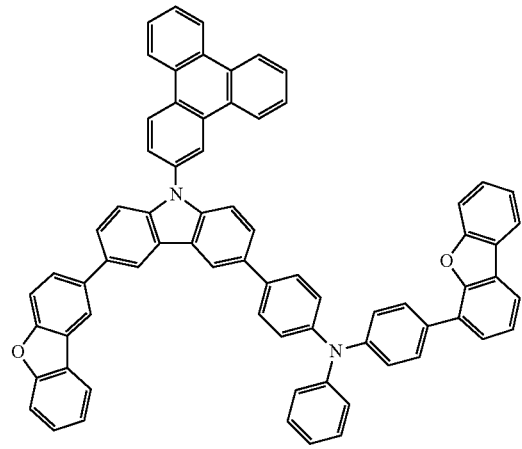
[A-98]
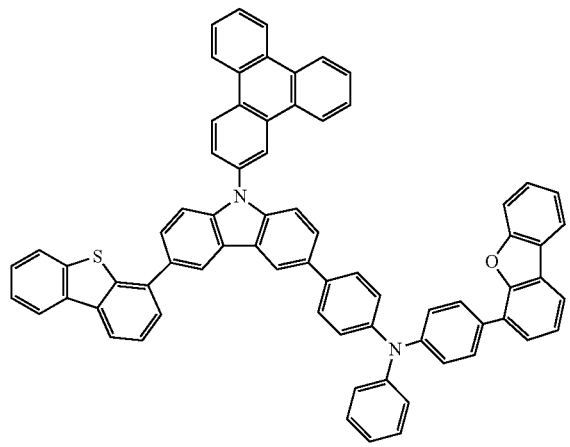
[A-99]
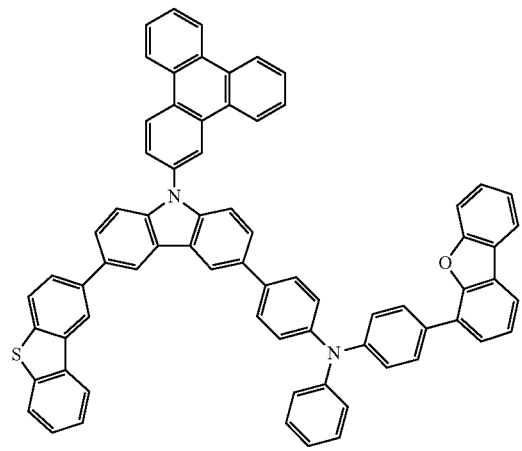
[A-100]
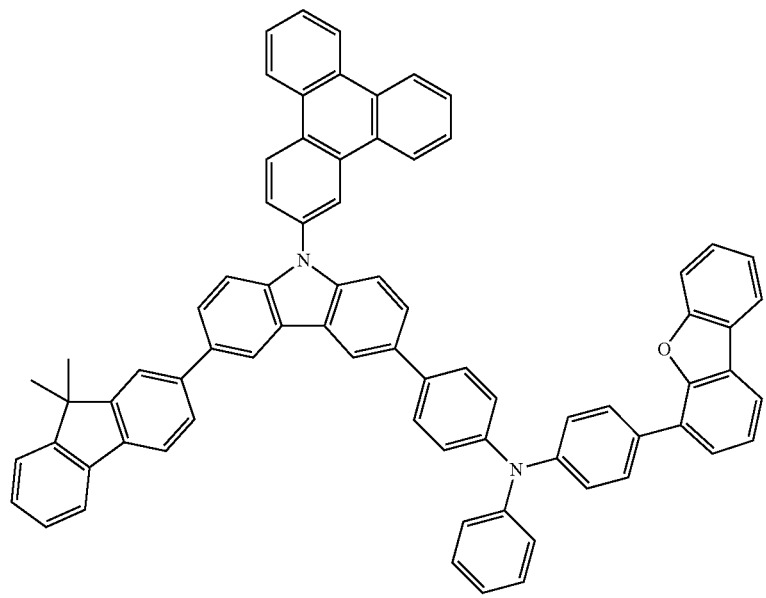

-continued
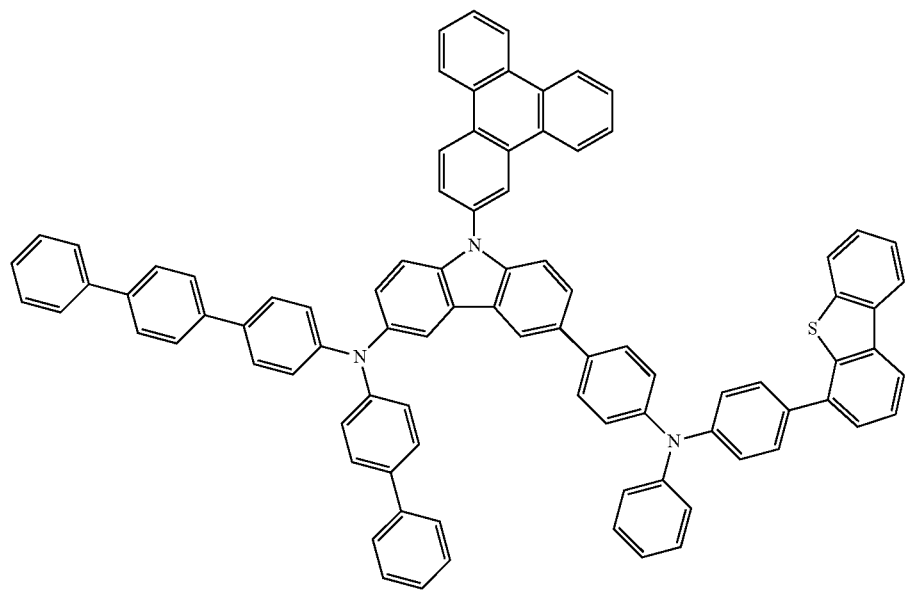
[A-101]
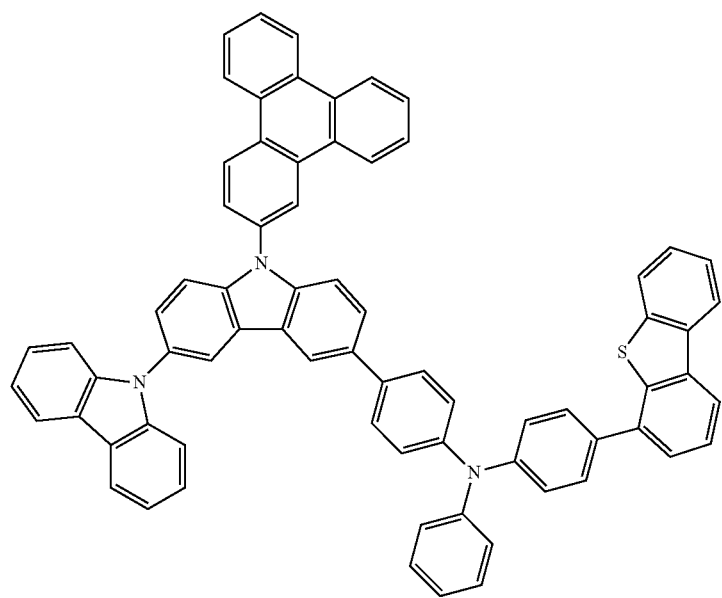
[A-102]

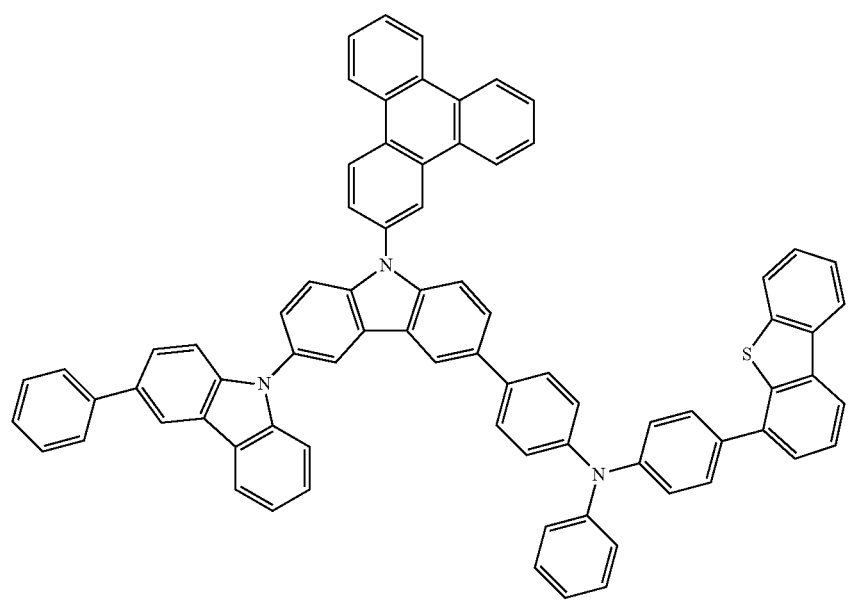
[A-103]
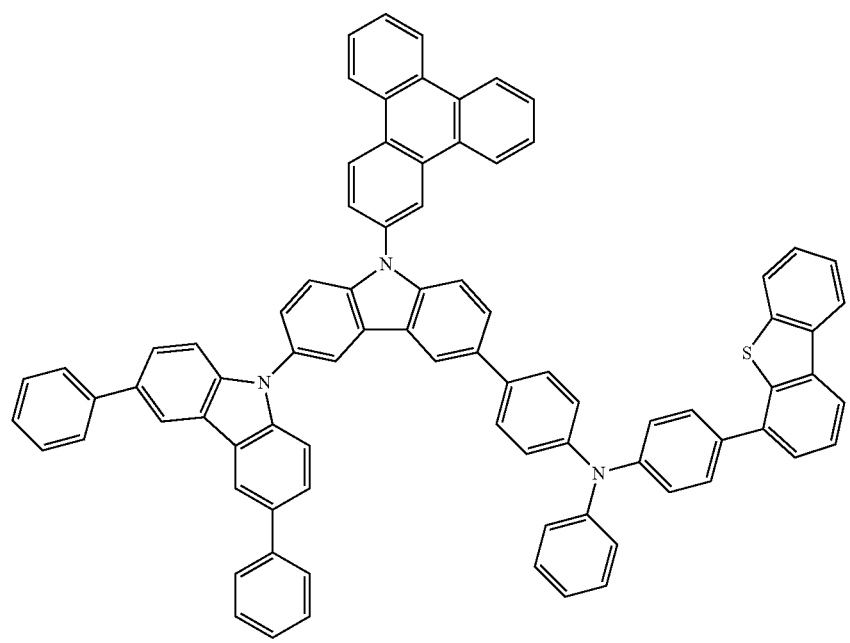
[A-104]

-continued
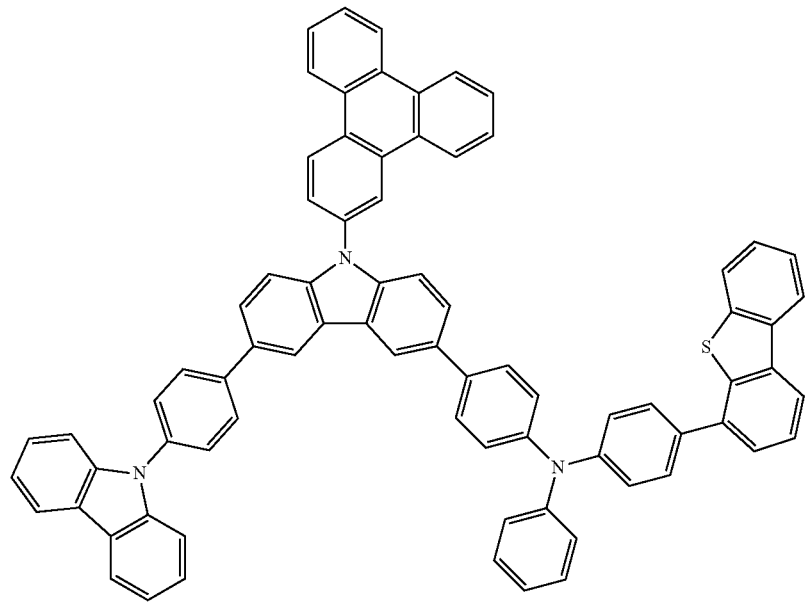
[A-105]
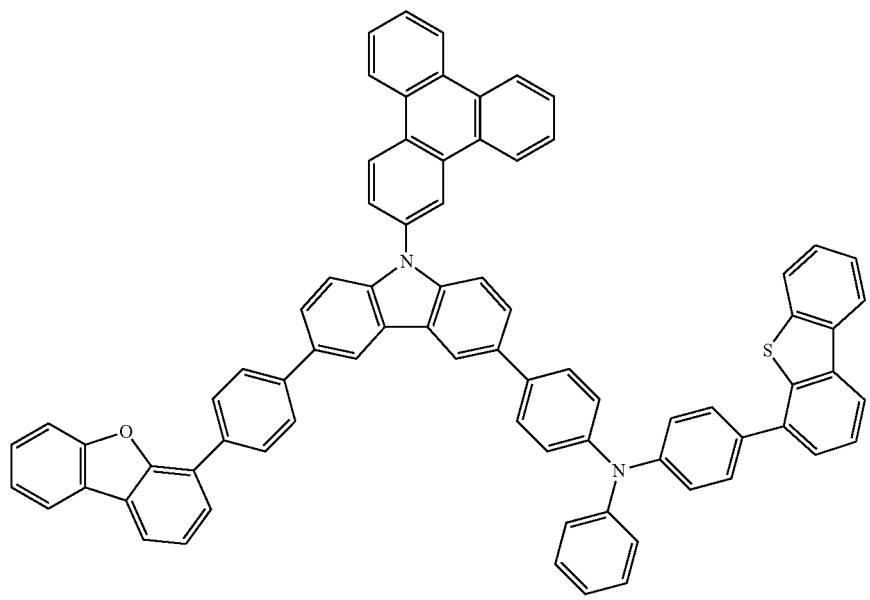
[A-106]

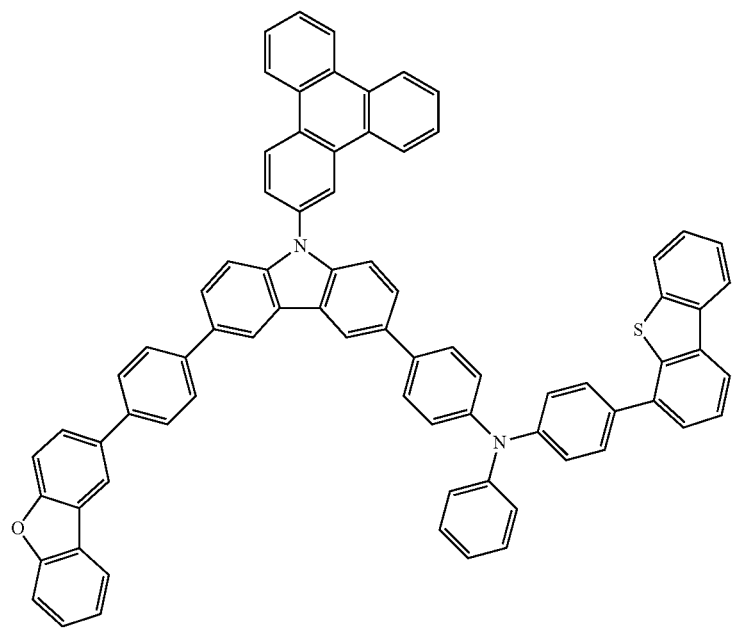
[A-107]
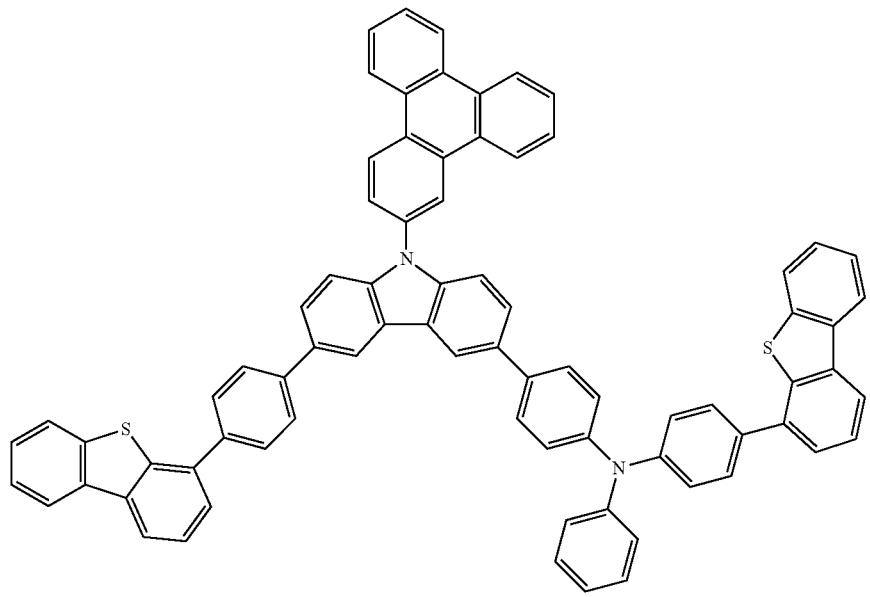
[A-108]

[A-109]
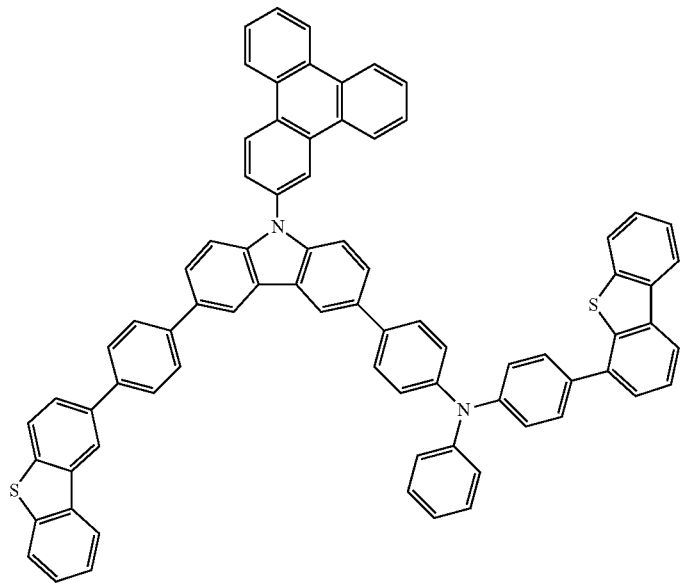
[A-110]
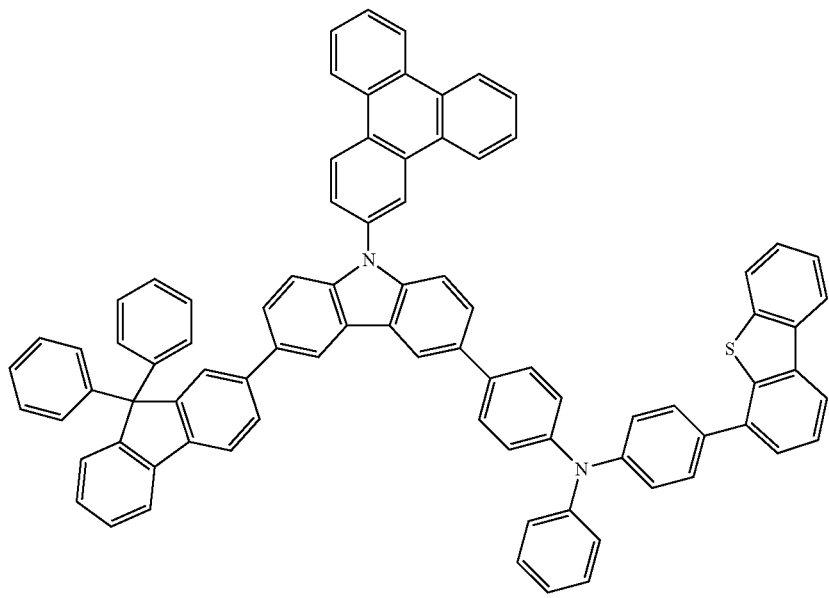
[A-111]
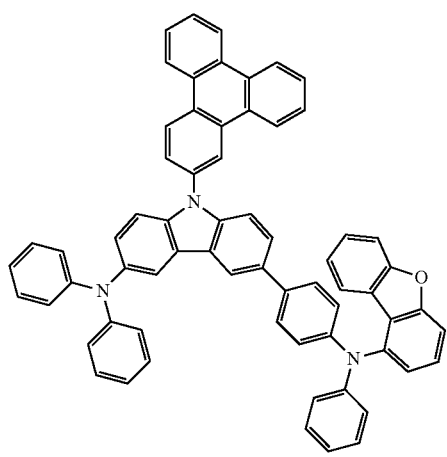
[A-112]
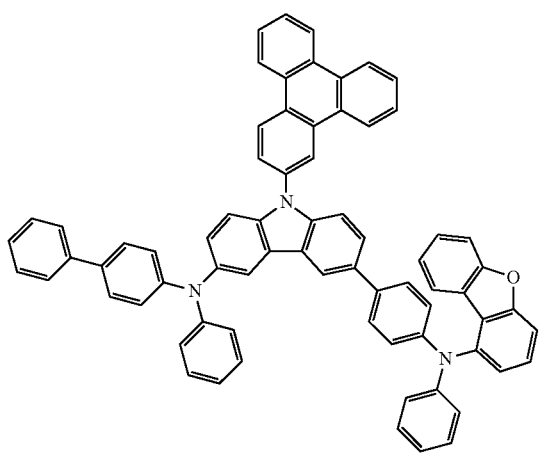

-continued
[A-113]
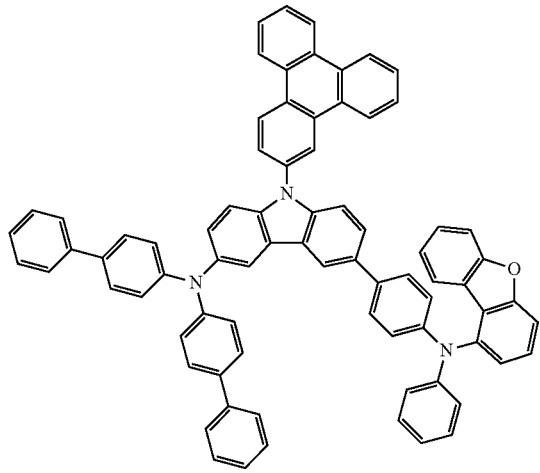
[A-114]
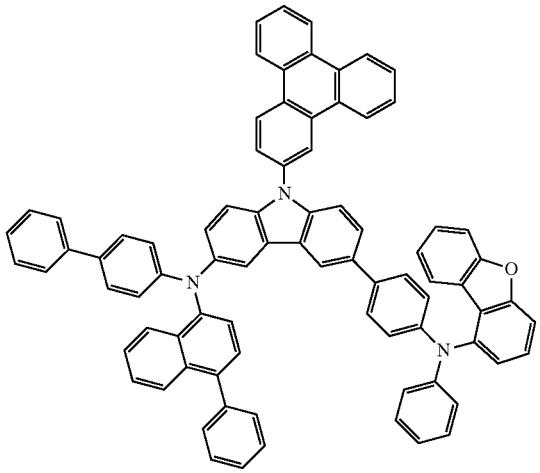
[A-115]
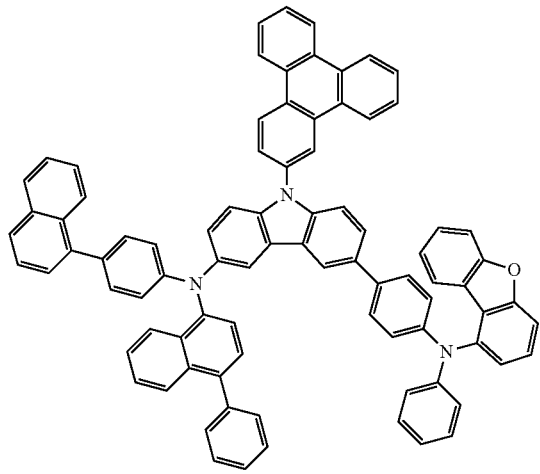
[A-116]
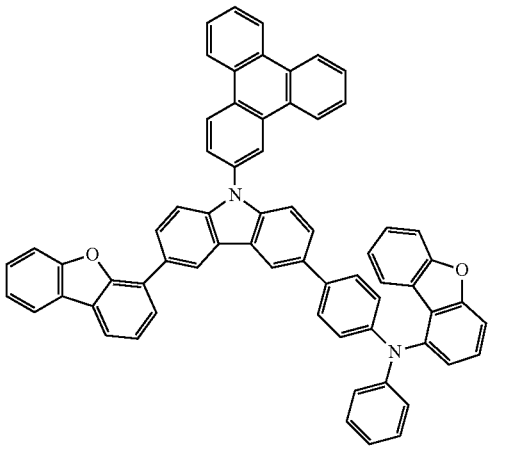
[A-117]
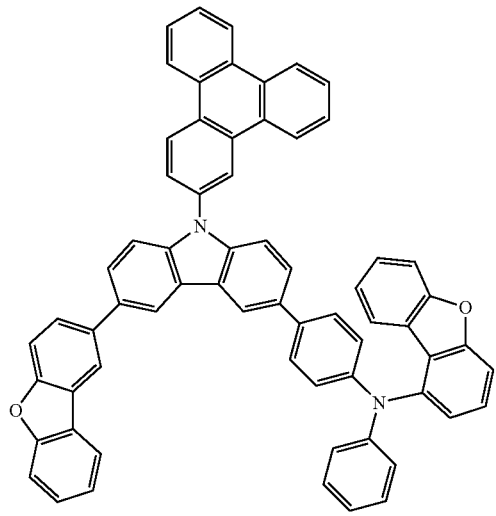
[A-118]
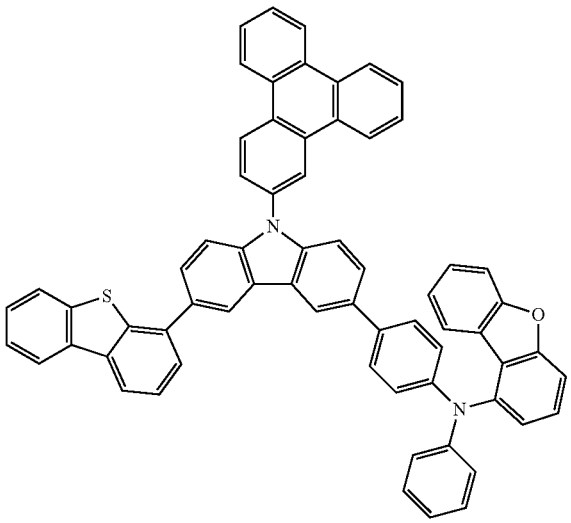

-continued
[A-119]
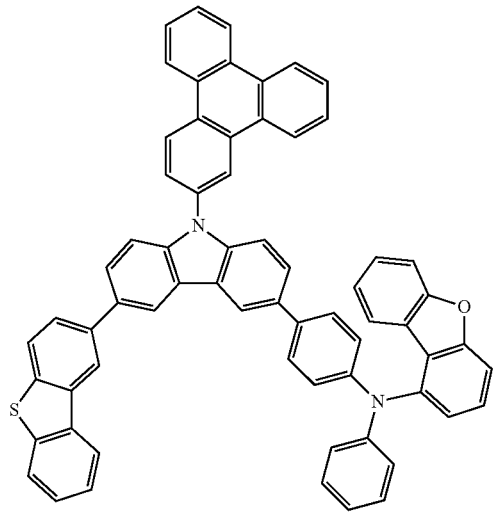
[A-120]
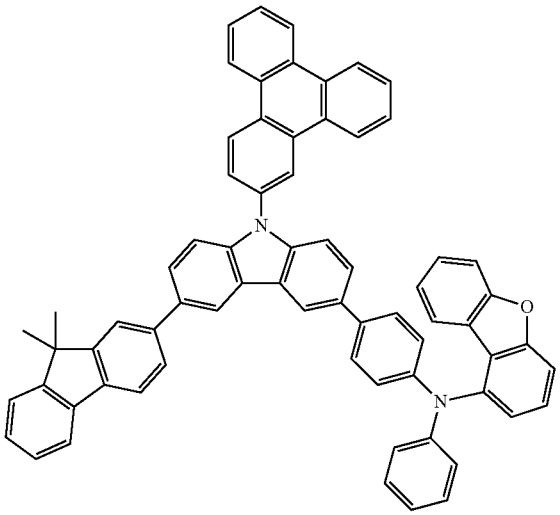
[A-121]
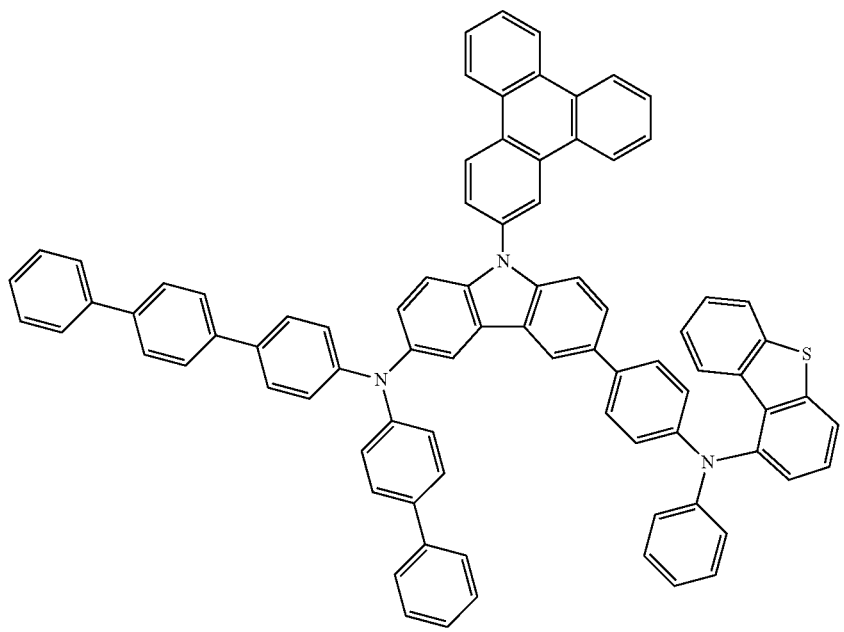
[A-122]
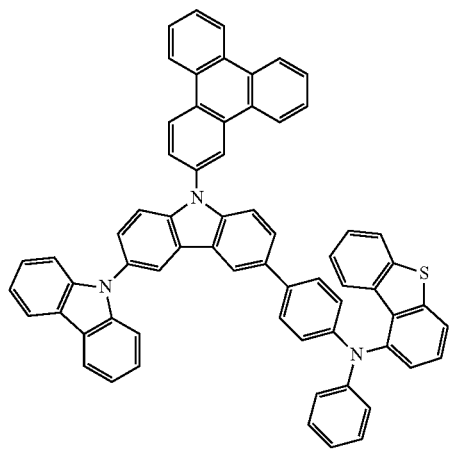
[A-123]
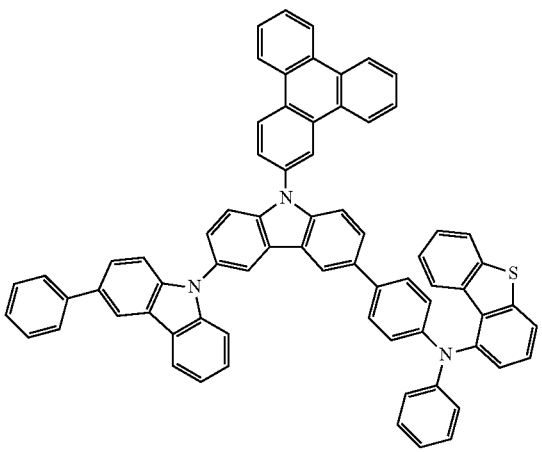

-continued
[A-124]
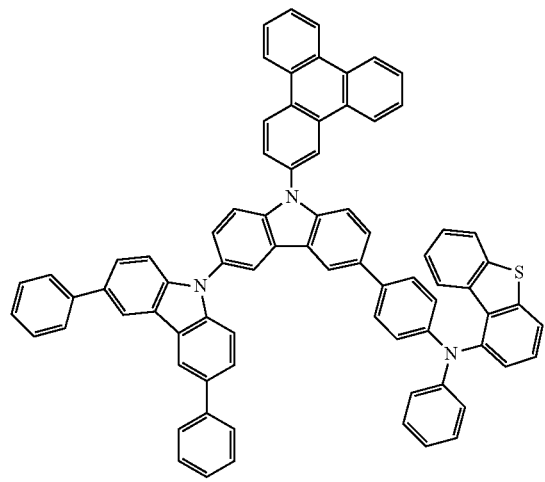
[A-125]
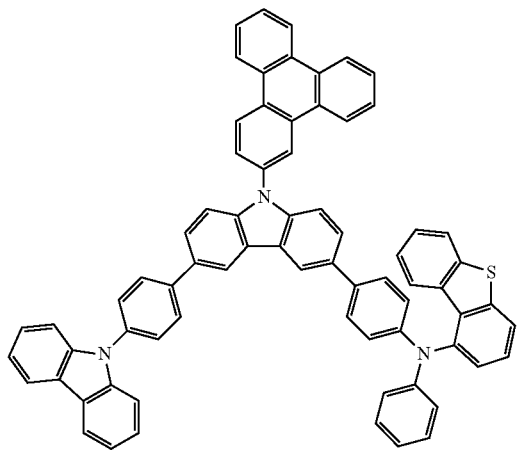
[A-126]
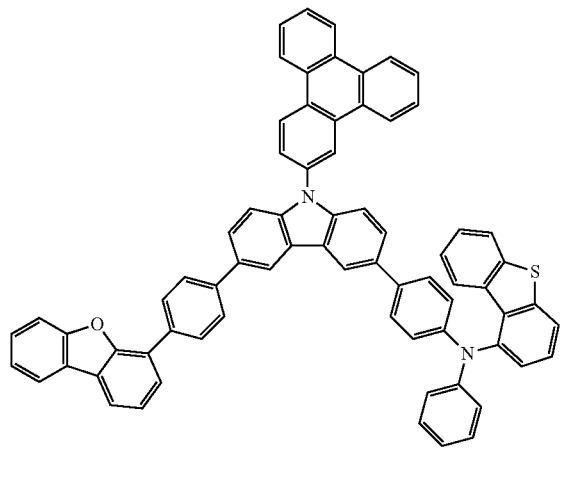
[A-127]
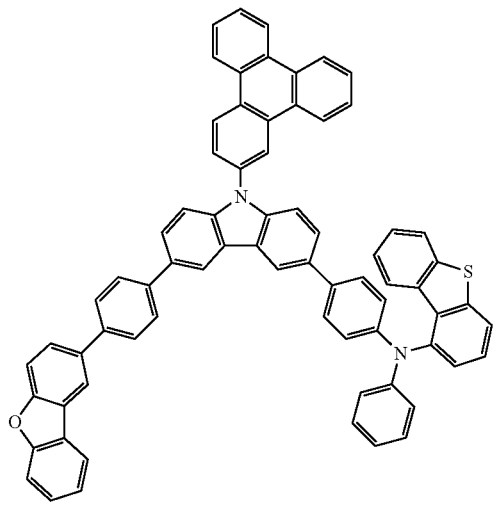
[A-128]
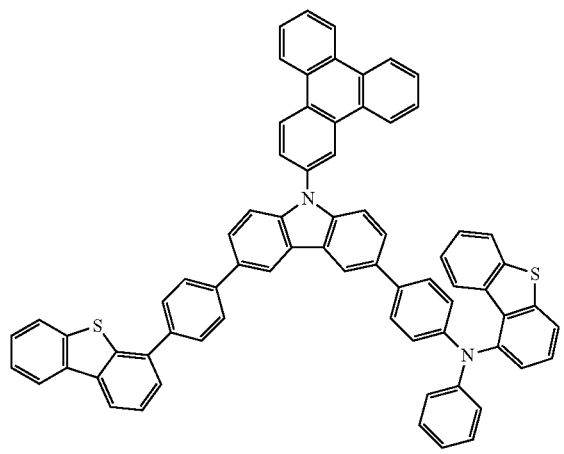
[A-129]
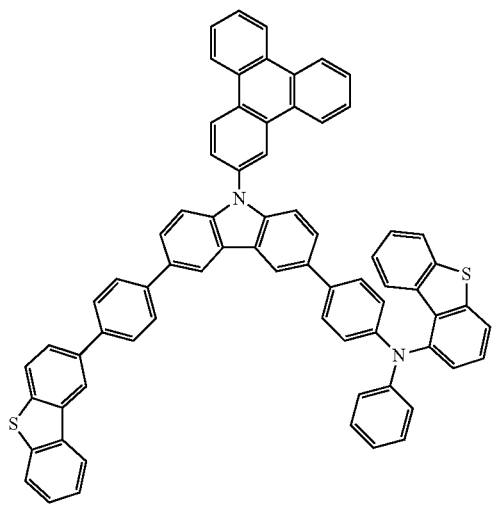

-continued
[A-130]
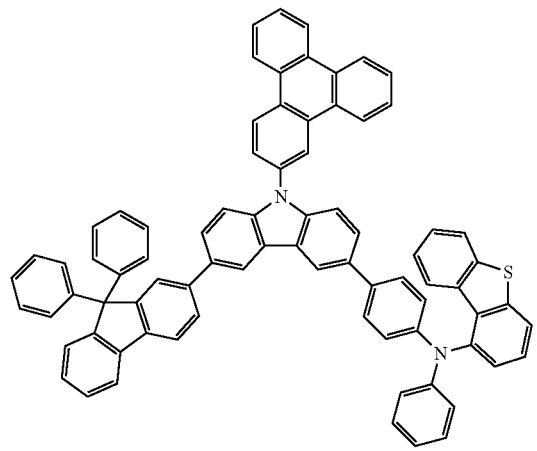
[A-131]
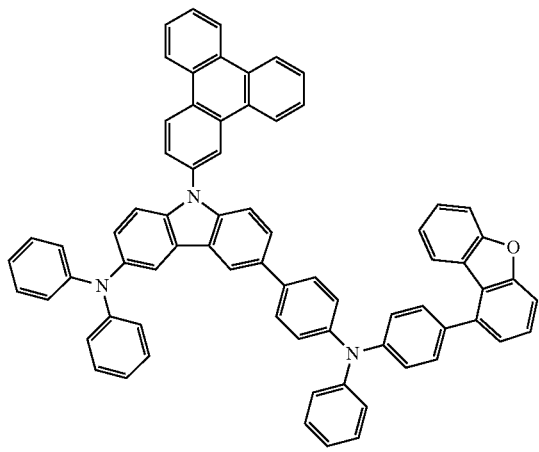
[A-132]
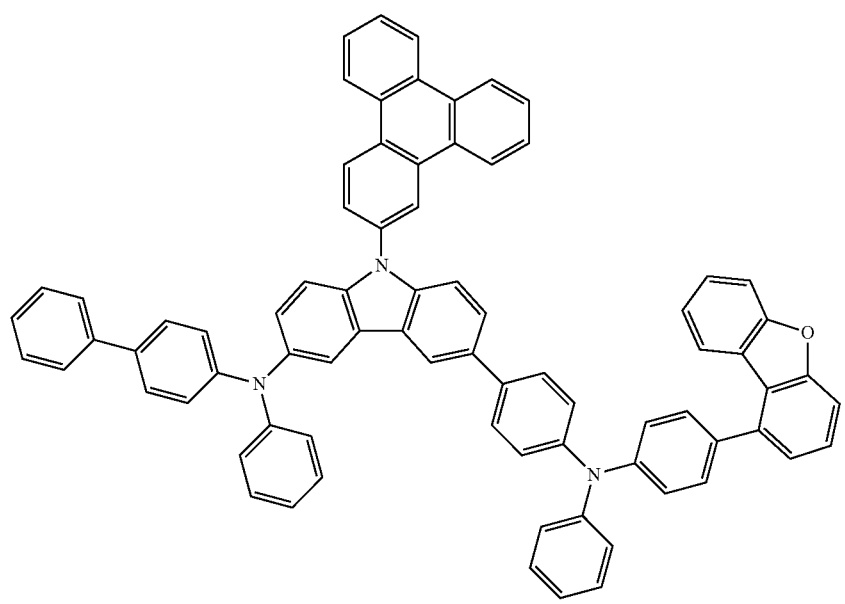

-continued
[A-133]
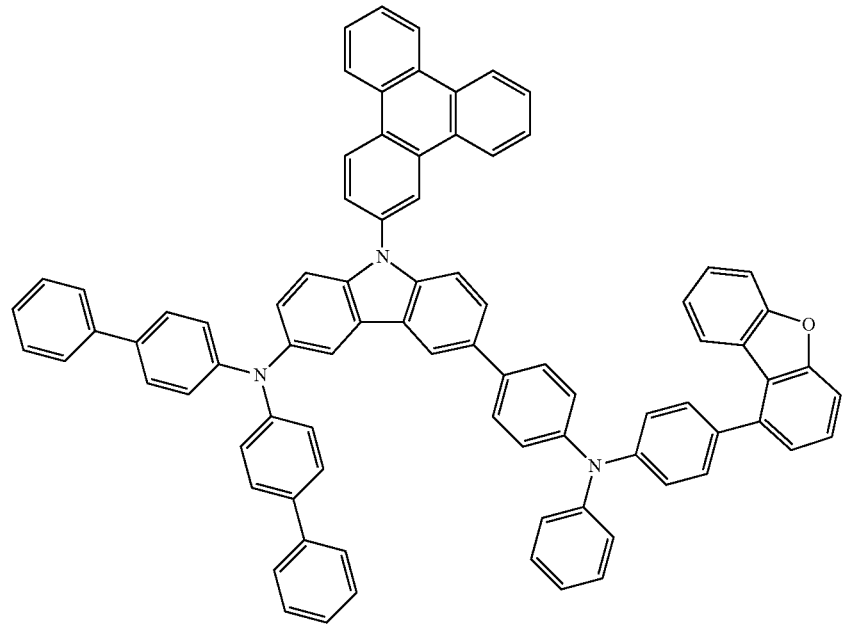
[A-134]
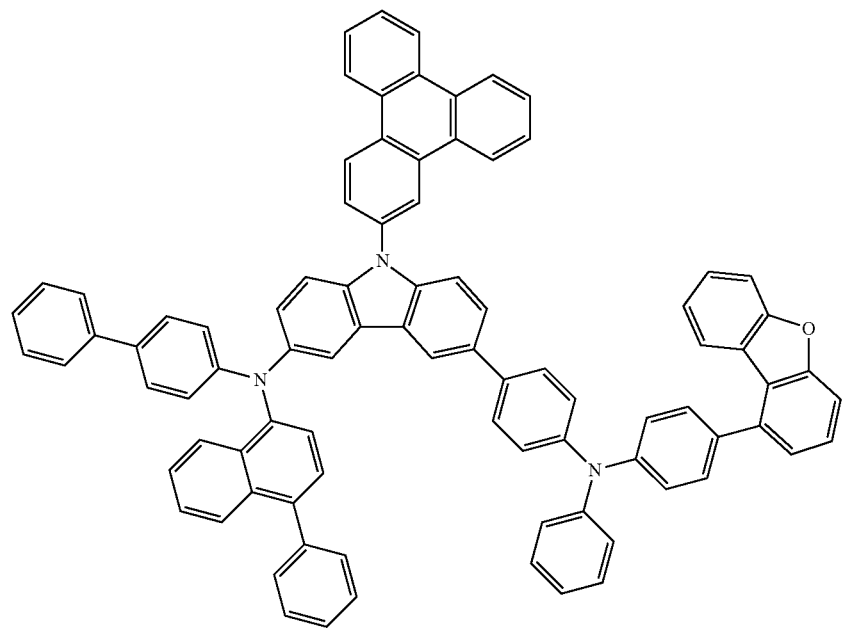

[A-135]
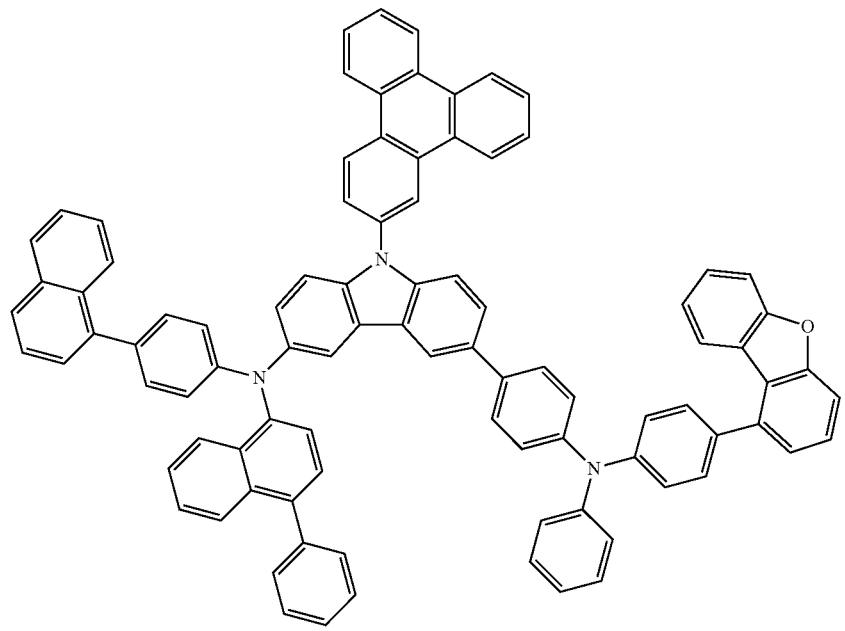
[A-136]
[A-137]
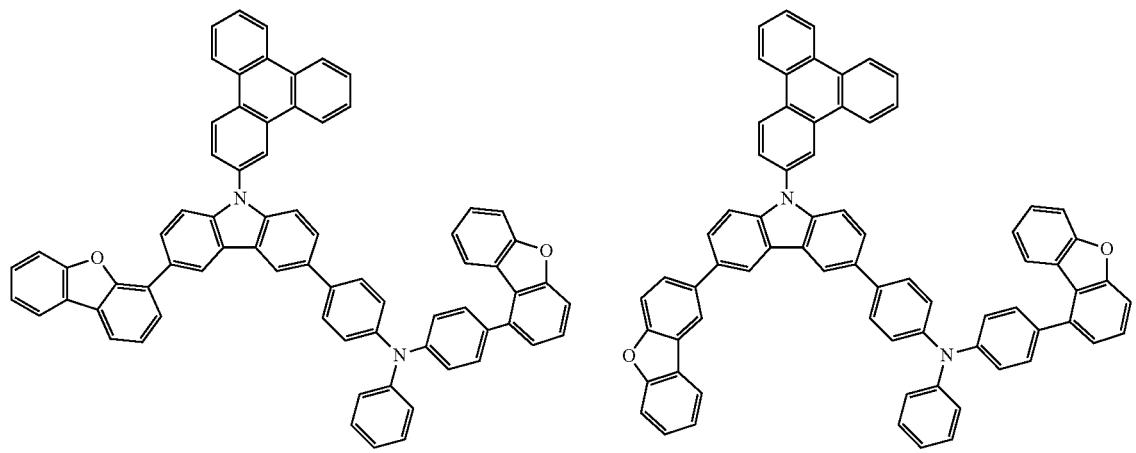
[A-138]
[A-139]
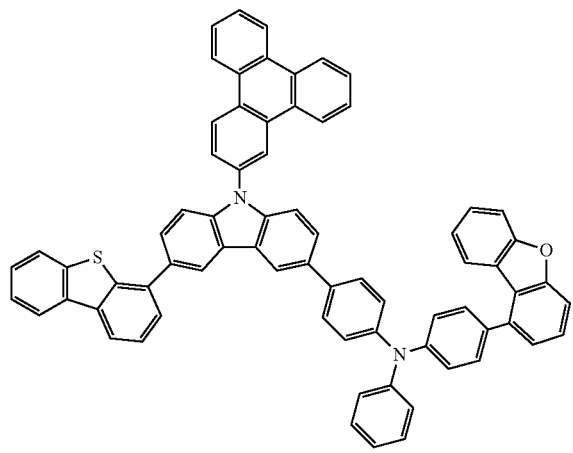
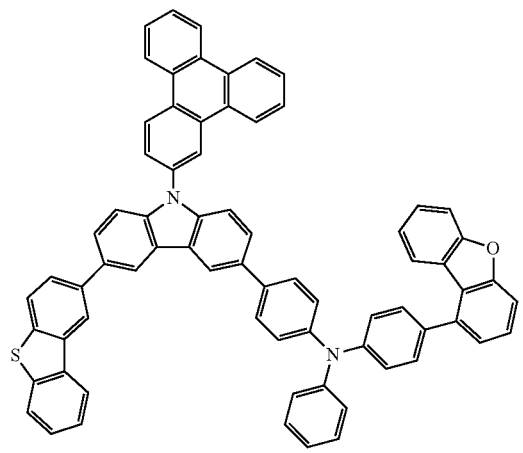

[A-140]
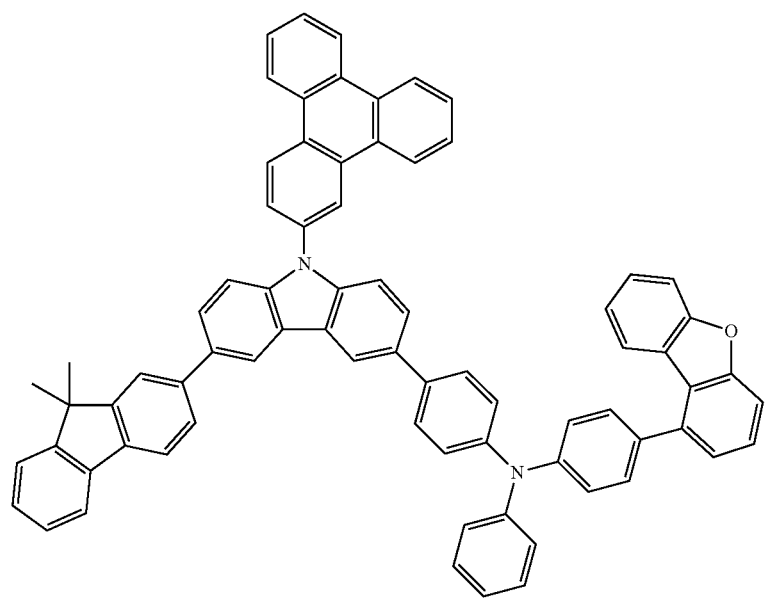
[A-141]
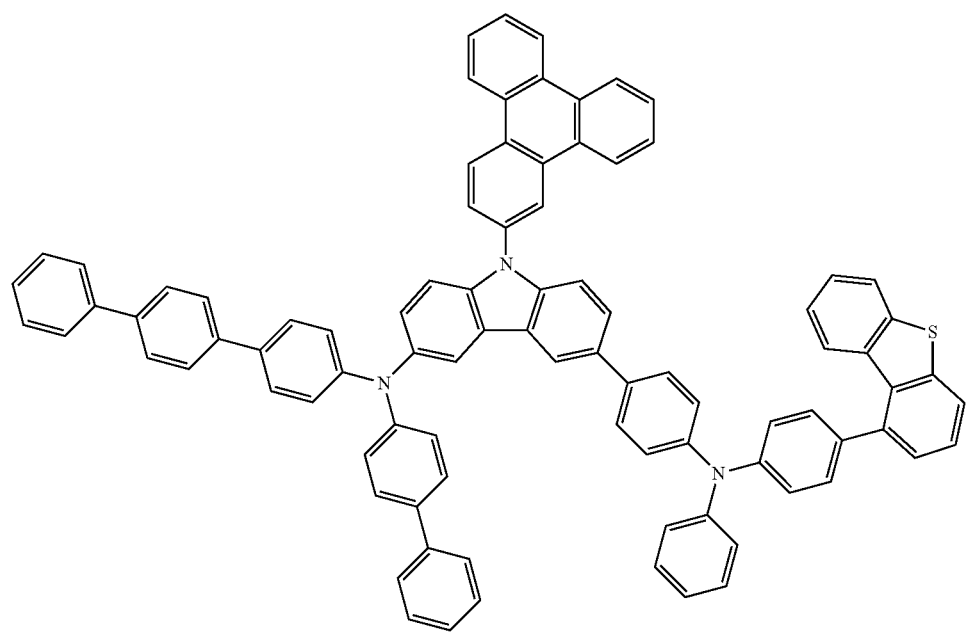

[A-142]
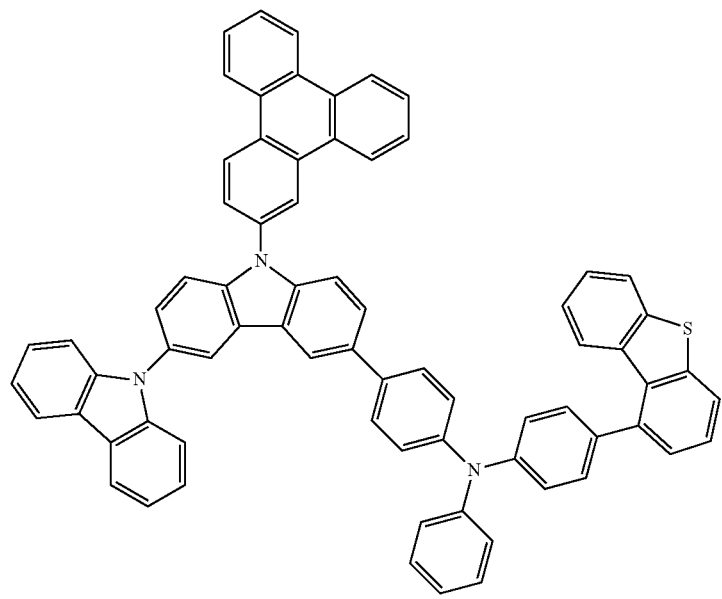
[A-143]
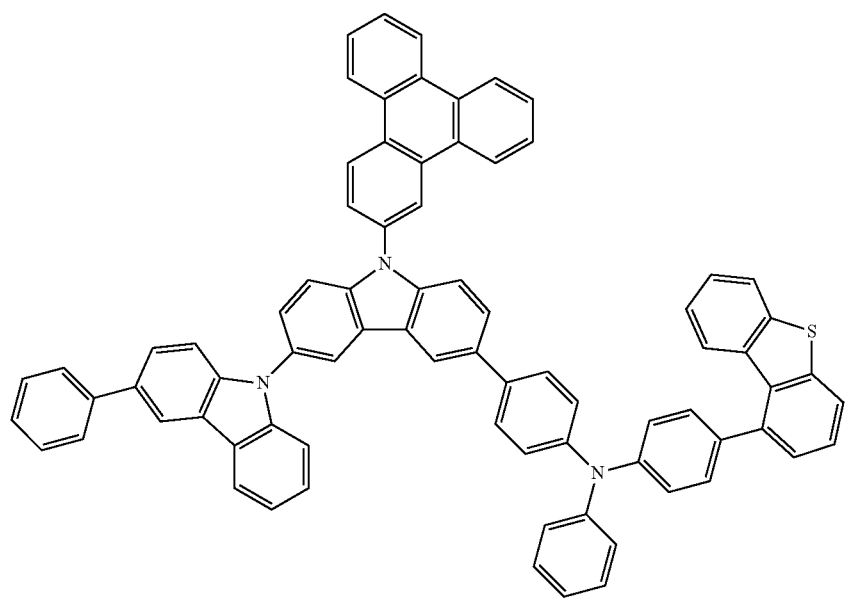

-continued
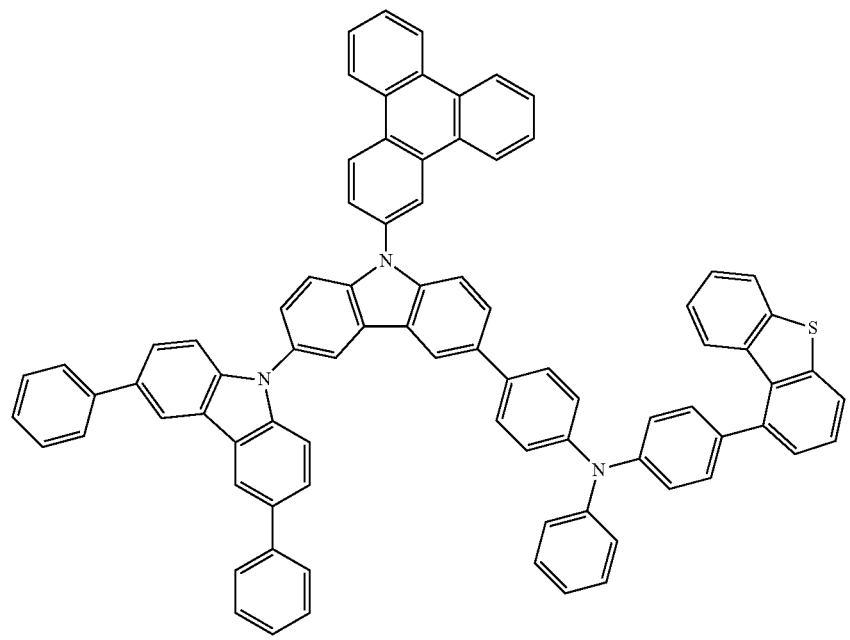
[A-144]
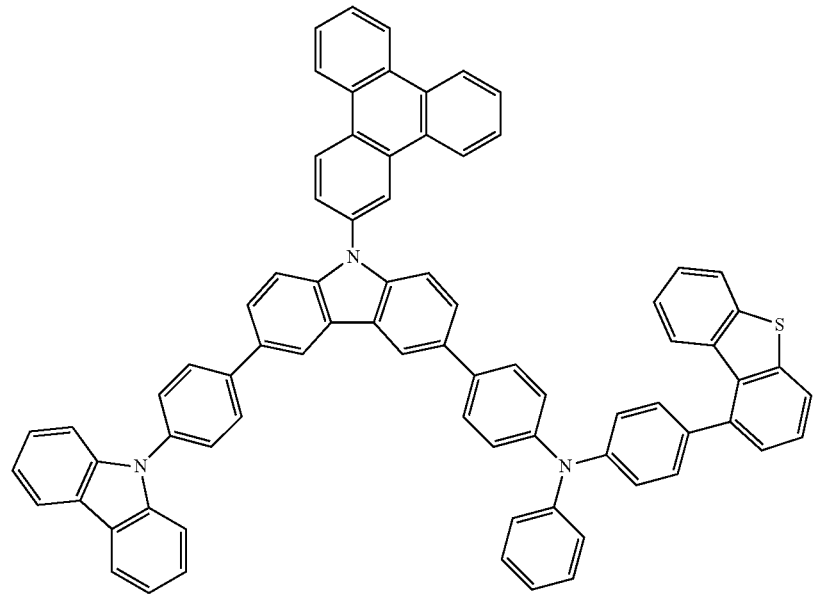
[A-145]

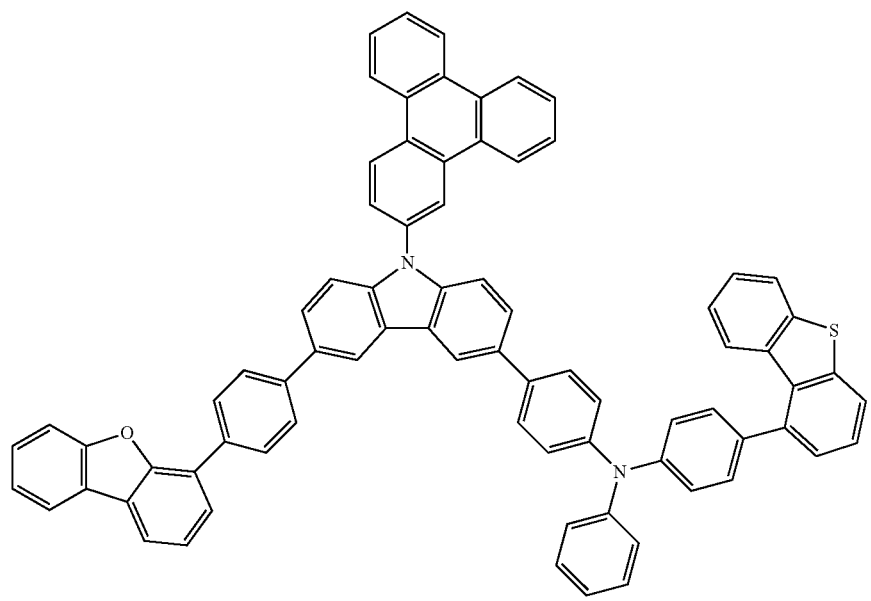
[A-146]
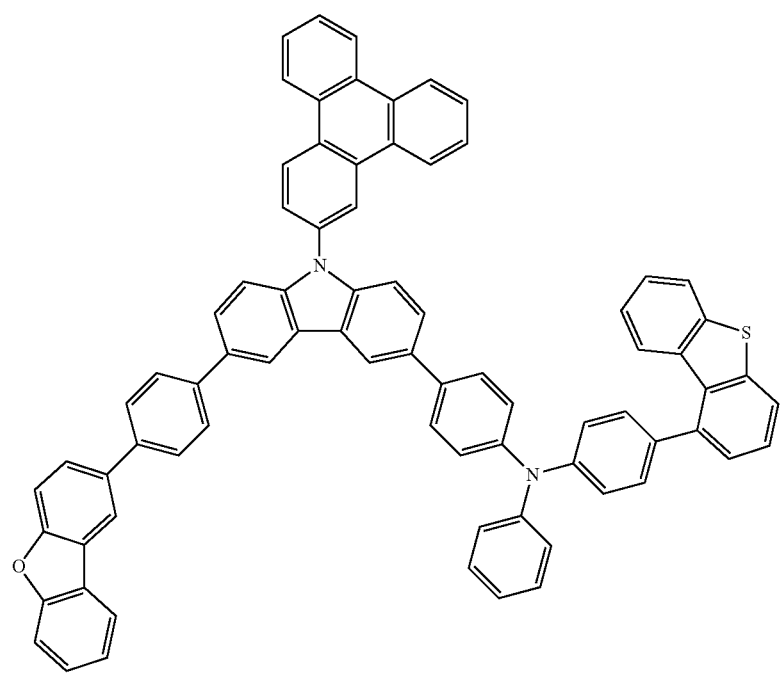
[A-147]

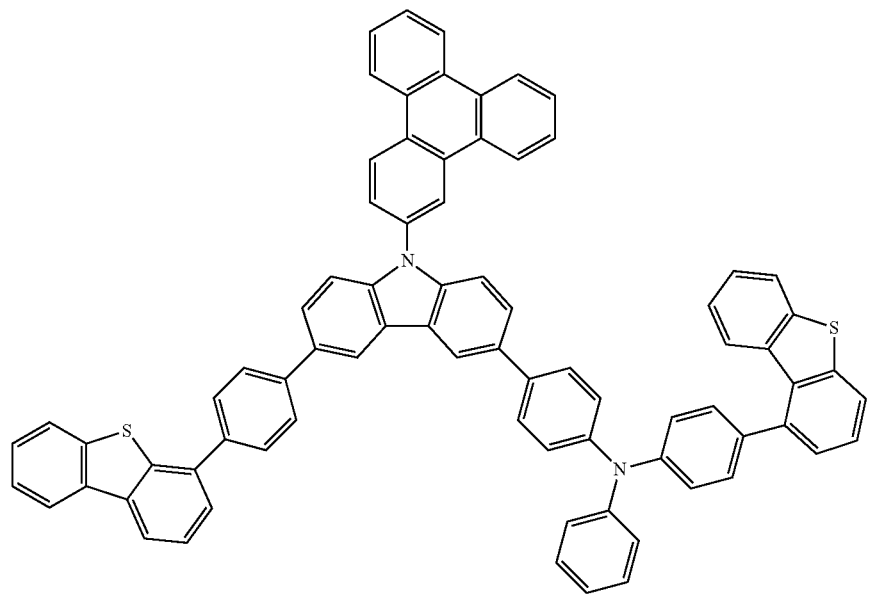
[A-148]
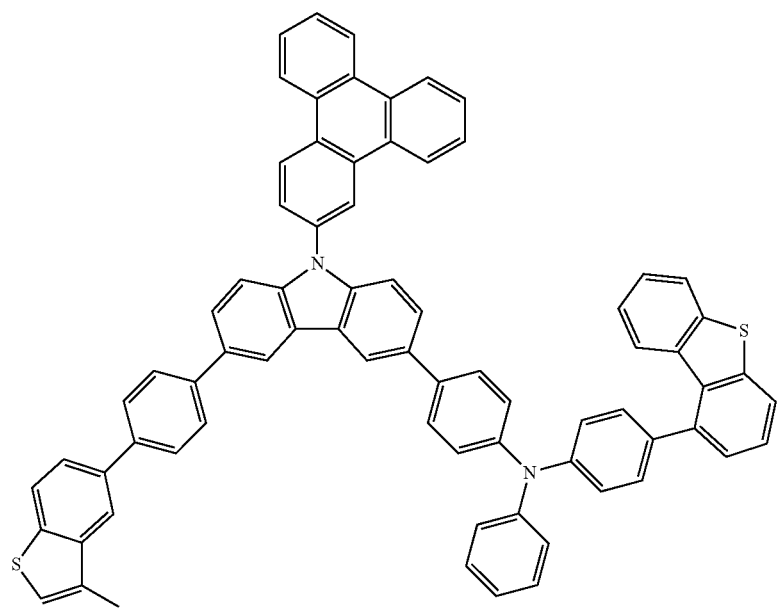
[A-149]

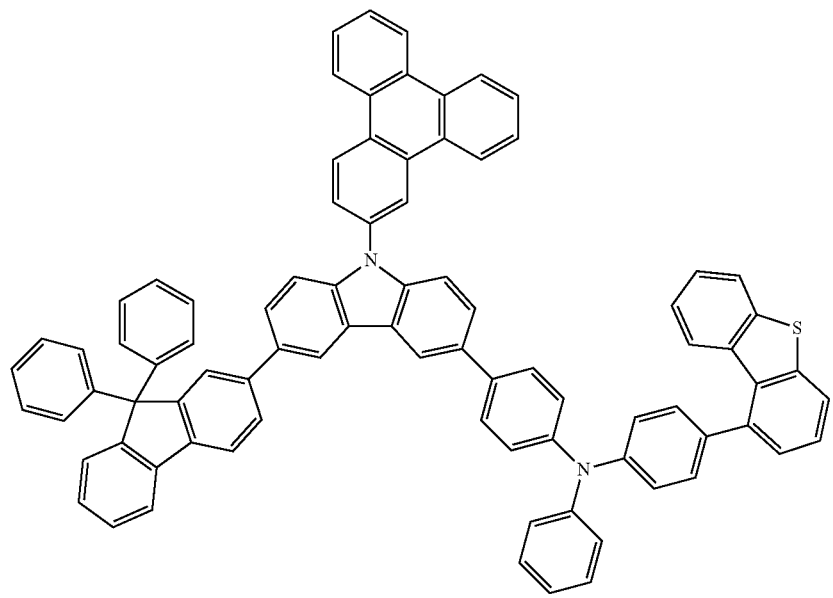
[A-150]
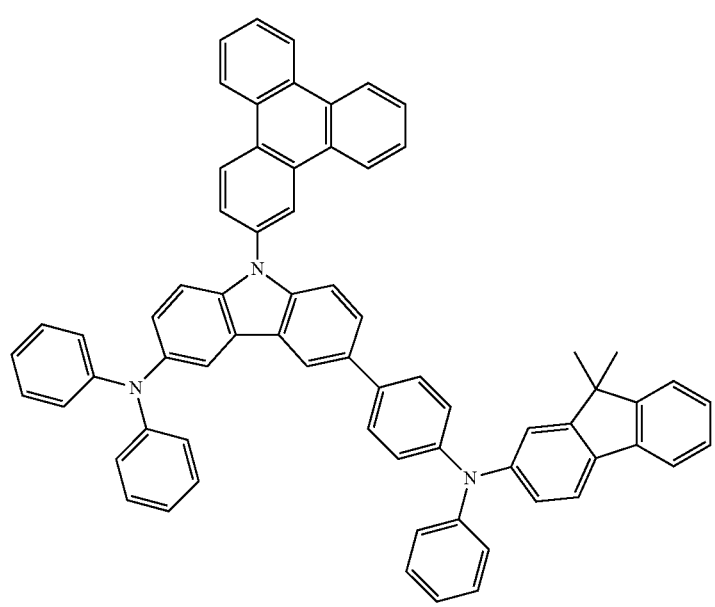
[A-151]

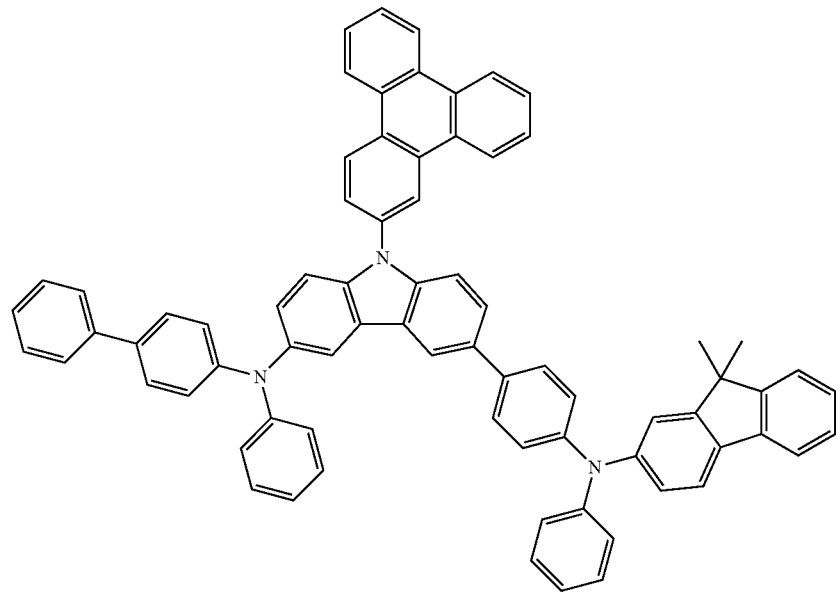
[A-152]
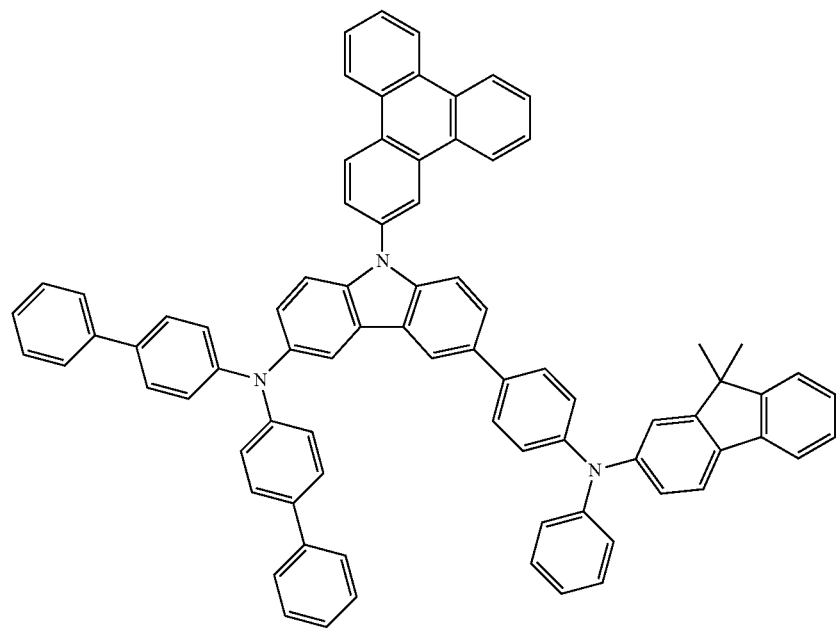
[A-153]

[A-154]
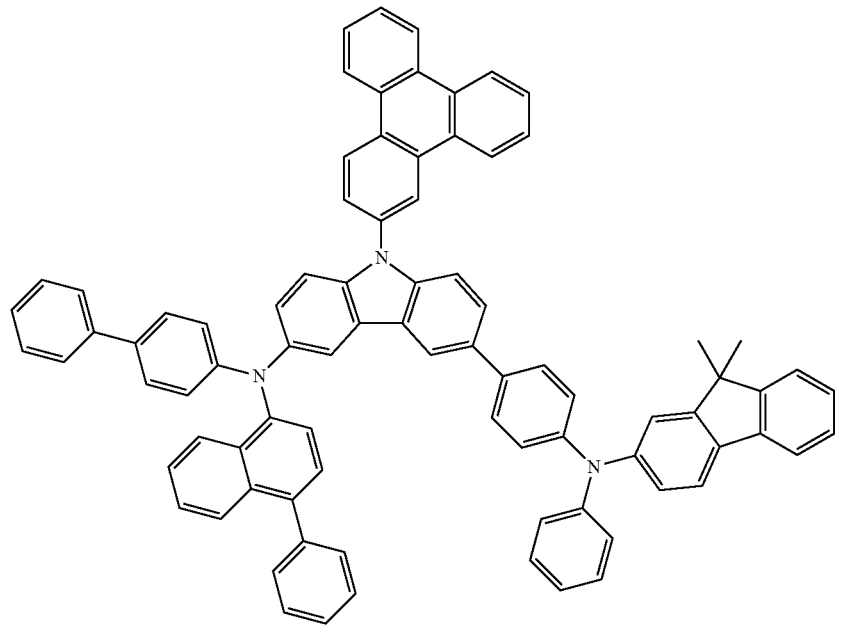
[A-155]
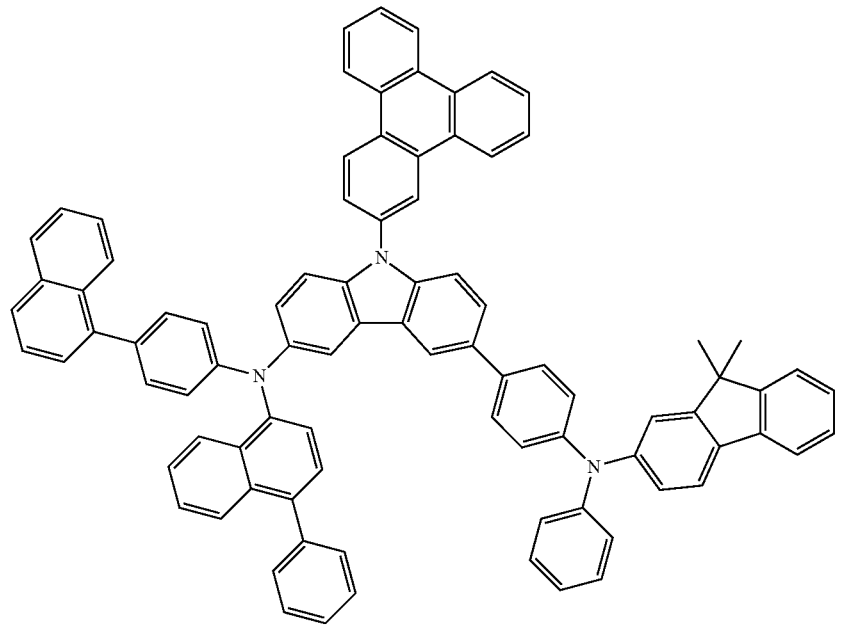

-continued
[A-156]
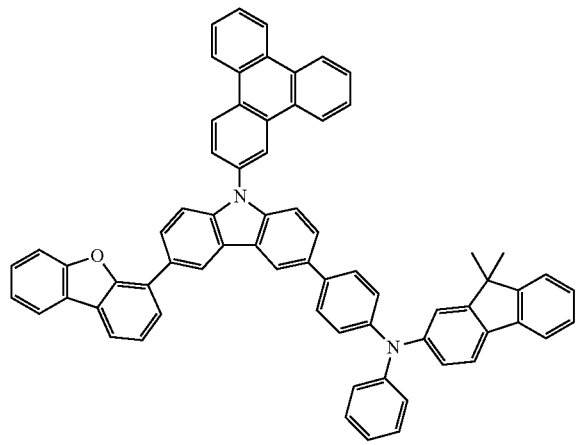
[A-157]
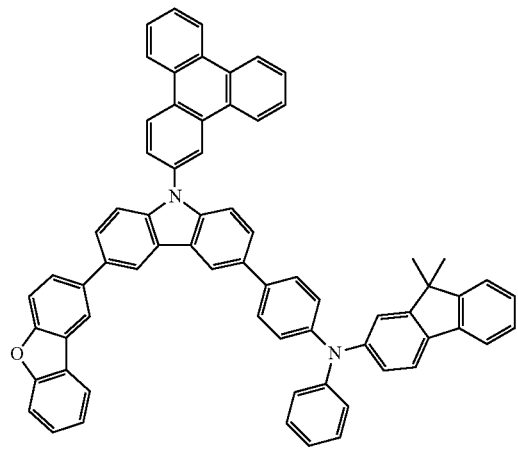
[A-158]
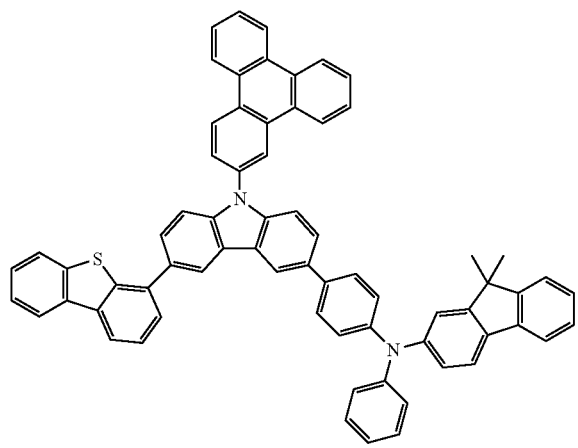
[A-159]
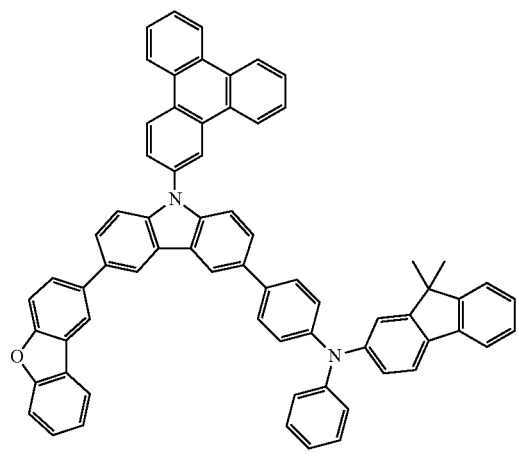
[A-160]
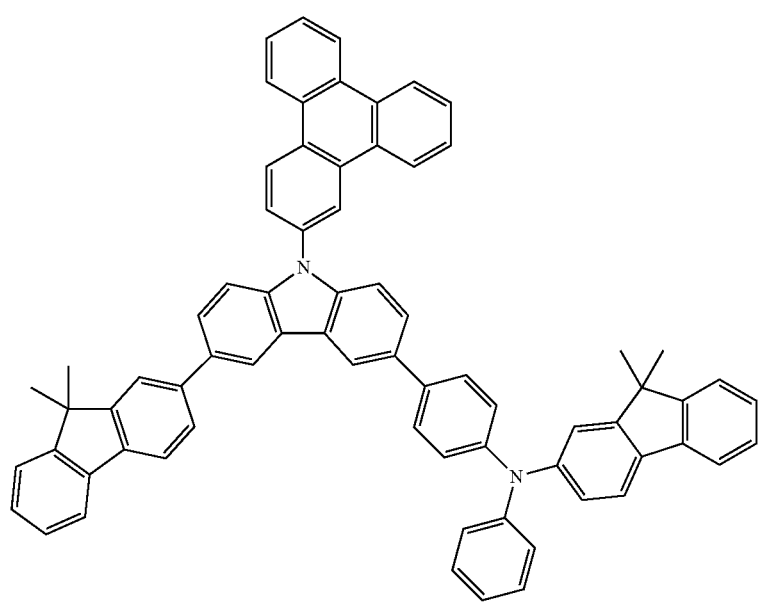

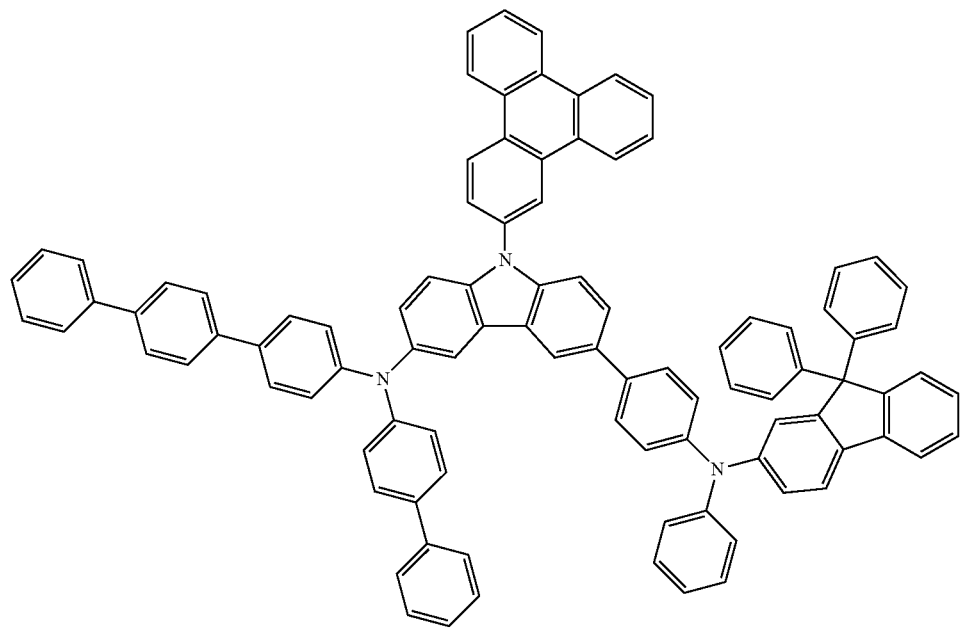
[A-161]
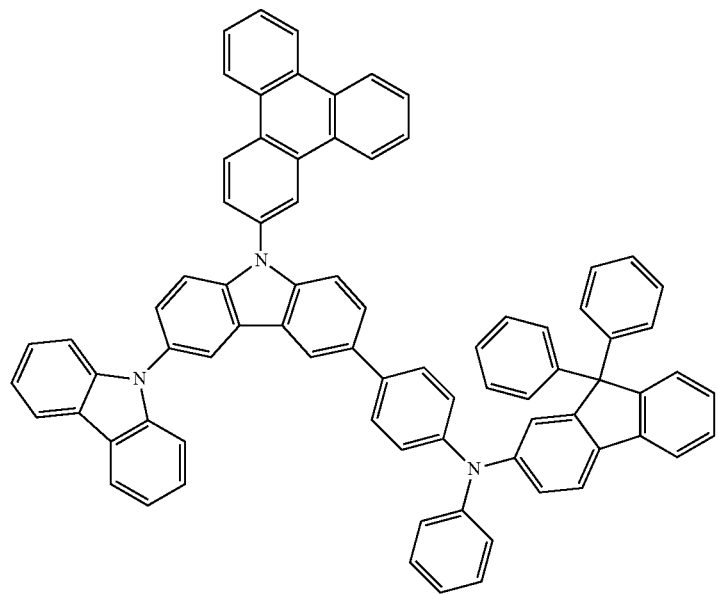
[A-162]

-continued
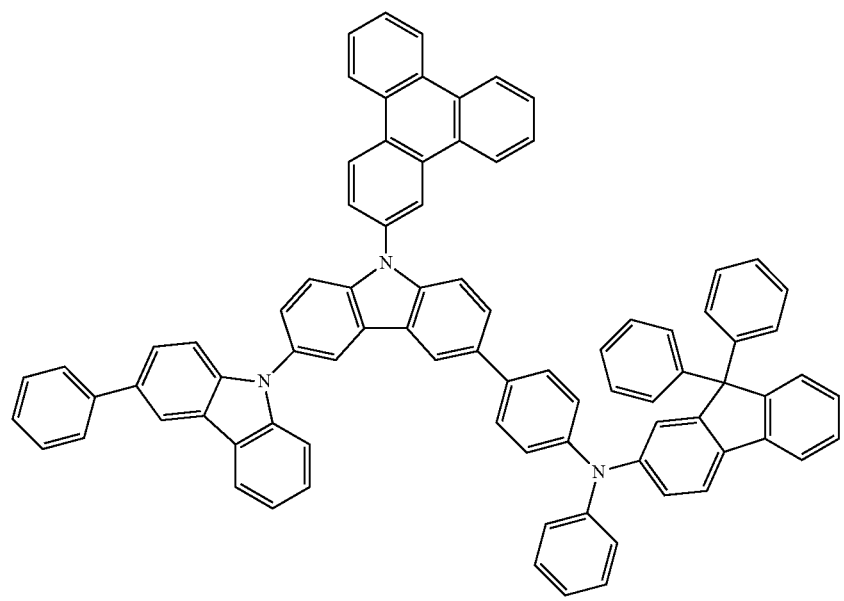
[A-163]
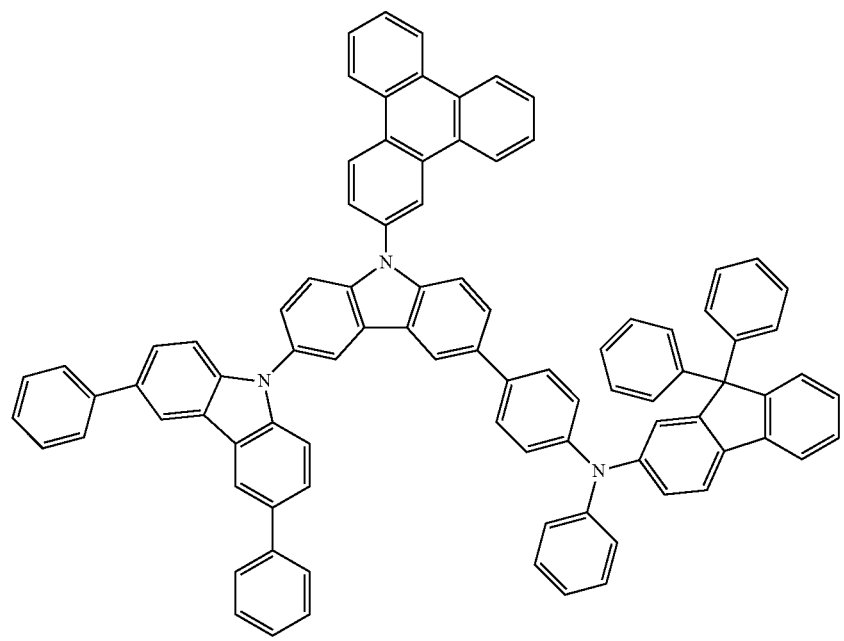
[A-164]

-continued
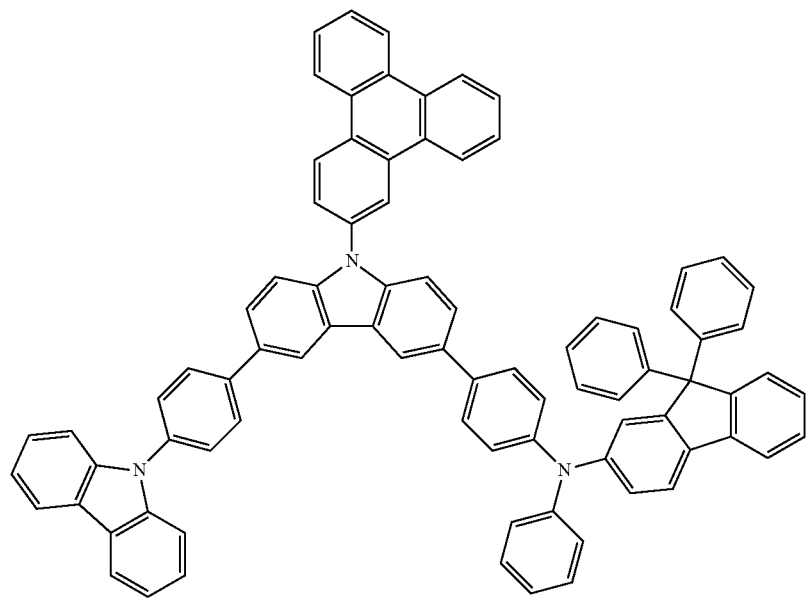
[A-165]
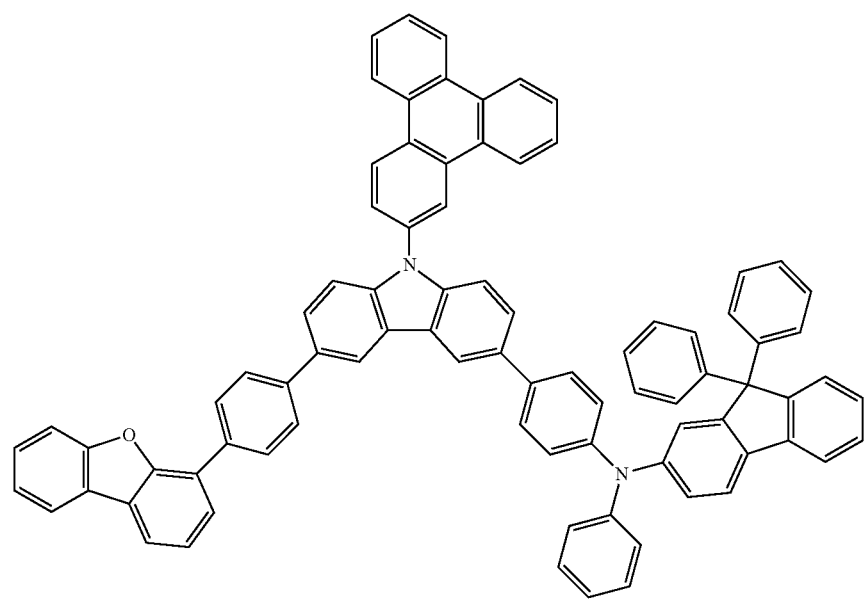
[A-166]

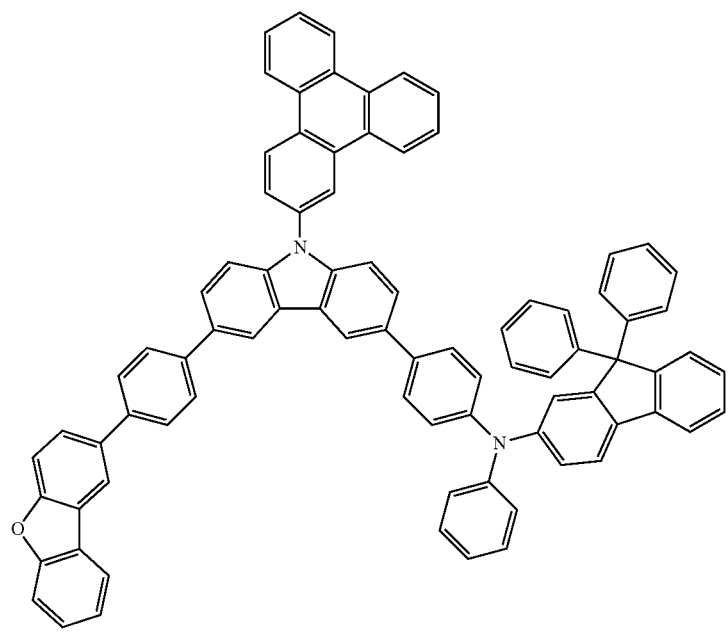
[A-167]
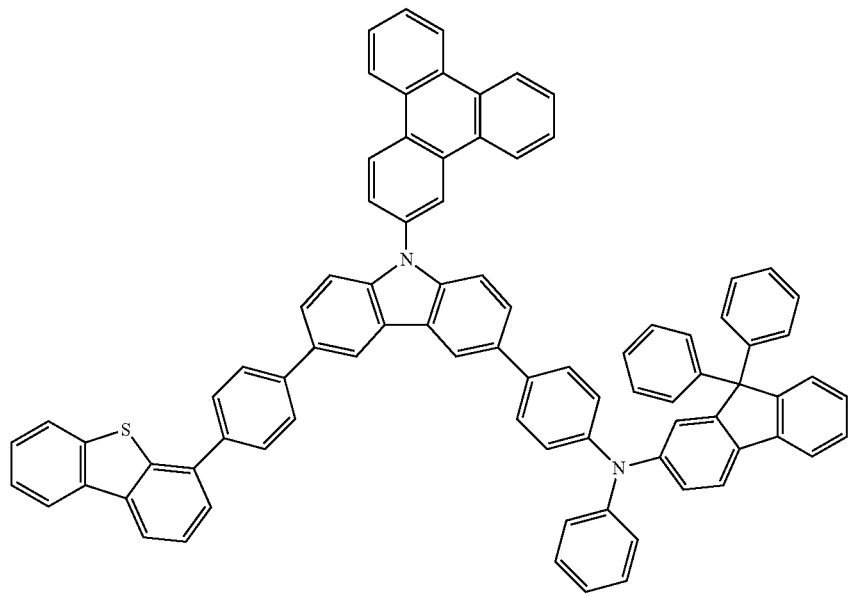
[A-168]

-continued
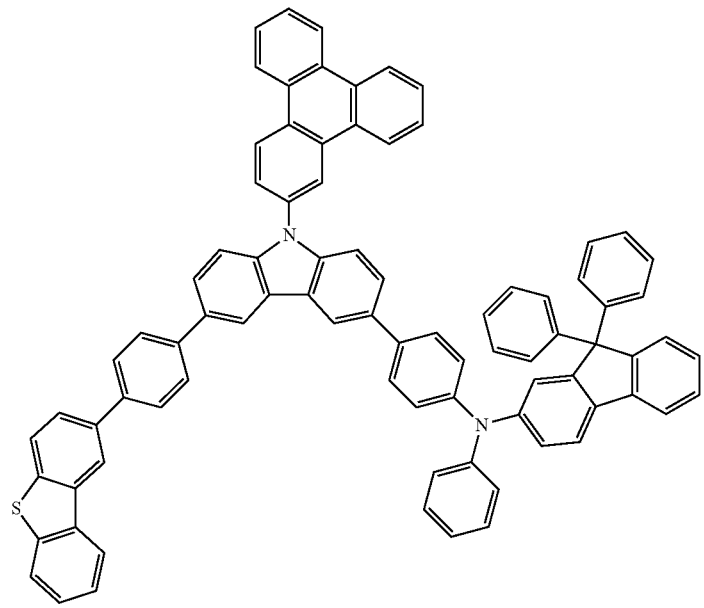
[A-169]
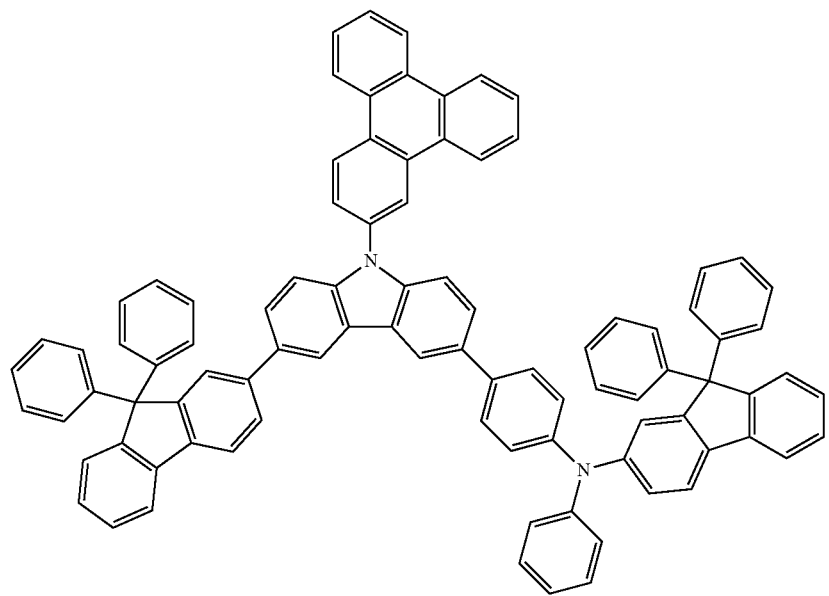
[A-170]

-continued
[A-171]
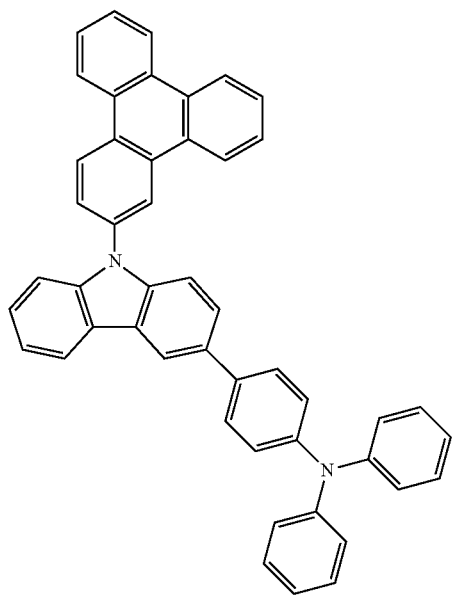
[A-172]
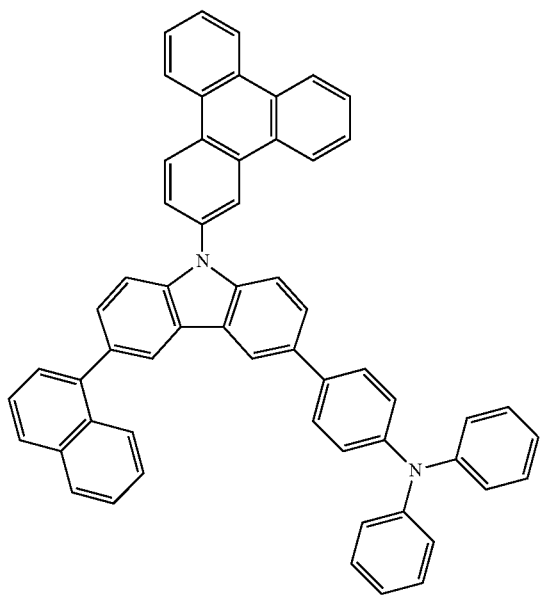
[A-173]
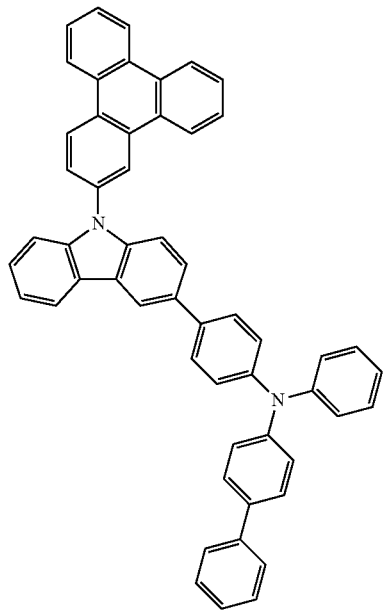
[A-174]
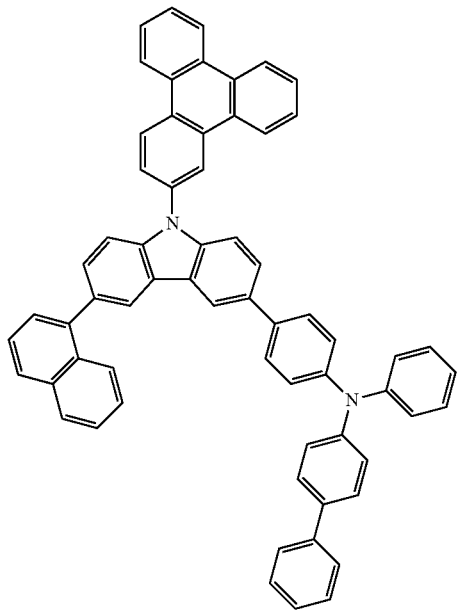

-continued
311 [A-175]
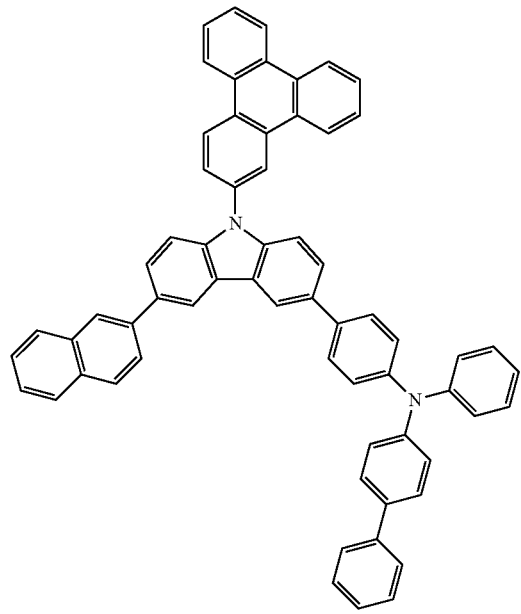
312 [A-176]
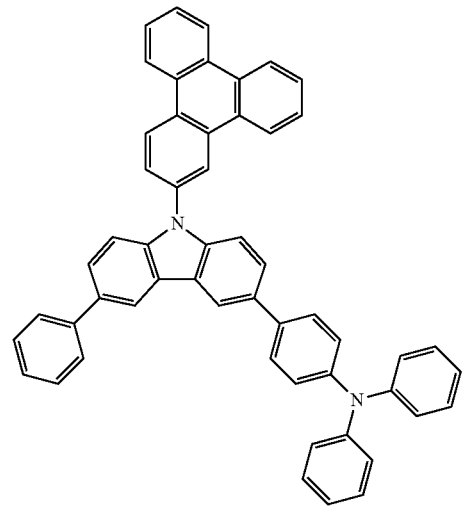
[A-177]
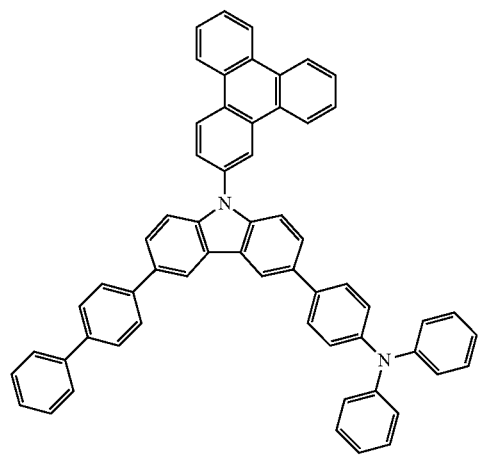
[A-178]
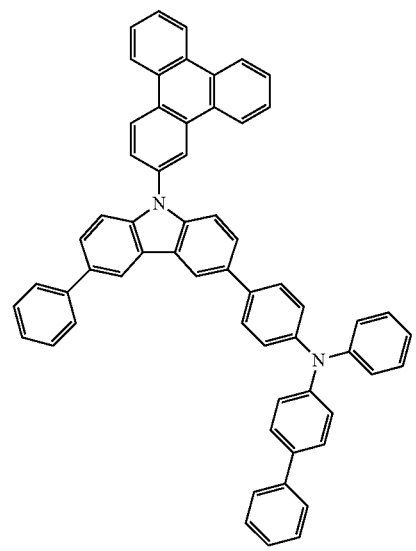

313                                    314
-continued
[A-179]
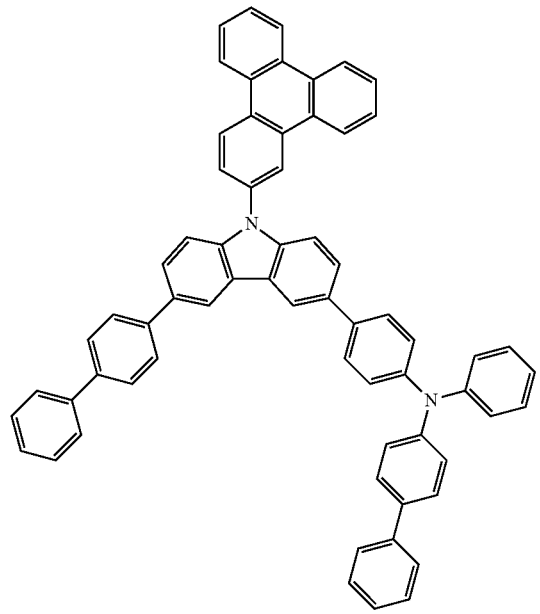
[A-180]
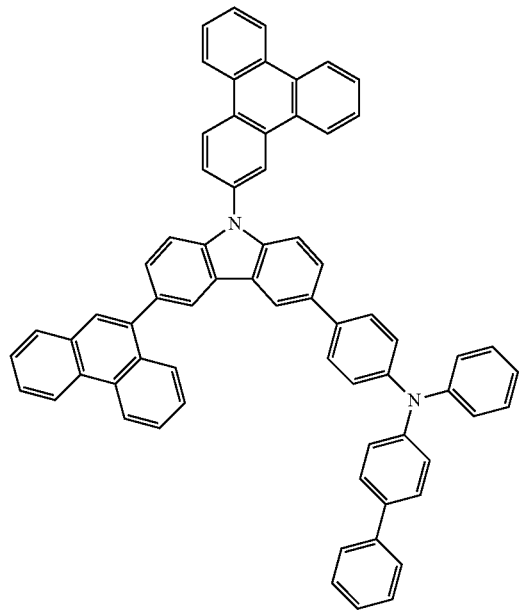
[A-181]
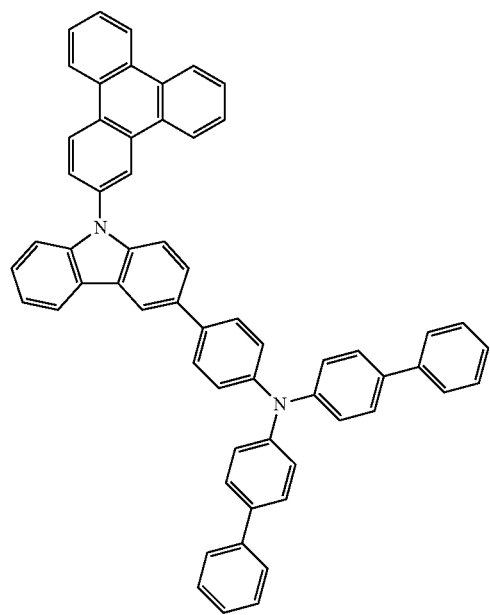
[A-182]
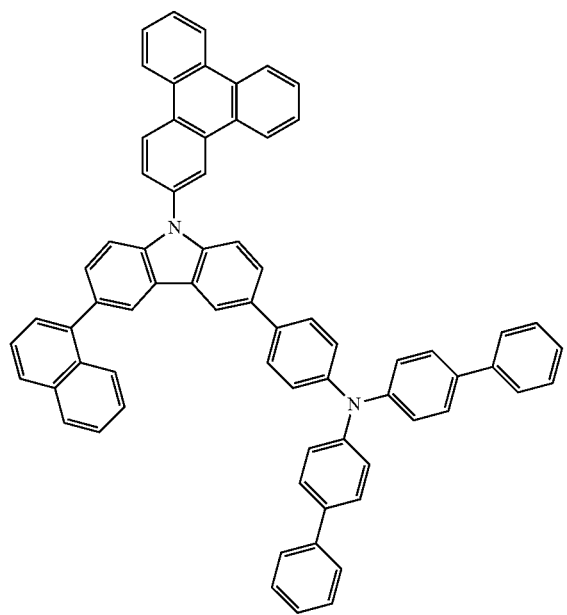

-continued
[A-183]
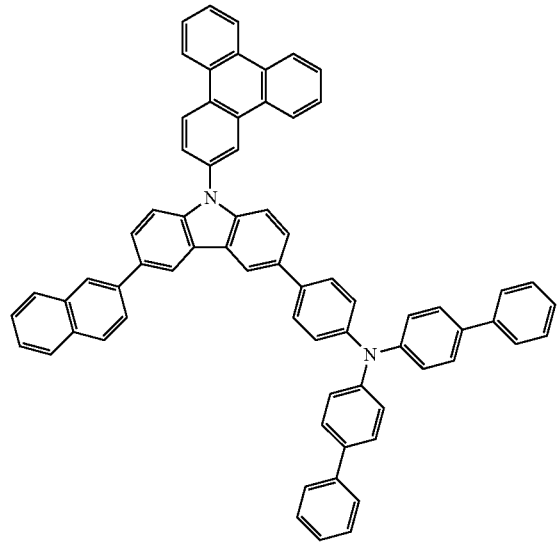
[A-184]
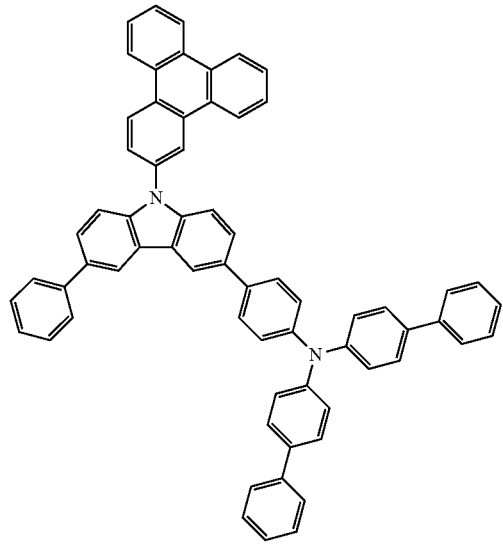
[A-185]
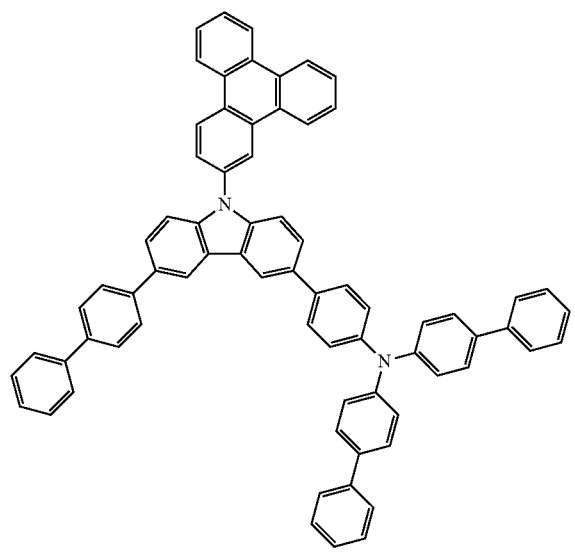
[A-186]
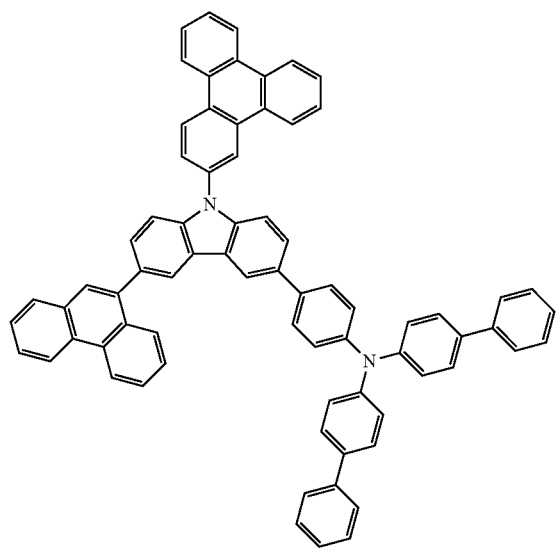

-continued
[A-187]
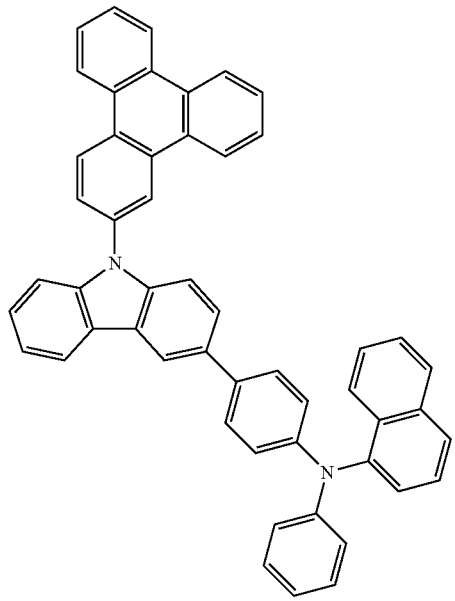
[A-188]
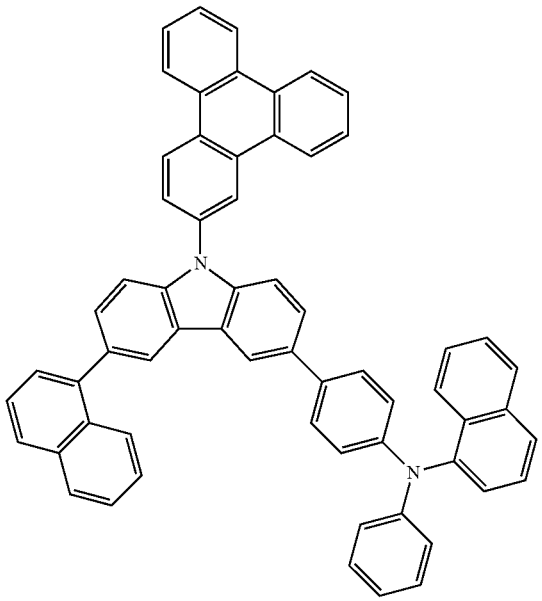
[A-189]
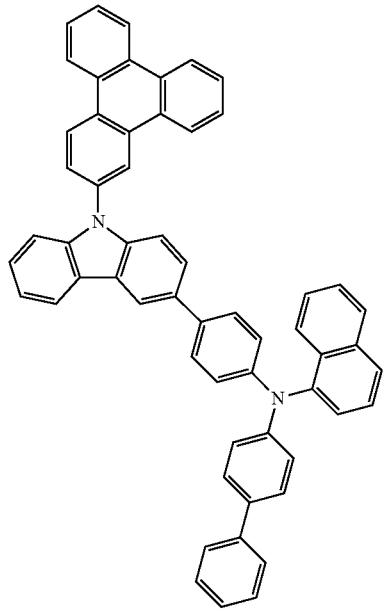
[A-190]
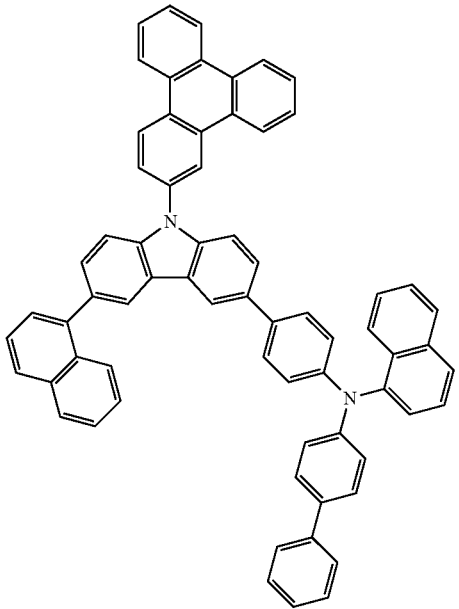

-continued
[A-191]
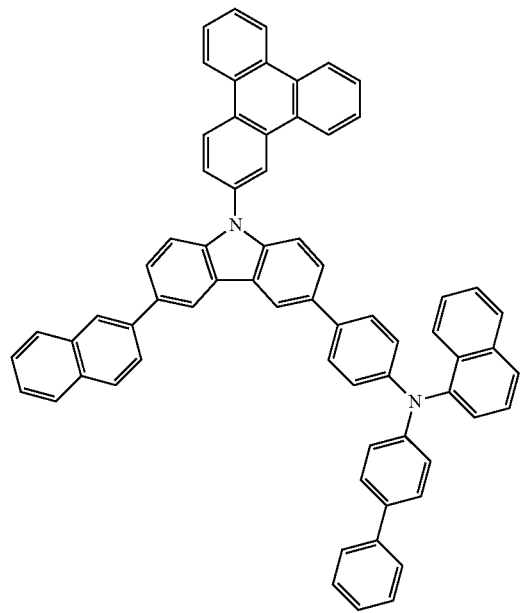
[A-192]
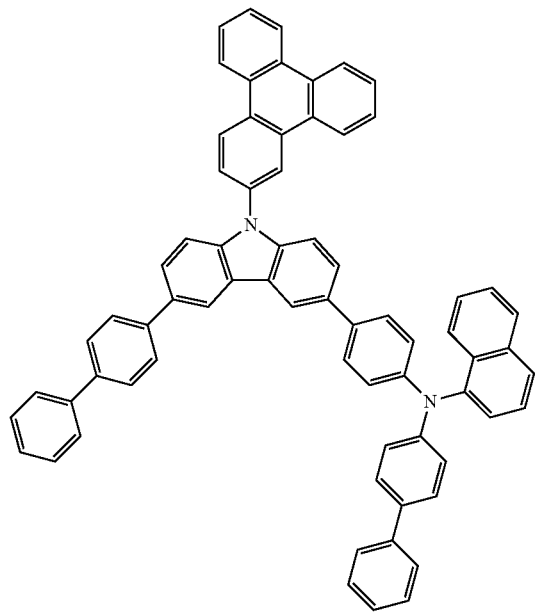
[A-193]
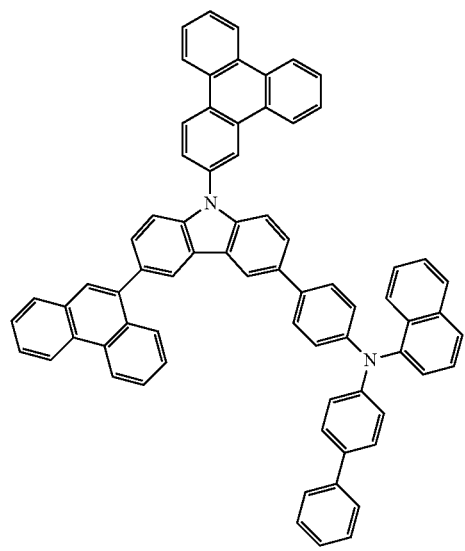
[A-194]
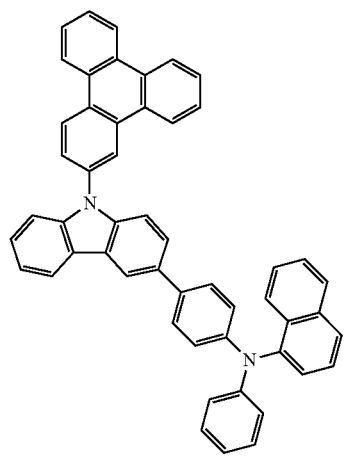

321
[A-195]
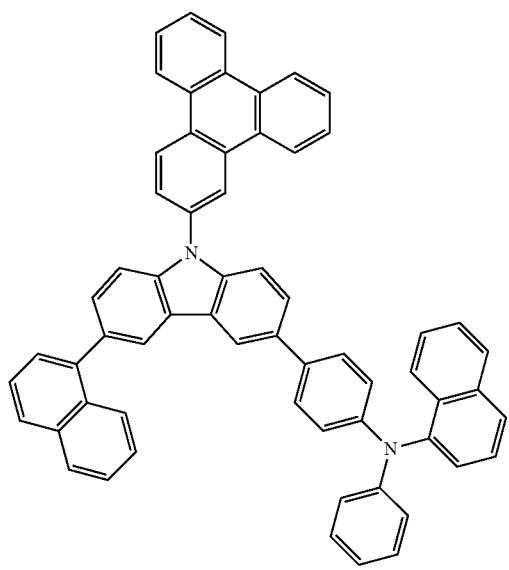
322
[A-196]
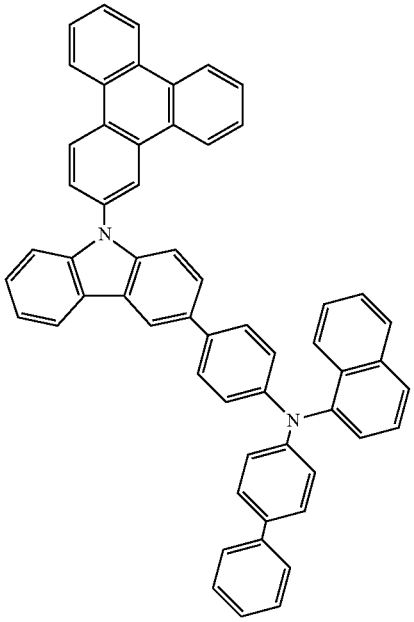
[A-197]
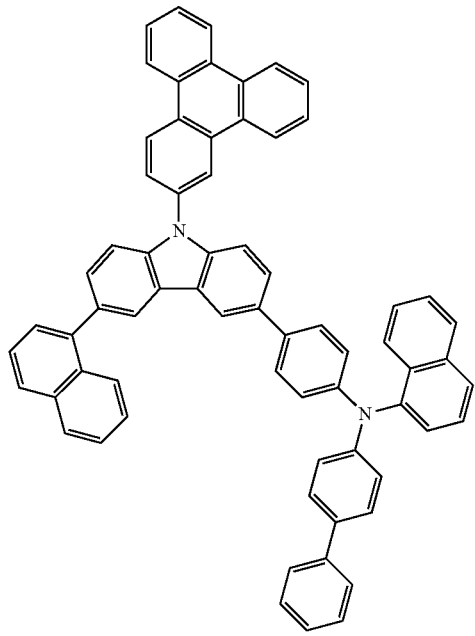
[A-198]
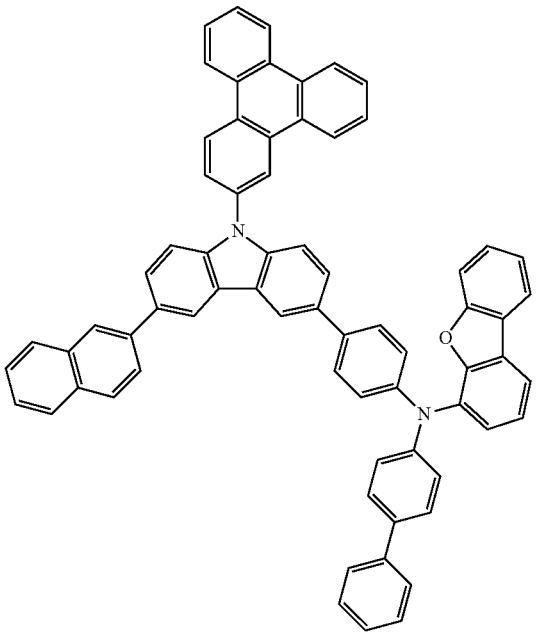

[A-199]
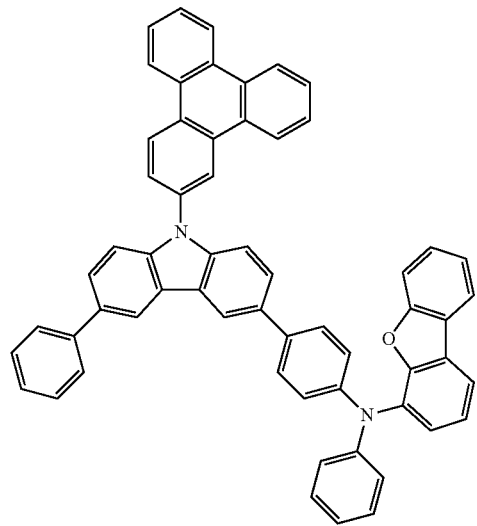
[A-200]
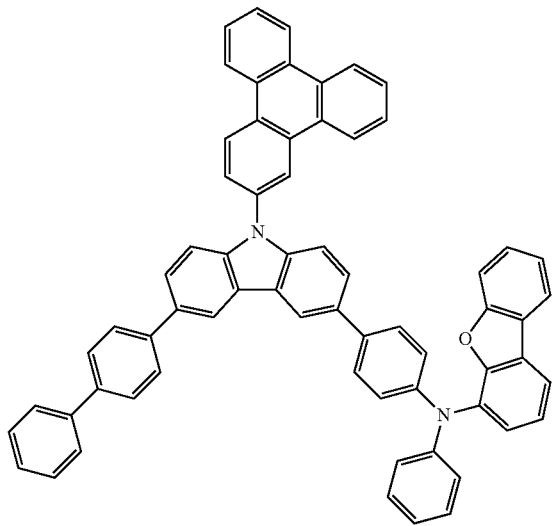
[A-201]
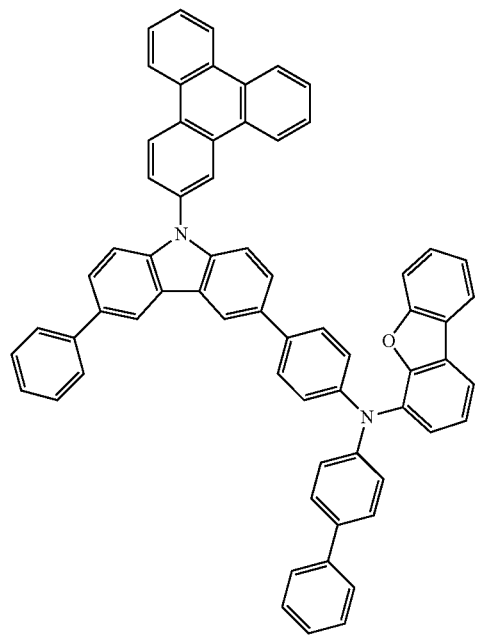
[A-202]
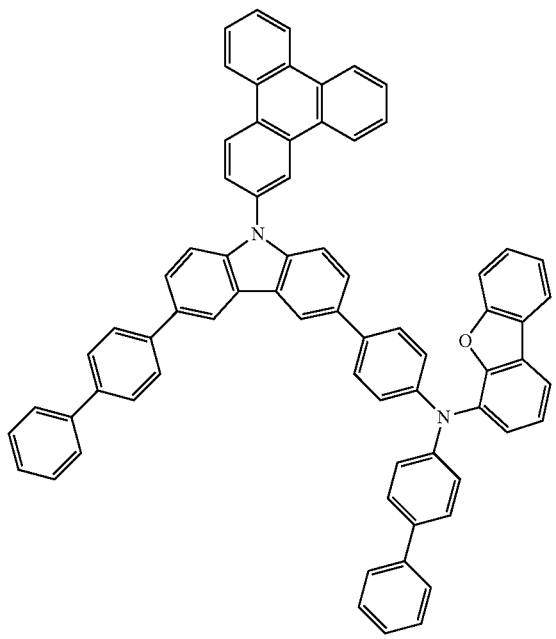

-continued
[A-203]
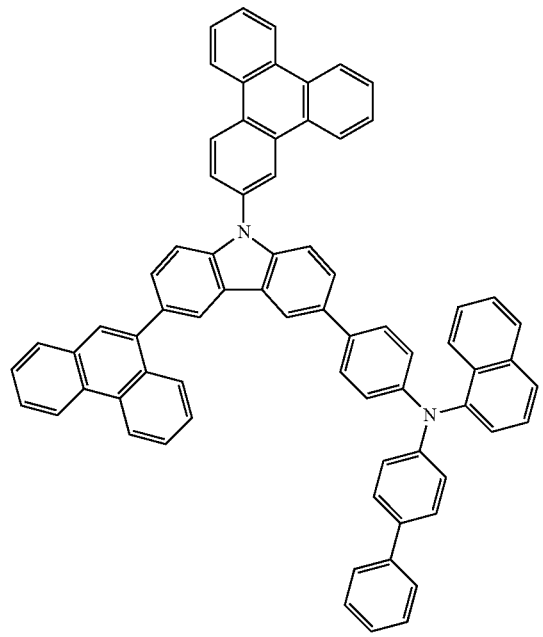
[A-204]
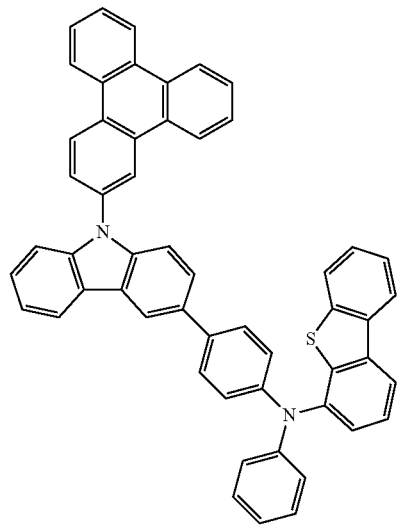
[A-205]
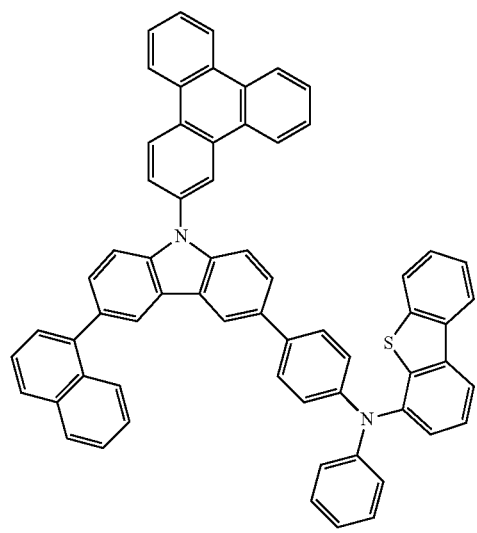
[A-206]
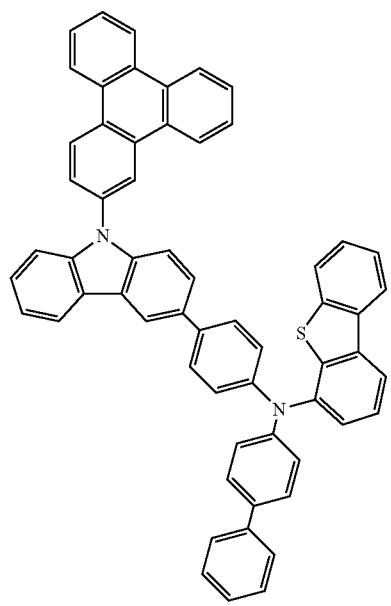

-continued
[A-207]
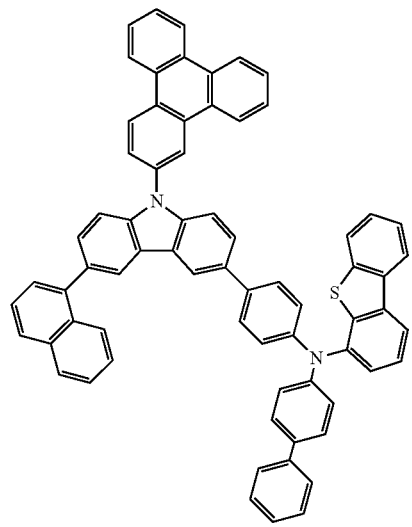
[A-208]
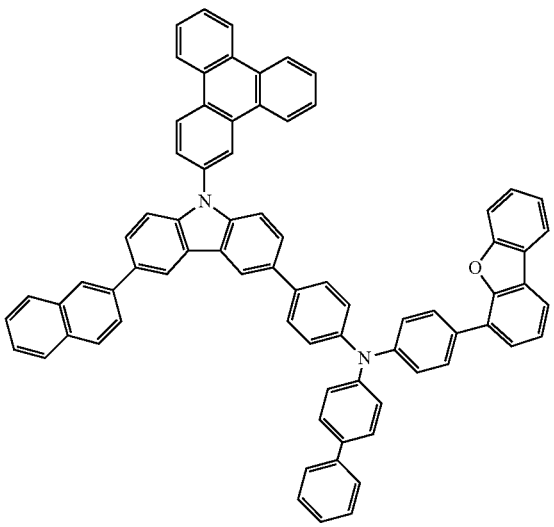
[A-209]
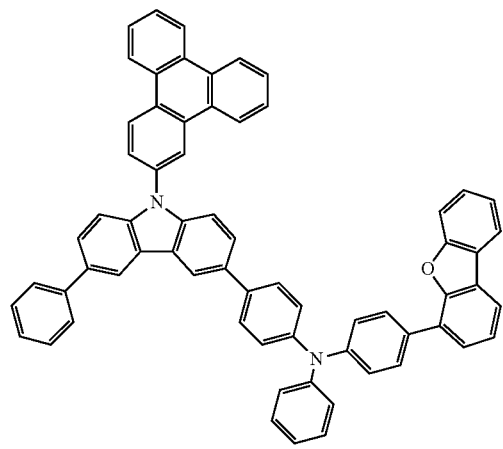
[A-210]
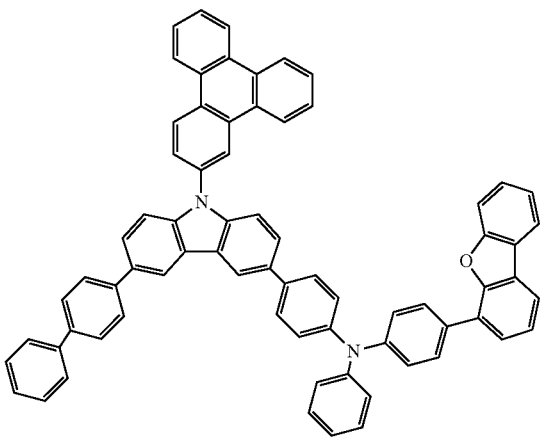
[A-211]
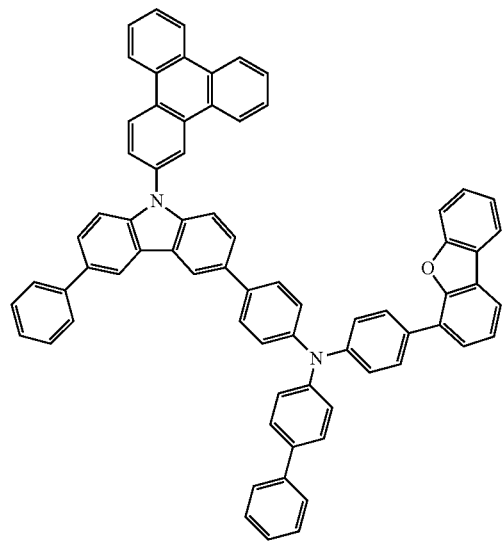
[A-212]
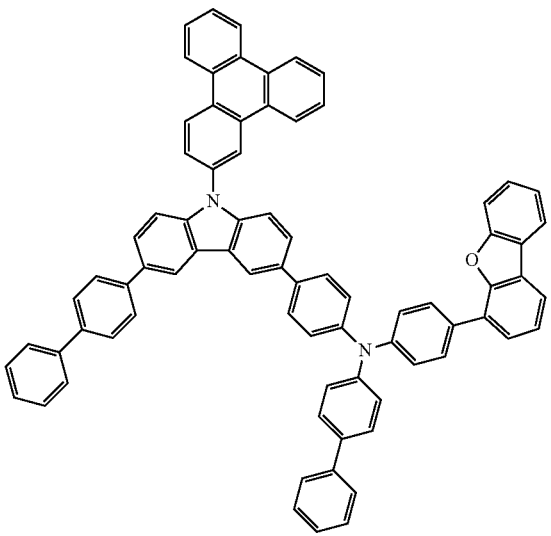

[A-213]
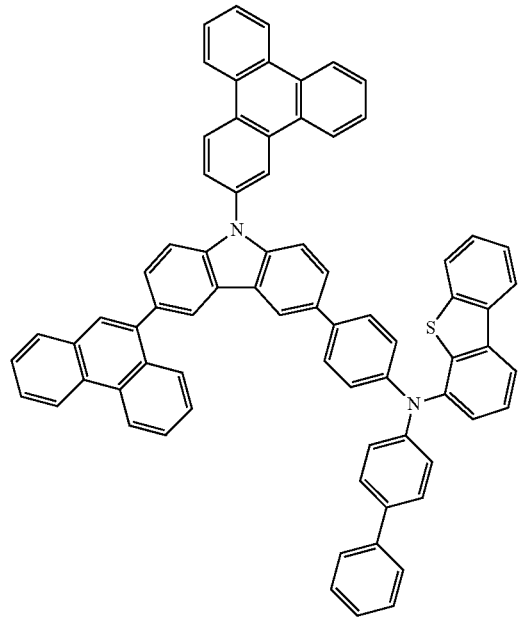
[A-214]
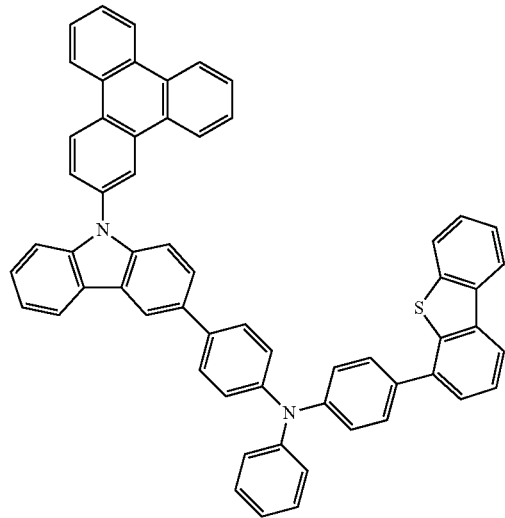
[A-215]
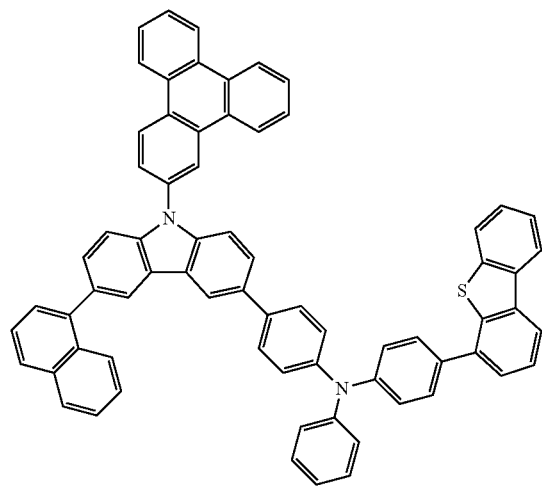
[A-216]
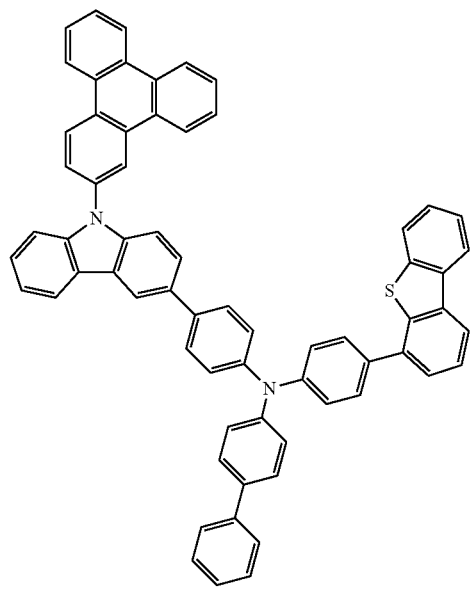

-continued
[A-217]
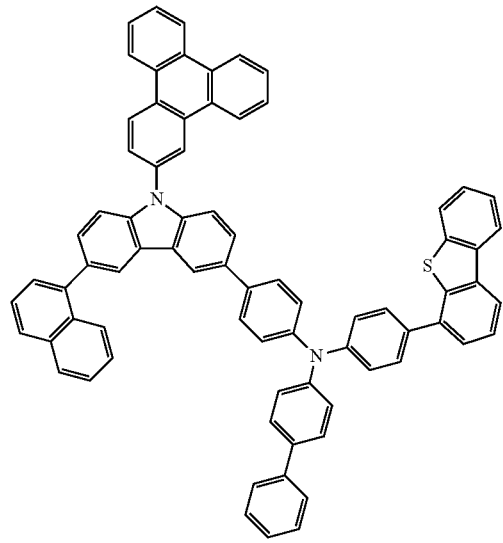
[A-218]
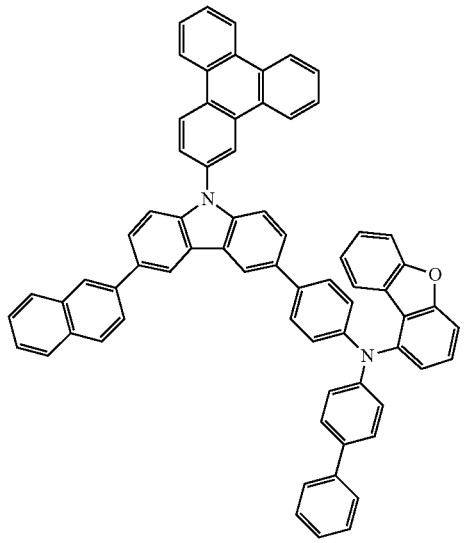
[A-219]
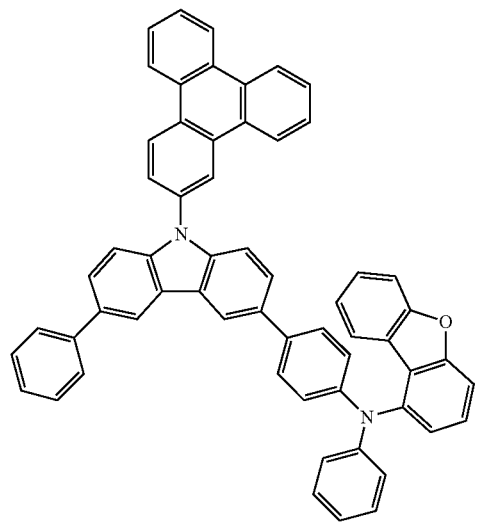
[A-220]
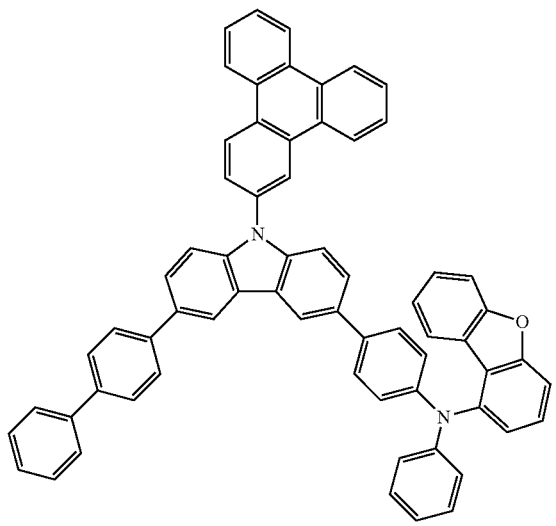

-continued
333 [A-221]
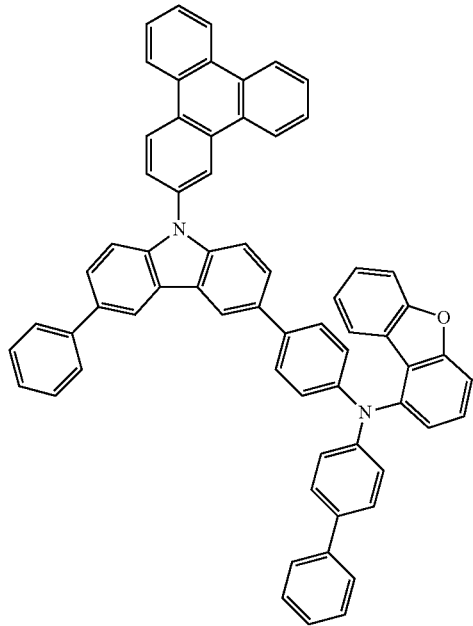
334 [A-222]
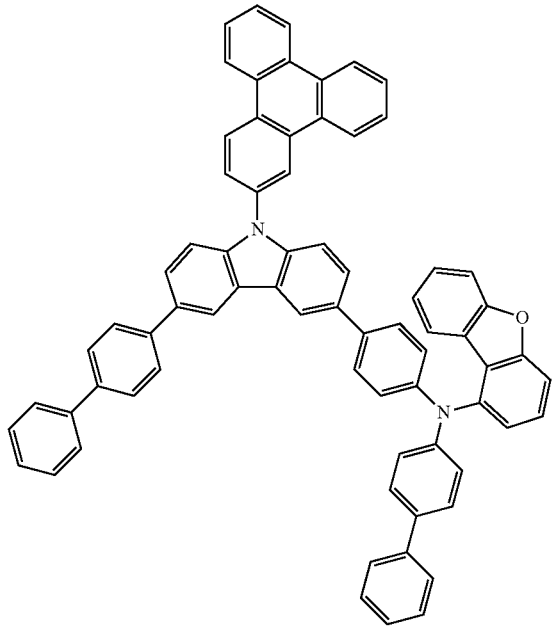
[A-223]
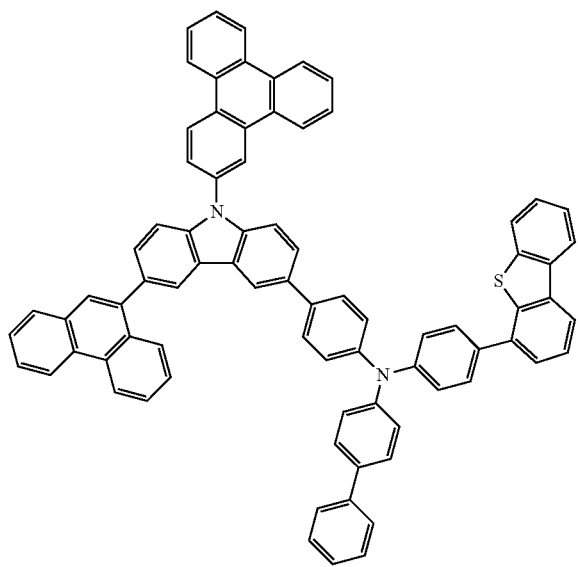
[A-224]
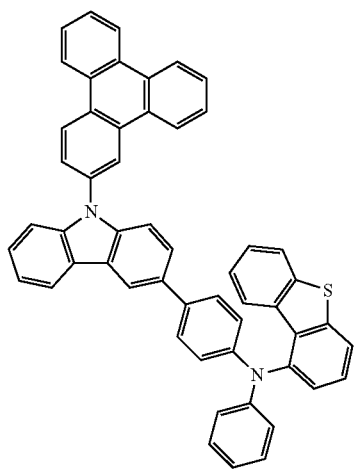

-continued
[A-225]
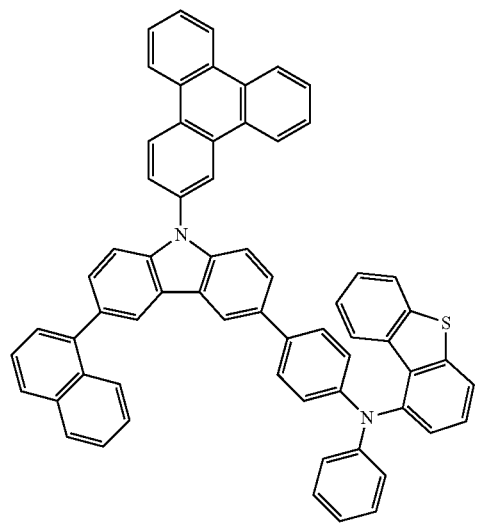
[A-226]
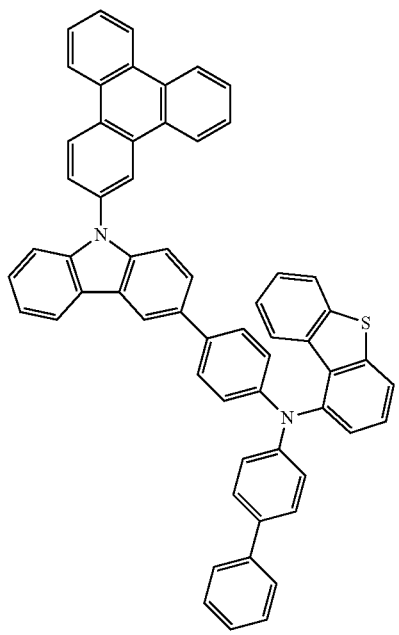
[A-227]
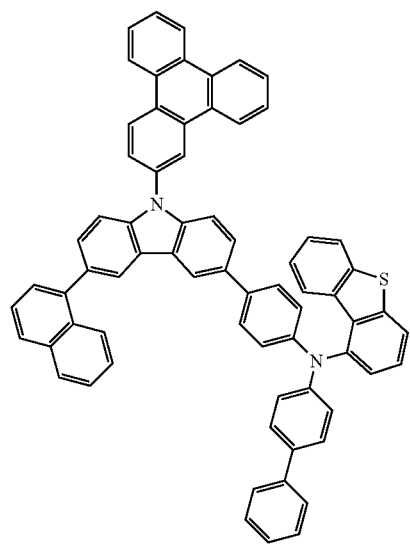
[A-228]
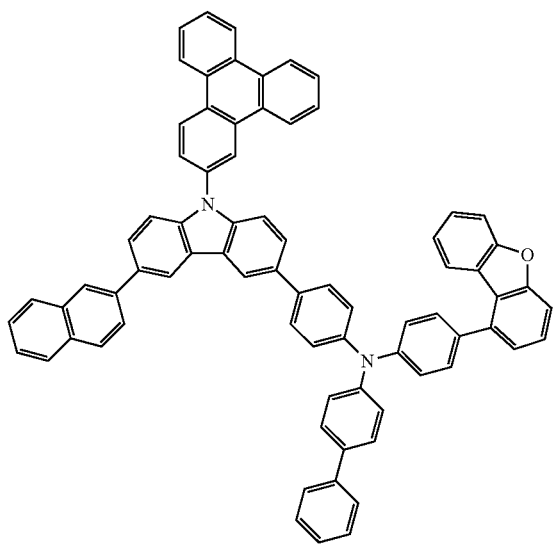
[A-229]
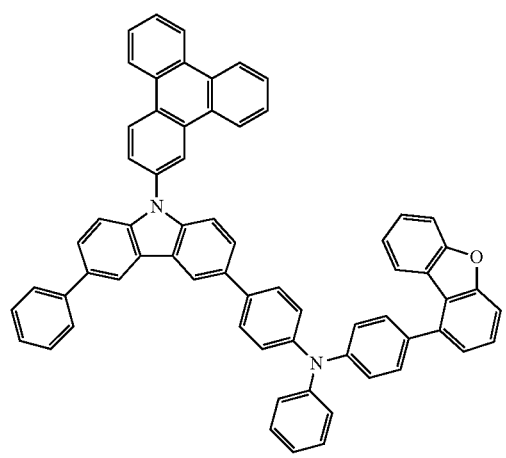
[A-230]
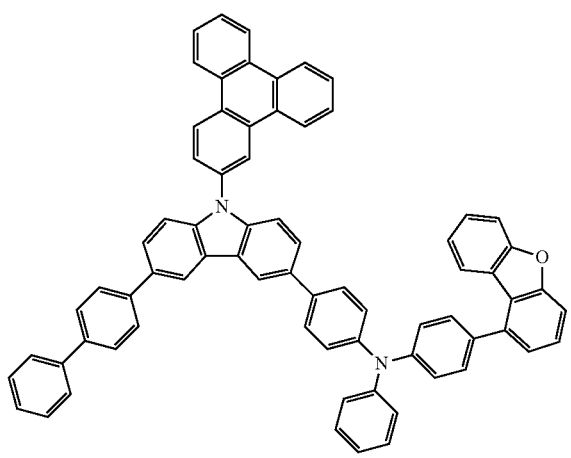

-continued
[A-231]
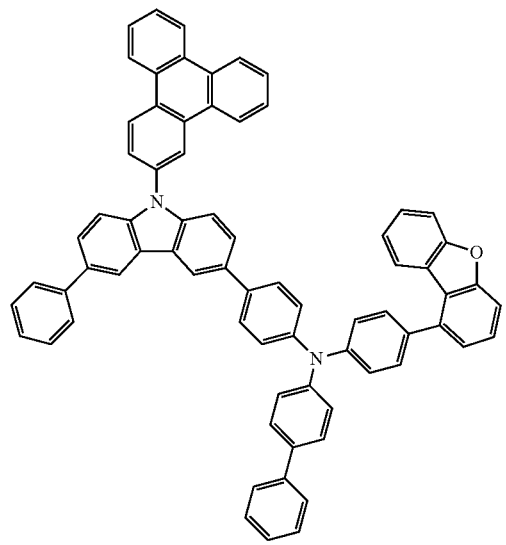
[A-232]
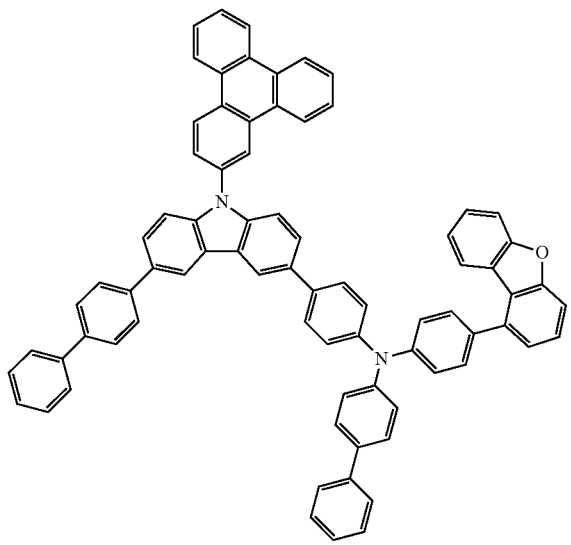
[A-233]
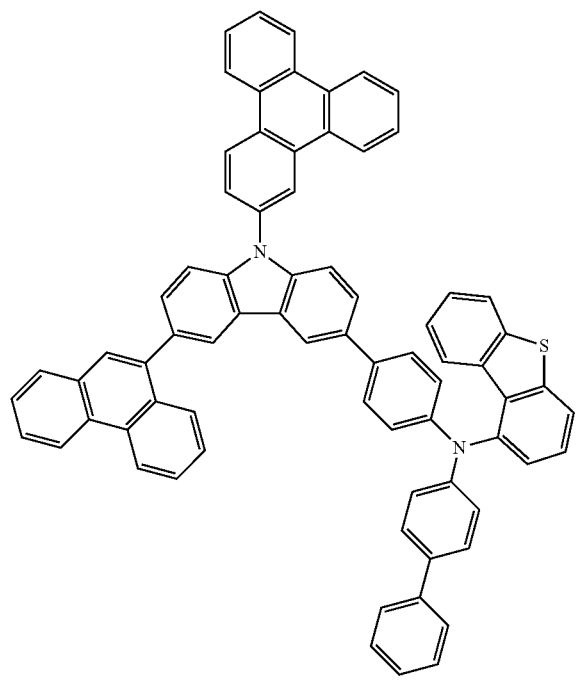
[A-234]
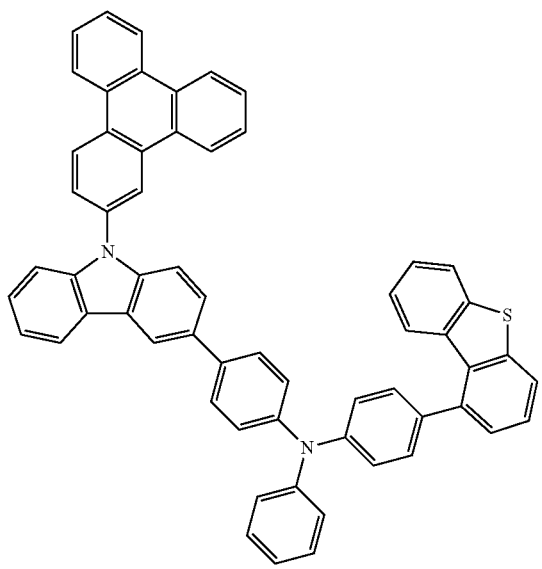

[A-235]
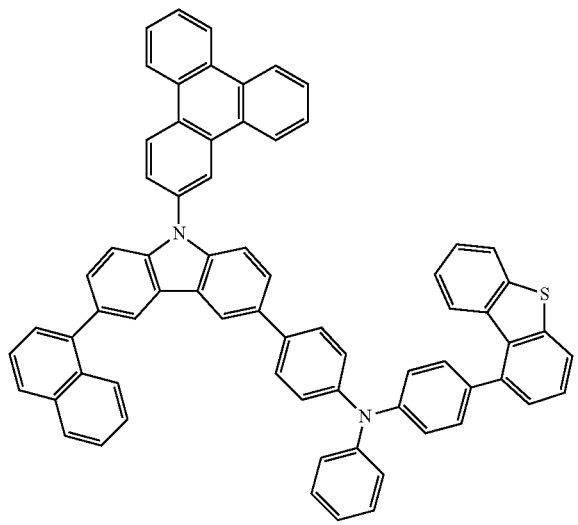
[A-236]
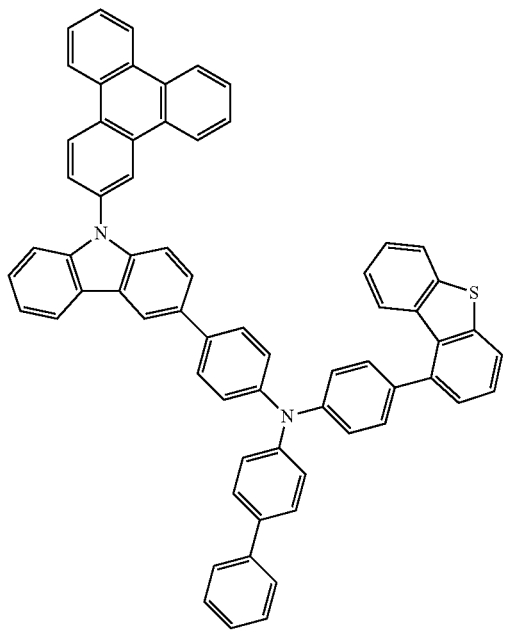
[A-237]
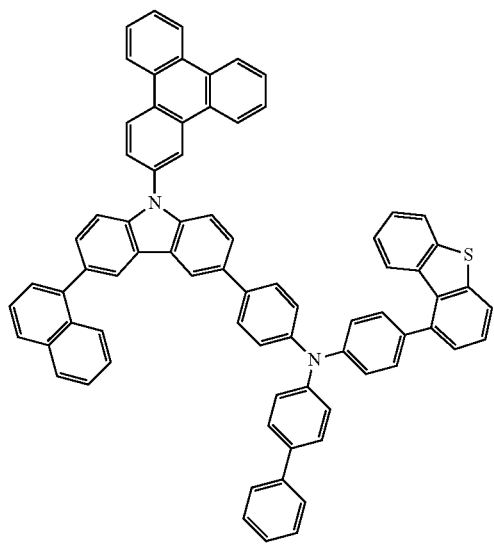
[A-238]
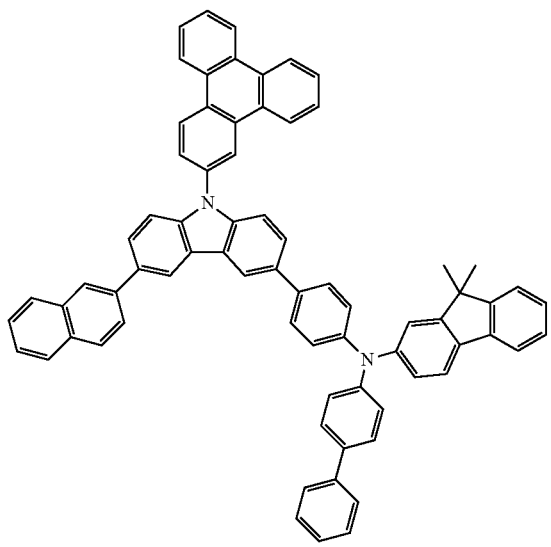

-continued
[A-239]
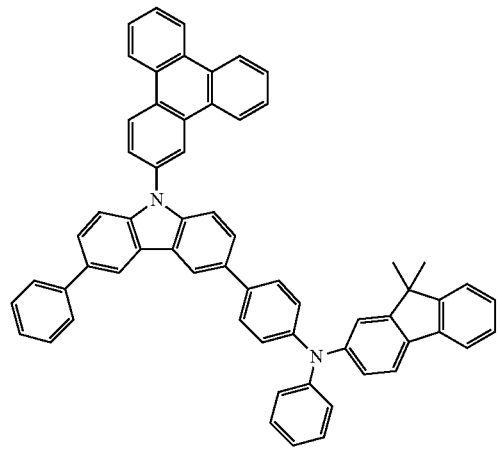
[A-240]
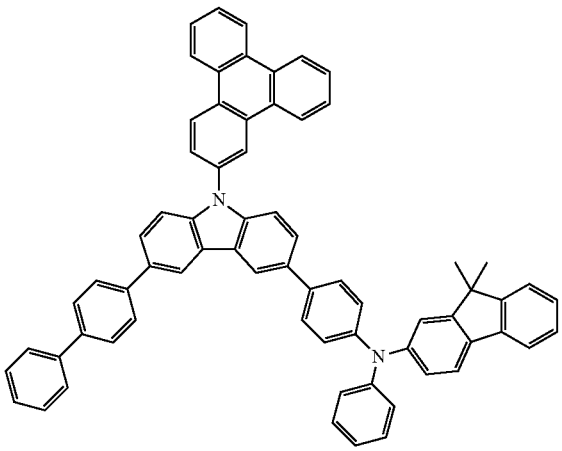
[A-241]
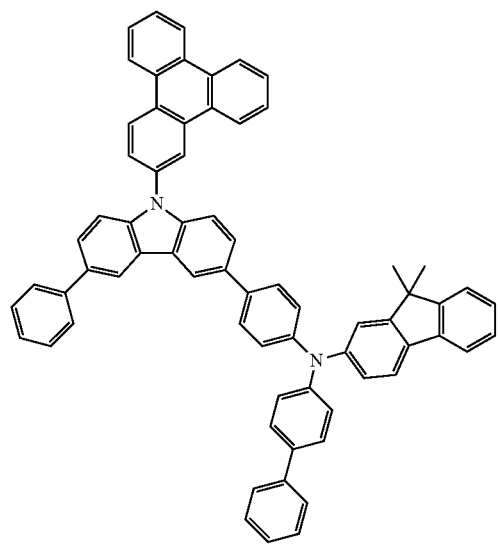
[A-242]
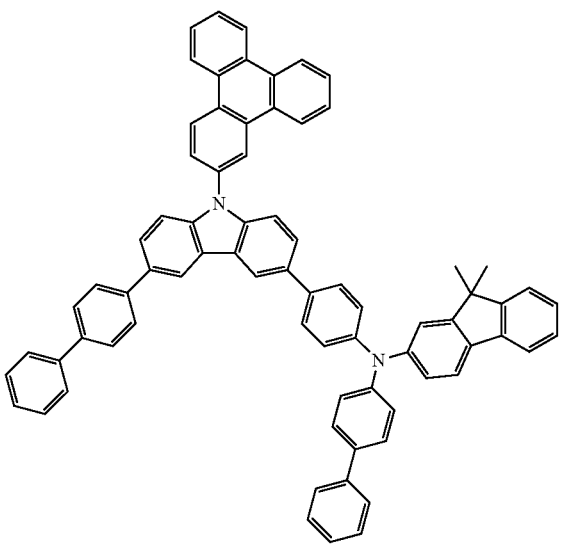
[A-243]
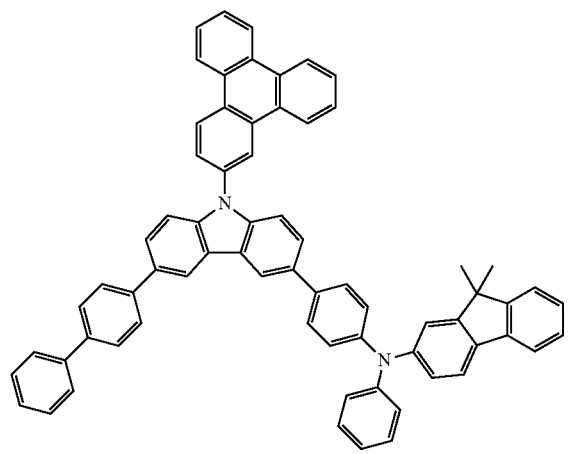
[A-244]
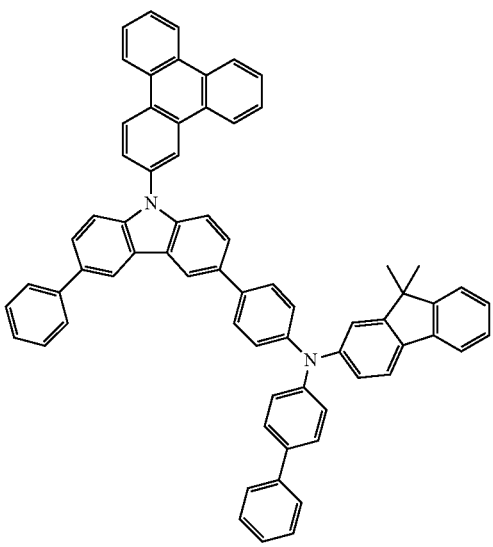

[A-245]
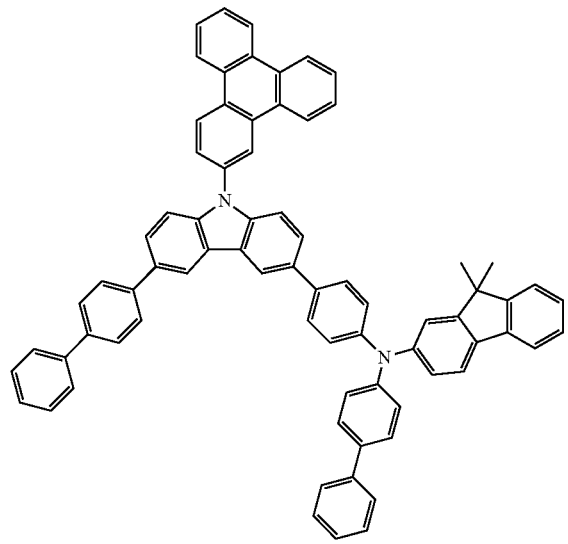
[A-246]
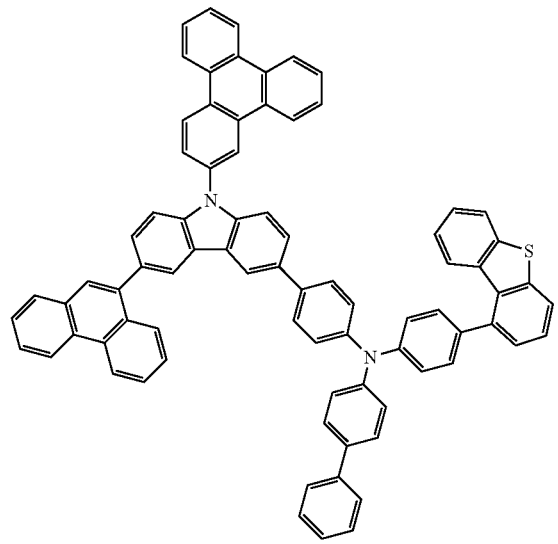
[A-247]
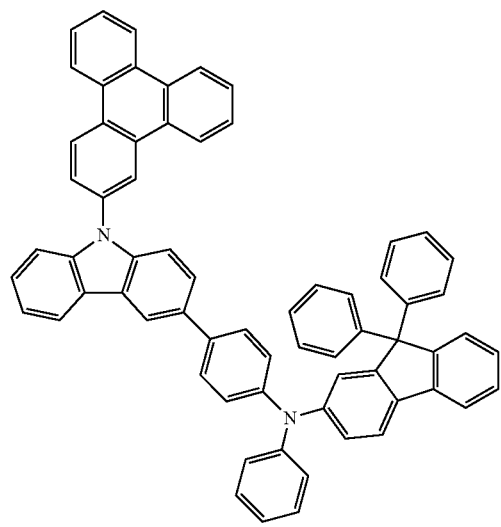
[A-248]
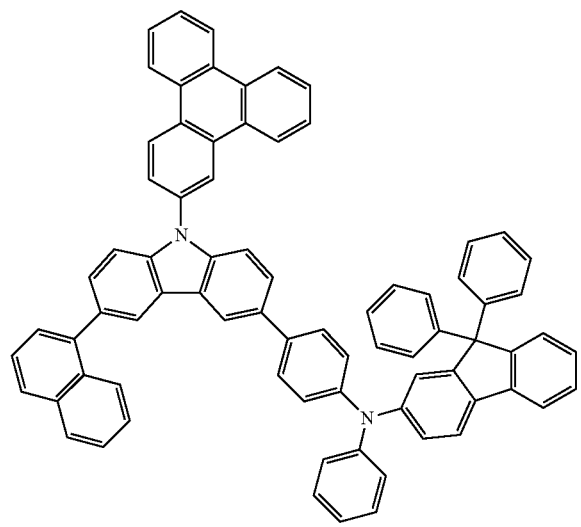

[A-249]
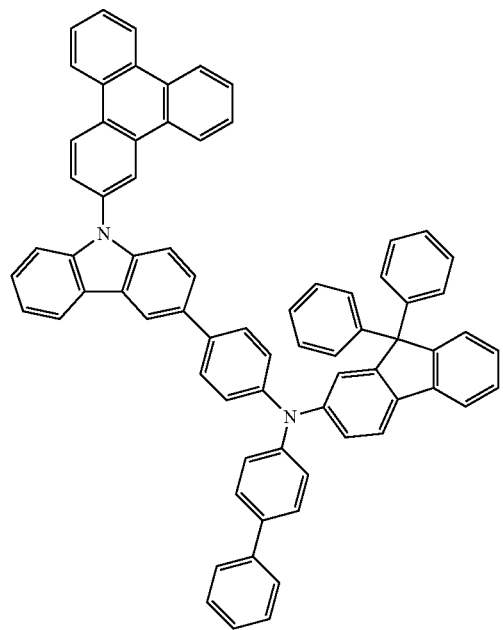
[A-250]
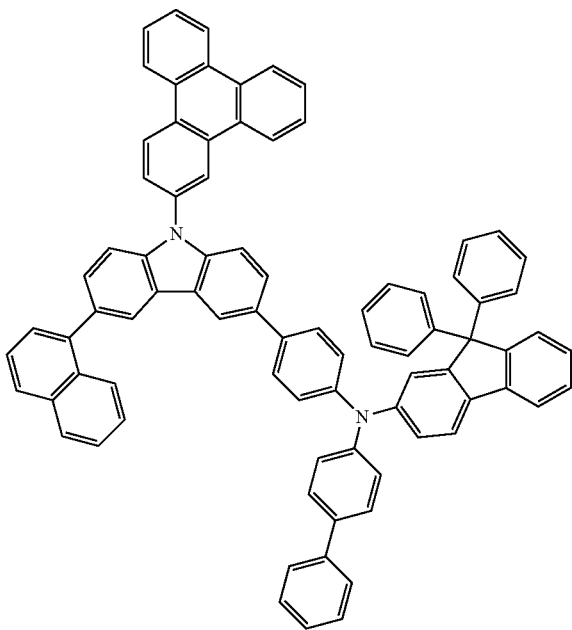
[A-251]
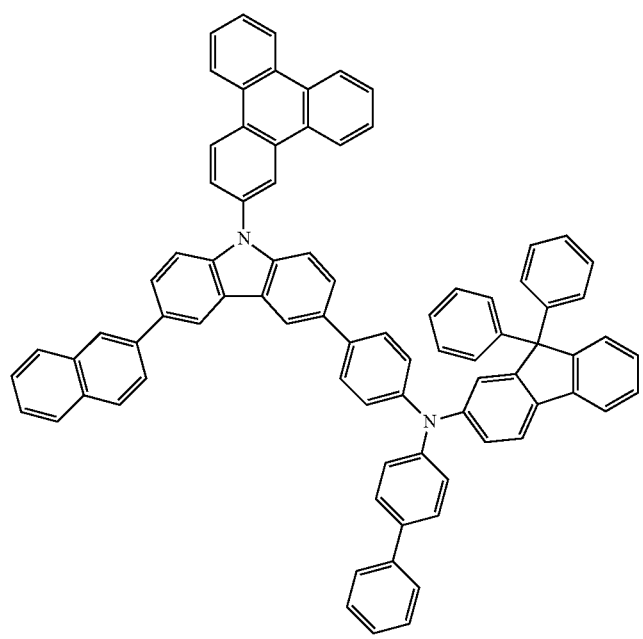

The compound for an organic photoelectric device represented by the above Chemical Formula 1 may be represented by one of the following Chemical Formulae A-252 to A-336.
[A-252]
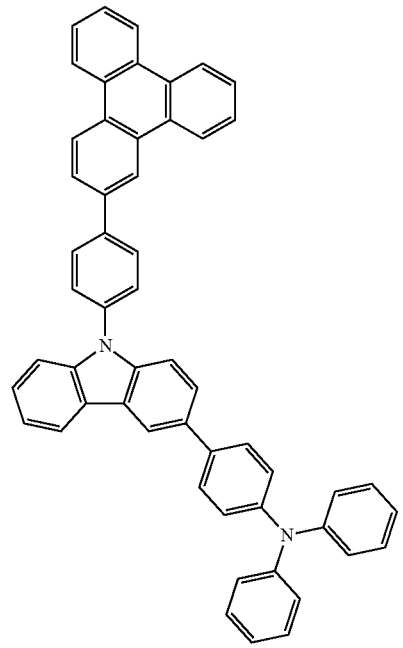
[A-253]
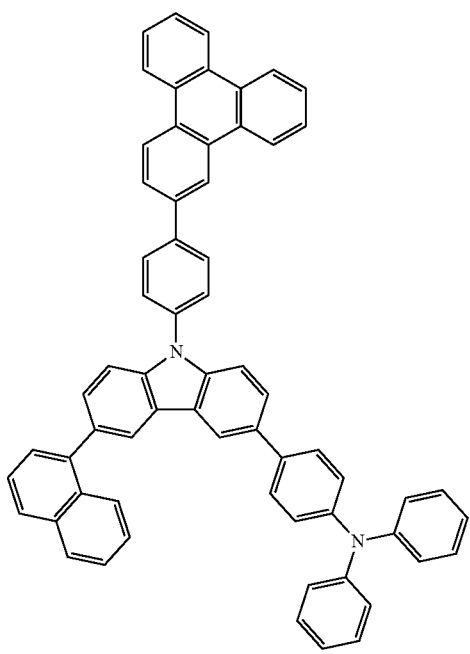
[A-254]
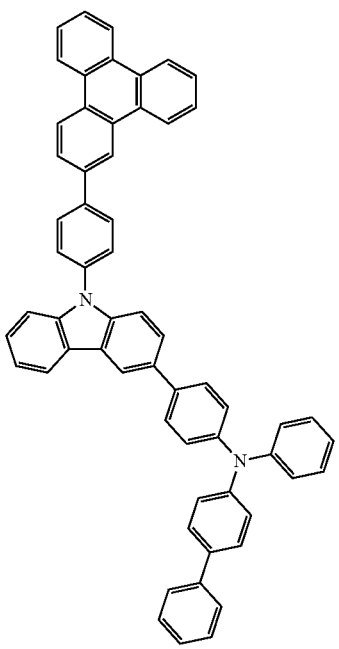
[A-255]
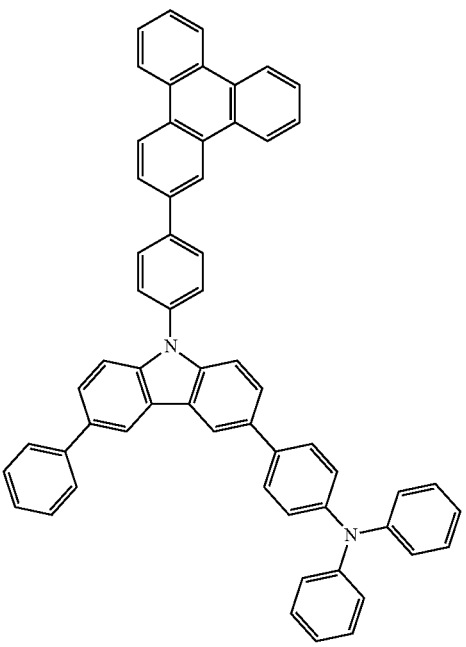

[A-256]
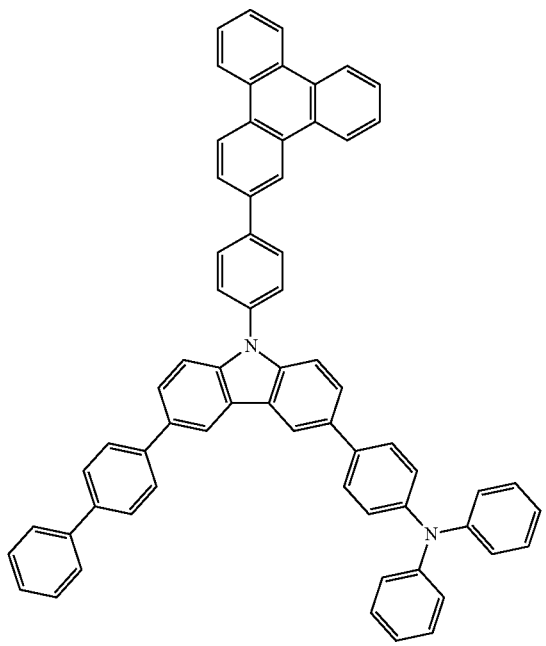
[A-258]
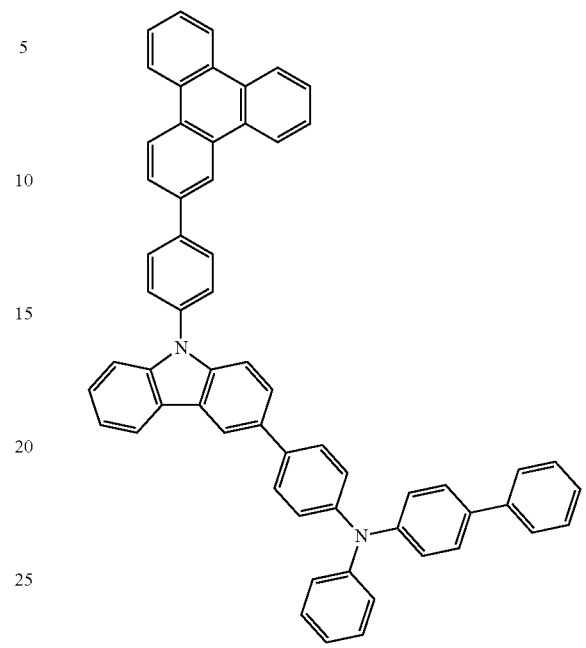
[A-257]
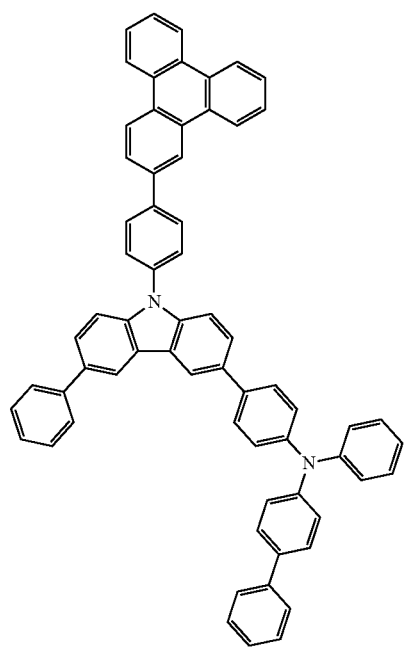
[A-259]
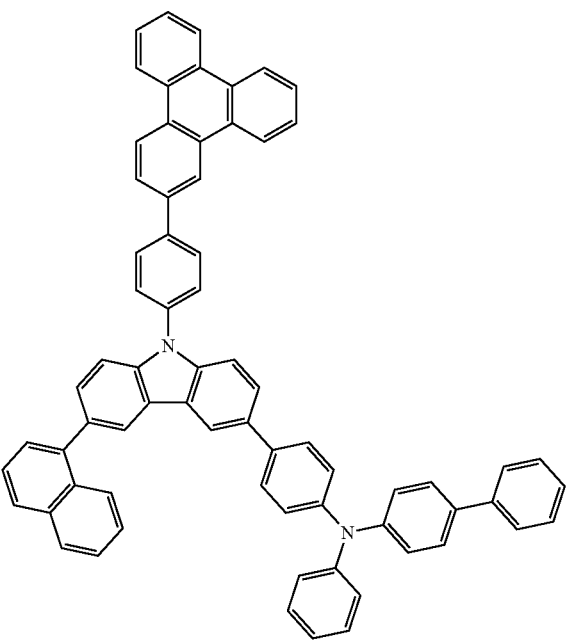

[A-260]
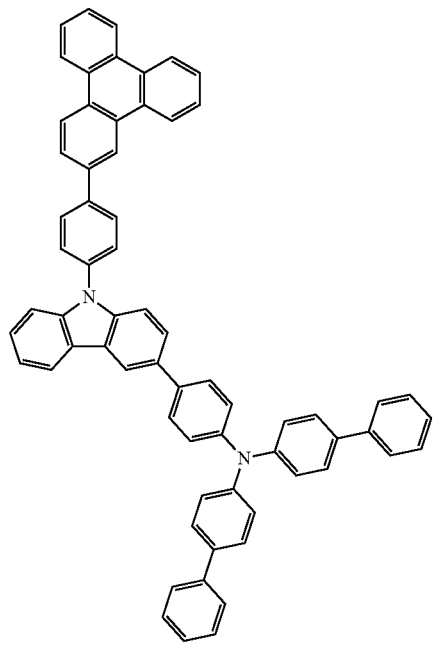
[A-262]
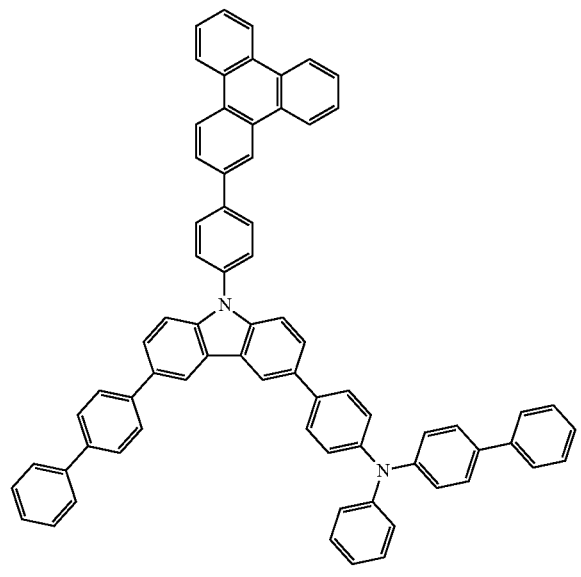
[A-261]
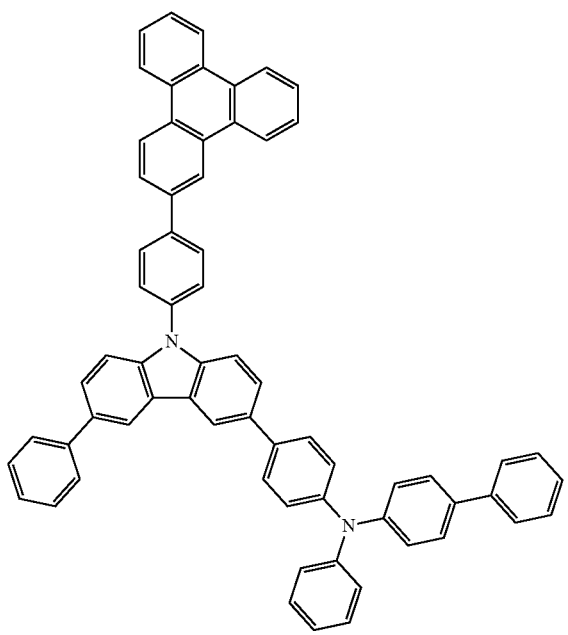
[A-263]
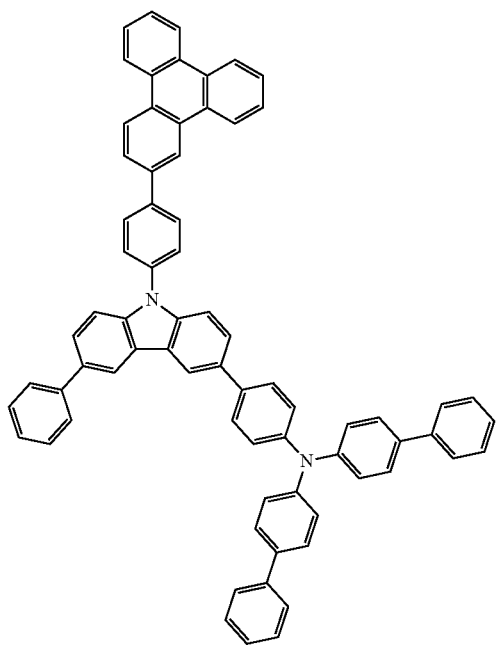

[A-264]
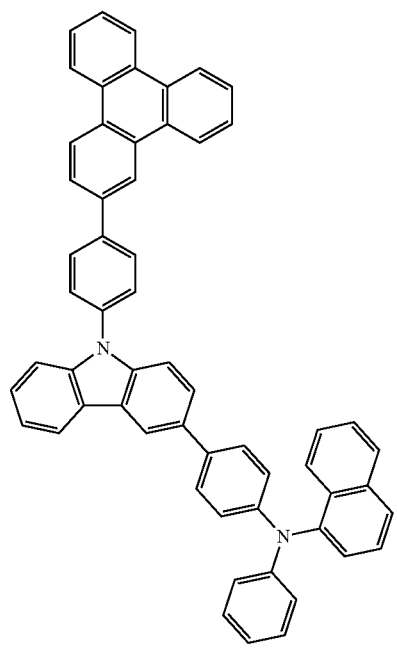
[A-266]
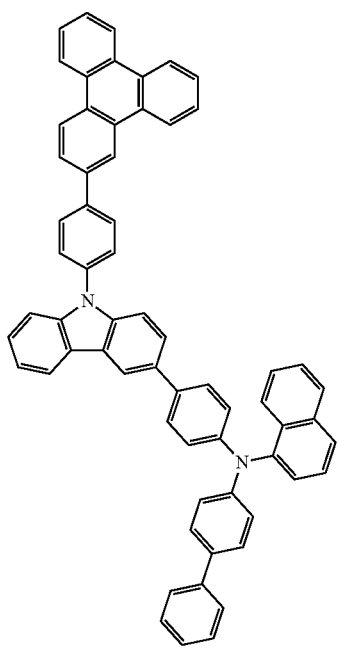
[A-265]
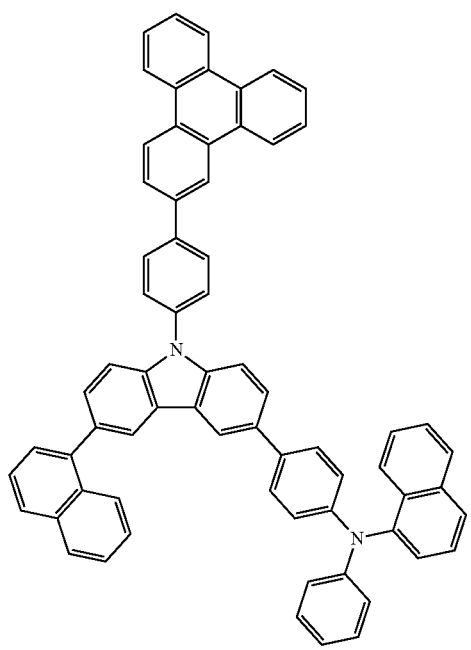
[A-267]
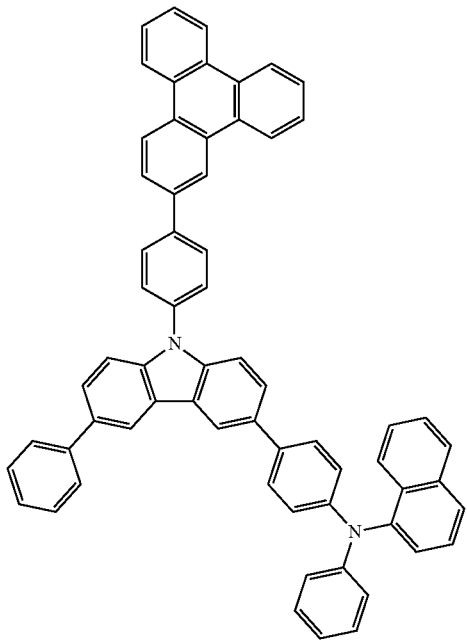

[A-268]
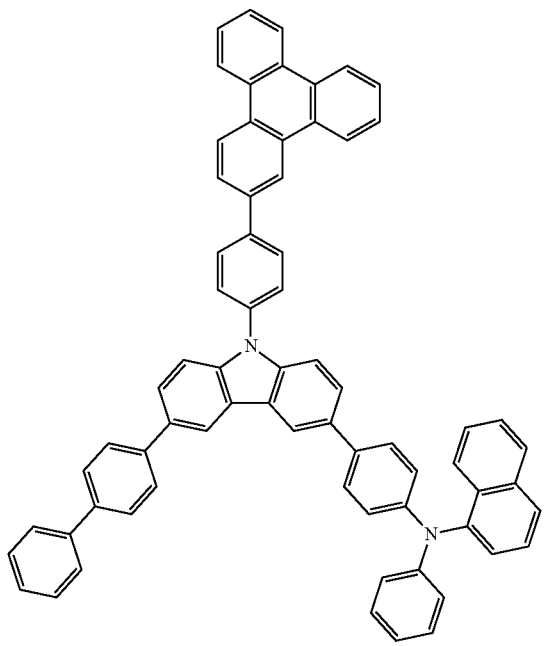
[A-270]
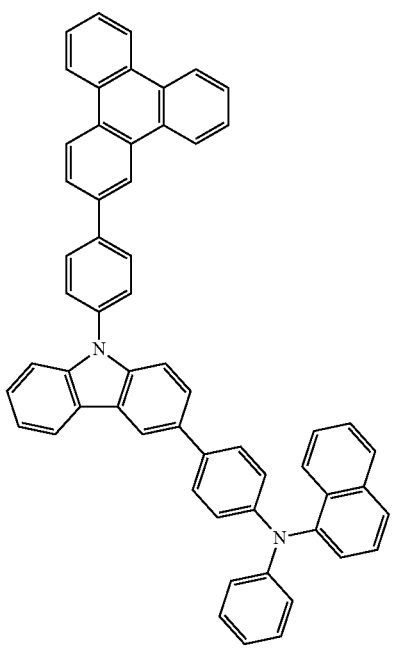
[A-269]
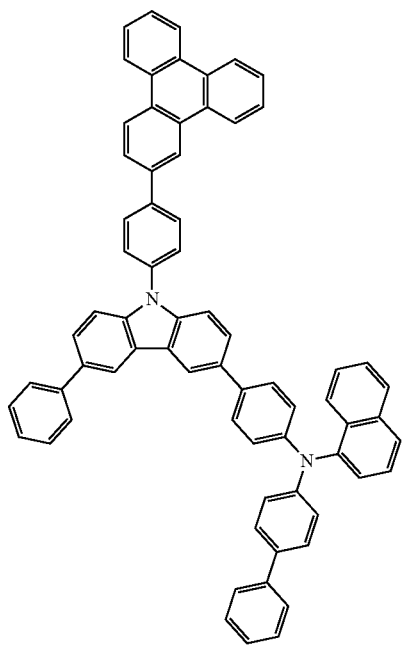
[A-271]
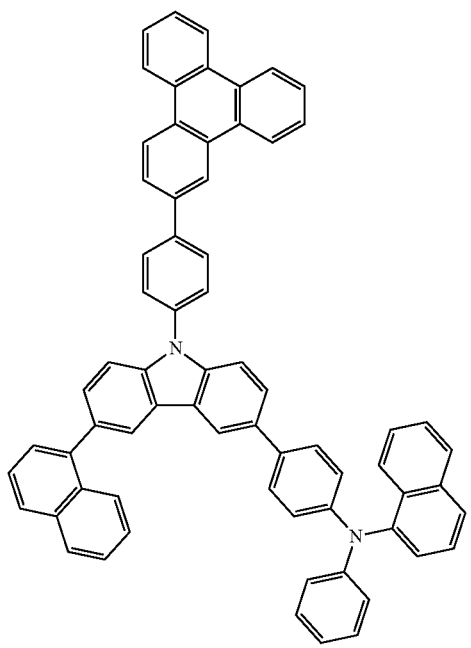

-continued
[A-272]
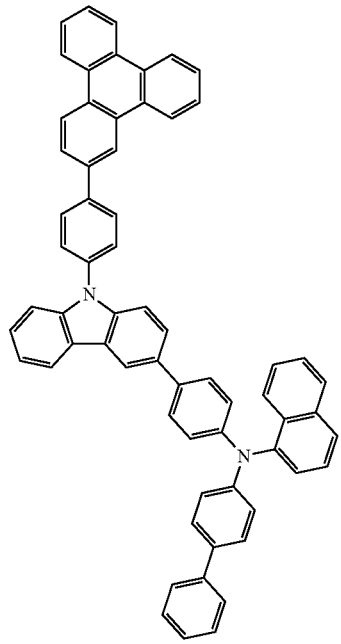
[A-273]
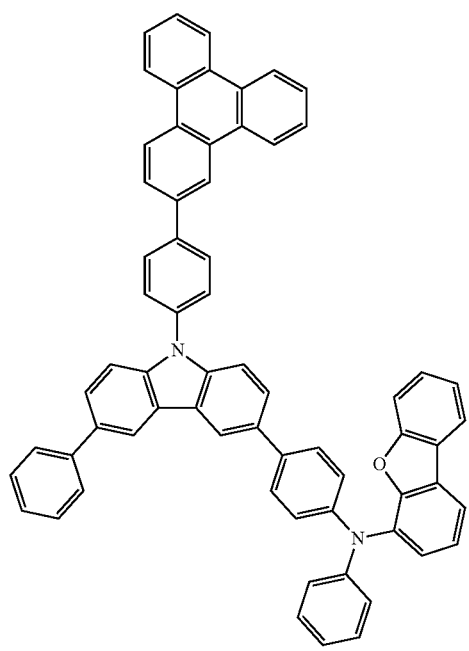
-continued
[A-274]
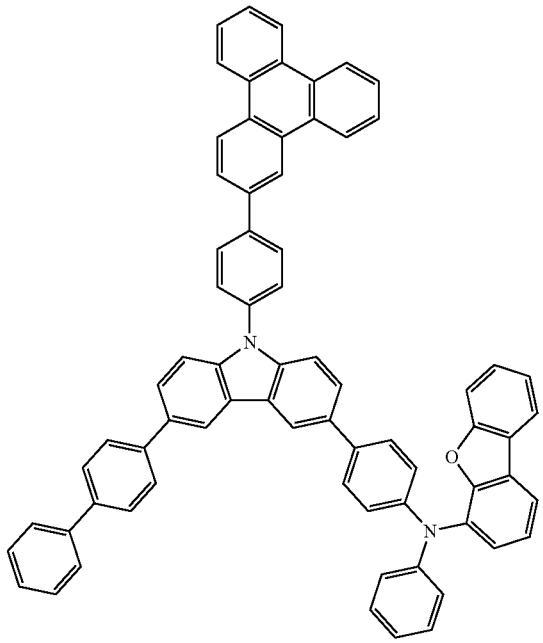
[A-275]
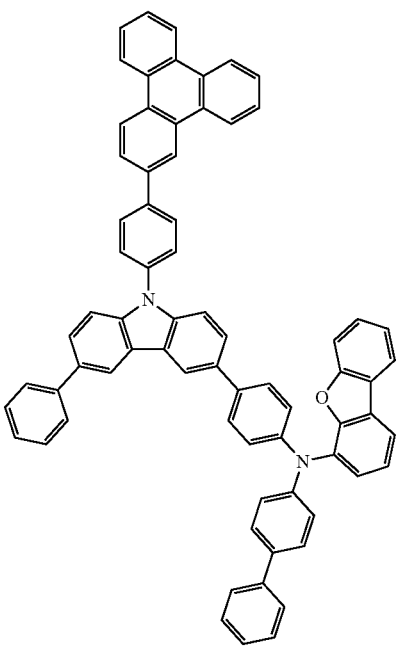

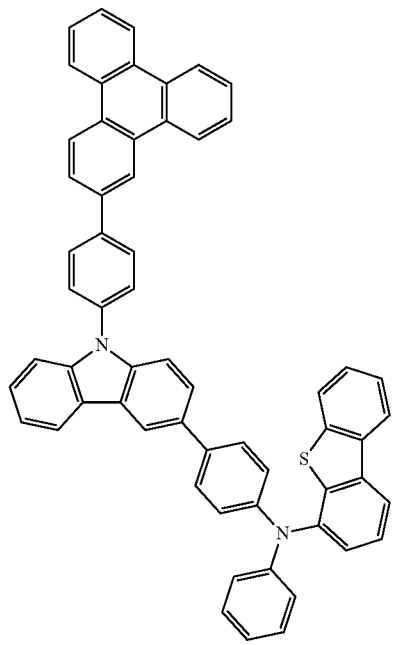
[A-276]
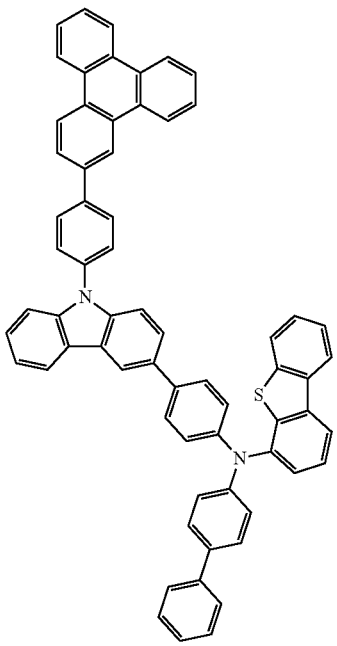
[A-278]
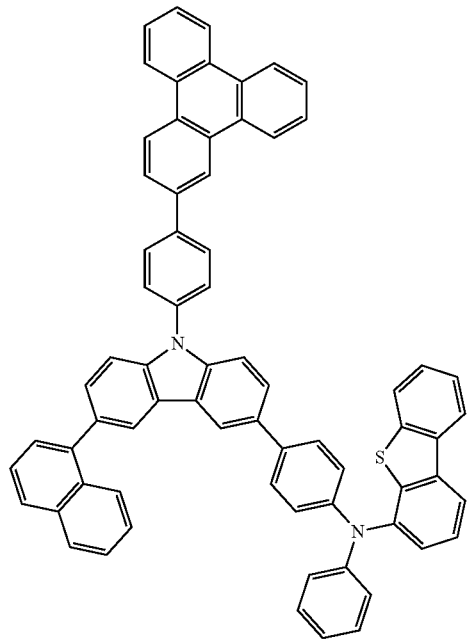
[A-277]
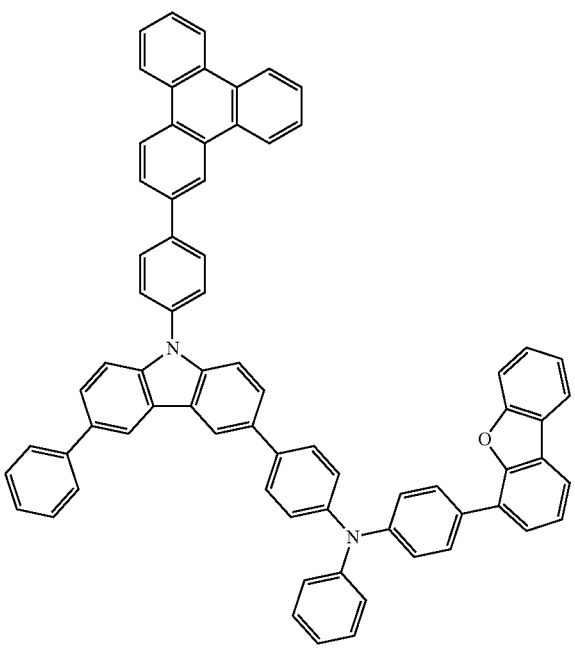
[A-279]

-continued
[A-280]
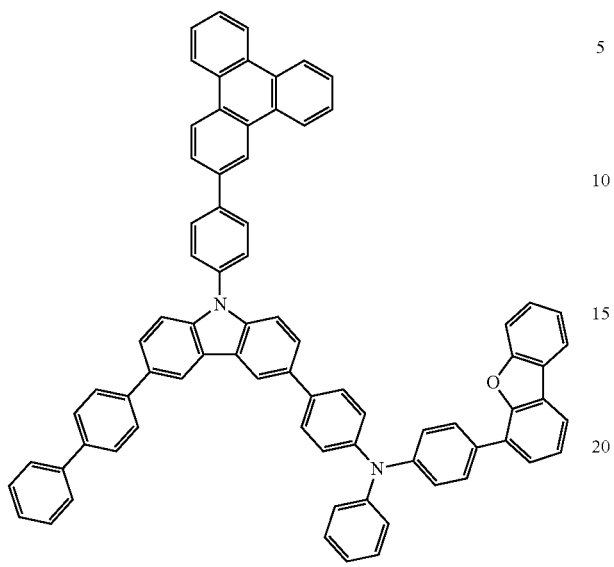
[A-281]
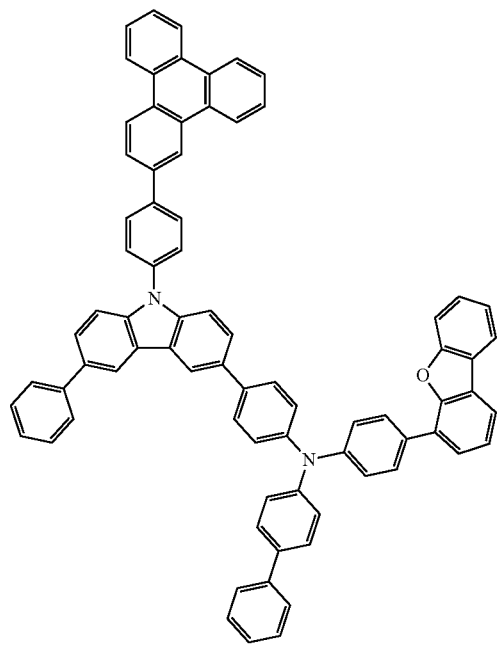
[A-282]
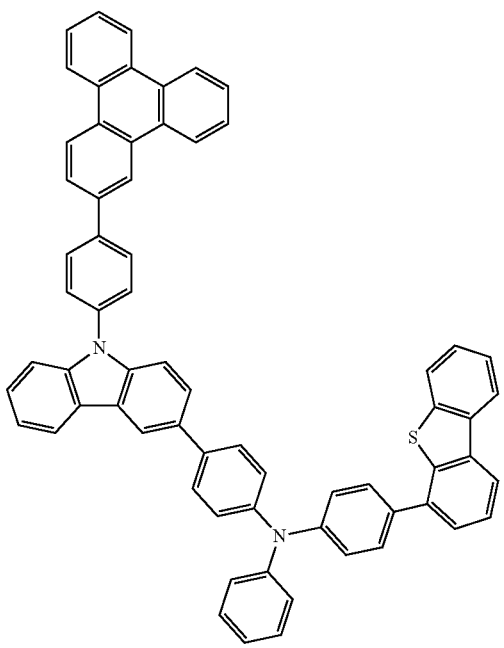
[A-283]
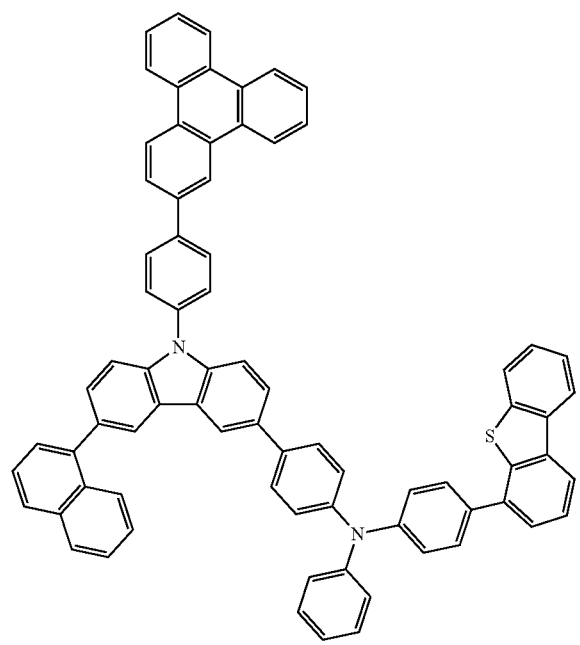

[A-284]
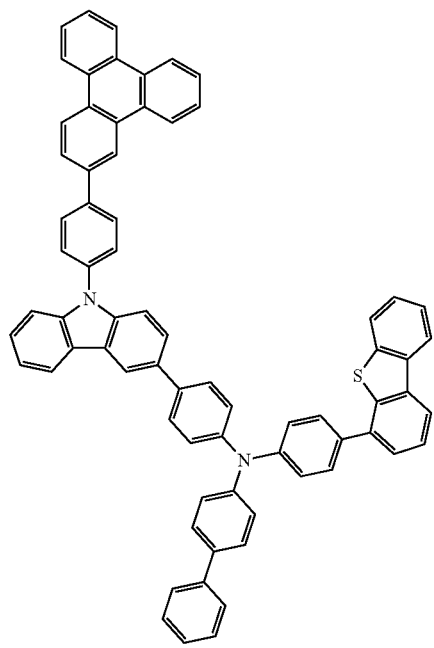
[A-285]
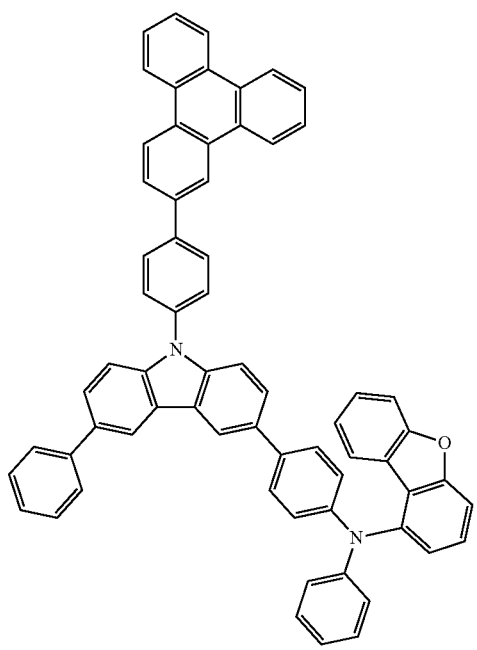
[A-286]
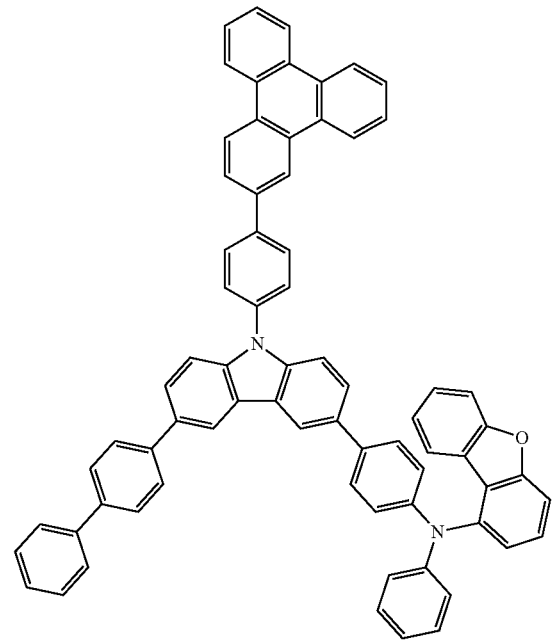
[A-287]
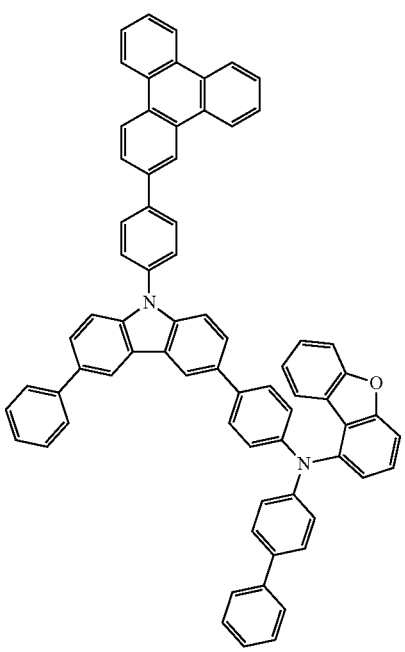

[A-288]
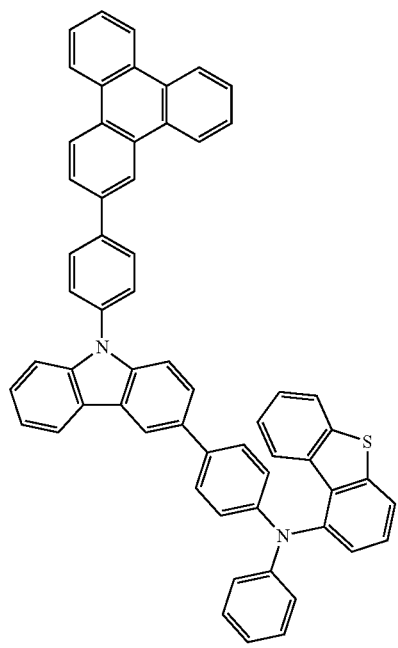
[A-290]
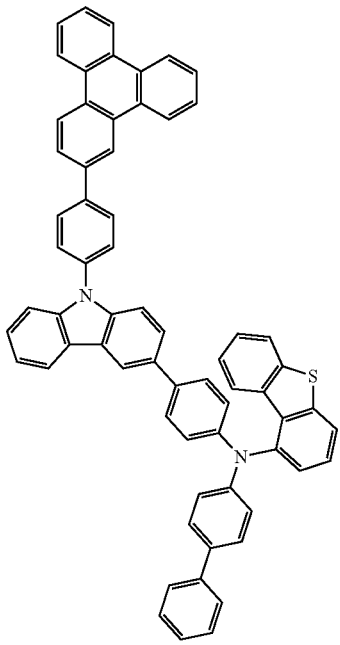
[A-289]
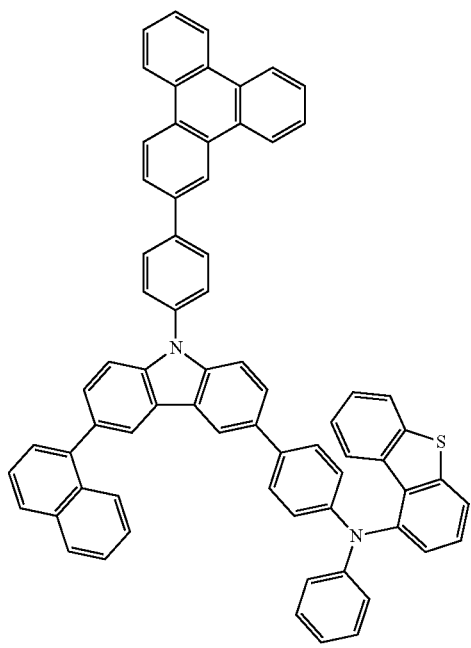
[A-291]
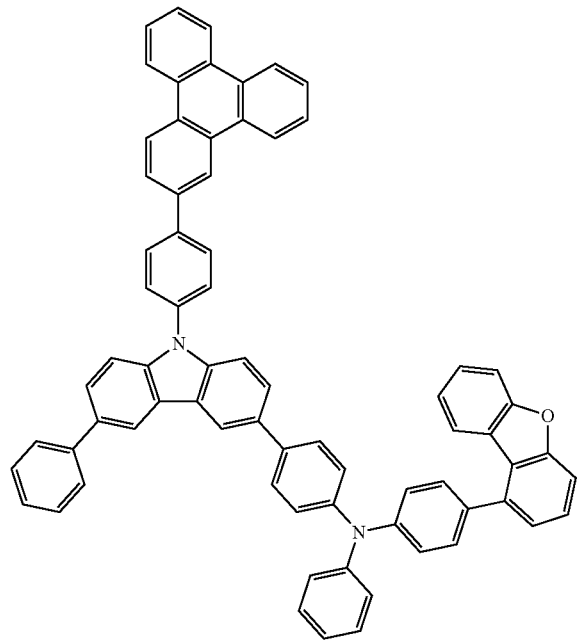

[A-292]
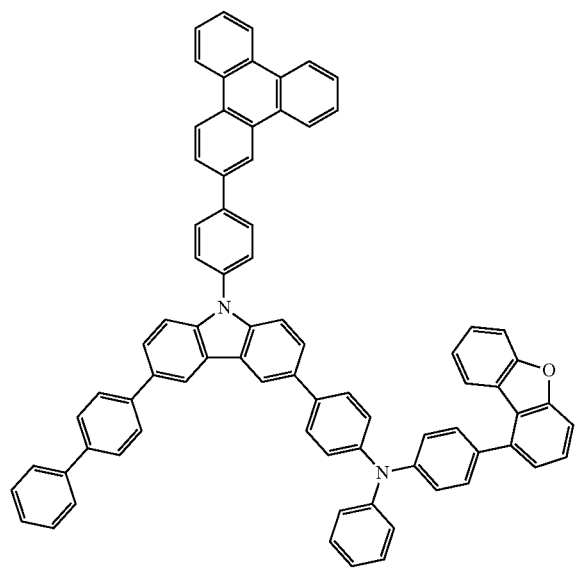
[A-293]
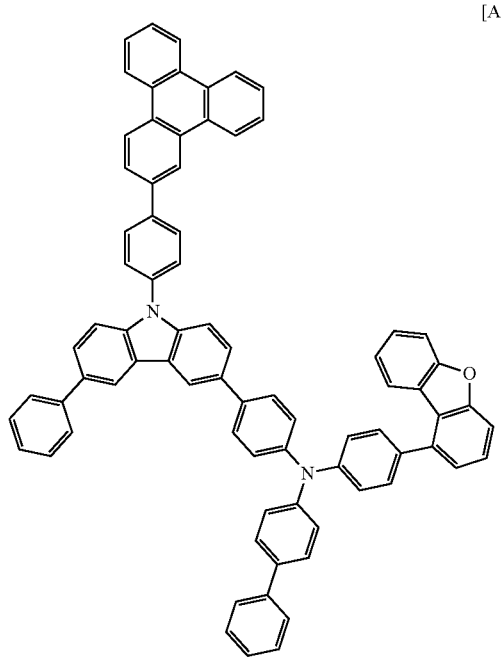
[A-294]
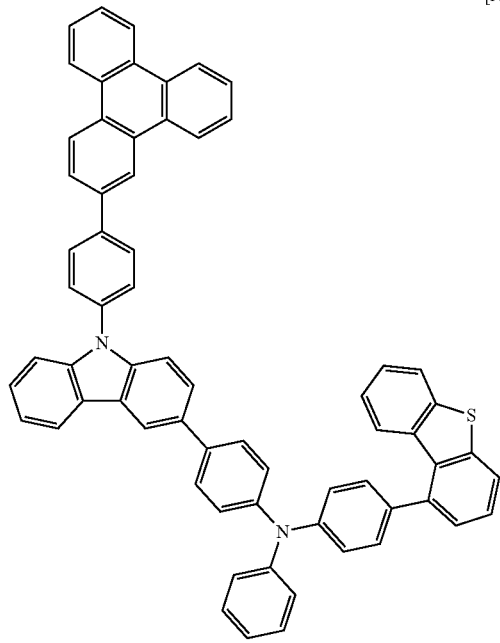
[A-295]
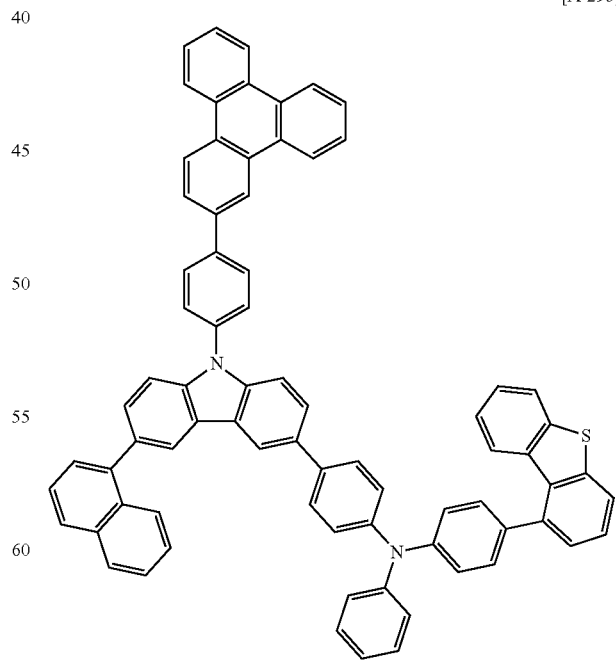

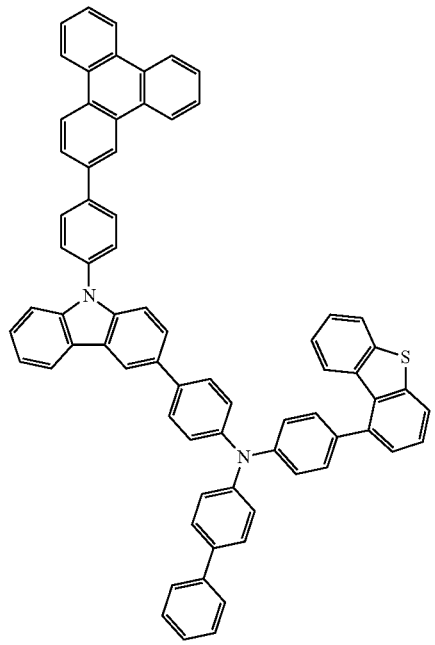
[A-296]
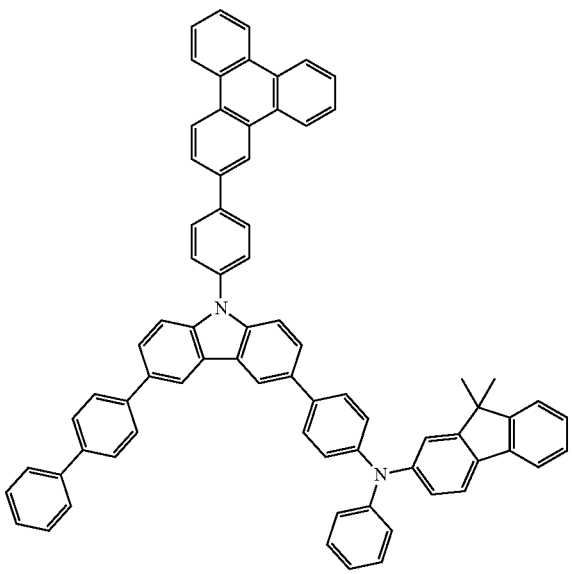
[A-298]
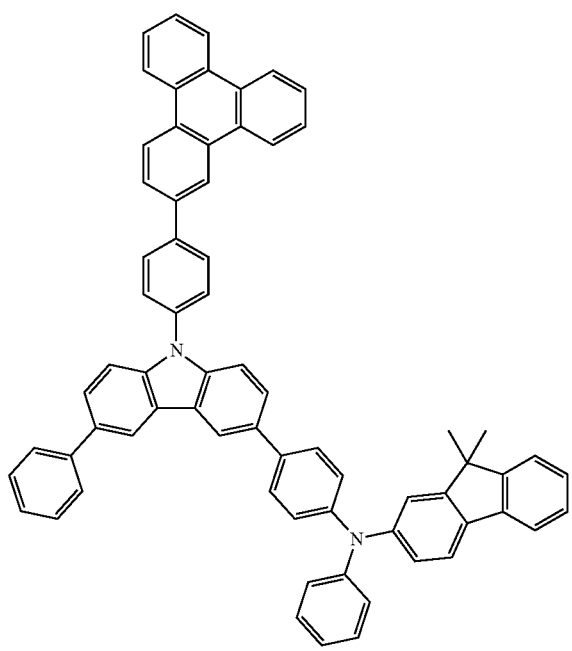
[A-297]
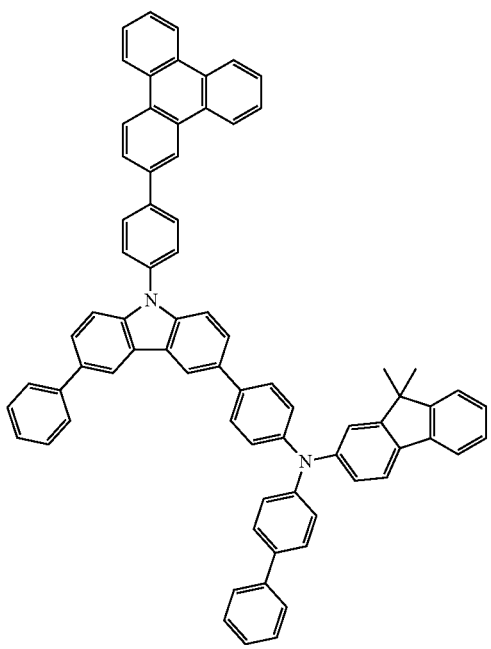
[A-299]

[A-300]
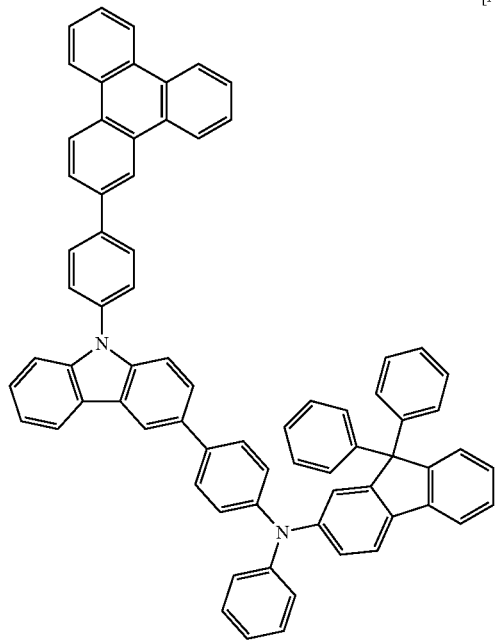
[A-302]
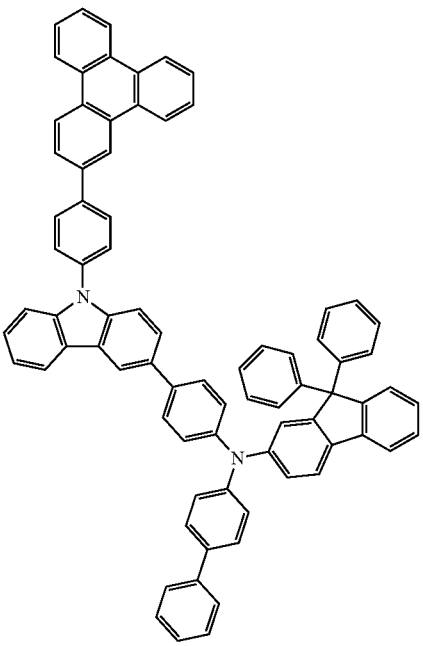
[A-301]
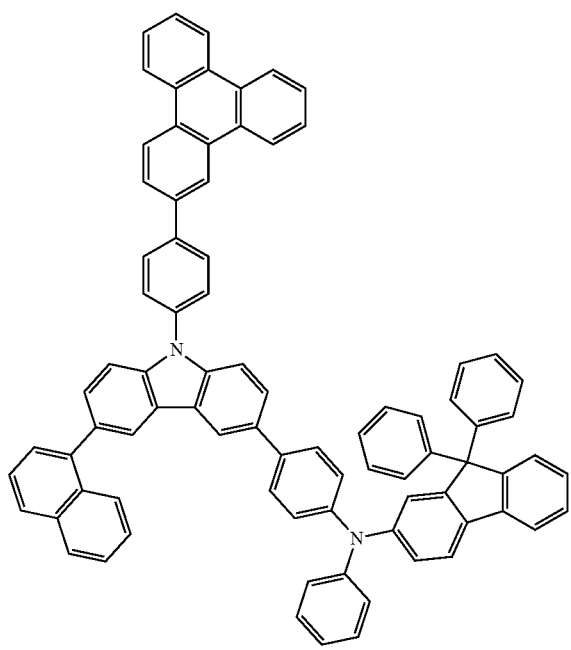
[A-303]
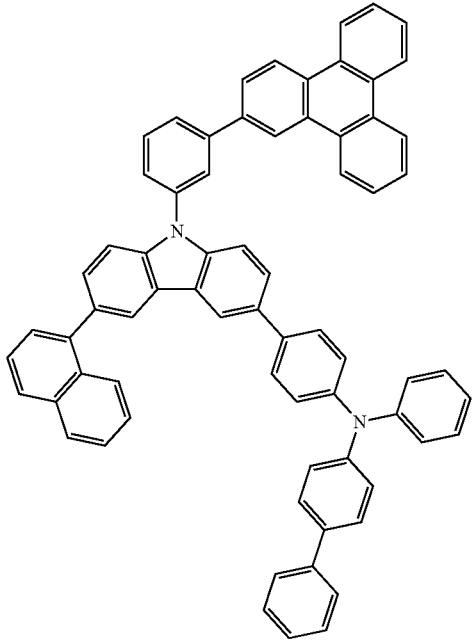

-continued
[A-304]
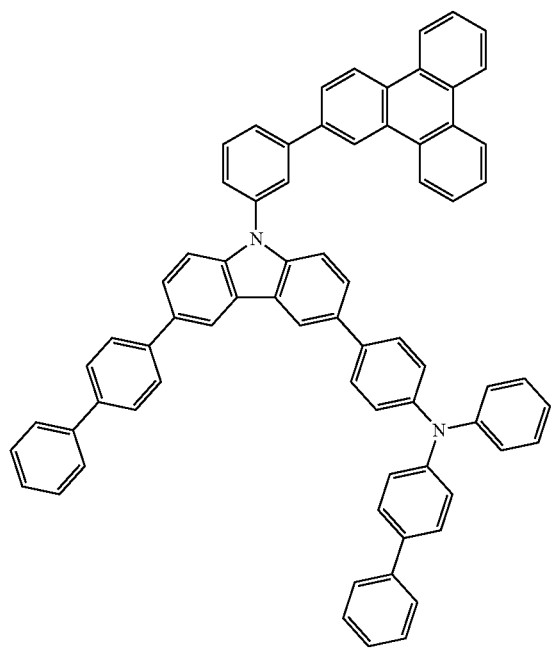
[A-306]
[A-305]
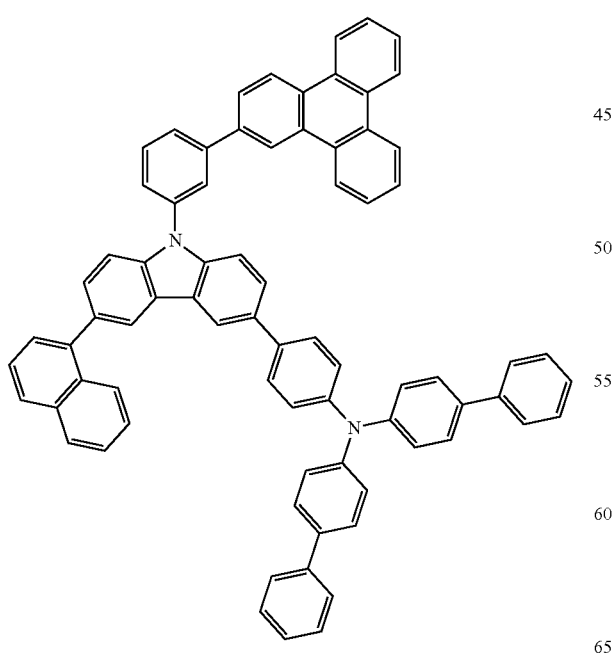
[A-307]
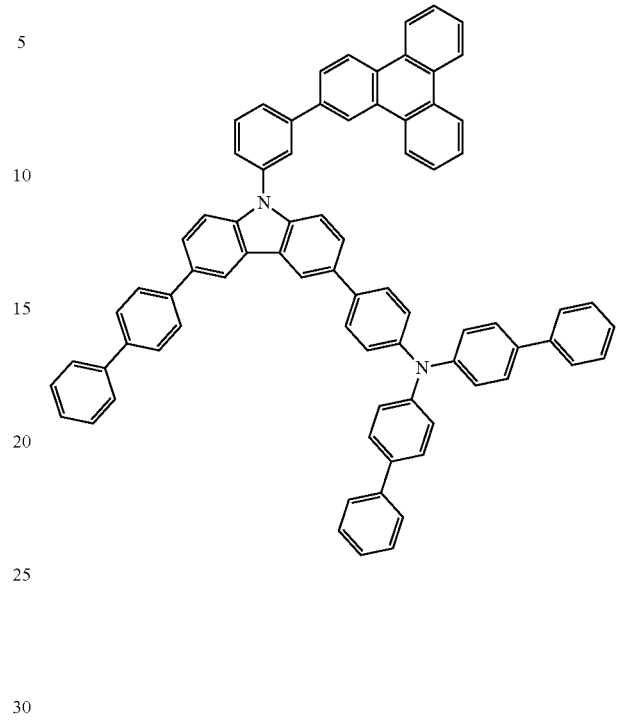

[A-308]
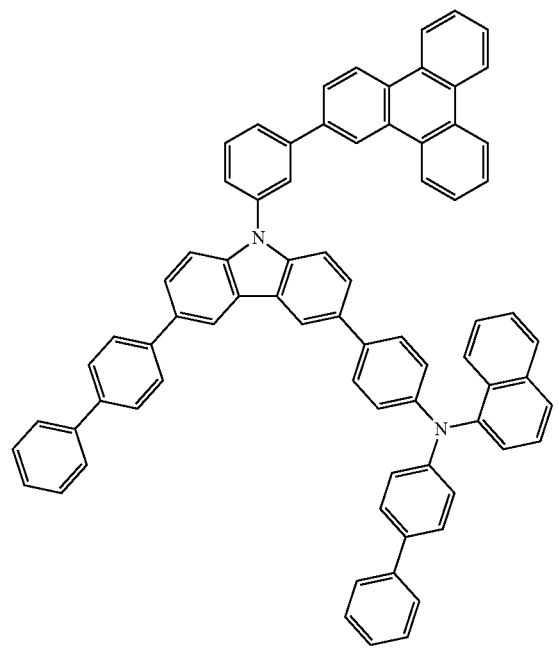
[A-310]
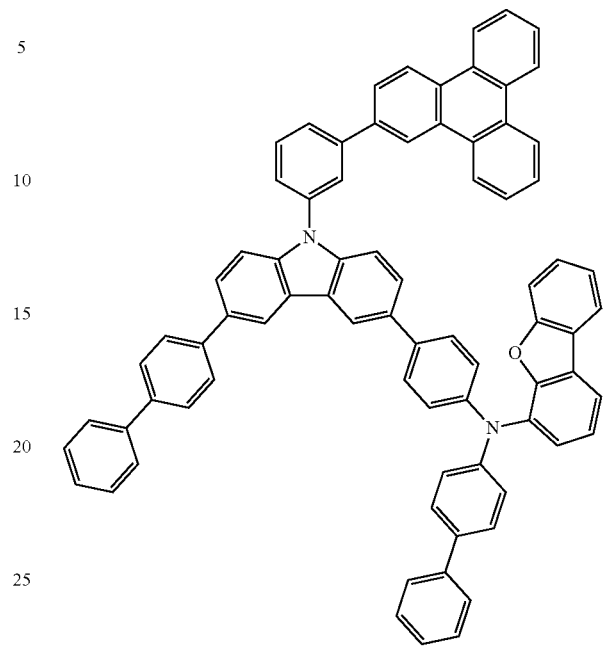
[A-309]
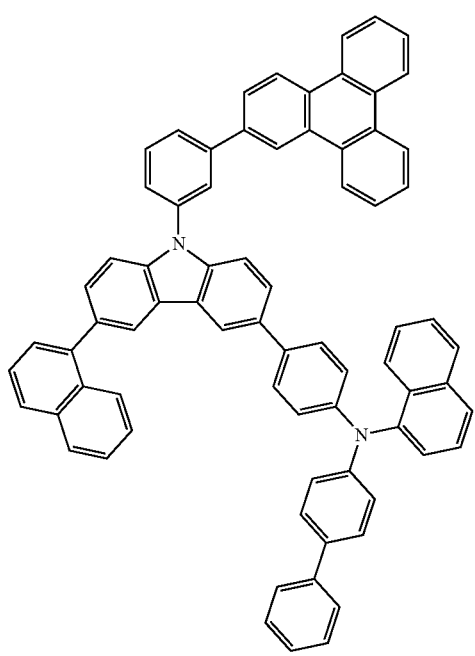
[A-311]
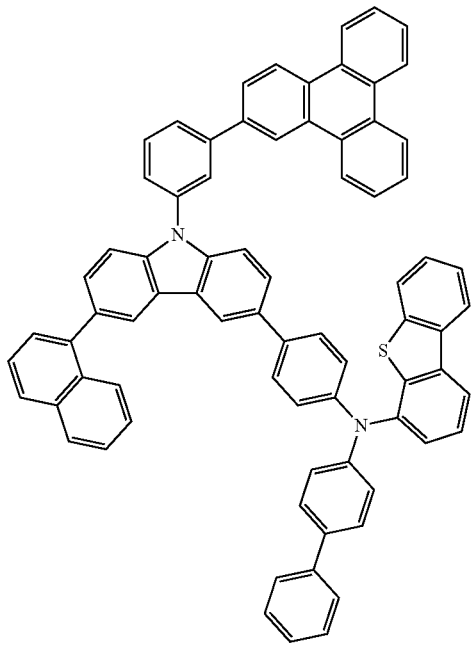

[A-312]
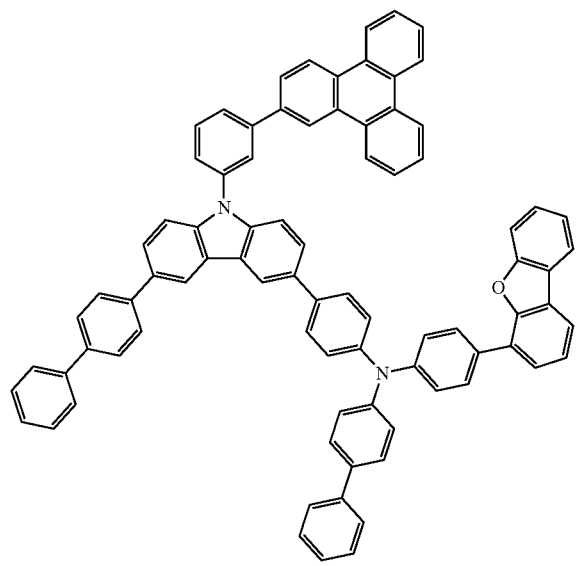
[A-313]
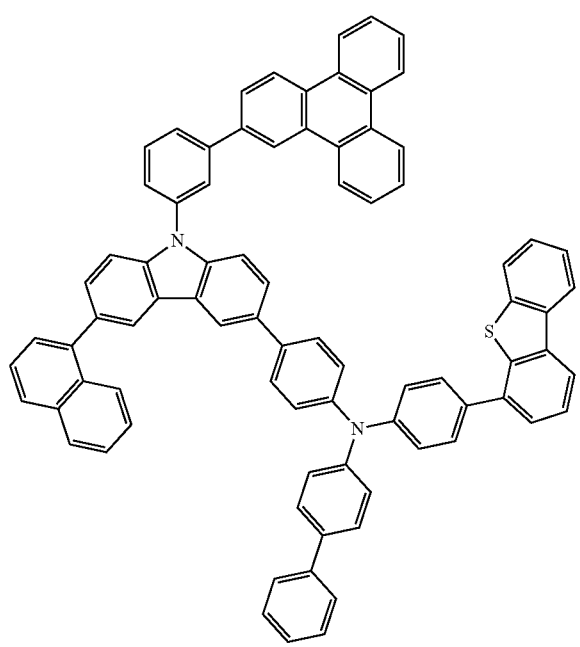
[A-314]
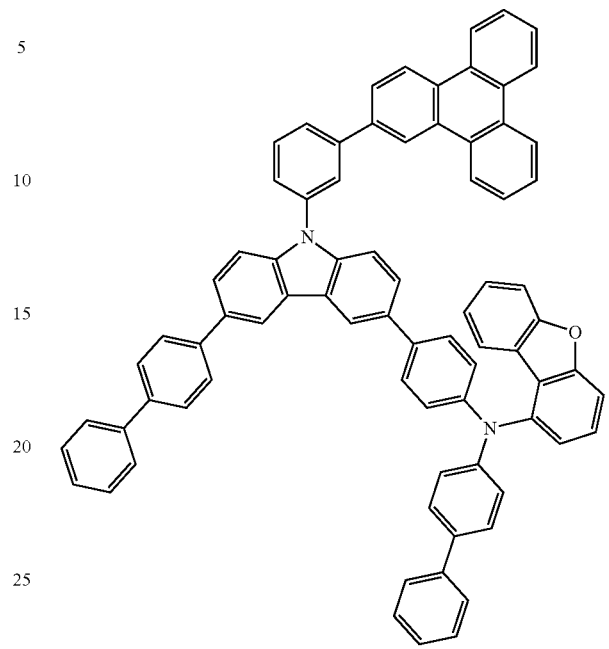
[A-315]
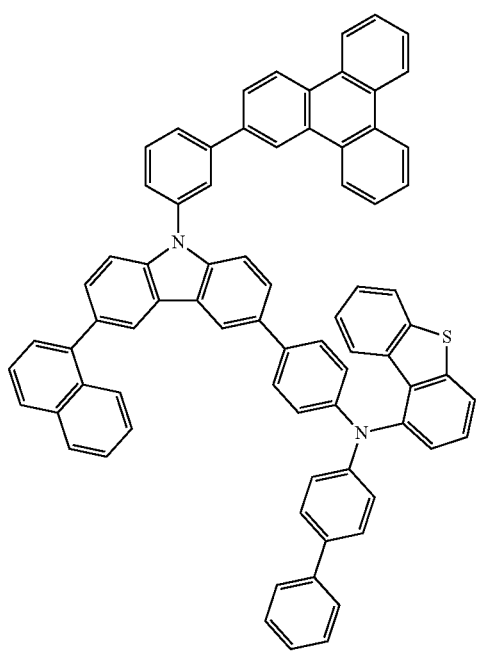

-continued
[A-316]
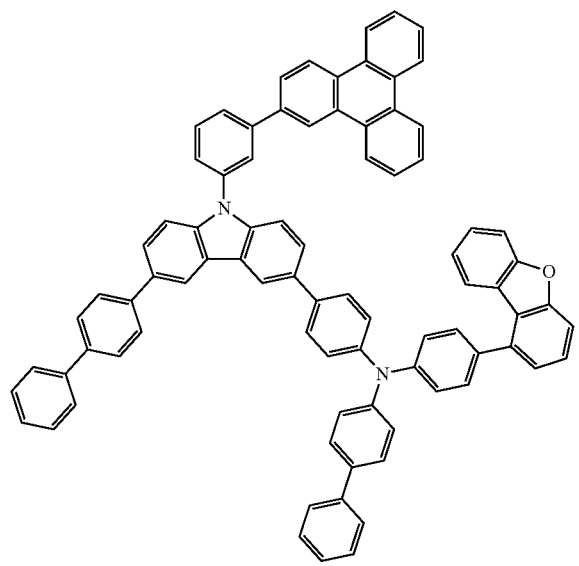
[A-318]
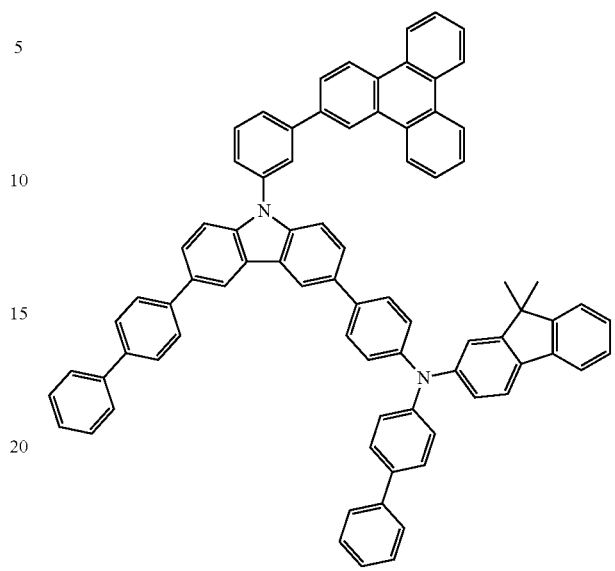
[A-317]
[A-319]
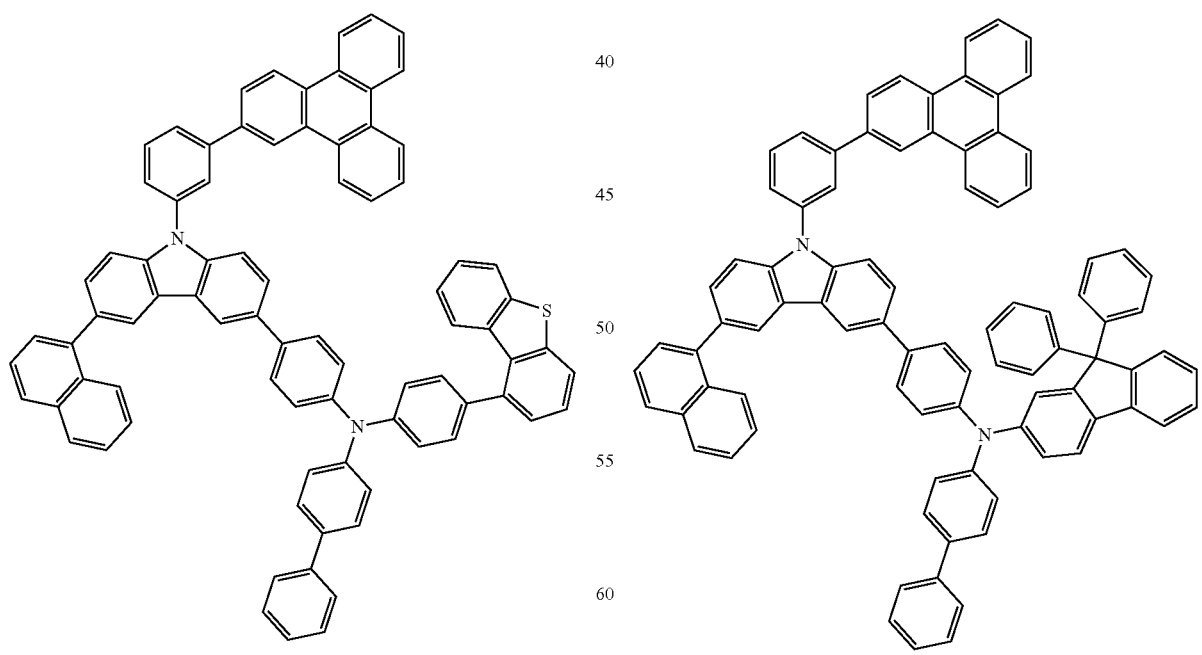

[A-320]
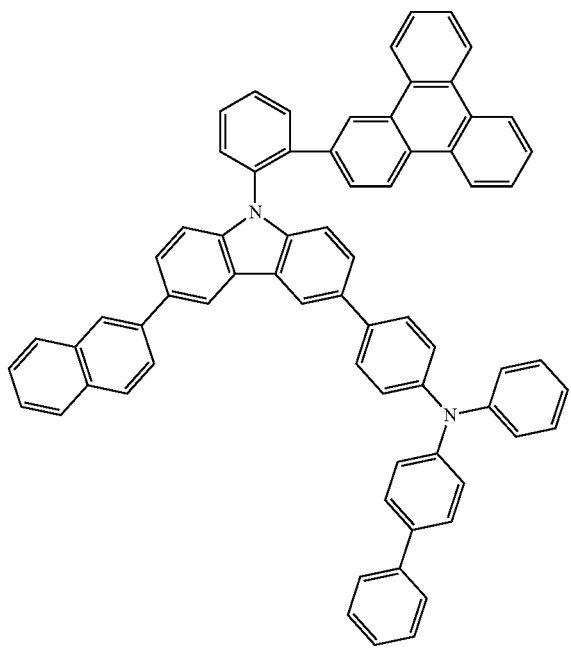
[A-321]
[A-322]
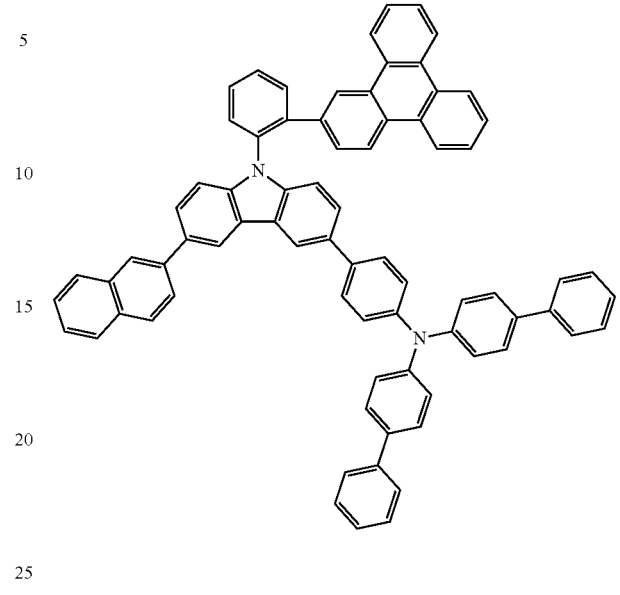
[A-323]
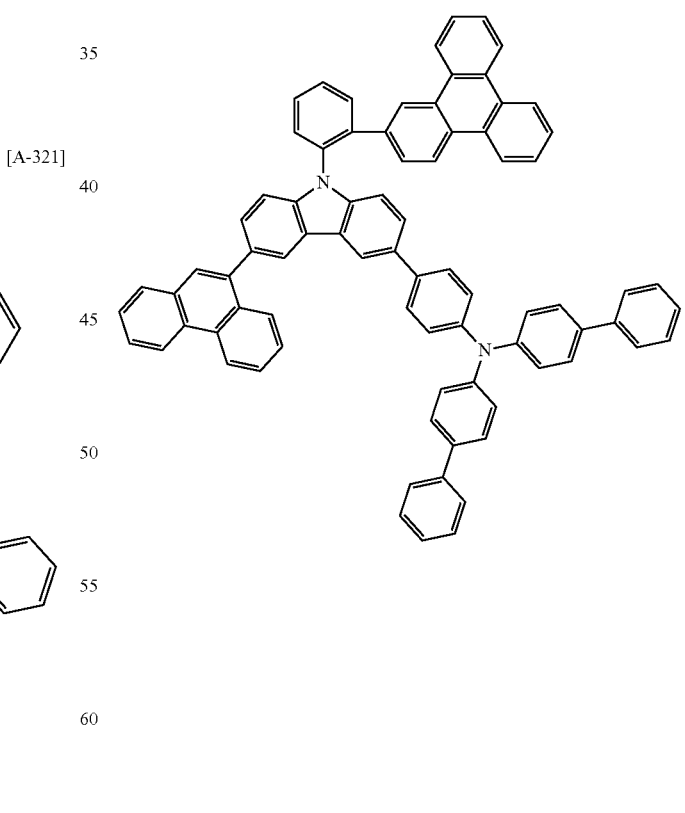

[A-324]
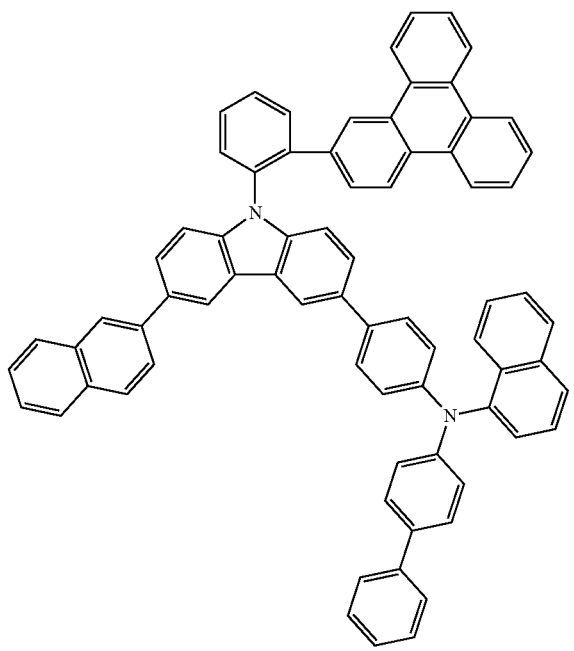
[A-326]
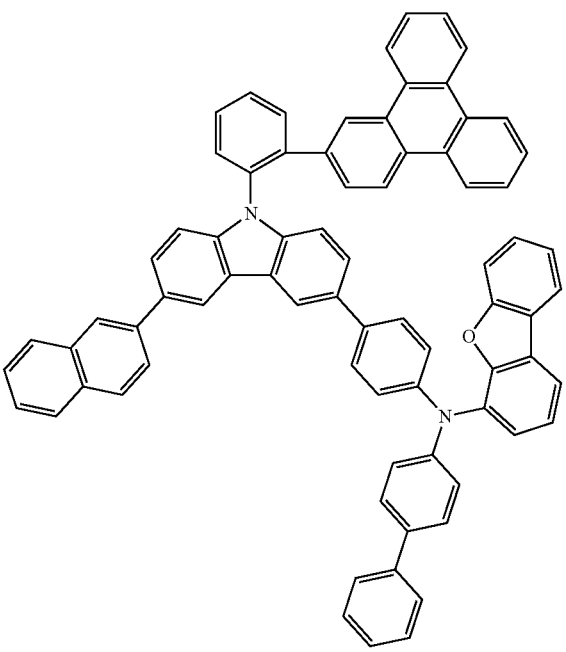
[A-325]
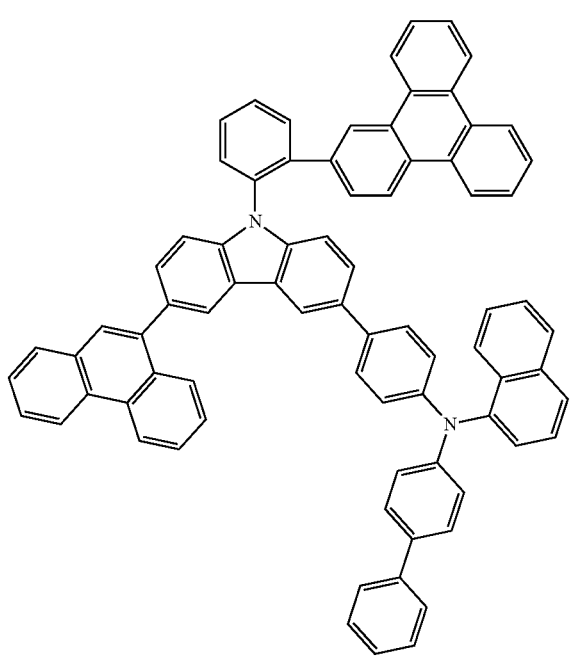
[A-327]
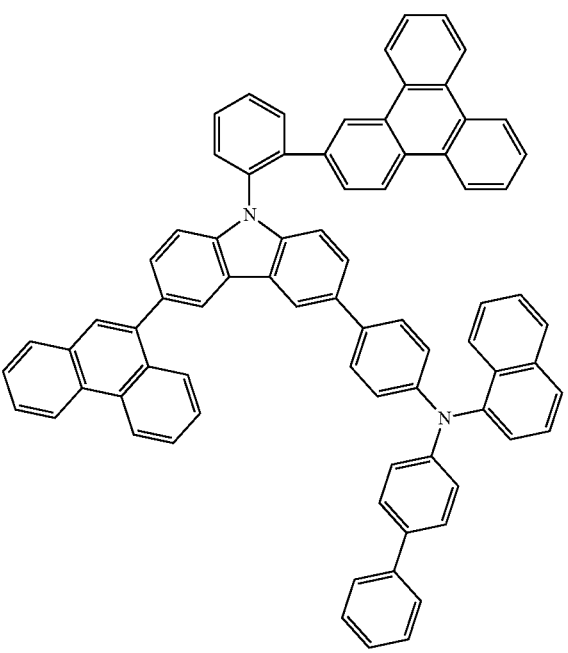

[A-328]
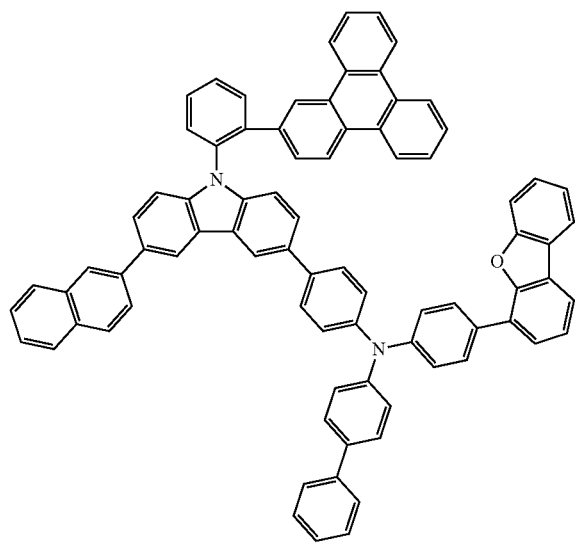
[A-330]
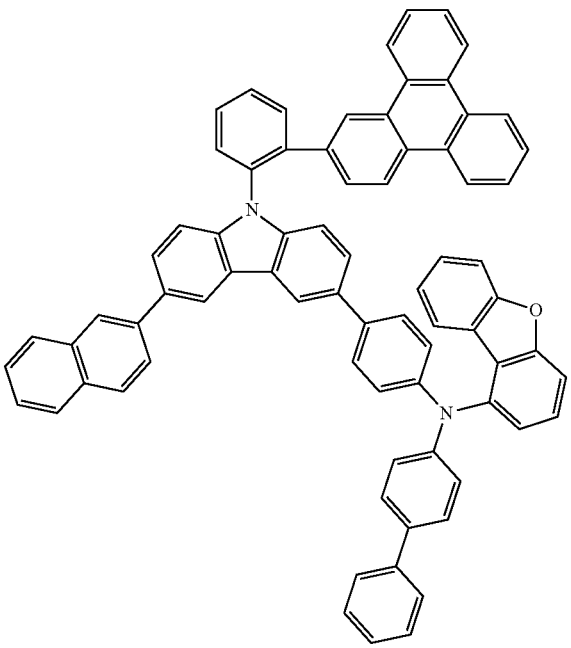
[A-329]
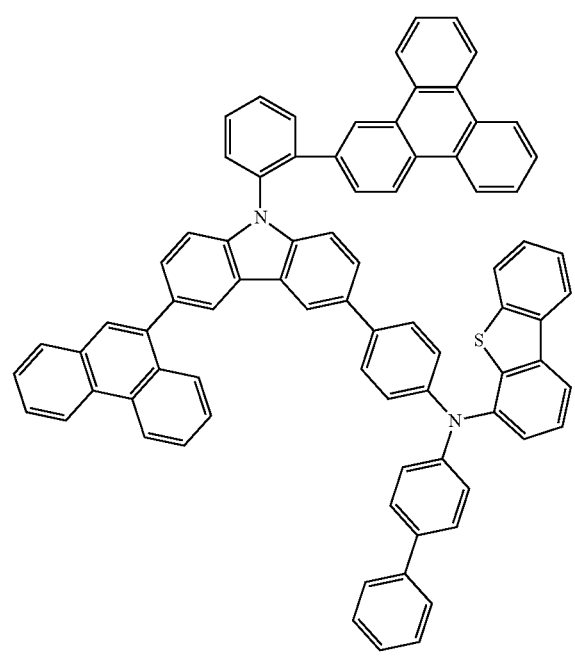
[A-331]
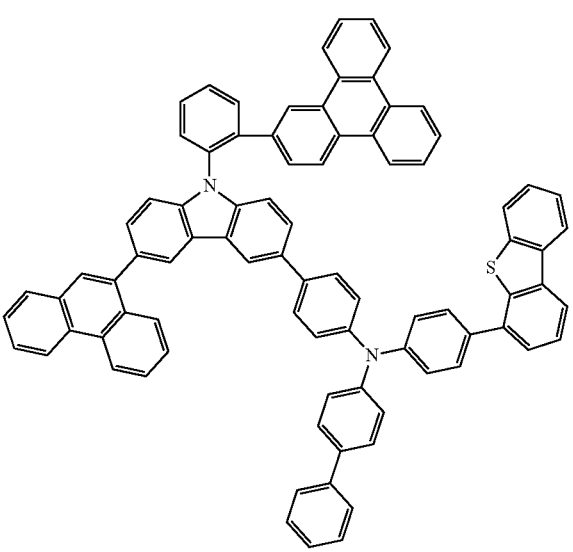

[A-332]
[A-334]
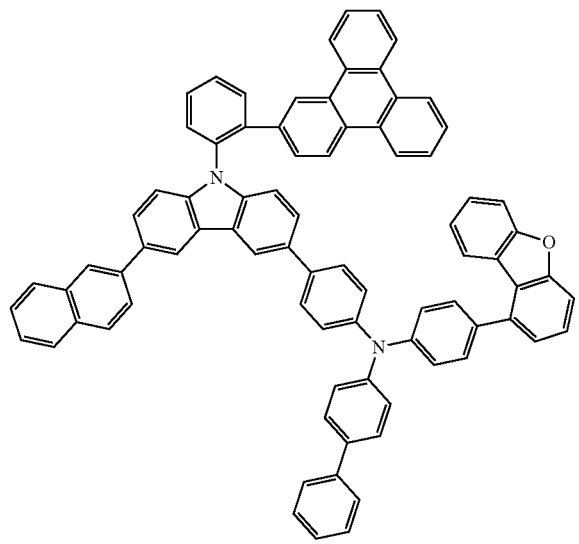
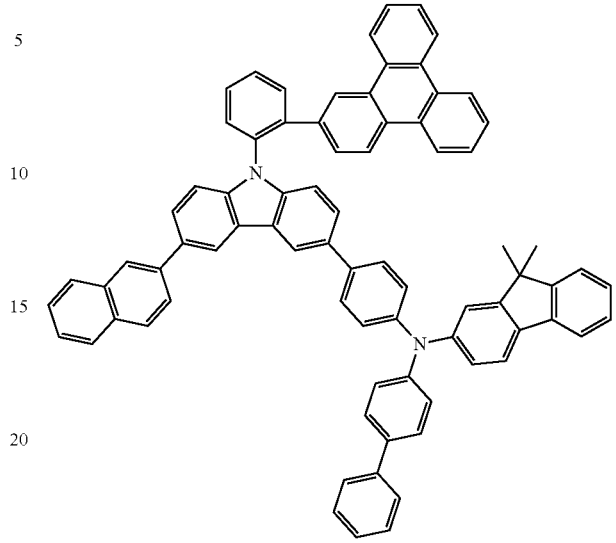
[A-333]
[A-335]
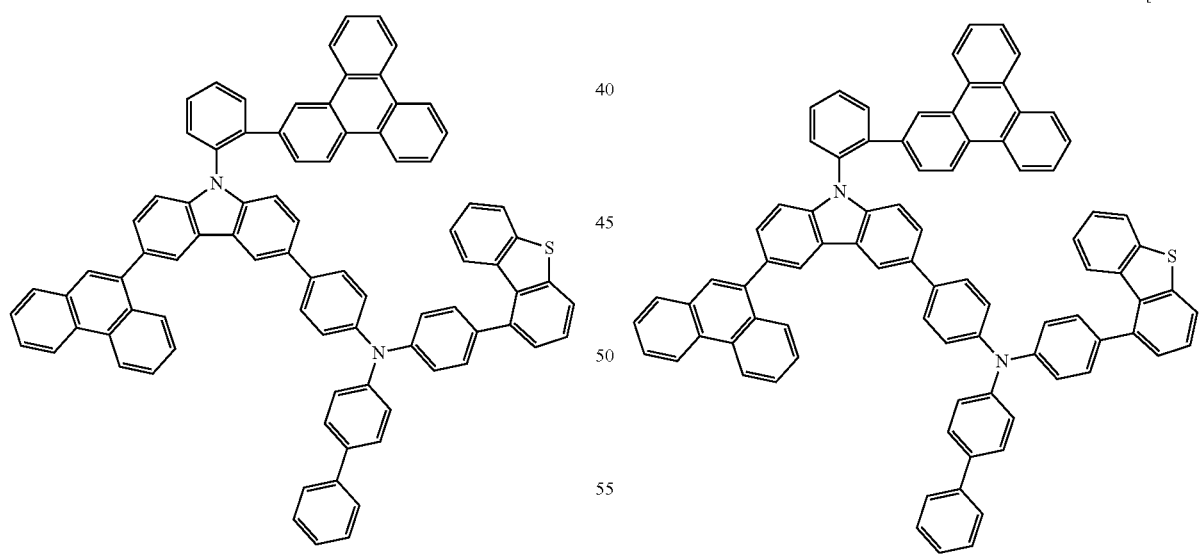

-continued

[A-336]

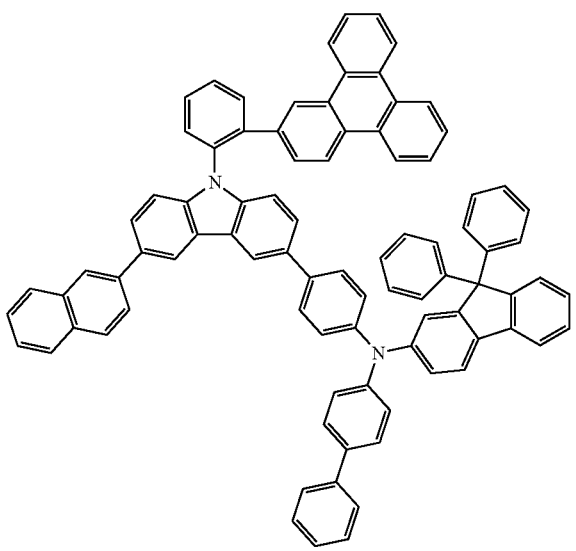

The compound for an organic photoelectric device including the above compounds may have a glass transition temperature of about 110° C. or more and a thermal decomposition temperature of about 400° C. or more, indicating improved thermal stability. Thus, it may be possible to provide an organic photoelectric device with high efficiency.

The compound for an organic photoelectric device including the above compounds may play a role for emitting light or injecting and/or transporting electrons, and also act as a light emitting host with an appropriate dopant. In an implementation, the compound for an organic photoelectric device may be used as a phosphorescent or fluorescent host material, a blue light emitting dopant material, or an electron transport material.

The compound for an organic photoelectric device according to an embodiment may be used for an organic thin layer. Thus, it may provide improvements in the life-span characteristic, efficiency characteristic, electrochemical stability, and thermal stability of an organic photoelectric device, and decrease the driving voltage.

According to another embodiment, an organic photoelectric device that includes the compound for an organic photoelectric device is provided. The organic photoelectric device may include an organic light emitting diode, an organic solar cell, an organic transistor, an organic photo conductor drum, an organic memory device, or the like. For example, the compound for an organic photoelectric device according to an embodiment may be included in an electrode or an electrode buffer layer in an organic solar cell to improve the quantum efficiency, or it may be used as an electrode material for a gate, a source-drain electrode, or the like in an organic transistor.

According to another embodiment, an organic light emitting diode includes an anode, a cathode, and one or more organic thin layers between the anode and the cathode. At least one of the organic thin layers may include the compound for an organic photoelectric device according to an embodiment.

The organic thin layer that may include the compound for an organic photoelectric device may include a layer selected from the group of an emission layer, a hole transport layer (HTL), a hole injection layer (HIL), an electron transport layer (ETL), an electron injection layer (EIL), a hole blocking layer, and a combination thereof The at least one layer includes the compound for an organic photoelectric device according to an embodiment. For example, the compound for an organic photoelectric device according to an embodiment may be included in an electron transport layer (ETL) or an electron injection layer (EIL). In addition, when the compound for an organic photoelectric device is included in the emission layer, the compound for an organic photoelectric device may be included as a phosphorescent or fluorescent host, or as a fluorescent blue dopant material.

FIGS. 1 to 5 are cross-sectional views showing organic light emitting diodes including the compound for an organic photoelectric device according to embodiments.

In the example embodiments shown in FIGS. 1 to 5, organic light emitting diodes 100, 200, 300, 400, and 500 include at least one organic thin layer 105 interposed between an anode 120 and a cathode 110.

The anode 120 may include an anode material having a large work function to help hole injection into an organic thin layer. The anode material may include one or more of, e.g., a metal (such as one or more of nickel, platinum, vanadium, chromium, copper, zinc, and gold, or alloys thereof); a metal oxide (such as one or more of zinc oxide, indium oxide, indium tin oxide (ITO), or indium zinc oxide (IZO)); a bonded metal and oxide (such as one or more of ZnO:Al or $SnO_2$:Sb); a conductive polymer (such as one or more of poly(3-methylthiophene), poly[3,4-(ethylene-1,2-dioxy)thiophene] (PEDT), polypyrrole, or polyaniline); or the like. In an implementation, a transparent electrode including indium tin oxide (ITO) is included as an anode.

The cathode 110 may include a cathode material having a small work function to help electron injection into an organic thin layer. The cathode material may include, e.g., a metal (such as one or more of magnesium, calcium, sodium, potassium, titanium, indium, yttrium, lithium, gadolinium, aluminum, silver, tin, lead, or alloys thereof); a multi-layered material (such as one or more of LiF/Al, Liq/Al, $LiO_2$/Al, LiF/Ca, LiF/Al, or $BaF_2$/Ca), or the like. In an implementation, a metal electrode including aluminum is included as a cathode.

In the example shown in FIG. 1, the organic light emitting diode 100 includes an organic thin layer 105 including only an emission layer 130.

Figure 2:
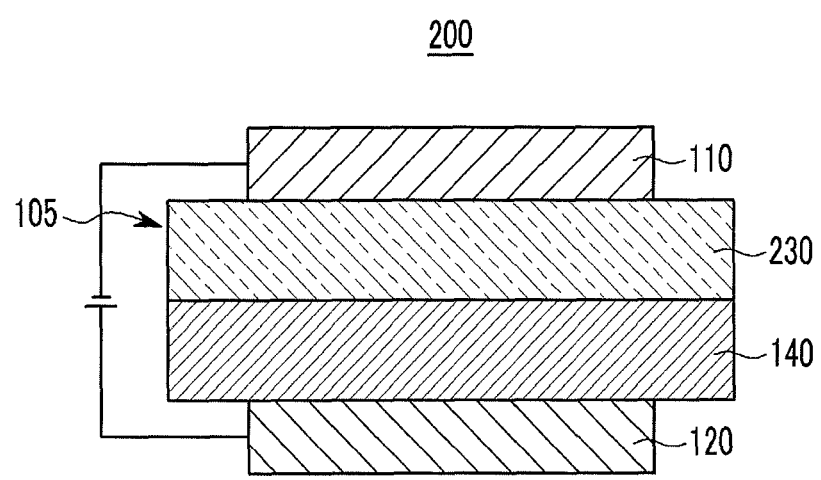

In the example shown in FIG. 2, a double-layered organic light emitting diode 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and hole transport layer (HTL) 140. The emission layer 130 may also function as an electron transport layer (ETL), and the hole transport layer (HTL) 140 layer may have an excellent binding property with a transparent electrode such as ITO or an excellent hole transport capability.

Figure 3:
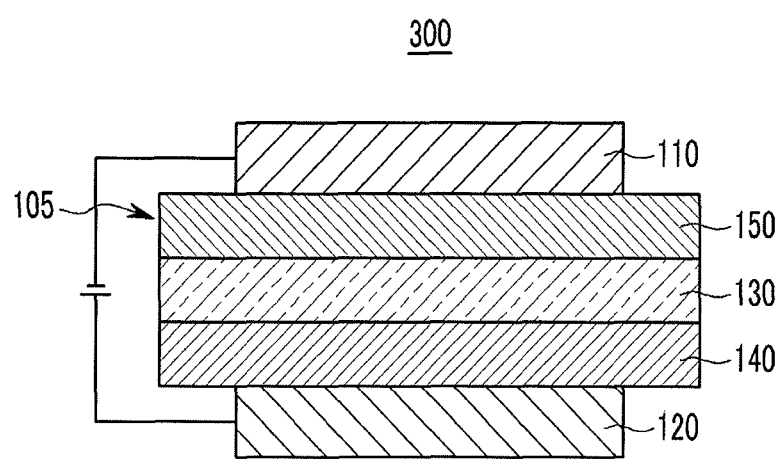

In the example shown in FIG. 3, a three-layered organic light emitting diode 300 includes an organic thin layer 105 including an electron transport layer (ETL) 150, an emission layer 130, and a hole transport layer (HTL) 140. The emission layer 130 is independently installed, and layers having an excellent electron transport capability or an excellent hole transport capability may be separately stacked.

Figure 4:
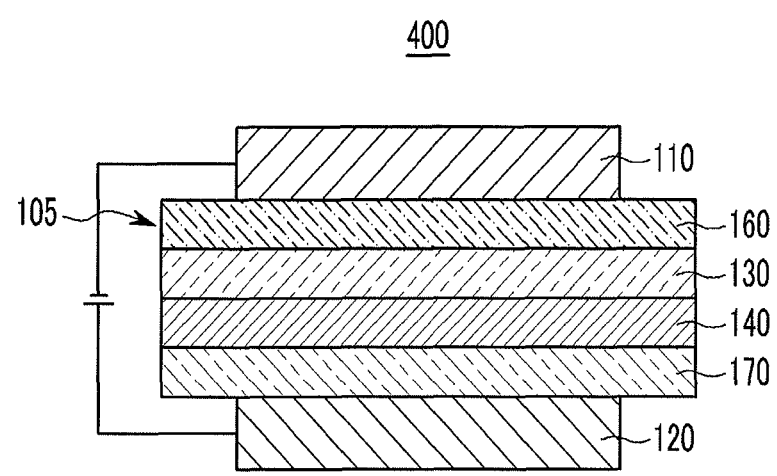

In the example shown in FIG. 4, a four-layered organic light emitting diode 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
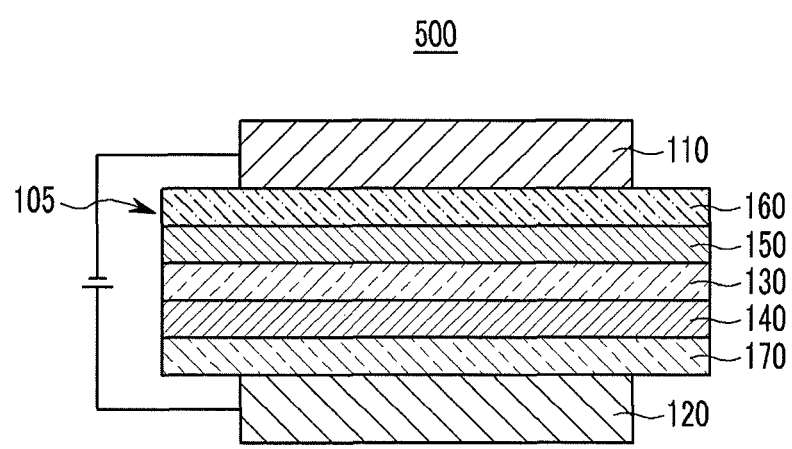

In the example shown in FIG. 5, a five layered organic light emitting diode 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from the group of an electron transport layer (ETL) 150, an electron injection layer (EIL) 160, emission layers 130 and 230, a hole transport layer (HTL) 140, a hole injection layer (HIL) 170, and combinations thereof includes a compound for an organic optoelectronic device according to an embodiment. The compound for an organic optoelectronic device may be used for an electron transport layer (ETL) 150 including the electron transport layer (ETL) 150 or electron injection layer (EIL) 160. When it is used for the electron transport layer (ETL), it may be possible to provide an organic photoelectric device having a simpler structure by eliminating an additional hole blocking layer (not shown).

When the compound for an organic photoelectric device is included in the emission layers 130 and 230, the material for the organic photoelectric device may be included as, e.g., a phosphorescent or fluorescent host or a fluorescent blue dopant.

The organic light emitting diode may be fabricated by, e.g.,: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

Another embodiment provides a display device including an organic light emitting diode according to an embodiment.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

(Preparation of Compound for Organic Photoelectric Device)

Synthesis of intermediates A, B-a, B-b, C, D, G, and H

Intermediates A, B-a, B-b, C, and D were synthesized according to the following Reaction Scheme 1.

[Reaction Scheme 1]

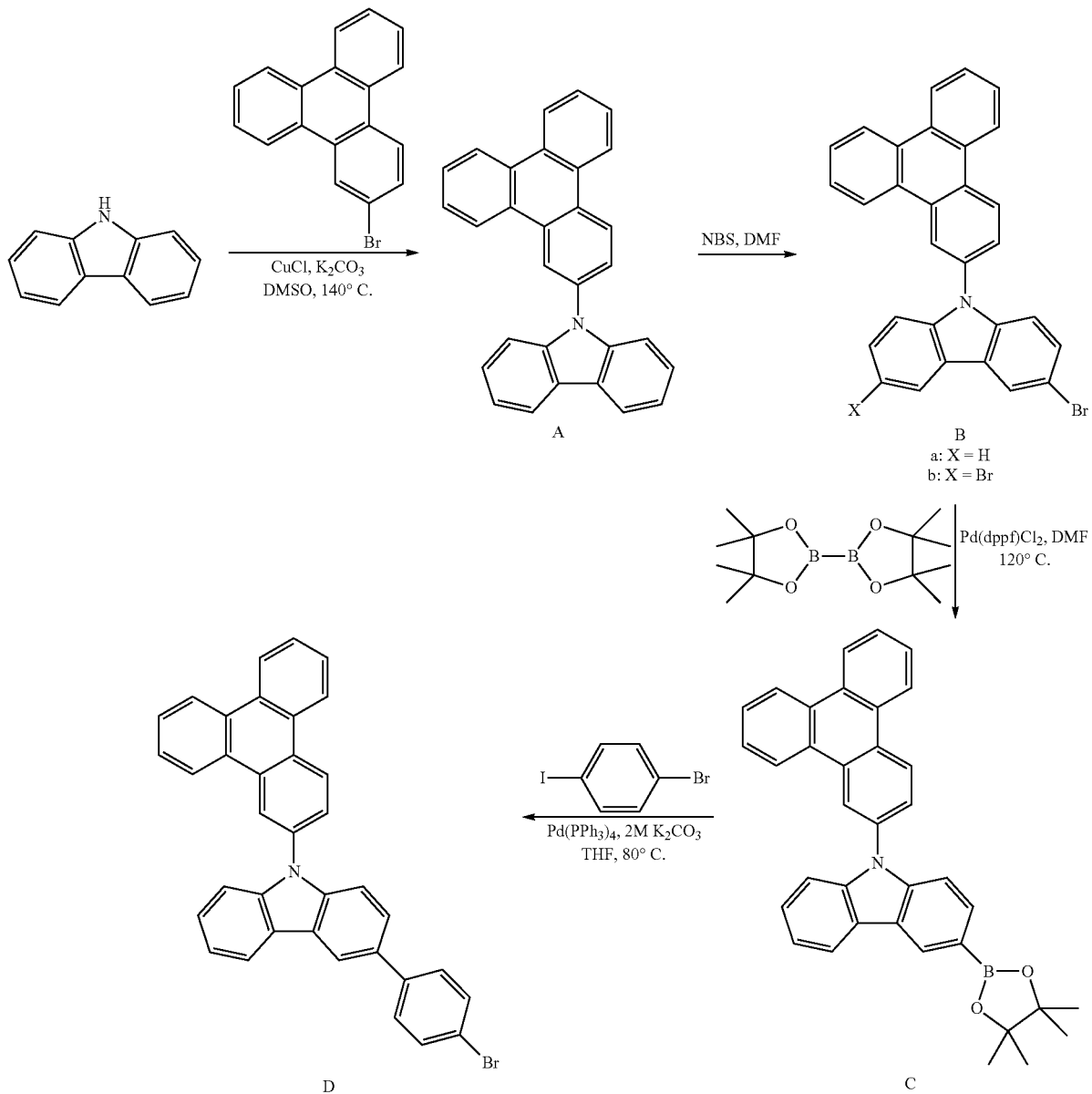

Synthesis of Intermediate A 20 g of carbazole, and 38.6 g of 2-bromotriphenylene were dissolved in 200 mL of DMSO. The resultant solution was added to a mixed reaction solution prepared by dissolving 14.2 g of CuCl and 24.8 g of $K_2CO_3$. The mixture was agitated at 140° C. for 24 hours and then adsorption-filtered using Celite. The filtered solution was concentrated under a reduced pressure condition and then purified using a silica gel column chromatography. The purified product was recrystallized under a hexane or ether/methanol condition, respectively obtaining 29.4 g of a desired product (62.4%, GC-Mass (M+H+)=393.5).

Synthesis of Intermediate B-a 25 g of the intermediate A was dissolved in 200 mL of DMF, and a solution prepared by dissolving 11.6 g of NBS (N-bromosuccinimide) in 20 mL of DMF was added thereto in a dropwise fashion. The mixture was reacted at room temperature for 16 hours and added to 1 L of MeOH. Then, a produced precipitate was filtered. Next, 500 mL of MeOH was to the filtered solution, and a newly produced precipitate was filtered. The obtained precipitate was recrystallized in hexane, obtaining 30 g of a desired product (97%, GC-Mass (M+H+)=484.19).

Synthesis of Intermediate B-b 25 g of the intermediate A was dissolved in 200 mL of DMF, and a solution prepared by dissolving 23.2 g of NBS (N-bromosuccinimide) in 40 mL of DMF was added thereto in a dropwise fashion. The mixture was reacted at room temperature for 16 hours and added to 1 L of MeOH, and a produced precipitate was filtered. Then, 500 mL of MeOH was added to the filtered solution, and a newly produced precipitate was filtered. The obtained precipitate was recrystallized in hexane, obtaining 40.8 g of a desired product (95%, GC-Mass (M+H+)=549.10).

Synthesis of Intermediate C 30 g of the intermediate B-a and 23.6 g of bispinacolatodiborane were dissolved in 400 mL of DMF, and 2.3 g of Pd(dppf)C12 and 24.4 g of potassium acetate ($CH_3COOK$) as a catalyst were added thereto. The resulting mixture was heated in a reflux condenser under a nitrogen atmosphere up to 120° C. and reacted for 18 hours, and the DMF was removed under a reduced pressure. The remaining reactant was dissolved in $CH_2Cl_2$ and filtered through a filter filled with Celite. The filtered reactant was concentrated under a reduced pressure. The concentrated reactant was primarily purified using a silica gel column chromatography and then recrystallized in hexane, obtaining 28.3 g of a desired product (75.2%, LC-Mass (M+H+)=531.56).

Synthesis of Intermediate D 25 g of the intermediate C, 14 g of 4-iodo-1-bromobenzene, and 2.7 g of tetrakistriphenylphosphine palladium were dissolved in 300 mL of THF, and 118 mL of $K_2CO_3$ in a concentration of 2M was added thereto. The mixture was heated up to 80° C. in a reflux condenser under a nitrogen atmosphere and agitated for 15 hours. Next, a water layer was removed using a separatory funnel, and THF was removed under a reduced pressure condition. The remaining product was dissolved in $CH_2Cl_2$, and charcoal powder was added thereto. The mixture was agitated. The agitated reactant was filtered through a filter filled with Celite and concentrated under a reduced pressure. The concentrated reactant was purified using a silica gel column chromatography, obtaining 22 g of a product (85%, LC-Mass (M+H+)=550.9).

Intermediates G and H were synthesized through the following reaction scheme 2.

[Reaction Scheme 2]

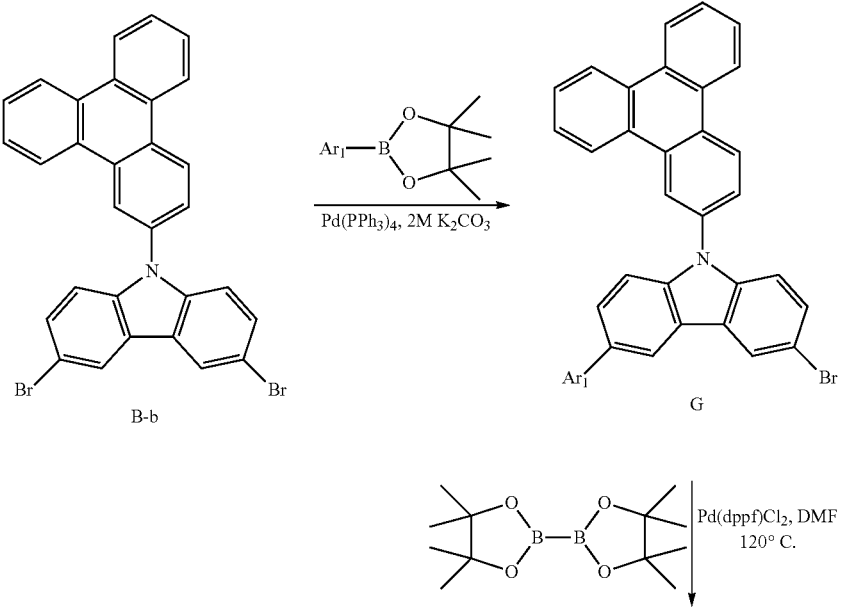

-continued

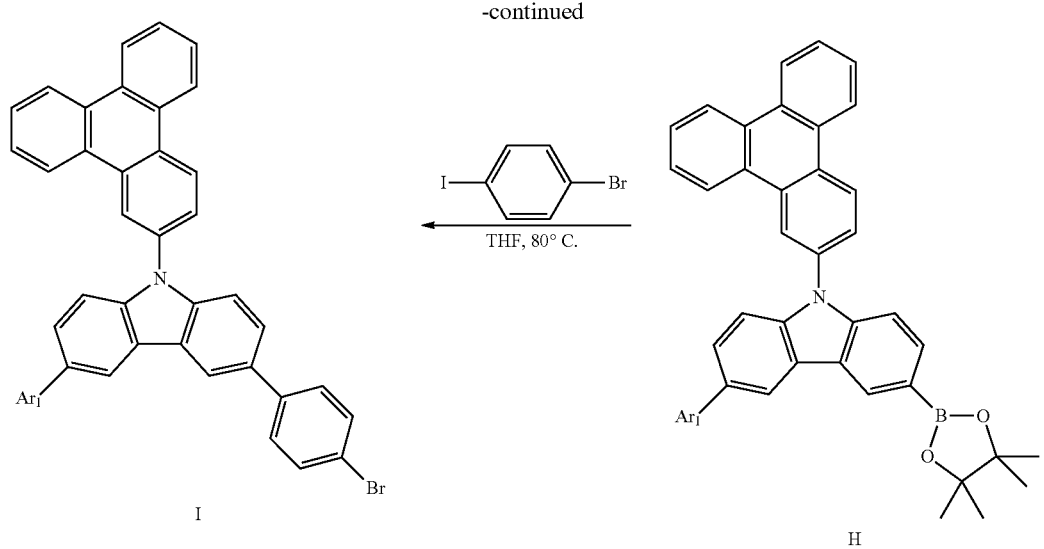

Synthesis of Intermediate G 1.1 equivalent of an aryl boronic ester and 0.05 equivalent of tetrakistriphenylphosphine palladium were added to the intermediate B-b dissolved THF, and 3 equivalents of $K_2CO_3$ in a concentration of 2M was added thereto. The mixture was heated up to 80° C. in a reflux condenser under a nitrogen atmosphere and agitated for 15 hours. Then, a water layer was removed using a separatory funnel, and the THF was removed under a reduced pressure condition. The remaining reactant was dissolved in $CH_2Cl_2$, and charcoal powder was added thereto. The mixture was agitated. The agitated reactant was filtered through a filter filled with Celite and concentrated under a reduced pressure. The concentrated reactant was purified using a silica gel column chromatography, obtaining a product G.

Synthesis of Intermediate H

The intermediate G and 1.2 equivalent of bispinacolatodiborane were dissolved in DMF, and 0.05 equivalent of Pd(dppf)Cl$_2$ and 2 equivalent of potassium acetate (CH$_3$COOK) as a catalyst were added thereto. The mixture was heated up to 120° C. in a reflux condenser under a nitrogen atmosphere and then reacted for 18 hours to remove the DMF under a reduced pressure. The remaining reactant was dissolved in $CH_2Cl_2$. The solution was filtered through a filter filled with Celite and concentrated under a reduced pressure. The concentrated reactant was primarily purified using a silica gel column chromatography and recrystallized in hexane, obtaining a product H.

Synthesis of Intermediate I

The intermediate H, 1.1 equivalent of 4-iodo-1-bromobenzene, and 0.05 equivalent of tetrakistriphenylphosphine palladium was dissolved in THF, and 3 equivalents of $K_2CO_3$ in a concentration of 2M was added thereto. The mixture was heated up to 80° C. in a reflux condenser under a nitrogen atmosphere and then agitated for 15 hours. Then, a water layer was removed using a separatory funnel, and the THF was removed under a reduced pressure condition. The obtained reactant was dissolved in $CH_2Cl_2$, and charcoal powder was added thereto. The mixture was agitated. The agitated reactant was filtered through a filter filled with Celite and then concentrated under a reduced pressure. The concentrated reactant was purified using a silica gel column chromatography, obtaining a desired product I.

Example 1

Synthesis of Compound Represented by Chemical Formula 6

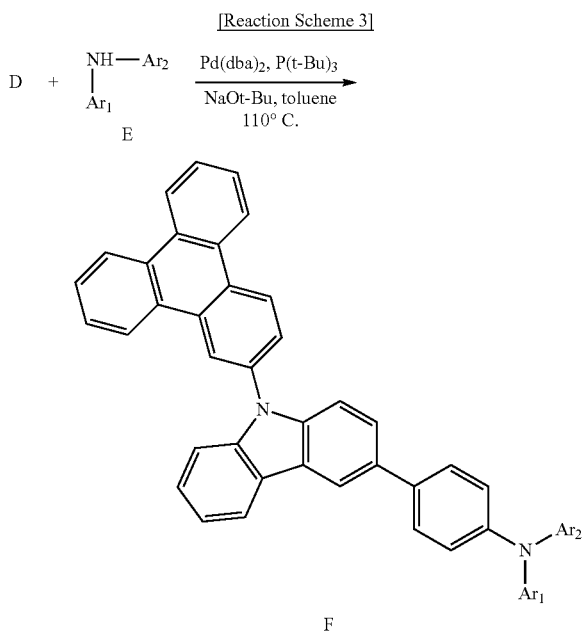

Specific product examples depending on kinds of the intermediate E are provided in the following Table 1.

| Ar1 | Ar2 | Structure of product |
|---|---|---|
| E-1  | 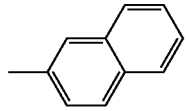 | [Chemical Formula 6] 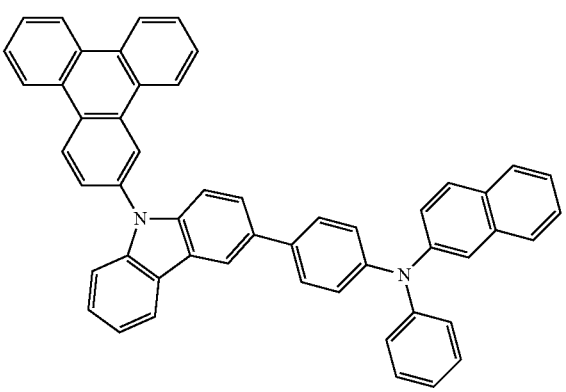 |
| E-2 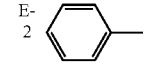 | 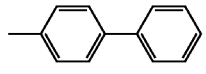 | [Chemical Formula 7] 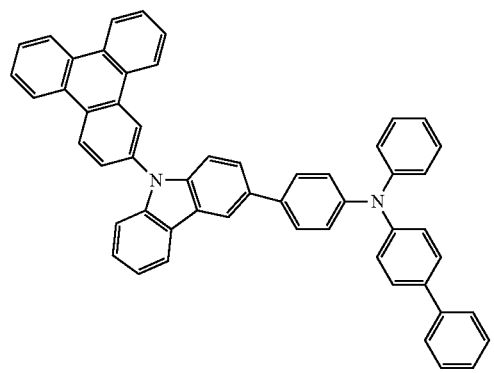 |
| E-3 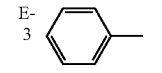 | 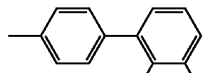 | [Chemical Formula 8] 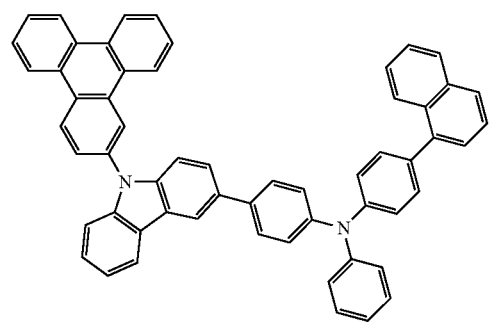 |
| E-4 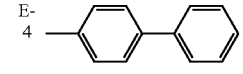 | 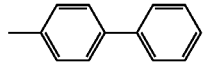 | [Chemical Formula 9] 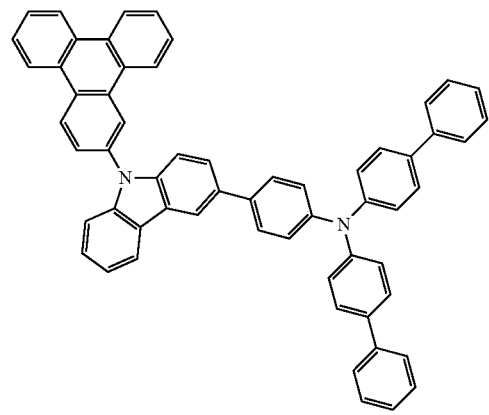 |

| Ar1 | Ar2 | Structure of product |
|---|---|---|
| E-5 | | [Chemical Formula 10] |
| E-6 | | [Chemical Formula 11] |
| E-7 | | [Chemical Formula 12] |

| Ar1 | Ar2 | Structure of product |
|---|---|---|
| E-8 [biphenyl structure] | [methyldibenzothiophene structure] | [Chemical Formula 13] [product structure] |

5.5 g of the intermediate E-1 and 14.5 g of the intermediate D provided in Table 1 were put in a 250 ml 2-necked round-bottomed flask, and 60 mL of toluene was filled therein to dissolve the reactants. Then, 2.9 g of sodium tert-butoxide, 0.72 g of Pd(dba)2 [(tris(dibenzylidine acetone)dipalladium (0))], and 0.31 g of tri(tert-butyl)phosphine were subsequently added to the reactant, and the mixture was reacted at 110° C. for 12 hours. When the reaction was complete, the reaction mixture was cooled down to room temperature, and 100 ml of distilled water was added thereto to extract an organic layer. The organic layer was dried with MgSO4, dried, and treated through silica gel column chromatography. Herein, the obtained eluate was concentrated and dried, obtaining 12 g (69.7%) of a solid product. The solid product was identified using LC/MS.

Example 3

Synthesis of Compound Represented by Chemical Formula 8

A compound represented by Chemical Formula 7 was synthesized according to the same method as Example 1, except for using the intermediate E-3 provided in Table 1, and identified using LC/MS.

Example 2

Synthesis of Compound Represented by Chemical Formula 7

A compound represented by Chemical Formula 7 was synthesized according to the same method as Example 1, except for using the intermediate E-2 provided in Table 1, and identified using LC/MS.

Example 4

Synthesis of Compound Represented by Chemical Formula 14

[Reaction Scheme 4]

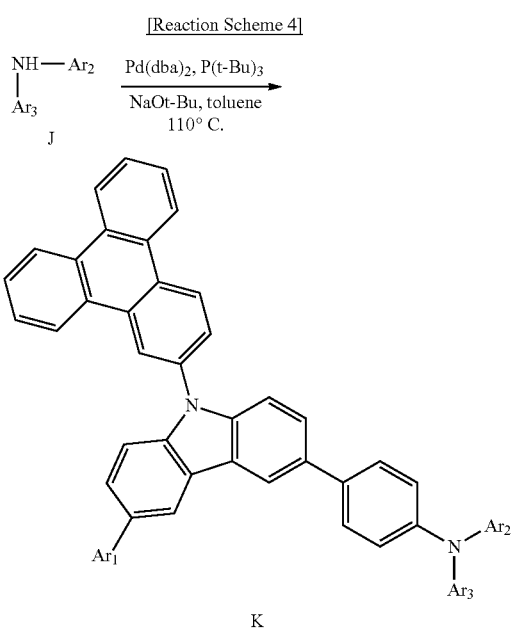

For the above Reaction Scheme 4, specific product examples depending on the intermediates I and J are provided in the following Table 2.

TABLE 2
| Ar1 of I | Ar2 of J | Ar3 of J | Structure of product |
|---|---|---|---|
| I-1 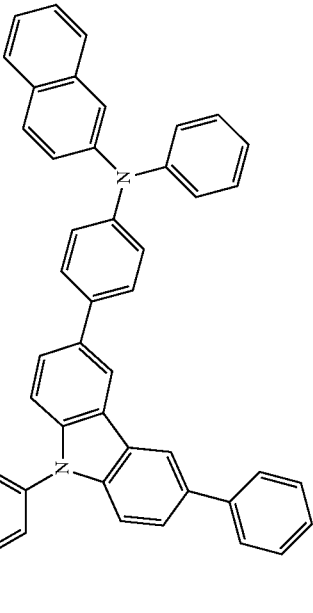 | J-1 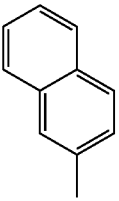 | 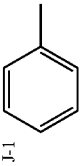 | [Chemical Formula 14] |

TABLE 2-continued

| Ar1 of I | Ar2 of J | Ar3 of J | Structure of product |
|---|---|---|---|
| I-2 (phenyl) | J-2 (phenyl) | biphenyl | [Chemical Formula 15] |

TABLE 2-continued

| Ar1 of I | Ar2 of J | Ar3 of J | Structure of product |
|---|---|---|---|
| I-3 | J-3 | | [Chemical Formula 16] |

TABLE 2-continued
| Ar1 of I | Ar2 of J | Ar3 of J | Structure of product |
|---|---|---|---|
| I-4 | J-4 | | [Chemical Formula 17] 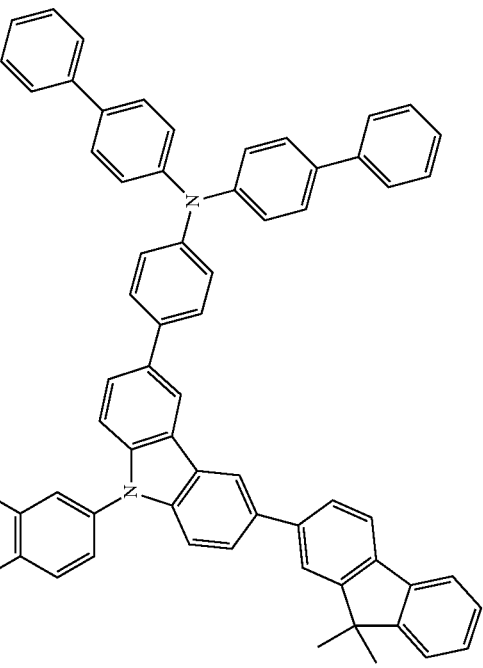 |

TABLE 2-continued

| Ar1 of I | Ar2 of J | Ar3 of J | Structure of product |
|---|---|---|---|
| I-5 | J-5 | | [Chemical Formula 18] |

5.5 g of the intermediate J-1 and 16.45 g of the intermediate I-1 provided in Table 2 were put in a 250 ml 2-necked round-bottomed flask, and 60 mL of toluene was filled therein to dissolve the reactants. Then, 2.9 g of sodium tert-butoxide, 0.72 g of Pd(dba)$_2$ [(tris(dibenzylidine acetone)dipalladium (0))], and 0.31 g of tri(tert-butyl)phosphine were subsequently added to the reactor, and the mixture was reacted at 110° C. for 12 hours. When the reaction was complete, the reaction mixture was cooled down to room temperature, and 100 ml of distilled water was added thereto, to extract an organic layer. The organic layer was dried with MgSO$_4$, concentrated, and treated through a silica gel column chromatography. Here, the obtained eluate was concentrated and dried, obtaining 13.5 g (75.3%) of a desired solid compound. The compound was identified using LC/MS.

Example 5

Synthesis of Compound Represented by Chemical Formula 15

A compound represented by Chemical Formula 15 was synthesized according to the same method as Example 4, except for using the intermediates I-2 and J-2 provided in Table 2, and identified using LC/MS.

Fabrication of Organic Light Emitting Diode

Example 6

A glass substrate coated with a 1500 Å-thick ITO (Indium tin oxide) thin film was washed with a distilled water and ultrasonic wave. When completely washed with distilled water, the glass substrate was cleaned with an ultrasonic wave using a solvent such as isopropyl alcohol, acetone, methanol, and the like, then moved to a plasma cleaner and cleaned using oxygen plasma for 5 minutes, and moved to a vacuum depositor. This ITO transparent electrode was used as a positive electrode, and 4,4'-bis[N-[4-{N,N-bis(3-methylphenyl)amino}-phenyl]-N-phenylamino]biphenyl (DNTPD) was vacuum deposited thereon to form a 600 Å-thick hole injection layer (HIL). Then, the compound according to Example 1 was vacuum-deposited on the hole injection layer to form a 300 Å-thick hole transport layer (HTL). On the hole transport layer (HTL), a 250A-thick emission layer was formed by vacuum-depositing 9,10-di-(2-naphthyl)anthracene (ADN) as a host and 3 wt % of 2,5,8,11-tetra(tert-butyl)perylene (TBPe) as a dopant.

Next, Alq3 was vacuum-deposited on the emission layer to form a 250 Å-thick electron transport layer (ETL). On the electron transport layer (ETL), 10 Å-thick LiF and 1000 Å-thick Al were sequentially vacuum-deposited, forming a cathode and thereby fabricating an organic light emitting diode.

The organic light emitting diode had a five-layered organic thin film, specifically, Al 1000 Å/LiF 10 Å/Alq3 250 Å/EML[ADN:TBPe=97:3] 250 Å/HTL 300 Å/DNTPD 600 Å/ITO 1500 Å.

Example 7

An organic light emitting diode was fabricated according to the same method as Example 6 except for using the compound according to Example 2 instead of the one according to Example 1.

Example 8

An organic light emitting diode was fabricated according to the same method as
Example 6 except for using the compound according to Example 4 instead of the one according to Example 1.

Comparative Example 1

An organic light emitting diode was fabricated according to the same method as Example 6 except for using NPB instead of the compound according to Example 1. The structure of the NPB is provided as follows.

Comparative Example 2

An organic light emitting diode was fabricated according to the same method as Example 6 except for using HT1 instead of the compound according to Example 1. The structure of the HT1 is provided as follows.

Comparative Example 3

An organic light emitting diode was fabricated according to the same method as Example 6 except for using HT2 instead of the compound according to Example 1. The structure of the HT2 is provided as follows.

The structures of the DNTPD, ADN, TBPe, NPB, HT1, and HT2 used to fabricate an organic light emitting diode are provided as follows.

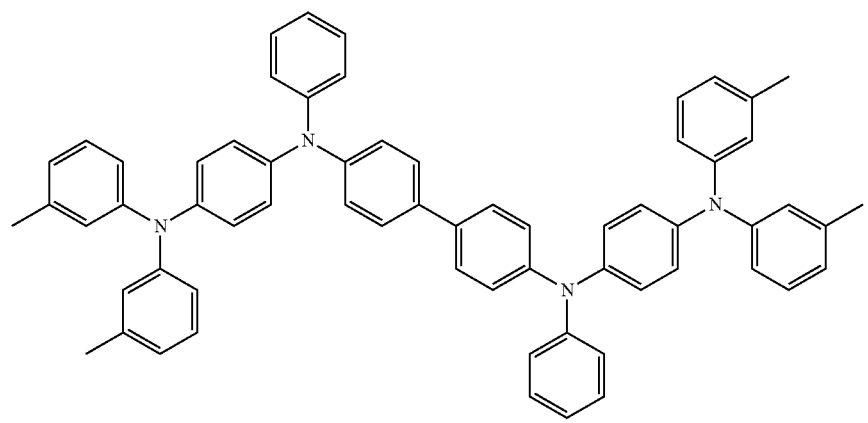

[DNTPD]

-continued
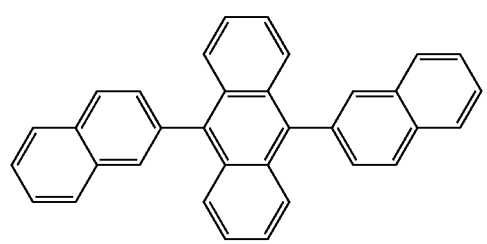
[ADN]
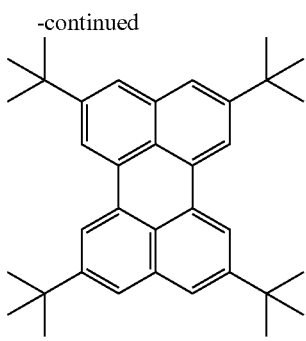
[TBPe]
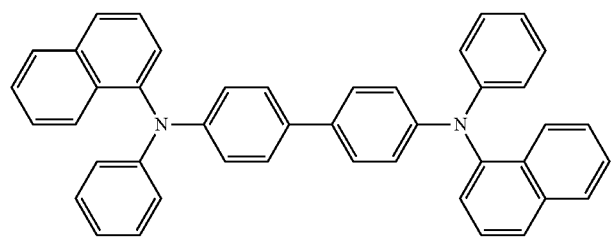
[NPB]
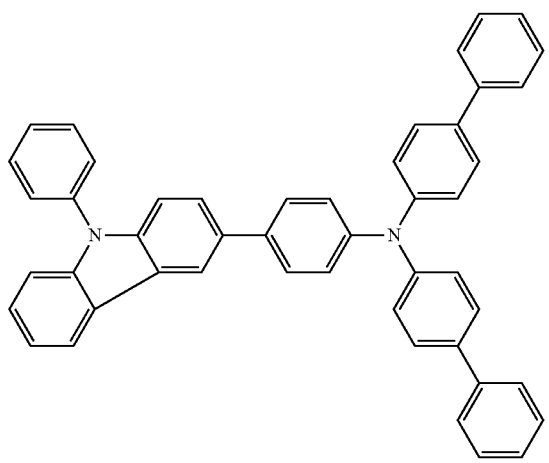
[HT1]
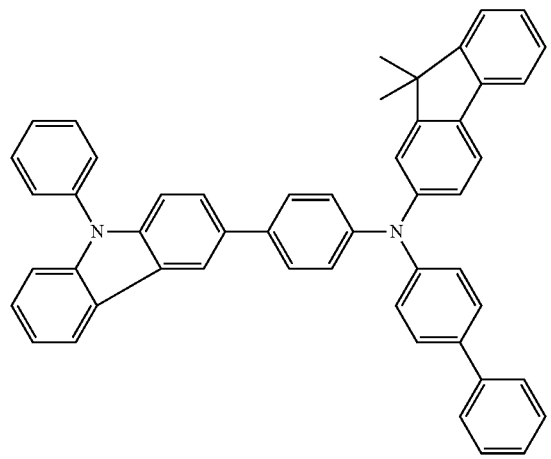
[HT2]

(Performance measurement of Organic light emitting diode)

Each organic light emitting diode according to Examples 6, 7, and 8 and Comparative Examples 1, 2, and 3 was measured regarding current density and luminance changes depending on voltage and luminous efficiency. Specific measurement methods were as follows, and the results are shown in the following Table 3.

(1) Measurement of Current density change depending on Voltage change

The fabricated organic light emitting diodes were measured for current value flowing in the unit device while increasing the voltage from 0 V to 10 V using a current-voltage meter (Keithley 2400), and the measured current value was divided by area to provide the result.

(2) Measurement Of luminance change depending on voltage change

The fabricated organic light emitting diodes were measured for luminance while increasing the voltage form 0V to 10V using a luminance meter (Minolta Cs 1000A).

(3) Measurement of Luminous efficiency

Current efficiency (cd/A) and electric power efficiency (1 m/W) at the same luminance (1000 cd/m$^2$) were calculated by using luminance and current density from the items (1) and (2) and voltage.

(4) Color coordinate was Measured using luminance meter (Minolta Cs100A).

TABLE 3

| | Compound in hole transport layer (HTL) | Driving voltage (V) | Color coordinate | Luminous efficiency (cd/A) |
|---|---|---|---|---|
| Comparative Example 1 | NPB | 7.1 | (0.138, 0.276) | 4.9 |
| Comparative Example 2 | HT1 | 6.6 | (0.134, 0.142) | 5.7 |
| Comparative Example 3 | HT2 | 6.4 | (0.135, 0.145) | 5.9 |
| Example 6 | Chemical Formula 6 | 6.2 | (0.133, 0.140) | 6.3 |
| Example 7 | Chemical Formula 7 | 6.3 | (0.134, 0.140) | 6.4 |
| Example 8 | Chemical Formula 14 | 6.2 | (0.133, 0.139) | 6.2 |

According to the results of Table 3, the compounds according to Examples 6, 7, and 8 were used to form a hole transport layer (HTL) for an organic light emitting diode, and decreased driving voltage of organic light emitting diodes and improved luminous efficiency of the organic light emitting diodes.

Specifically, the driving voltage was at most about 0.9V decreased, and the efficiency was up to 1.3 times increased. Accordingly, the compounds may be used to fabricate an organic light emitting diode having excellent hole injection and transport capability, low voltage, high efficiency, high luminance, and long life-span. These driving voltage and luminous efficiency results of the example embodiments are practical for a commercially-available device.

By way of summation and review, examples of an organic optoelectronic device may include an organic photoelectric device, an organic light emitting diode, an organic solar cell, an organic photo conductor drum, an organic transistor, or the like, which use one or more of a hole injecting or transport material, an electron injecting or transport material, or a light emitting material.

For example, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer may include a multi-layer including different materials, e.g., one or more of a hole injection layer (HIL), a hole transport layer (HTL), an emission layer, an electron transport layer (ETL), or an electron injection layer (EIL), in order to improve efficiency and stability of an organic photoelectric device.

In an organic light emitting diode, when a voltage is applied between an anode and a cathode, holes from the anode and electrons from the cathode may be injected to an organic material layer and recombine to generate excitons having high energy. The generated excitons may generate light having certain wavelengths while shifting to a ground state.

A phosphorescent light emitting material may be used for a light emitting material of an organic light emitting diode, as may be a fluorescent light emitting material. A phosphorescent material may emits light by transporting the electrons from a ground state to an exited state, non-radiance transiting of a singlet exciton to a triplet exciton through intersystem crossing, and transiting a triplet exciton to a ground state to emit light.

In an organic light emitting diode, an organic material layer may include a light emitting material and a charge transport material, e.g., one or more of a hole injection material, a hole transport material, an electron transport material, an electron injection material, or the like.

The light emitting material may be classified as, e.g., blue, green, or red light emitting materials according to emitted colors, or yellow and orange light emitting materials to emit colors approaching natural colors.

When one material is used as a light emitting material, a maximum light emitting wavelength may be shifted to a long wavelength or color purity may decrease because of interactions between molecules, or device efficiency may decrease because of a light emitting quenching effect. Therefore, a host/dopant system may be included as a light emitting material in order to improve color purity and increase luminous efficiency and stability through energy transfer.

A material constituting an organic material layer, for example a hole injection material, a hole transport material, a light emitting material, an electron transport material, an electron injection material, and a light emitting material such as a host and/or a dopant, should be stable and have good efficiency. Development of an organic material layer forming material for an organic light emitting diode is ongoing. Material development is may also provide benefits for other organic photoelectric devices.

A low molecular organic light emitting diode may be manufactured as a thin film in a vacuum deposition method and may have good efficiency and life-span performance. A polymer organic light emitting diode may be manufactured in an inkjet or spin coating method may have an advantage of low initial cost and being suitable for large-sized substrates.

Both low molecular organic light emitting and polymer organic light emitting diodes may provide a self-light emitting display with high speed response, wide viewing angle, ultra-thin, high image quality, durability, large driving temperature range, etc. They may have good visibility due to self-light emitting characteristic compared with a conventional LCD (liquid crystal display) and have an advantage of decreasing thickness and weight of LCD up to a third, because they may omit a backlight. In addition, since they may have a response speed 1000 times faster than an LCD, they may realize a perfect motion picture without after-image. They have been developed to have 80 times the efficiency and more than 100 times the life-span since they came out for the first time in the late 1980s. Recently, they have been made larger, e.g., a 40-inch organic light emitting diode panel. It would be benefial if they were simultaneously to have improved luminous efficiency and life-span in order to be larger. Luminous efficiency may be obtained through smooth combination between holes and electrons in an emission layer. However, an organic material may in general have slower electron mobility than hole mobility. Thus, inefficient combination between holes and electrons could. Increasing electron injection and mobility from a cathode and simultaneously preventing movement of holes is expected to be beneficial.

Improved life-span may be obtained if a material crystallization caused by Joule heating generated during device operating is reduced or be prevented. Accordingly, there has been a strong need for an organic compound having excellent electron injection and mobility, and high electrochemical stability.

As described above, a compound for an organic photoelectric or optoelectronic device may act as light emission and/or electron injection and/or transport material, and may also act as a light emitting host along with a dopant. Thus, an organic light emitting diode having excellent life-span, high luminous efficiency at a low driving voltage, driving voltage, electrochemical stability, and/or thermal stability may be provided. A display device including the organic light emitting diode may also be provided.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope according to an embodiment as set forth in the following claims.

<Description of Symbols>

| | |
|---|---|
| 100: organic light emitting diode | 110: cathode |
| 120: anode | 105: organic thin layer |
| 130: emission layer | 140: hole transport layer (HTL) |
| 150: electron transport layer (ETL) | 160: electron injection layer (EIL) |
| 170: hole injection layer (HIL) | 230: emission layer + electron transport layer (ETL) |

What is claimed is:

1. A compound for an organic photoelectric device, the compound being represented by the following Chemical Formula 1:

[Chemical Formula 1]

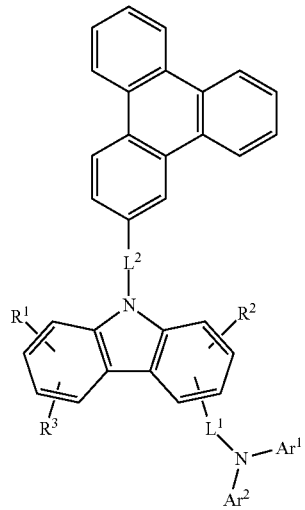

wherein, in Chemical Formula 1, $L^1$ and $L^2$ are each independently a single bond, a substituted or unsubstituted C2 to C6 alkenylene group, a substituted or unsubstituted C2 to C6 alkynylene group, a substituted or unsubstituted C6 to C30 arylene group, or a substituted or unsubstituted C2 to C30 heteroarylene group, $R^1$ to $R^3$ are each independently hydrogen, a substituted or substituted C1 to C6 alkyl group, a substituted or unsubstituted C6 to C3 aryl group, or a substituted or unsubstituted C2 to C30 heteroaryl group, and $Ar^1$ and $Ar^2$ are each independently a substituted or unsubstituted C6 to C30 aryl group, or a substituted or unsubstituted C2 to C30 heteroaryl group.

2. The compound as claimed in claim 1, wherein the $Ar^1$ and $Ar^2$ are each independently a substituted or unsubstituted phenyl group, a substituted or unsubstituted naphthalenyl group, a substituted or unsubstituted fluorenyl group, a substituted or unsubstituted biphenyl group, a substituted or unsubstituted dibenzofuranyl group, a substituted or unsubstituted dibenzothiophenyl group, a substnuted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzocuranyl group, a substituted or unsubstituted benzothiophenyl group, a substituted or unsubstituted benzimidazolyl group, a substituted or unsubstituted indolyl group, a substituted or MS ubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenaziny group, a substituted or unsubstituted phenothiazinyl group, or a substituted or unsubstituted phenoxazinyl group.

3. The compound as claimed in claim wherein the compound is represented by one of the following Chemical Formulae 2 to 4;

[Chemical Formula 2]

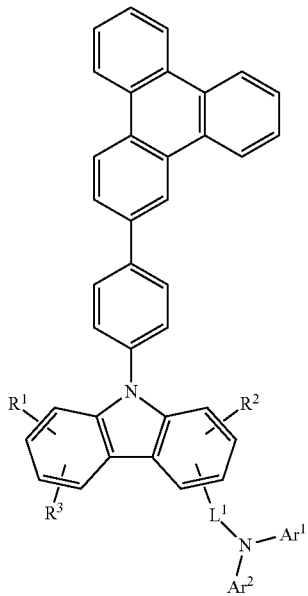

[Chemical Formula 3]

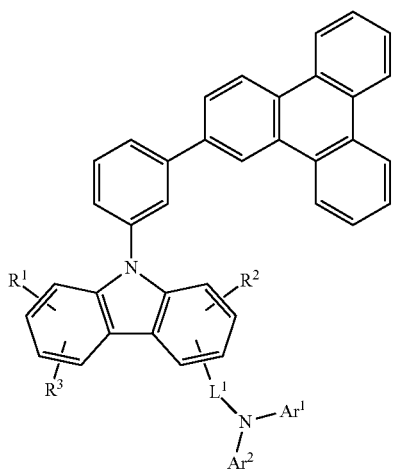

[Chemical Formula 4]

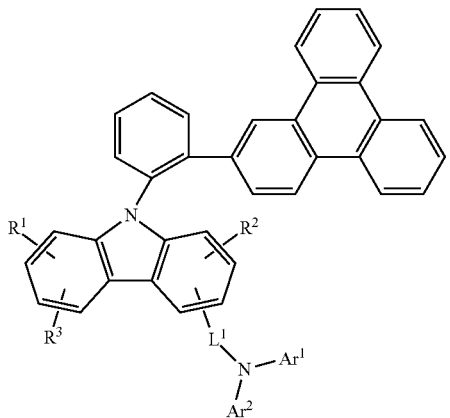

wherein, in Chemical formulae 2 to 4,
L$^1$ is a single bond, a substituted or unsubstituted C2 to C6 alkenylene group, a substituted or unsubstituted C2 to C6 alkynylene group, a substituted or unsubstituted C6 to C30 arylene group, or a substituted or unsubstituted C2 to C30 heteroarylene group,
R$^1$ to R$^3$ are independently hydrogen, a substituted or unsubstituted C1 to C6 alkyl group, a substituted or unsubstituted C6 to C30 aryl group, or a substituted or unsubstituted C2 to C30 heteroaryl group, and
Ar$^1$ and Ar$^2$ are each independently a substituted or insubstituted C6 to C30 aryl group, or a substituted or unsubstituted C2 to C30 heteroaryl group.

4. The compouund as claimed in claim 3, wherein the Ar$^1$ and Ar$^2$ are each a substituted or unsubstituted phenyl group, a substituted or unsubstituted naphthalenyl group, a substituted or unsubstituted fluorenyl group, substituted or unsubstituted biphenyl group, a substituted or unsubstituted dibenzofuranyl group, a substituted or unsubstituted dibenzothiophenyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terpheny group, a substituted or unsubstituted chrysenyl group, a substituted unsubstituted triphelenyl group, a substituted or unsubstituted perylenyl group, a substituted or unsubstituted indenyl group, a substituted or uusubstituted furanyl group, a substituted car unsubstituted thiophen of group, a substituted or unsubstituted pyrrolyl group, a substituted or unsubstituted pyrazolyl group, a substituted or uunsuubstiituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstiuted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted soqumohnyl group, a substituted or unsubstituted quinazolinyl group, a substituted or unsubstituted quinoxalinytl group, a substituted or unsubstituted naphthyridinyl group, a substituted or unsubstituted benzoxazinyl group a substituted or unsubstituted benzthiazinyl group, a substituted or unsubstituted acridinyl group a substituted or unsubstituted phenazinyl group, a substituted or unsubstituted phenothiazinyl group, or a substltuted or unsubstituted phenoxazinyl.

5. The compound as claimed in claim 1, wherein the compound is represented by the following Chemical Formula 5:

[Chemical Formula 5]

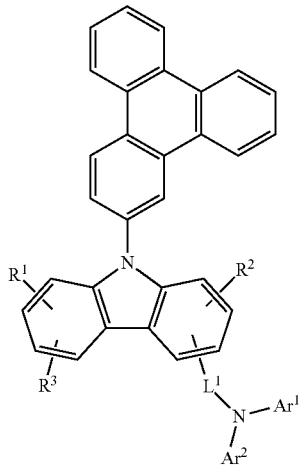

wherein, in Chemical Formula 5,
- $L^1$ is a single bond, a substituted or unsubstituted C2 to C6 alkenylene group, a substituted or unsubstituted C2 to C6 alkynylene group, a substituted or unsubstituted C6 to C30 alylene group, or a substituted or unsubstituted C2 to C30 heteroarylene group,
- $R^1$ to $R^3$ are each independently hydrogen, a substituted or unsubstituted C1 to C6 alkyl group, a substituted or unsubstituted C6 to C30 aryl group, or a substituted or unsubstituted C2 to C30 heteroaryl group, and
- $Ar^1$ and $Ar^2$ are each independently a substituted or unsubstituted $C^6$ to C30 aryl group, or a substituted or unsubstituted C2 to C30 heteroaryl group.

6. The compound as claimed in claim 5, wherein the $Ar^1$ and $Ar^2$ are each independently a substituted or unsubstituted phenyl group, a substituted or unsubstituted naphthalenyl group, a substituted or unsubstituted fluorenyl group, a substituted or unsubstituted biphenyl group, a substituted or unsubstituted dibenzoftiranyl group, a substituted or unsubstituted dibenzothiophenyi group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unstibstituted p-terphenyl group, a substituted or unsubstituted m-terphenyl group, a substituted or unsubstituted chrysenyl group, a substituted or unsubstituted triphenylenyl group, a substituted or unsubstituted petylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl tuoup, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiopheayl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstitutedphenazinyl group, a substituted or unsubstituted phenothiazinyl group, or a substituted or unsubstituted phenoxazinyl group.

7. A compound for an organic photoelectric device, the compound being represented by one of the following Chemical Formulae 6 to 18 or A-1 to A-251:

[Chemical Formula 6]

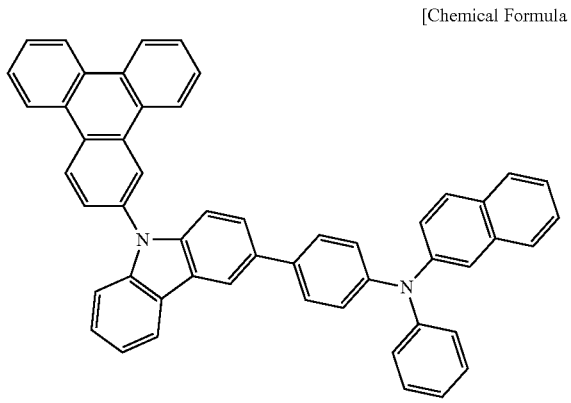

[Chemical Formula 7]

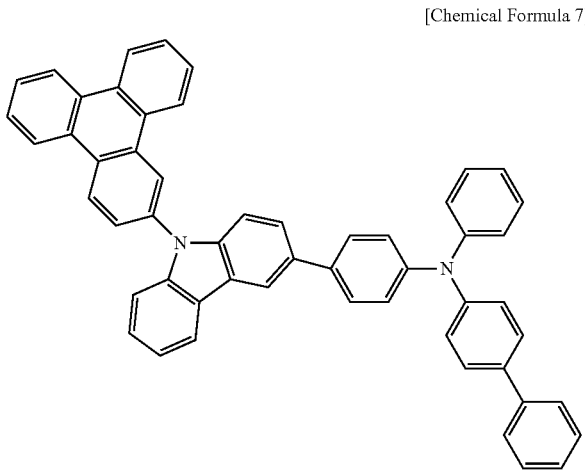

-continued
[Chemical Formula 8]
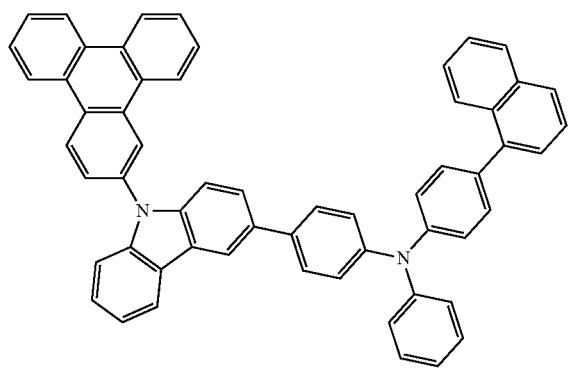
[Chemical Formula 9]
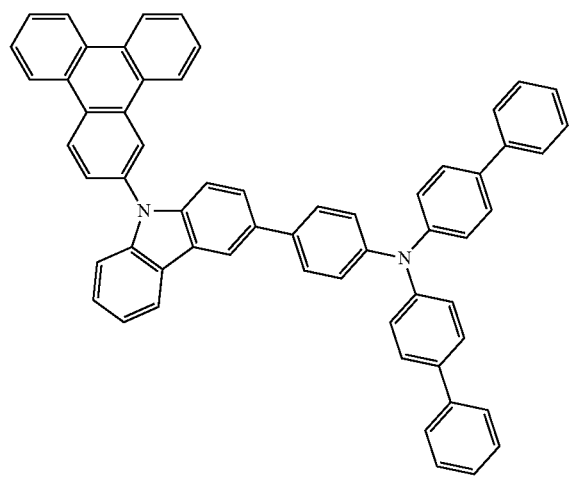
[Chemical Formula 10]
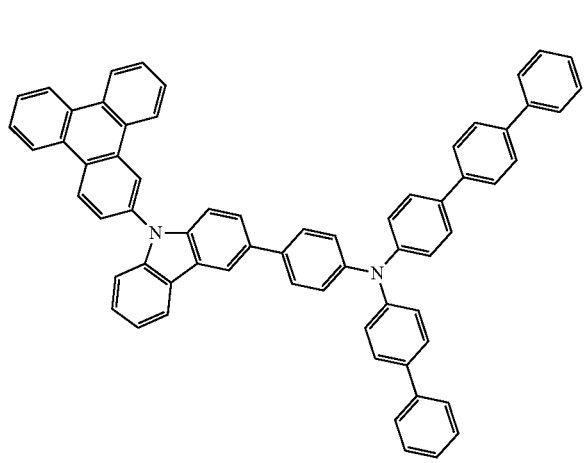
[Chemical Formula 11]
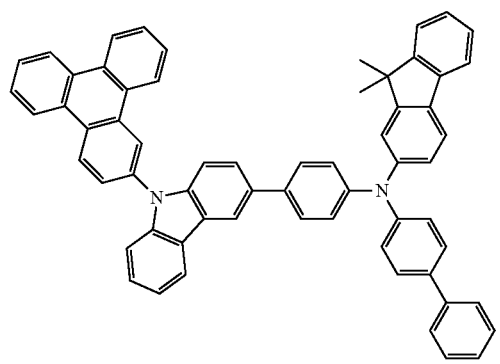
[Chemical Formula 12]
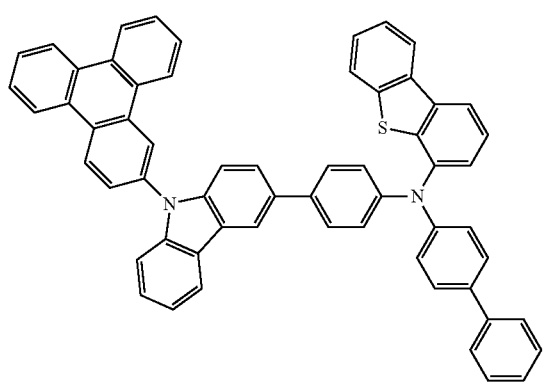
[Chemical Formula 13]
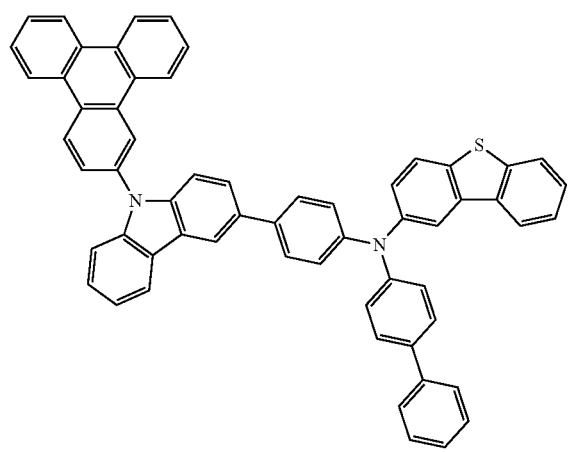

[Chemical Formula 14]
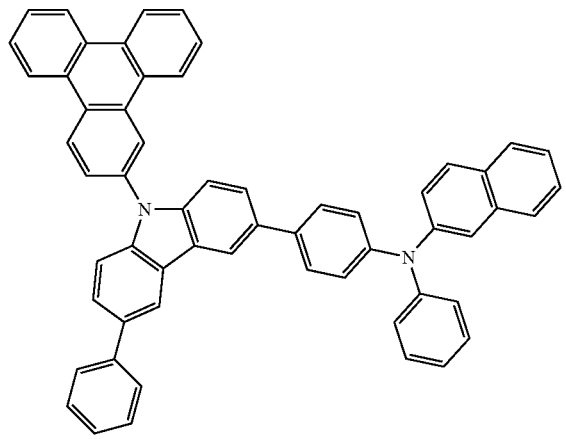
[Chemical Formula 15]
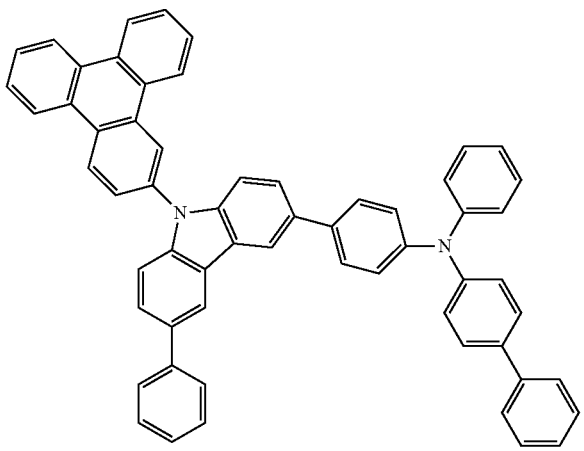
[Chemical Formula 16]
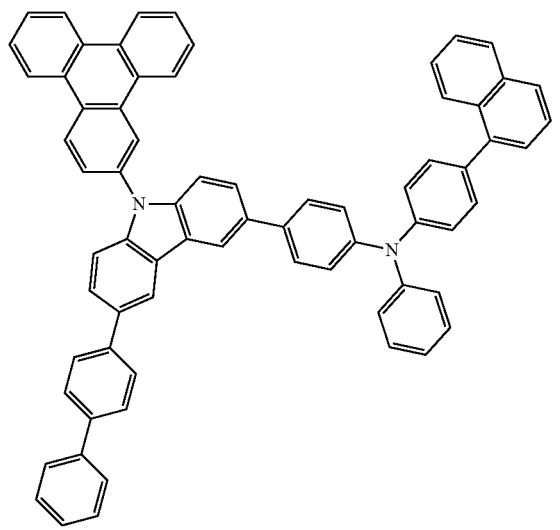
[Chemical Formula 17]
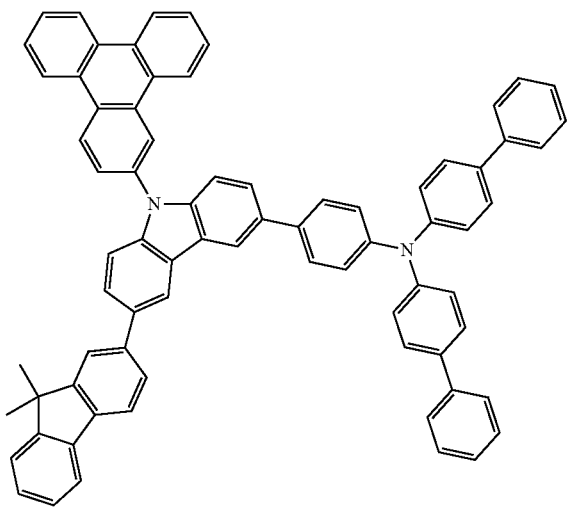
[Chemical Formula 18]
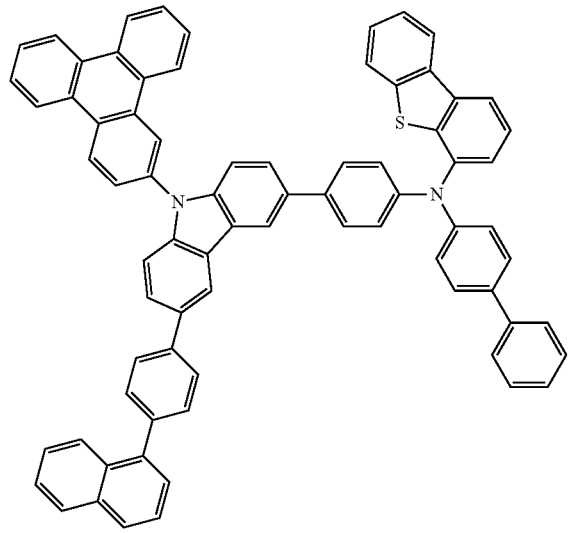
[A-1]
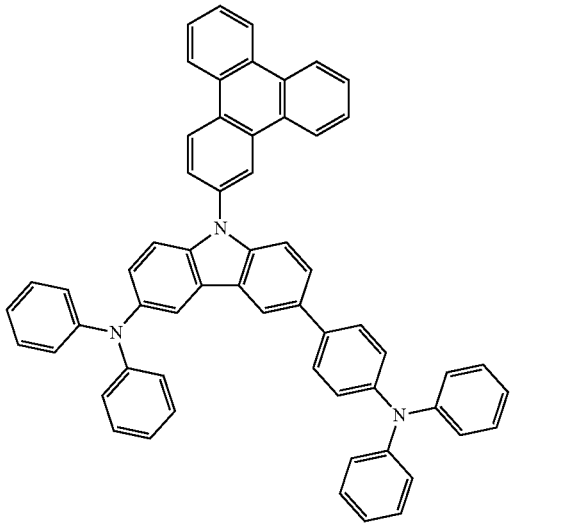

-continued
[A-2]
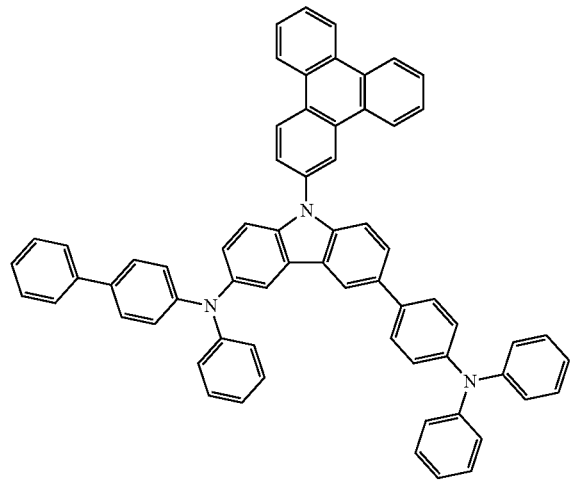
[A-3]
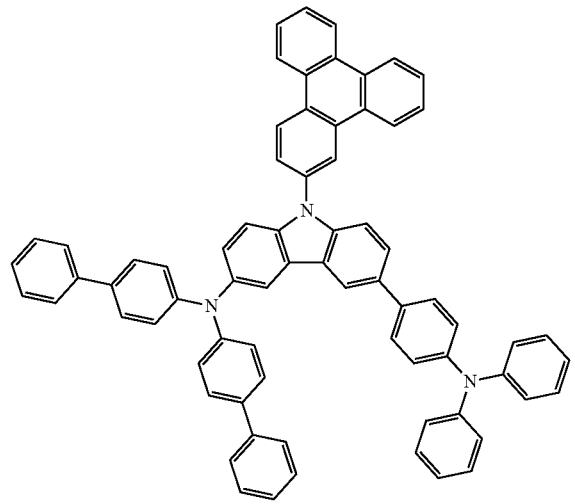
[A-4]
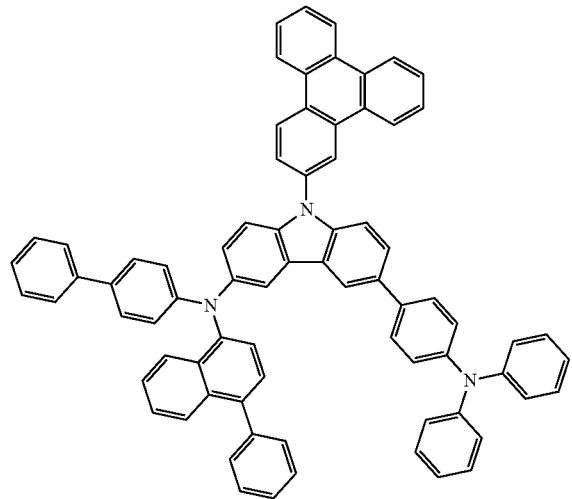
[A-5]
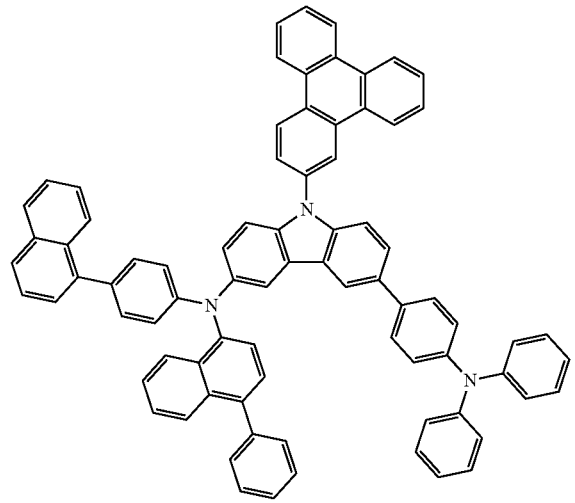
[A-6]
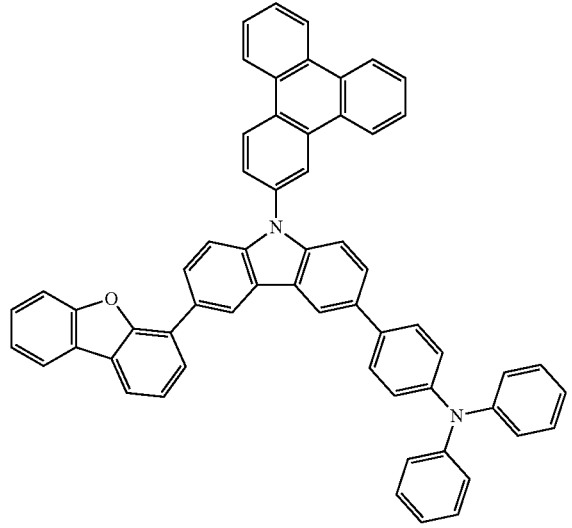
[A-7]
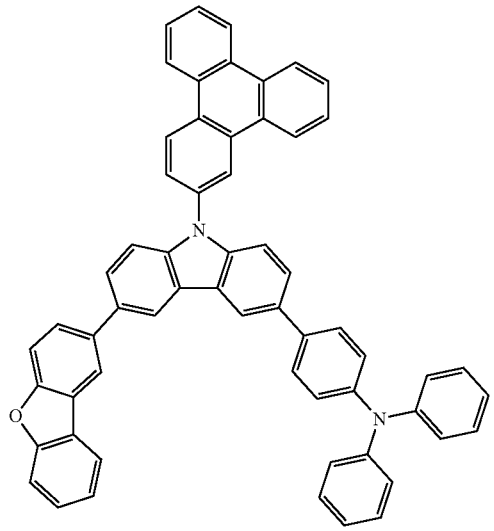

431 432
-continued
[A-8] 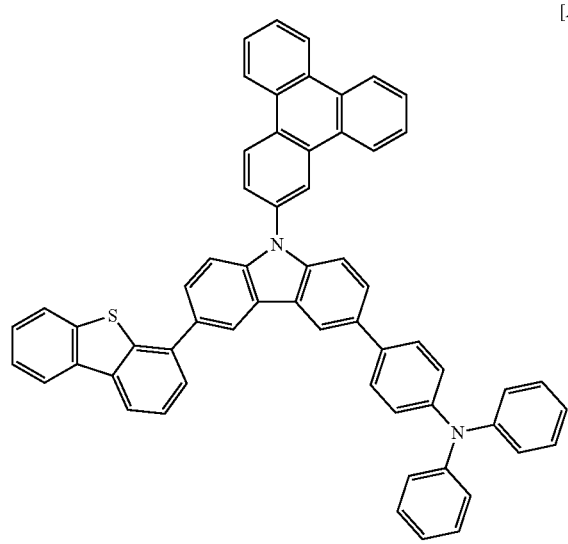
[A-9] 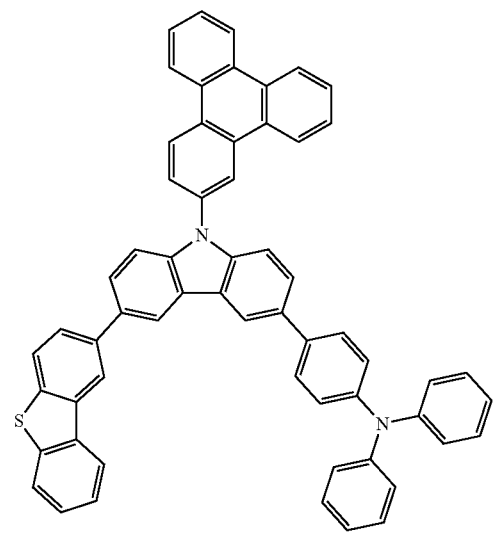
[A-10] 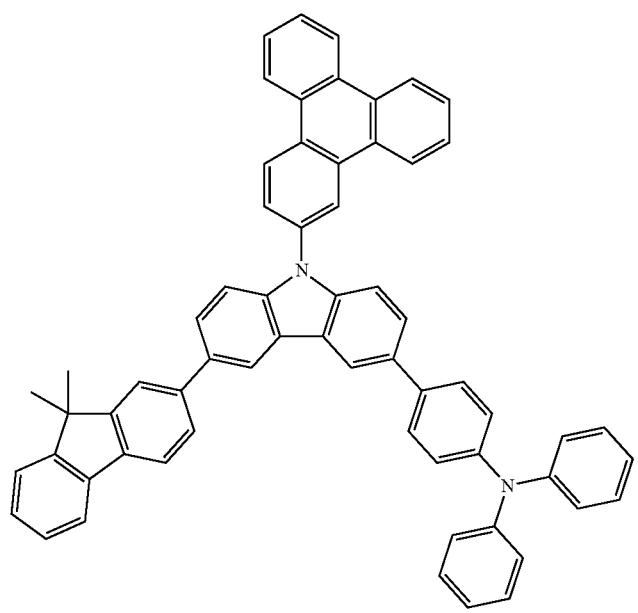

-continued
[A-11]
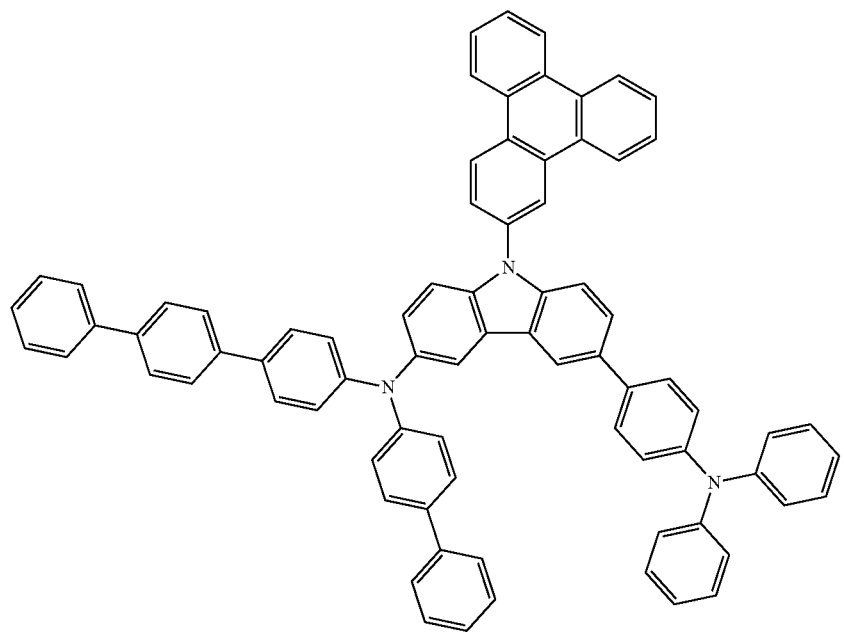
[A-12]
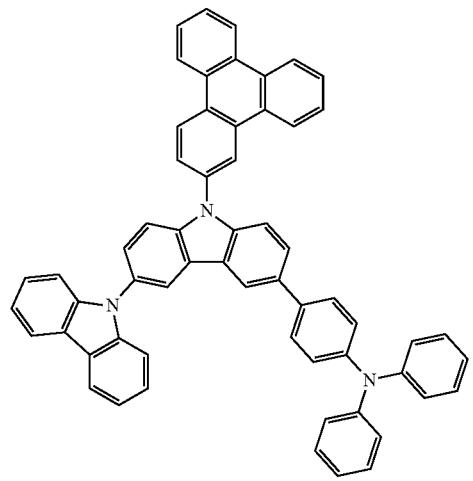
[A-13]
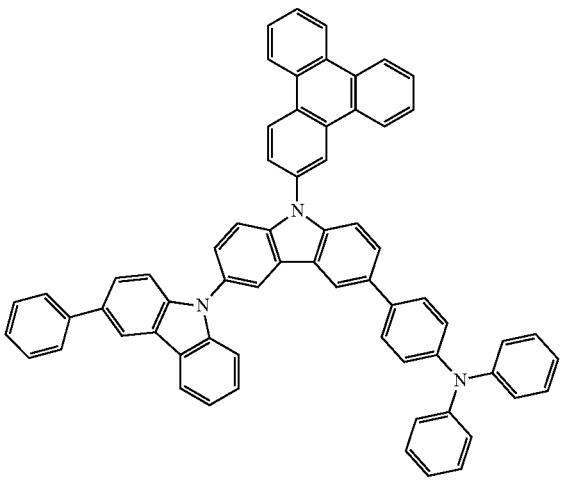
[A-14]
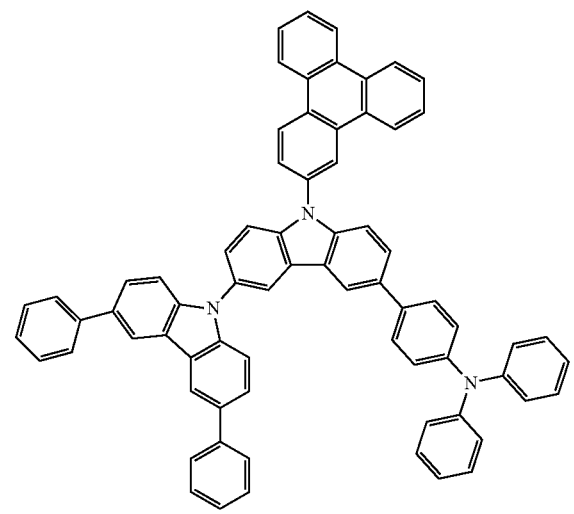
[A-15]
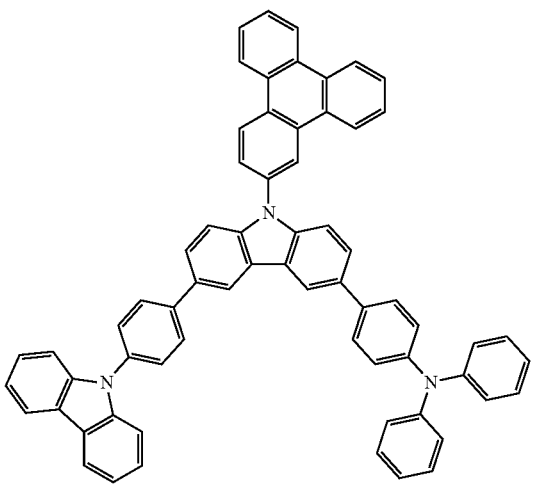

-continued
[A-16]
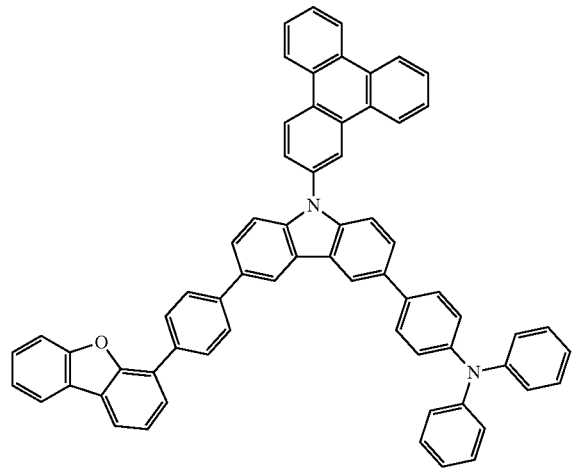
[A-17]
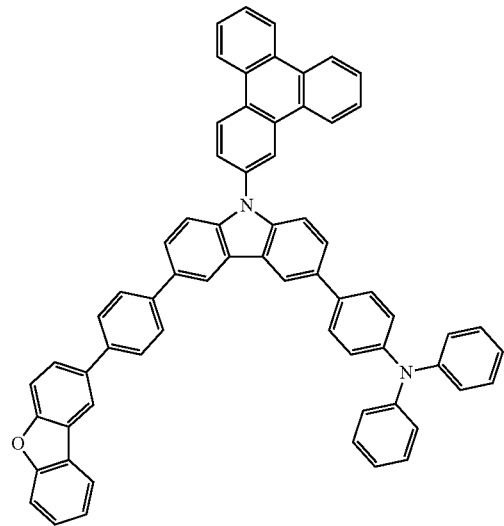
[A-18]
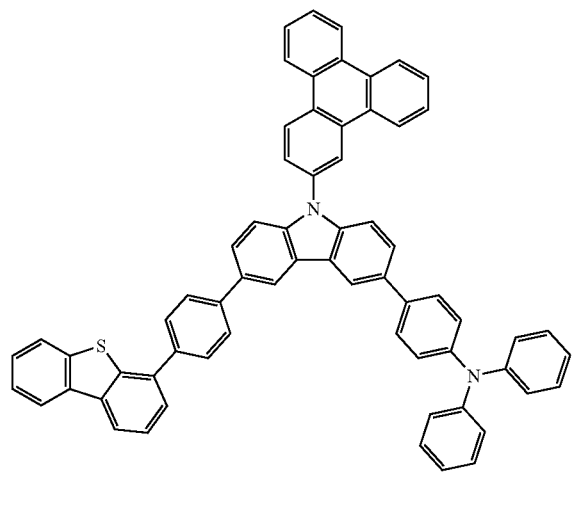
[A-19]
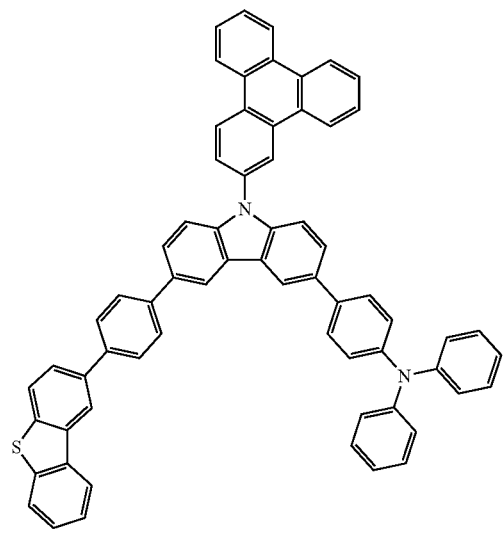
[A-20]
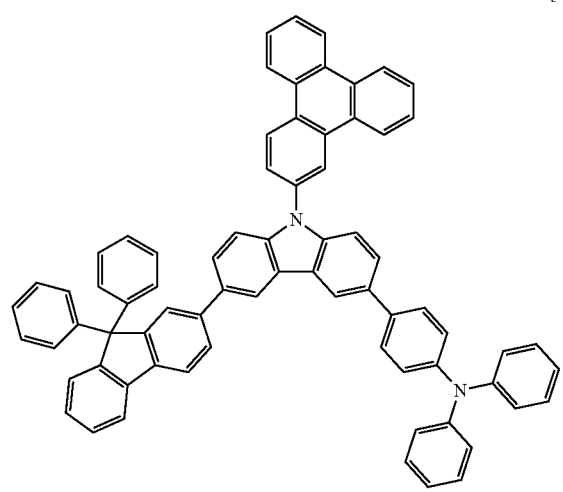
[A-21]
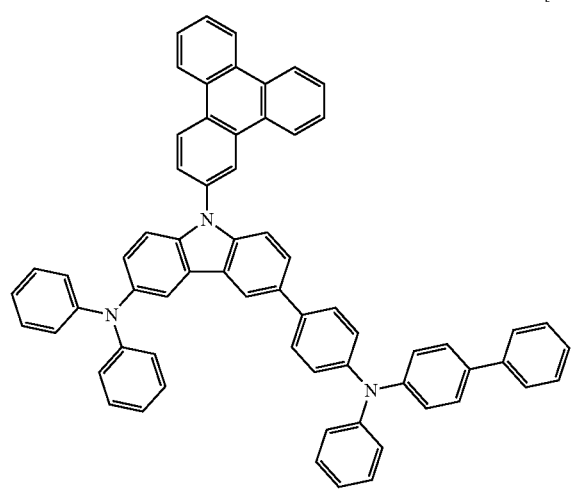

[A-22]
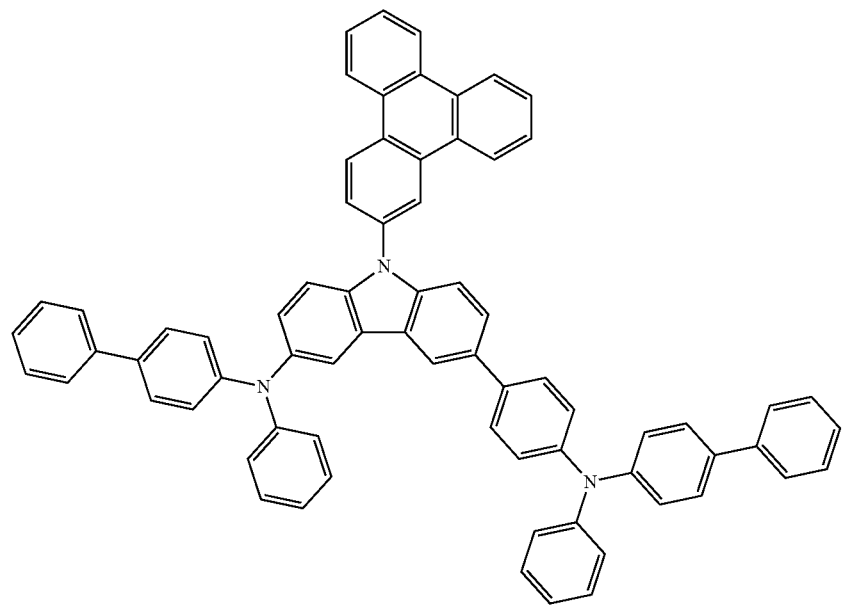
[A-23]
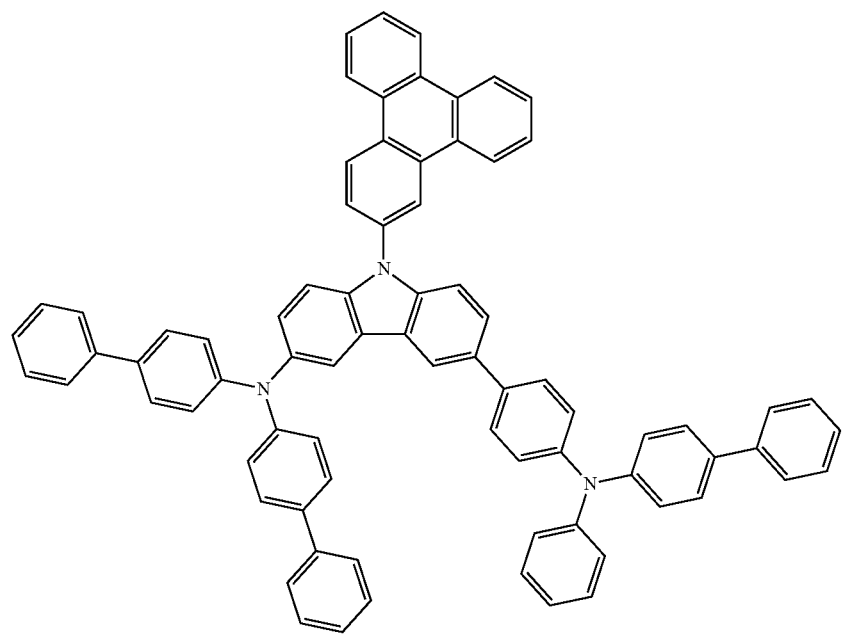

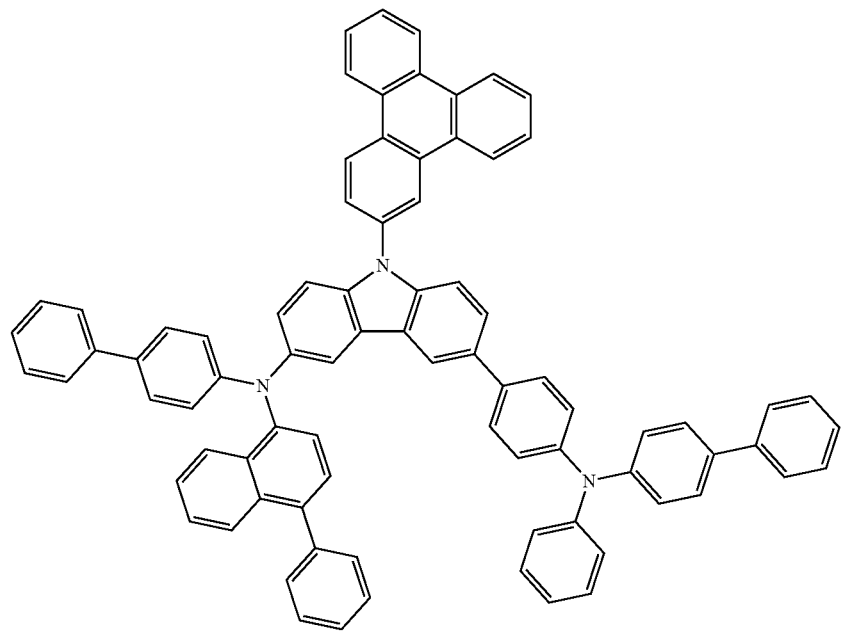
[A-24]
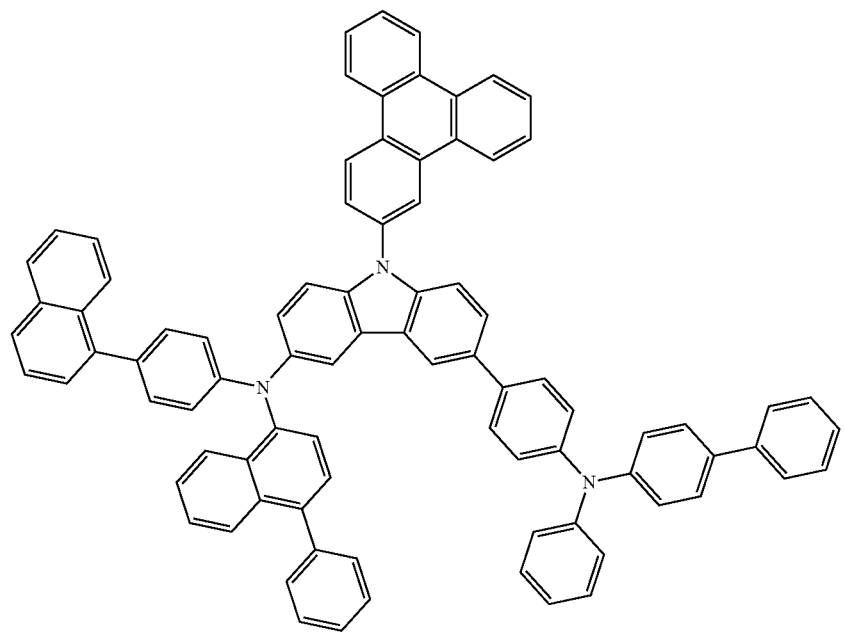
[A-25]

-continued
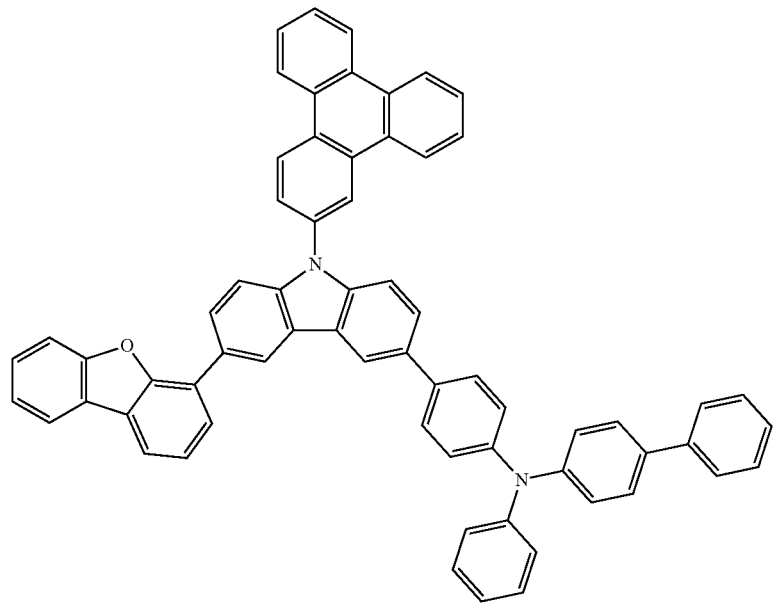
[A-26]
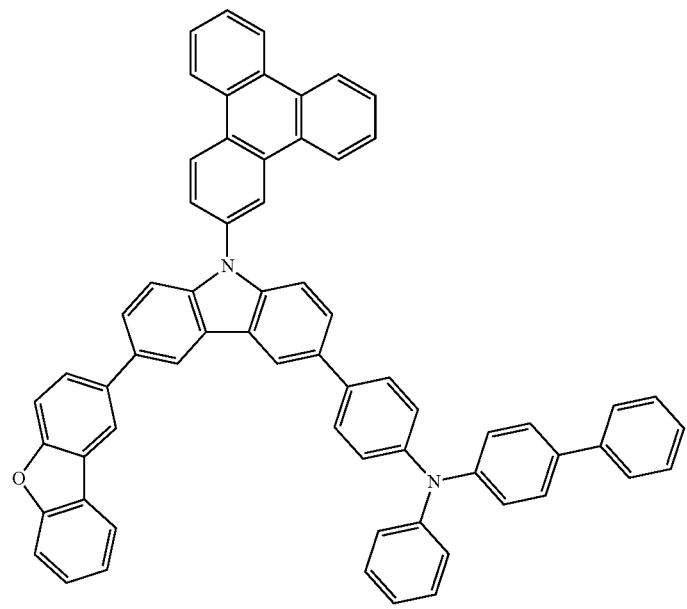
[A-27]

[A-28]
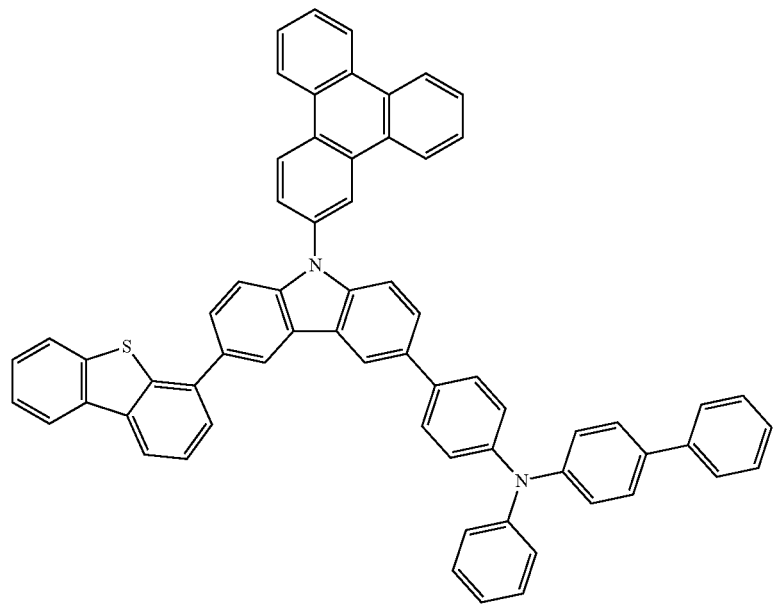
[A-29]
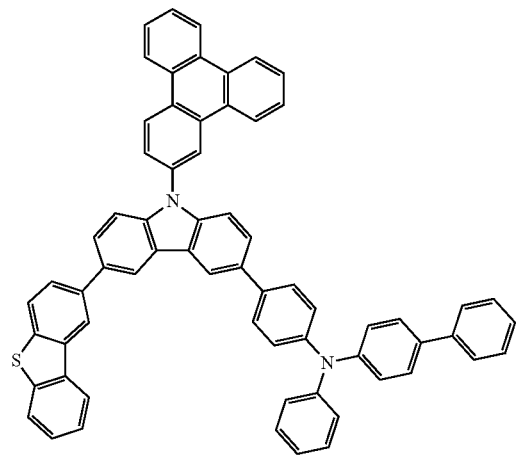
[A-30]
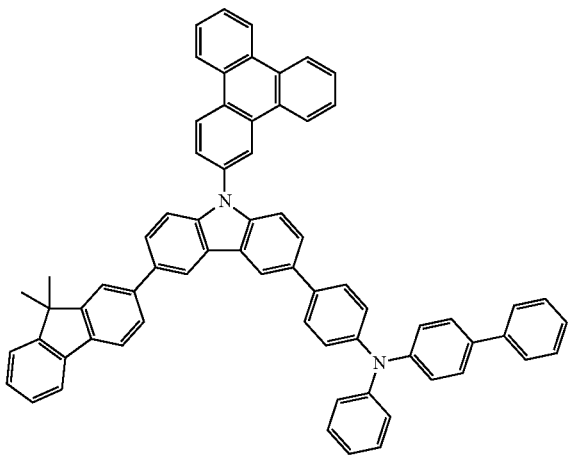

-continued
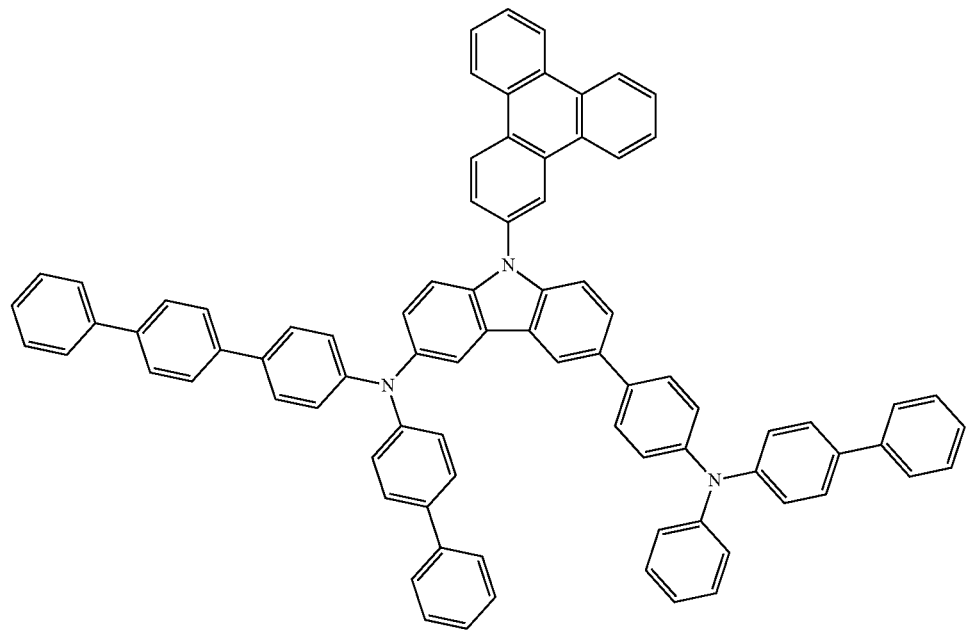
[A-31]
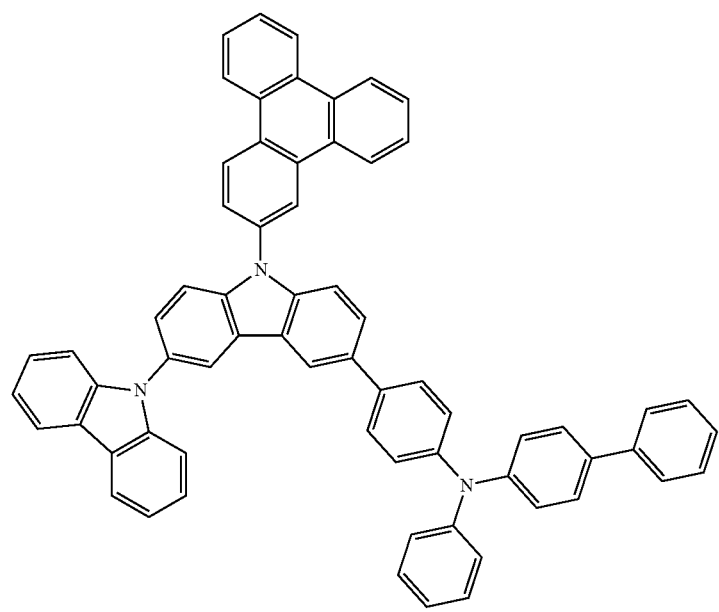
[A-32]

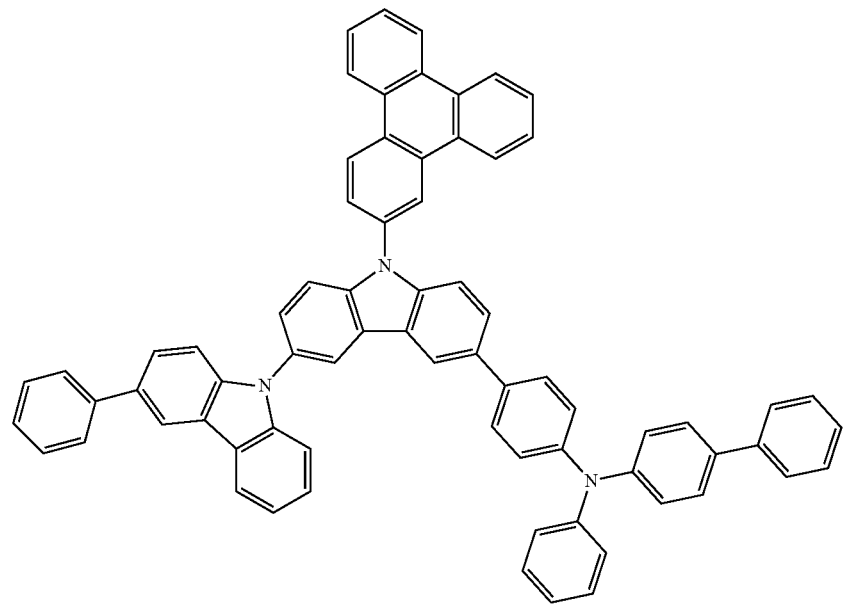
[A-33]
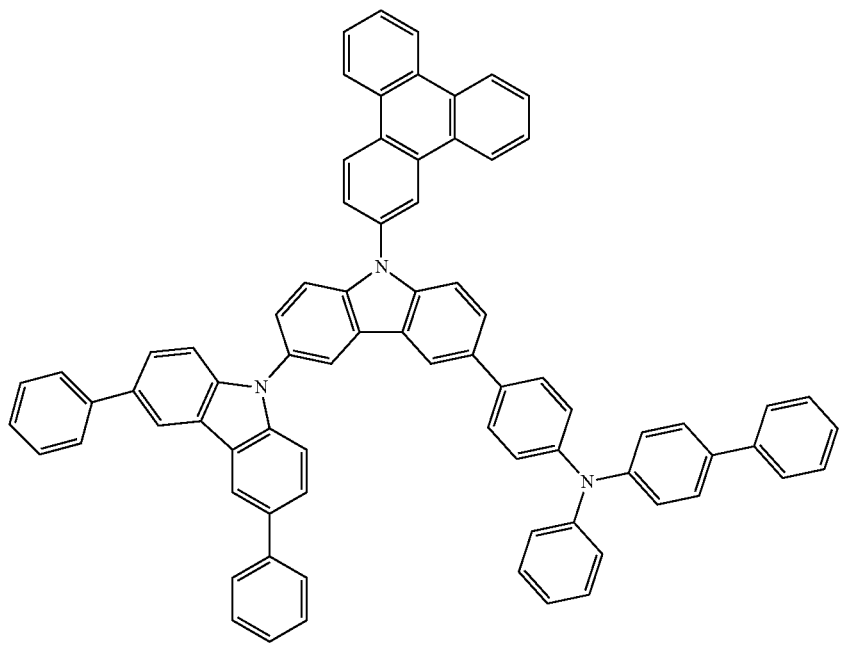
[A-34]

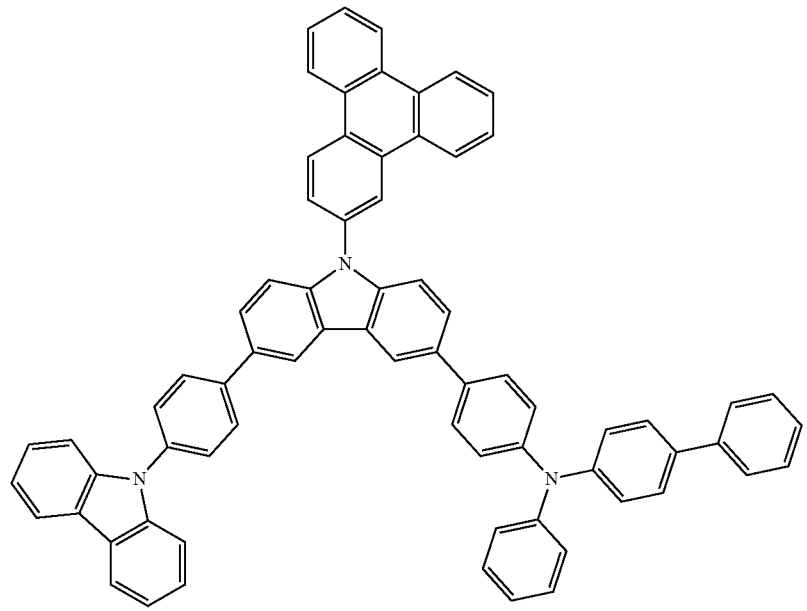
[A-35]
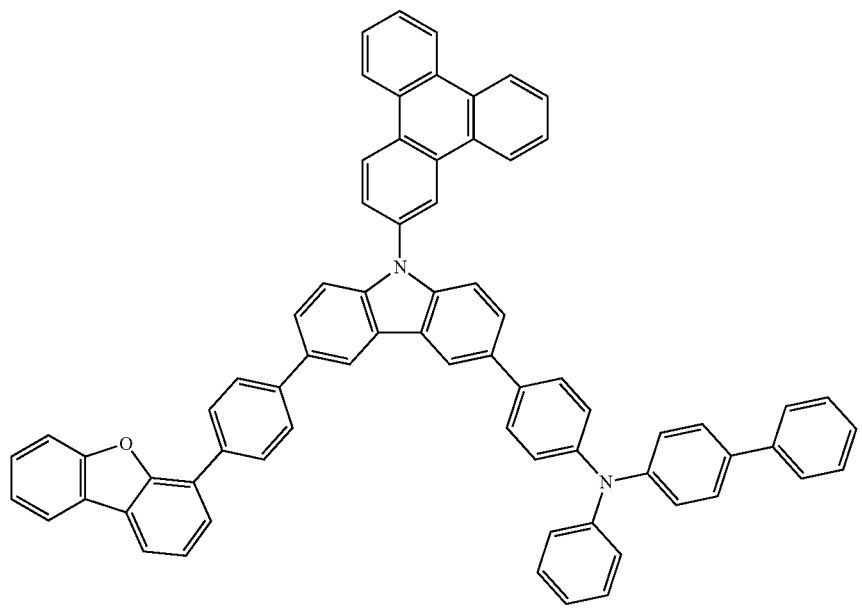
[A-36]

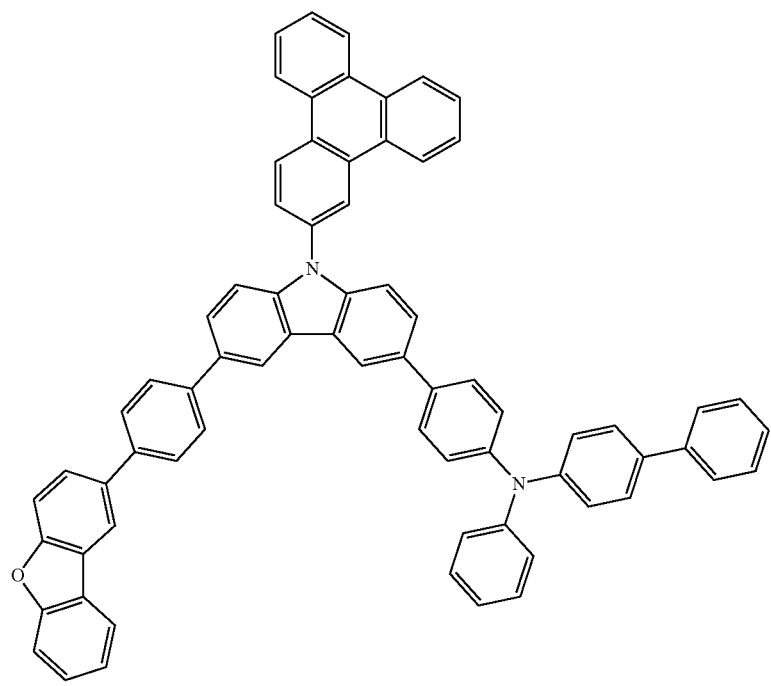
[A-37]
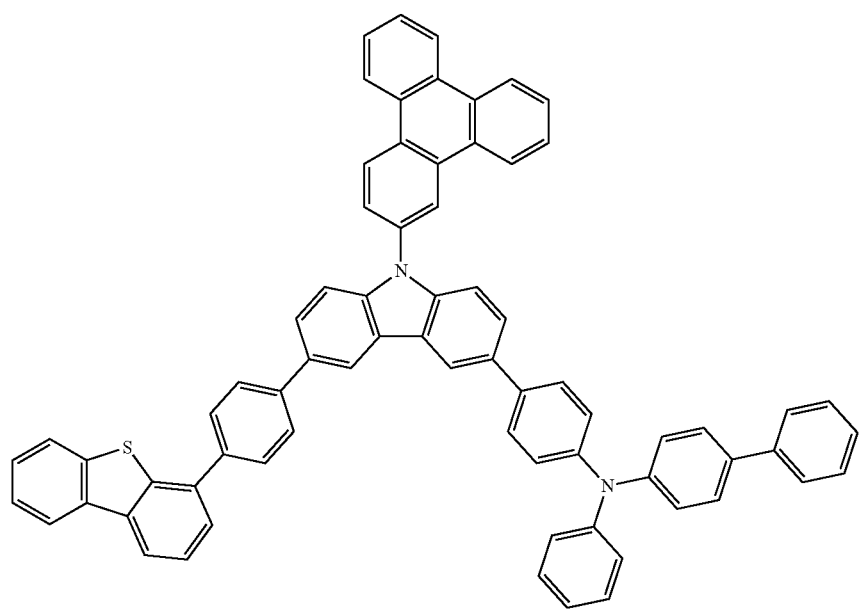
[A-38]

[A-39]
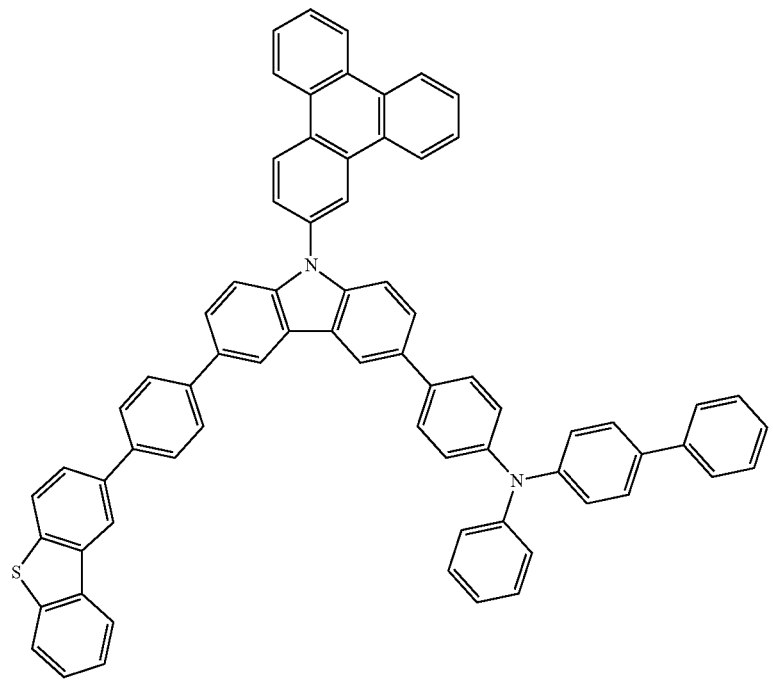
[A-40]
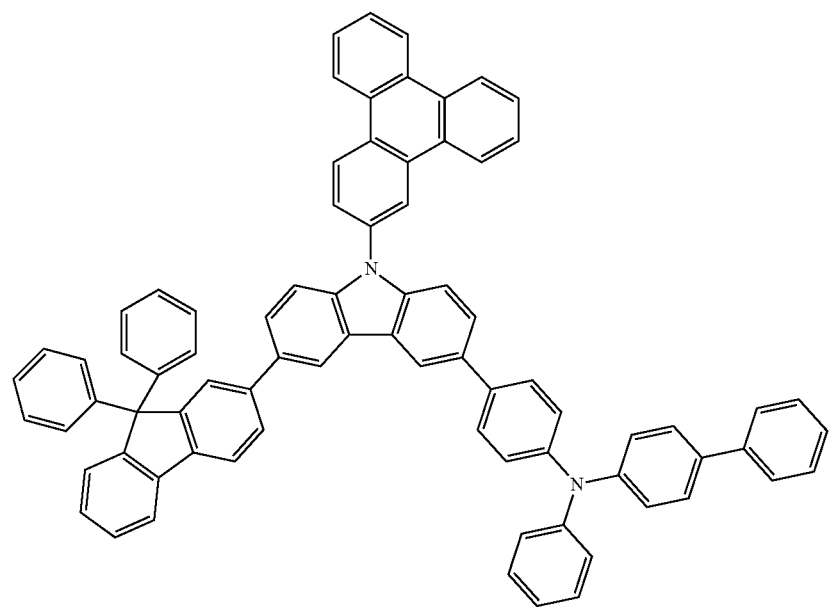

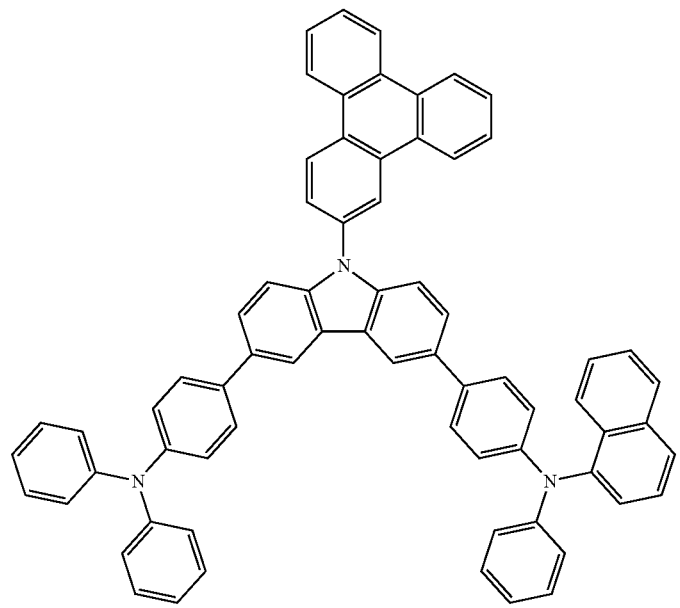
[A-41]
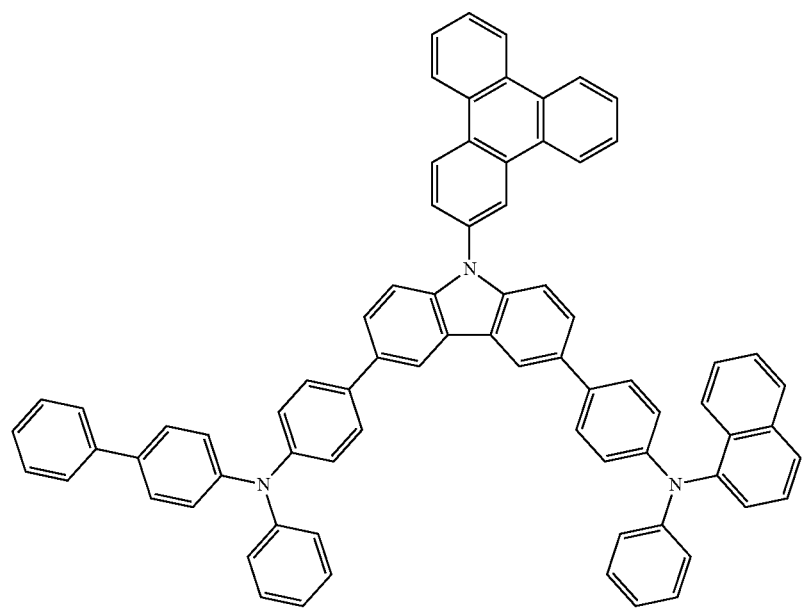
[A-42]

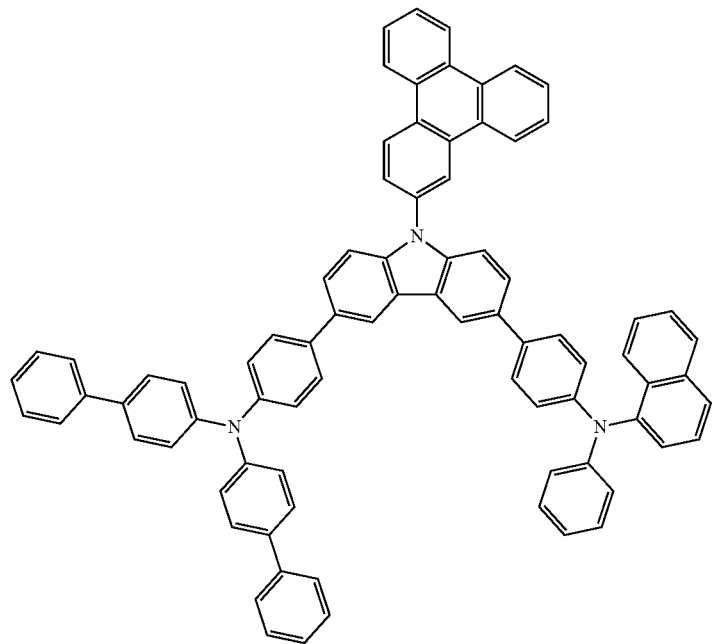
[A-43]
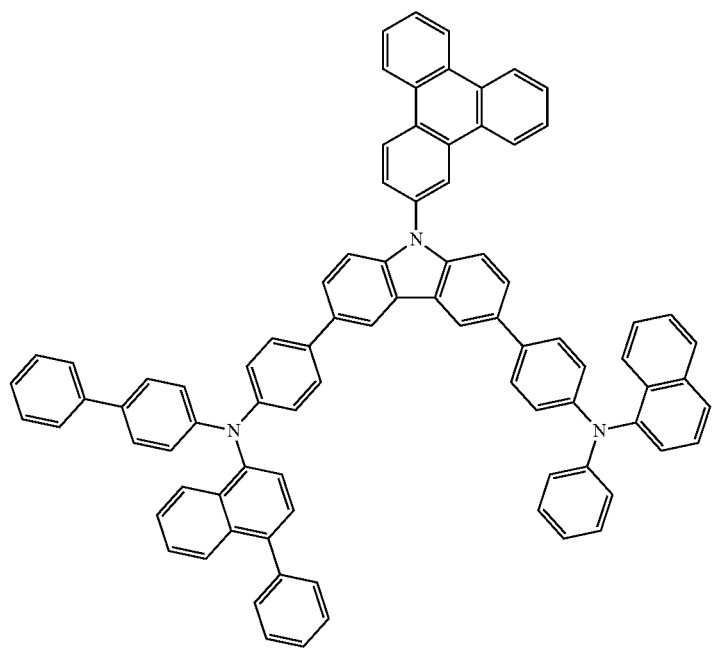
[A-44]

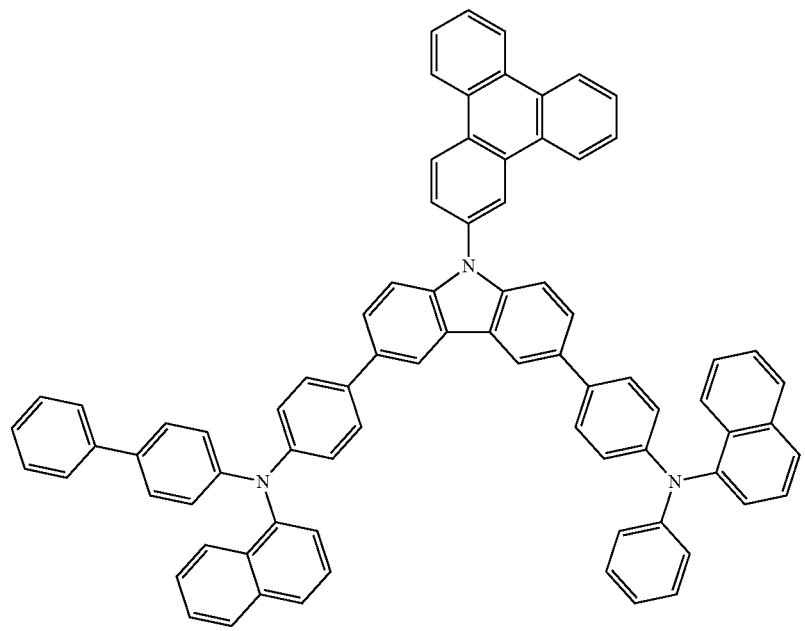
[A-45]
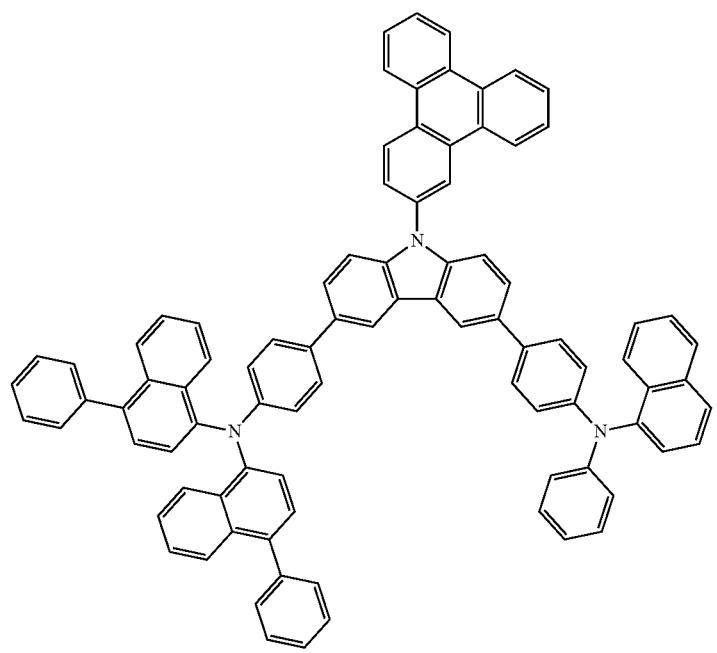
[A-46]

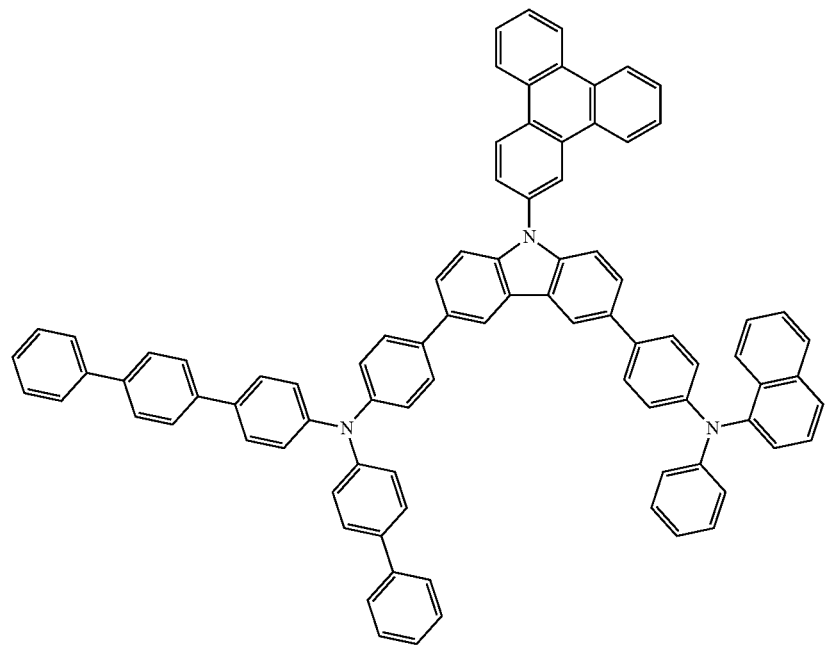
[A-47]
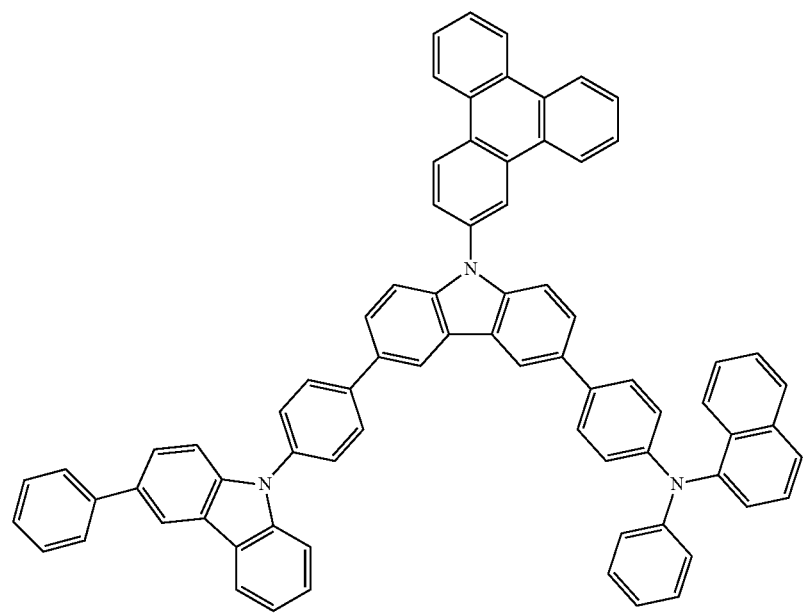
[A-48]

[A-49]
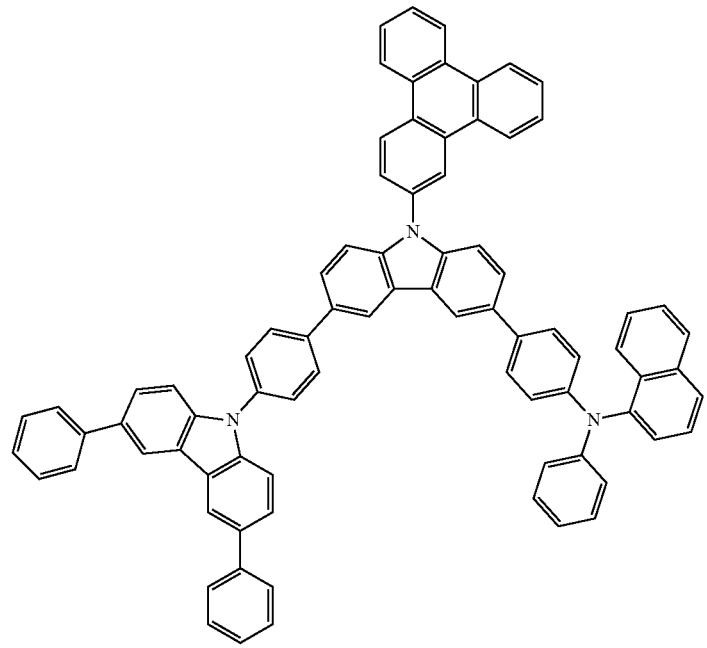
[A-50]
[A-51]
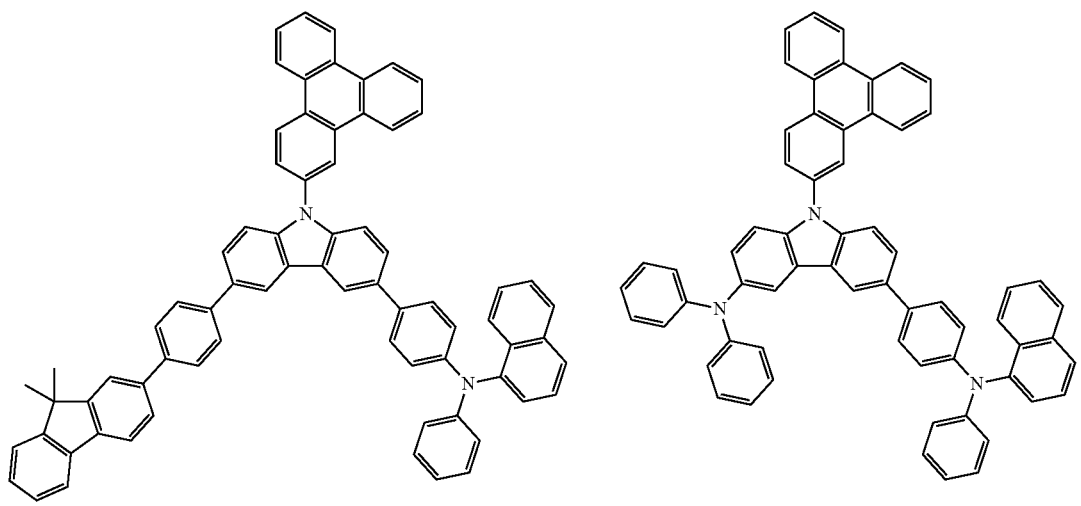

-continued
[A-52]
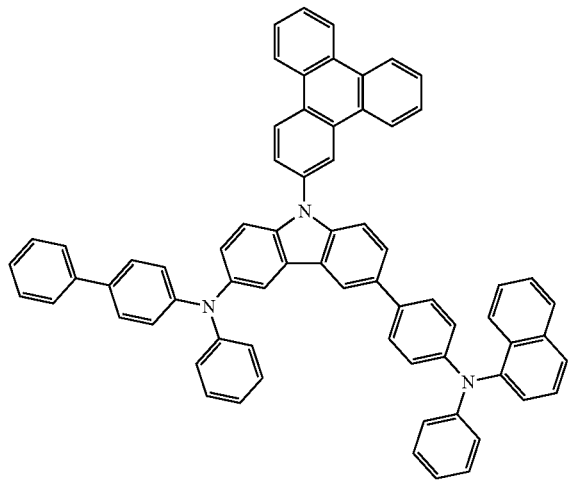
[A-53]
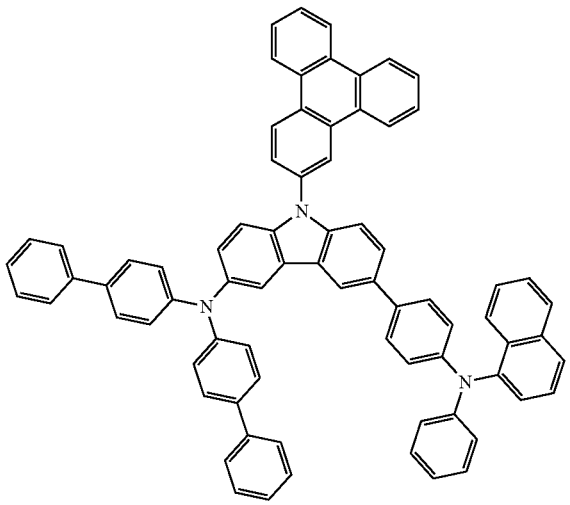
[A-54]
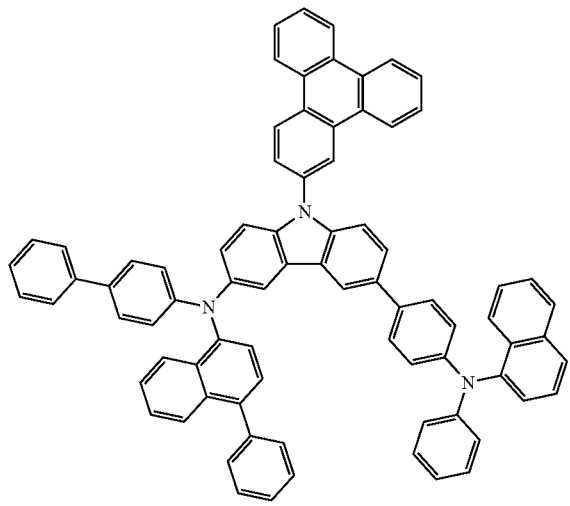
[A-55]
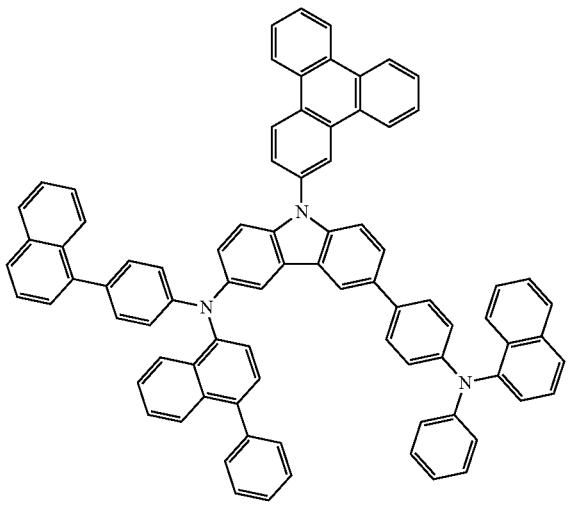
[A-56]
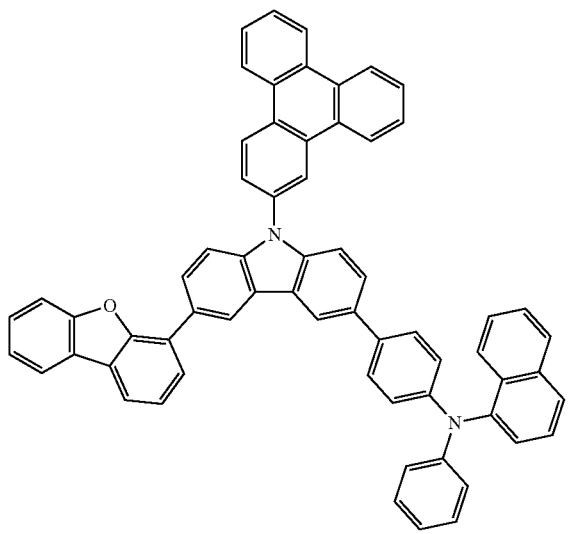
[A-57]
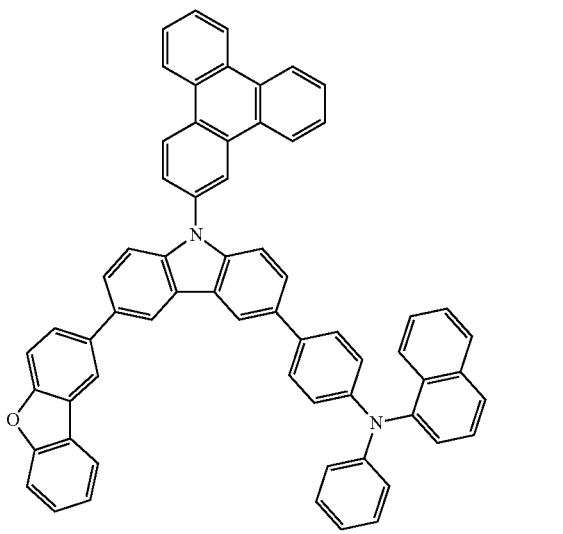

467
-continued
[A-58]
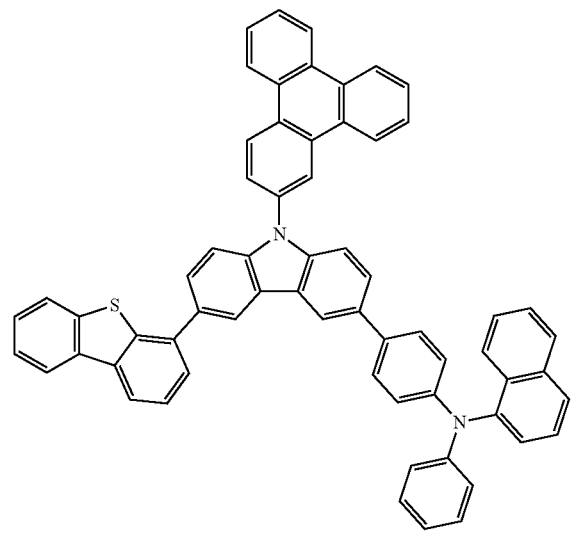
[A-59]
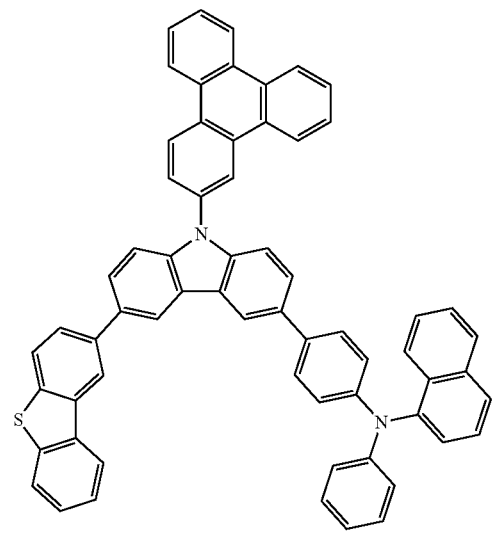
[A-60]
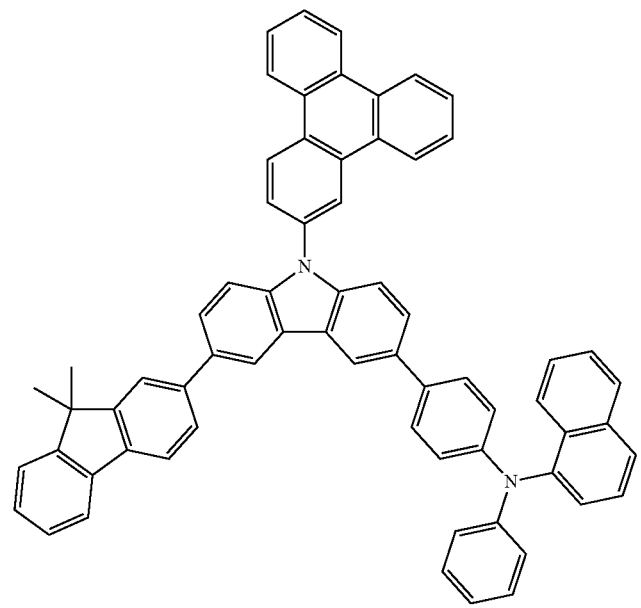

-continued
[A-61]
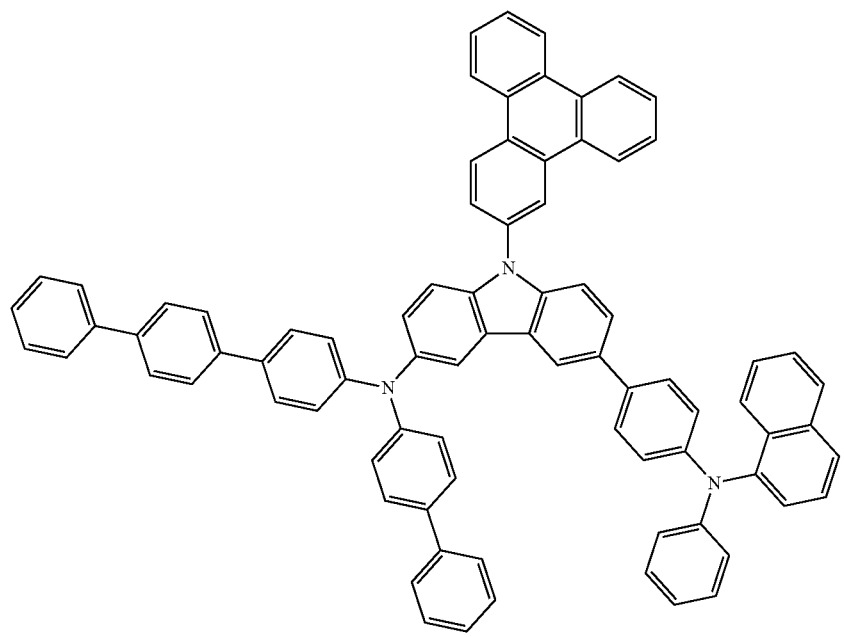
[A-62]
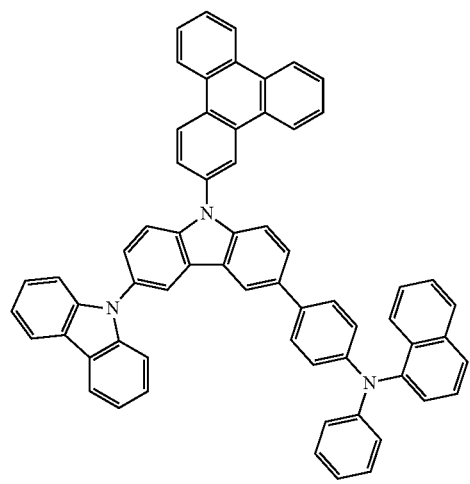
[A-63]
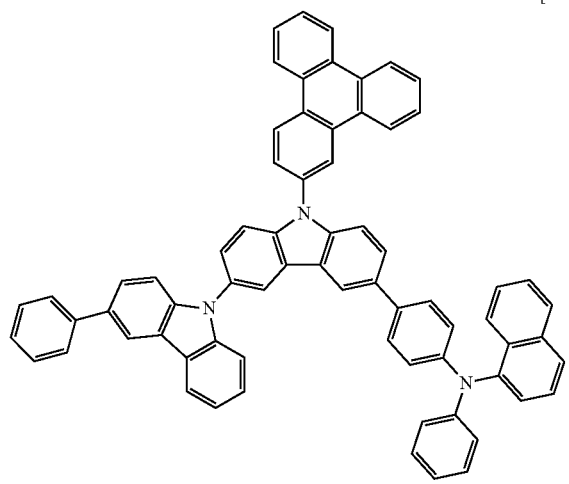
[A-64]
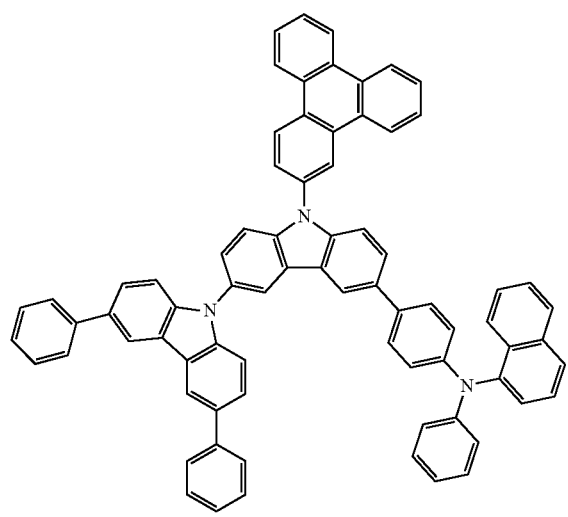
[A-65]
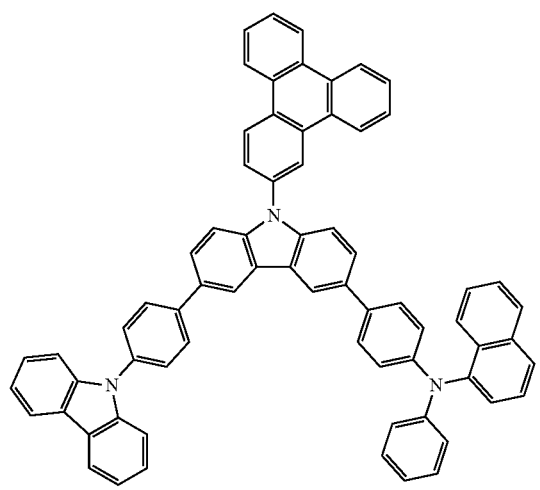

-continued
[A-66]
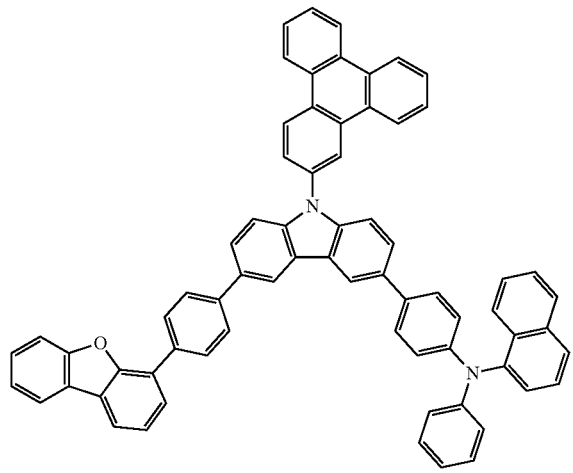
[A-67]
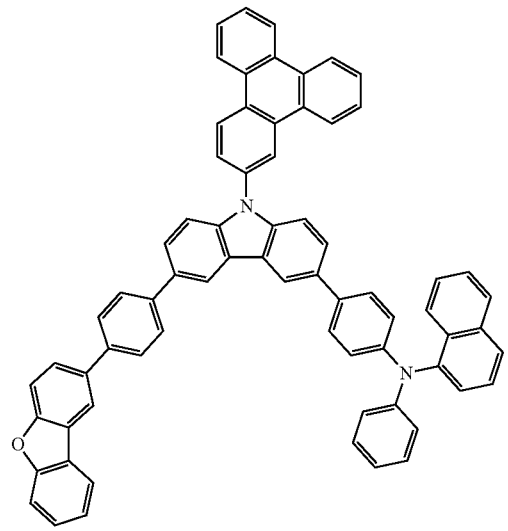
[A-68]
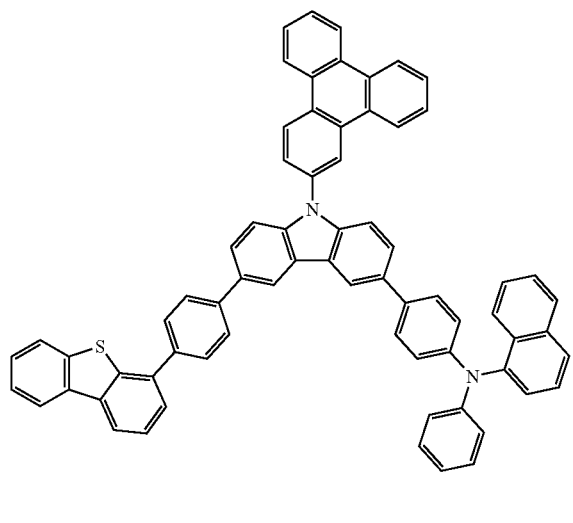
[A-69]
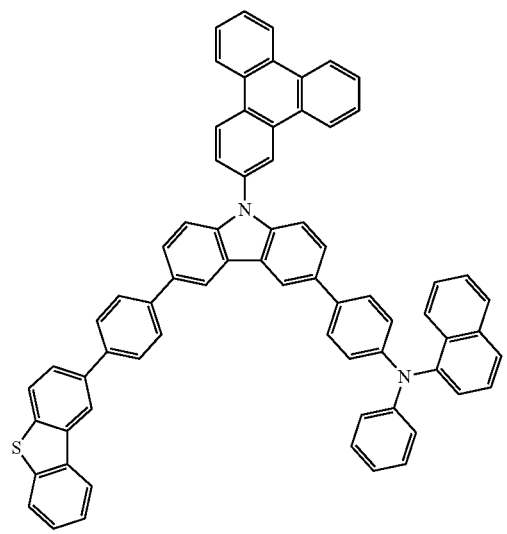
[A-70]
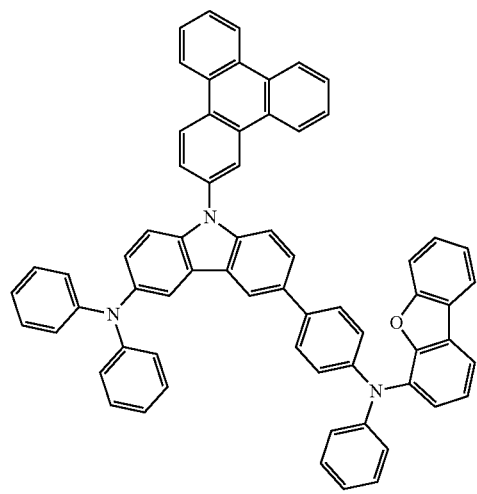
[A-71]
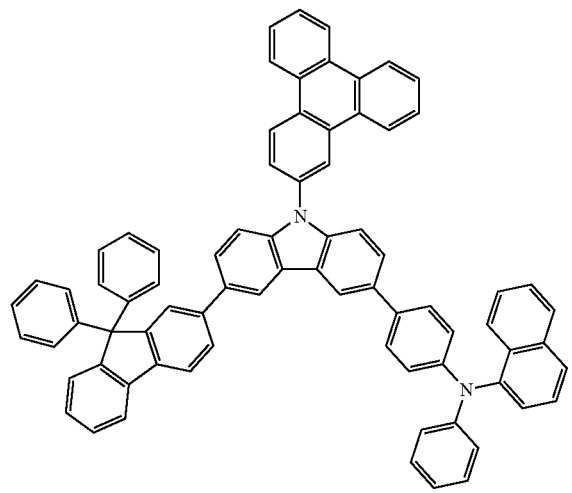

-continued
[A-72]
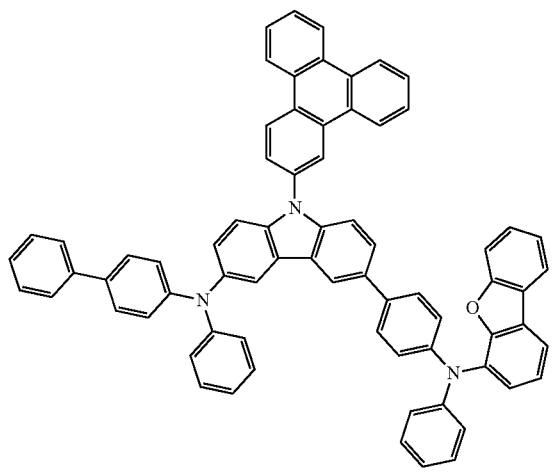
[A-73]
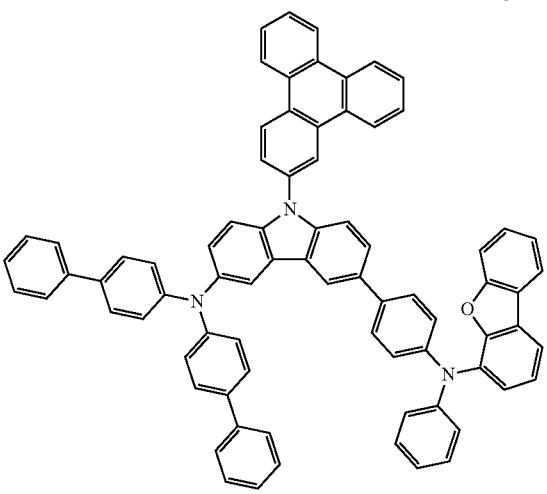
[A-74]
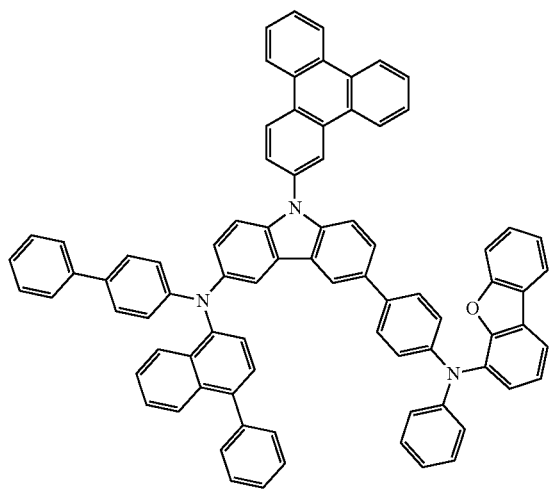
[A-75]
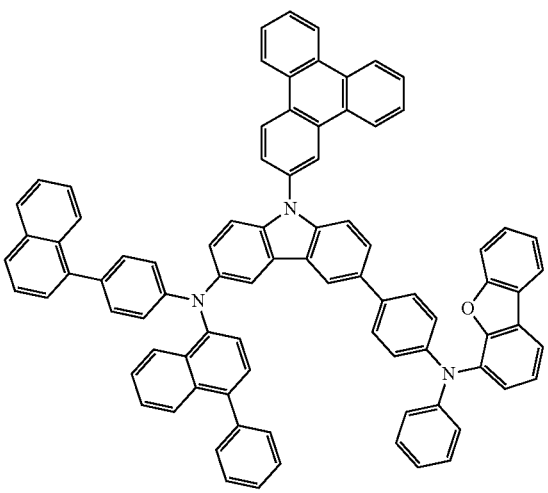
[A-76]
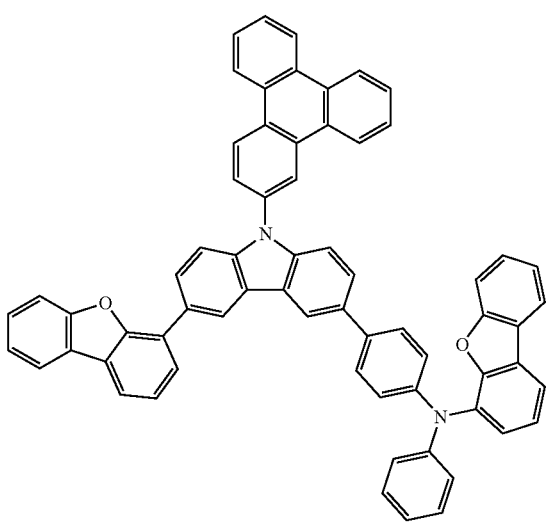
[A-77]
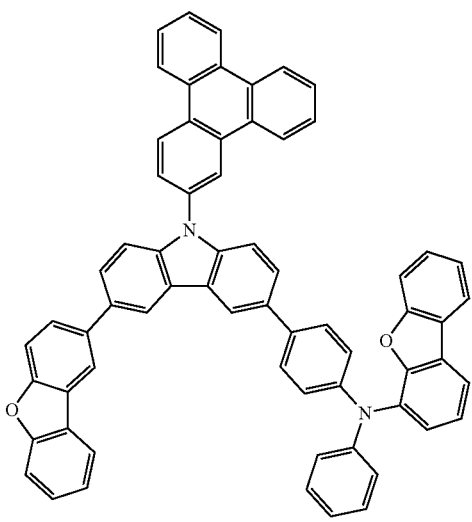

[A-78]
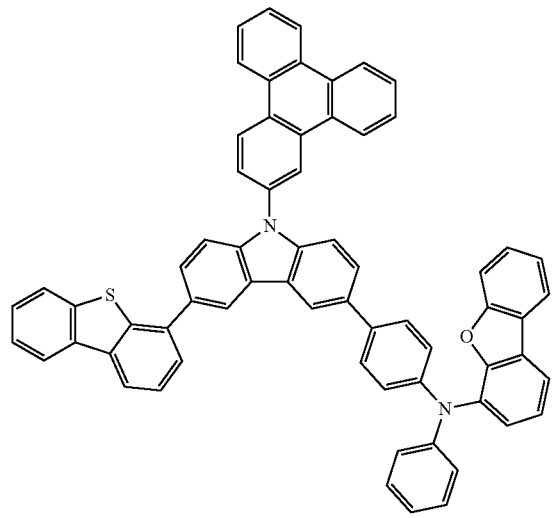
[A-79]
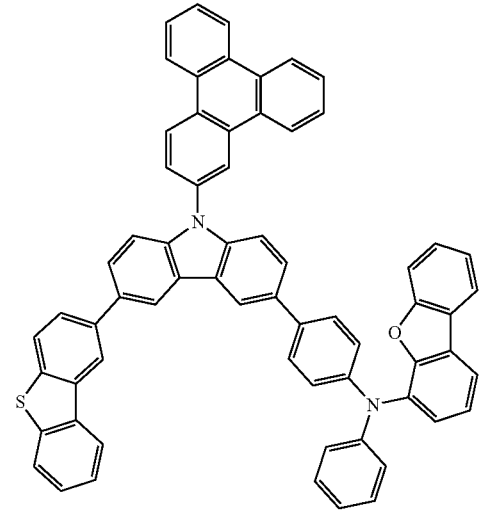
[A-80]
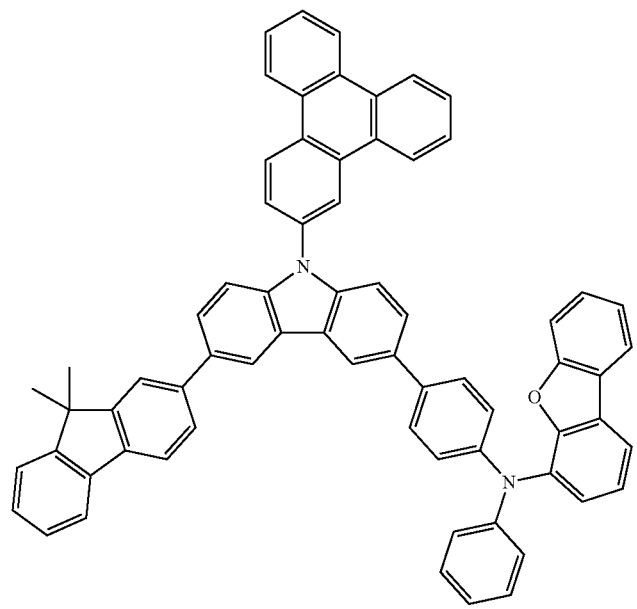

-continued
[A-81]
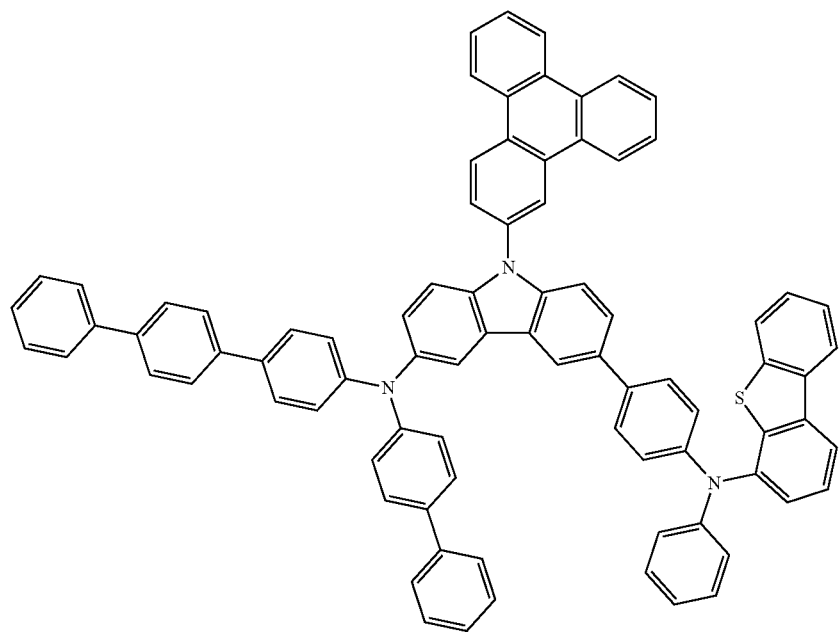
[A-82]
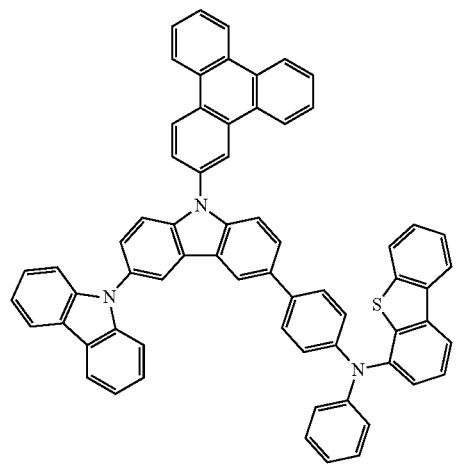
[A-83]
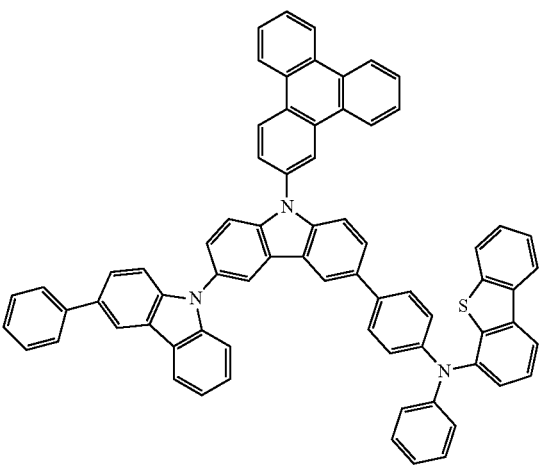
[A-84]
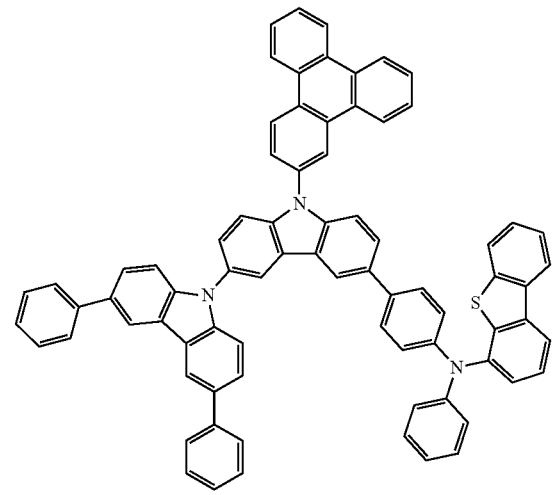
[A-85]
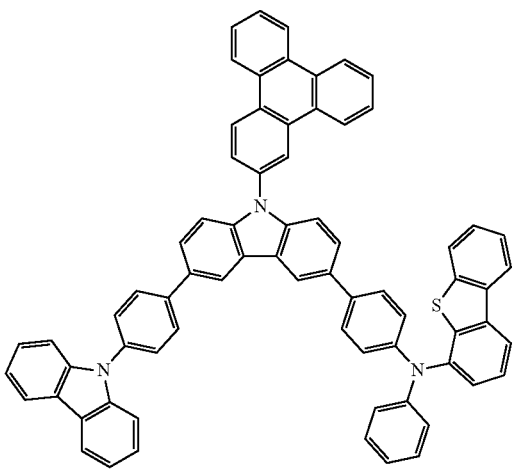

-continued
[A-86]
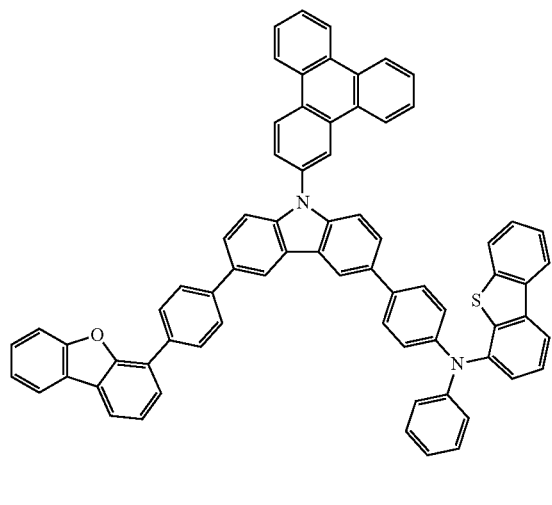
[A-87]
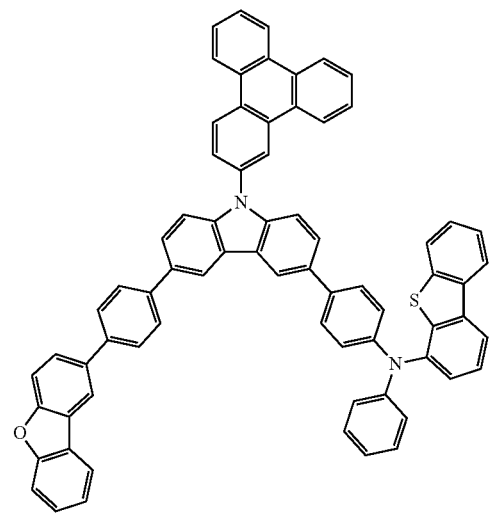
[A-88]
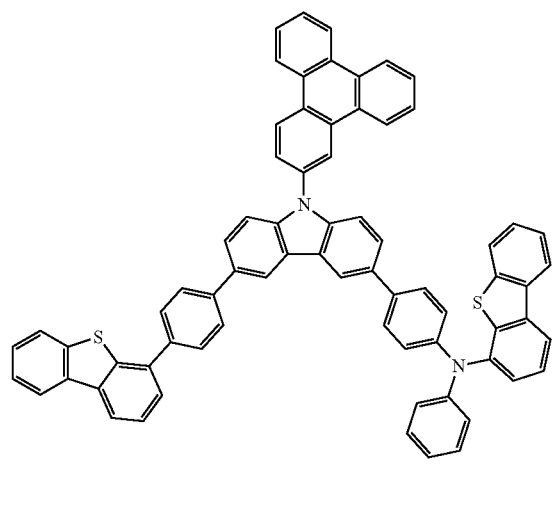
[A-89]
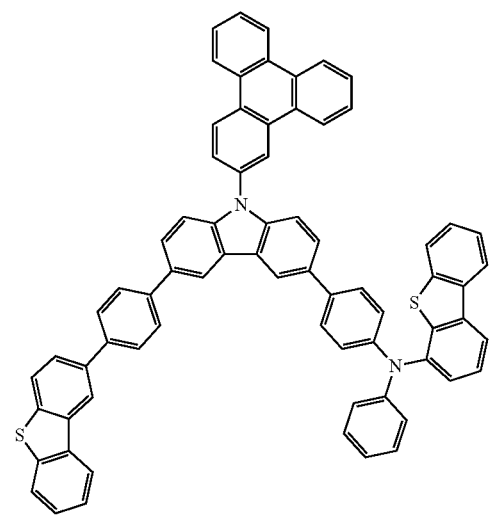
[A-90]
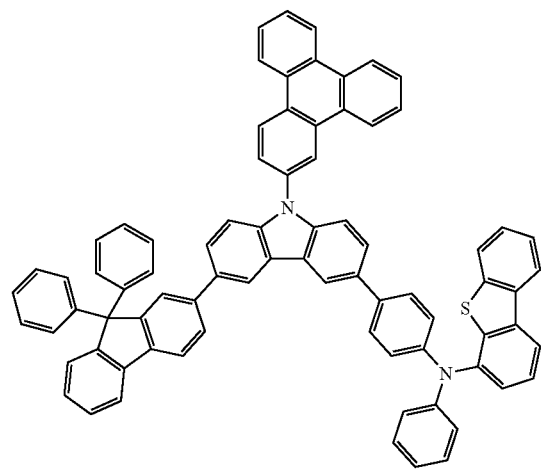
[A-91]
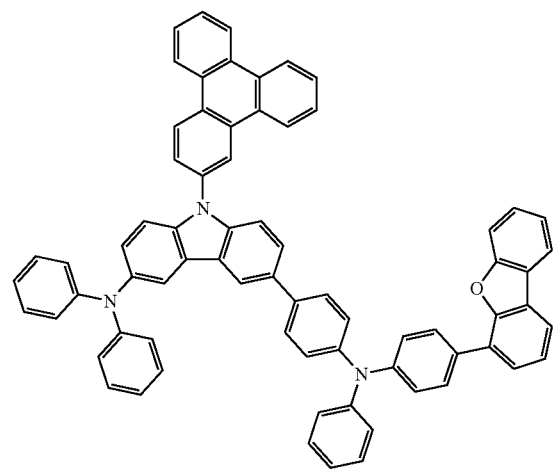

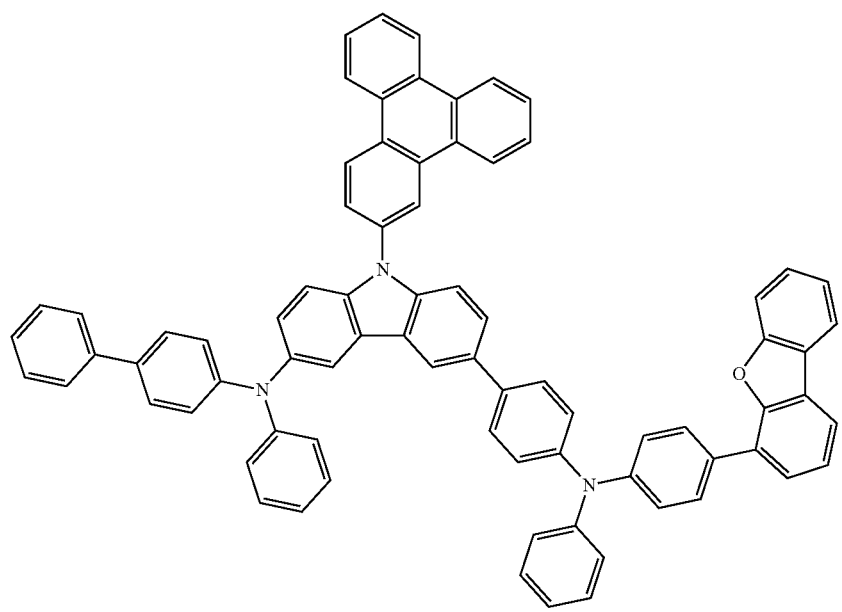
[A-92]
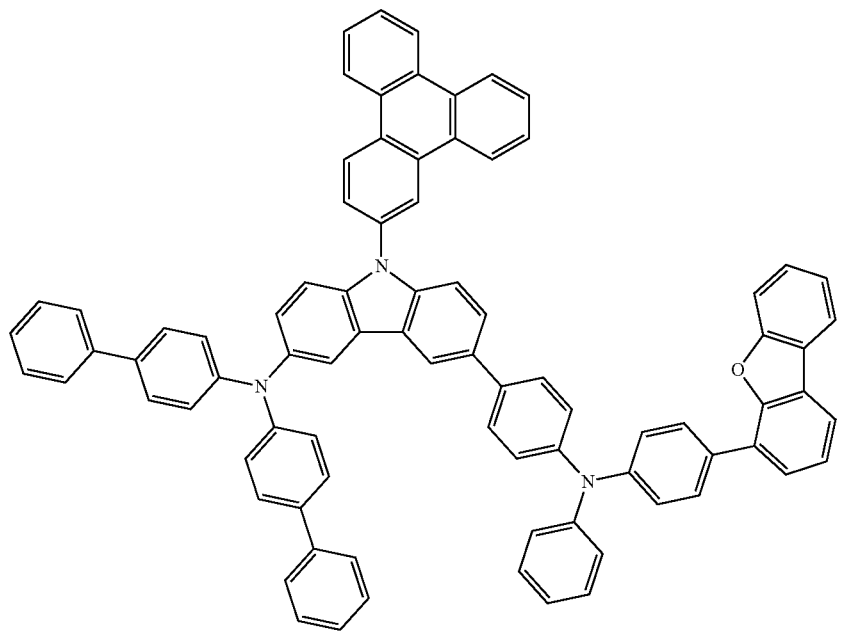
[A-93]

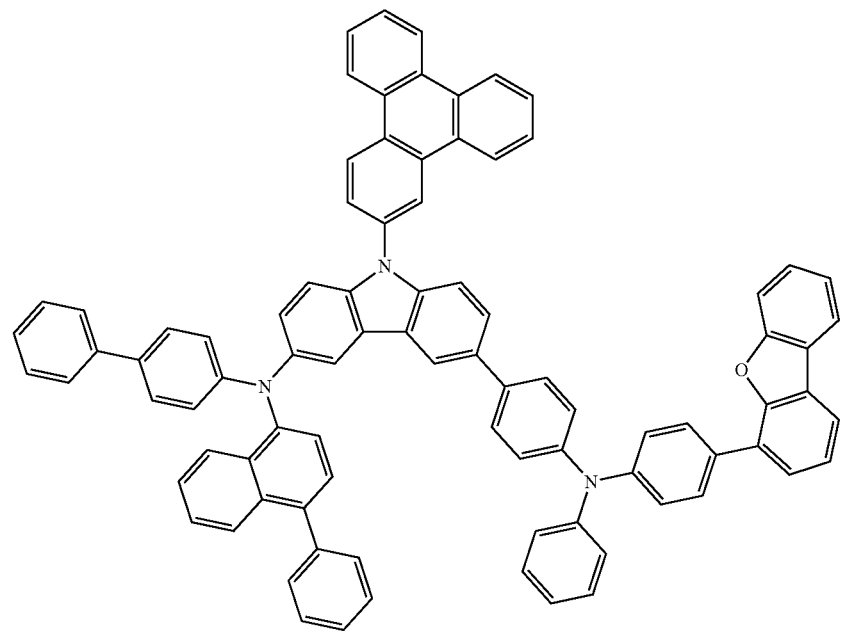
[A-94]
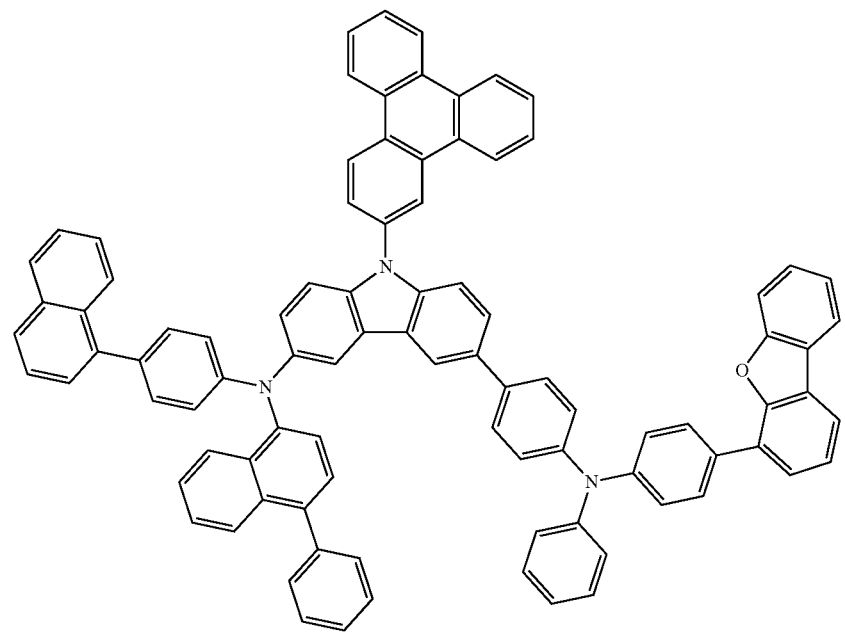
[A-95]

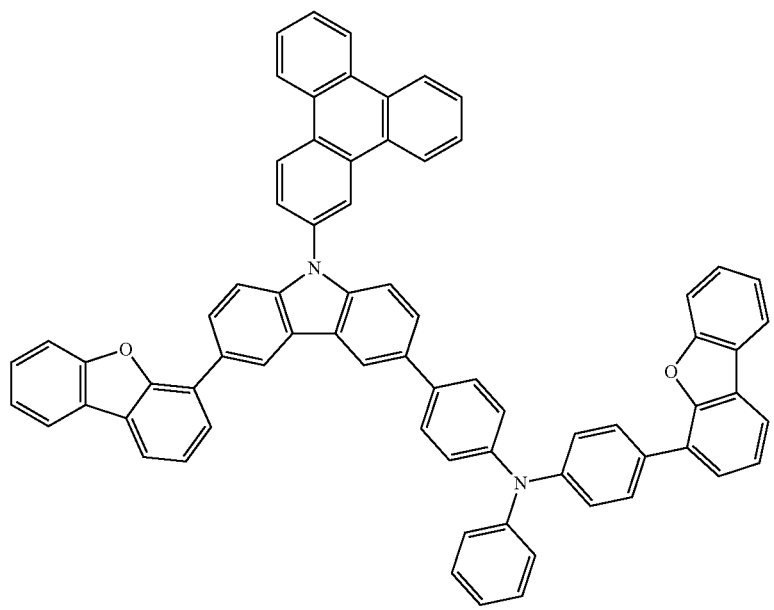
[A-96]
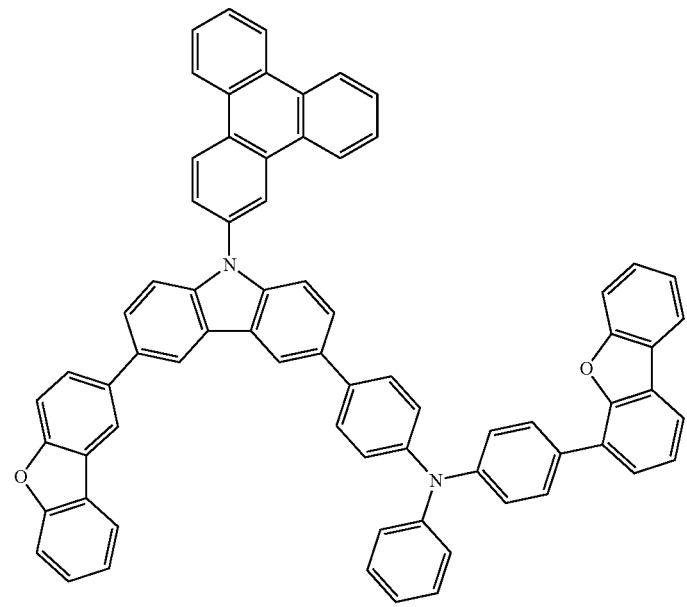
[A-97]

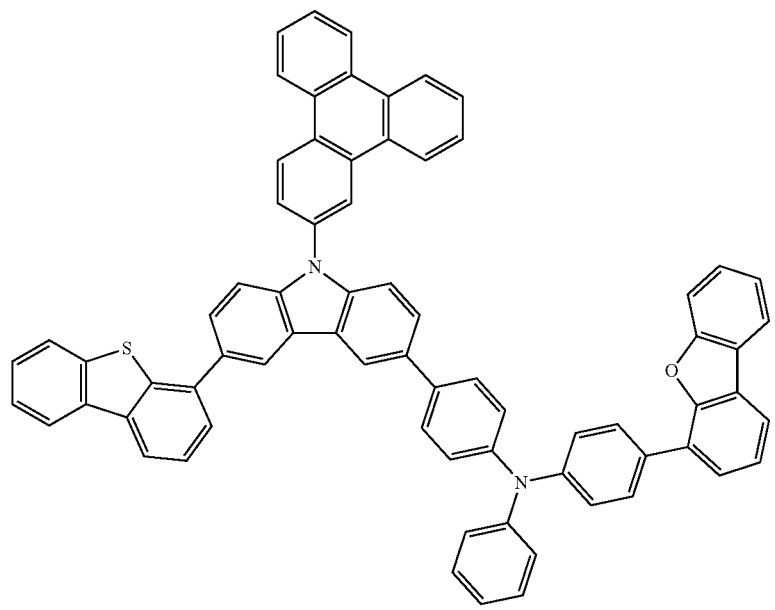
[A-98]
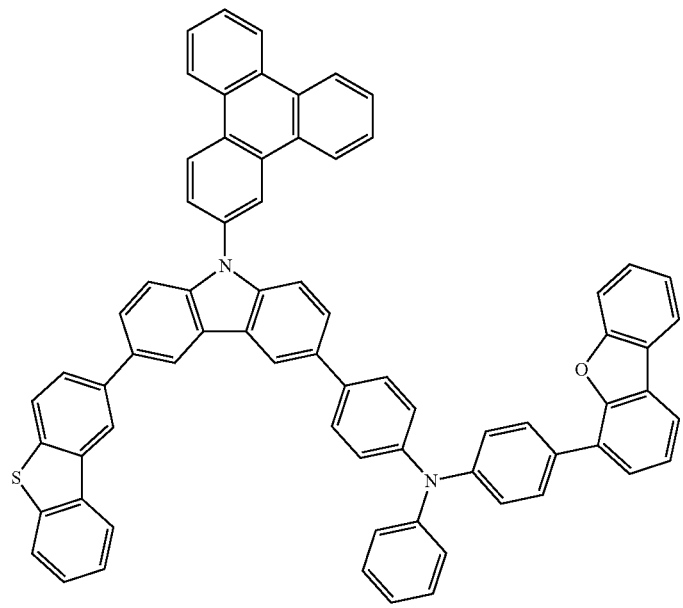
[A-99]

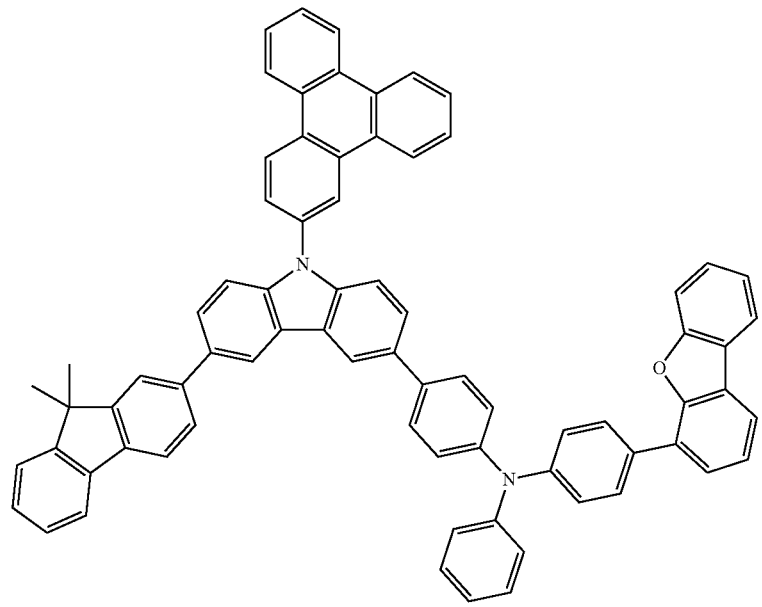
[A-100]
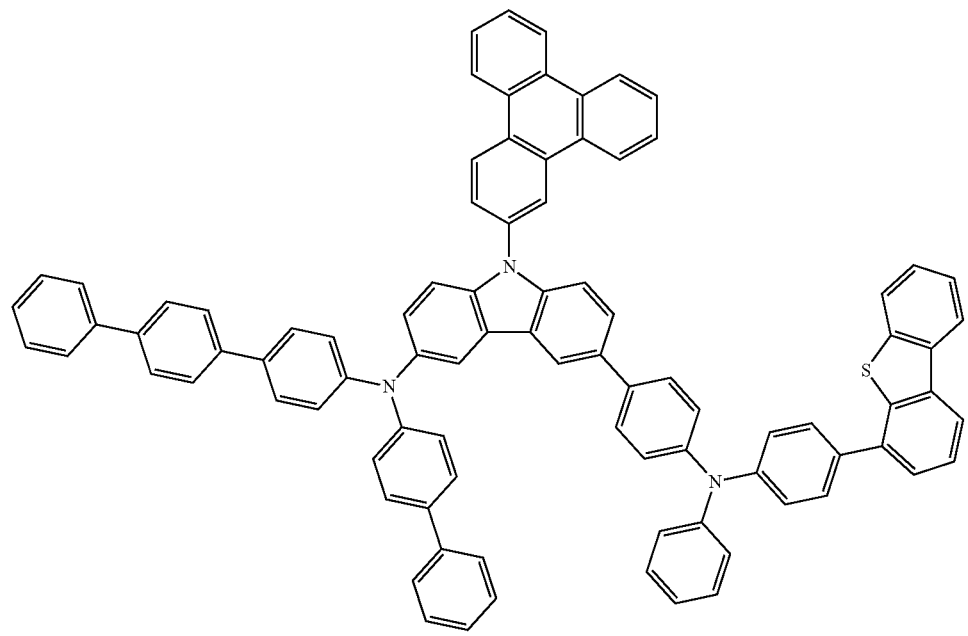
[A-101]

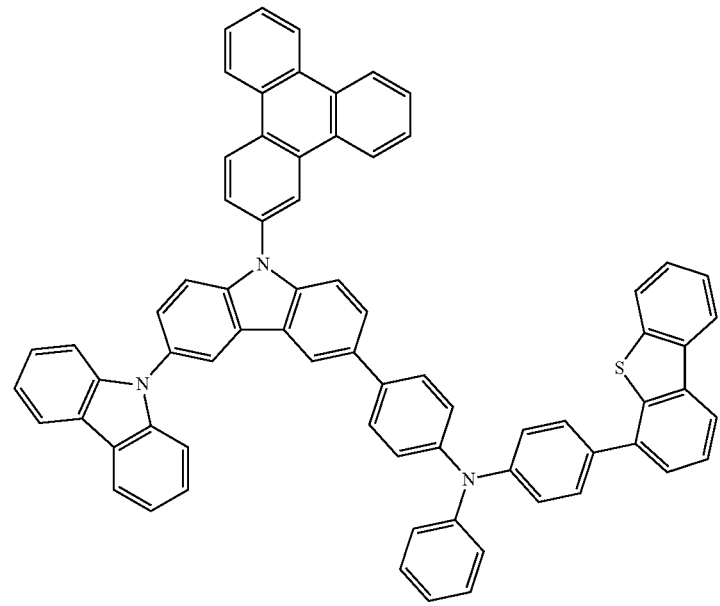
[A-102]
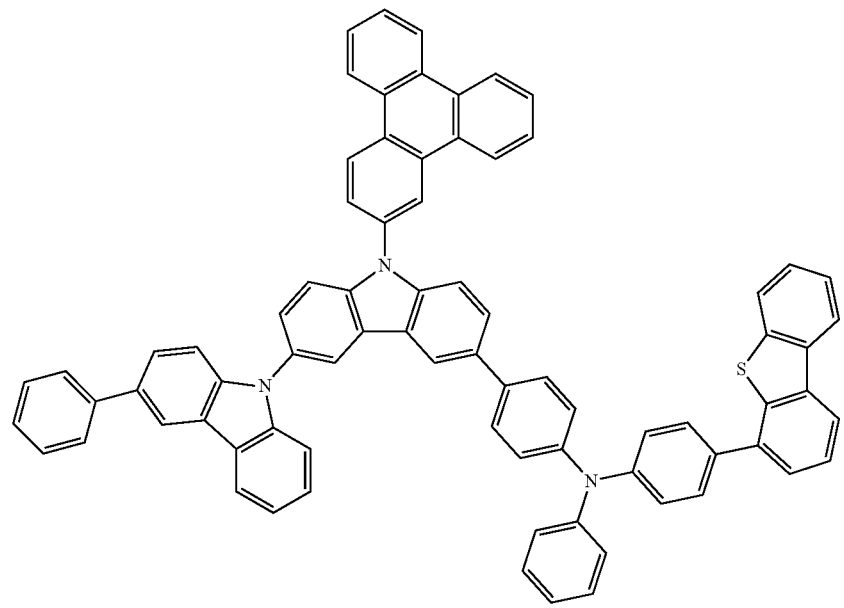
[A-103]

-continued
[A-104]
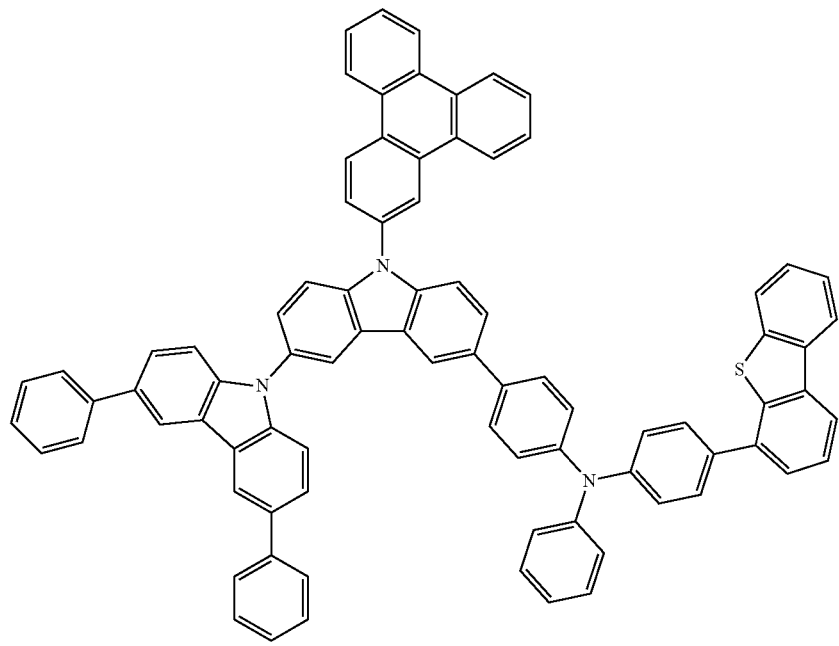
[A-105]
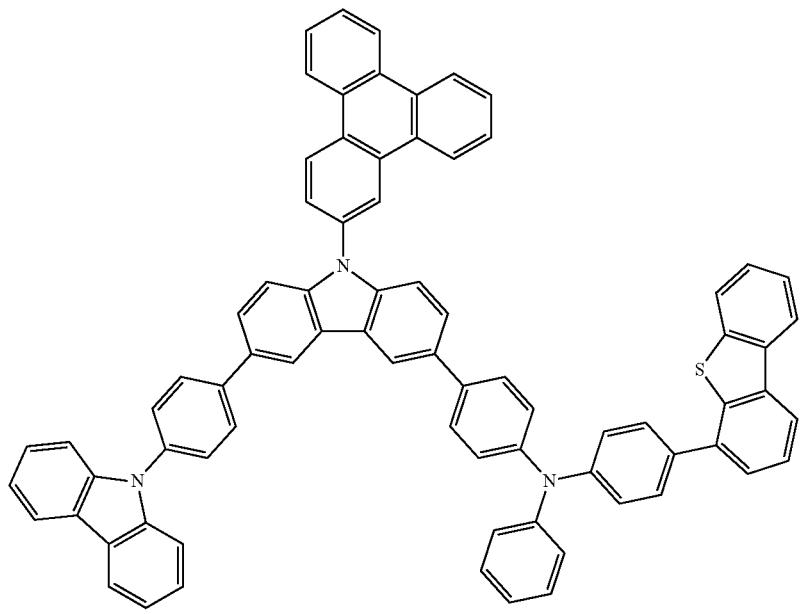

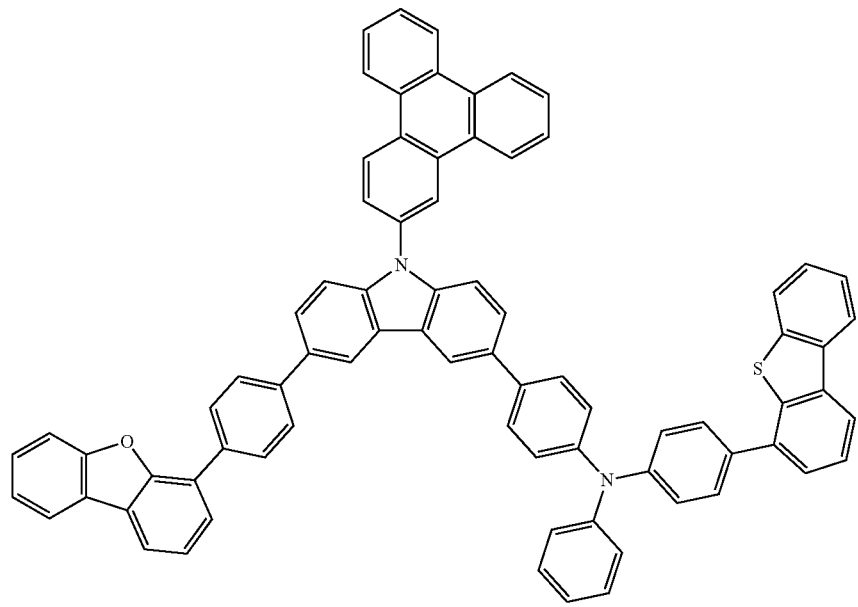
[A-106]
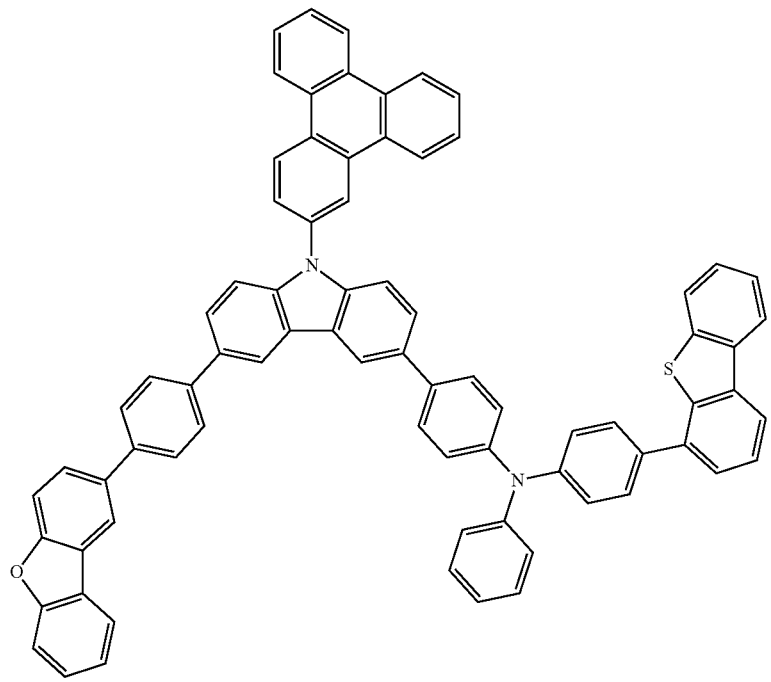
[A-107]

-continued
[A-108]
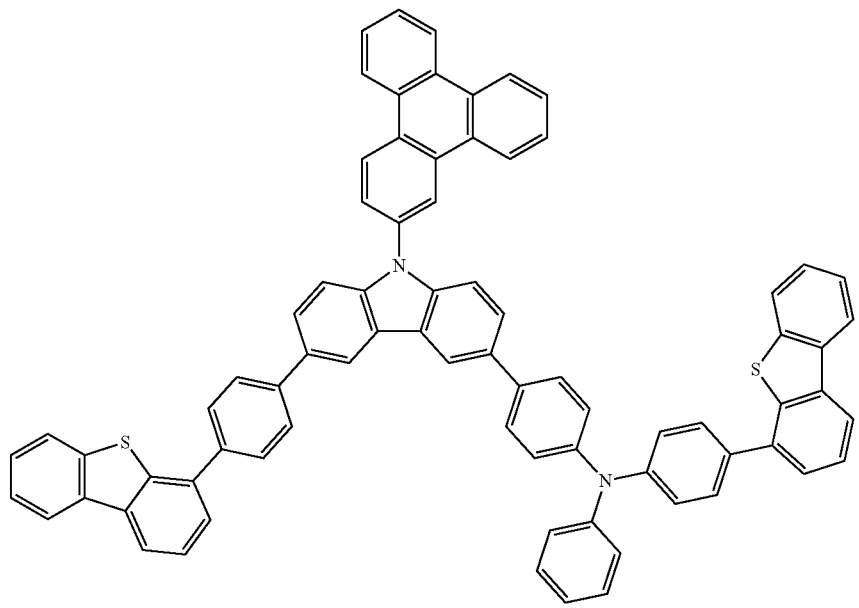
[A-109]
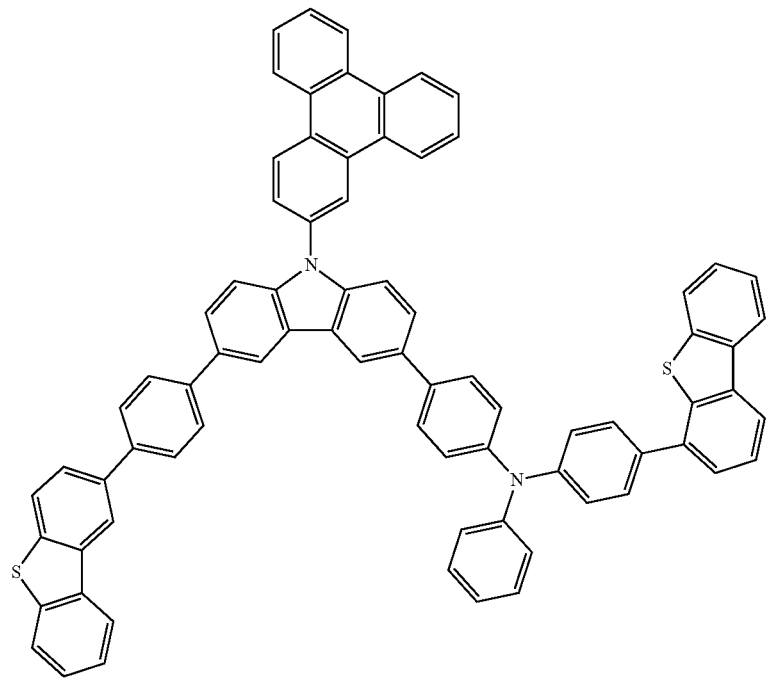

[A-110]
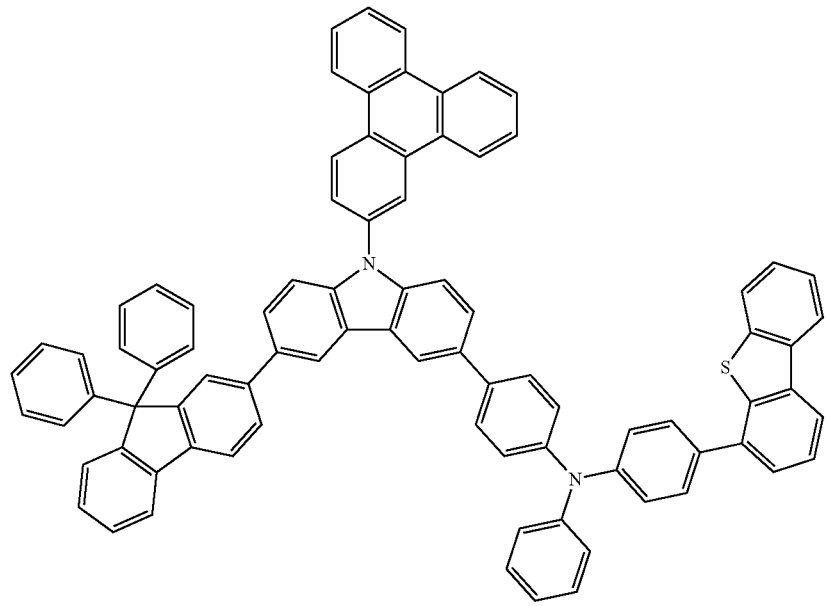
[A-111]
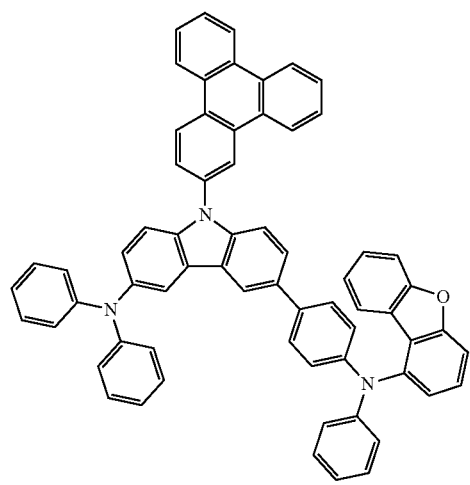
[A-112]
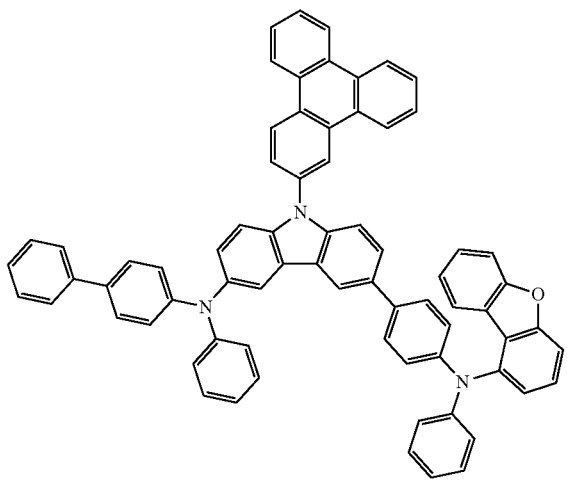
[A-113]
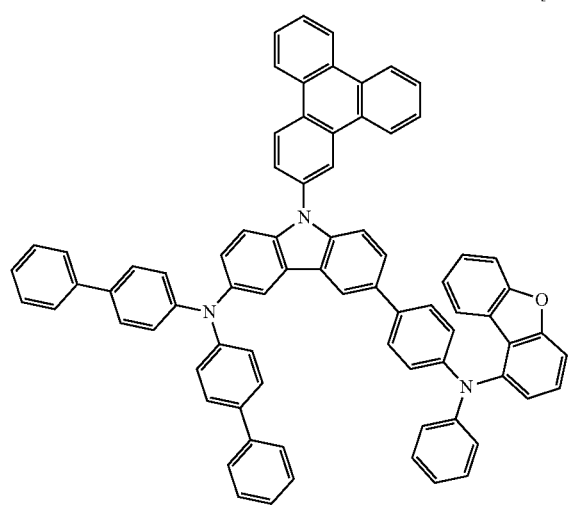
[A-114]
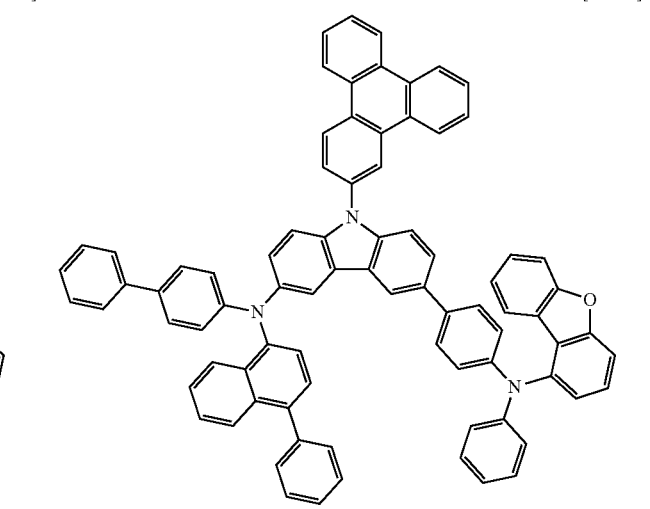

-continued
[A-115]
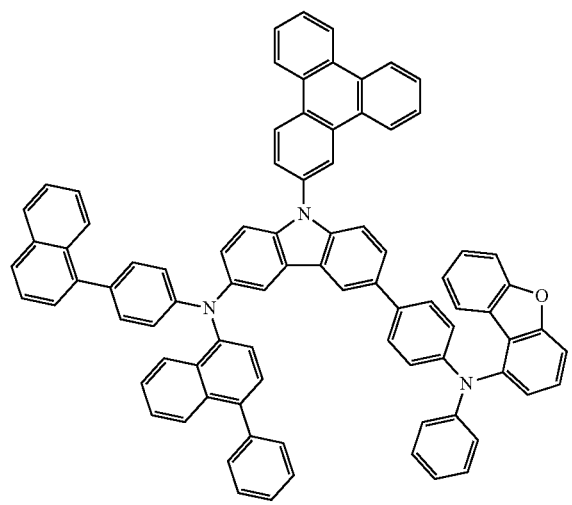
[A-116]
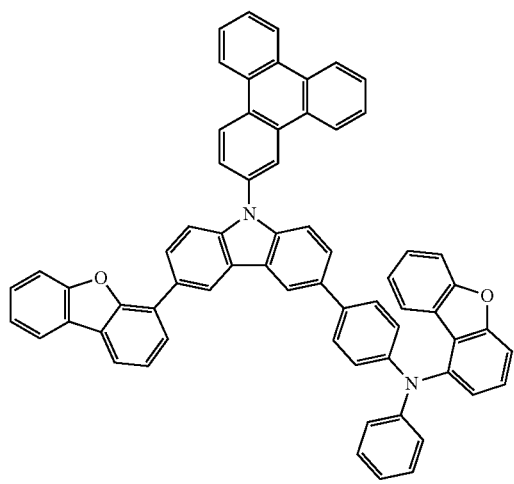
[A-117]
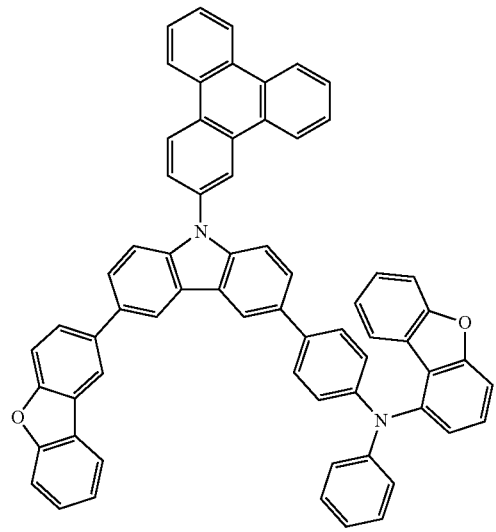
[A-118]
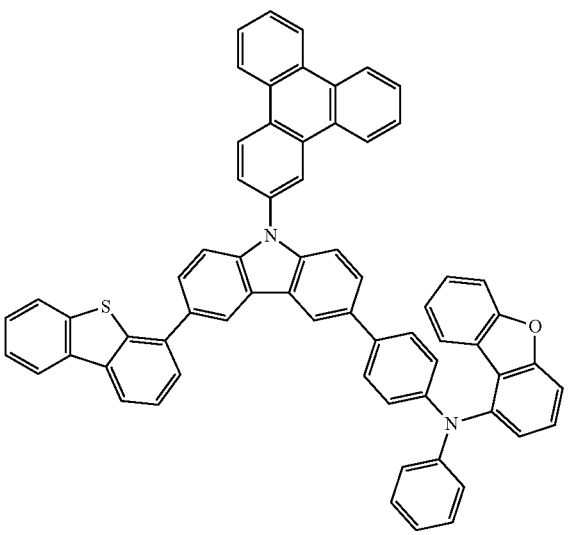
[A-119]
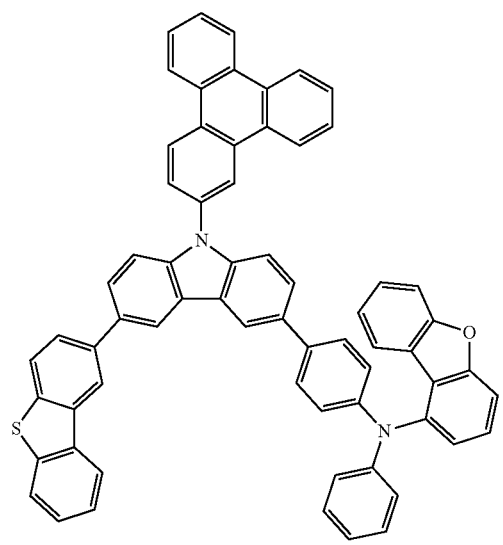
[A-120]
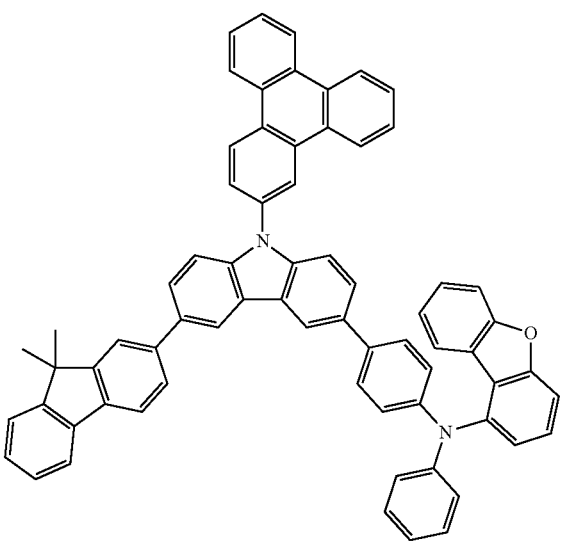

-continued
[A-121]
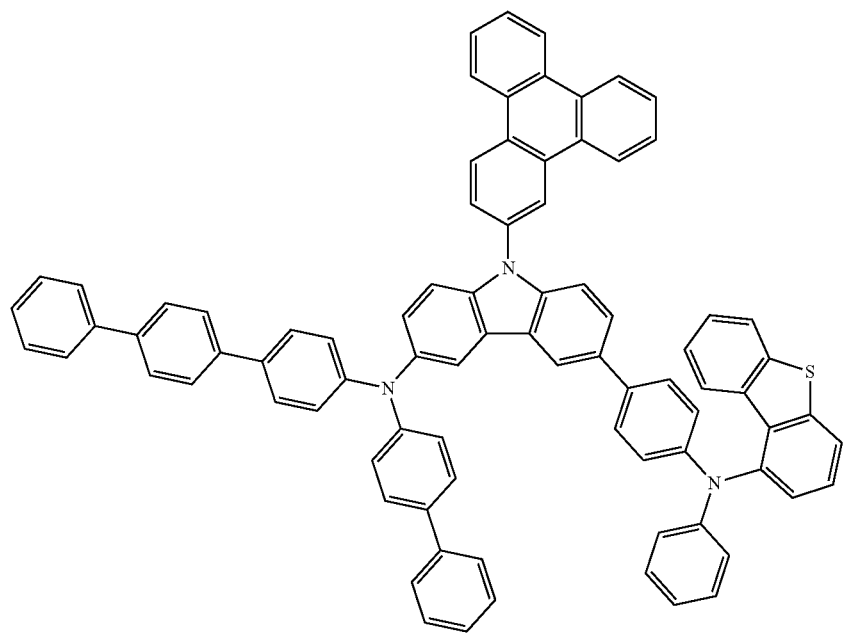
[A-122]
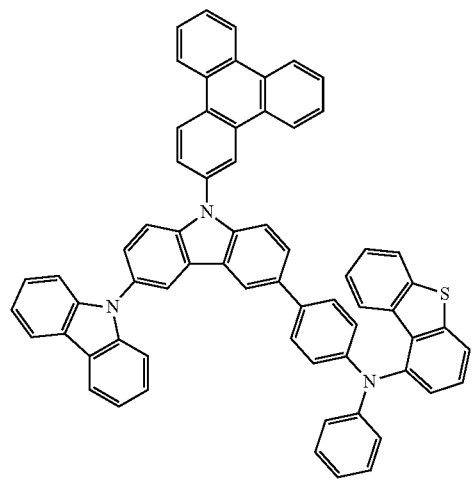
[A-123]
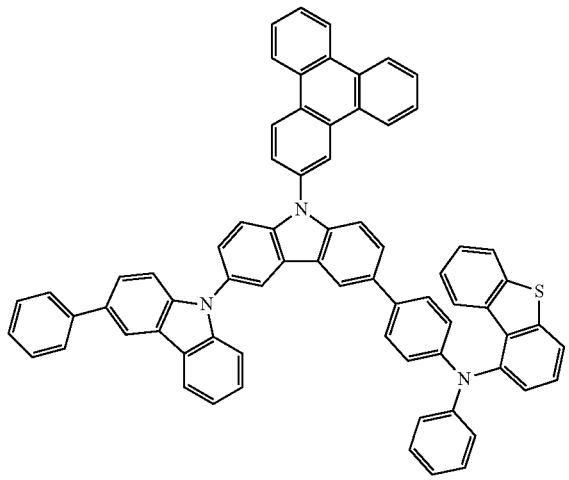
[A-124]
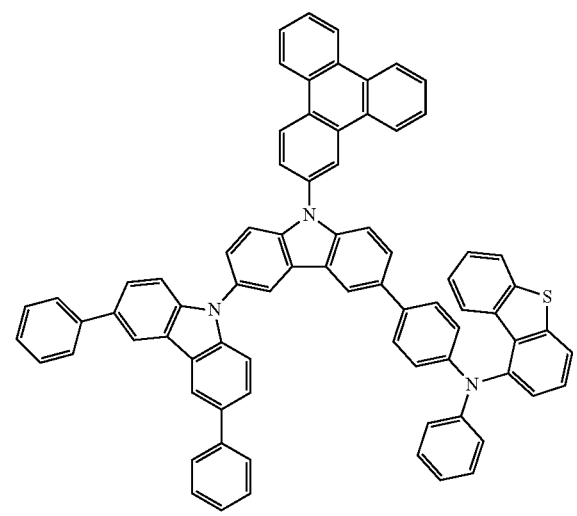
[A-125]
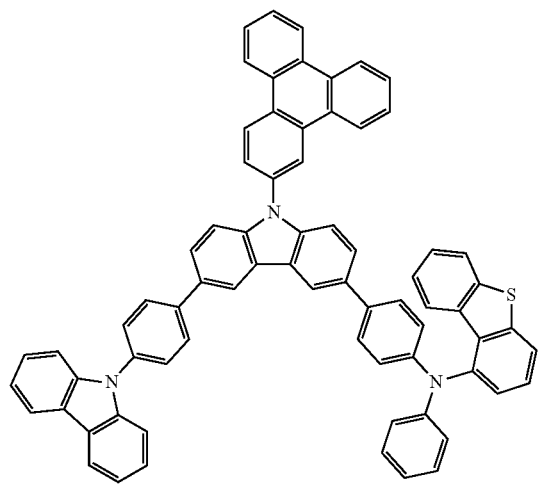

-continued
[A-126]
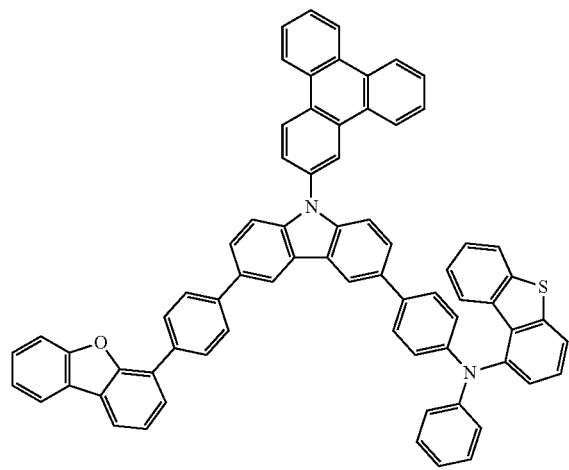
[A-127]
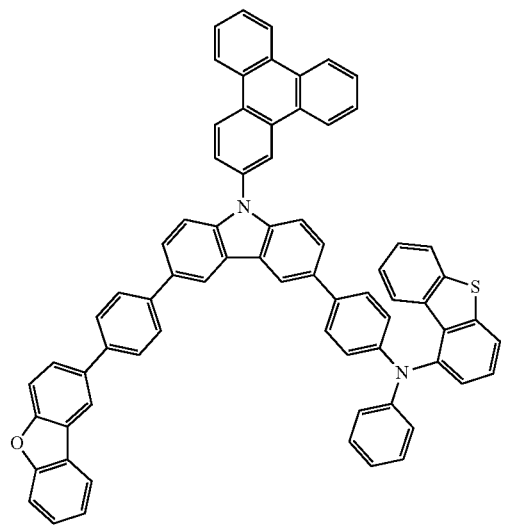
[A-128]
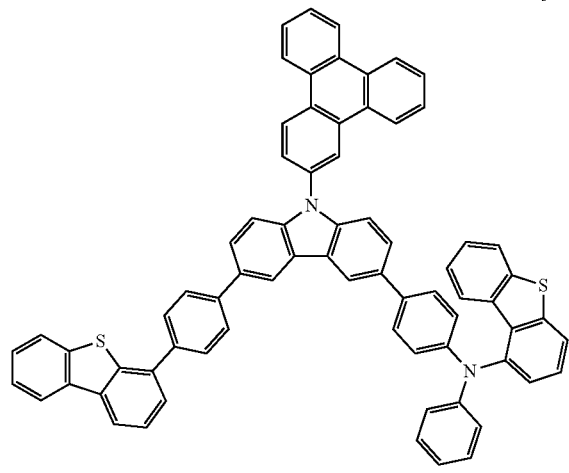
[A-129]
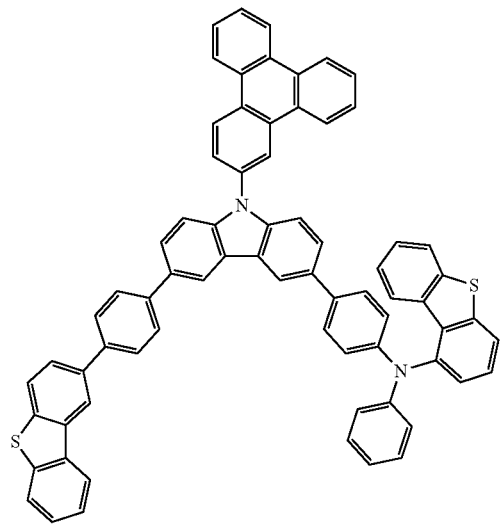

[A-130]
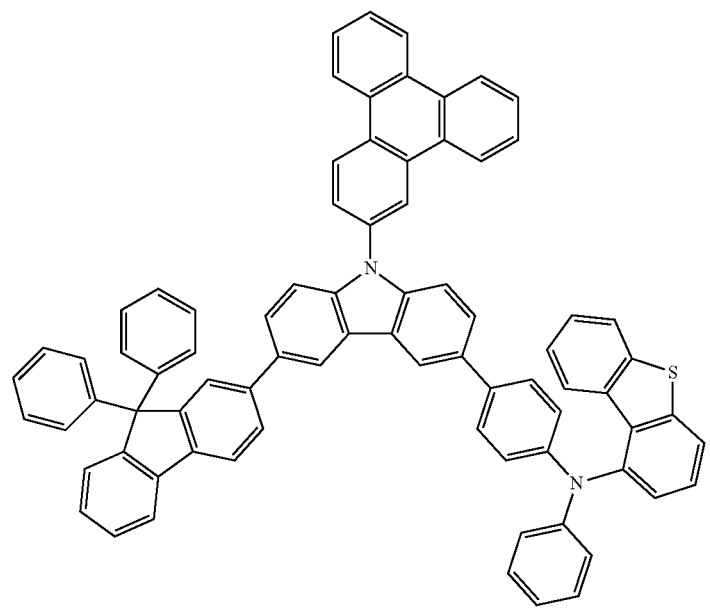
[A-131]
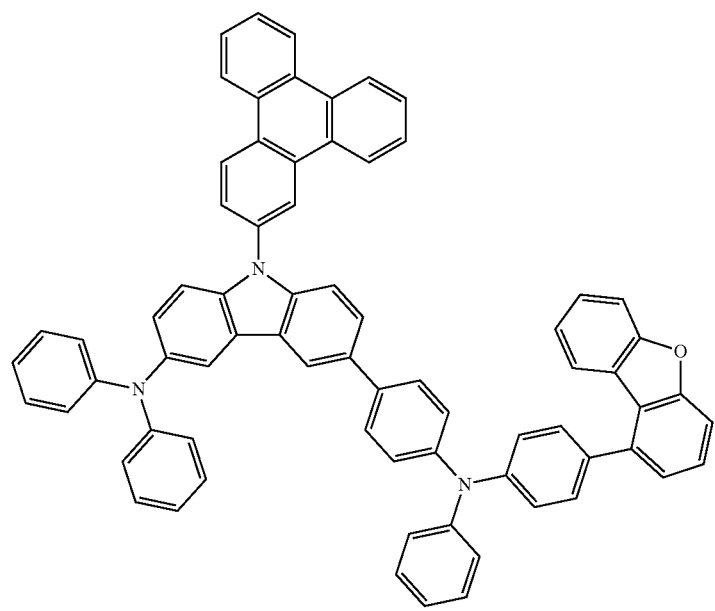

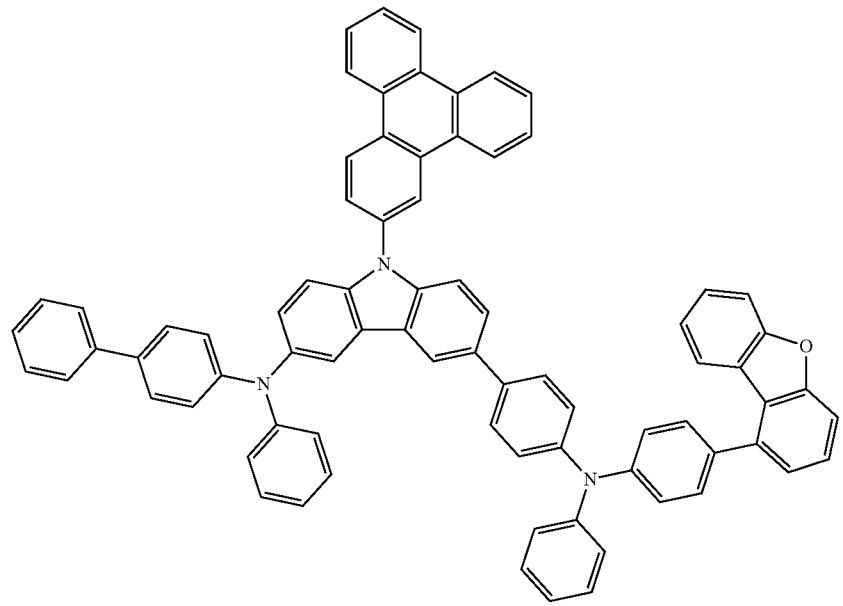
[A-132]
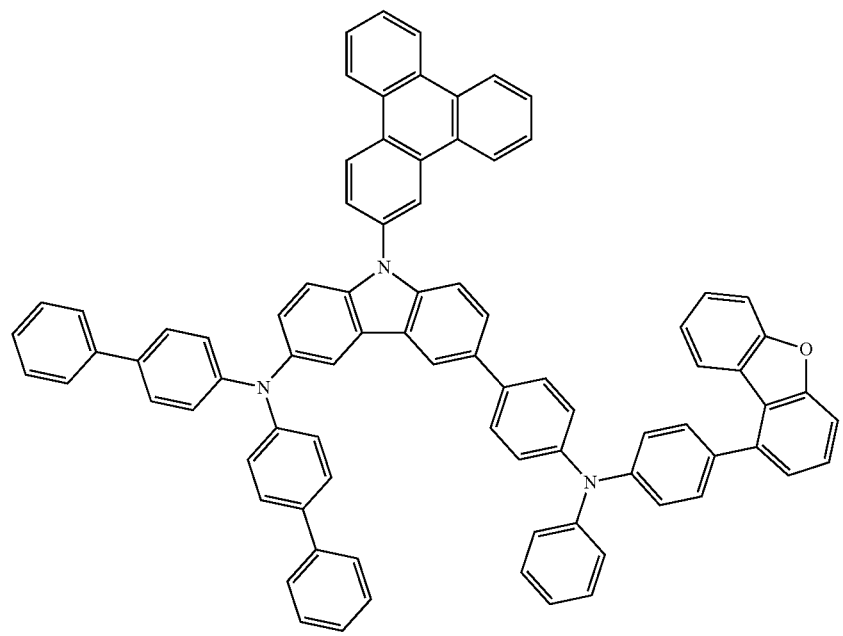
[A-133]

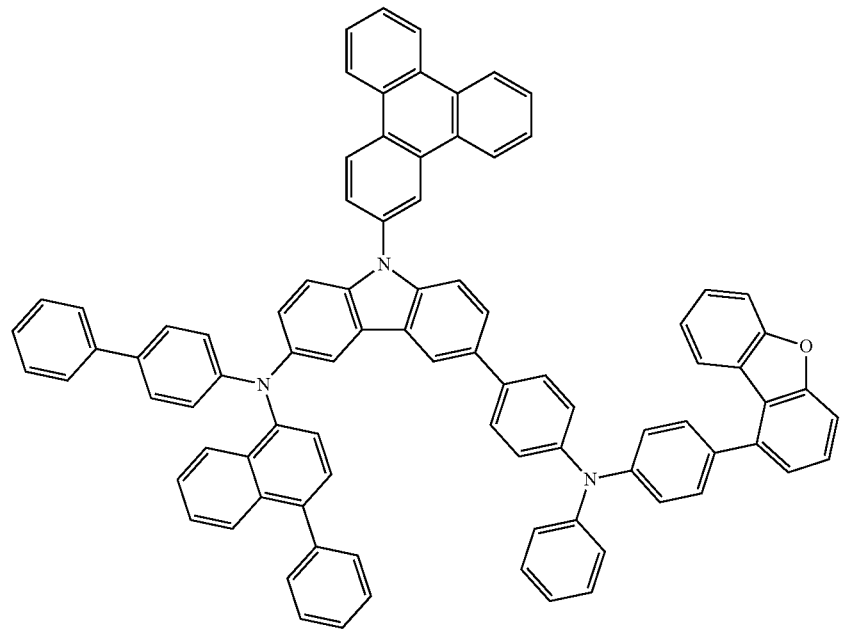
[A-134]
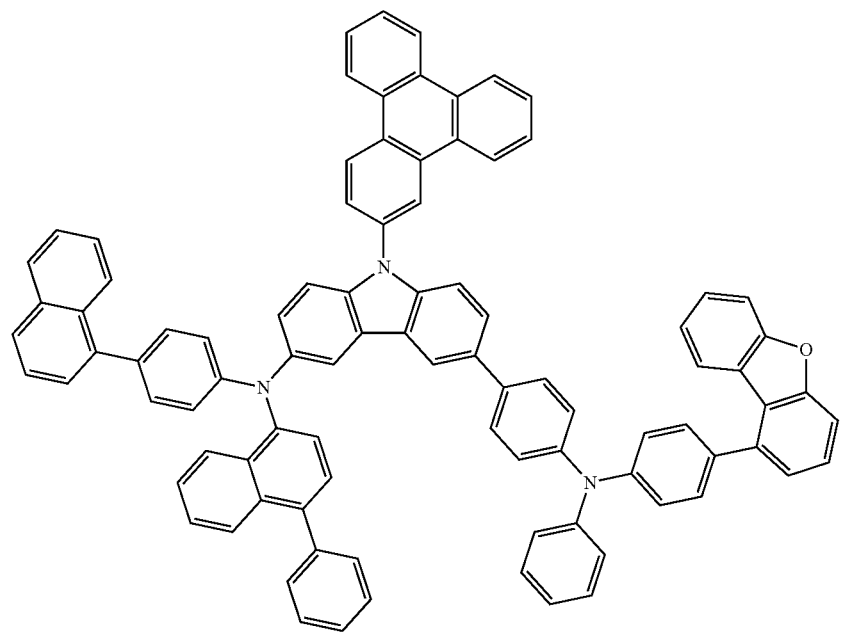
[A-135]

-continued
[A-136]
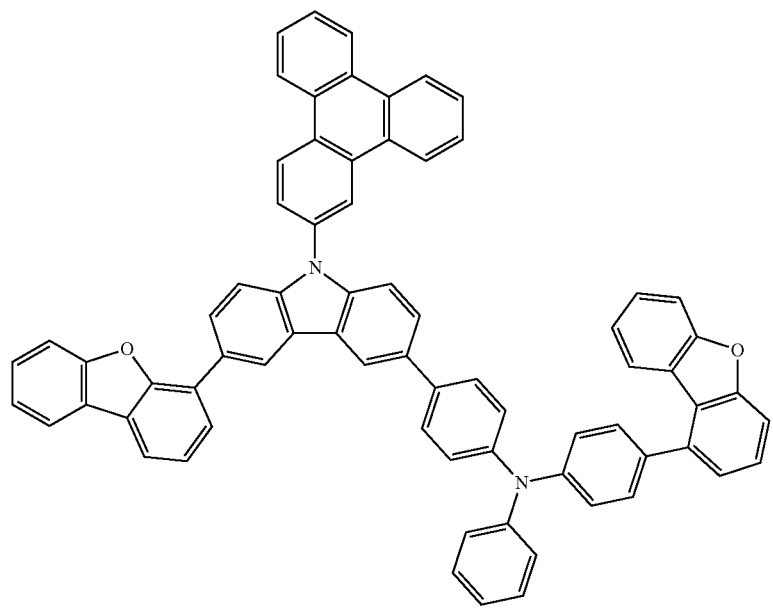
[A-137]
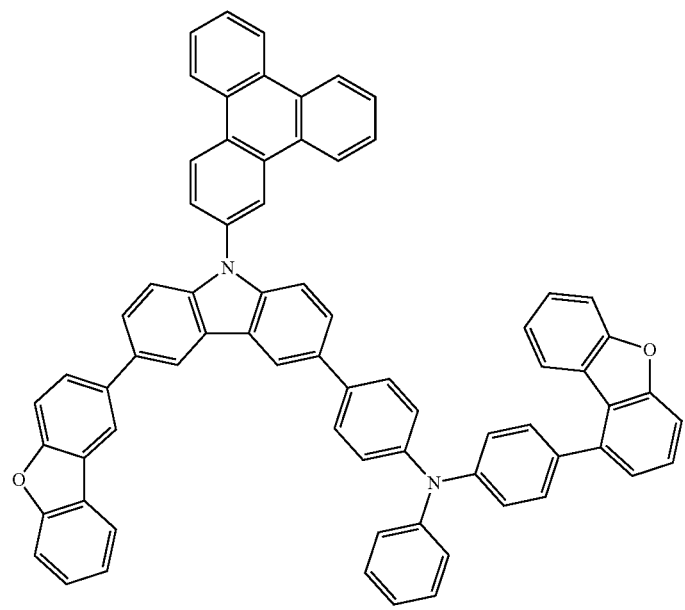

-continued
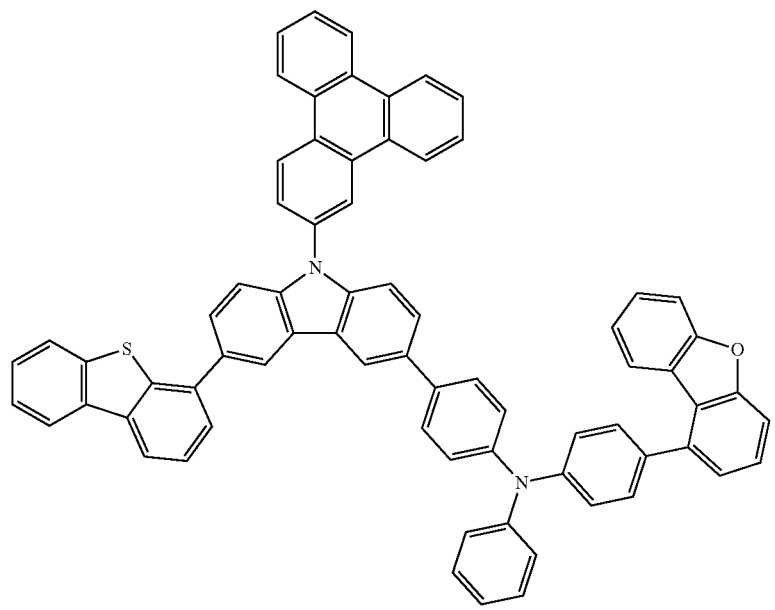
[A-138]
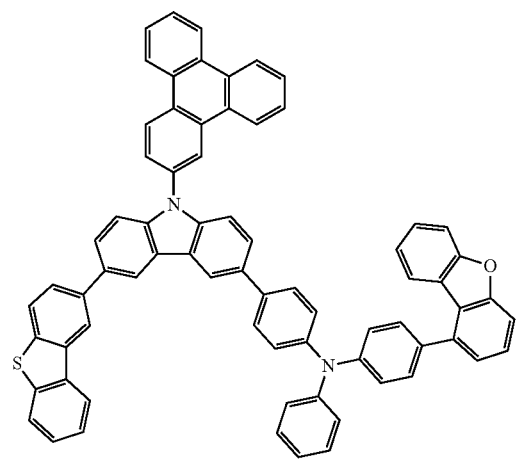
[A-139]
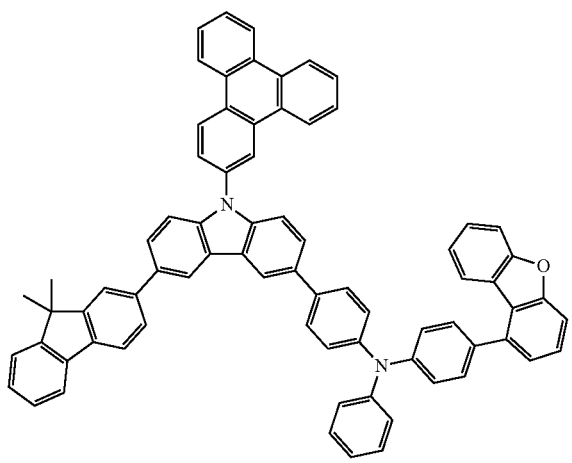
[A-140]

-continued
[A-141]
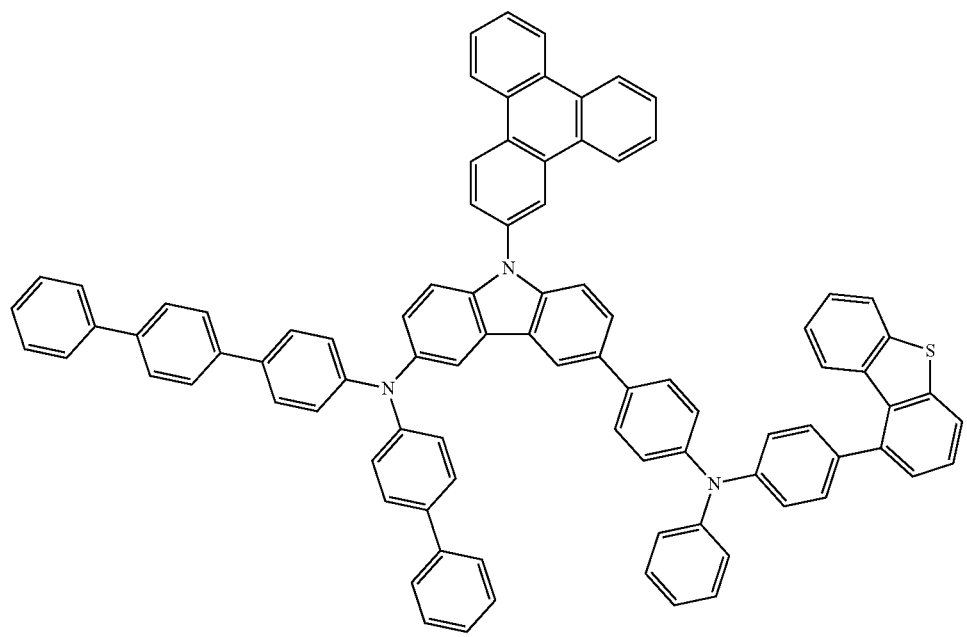
[A-142]
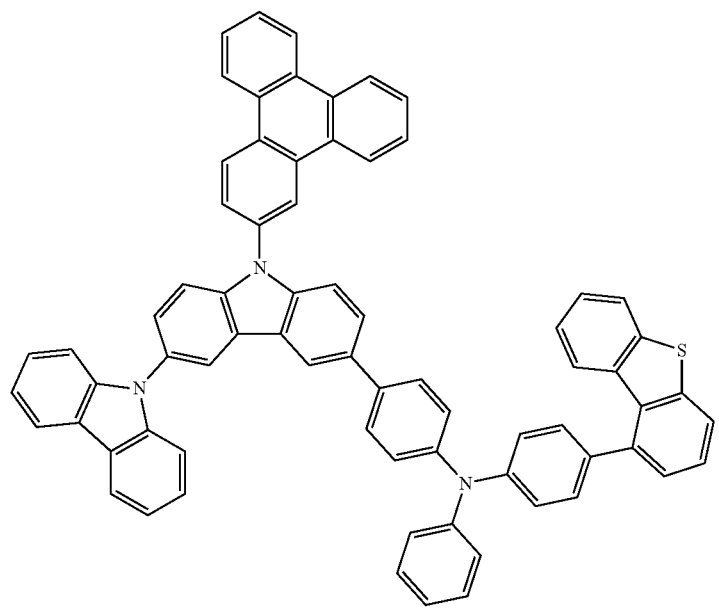

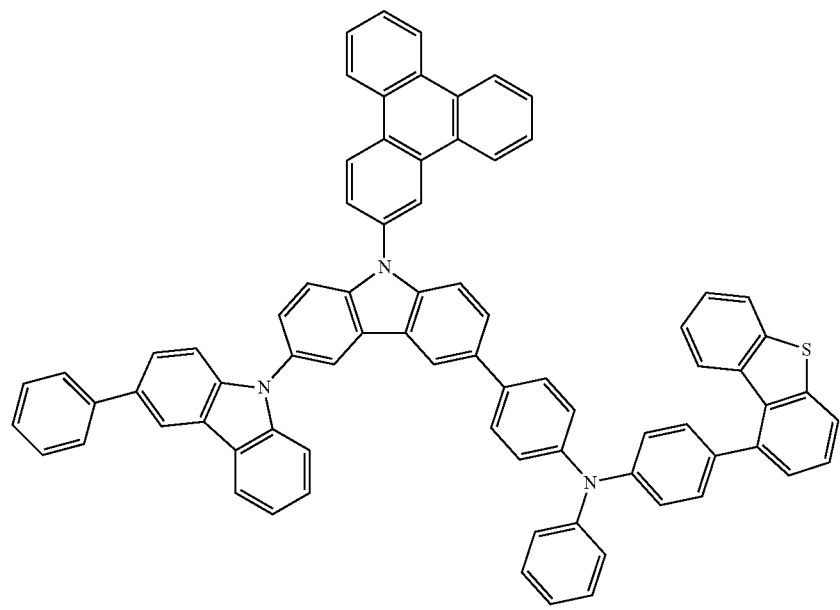
[A-143]
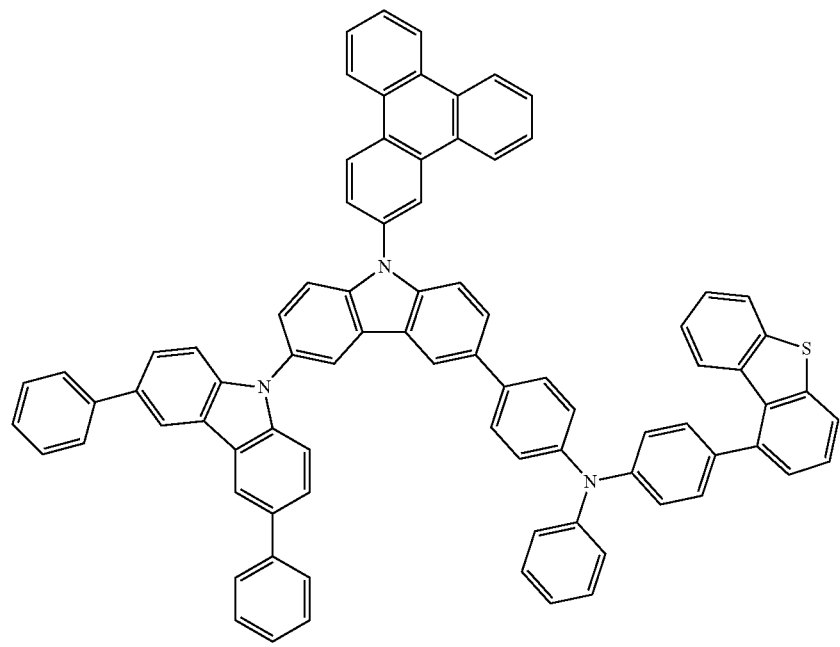
[A-144]

-continued
[A-145]
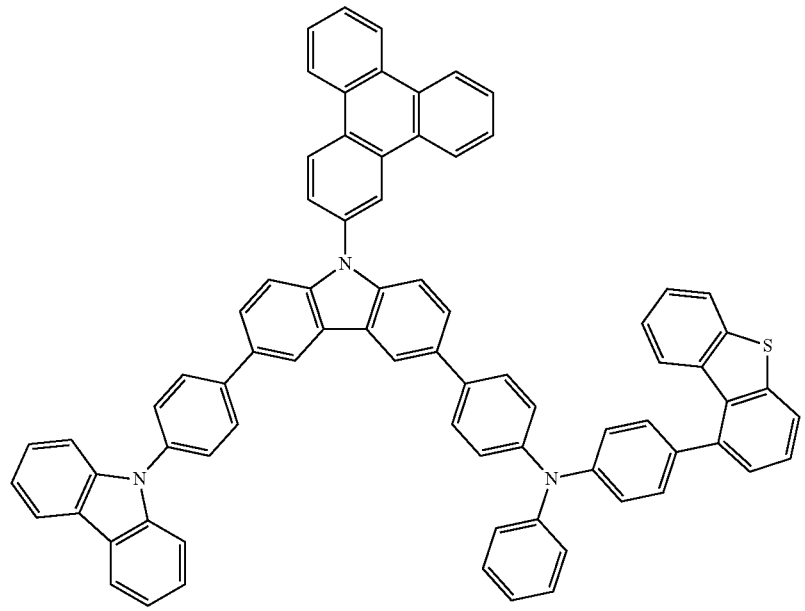
[A-146]
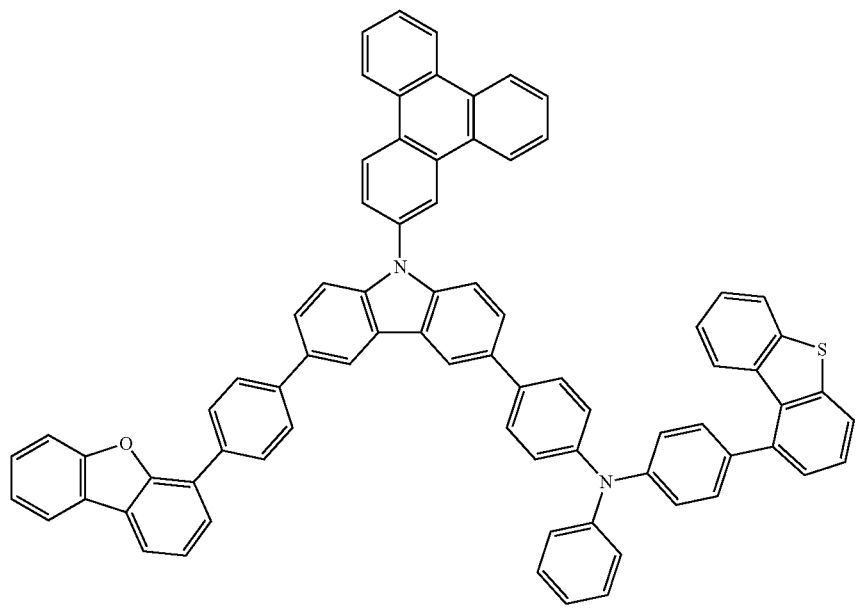

-continued
[A-147]
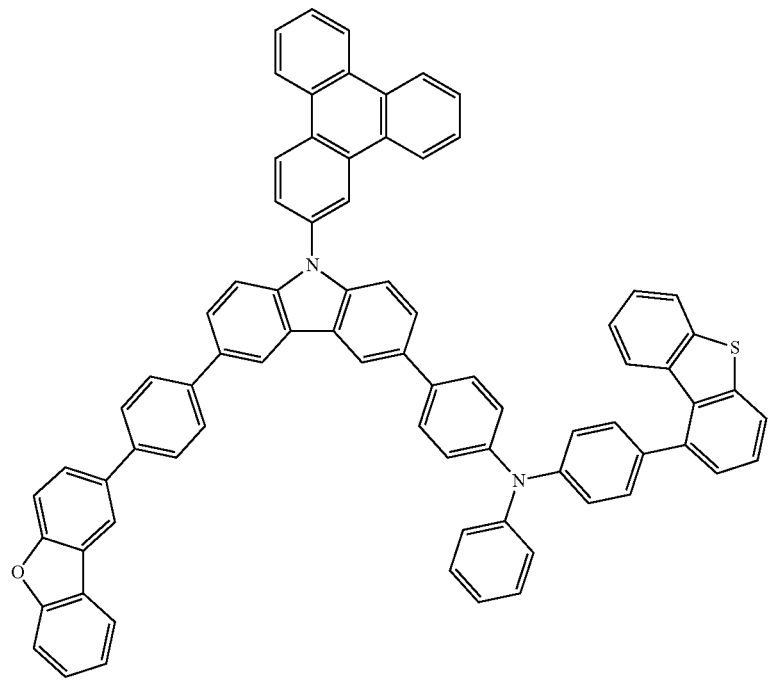
[A-148]
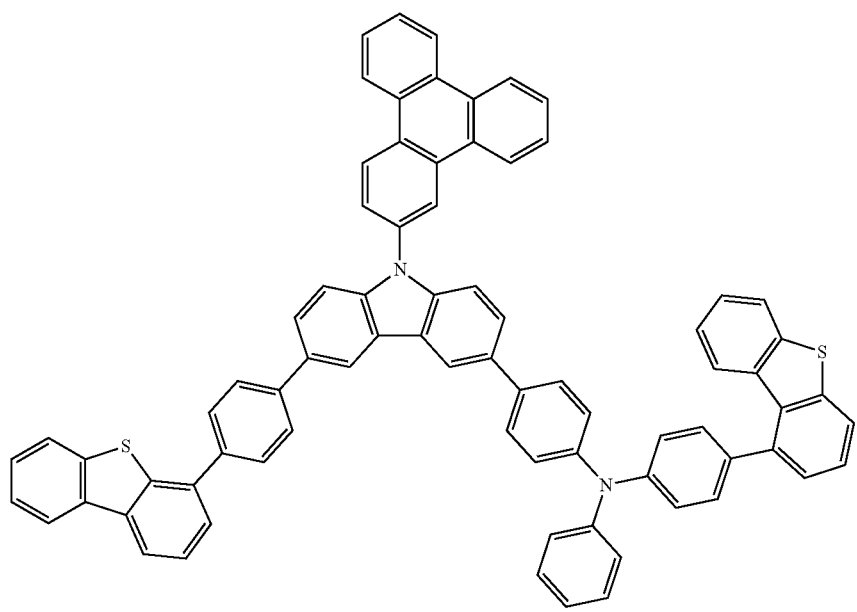

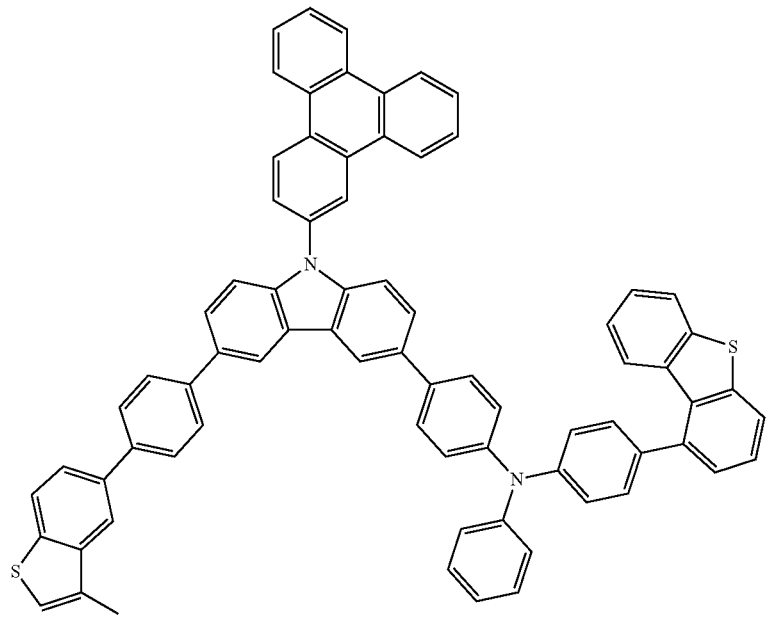
[A-149]
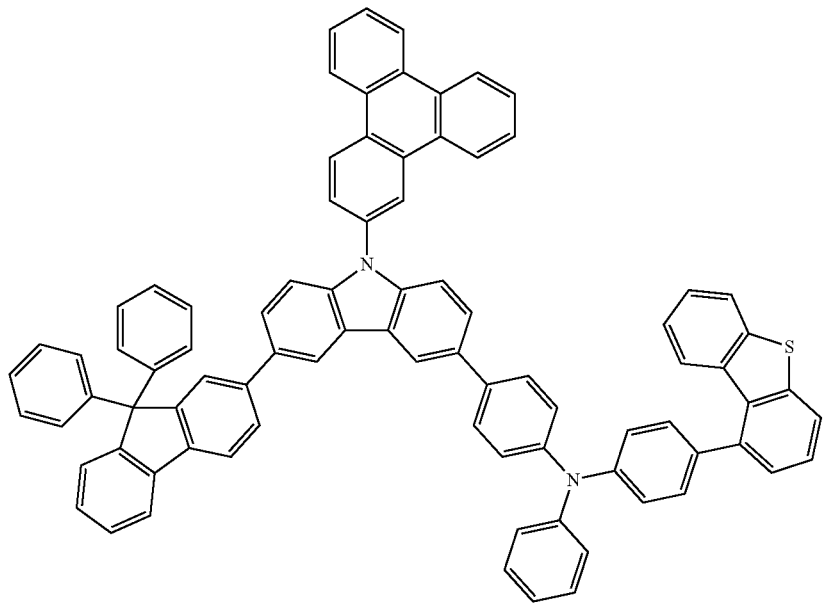
[A-150]

-continued
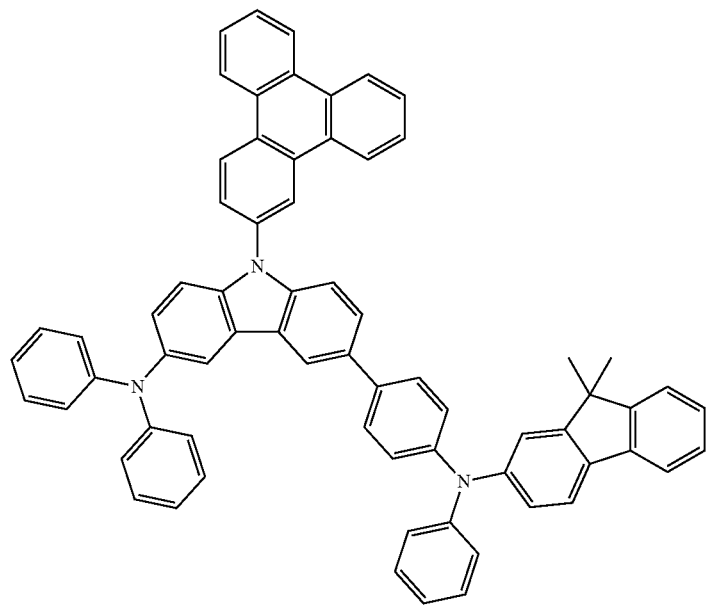
[A-151]
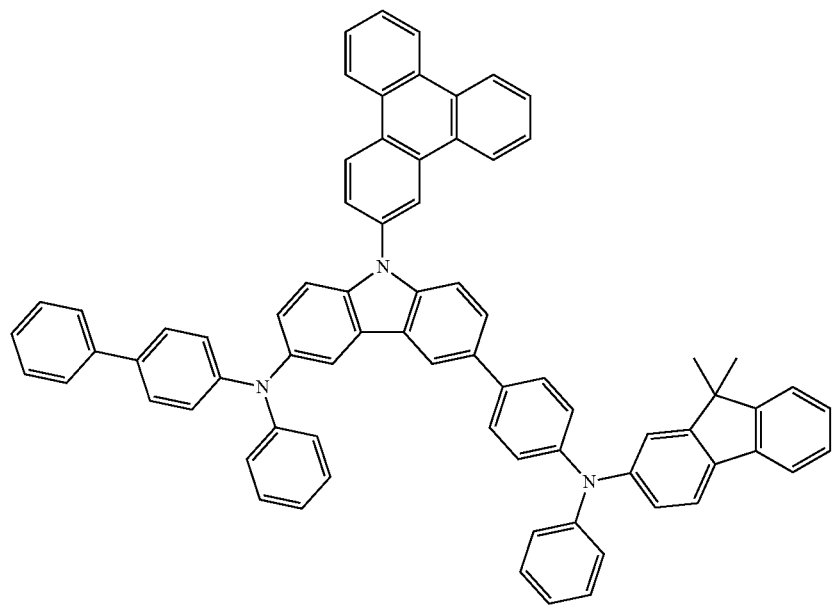
[A-152]

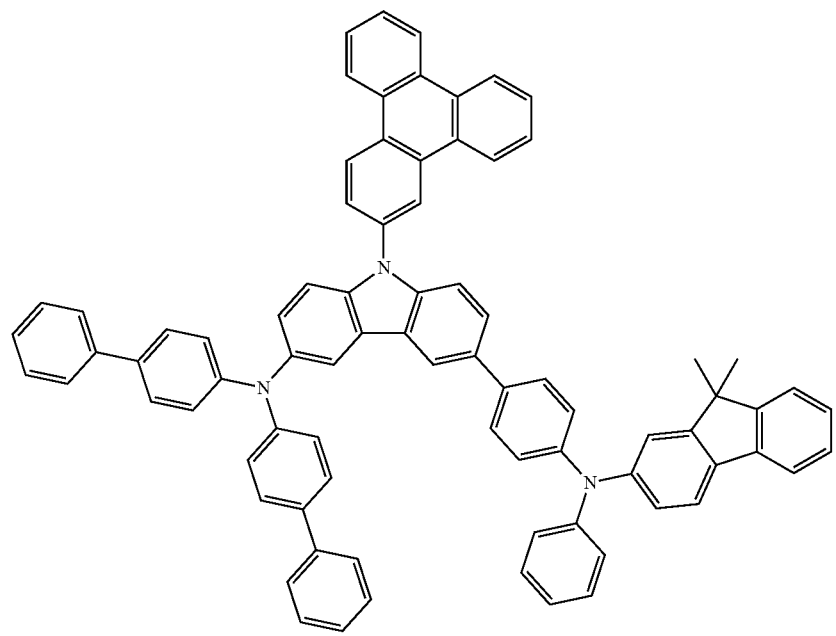
[A-153]
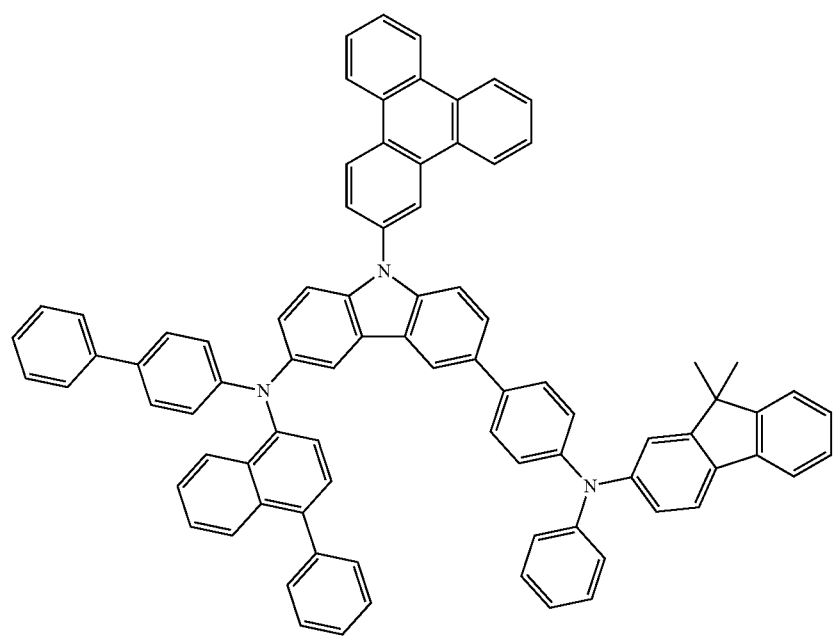
[A-154]

-continued
[A-155]
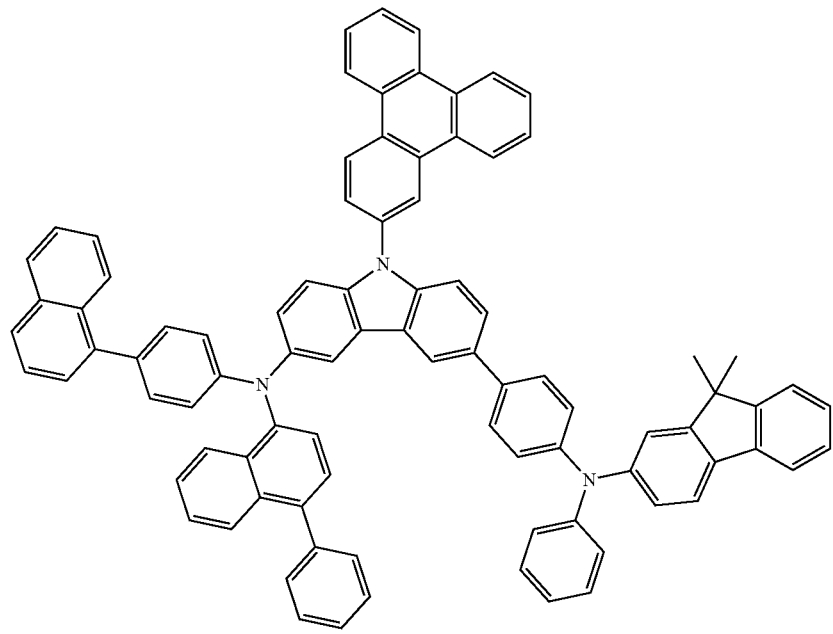
[A-156] [A-157]
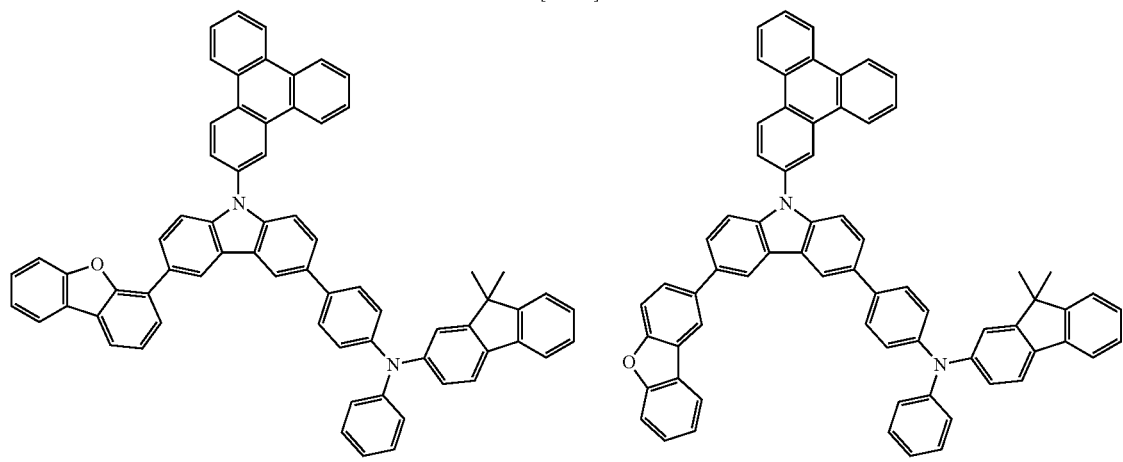
[A-158] [A-159]
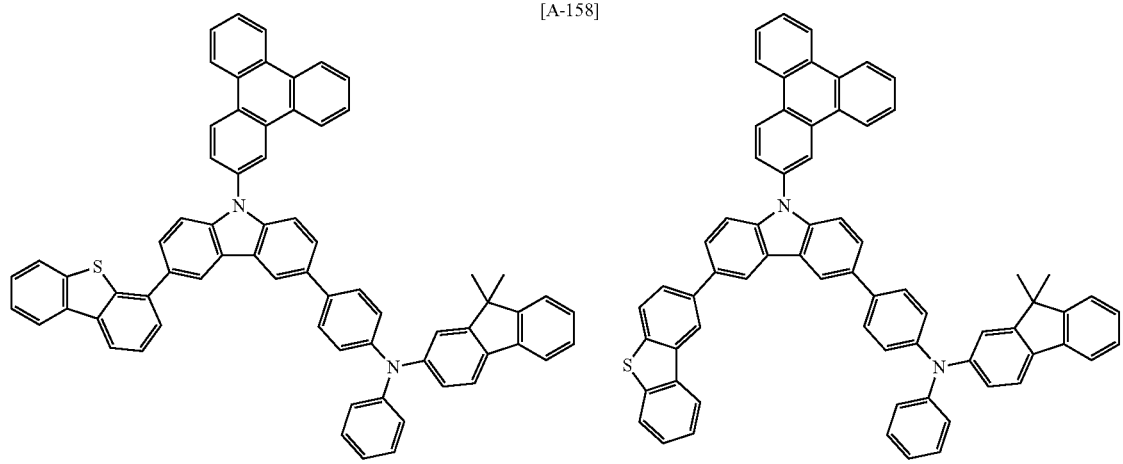

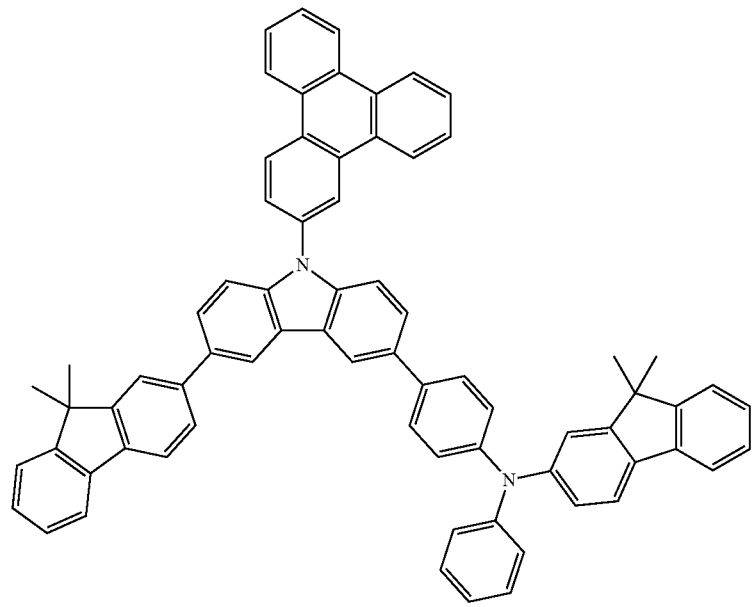
[A-160]
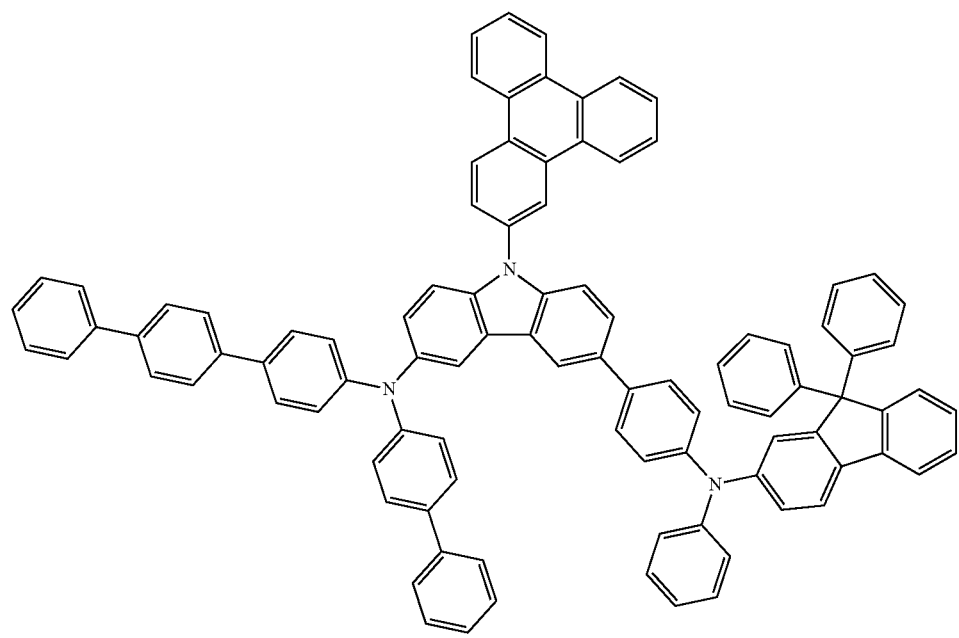
[A-161]

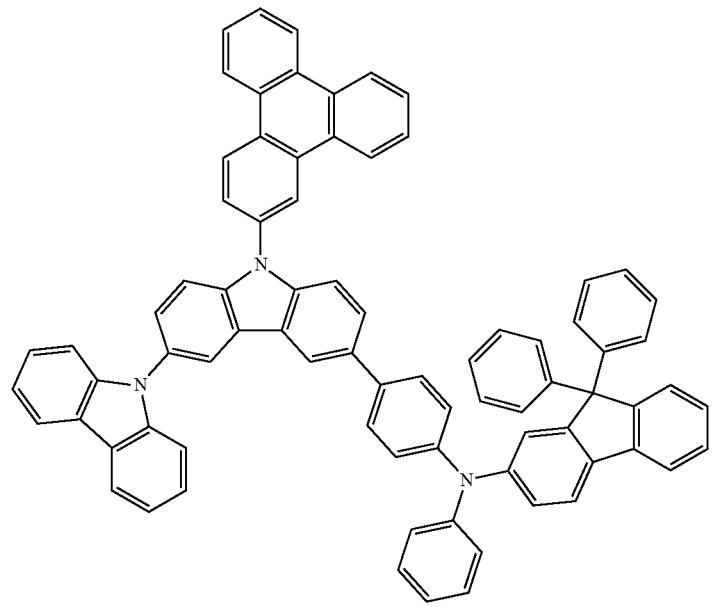
[A-162]
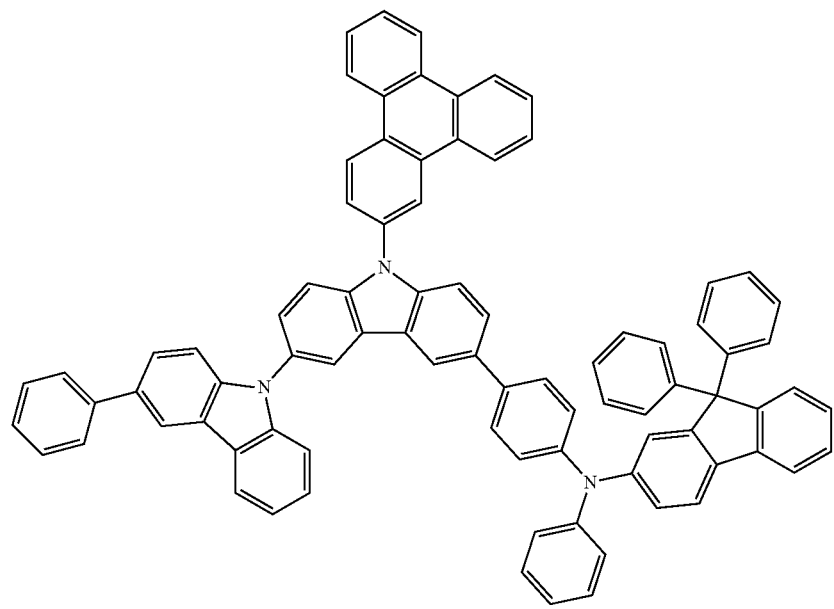
[A-163]

[A-164]
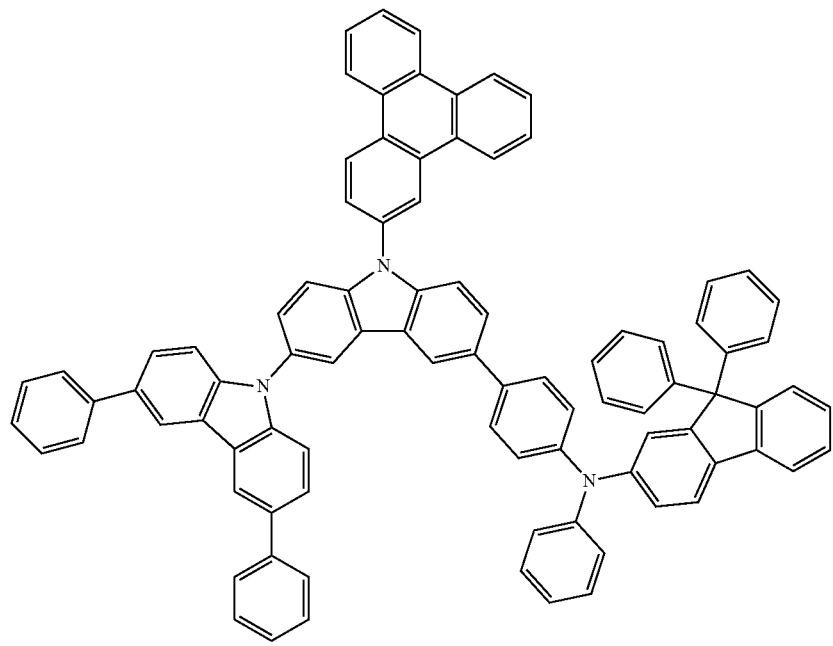
[A-165]
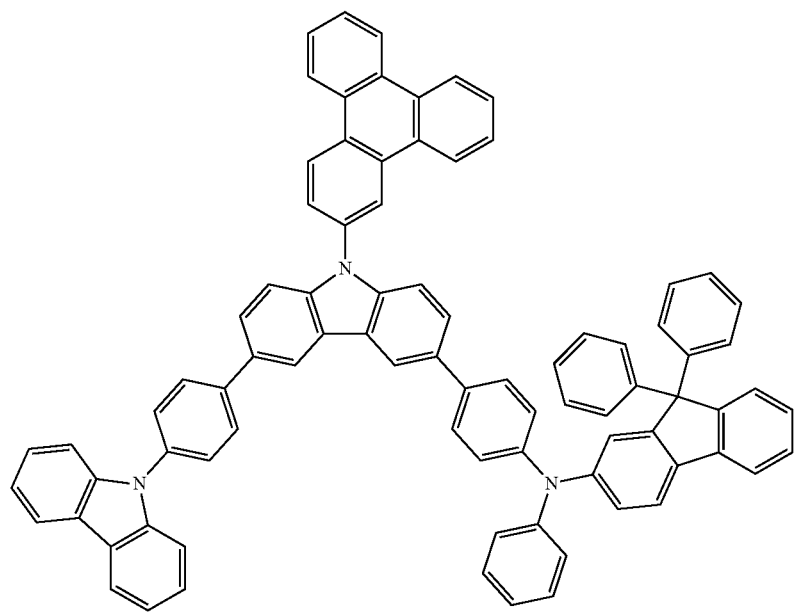

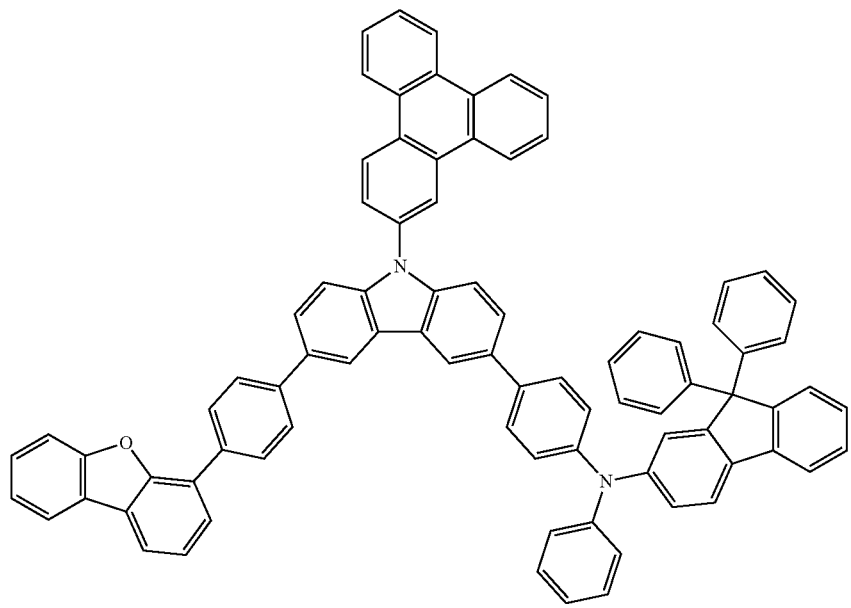
[A-166]
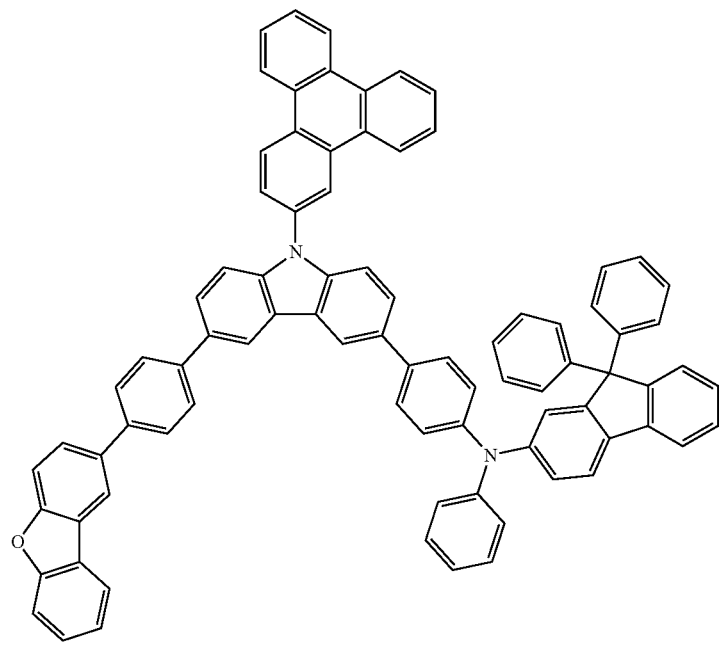
[A-167]

-continued
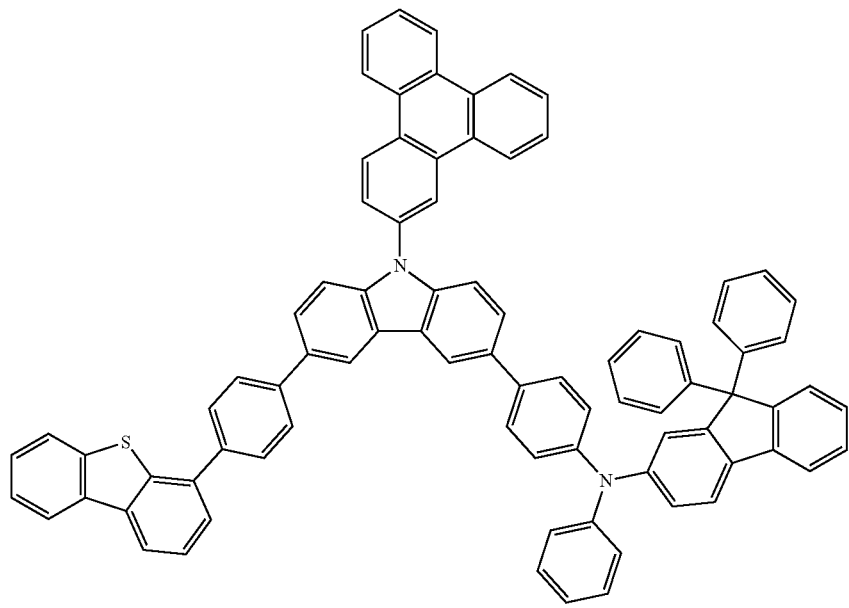
[A-168]
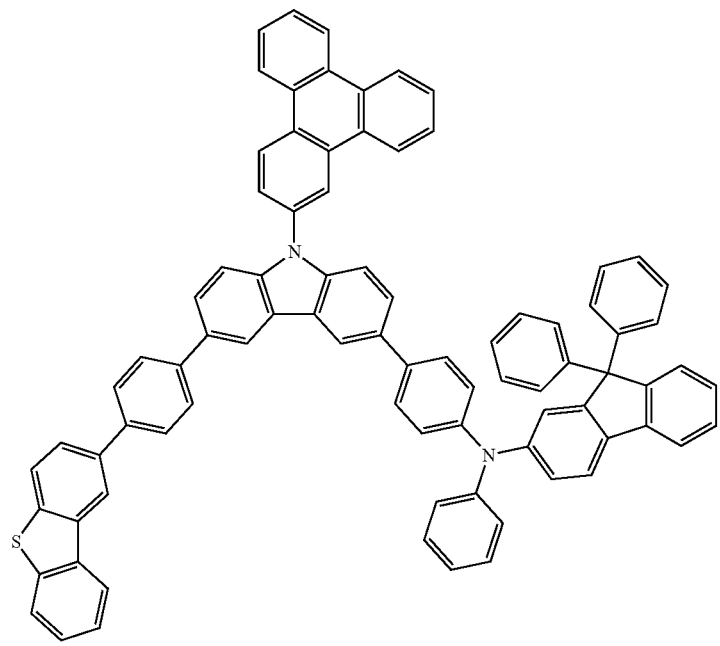
[A-169]

[A-170]
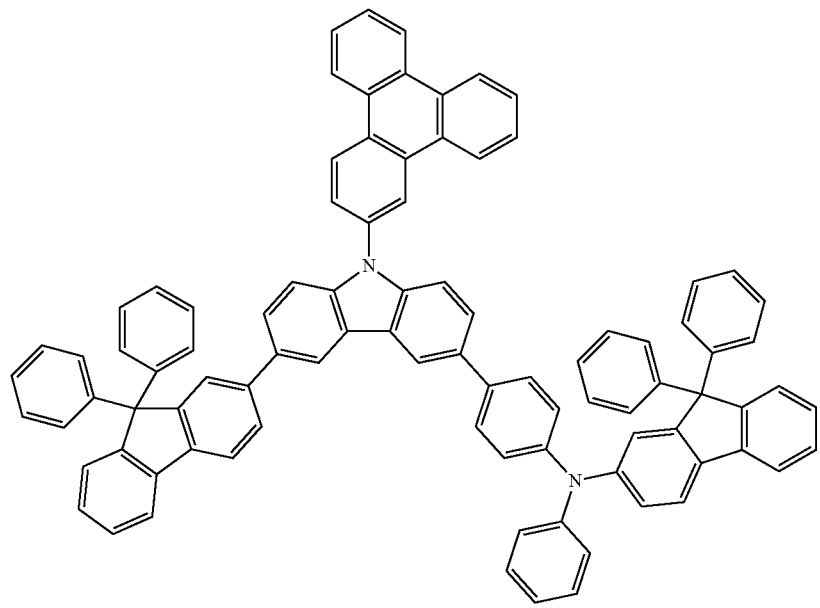
[A-171]
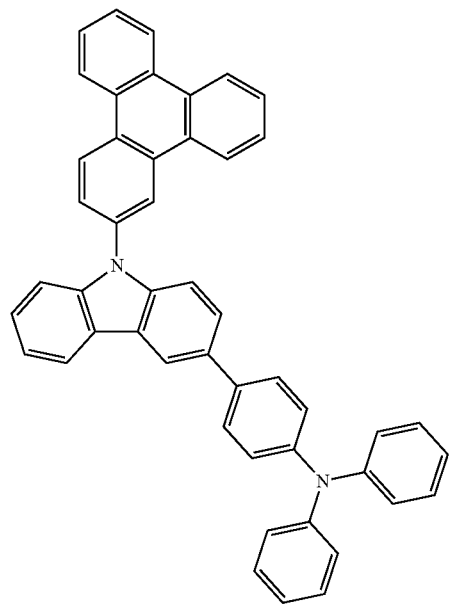
[A-172]

-continued
[A-173]
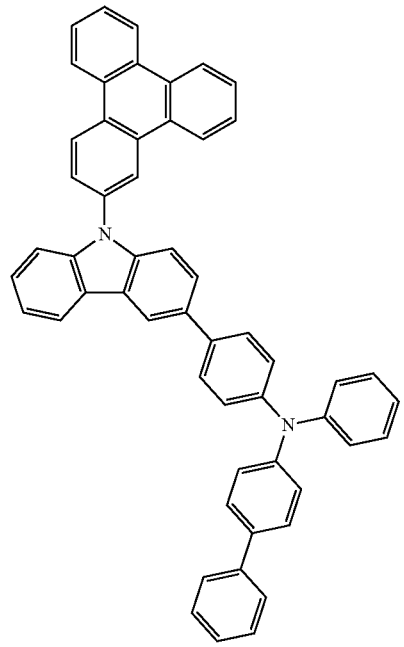
[A-174]
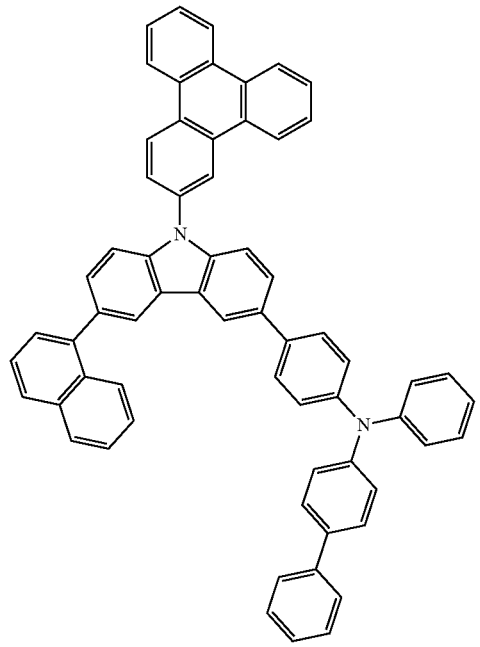
[A-175]
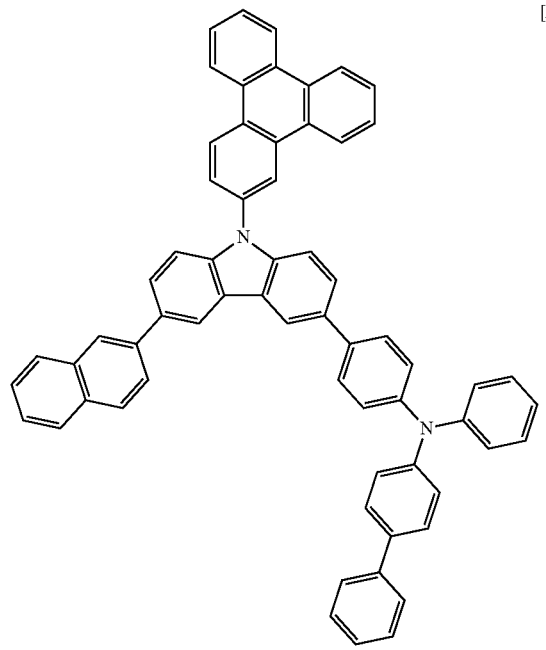
[A-176]
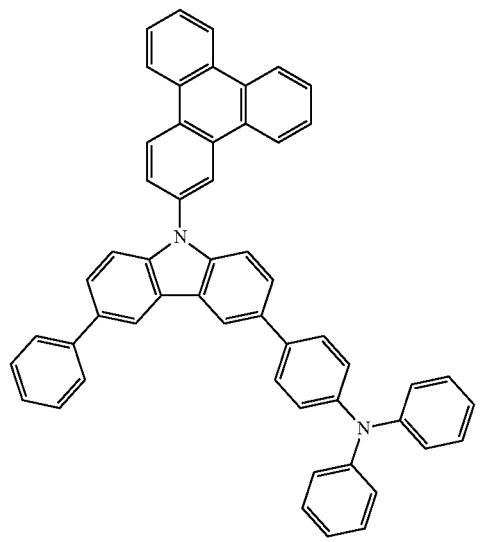

-continued
[A-177]
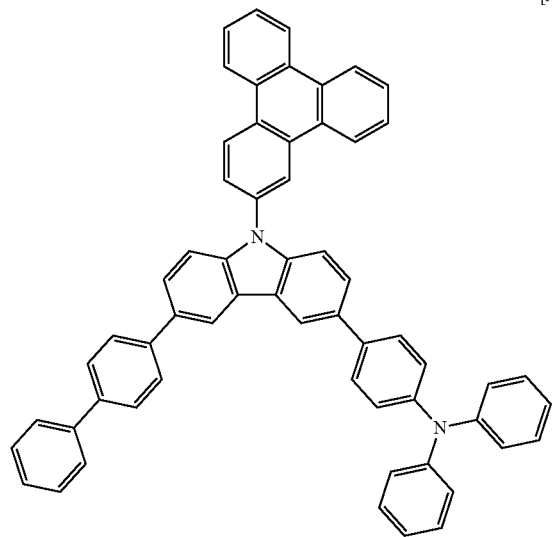
547
[A-178]
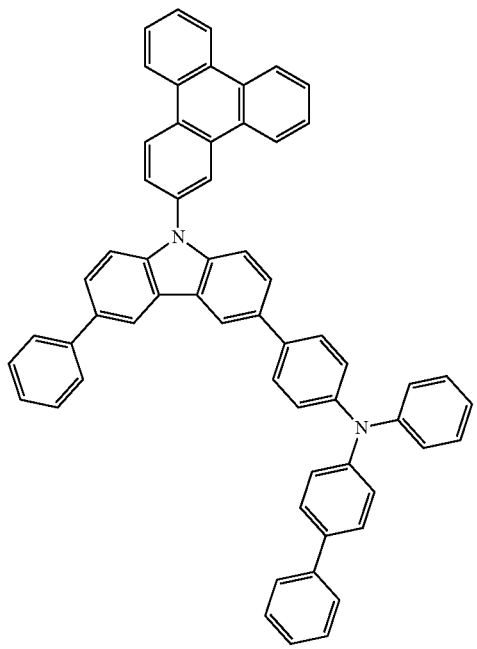
548
[A-179]
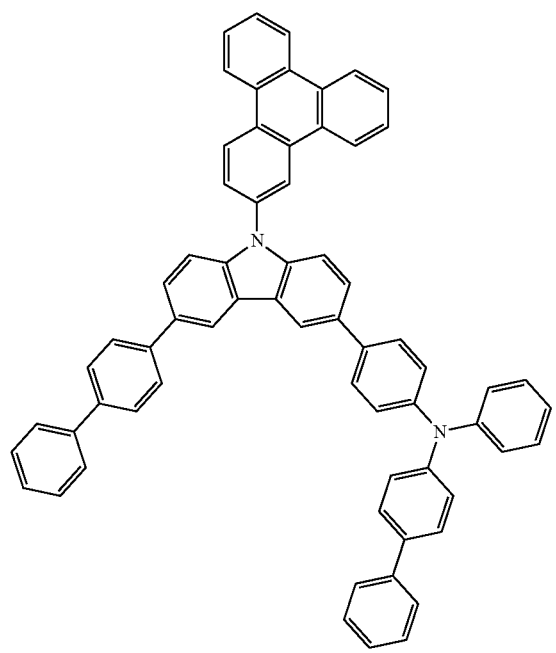
[A-180]
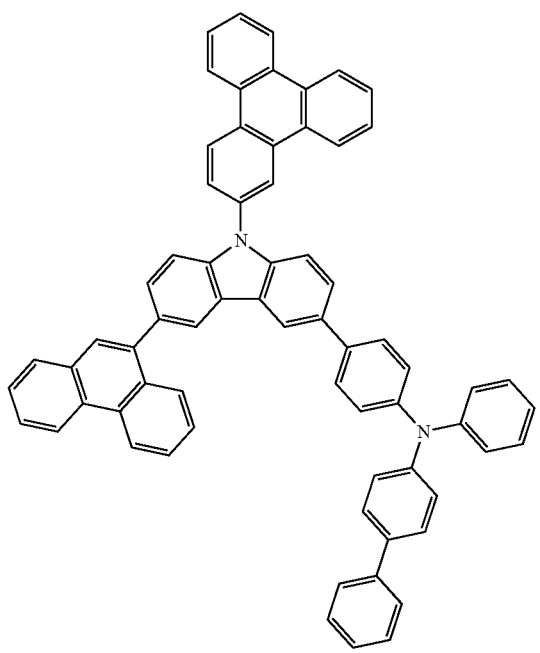

[A-181]
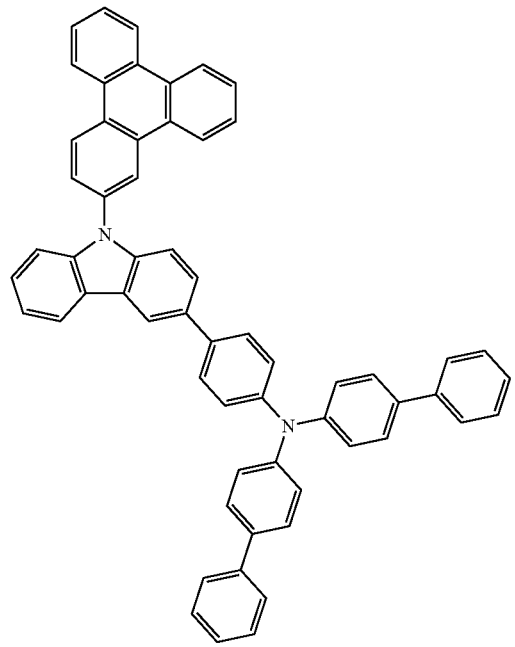
[A-182]
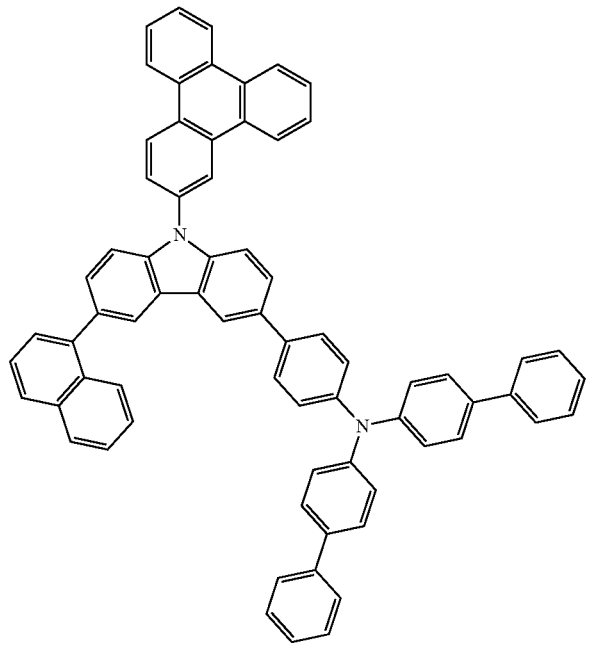
[A-183]
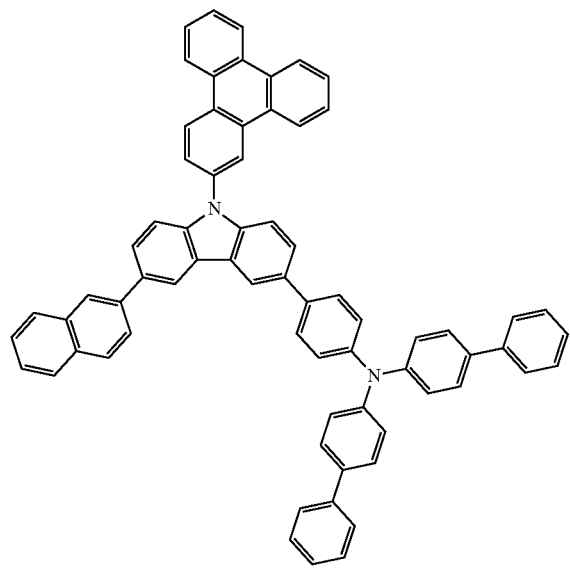
[A-184]
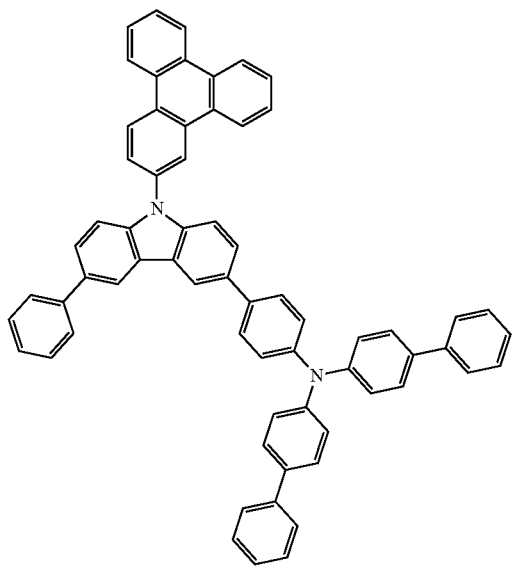

551 552
-continued
[A-185]
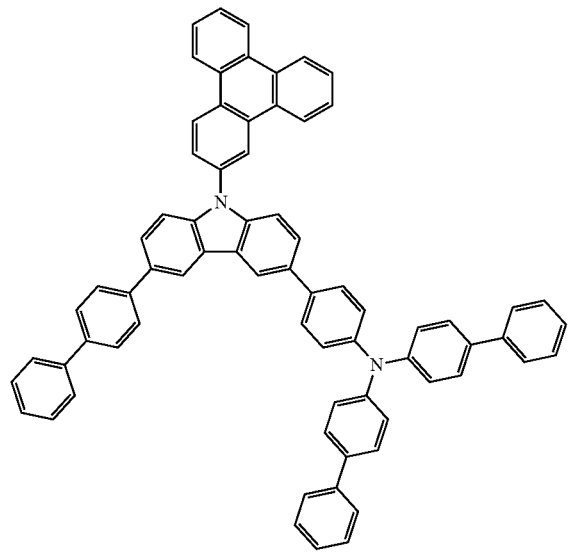
[A-186]
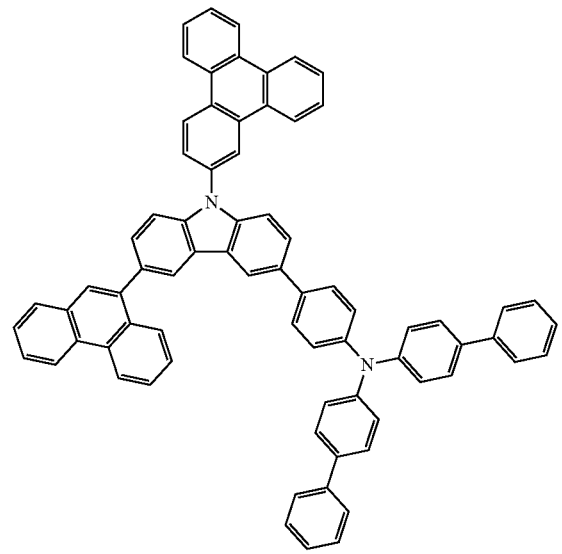
[A-187]
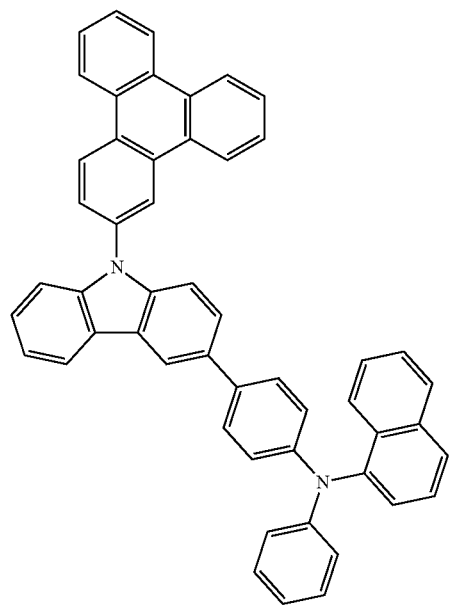
[A-188]
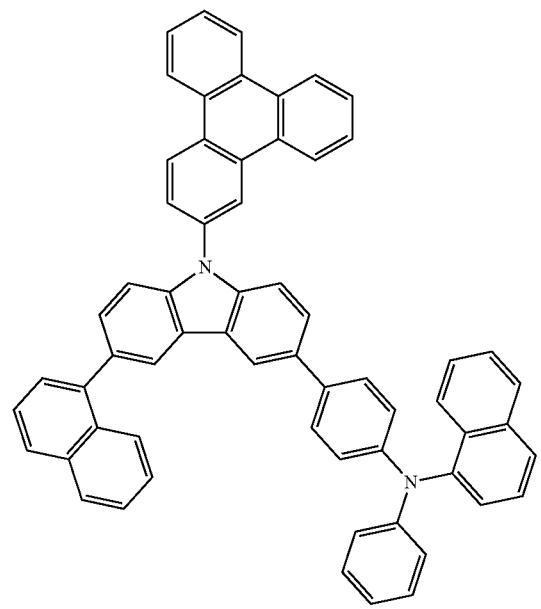

-continued
[A-189]
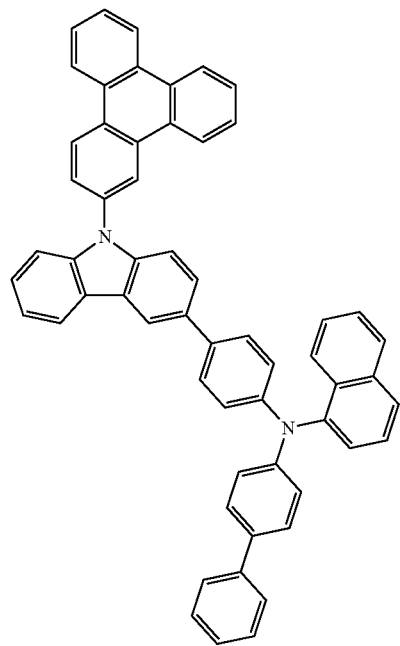
[A-190]
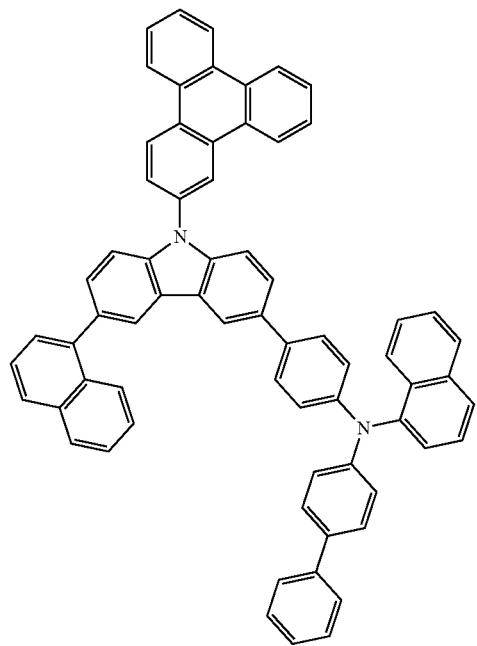
[A-191]
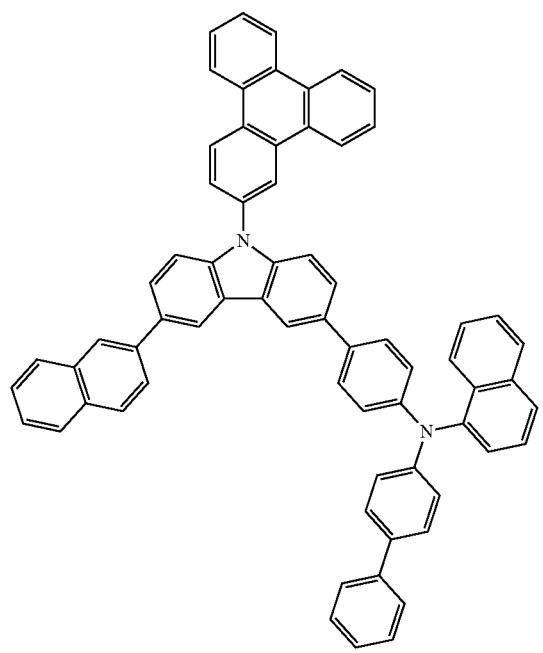
[A-192]
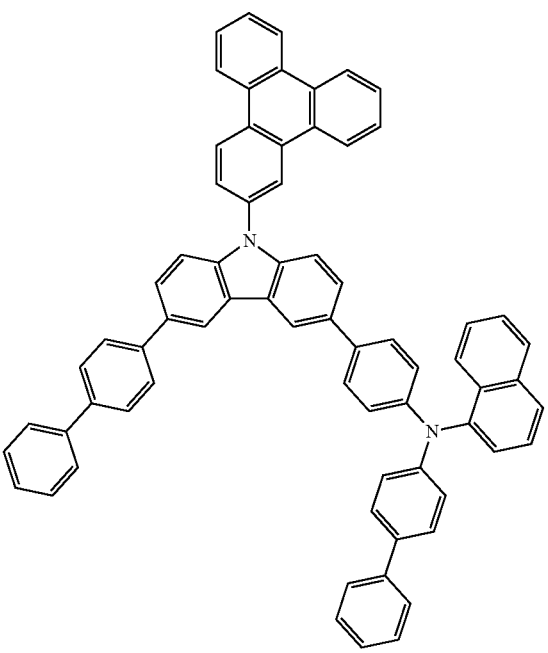

-continued
[A-193]
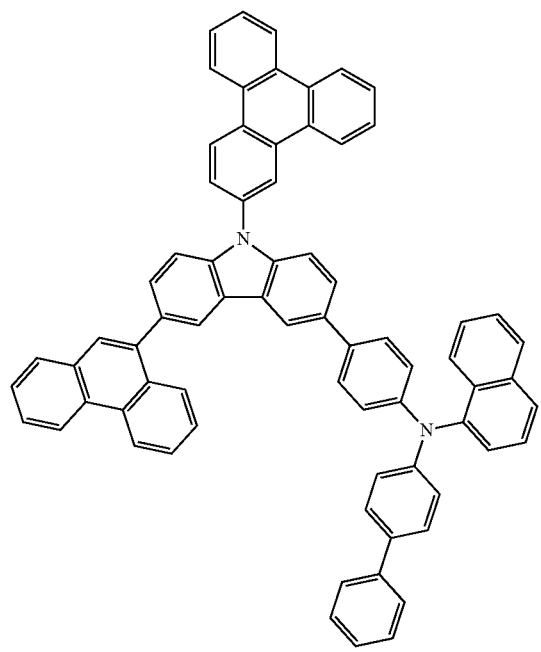
[A-194]
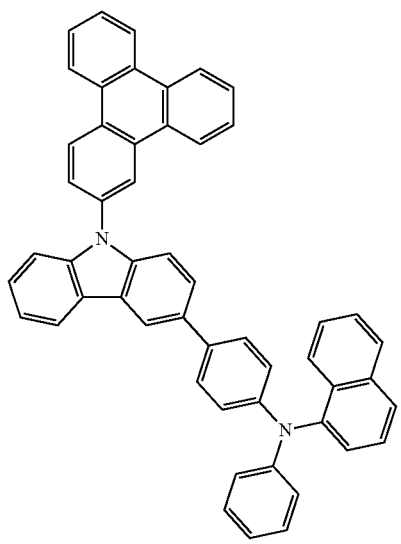
[A-195]
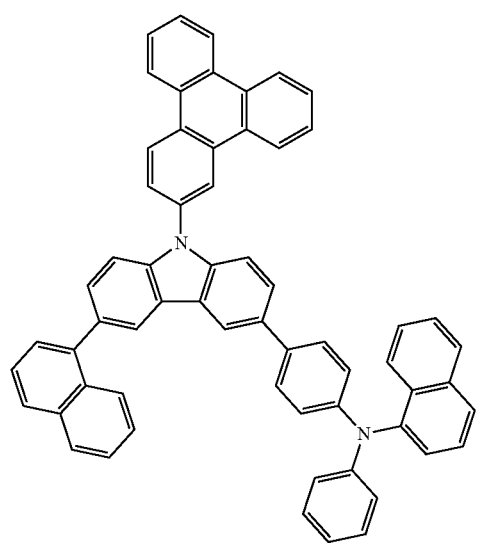
[A-196]
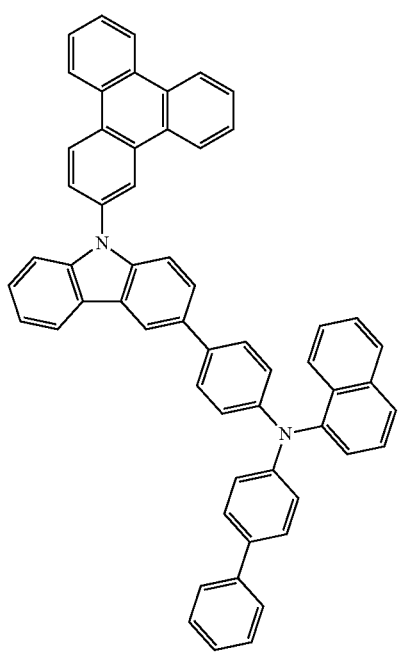

-continued
[A-197]
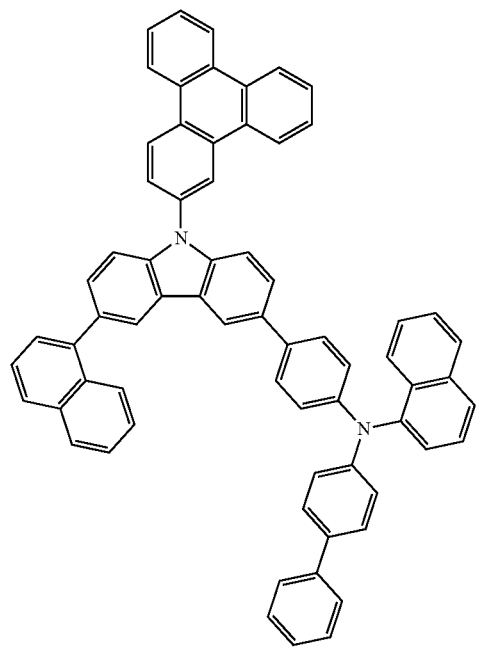
[A-198]
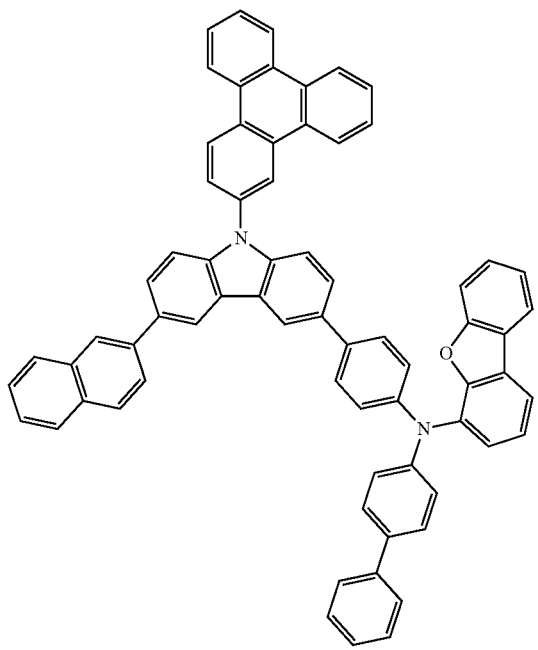
[A-199]
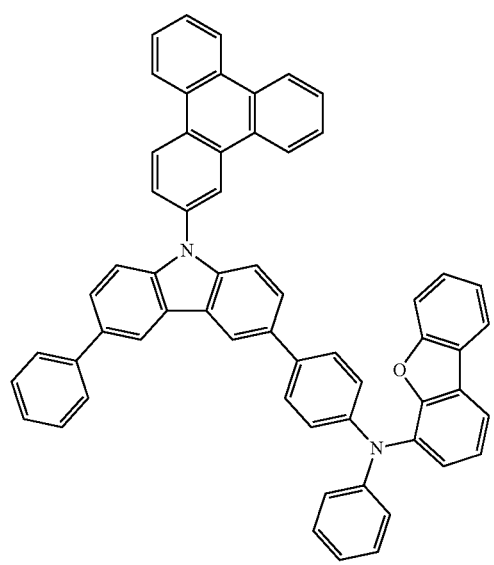
[A-200]
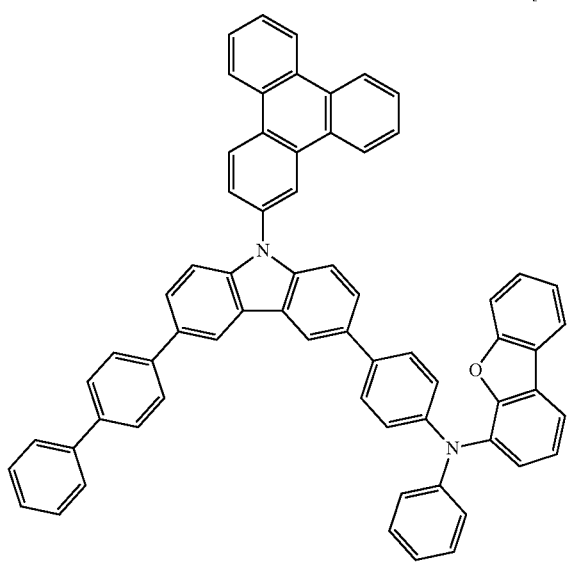

[A-201]
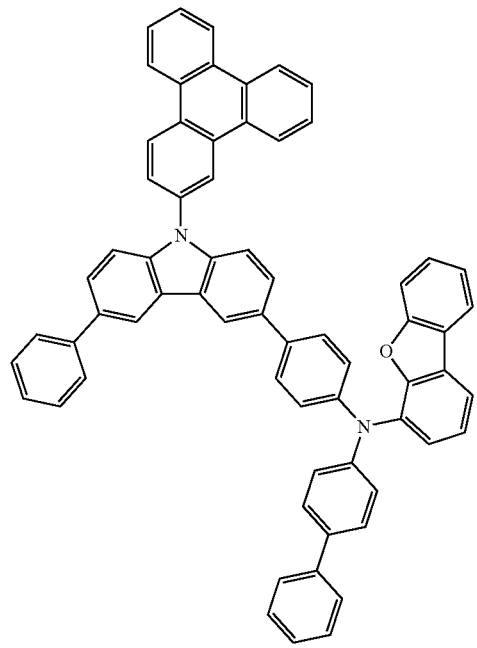
[A-202]
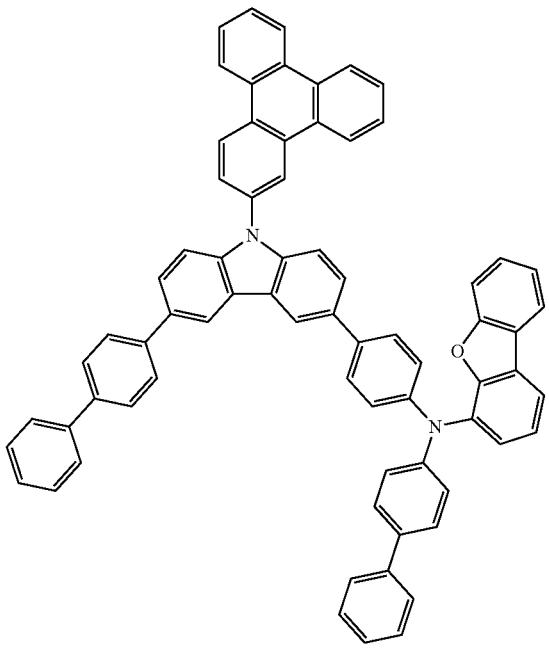
[A-203]
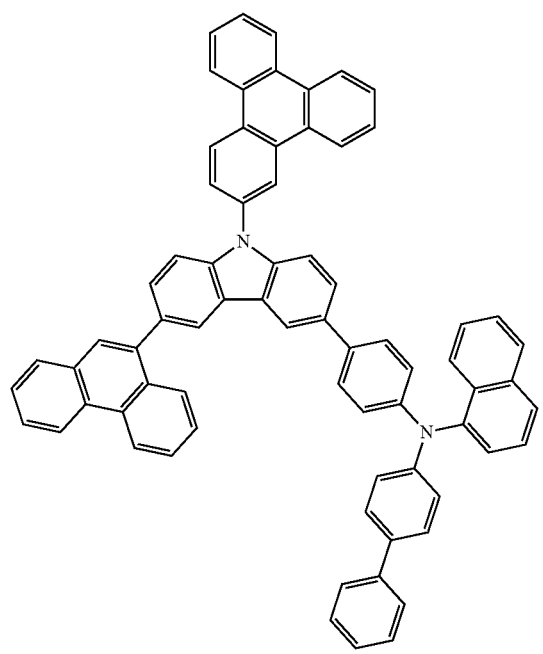
[A-204]
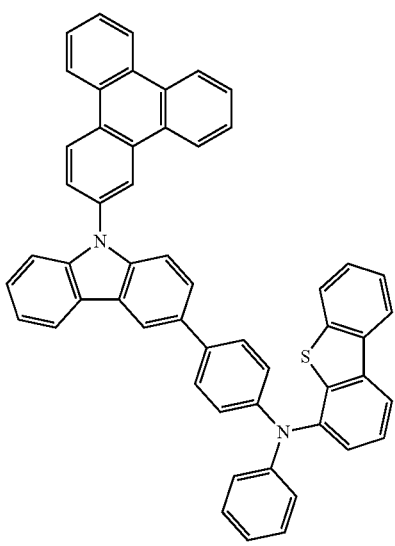

-continued
[A-205]
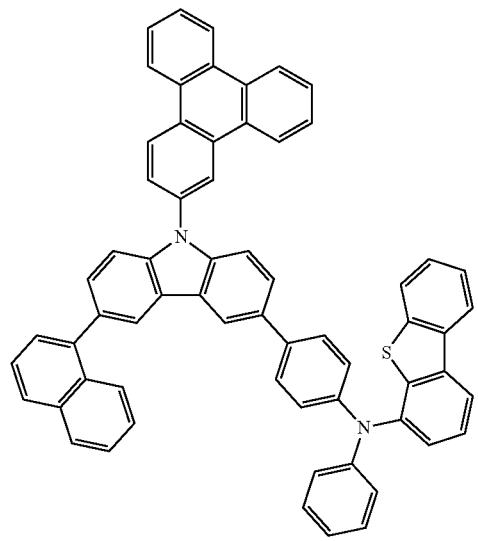
[A-206]
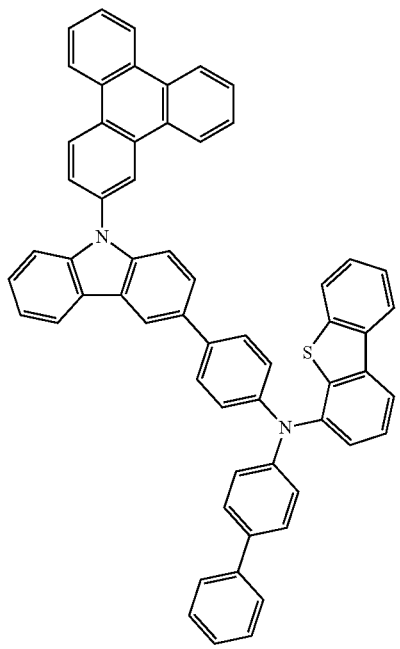
[A-207]
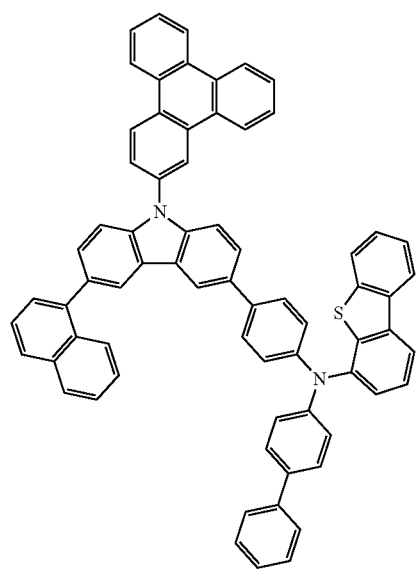
[A-208]
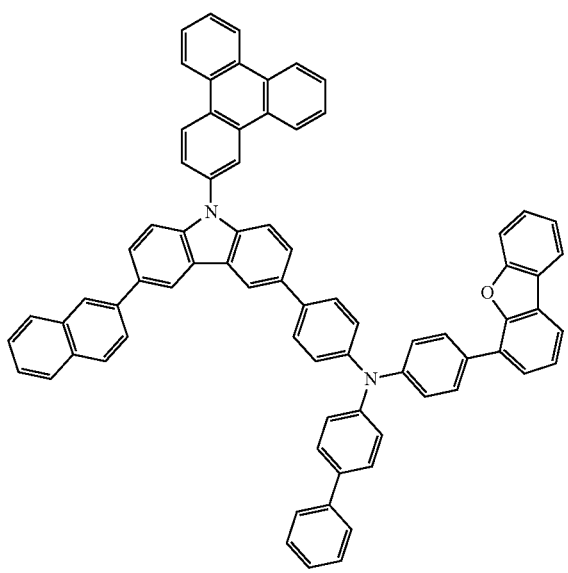

-continued
[A-209]
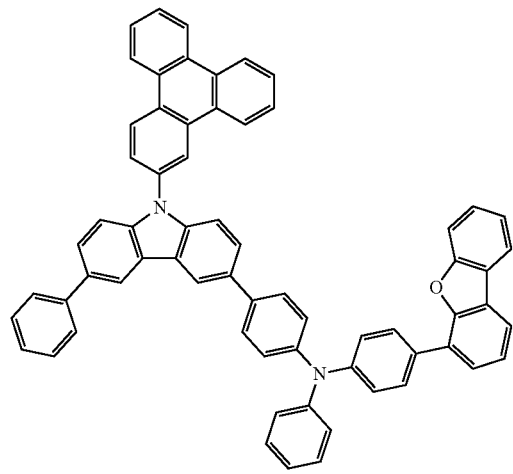
[A-210]
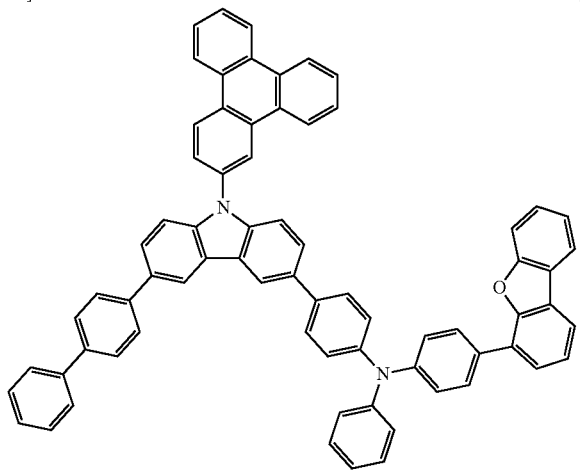
[A-211]
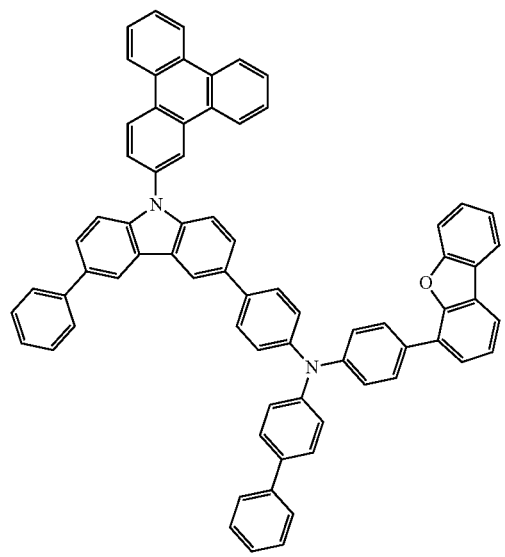
[A-212]
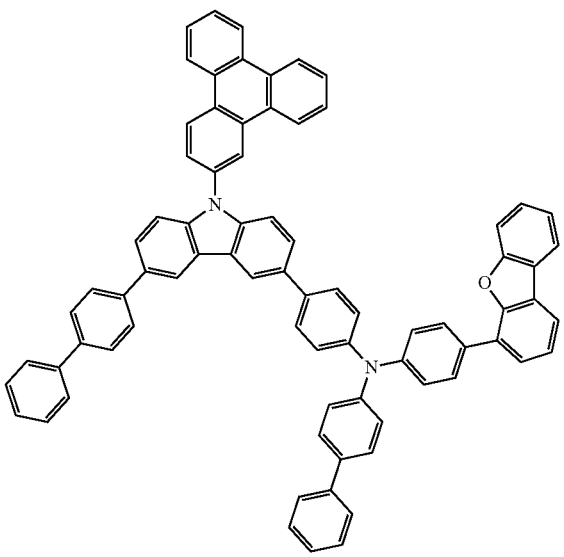

[A-213]
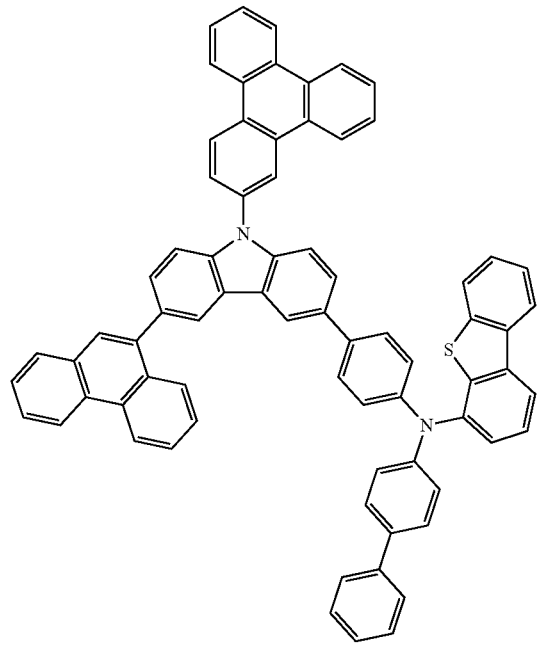
[A-214]
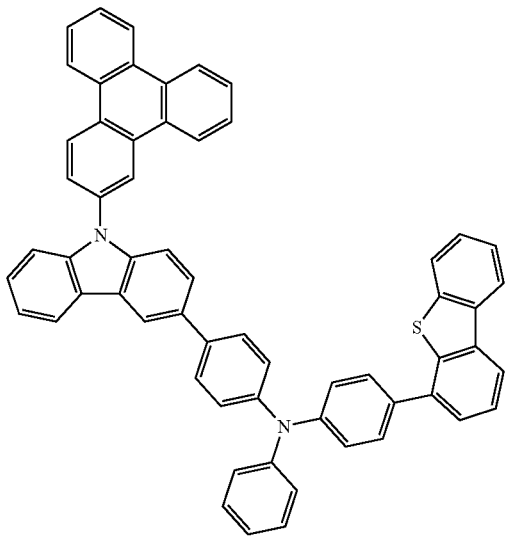
[A-215]
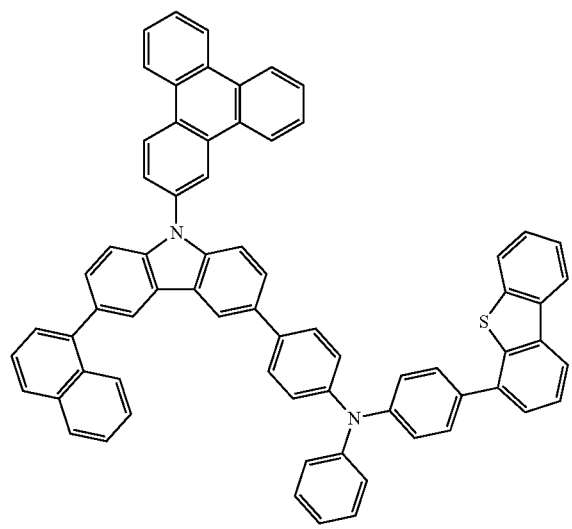
[A-216]
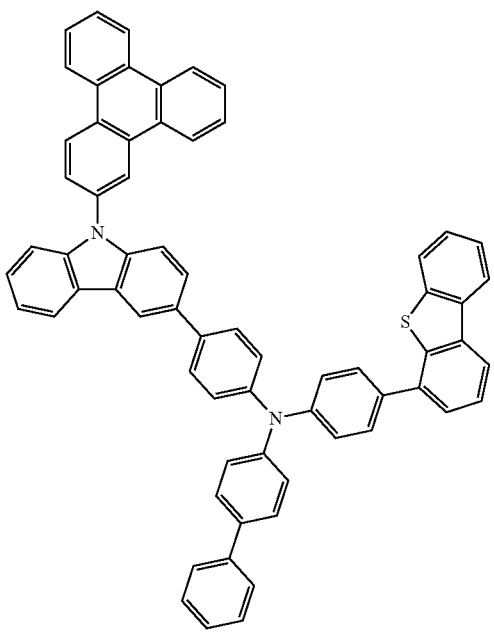

-continued
[A-217]
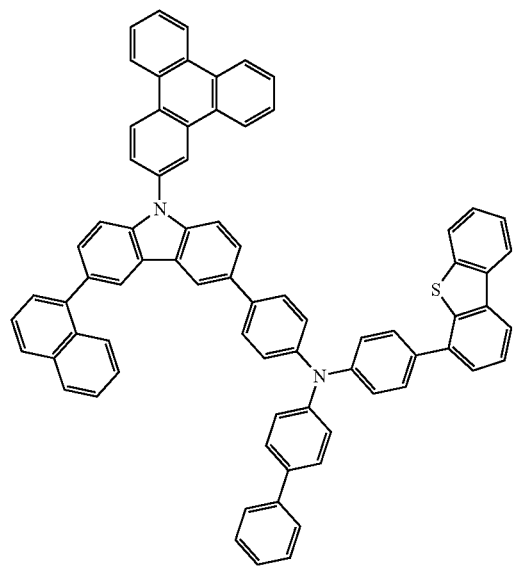
[A-218]
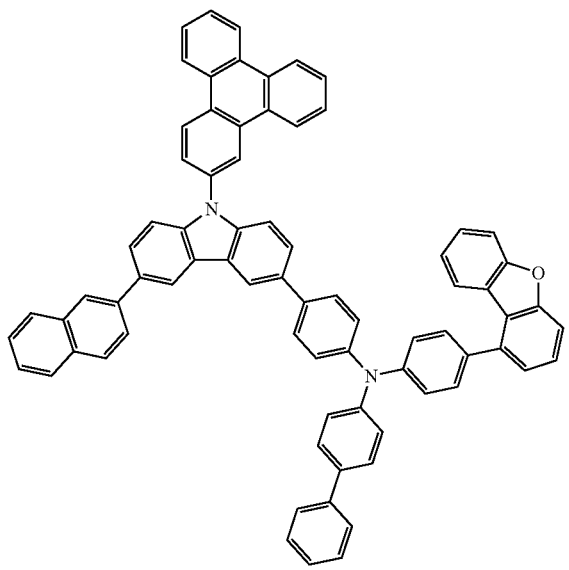
[A-219]
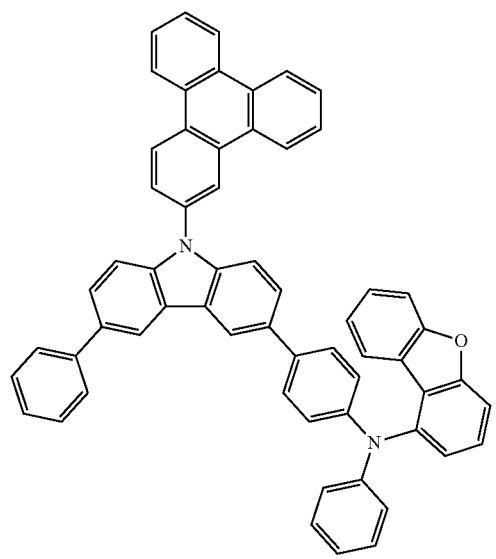
[A-220]
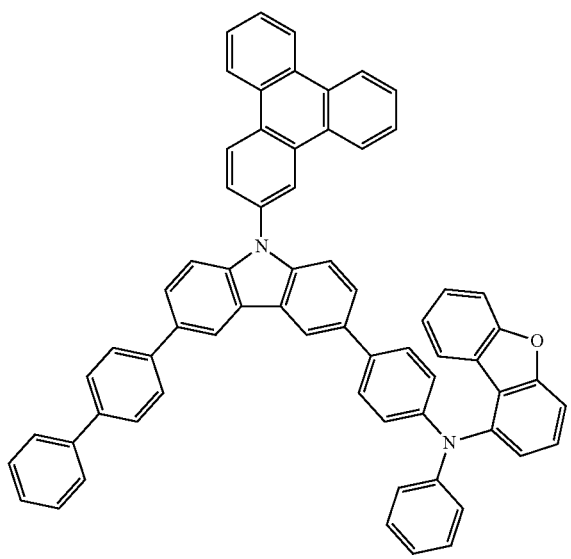

-continued
[A-221]
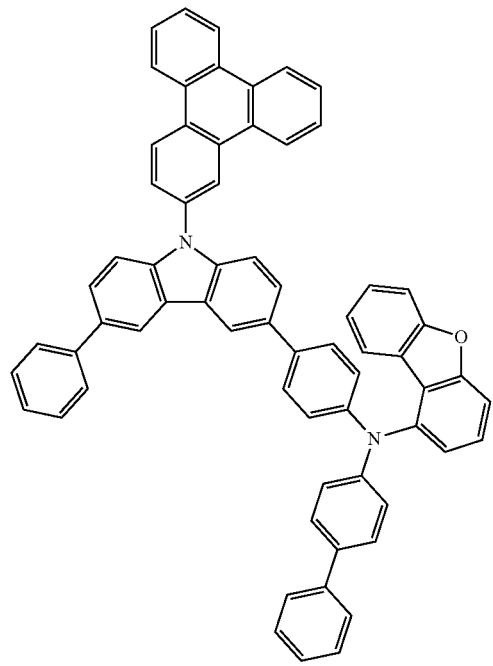
[A-222]
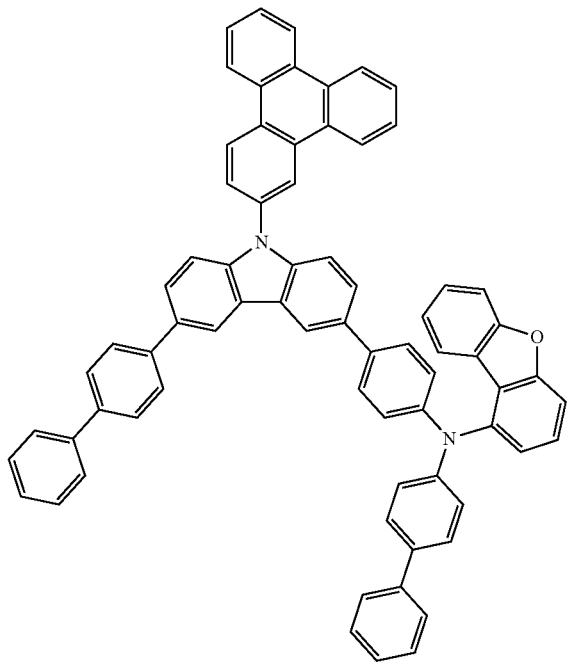
[A-223]
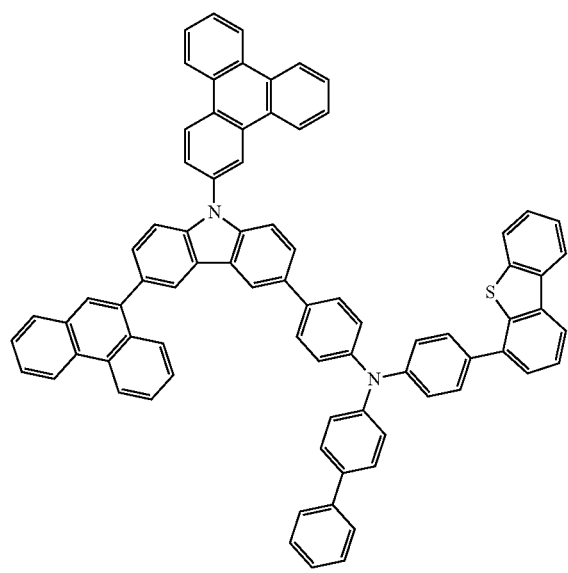
[A-224]
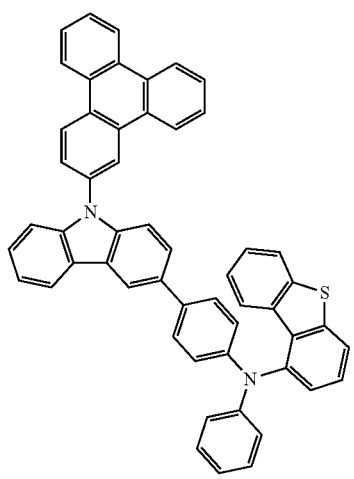

-continued
[A-225]
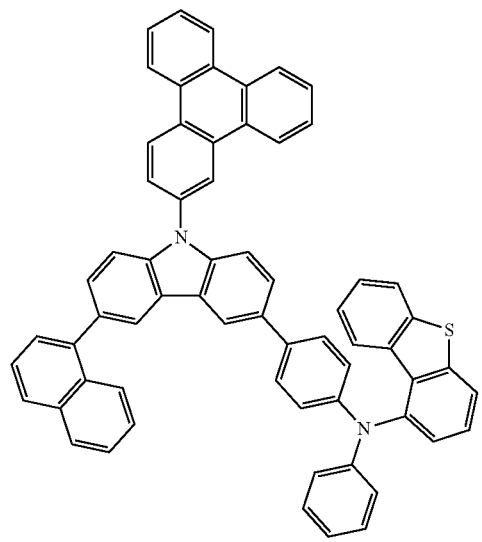
[A-226]
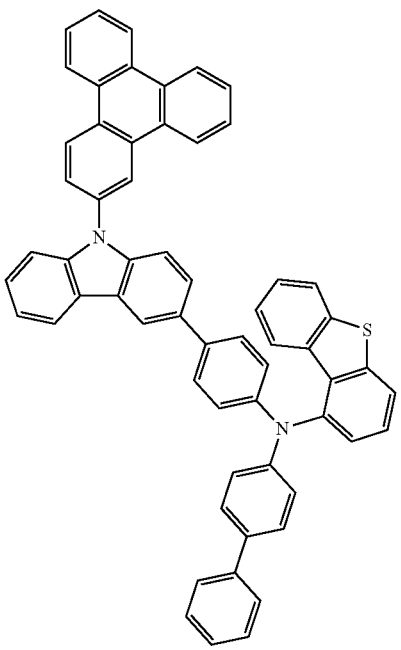
[A-227]
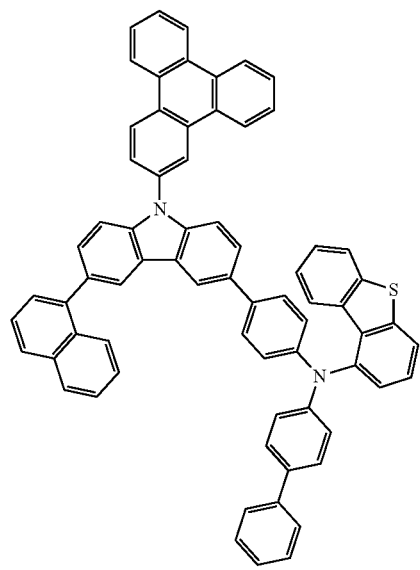
[A-228]
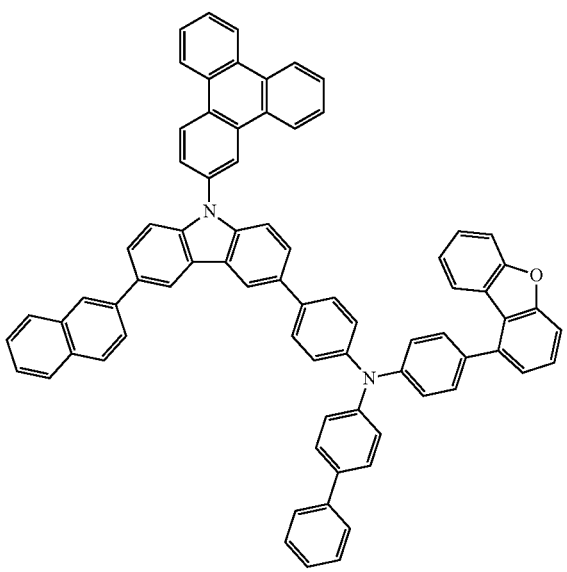

-continued
[A-229]
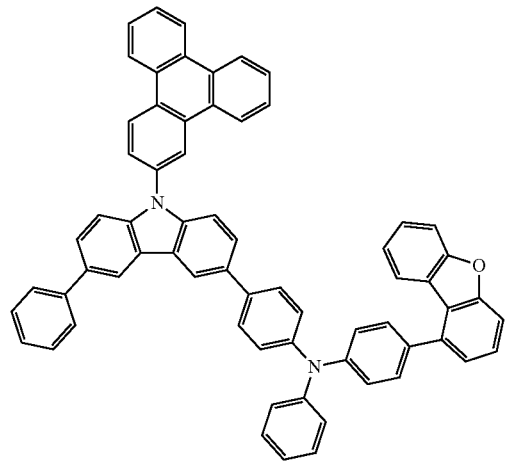
[A-230]
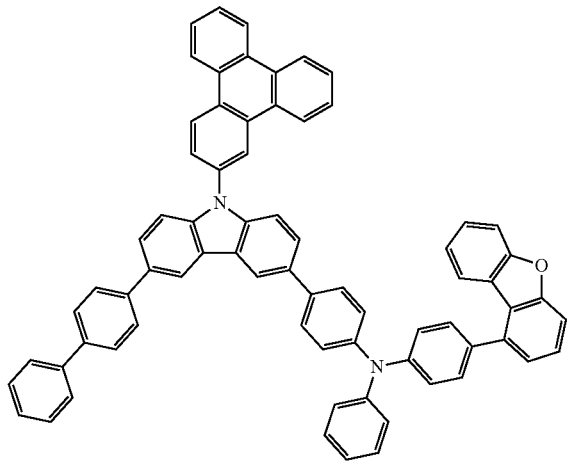
[A-231]
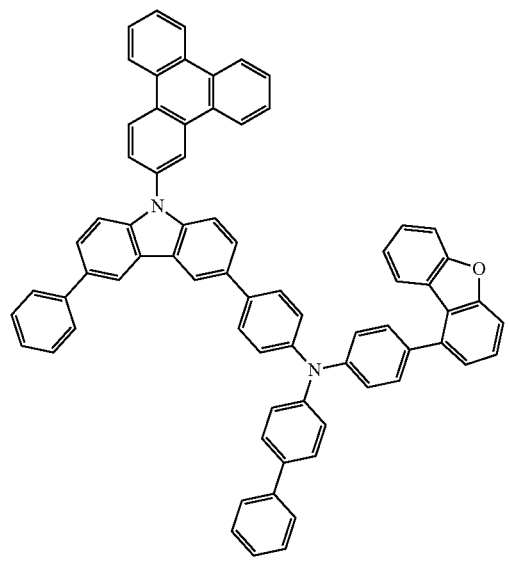
[A-232]
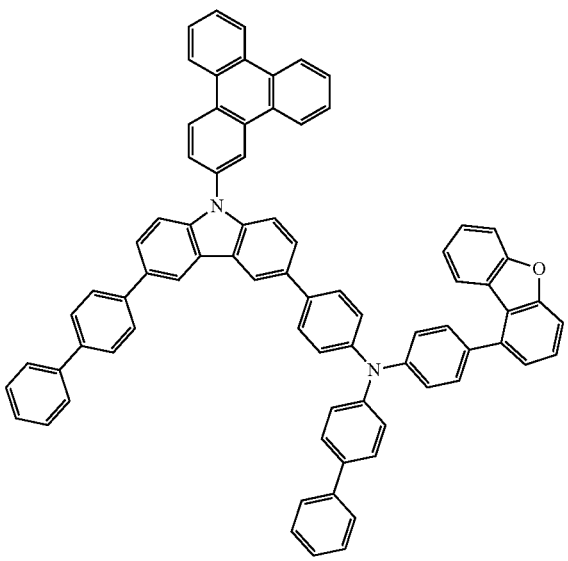

-continued
[A-233]
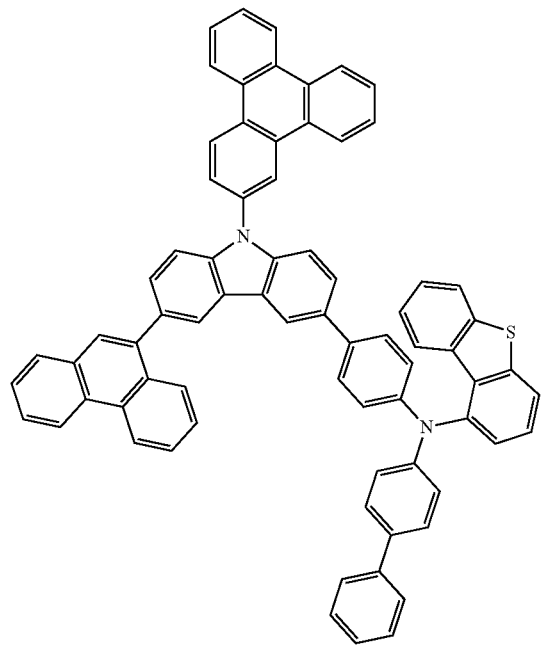
[A-234]
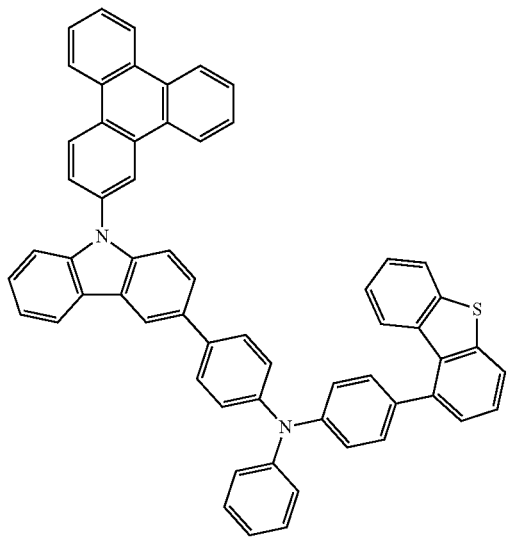
[A-235]
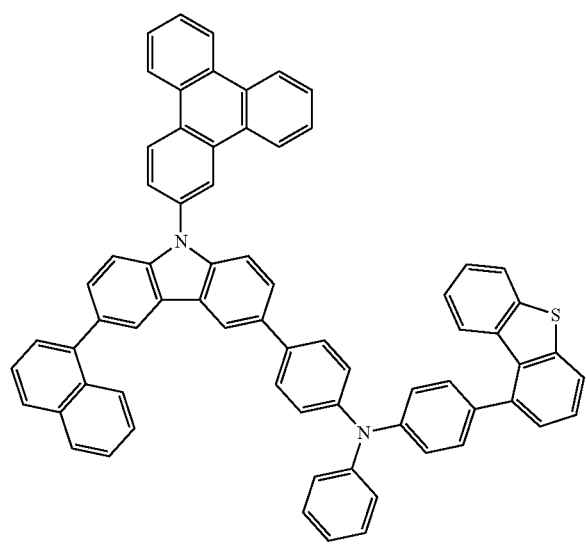
[A-236]
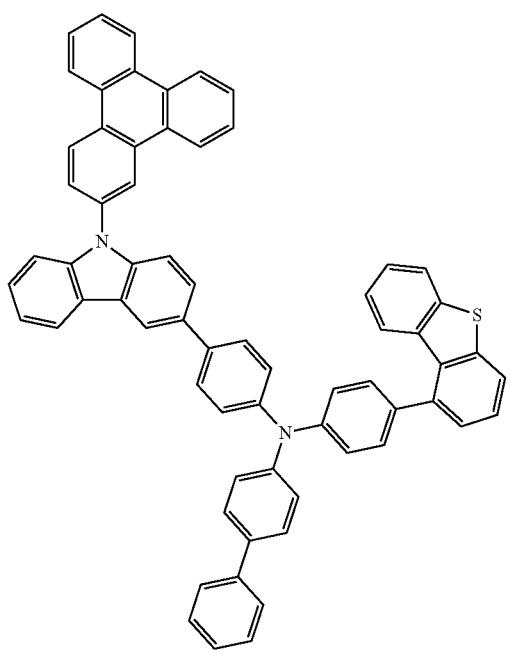

-continued
[A-237]
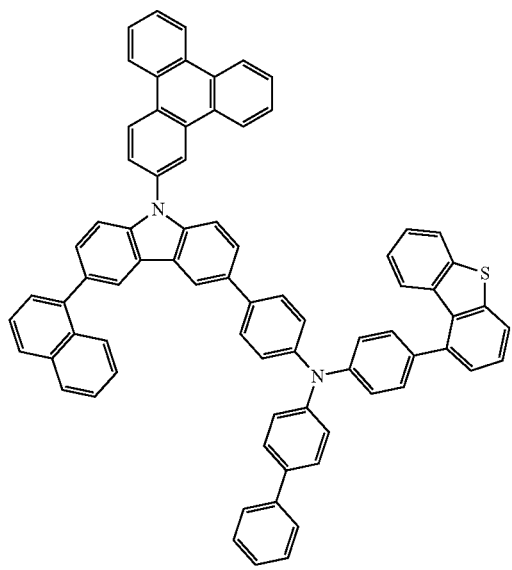
[A-238]
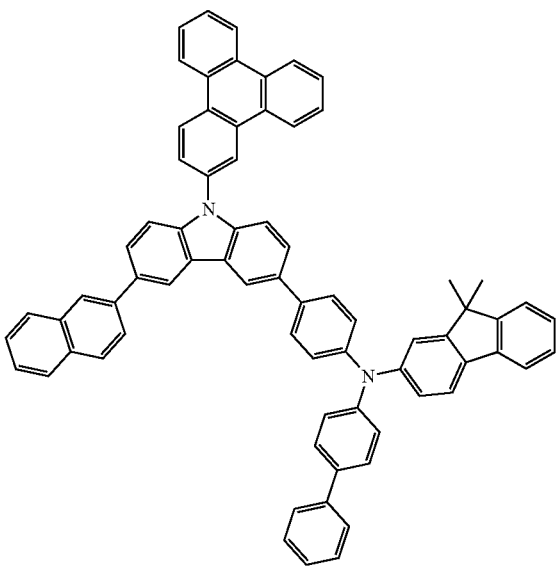
[A-239]
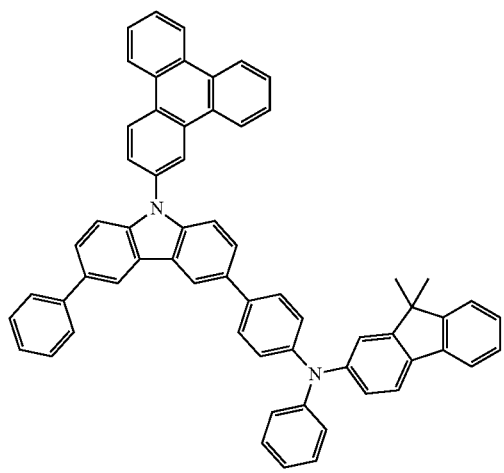
[A-240]
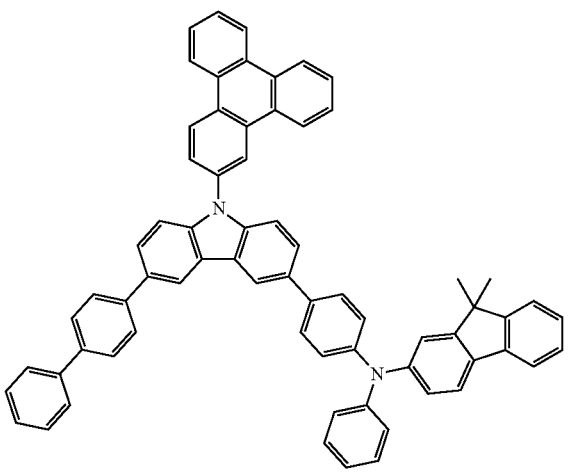
[A-241]
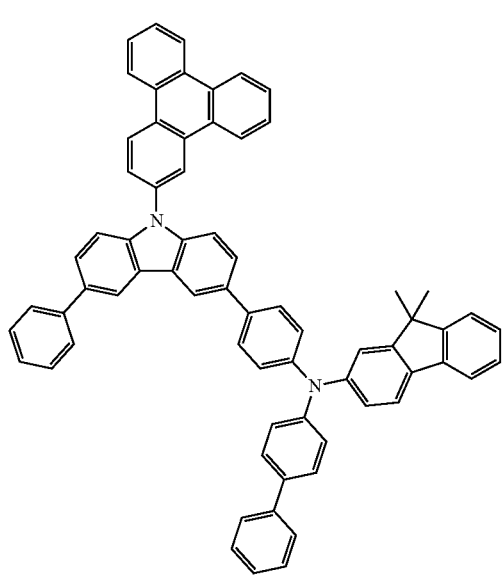
[A-242]
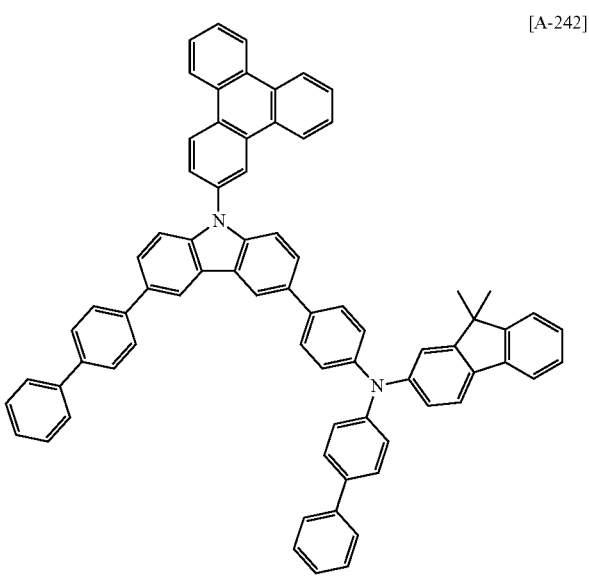

-continued
[A-243]
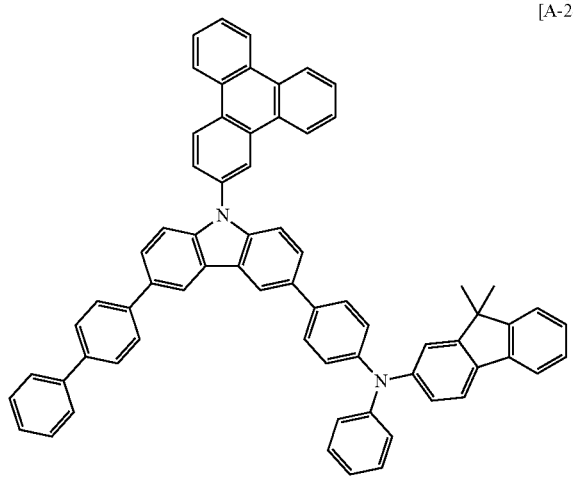
[A-244]
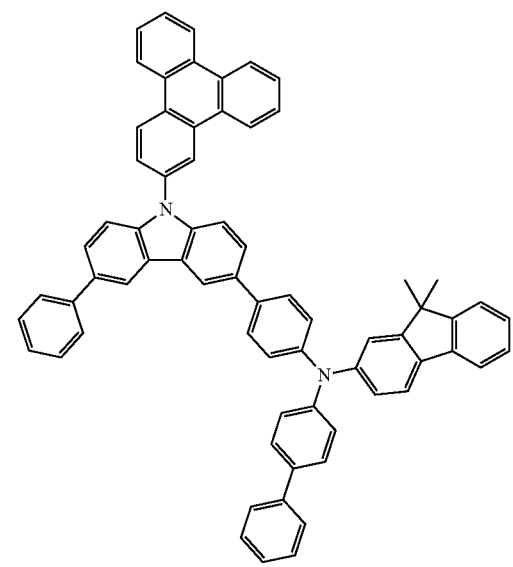
[A-245]
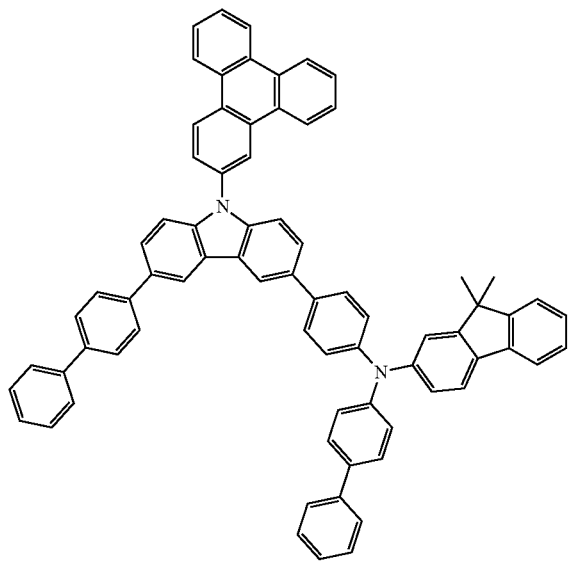
[A-246]
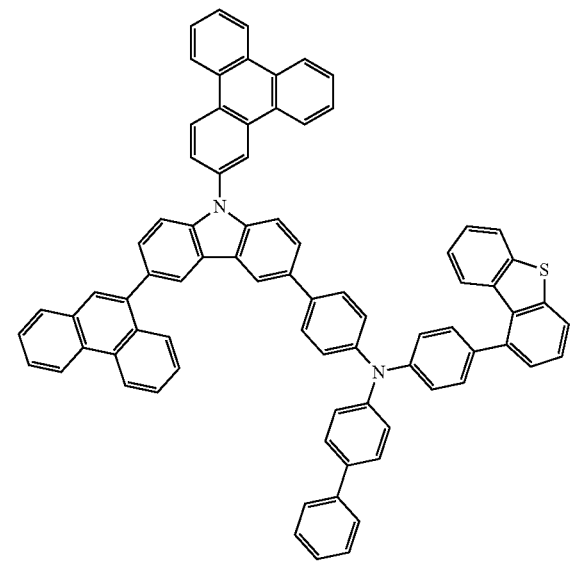
[A-247]
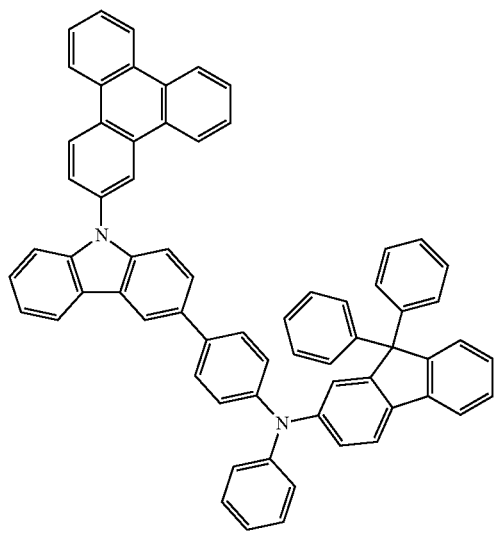
[A-248]
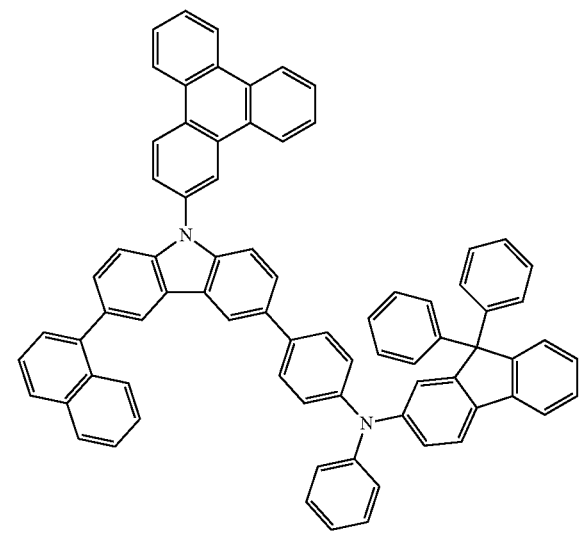

[A-249]
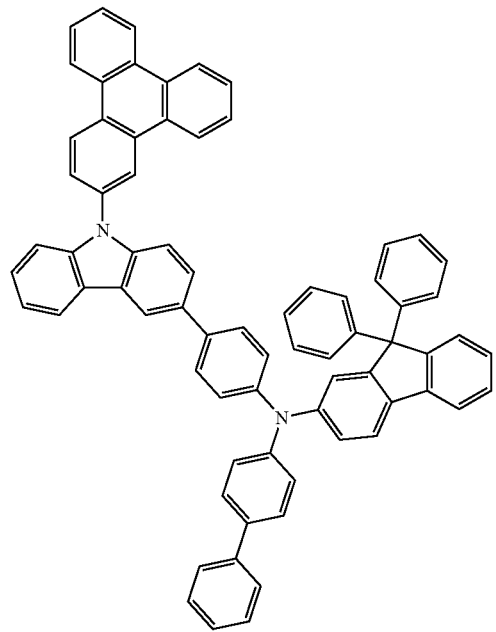
[A-250]
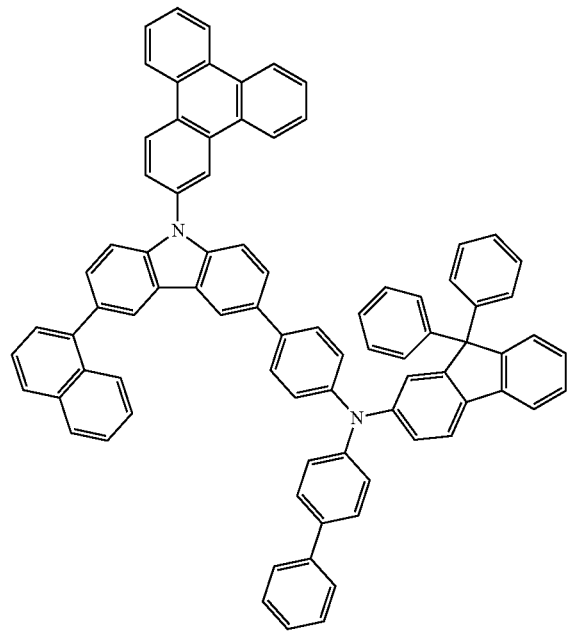
[A-251]
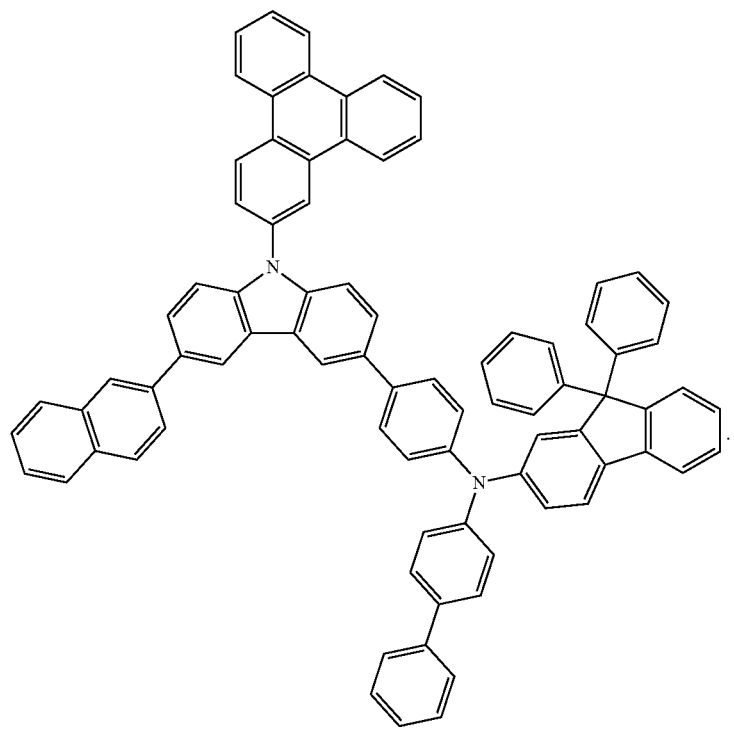

8. A compound for an organic photoelectric device, the compound being represented by one of the following Chemical Formulae A-252 to A-336:
[A-252]
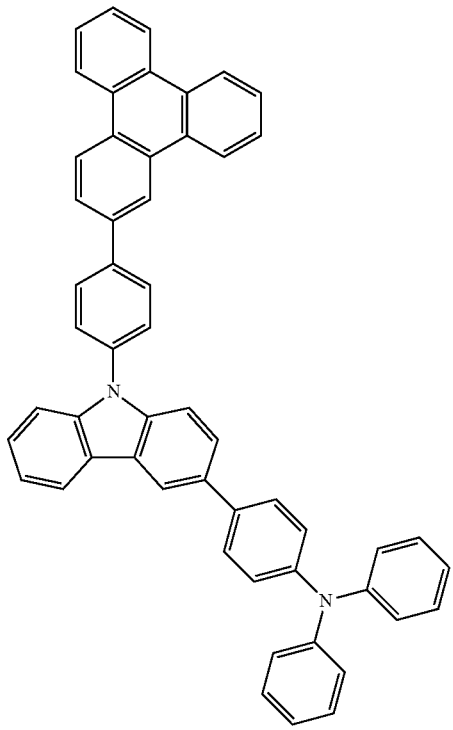
[A-253]
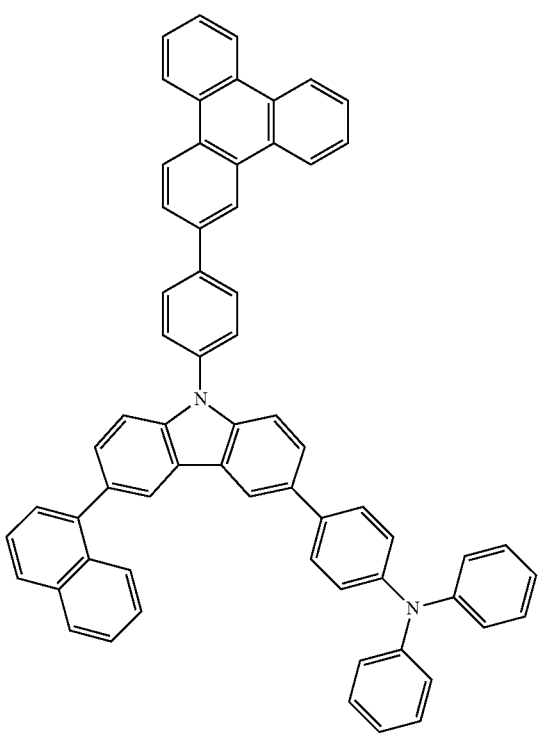
[A-254]
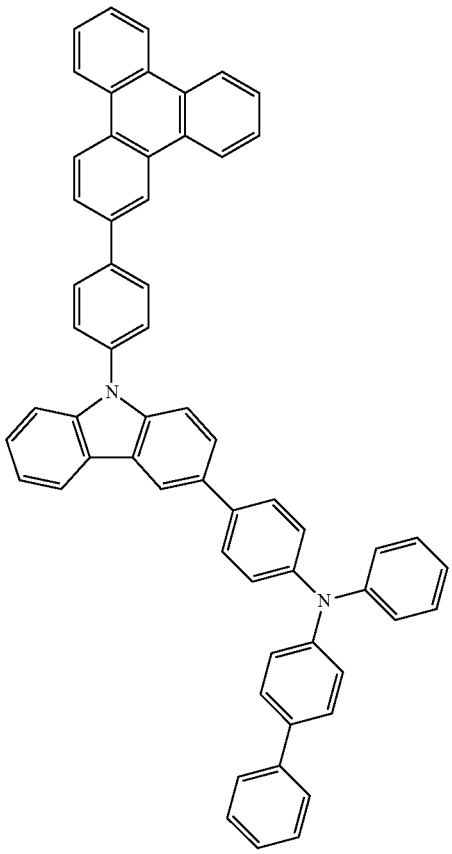
[A-255]
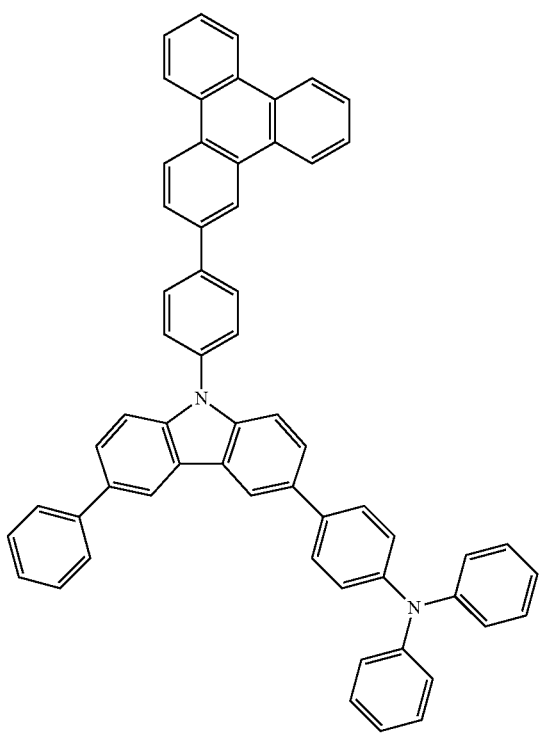

[A-256]
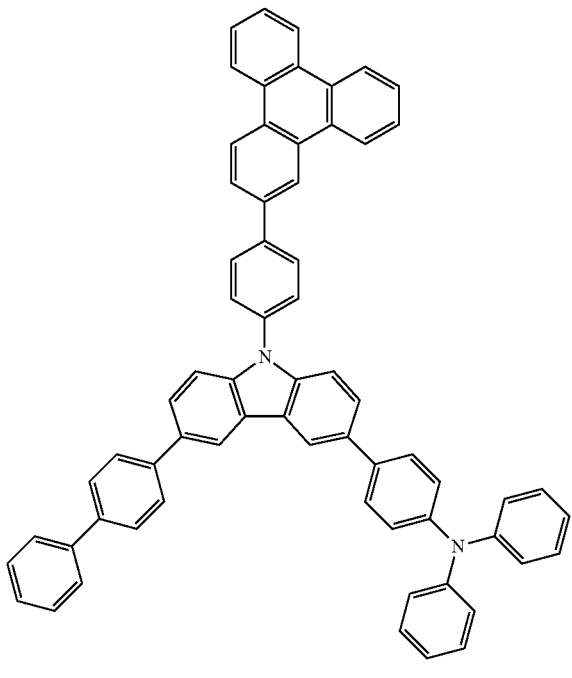
[A-257]
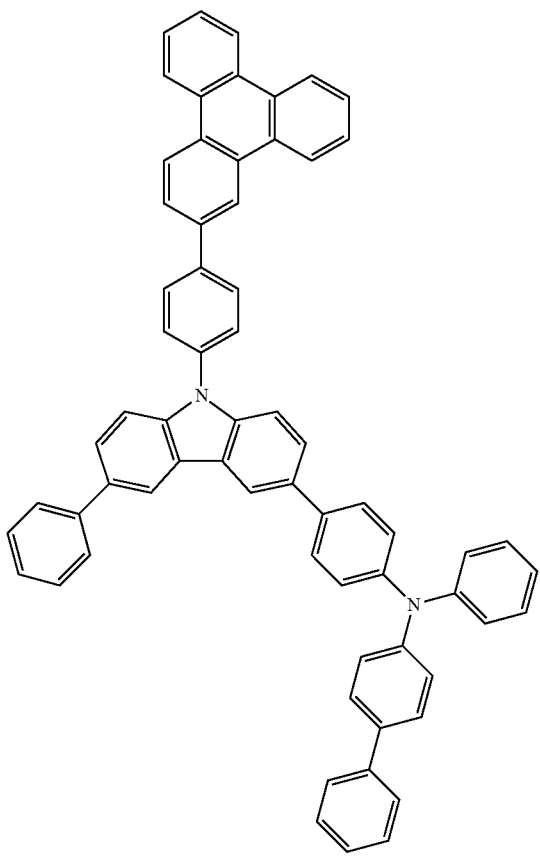
[A-258]
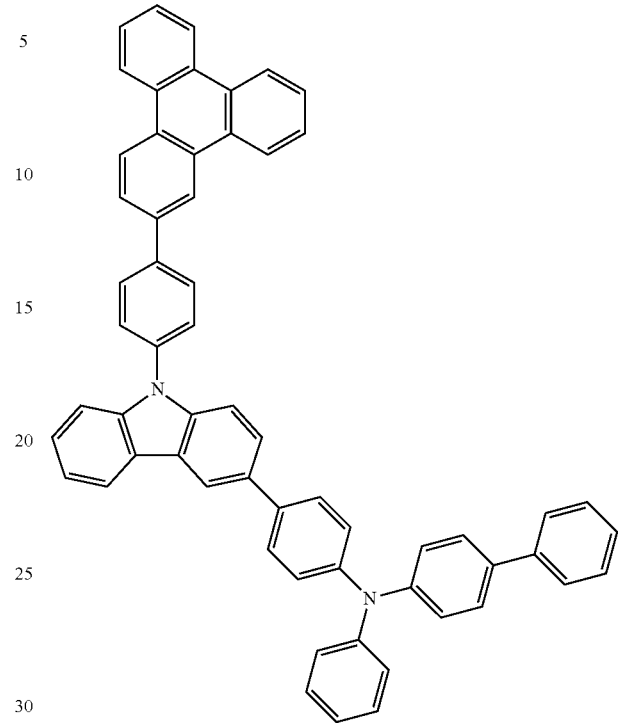
[A-259]
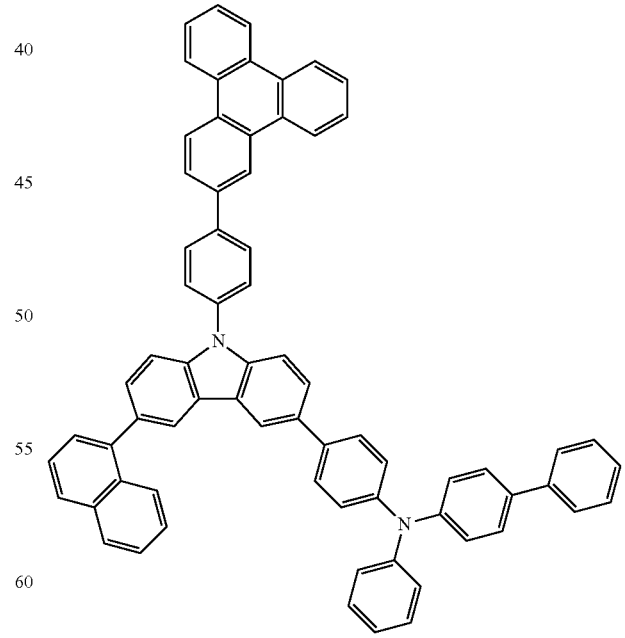

[A-260]
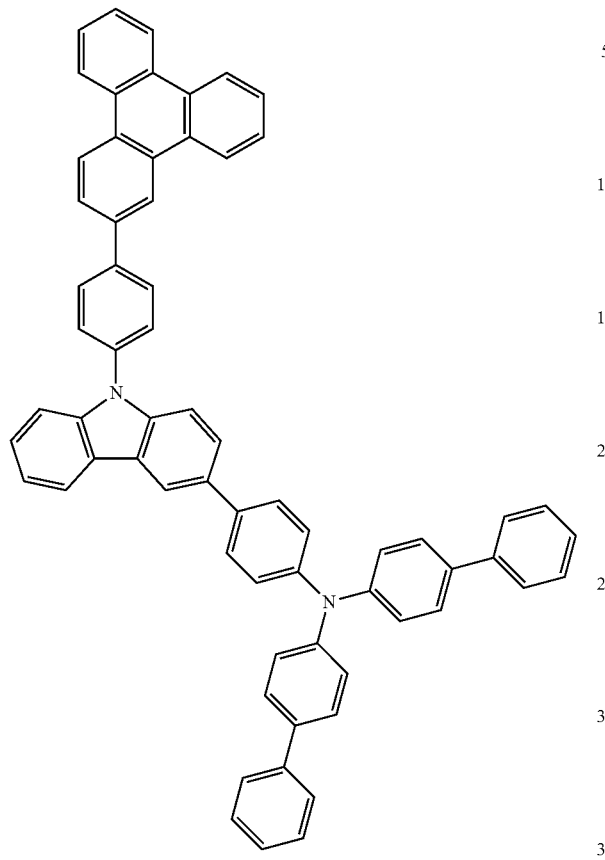
[A-261]
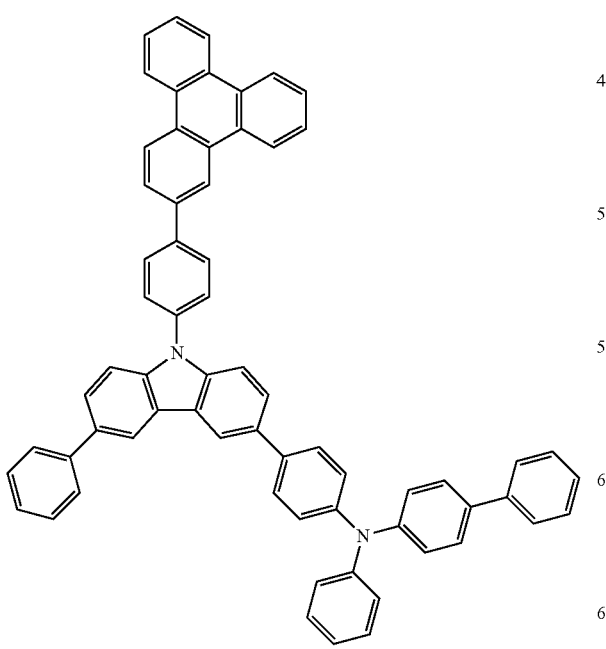
[A-262]
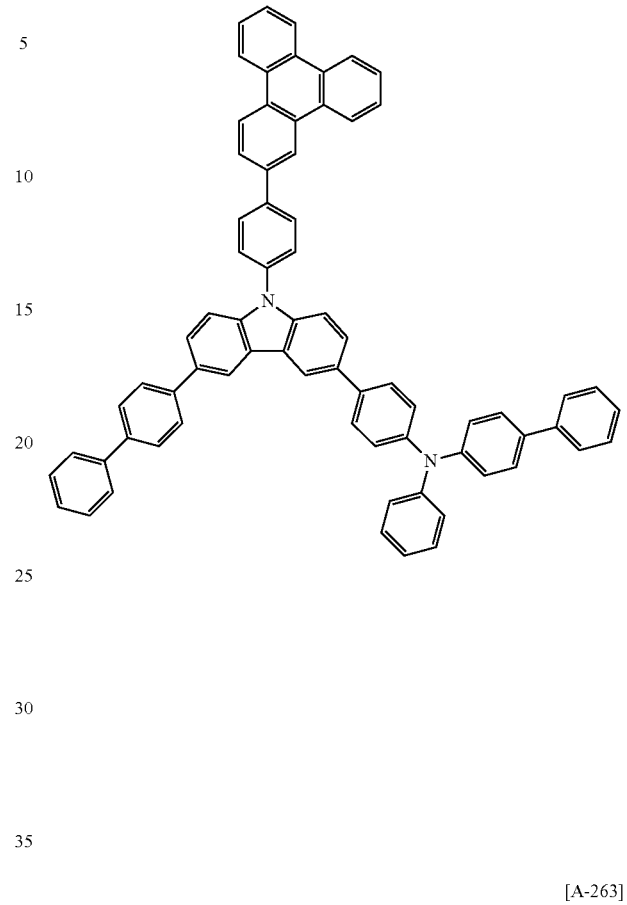
[A-263]

[A-264]
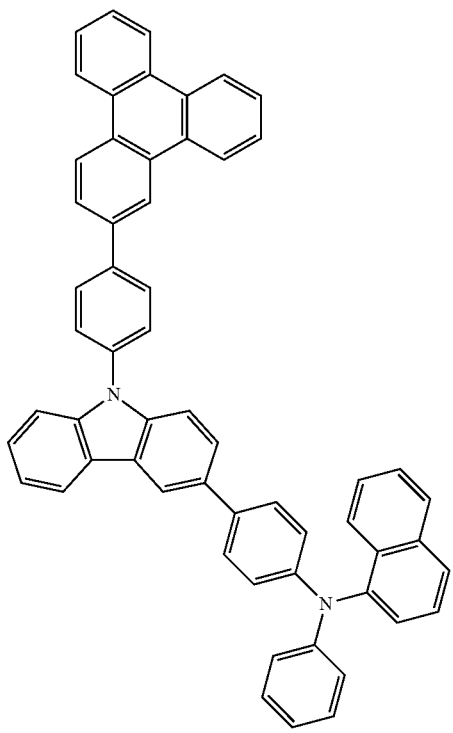
[A-266]
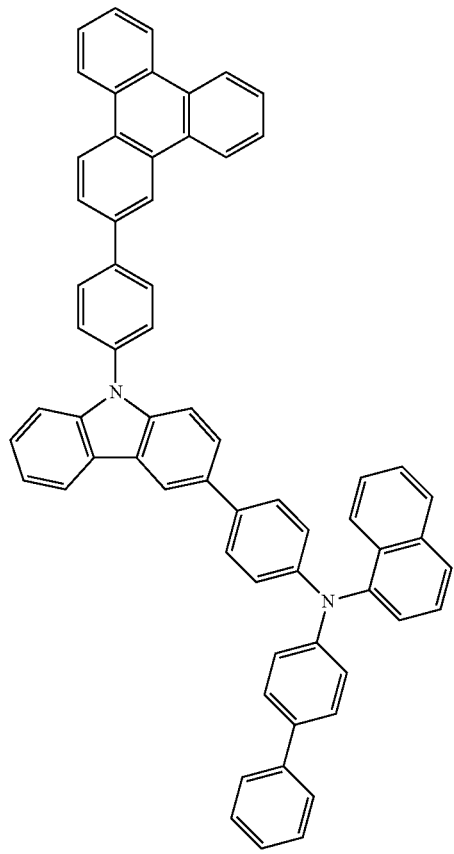
[A-265]
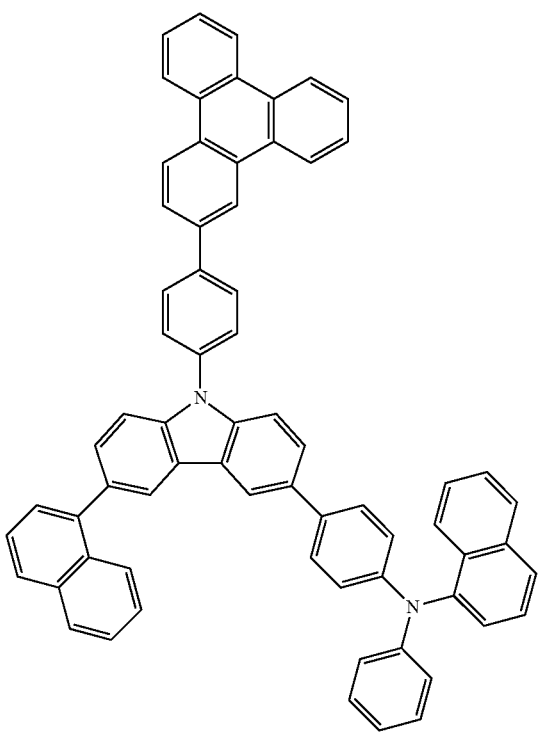
[A-267]
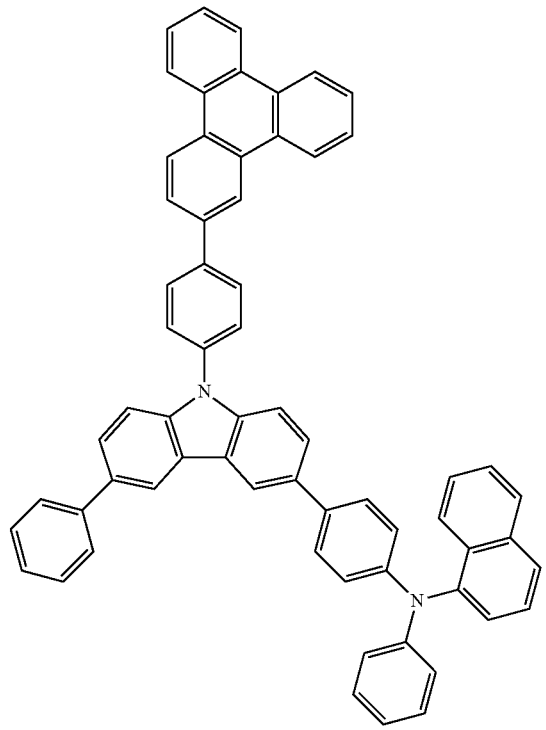

[A-268]
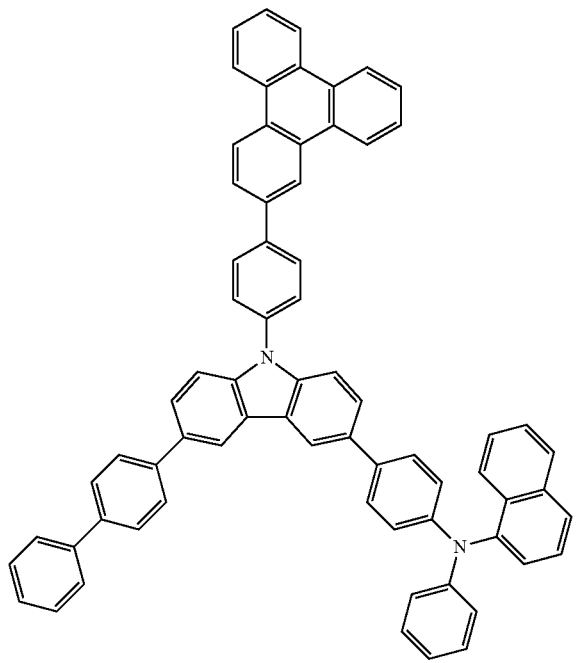
[A-270]
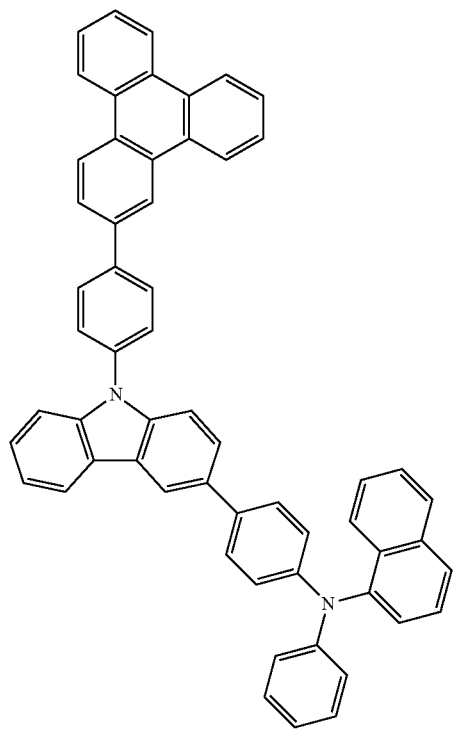
[A-269]
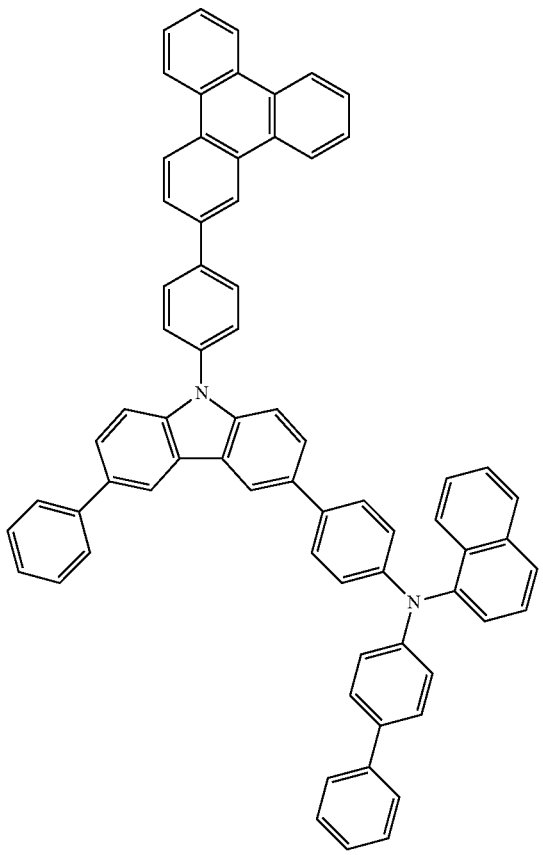
[A-271]
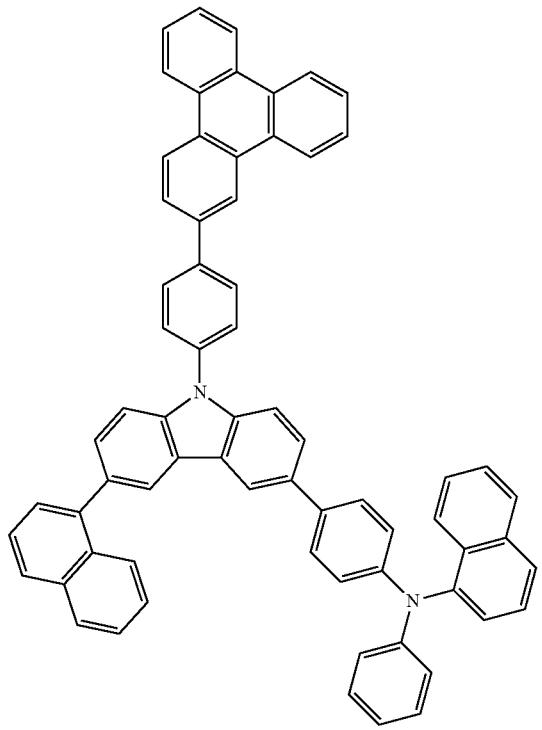

[A-272]
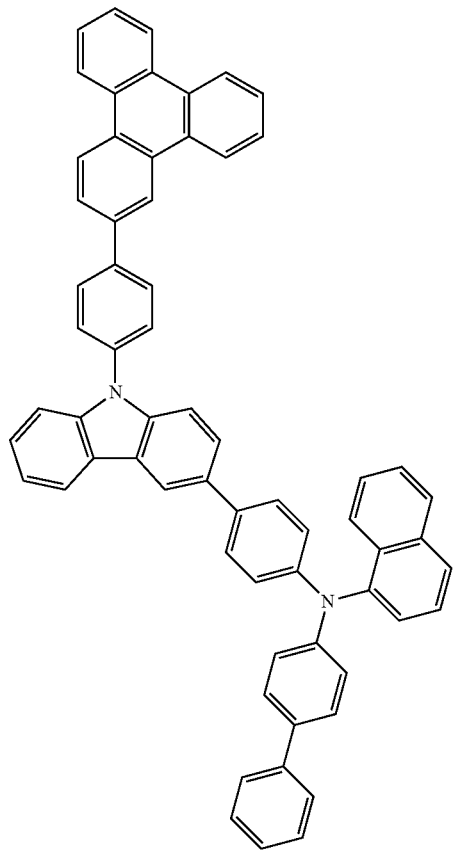
[A-273]
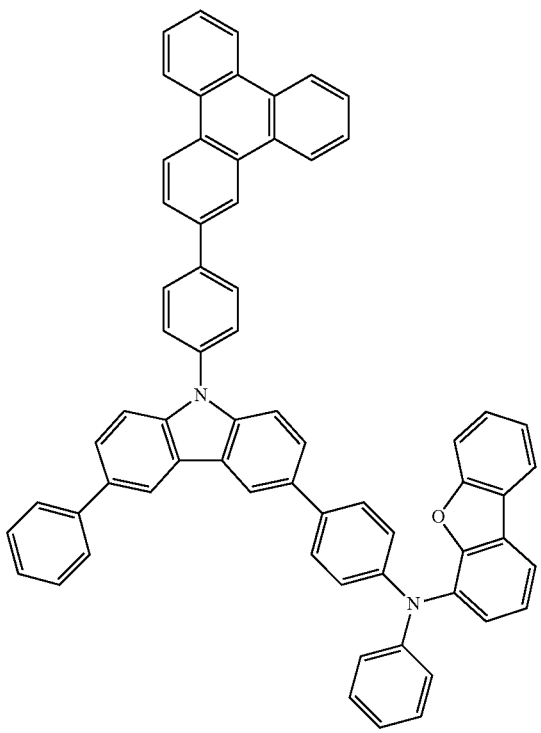
[A-274]
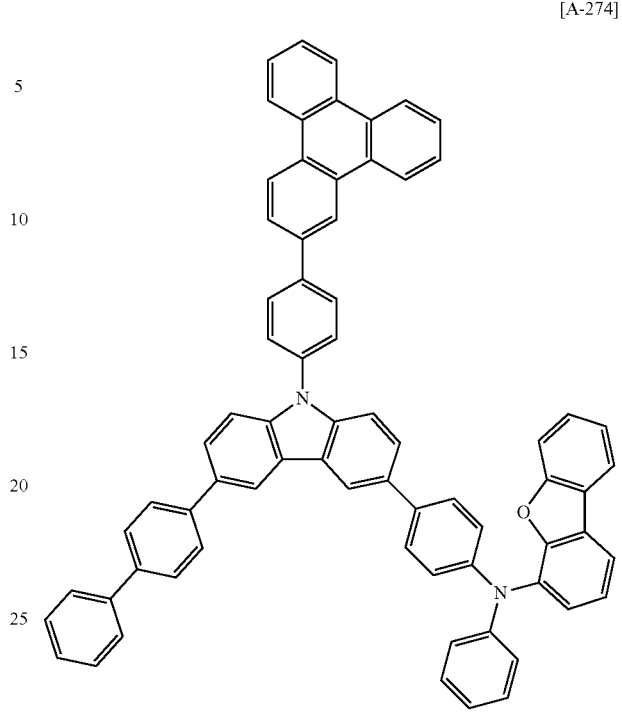
[A-275]
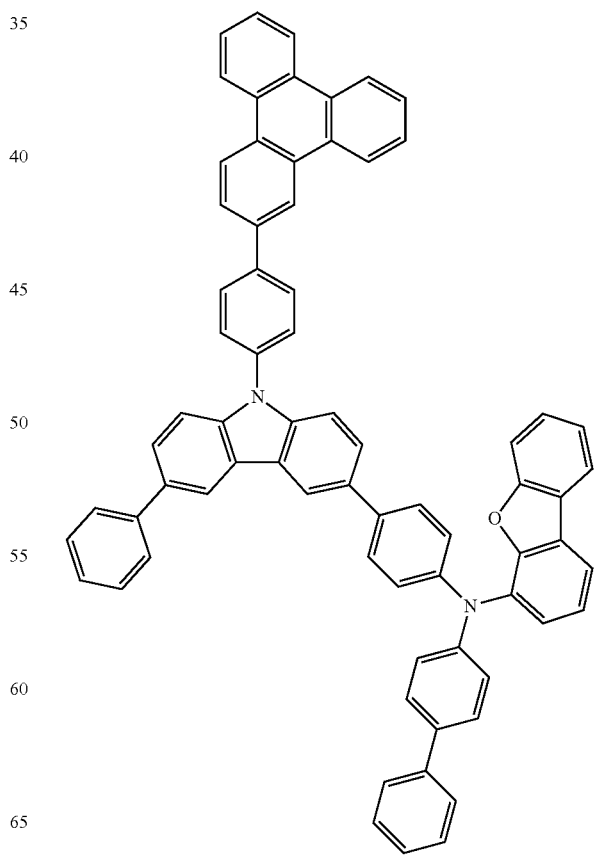

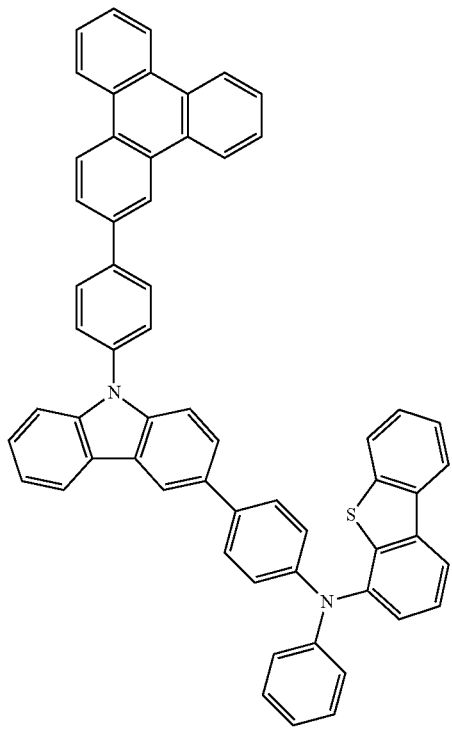
[A-276]
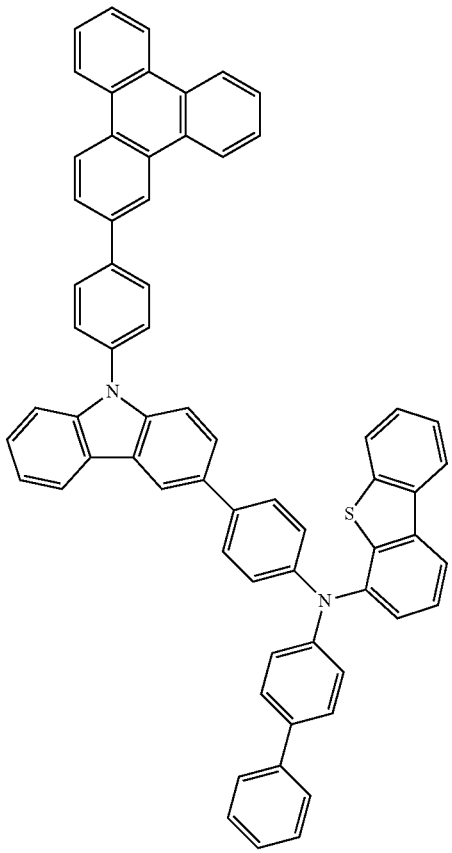
[A-278]
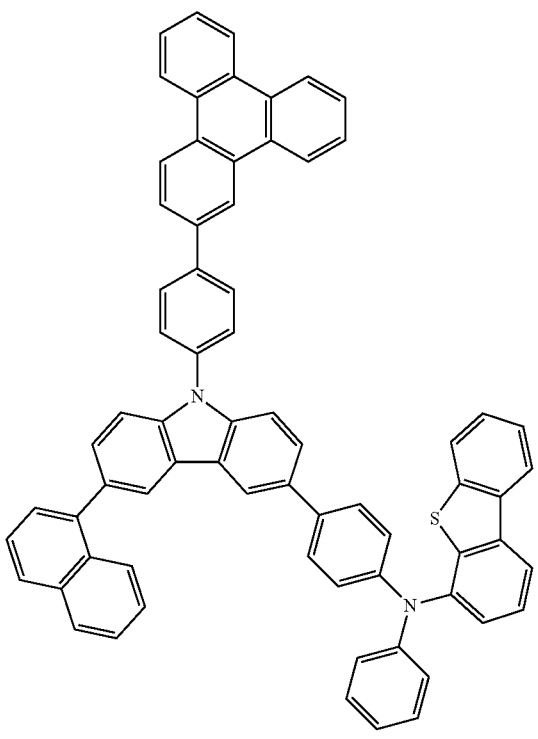
[A-277]
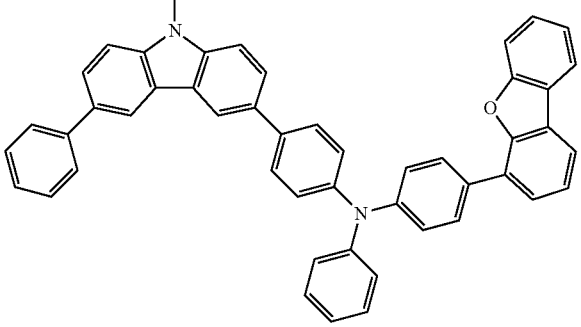
[A-279]

[A-280]
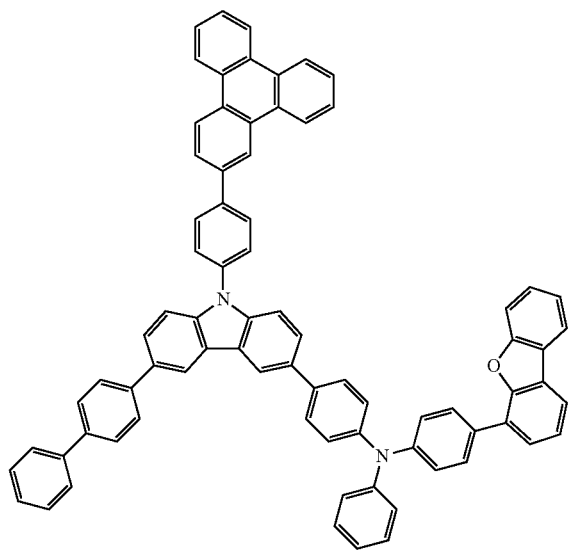
[A-281]
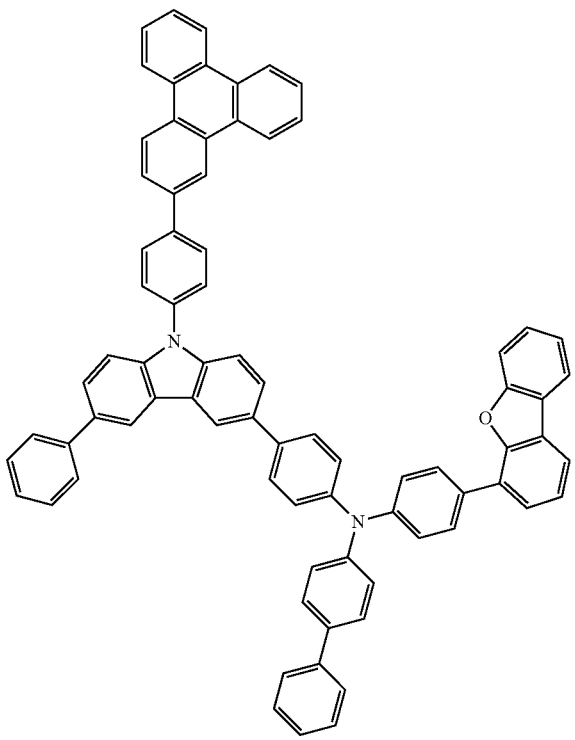
[A-282]
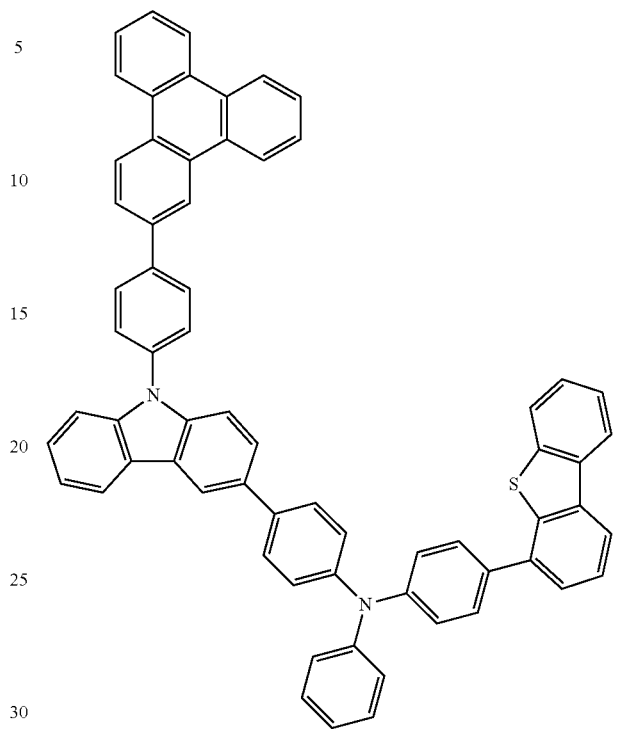
[A-283]
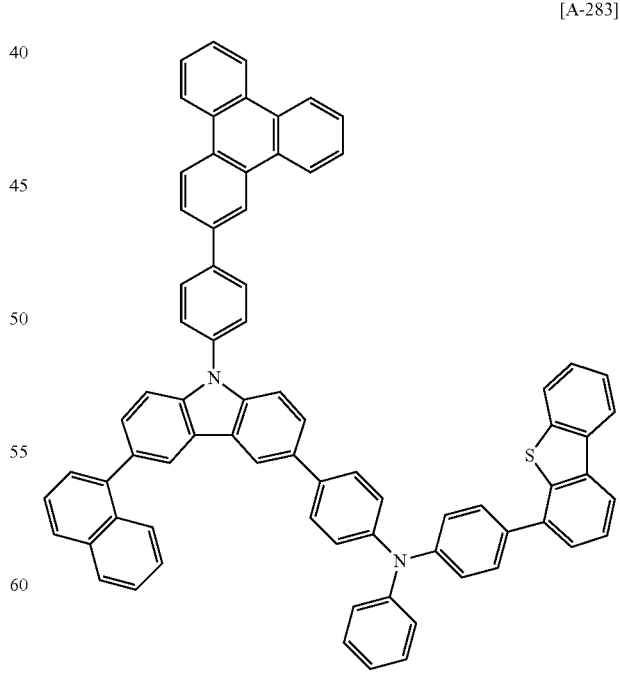

[A-284]
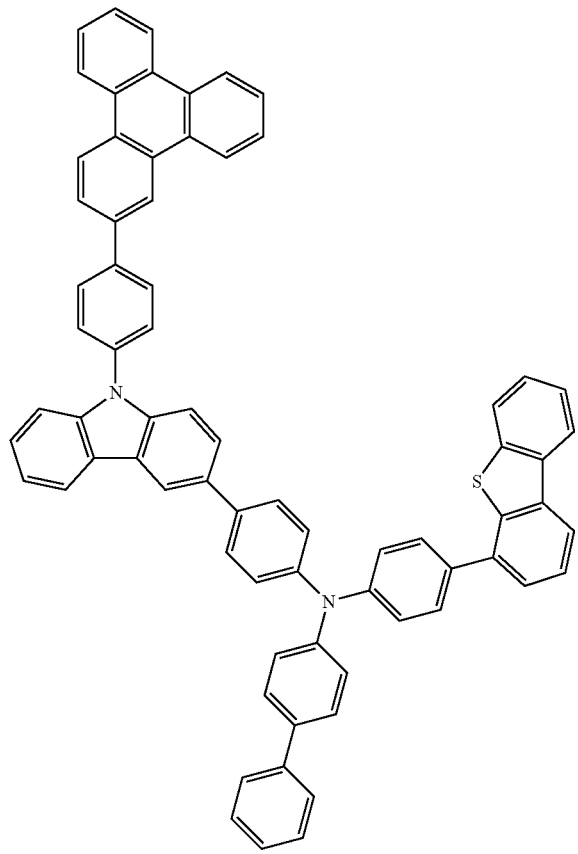
[A-285]
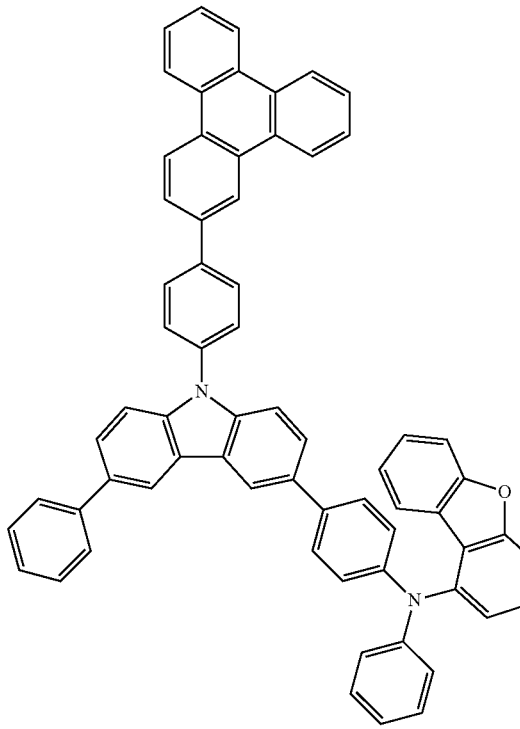
[A-286]
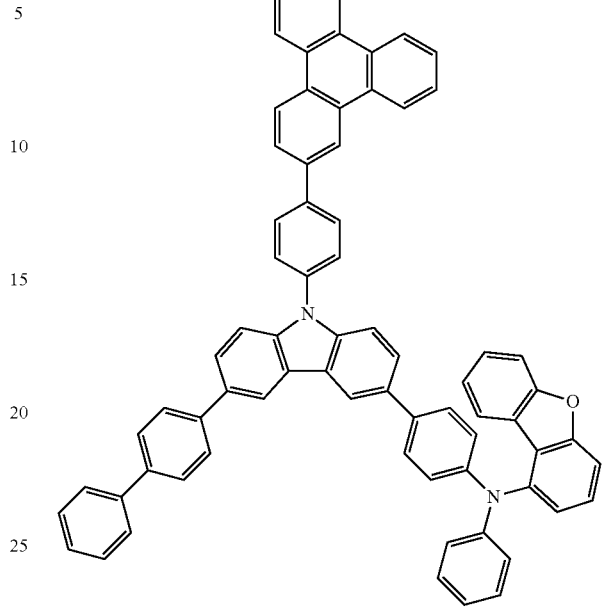
[A-287]
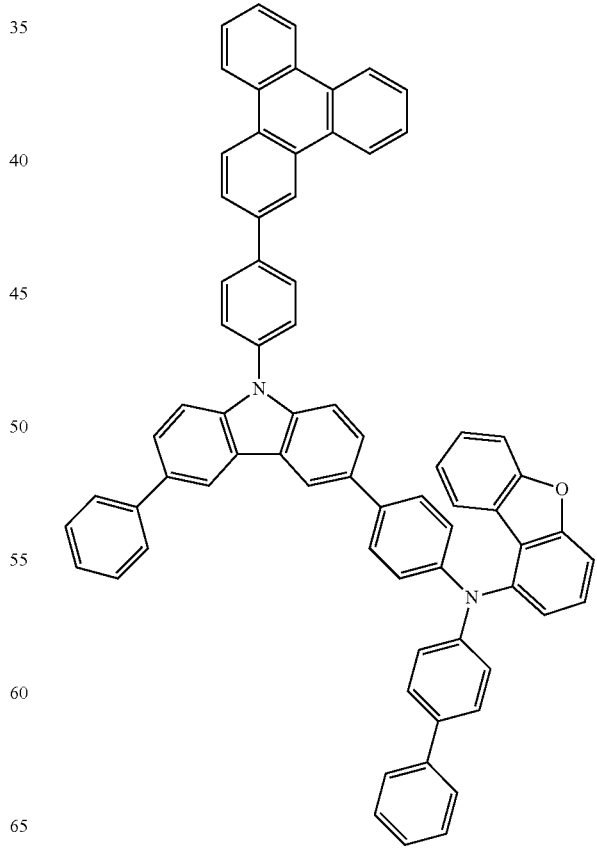

[A-288]
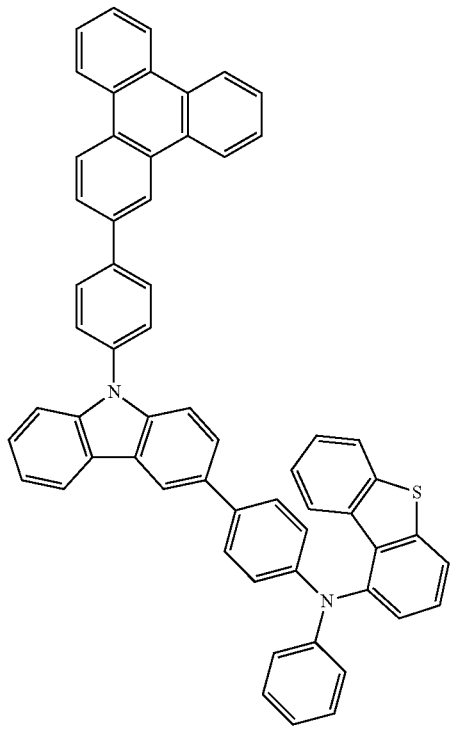
[A-289]
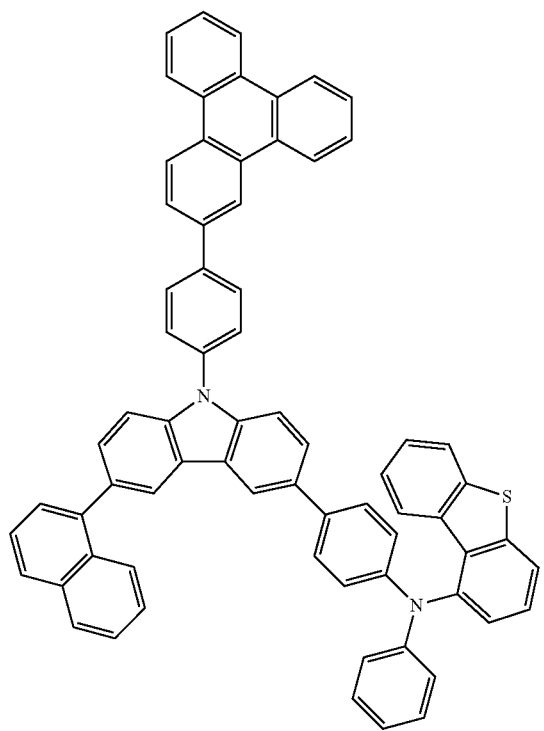
[A-290]
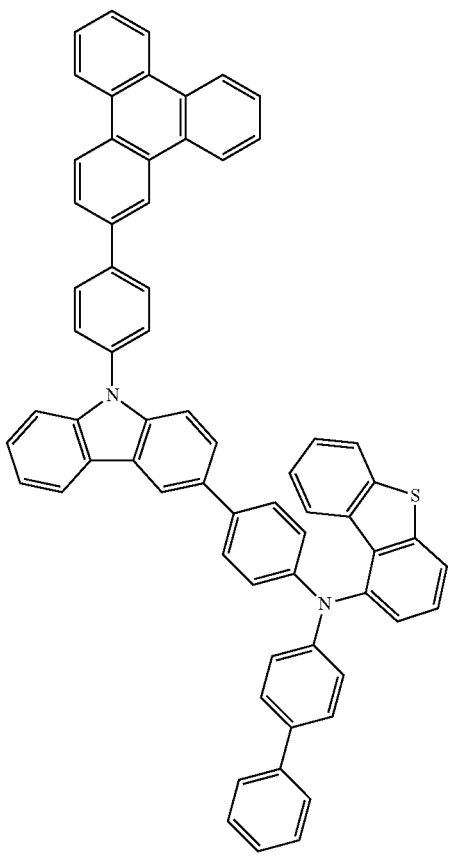
[A-291]
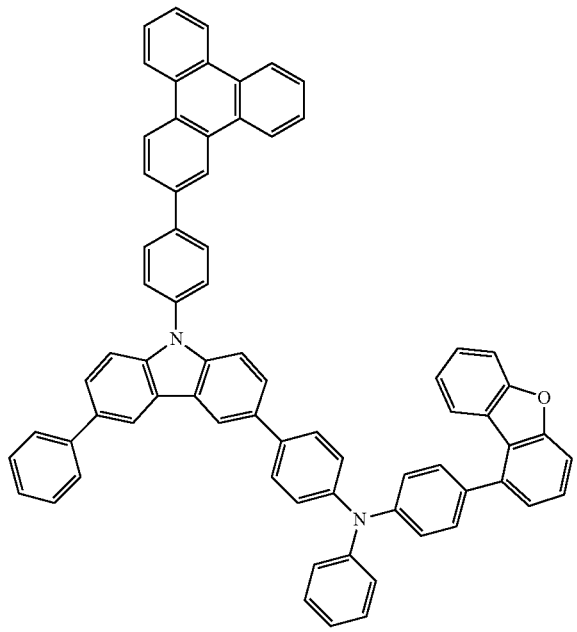

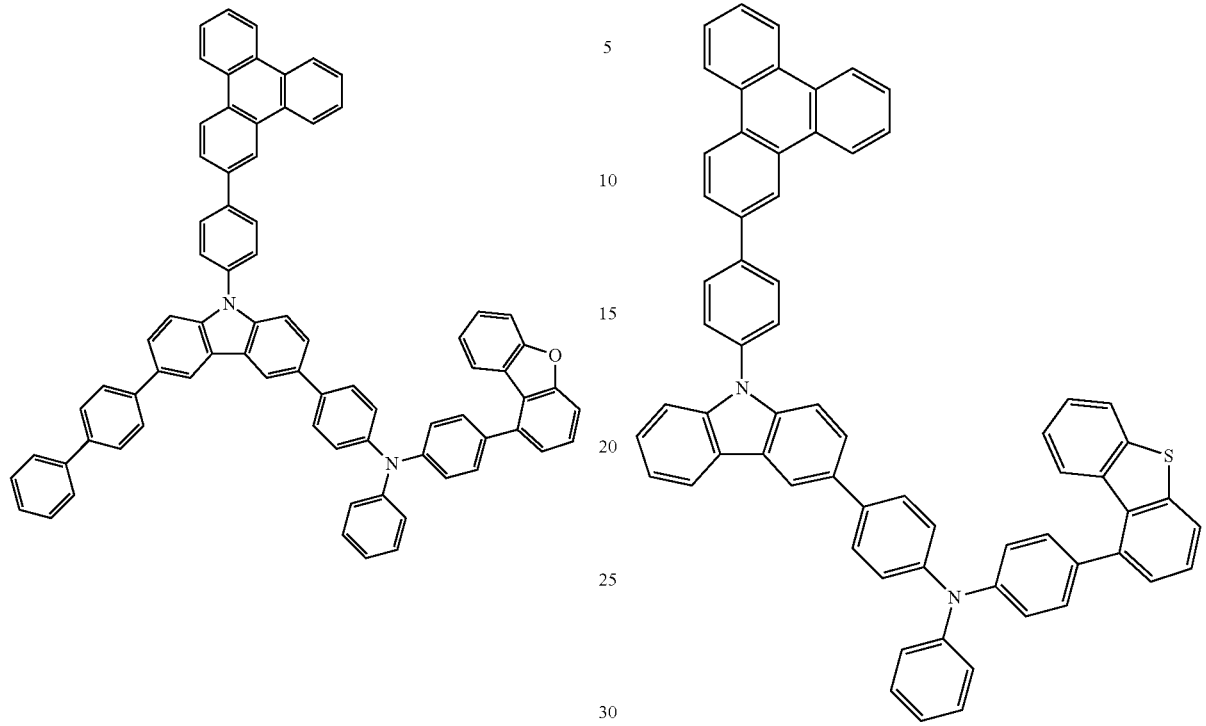
[A-292]
[A-293]
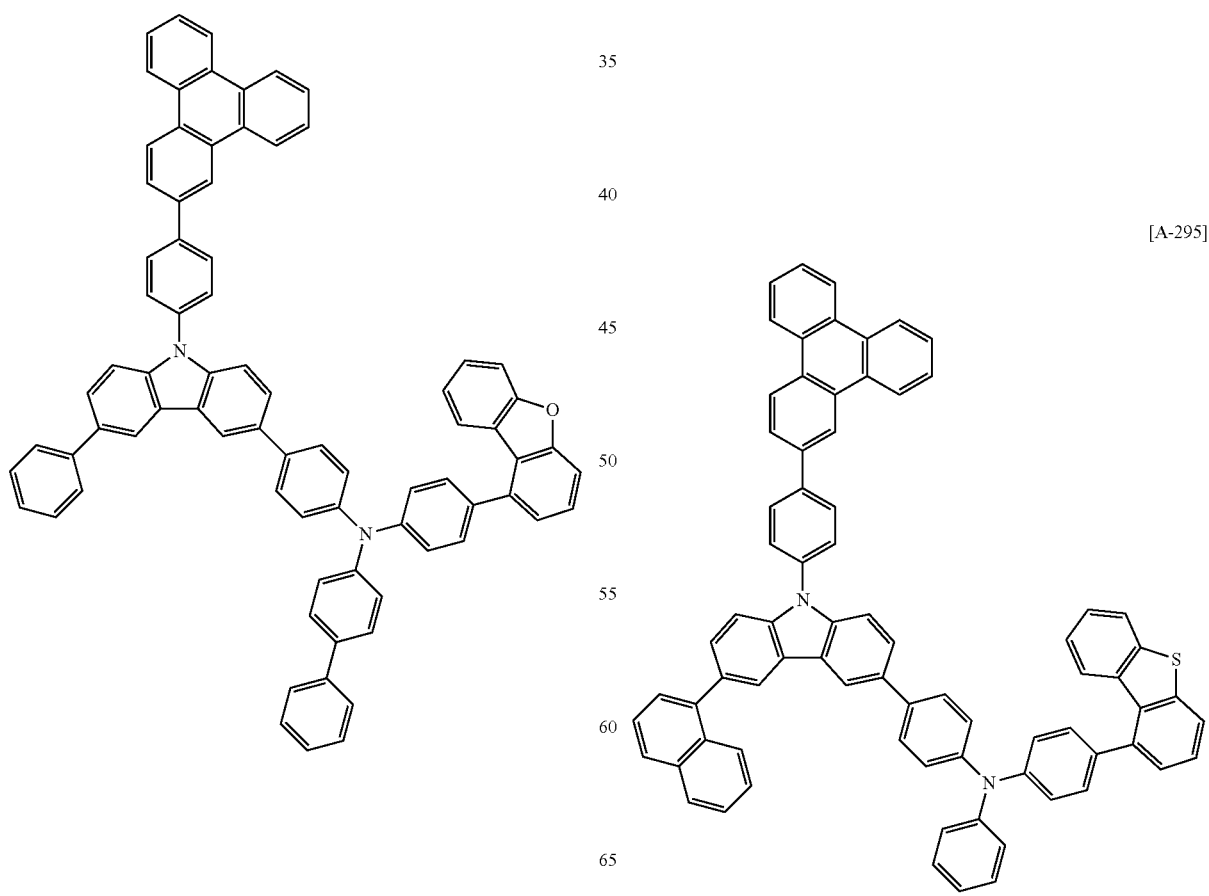
[A-294]
[A-295]

[A-296]
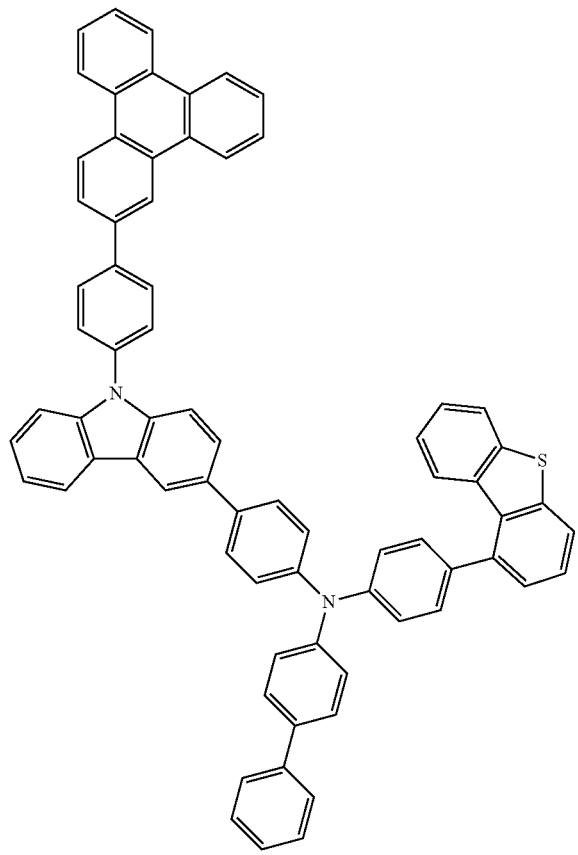
[A-297]
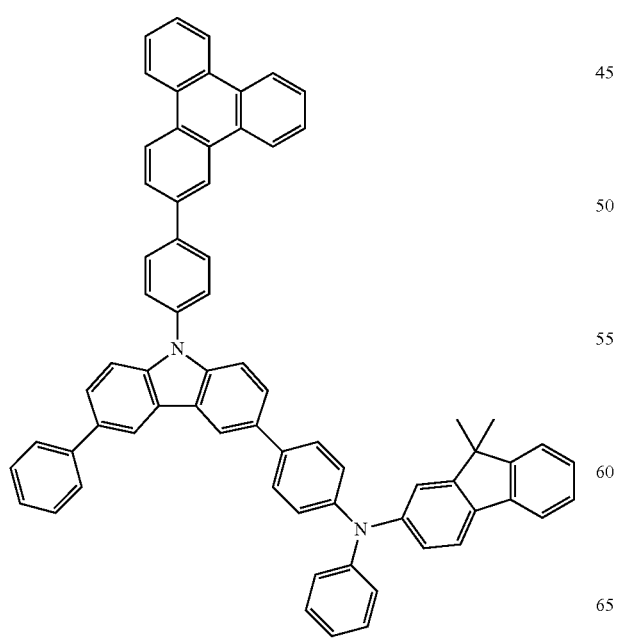
[A-298]
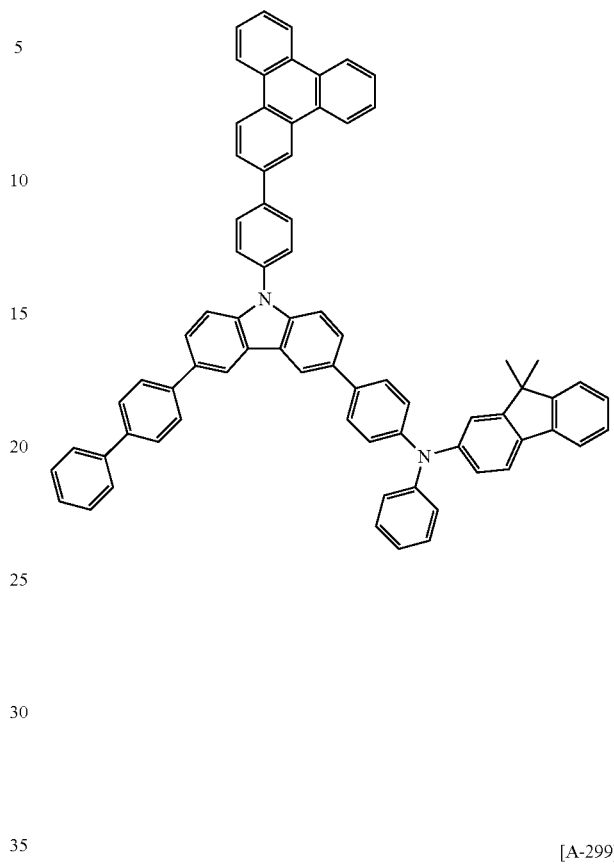
[A-299]
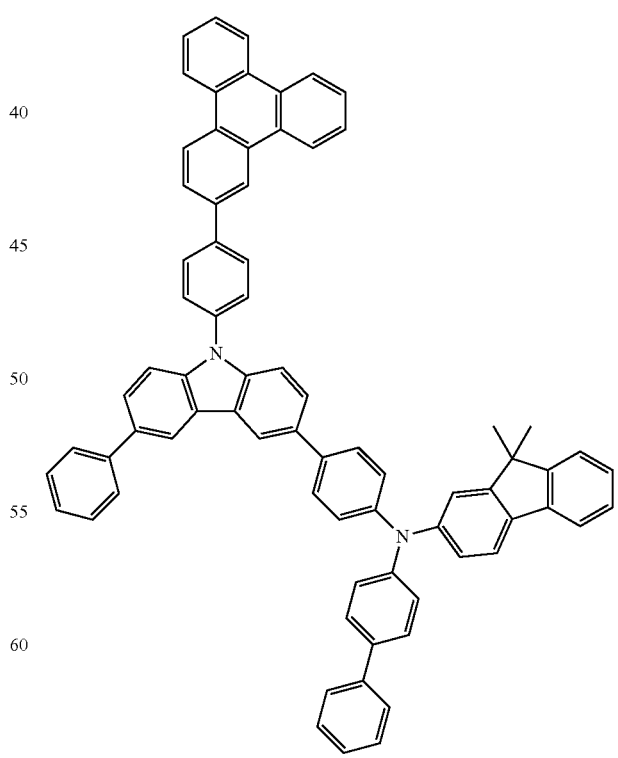

[A-300]
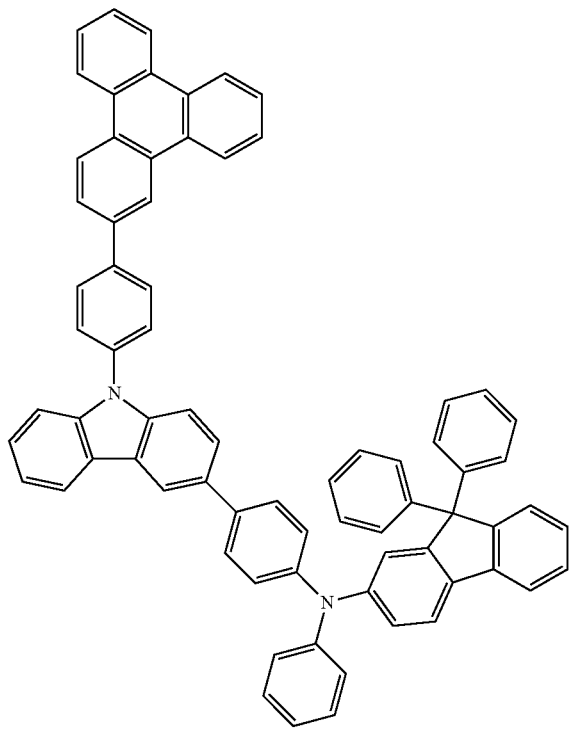
[A-302]
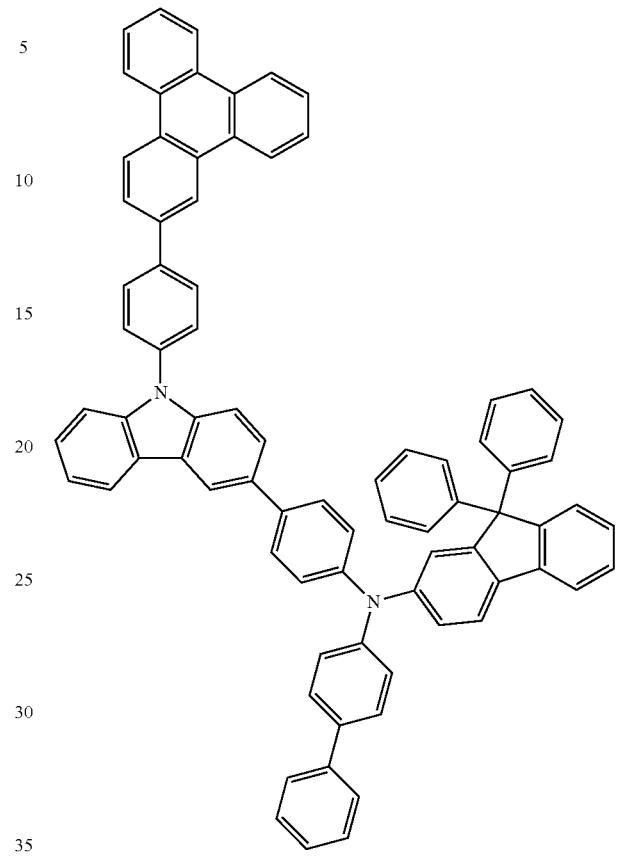
[A-301]
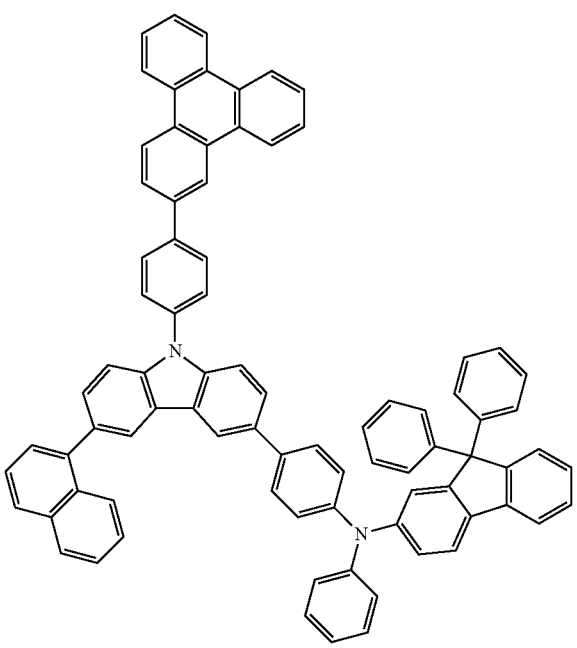
[A-303]
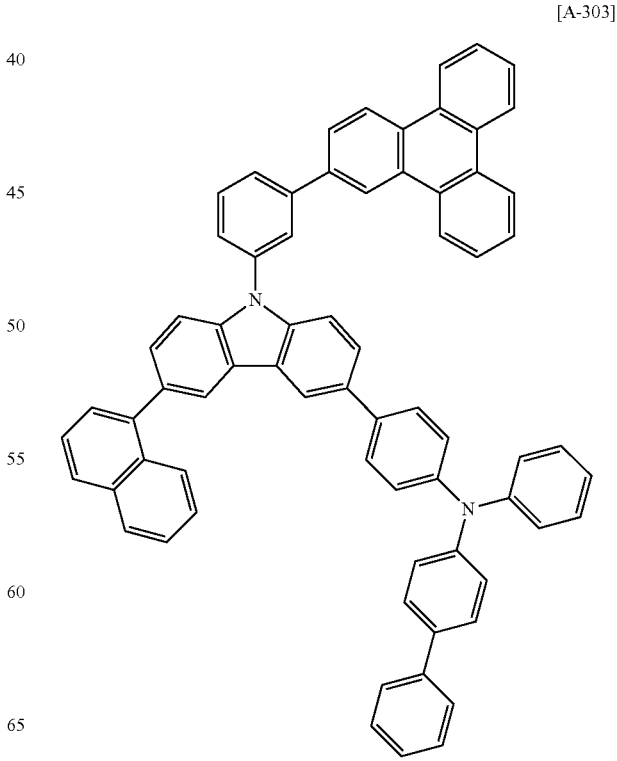

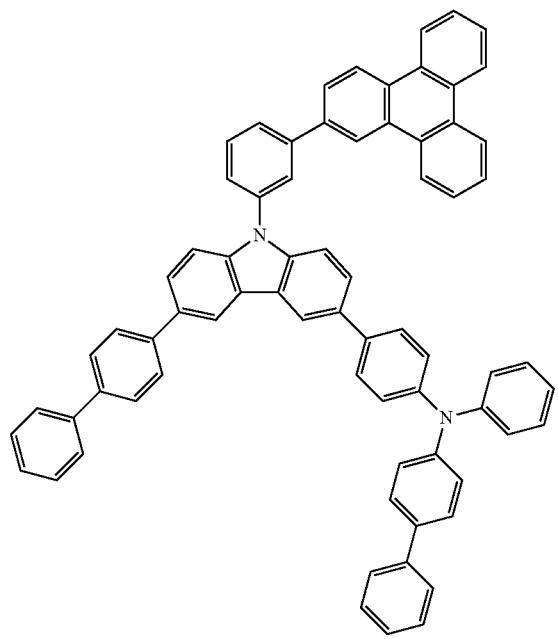
[A-304]
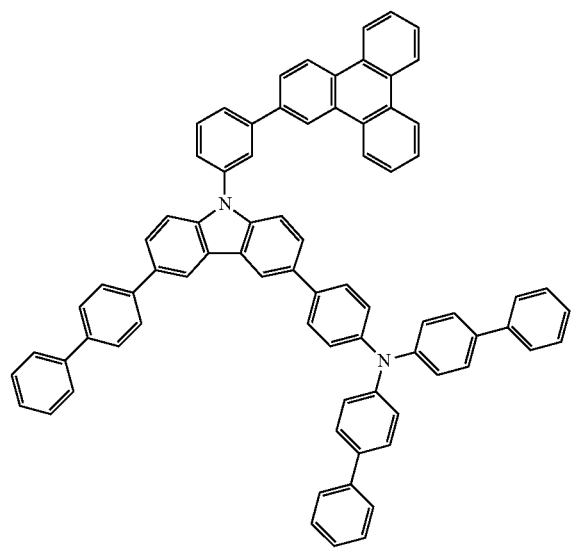
[A-306]
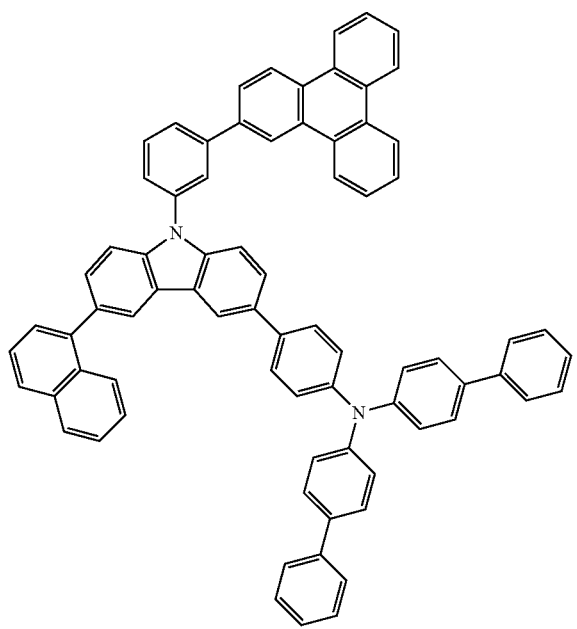
[A-305]
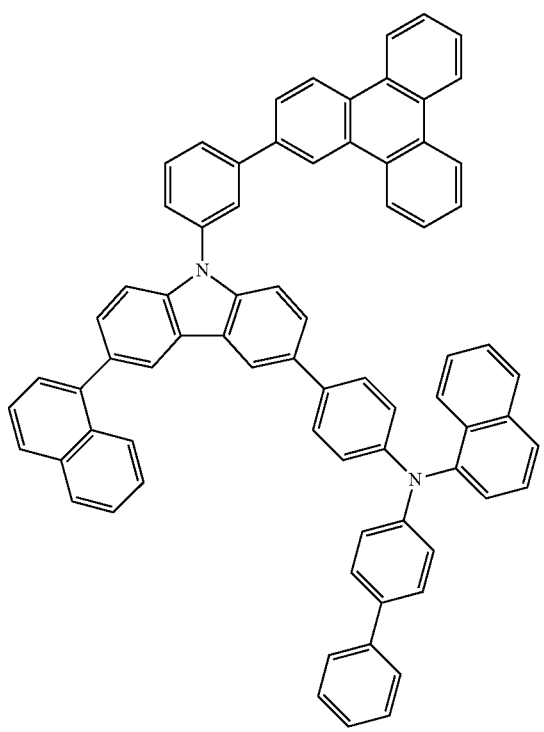
[A-307]

[A-308]
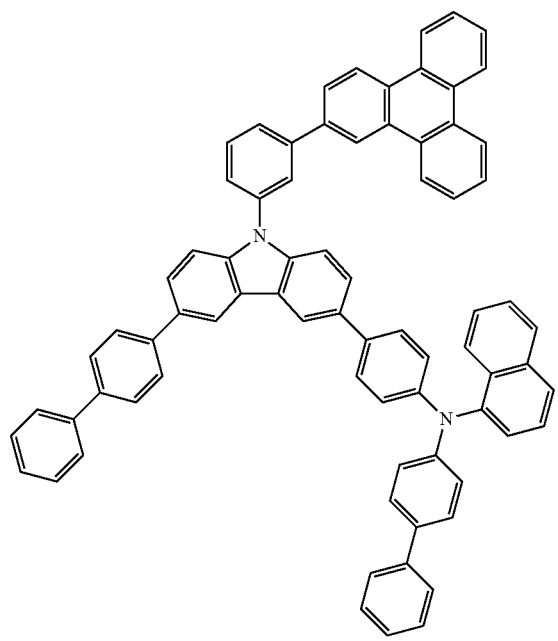
[A-310]
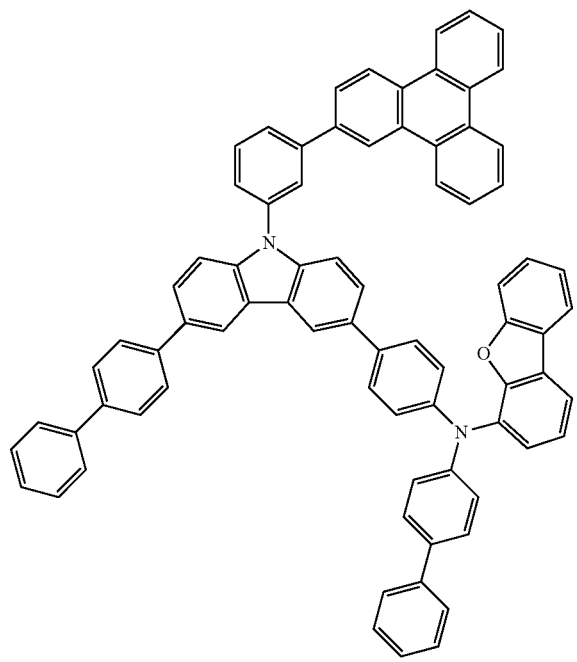
[A-309]
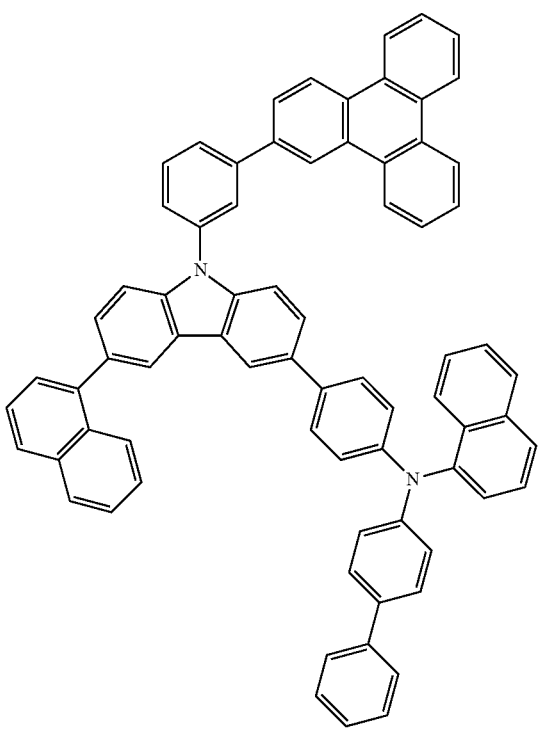
[A-311]
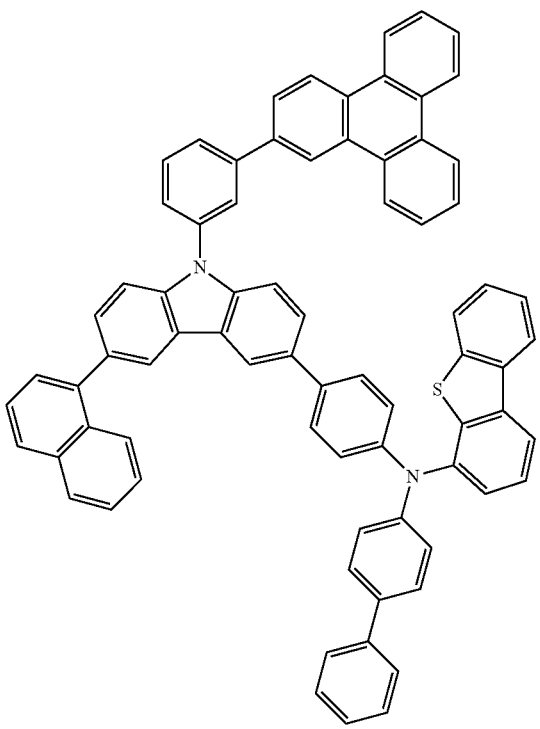

-continued
[A-312]
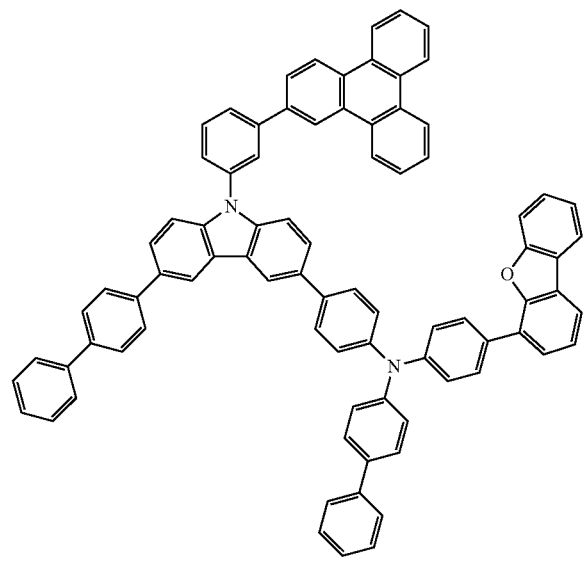
[A-314]
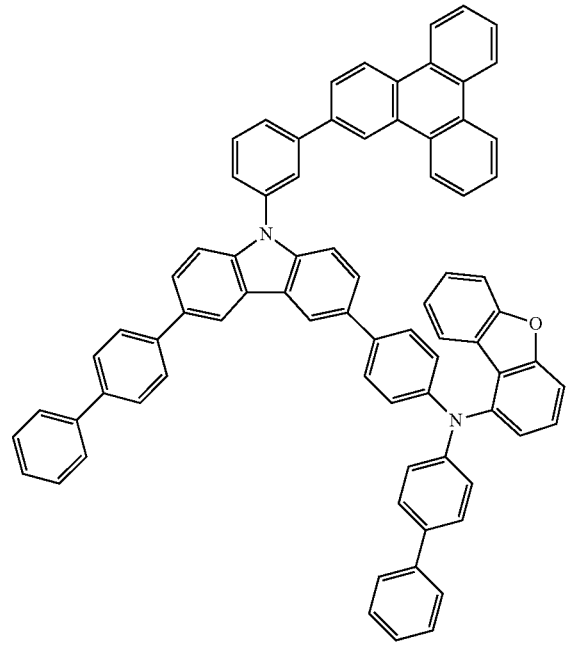
[A-313]
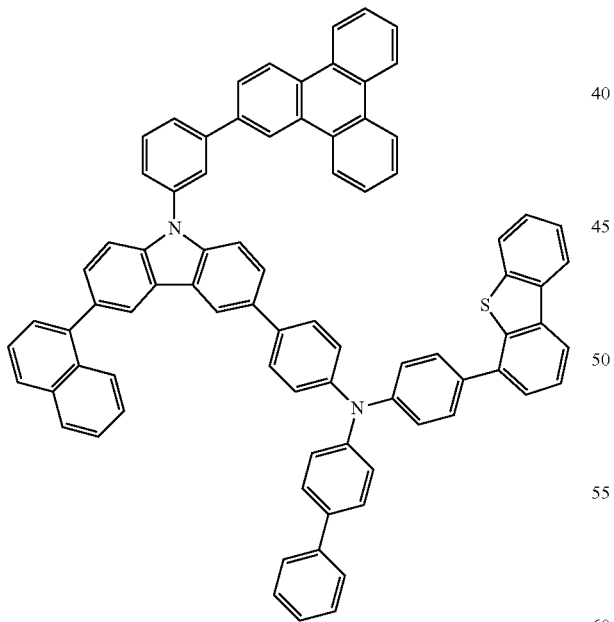
[A-315]
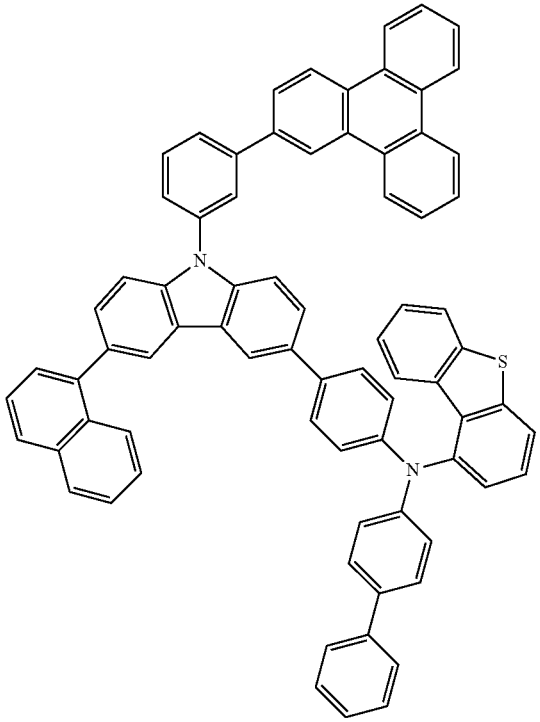

[A-316]
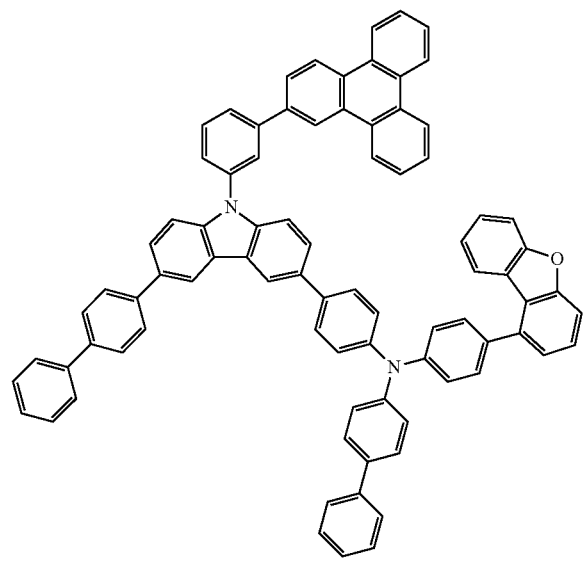
[A-318]
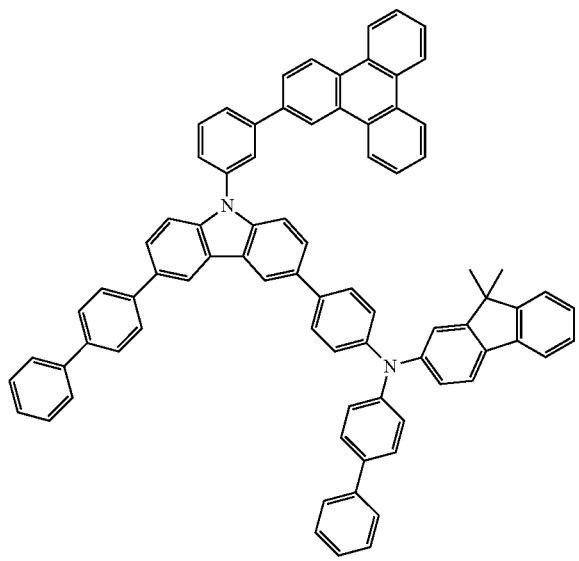
[A-317]
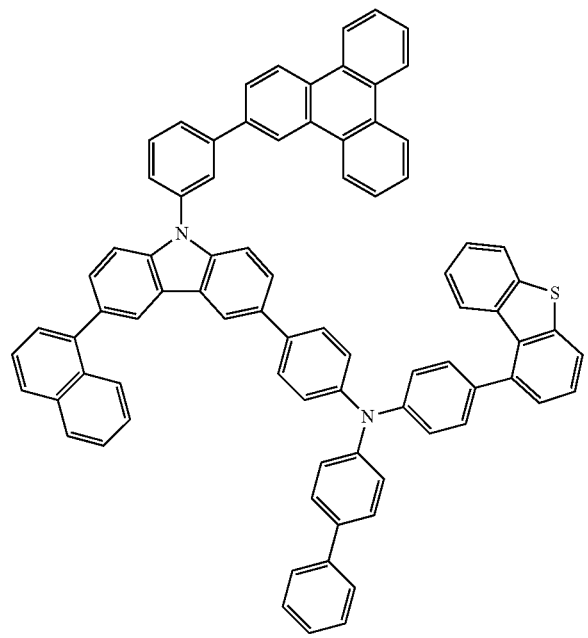
[A-319]
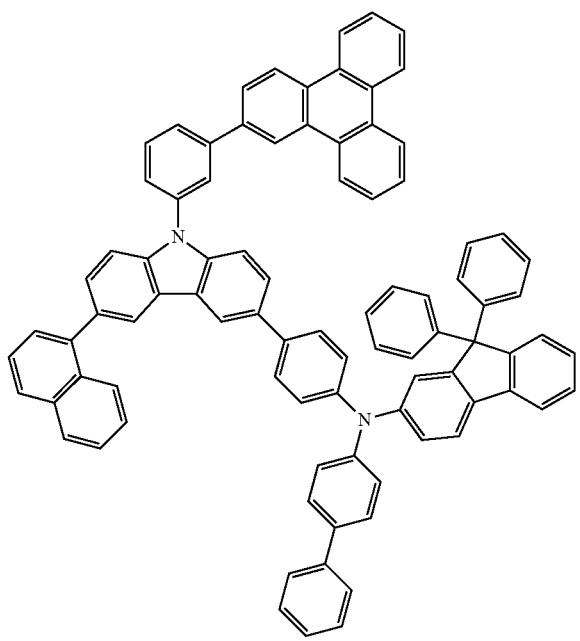

[A-320]
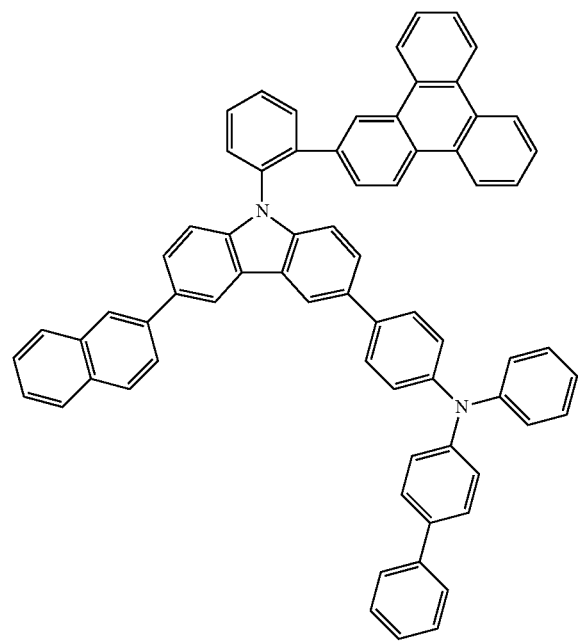
[A-322]
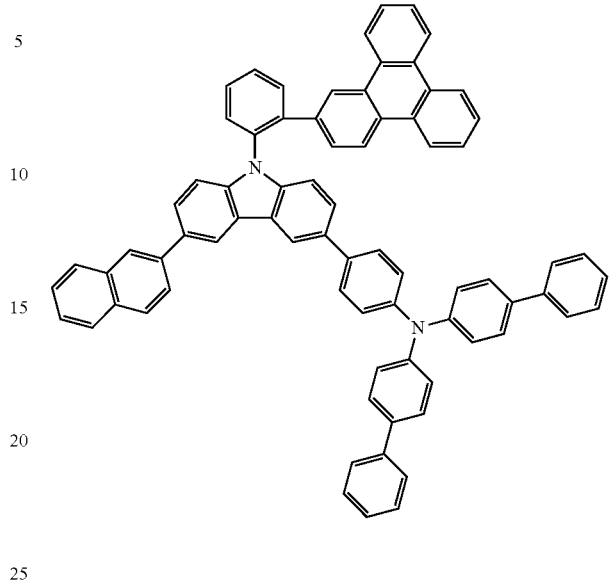
[A-321]
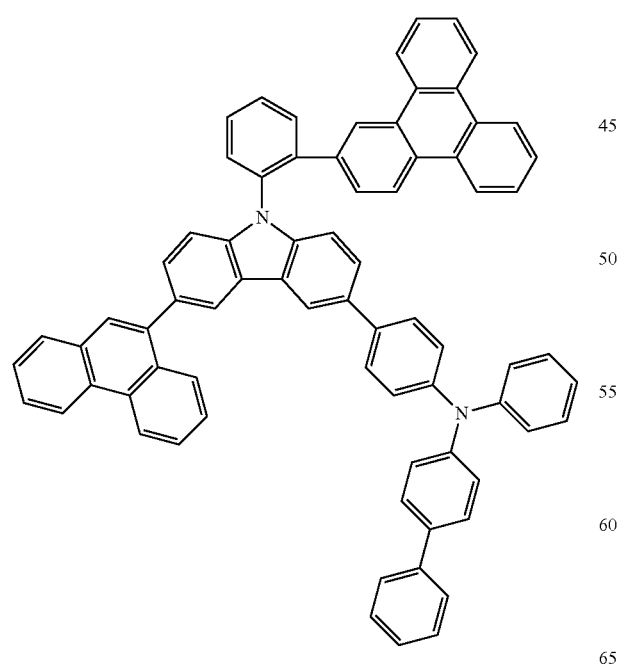
[A-323]

[A-324]
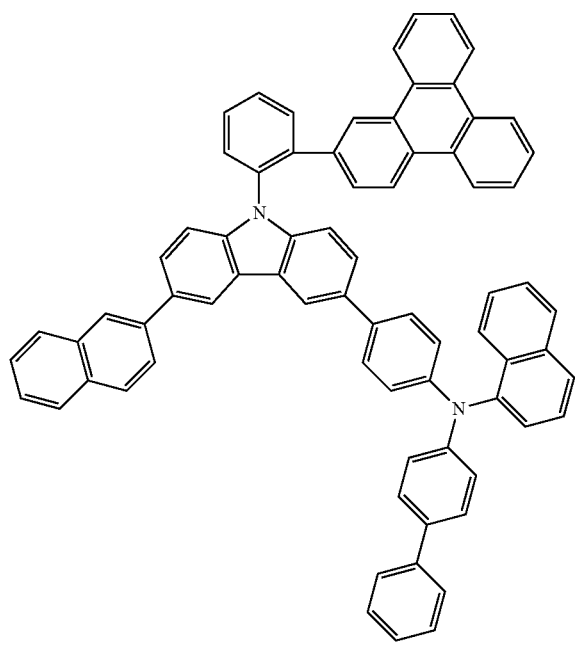
[A-326]
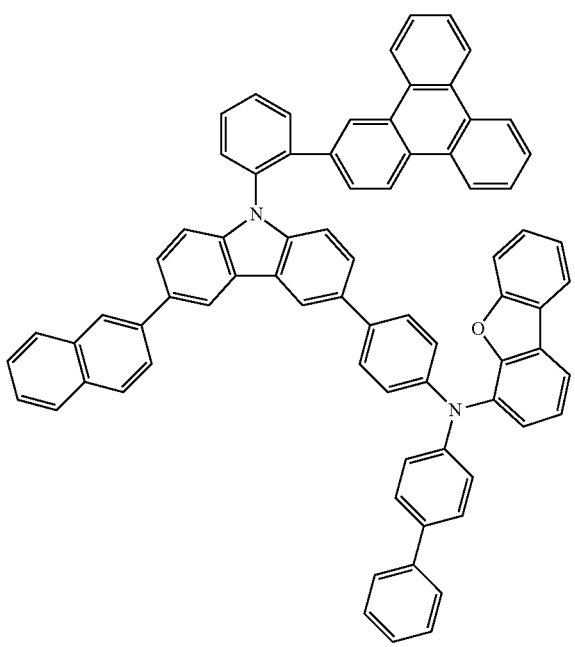
[A-325]
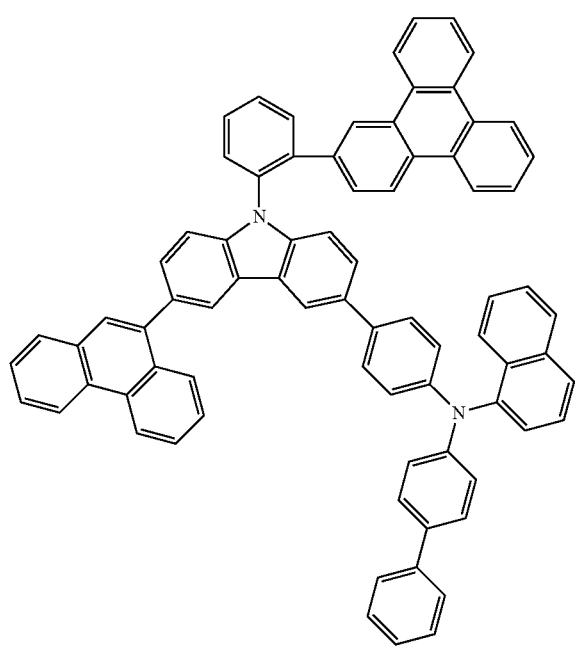
[A-327]
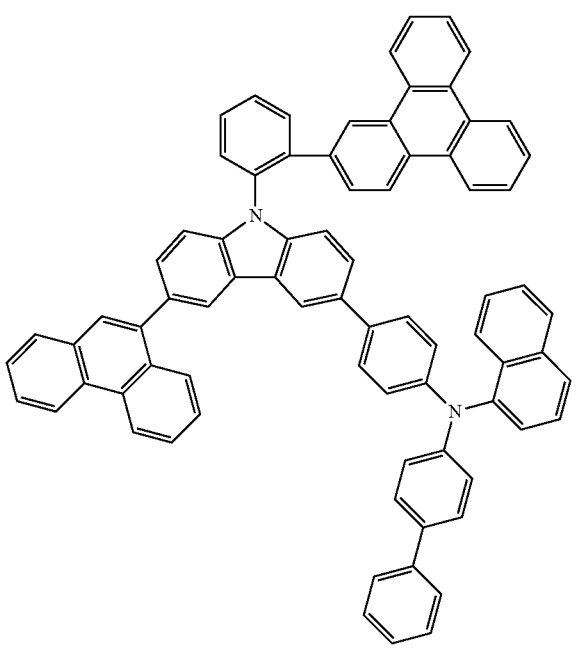

-continued
[A-328]
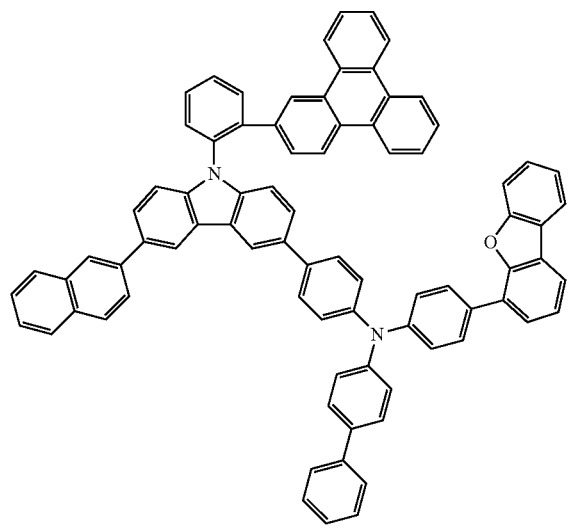
[A-329]
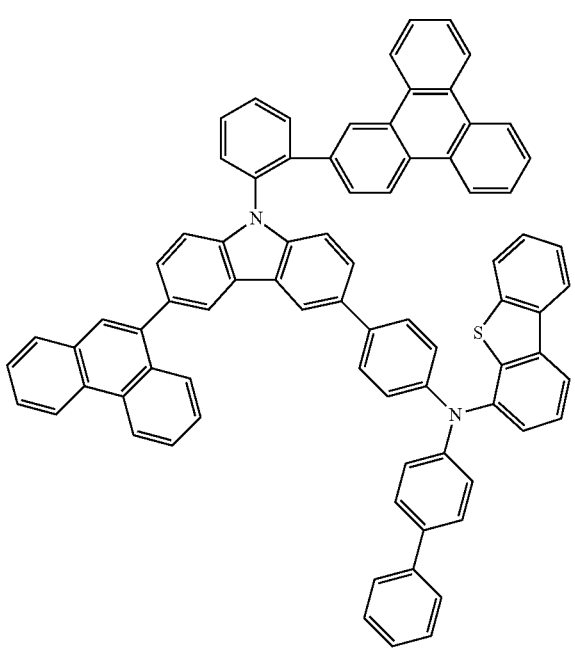
-continued
[A-330]
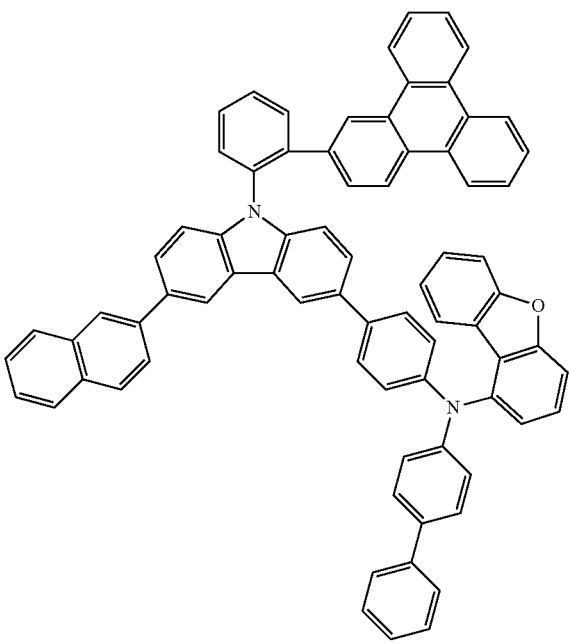
[A-331]
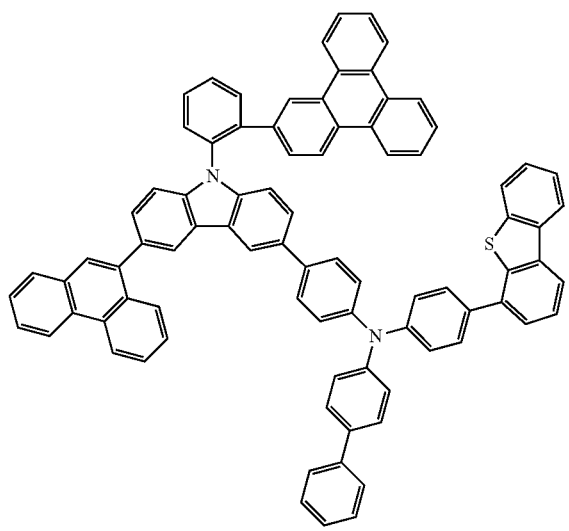

623
-continued

[A-332]

[A-333]

[A-334]

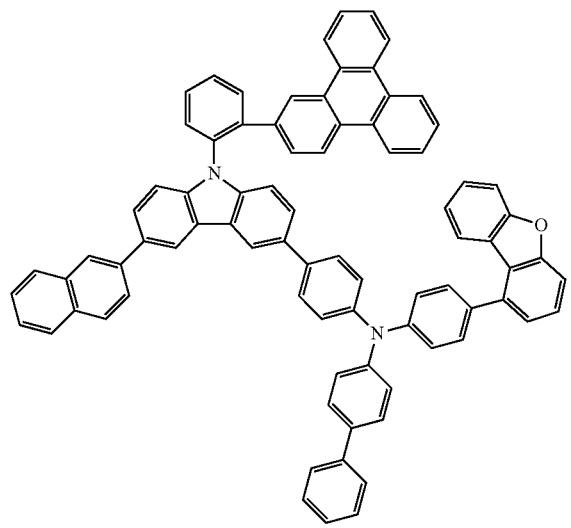

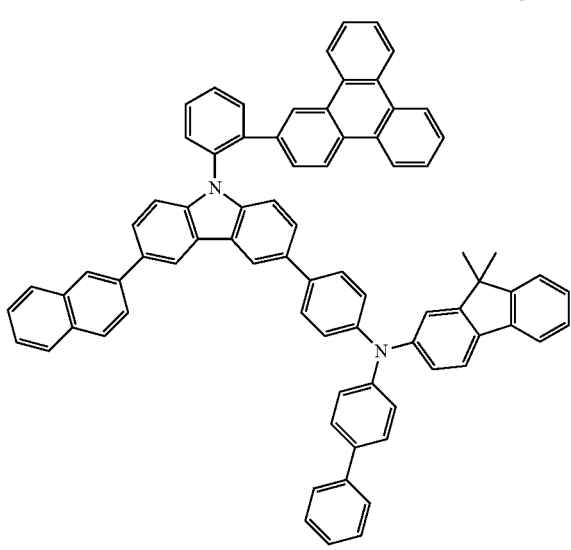

624
-continued

[A-335]

[A-336]

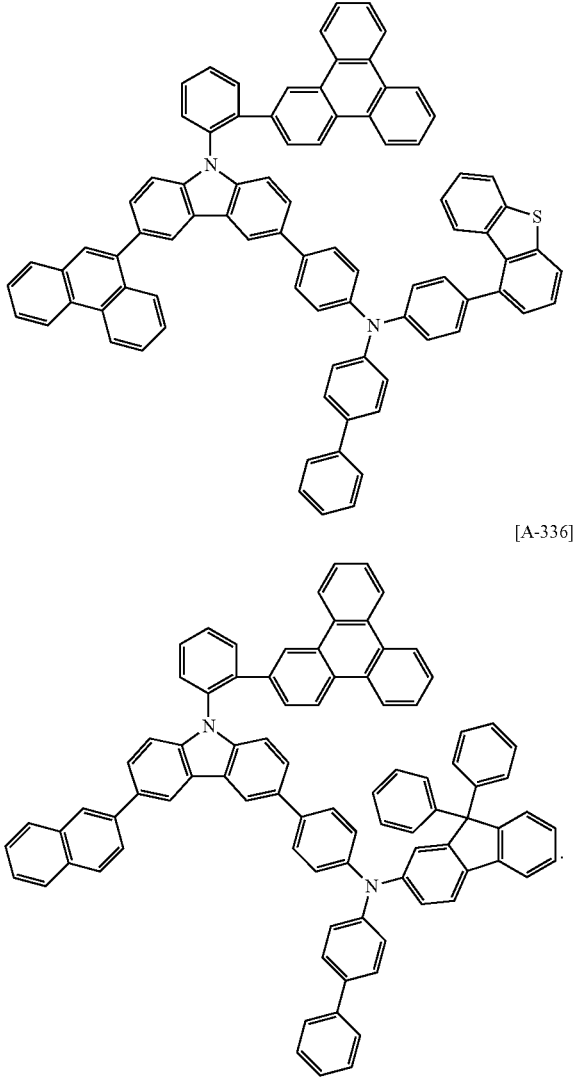

9. The compound as claimed in claim 1, wherein the organic photoelectric device is an organic light emitting diode, an organic solar cell, an organic transistor, an organic photo conductor drum, or an organic memory device.

10. An organic light emitting diode, comprising:
an anode, a cathode, and one or more organic thin layers between the anode and the cathode,
wherein at least one of the organic thin layers includes the compound as claimed in claim 1.

11. The organic light emitting diode as claimed in claim 10, wherein at least one of the organic thin layers includes an emission layer, a hole transport layer (HTL), a hole injection layer (HIL), an electron transport layer (ETL), an electron injection layer (EIL), a hole blocking layer, or a combination thereof.

12. The organic light emitting diode as claimed in claim 10, wherein the compound is included in an electron transport layer (ETL) or an electron injection layer (EIL).

13. The organic, light emitting diode as claimed in claim 10, wherein the compound is included in an emission layer.

14. The organic light emitting diode as claimed in claim 10, wherein the compound is a phosphorescent or fluorescent host material in an emission layer.

15. The organic light emitting diode as claimed in claim 10, wherein the compound is a fluorescent, blue dopant material in an emission layer.

16. A display device comprising the organic light emitting diode as claimed in claim 10.

* * * * *